(12) United States Patent
McCann et al.

(10) Patent No.: US 11,000,375 B2
(45) Date of Patent: May 11, 2021

(54) HEART VALVE SEALING DEVICES AND DELIVERY DEVICES THEREFOR

(71) Applicant: Edwards Lifesciences Corporation, Irvine, CA (US)

(72) Inventors: Alex Philip McCann, Lake Forest, CA (US); Grant Matthew Stearns, Tustin, CA (US); Eric Robert Dixon, Villa Park, CA (US); Yoon Hee Kwon, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 134 days.

(21) Appl. No.: 16/218,060

(22) Filed: Dec. 12, 2018

(65) Prior Publication Data

US 2020/0113691 A1    Apr. 16, 2020

Related U.S. Application Data

(60) Provisional application No. 62/744,031, filed on Oct. 10, 2018.

(51) Int. Cl.
*A61F 2/24*    (2006.01)
*A61B 17/00*    (2006.01)
(Continued)

(52) U.S. Cl.
CPC ...... *A61F 2/2466* (2013.01); *A61B 17/00234* (2013.01); *A61B 17/0469* (2013.01); *A61B 17/3468* (2013.01); *A61F 2/246* (2013.01); *A61F 2/2448* (2013.01); *A61F 2/2463* (2013.01); *A61B 17/0401* (2013.01);
(Continued)

(58) Field of Classification Search
CPC ............................. A61F 2/2454; A61F 2/2463
See application file for complete search history.

(56) References Cited

U.S. PATENT DOCUMENTS

| | | |
|---|---|---|
| 3,874,368 A | 4/1975 | King et al. |
| 4,340,091 A | 7/1982 | Skelton et al. |
| (Continued) | | |

FOREIGN PATENT DOCUMENTS

| | | |
|---|---|---|
| CN | 1142351 A | 2/1997 |
| EP | 0098100 A2 | 1/1984 |
| (Continued) | | |

OTHER PUBLICATIONS

Umaña et al.,""Bow-tie" mitral valve repair: an adjuvant technique for ischemic mitral regurgitation," Ann Thorac Surg. Nov. 1998;66(5):1640-6.

(Continued)

*Primary Examiner* — Suba Ganesan
(74) *Attorney, Agent, or Firm* — Thomas C. Richardson

(57) ABSTRACT

An exemplary valve repair device for repairing a native valve of a patient includes: a coaption element; a pair of paddles connected to the coaption element; a catch point formed by a portion of at least one of the coaption element and the pair of paddles when the paddles are in the open position; and a cover covering connected to the coaption element and the paddles for covering the catch point. The paddles are movable between an open position and a closed position and are configured to attach to the native valve of the patient.

29 Claims, 235 Drawing Sheets

(51) Int. Cl.
*A61B 17/04* (2006.01)
*A61B 17/34* (2006.01)

(52) U.S. Cl.
CPC .............. *A61B 2017/00243* (2013.01); *A61B 2017/00557* (2013.01); *A61B 2017/00783* (2013.01); *A61B 2017/00867* (2013.01); *A61B 2017/0464* (2013.01); *A61F 2/2445* (2013.01); *A61F 2210/0014* (2013.01); *A61F 2220/0016* (2013.01); *A61F 2220/0041* (2013.01); *A61F 2220/0091* (2013.01); *A61F 2230/0093* (2013.01); *A61F 2240/001* (2013.01); *A61F 2250/0003* (2013.01)

(56) References Cited

U.S. PATENT DOCUMENTS

| | | |
|---|---|---|
| 4,506,669 A | 3/1985 | Blake, III |
| 4,590,937 A | 5/1986 | Deniega |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,665 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,400 A | 10/1995 | Shichman et al. |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,575,971 B2 | 6/2003 | Hauck et al. |
| 6,626,930 B1 | 9/2003 | Allen et al. |
| 6,629,534 B1 | 10/2003 | St. Goar et al. |
| 6,695,866 B1 | 2/2004 | Kuehn et al. |
| 6,719,767 B1 | 4/2004 | Kimblad |
| 6,752,813 B2 | 6/2004 | Goldfarb et al. |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,011,669 B2 | 3/2006 | Kimblad |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,226,467 B2 | 6/2007 | Lucatero et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,704,269 B2 | 4/2010 | St. Goar et al. |
| 7,731,706 B2 | 6/2010 | Potter |
| 7,736,388 B2 | 6/2010 | Goldfarb et al. |
| 7,744,609 B2 | 6/2010 | Allen et al. |
| 7,748,389 B2 | 7/2010 | Salahieh et al. |
| 7,753,923 B2 | 7/2010 | St. Goar et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,811,296 B2 | 10/2010 | Goldfarb et al. |
| 7,824,443 B2 | 11/2010 | Salahieh et al. |
| 7,981,123 B2 | 7/2011 | Seguin |
| 7,988,724 B2 | 8/2011 | Salahieh et al. |
| 7,998,151 B2 | 8/2011 | St. Goar et al. |
| 8,029,518 B2 | 10/2011 | Goldfarb et al. |
| 8,052,592 B2 | 11/2011 | Goldfarb et al. |
| 8,052,750 B2 | 11/2011 | Tuval et al. |
| 8,057,493 B2 | 11/2011 | Goldfarb et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,123,703 B2 | 2/2012 | Martin et al. |
| 8,133,239 B2 | 3/2012 | Oz et al. |
| 8,147,542 B2 | 4/2012 | Maisano et al. |
| 8,172,856 B2 | 5/2012 | Eigler et al. |
| 8,187,299 B2 | 5/2012 | Goldfarb et al. |
| 8,206,437 B2 | 6/2012 | Bonhoeffer et al. |
| 8,216,256 B2 | 7/2012 | Raschdorf, Jr. et al. |
| 8,216,301 B2 | 7/2012 | Bonhoeffer et al. |
| 8,303,608 B2 | 11/2012 | Goldfarb et al. |
| 8,303,653 B2 | 11/2012 | Bonhoeffer et al. |
| 8,313,525 B2 | 11/2012 | Tuval et al. |
| 8,323,334 B2 | 12/2012 | Deem et al. |
| 8,343,174 B2 | 1/2013 | Goldfarb et al. |
| 8,348,995 B2 | 1/2013 | Tuval et al. |
| 8,348,996 B2 | 1/2013 | Tuval et al. |
| 8,409,273 B2 | 4/2013 | Thornton et al. |
| 8,414,643 B2 | 4/2013 | Tuval et al. |

(56) References Cited

U.S. PATENT DOCUMENTS

| | | |
|---|---|---|
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,500,761 B2 | 8/2013 | Goldfarb et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,734,505 B2 | 5/2014 | Goldfarb et al. |
| 8,740,918 B2 | 6/2014 | Seguin |
| 8,740,920 B2 | 6/2014 | Goldfarb et al. |
| 8,747,460 B2 | 6/2014 | Tuval et al. |
| 8,771,345 B2 | 7/2014 | Tuval et al. |
| 8,771,346 B2 | 7/2014 | Tuval et al. |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,945,177 B2 | 2/2015 | Dell et al. |
| 8,992,608 B2 | 3/2015 | Haug et al. |
| 9,011,468 B2 | 4/2015 | Ketai et al. |
| 9,034,032 B2 | 5/2015 | McLean et al. |
| 9,044,246 B2 | 6/2015 | Goldfarb et al. |
| 9,060,858 B2 | 6/2015 | Thornton et al. |
| 9,138,312 B2 | 9/2015 | Tuval et al. |
| 9,155,619 B2 | 10/2015 | Liu et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,427,237 B2 | 8/2016 | Oz et al. |
| 9,427,327 B2 | 8/2016 | Parrish |
| 9,439,763 B2 | 9/2016 | Geist et al. |
| 9,510,829 B2 | 12/2016 | Goldfarb et al. |
| 9,510,837 B2 | 12/2016 | Seguin |
| 9,510,946 B2 | 12/2016 | Chau et al. |
| 9,539,092 B2 | 1/2017 | Bourang et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0050693 A1 | 3/2003 | Quijano et al. |
| 2003/0069593 A1 | 4/2003 | Tremulis et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0034365 A1 | 2/2004 | Lentz et al. |
| 2004/0039442 A1 | 2/2004 | St. Goar et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0097979 A1 | 5/2004 | Svanidze et al. |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0033446 A1 | 2/2005 | Deem et al. |
| 2005/0049618 A1 | 3/2005 | Masuda et al. |
| 2005/0137686 A1 | 6/2005 | Salahieh et al. |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0240219 A1 | 10/2005 | Kahle et al. |
| 2005/0251183 A1 | 11/2005 | Buckman et al. |
| 2005/0267493 A1 | 12/2005 | Schreck et al. |
| 2005/0277959 A1 | 12/2005 | Cosgrove et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0038293 A1 | 2/2007 | St.Goar et al. |
| 2007/0093857 A1 | 4/2007 | Rogers et al. |
| 2007/0093890 A1 | 4/2007 | Eliasen et al. |
| 2007/0100356 A1 | 5/2007 | Lucatero et al. |
| 2007/0129737 A1 | 6/2007 | Goldfarb et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0167713 A1 | 7/2008 | Bolling |
| 2008/0167714 A1 | 7/2008 | St. Goar et al. |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0312664 A1 | 12/2008 | Bardsley et al. |
| 2008/0319455 A1 | 12/2008 | Harris et al. |
| 2009/0005863 A1 | 1/2009 | Goetz et al. |

(56) References Cited

U.S. PATENT DOCUMENTS

| | | |
|---|---|---|
| 2009/0024110 A1 | 1/2009 | Heideman et al. |
| 2009/0131680 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0275902 A1 | 11/2009 | Heeps et al. |
| 2009/0287304 A1 | 11/2009 | Dahlgren et al. |
| 2010/0022823 A1* | 1/2010 | Goldfarb ............ A61B 17/08 600/37 |
| 2010/0057192 A1 | 3/2010 | Celermajer |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0217283 A1 | 8/2010 | St. Goar et al. |
| 2010/0249497 A1 | 9/2010 | Peine et al. |
| 2010/0324595 A1 | 12/2010 | Linder et al. |
| 2011/0004227 A1 | 1/2011 | Goldfarb et al. |
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0257734 A1 | 10/2011 | Chalekian |
| 2011/0295281 A1 | 12/2011 | Mizumoto et al. |
| 2012/0022633 A1 | 1/2012 | Olson et al. |
| 2012/0041453 A1 | 2/2012 | Klingenbeck |
| 2012/0046741 A1 | 2/2012 | Tuval et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0123327 A1 | 5/2012 | Miller |
| 2012/0209318 A1 | 8/2012 | Qadeer |
| 2012/0277853 A1 | 11/2012 | Rothstein |
| 2013/0018372 A1 | 1/2013 | Sims et al. |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0039608 A1 | 2/2014 | Eidenschink |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0066693 A1 | 3/2014 | Goldfarb et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0222136 A1 | 8/2014 | Geist et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0094804 A1 | 4/2015 | Bonhoeffer et al. |
| 2015/0100116 A1 | 4/2015 | Mohl et al. |
| 2015/0105804 A1 | 4/2015 | Dell et al. |
| 2015/0105808 A1 | 4/2015 | Gordon et al. |
| 2015/0105857 A1 | 4/2015 | Bonhoeffer et al. |
| 2015/0148896 A1 | 5/2015 | Karapetian et al. |
| 2015/0157268 A1 | 6/2015 | Winshtein et al. |
| 2015/0182223 A1 | 7/2015 | Ketai et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257756 A1 | 9/2015 | Sauer |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008129 A1 | 1/2016 | Siegel |
| 2016/0008131 A1 | 1/2016 | Christianson et al. |
| 2016/0022970 A1 | 1/2016 | Forcucci et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0317290 A1 | 11/2016 | Chau et al. |
| 2016/0324634 A1 | 11/2016 | Gabbay |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100236 A1 | 4/2017 | Robertson et al. |
| 2017/0143330 A1 | 5/2017 | Basude et al. |
| 2017/0156725 A1 | 6/2017 | Hemmann |
| 2017/0231755 A1 | 8/2017 | Gloss et al. |
| 2017/0239048 A1 | 8/2017 | Goldfarb et al. |
| 2017/0252154 A1 | 9/2017 | Tubishevitz et al. |
| 2017/0281330 A1 | 10/2017 | Liljegren et al. |
| 2017/0348102 A1 | 12/2017 | Cousins et al. |
| 2018/0000582 A1 | 1/2018 | Tuval et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0126124 A1 | 5/2018 | Winston et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |

(56) References Cited

U.S. PATENT DOCUMENTS

| | | |
|---|---|---|
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2020/0113683 A1 | 4/2020 | Dale et al. |

FOREIGN PATENT DOCUMENTS

| | | |
|---|---|---|
| EP | 1281375 A2 | 2/2003 |
| EP | 0879069 B1 | 8/2003 |
| EP | 1301235 B1 | 10/2004 |
| EP | 1583577 B1 | 5/2007 |
| EP | 1408850 B1 | 9/2009 |
| EP | 0930845 B1 | 10/2009 |
| EP | 1624810 B1 | 3/2011 |
| EP | 1804686 B1 | 9/2015 |
| EP | 2266503 B1 | 1/2017 |
| EP | 2266504 B1 | 3/2017 |
| EP | 1624810 B1 | 7/2017 |
| FR | 2146050 A5 | 2/1973 |
| FR | 9711600 | 3/1997 |
| FR | 2 768 324 A1 | 3/1999 |
| WO | 9632882 A1 | 10/1996 |
| WO | 9802103 A1 | 1/1998 |
| WO | 9900059 A1 | 1/1999 |
| WO | 9913777 A1 | 3/1999 |
| WO | 0060995 A2 | 10/2000 |
| WO | 03001893 A2 | 1/2003 |
| WO | 2004103162 A2 | 12/2004 |
| WO | 2004103434 A2 | 12/2004 |
| WO | 2005112792 A2 | 12/2005 |
| WO | 2006116558 A2 | 11/2006 |
| WO | 2006047709 A3 | 7/2007 |
| WO | 2010098804 A1 | 9/2010 |
| WO | 2016110760 A1 | 7/2016 |
| WO | 2016183485 A1 | 11/2016 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |

OTHER PUBLICATIONS

Al Zaibag et al., "Percutaneous Balloon Valvotomy in Tricuspid Stenosis", British Heart Journal, vol. 57, No. 1, Jan. 1987.

Al-Khaja et al., "Eleven Years' Experience with Carpentier-Edwards Biological Valves in Relation to Survival and Complications", European Journal of Cardio-thoracic Surgery 3: pp. 305-311, 1989.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs." European Heart Journal (1992), 13, 704-708.

Andersen, H.R. "History of Percutaneous Aortic Valve Prosthesis," Herz No. 34. pp. 343-346. 2009.

Batista RJ et al., "Partial left ventriculectomy to treat end-stage heart disease", Ann Thorac Surg., vol. 64, Issue—3, pp. 634-638, Sep. 1997.

Beall AC Jr. et al.,"Clinical experience with a dacron velour-covered teflon-disc mitral-valve prosthesis", Ann Thorac Surg., vol. 5, Issue 5, pp. 402-410, May 1968.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, pp. 654-670, 1964.

Fucci et al., "Improved results with mitral valve repair using new surgical techniques", Eur J Cardiothorac Surg. 1995;Issue 9, vol. 11, pp. 621-626.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue—3, pp. 240-245, Mar. 1998.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Praz et al., "Compassionate use of the PASCAL transcatheter mitral valve repair system for patients with severe mitral regurgitation: a multicentre, prospective, observational, first-in-man study," Lancet vol. 390, pp. 773-780, 2017.

Rashkind et al., "Creation of an Atrial Septal Defect Wthout Thoracotomy: A Pallative Approach to Complete Transposition of the Great Arteries", The Journal of the American Medical Association, vol. 196, No. 11, pp. 173-174, Jun. 13, 1956.

Rashkind et al., "Historical Aspects of Interventional Cardiology: Past, Present, and Future", Texas Heart Institute Journal, Interventional Cardiology, pp. 363-367.

Reul RM et al., "Mitral valve reconstruction for mitral insufficiency", Prog Cardiovasc Dis., vol. 39, Issue—6, May-Jun. 1997.

Rosch, M.D., Josef, "The Birth, Early Years and Future of Interventional Radiology," J Vasc Interv Radiol 2003; 14:841-853.

(56) References Cited

OTHER PUBLICATIONS

Ross, D.N, "Aortic Valve Surgery", Surgery of the Aortic Valves, Guy's Hospital, London, pp. 192-197.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology: 176. pp. 535-538, 1990.

Serruys et al., "Stenting of Coronary Arteries. Are we the Sorcerer's Apprentice?", European Heart Journal, 10, 774-782, pp. 37-45, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida et al., "Modifications of Gianturco Expandable Wire Stents", Technical Note, American Roentgen Ray Society, pp. 1185-1187, May 1988.

Urban, Philip MD, "Coronary Artery Stenting", Editions Medecine et Hygiene, Geneve, pp. 1-47, 1991.

Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.

Wheatley, David J., "Valve Prosthesis", Rob & Smith's Operative Surgery, pp. 415-424, 1986.

\* cited by examiner

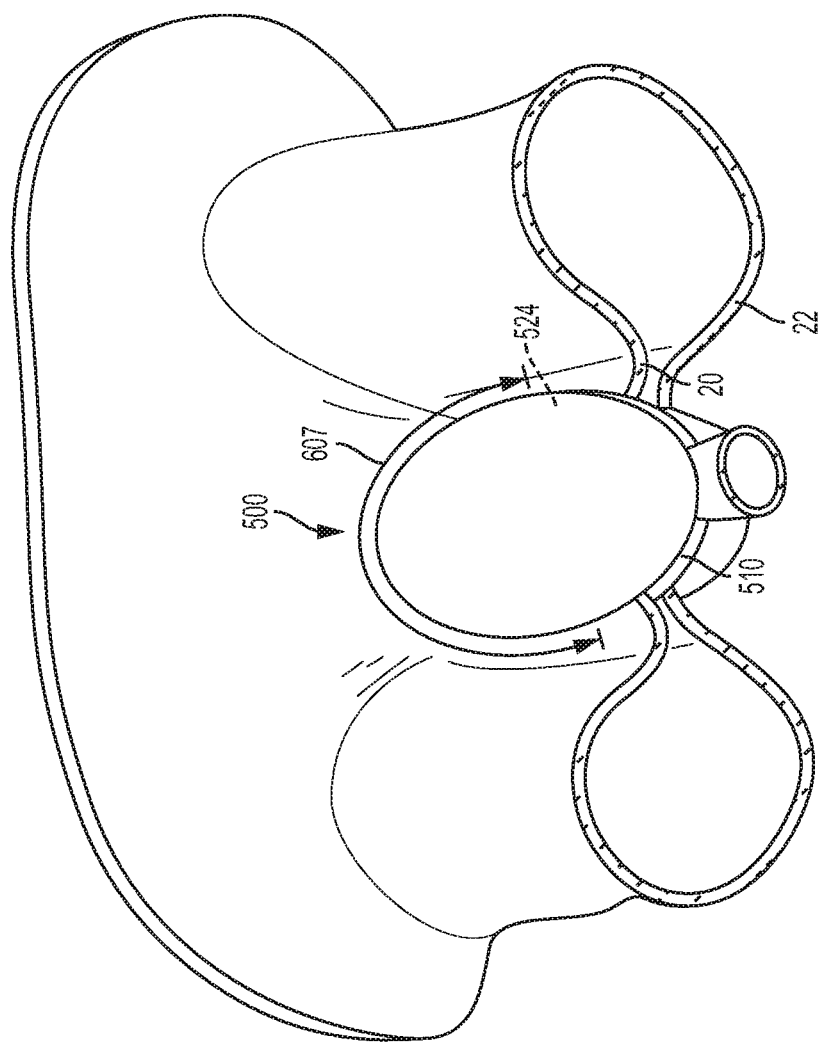

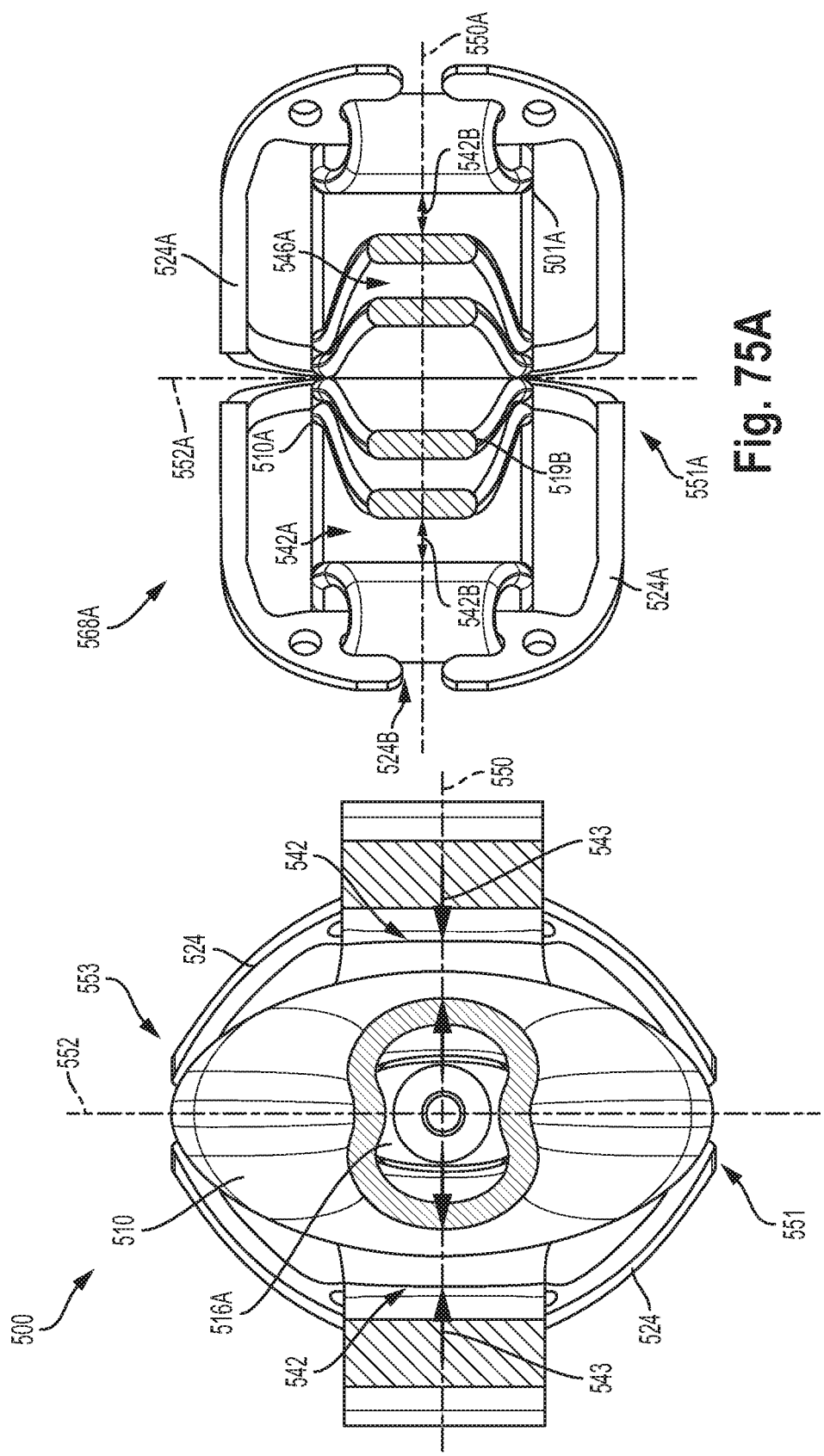

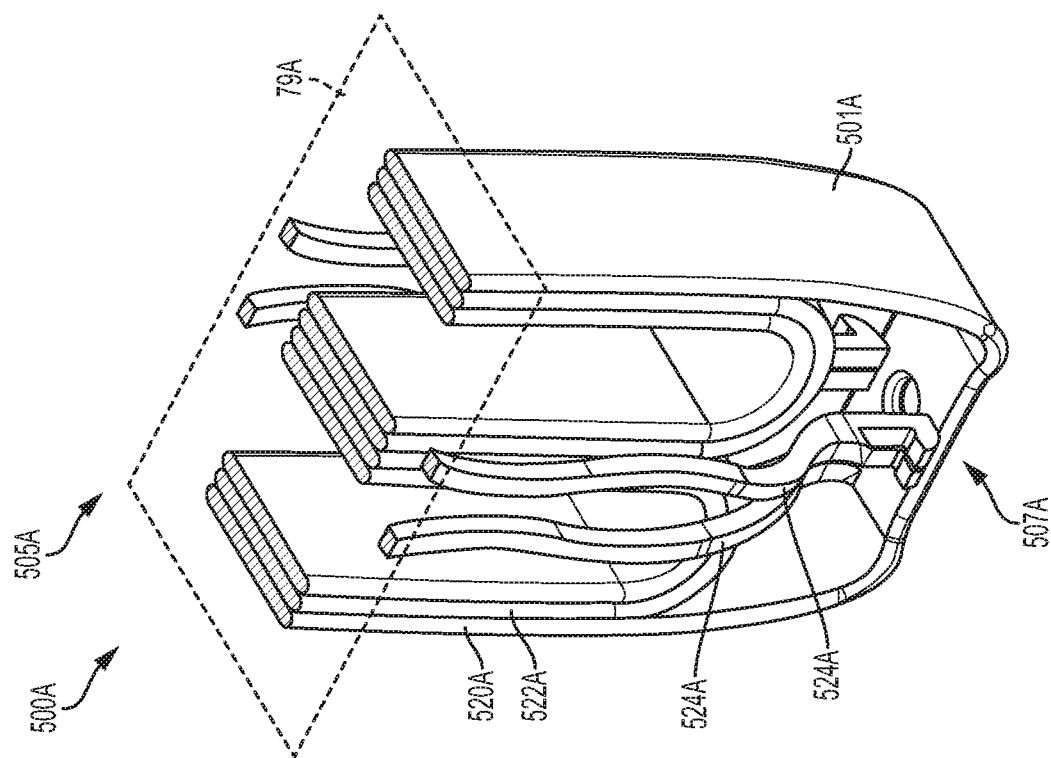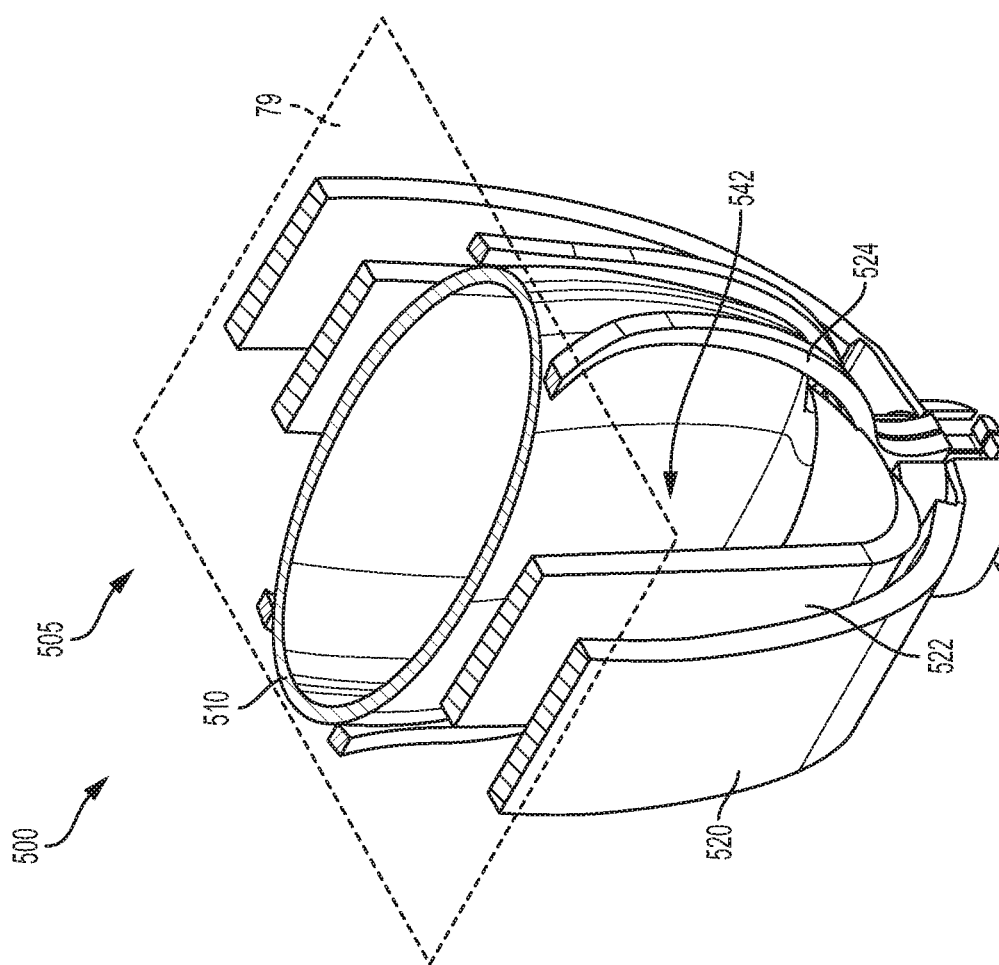

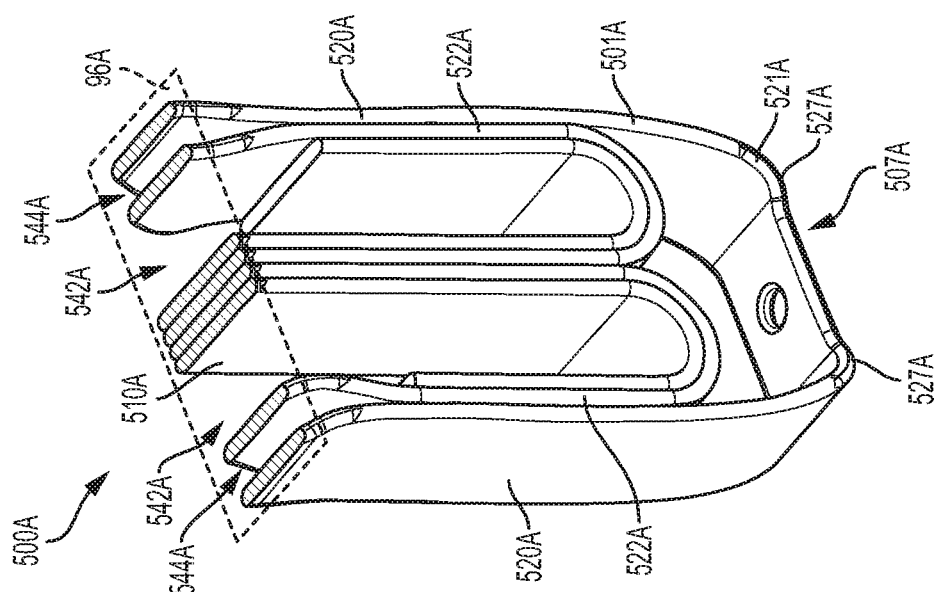
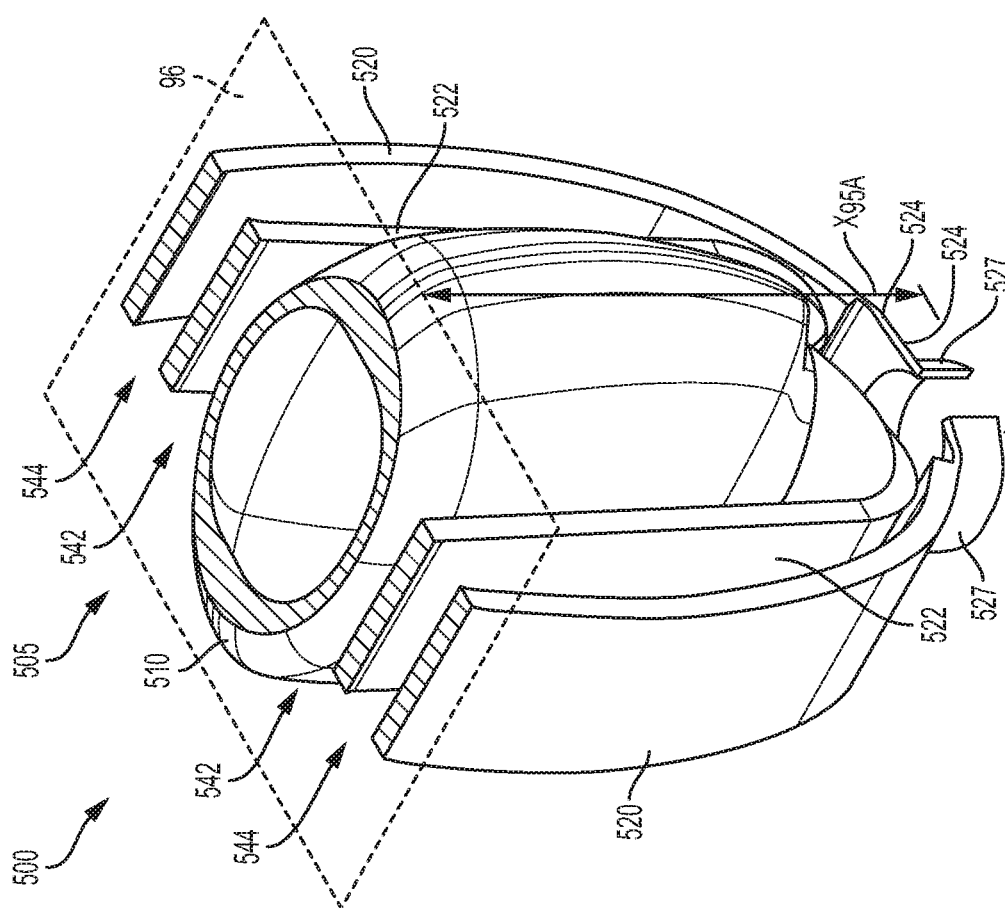

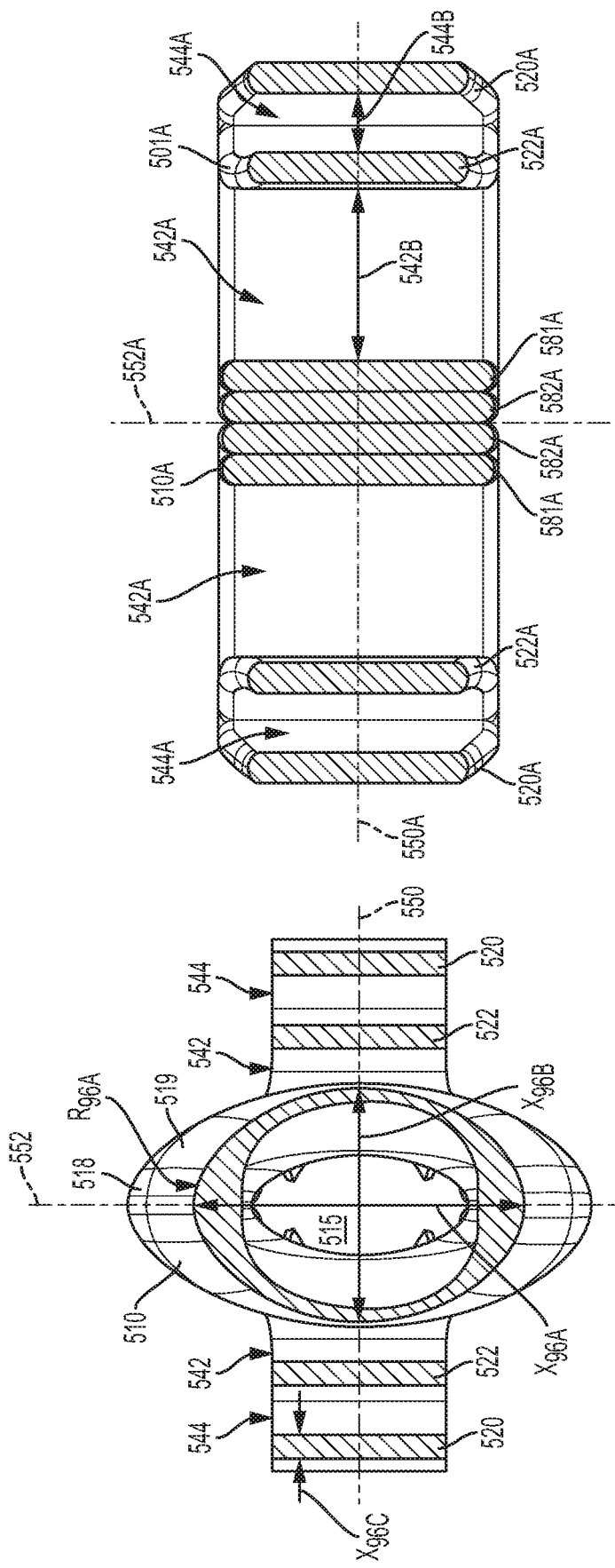

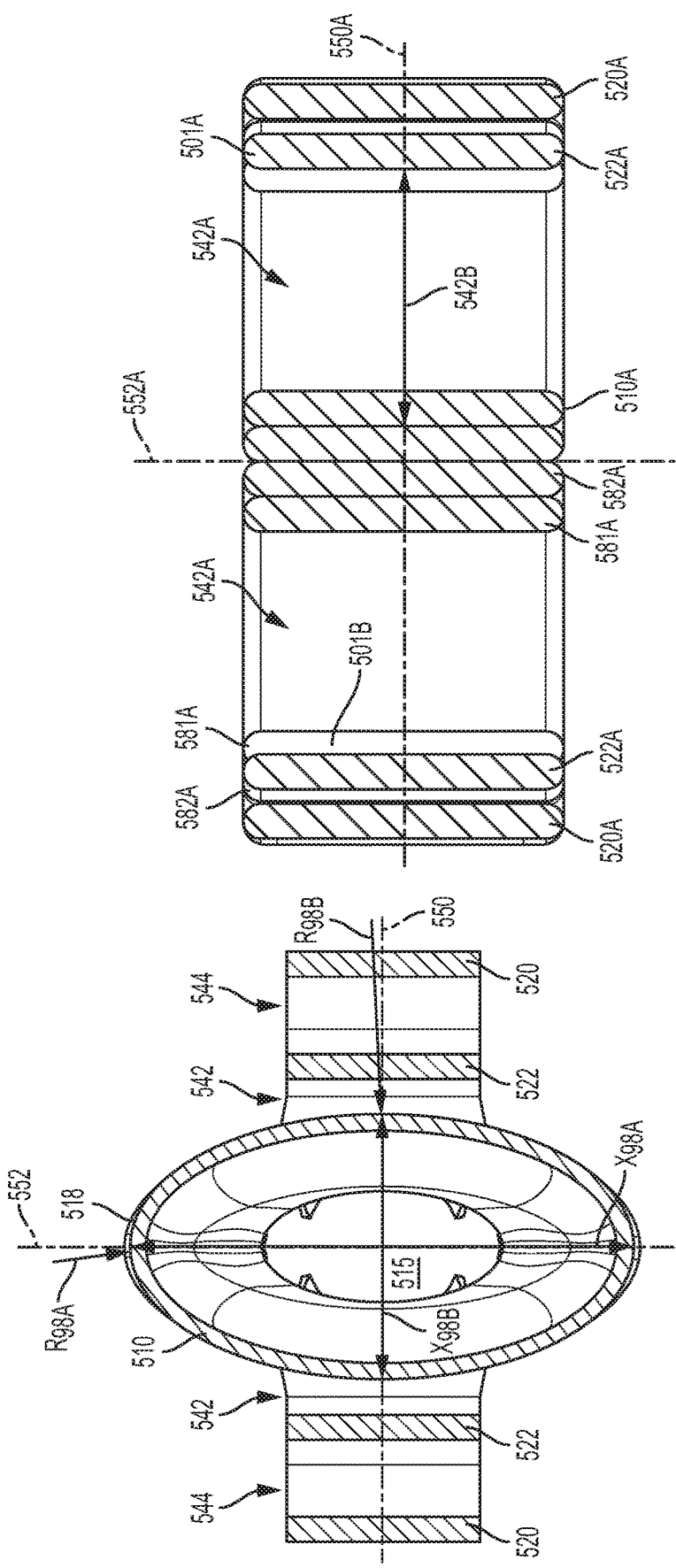

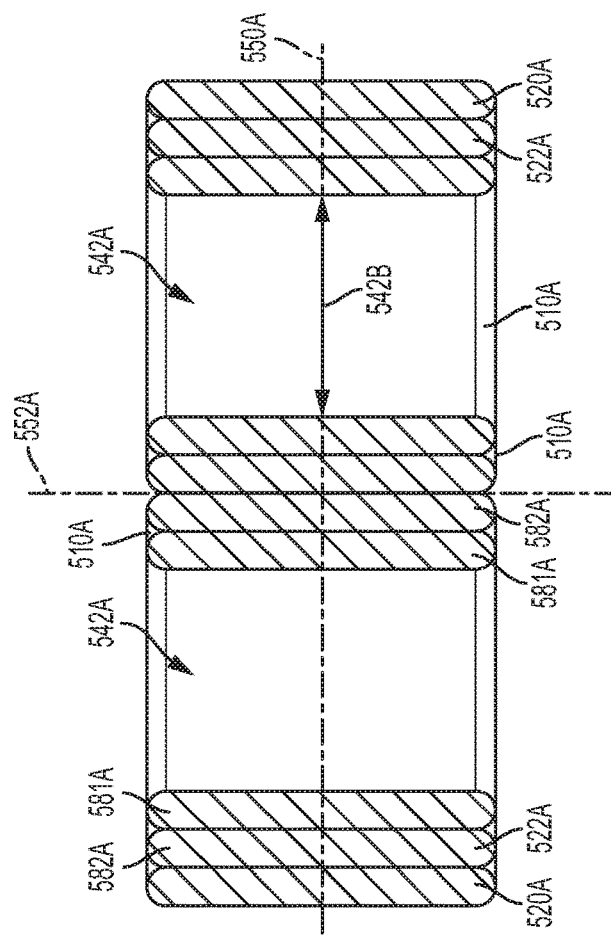
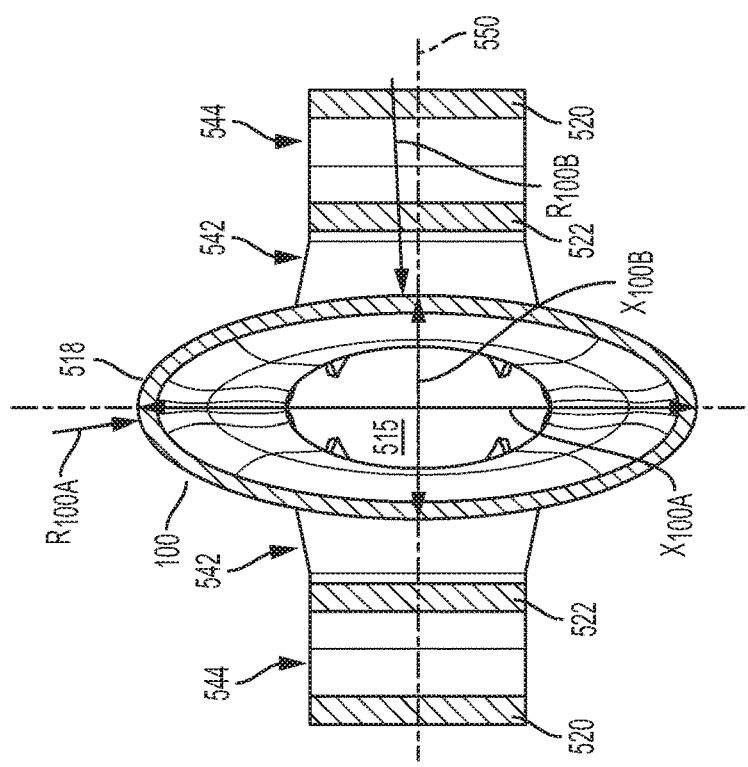
Fig. 100A
Fig. 100

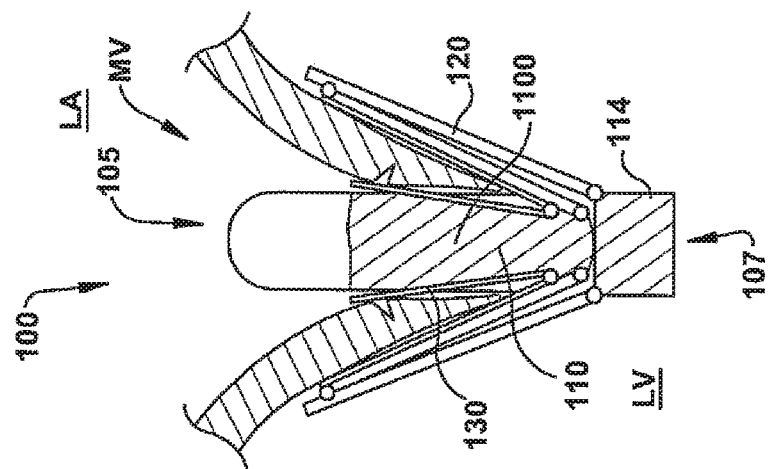
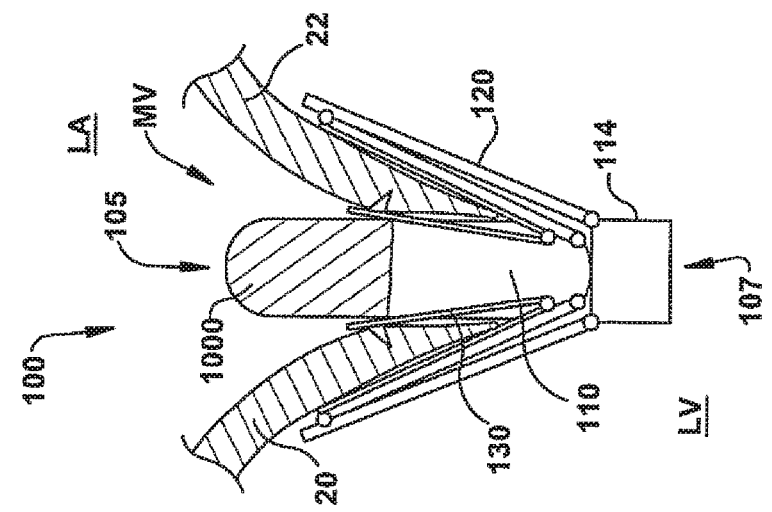
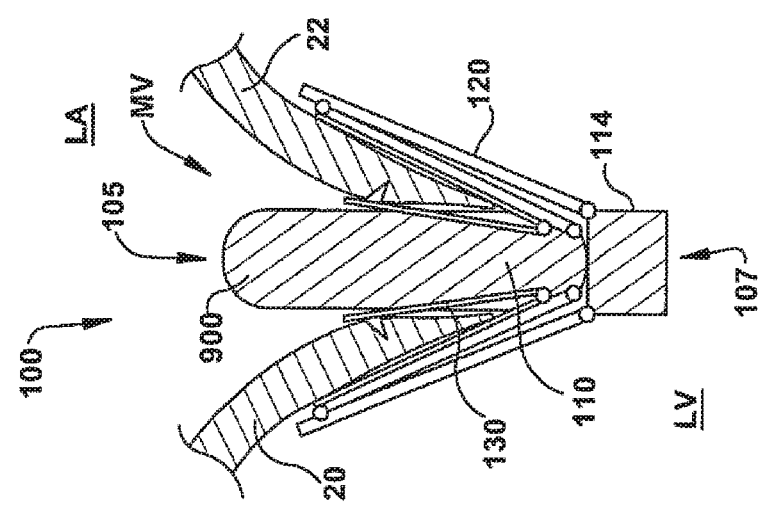

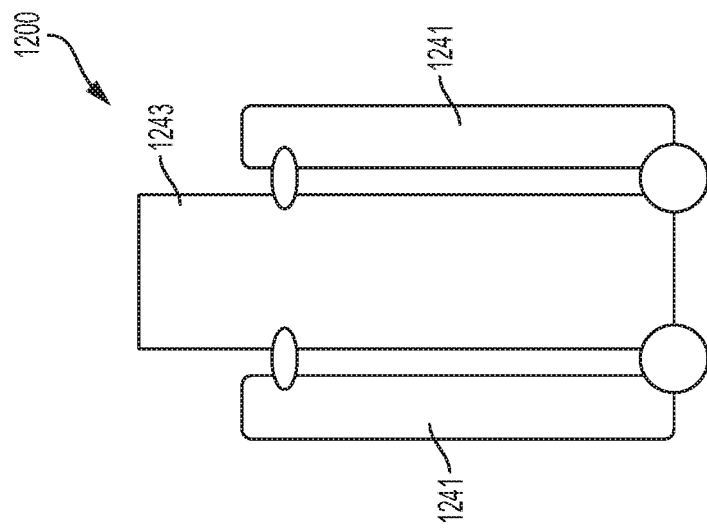
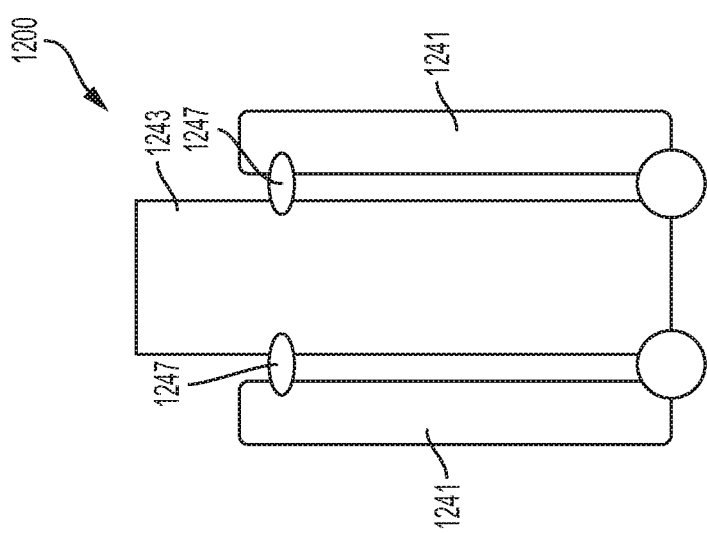

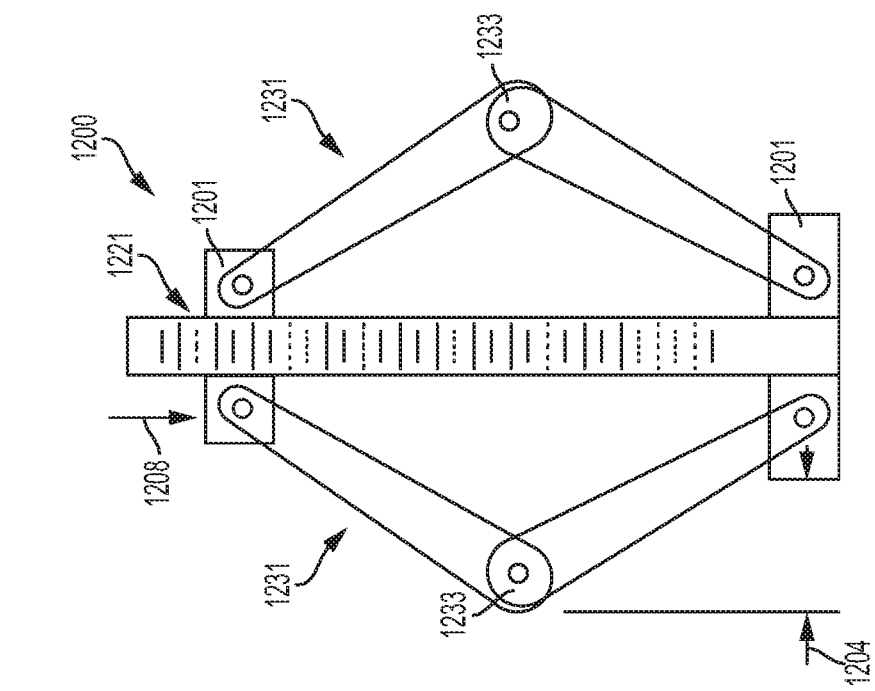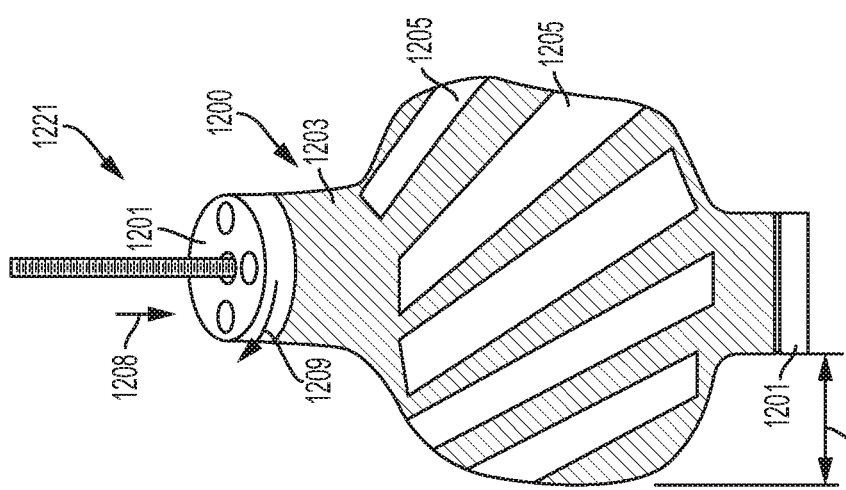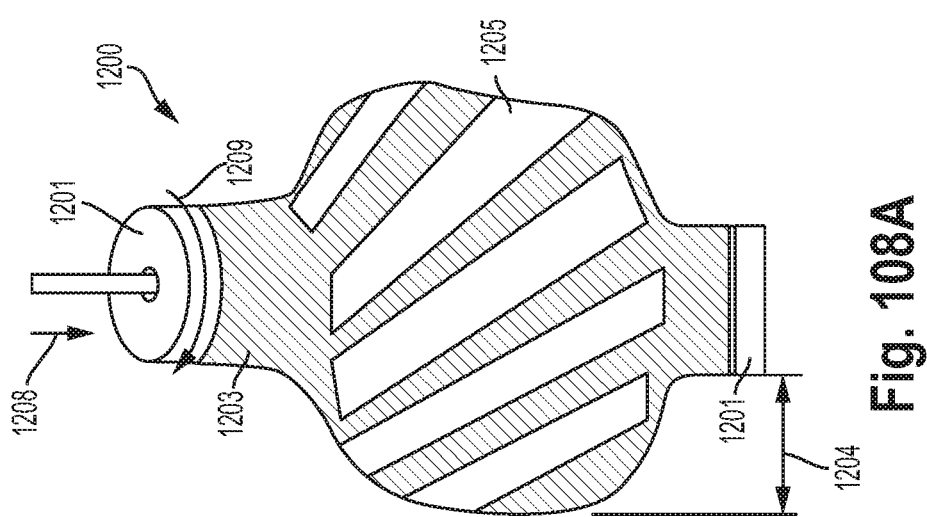

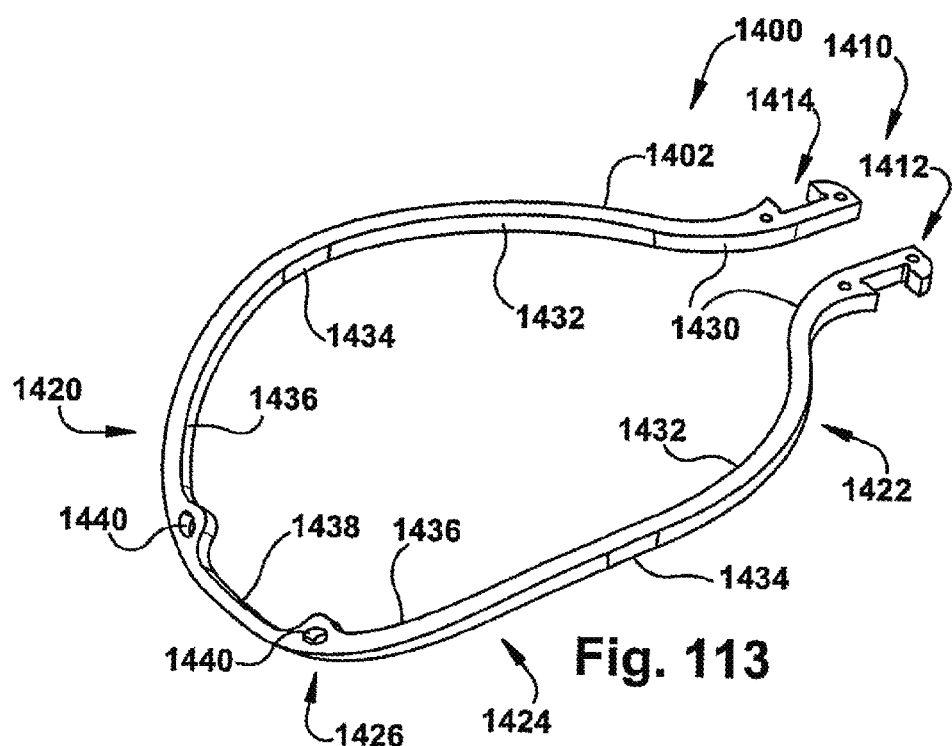

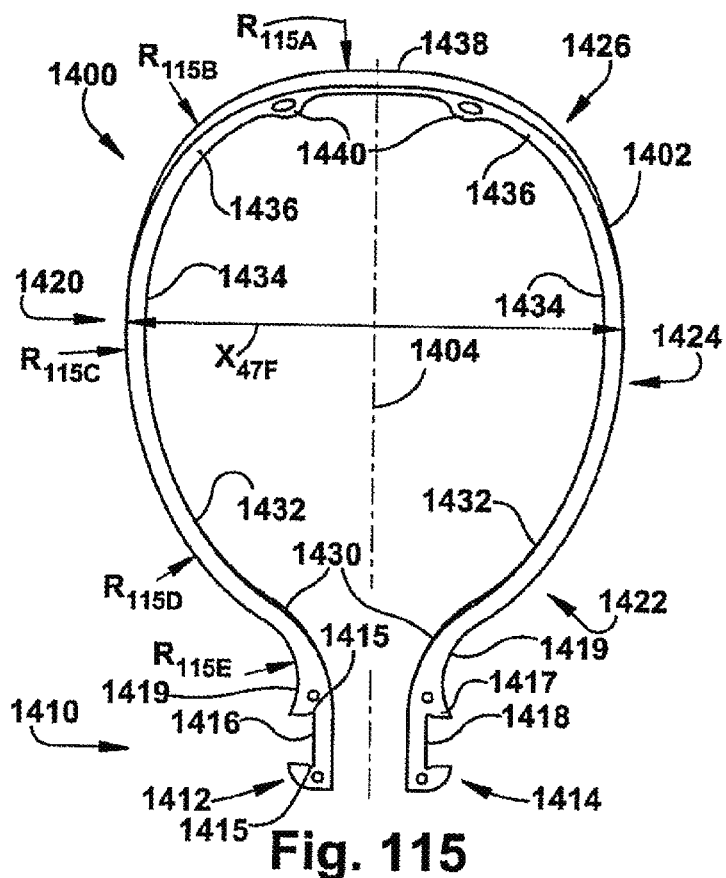
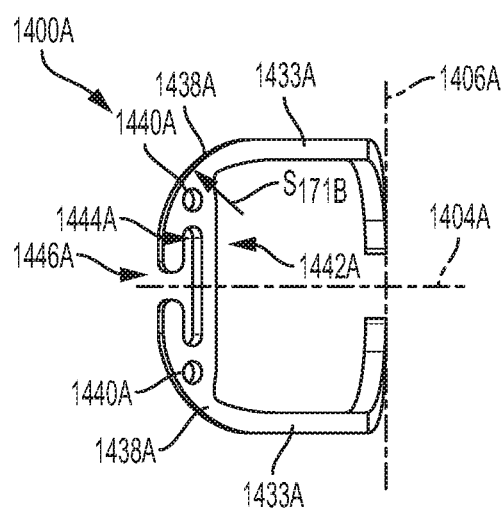
Fig. 115
Fig. 115A

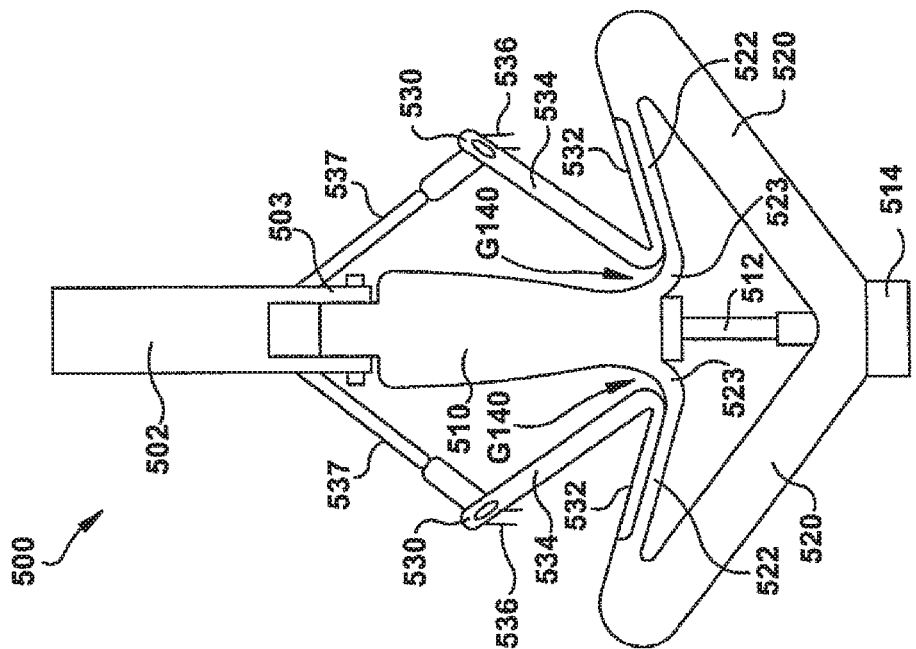
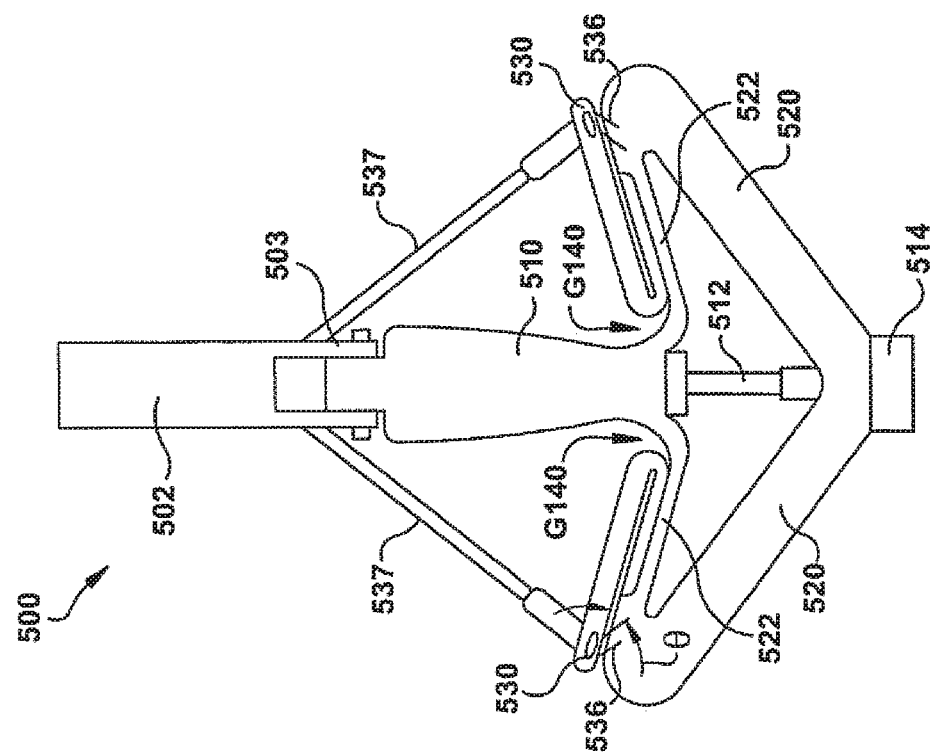
Fig. 138
Fig. 139

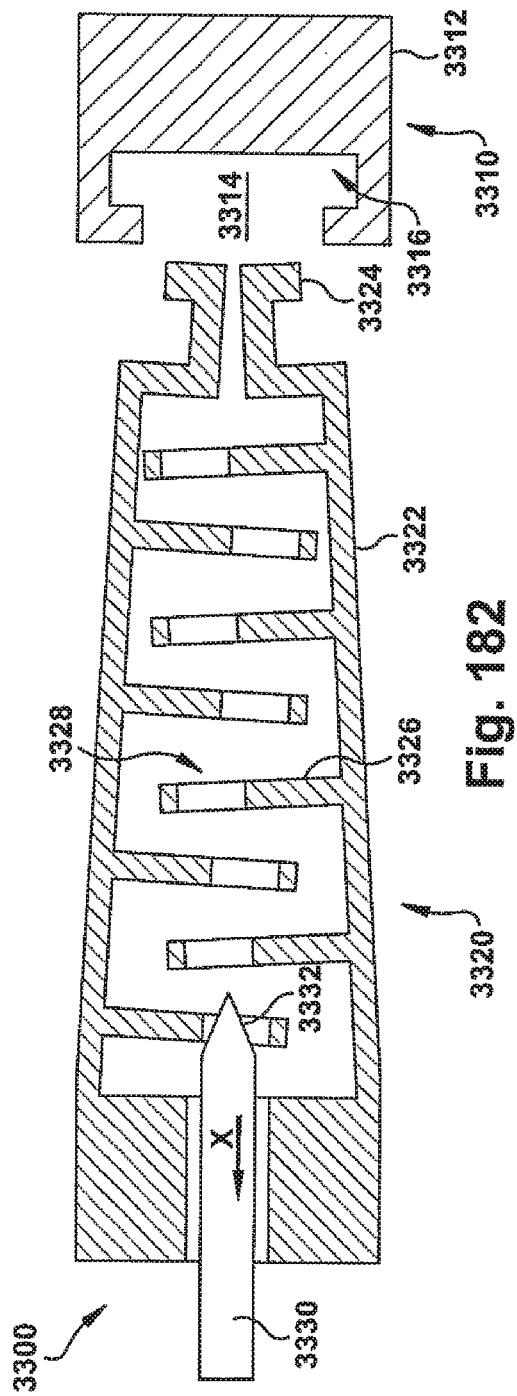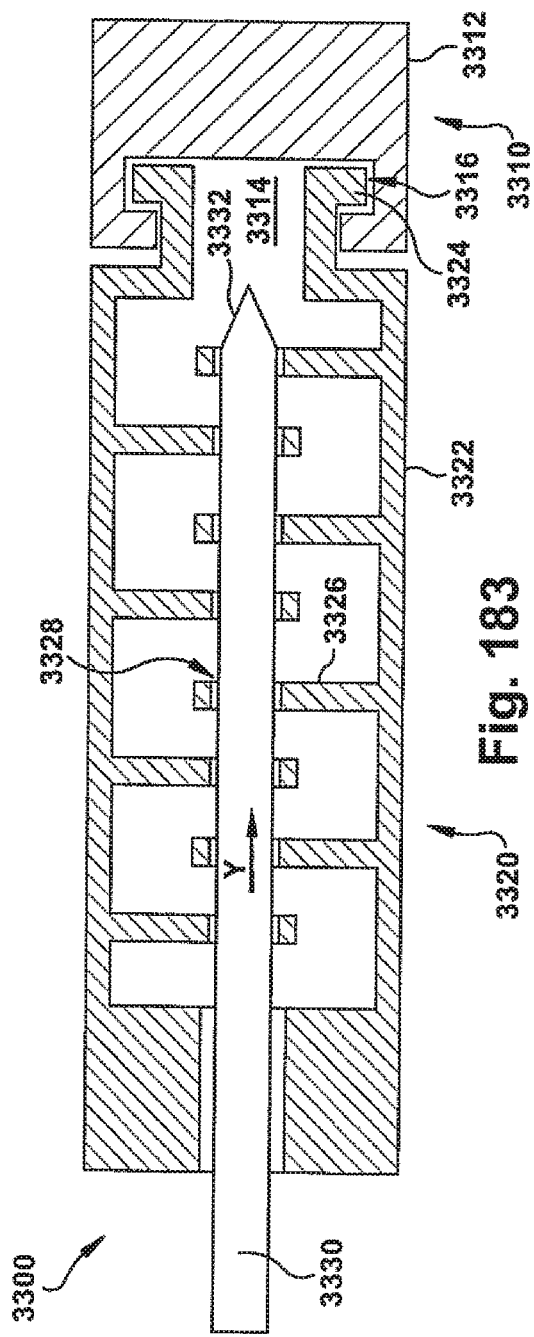

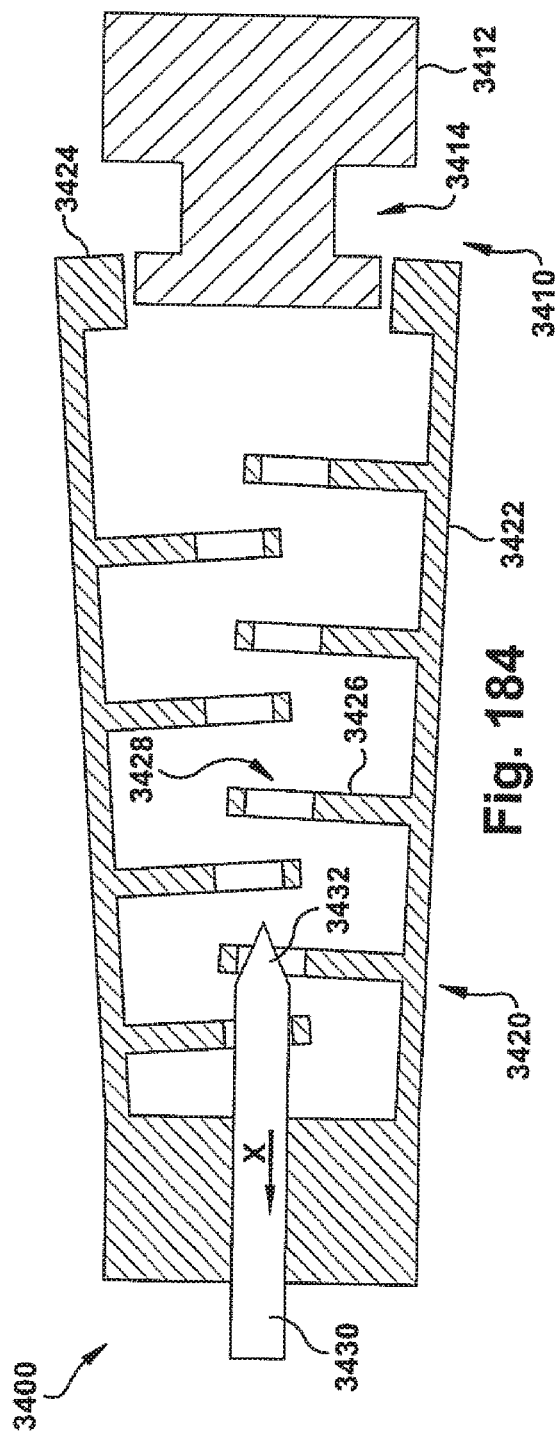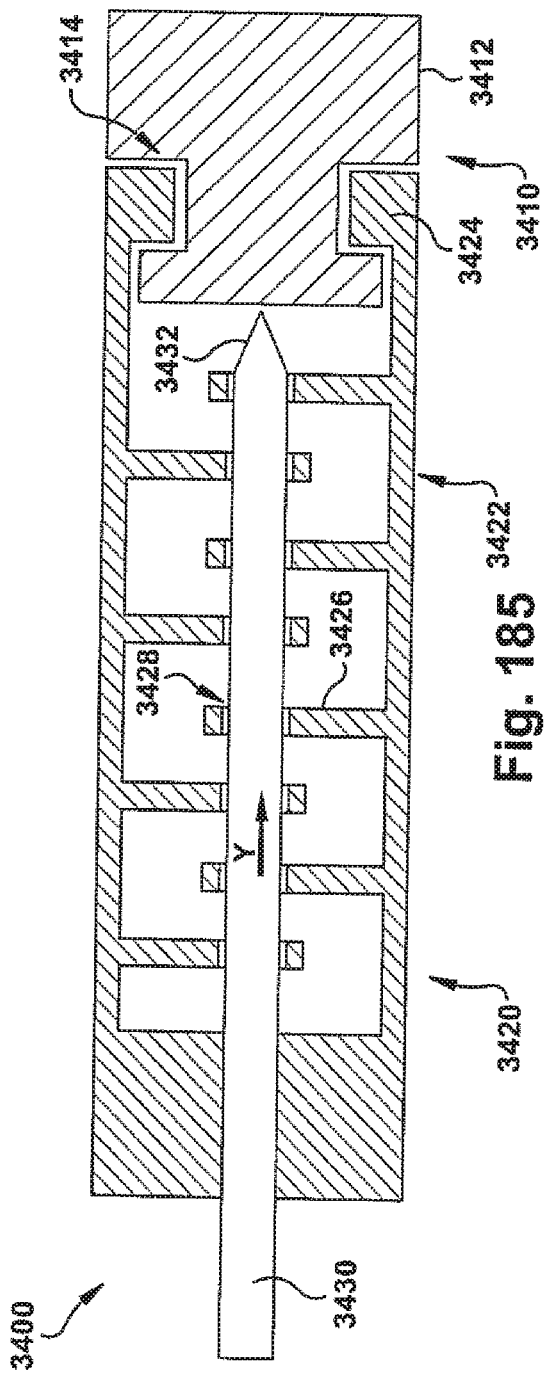

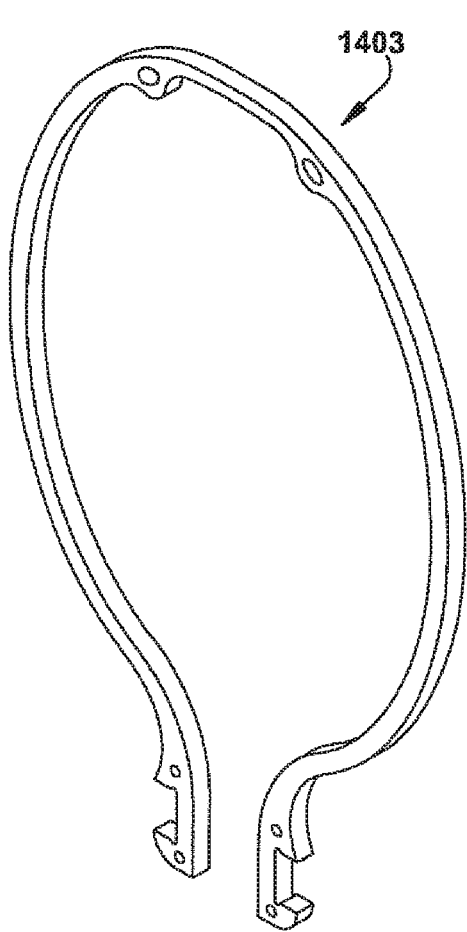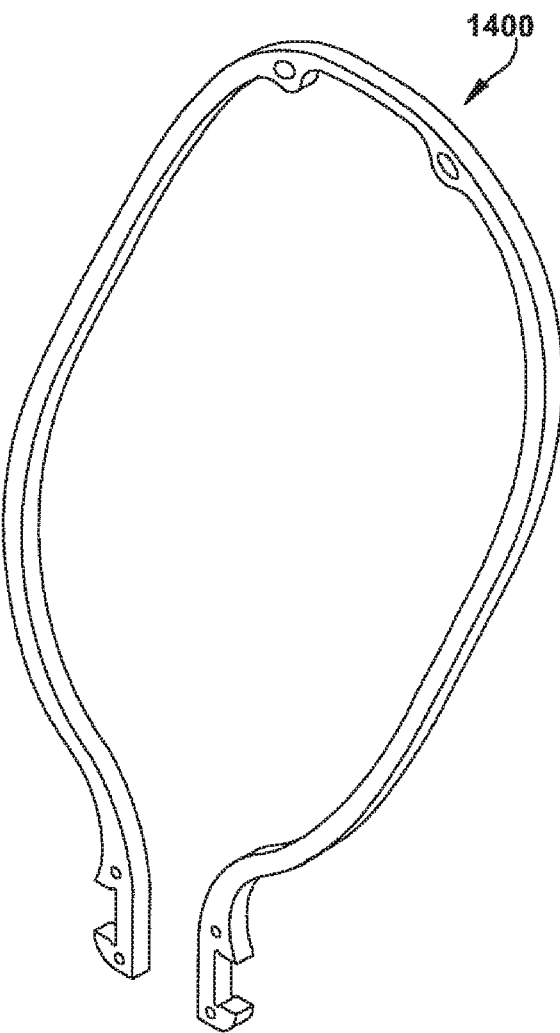
Fig. 191
Fig. 192

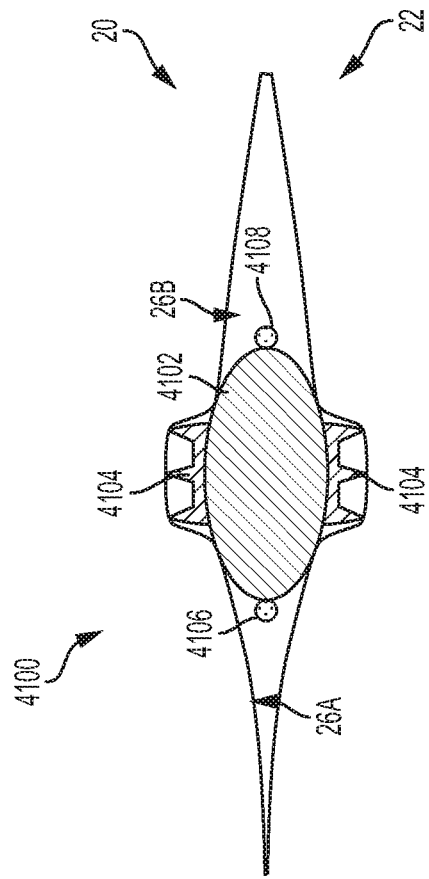
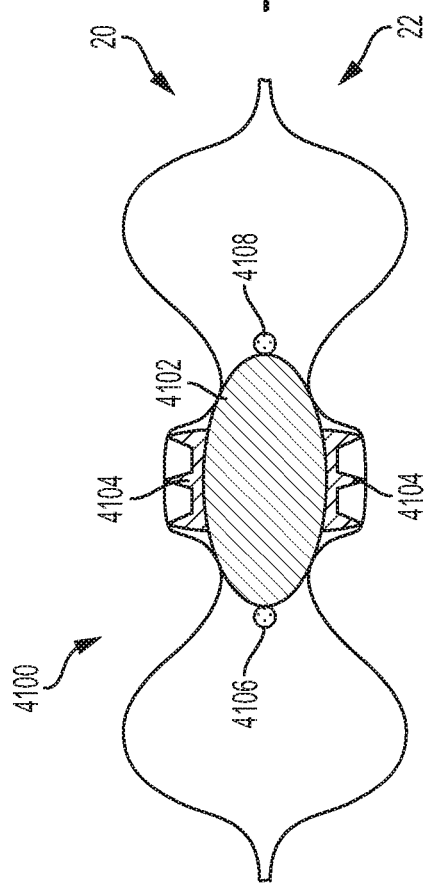

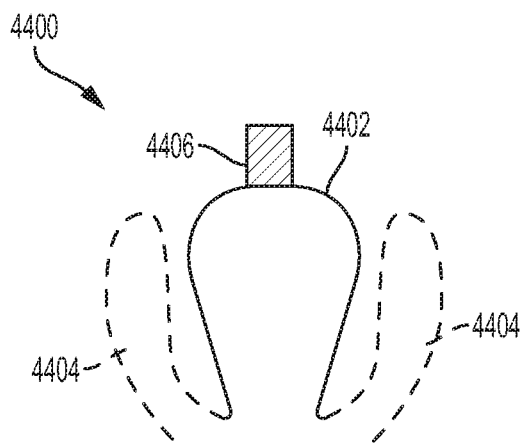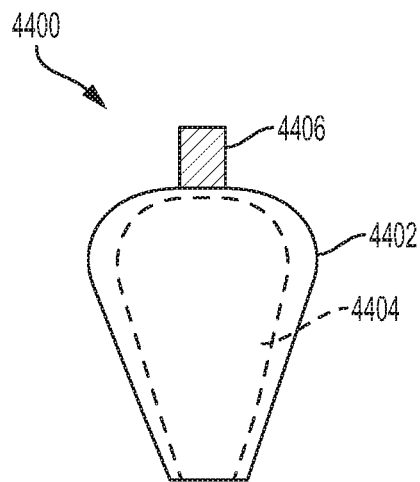
Fig. 212A    Fig. 212B
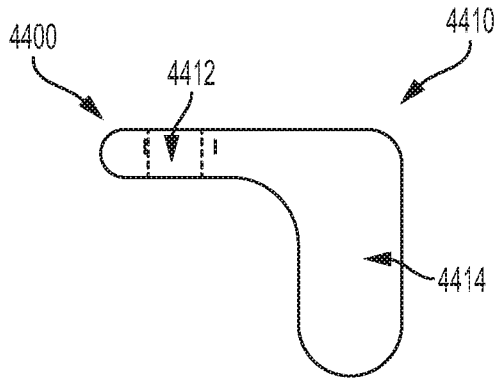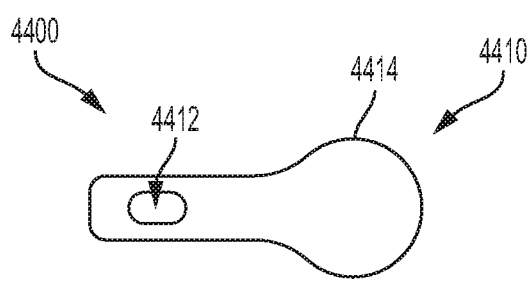
Fig. 213A    Fig. 213B
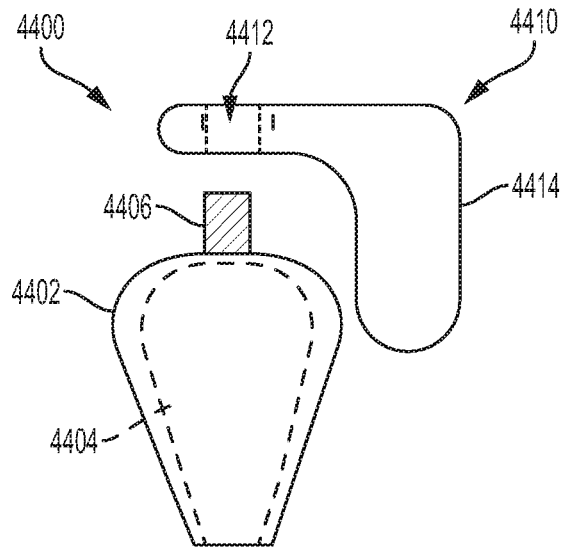
Fig. 214

HEART VALVE SEALING DEVICES AND DELIVERY DEVICES THEREFOR

CROSS-REFERENCE TO RELATED APPLICATIONS

This application claims priority to U.S. Provisional Application No. 62/744,031, filed Oct. 10, 2018, the contents of which are incorporated by reference in their entirety.

TECHNICAL FIELD

The present application relates generally to prosthetic devices and related methods for helping to seal native heart valves and prevent or reduce regurgitation therethrough, as well as devices and related methods for implanting such prosthetic devices.

BACKGROUND OF THE INVENTION

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, by congenital malformations, inflammatory processes, infectious conditions, or disease. Such damage to the valves can result in serious cardiovascular compromise or death. For many years the definitive treatment for such damaged valves was surgical repair or replacement of the valve during open heart surgery. However, open heart surgeries are highly invasive and are prone to many complications. Therefore, elderly and frail patients with defective heart valves often went untreated. More recently, transvascular techniques have been developed for introducing and implanting prosthetic devices in a manner that is much less invasive than open heart surgery. One particular transvascular technique that is used for accessing the native mitral and aortic valves is the transseptal technique. The transseptal technique comprises inserting a catheter into the right femoral vein, up the inferior vena cava and into the right atrium. The septum is then punctured and the catheter passed into the left atrium.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting sides of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the sides of the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is the most common form of valvular heart disease. Mitral regurgitation has different causes, such as leaflet prolapse, dysfunctional papillary muscles and/or stretching of the mitral valve annulus resulting from dilation of the left ventricle. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Central jet regurgitation occurs when the edges of the leaflets do not meet in the middle and thus the valve does not close and regurgitation is present.

Some prior techniques for treating mitral regurgitation in patients include surgically stitching the edges of the native mitral valve leaflets directly to one another. A catheter delivered clip has been used to attempt to clip the sides of the leaflets together at the end portions of the leaflets, similar to the surgical stitching method. However, this clip has shortcomings, since it can only be used to clip the middle of the leaflets where they overlap by about 2 mm or more. Alternately, attempts have been made to use multiple clips on the commissures of the mitral valve, where there may be more overlap of the leaflets. This technique results in a longer operation time and also joins the patient's leaflets at the sides, restricting blood flow. Additionally, both the surgical and clip treatments are thought to create stress on patient leaflets.

Despite these prior techniques, there is a continuing need for improved devices and methods for treating mitral valve regurgitation.

SUMMARY

Exemplary valve repair devices for repairing a native valve of a patient and methods of using the same are disclosed herein.

An exemplary valve repair device for repairing a native valve of a patient includes: a coaption element; a pair of paddles connected to the coaption element; a catch point formed by a portion of at least one of the coaption element and the pair of paddles when the paddles are in the open position; and a cover covering connected to the coaption element and the paddles for covering the catch point. The paddles are movable between an open position and a closed position and are configured to attach to the native valve of the patient.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures can be drawn to scale for some embodiments, the figures are not necessarily drawn to scale for all embodiments. Embodiments and other features and advantages of the present disclosure will be described and explained with additional specificity and detail through the use of the accompanying drawings in which:

FIG. 6C is a perspective view of a valve repair device attached to mitral valve leaflets with the coaption element in the gap of the mitral valve shown from a ventricular side of the mitral valve;

FIG. 75 shows a top cross-section view of the exemplary prosthetic device illustrated by FIG. 74;

FIG. 75A shows a top cross-section view of the exemplary prosthetic device illustrated by FIG. 74A;

FIG. 78 shows a sectioned perspective view of the implantable prosthetic device of FIG. 65 sectioned by cross-section plane 77;

FIG. 78A shows a sectioned perspective view of the implantable prosthetic device of FIG. 65A sectioned by cross-section plane 77A;

FIG. 90 shows a perspective view of a coapting portion and paddle portions of the implantable prosthetic device illustrated by FIG. 65;

FIG. 90A shows a perspective view of a coapting portion and paddle portions of the implantable prosthetic device illustrated by FIG. 65A;

FIG. 91 shows a front view of a coapting portion and paddle portions of the implantable prosthetic device illustrated by FIG. 65;

FIG. 91A shows a front view of a coapting portion and paddle portions of the implantable prosthetic device illustrated by FIG. 65A;

FIG. 92 shows a side view of a coapting portion and paddle portions of the implantable prosthetic device illustrated by FIG. 65;

FIG. 92A shows a side view of a coapting portion and paddle portions of the implantable prosthetic device illustrated by FIG. 65A;

FIG. 93 shows a top view of a coapting portion and paddle portions of the implantable prosthetic device illustrated by FIG. 65;

FIG. 93A shows a top view of a coapting portion and paddle portions of the implantable prosthetic device illustrated by FIG. 65A;

FIG. 94 shows a bottom view of a coapting portion and portions of the implantable prosthetic device illustrated by FIG. 65;

FIG. 94A shows a bottom view of a coapting portion and portions of the implantable prosthetic device illustrated by FIG. 65A;

FIG. 95 shows a sectioned perspective view of a coapting portion and paddle portions of the implantable prosthetic device illustrated by FIG. 65 with the section taken across plane 96;

FIG. 95A shows a sectioned perspective view of a coapting portion and paddle portions of the implantable prosthetic device illustrated by FIG. 65A with the section taken across plane 96A;

Figure 65:
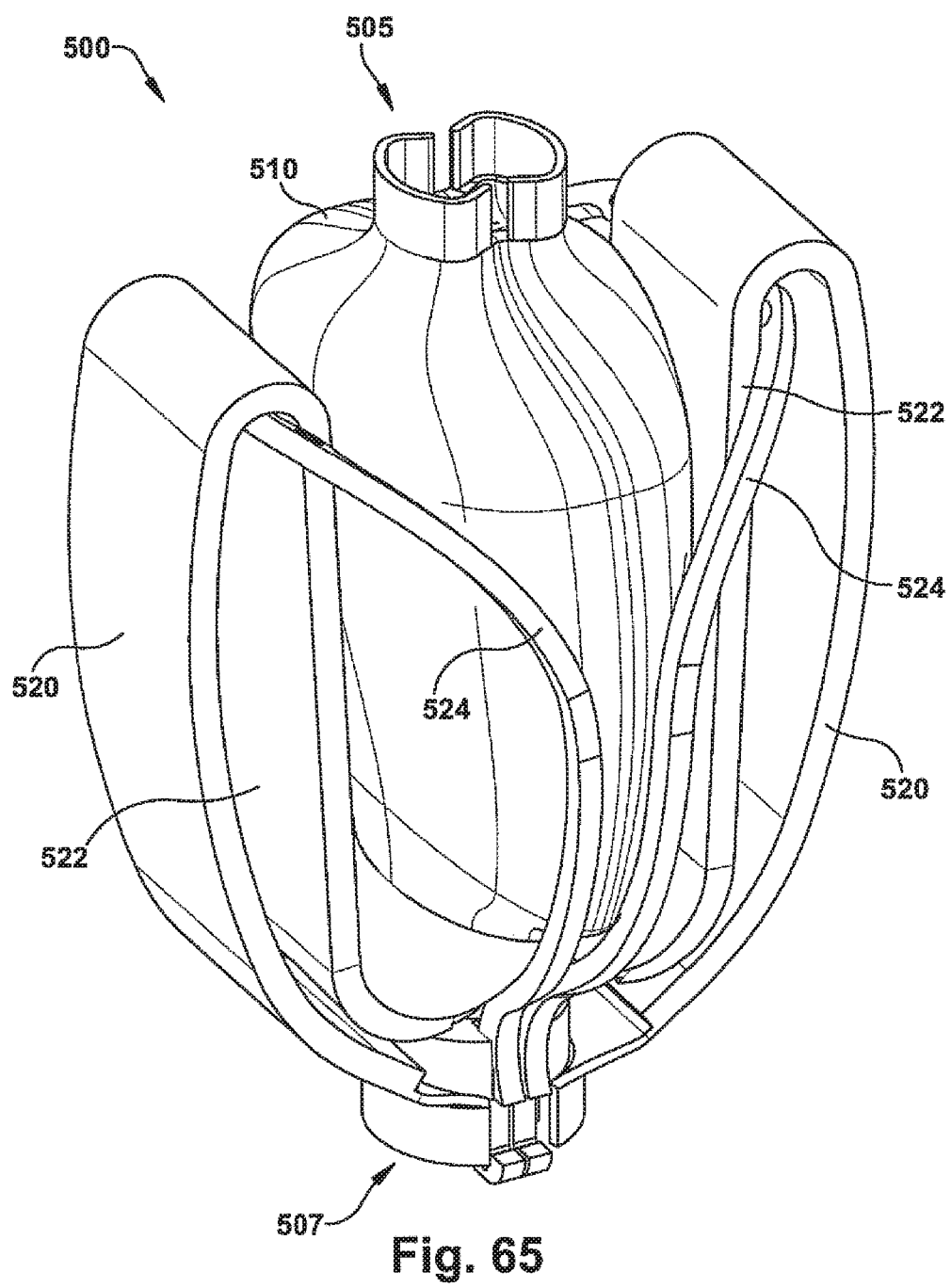
FIG. 65 shows a perspective view of an exemplary implantable prosthetic device in a closed position.
Figure 65A:
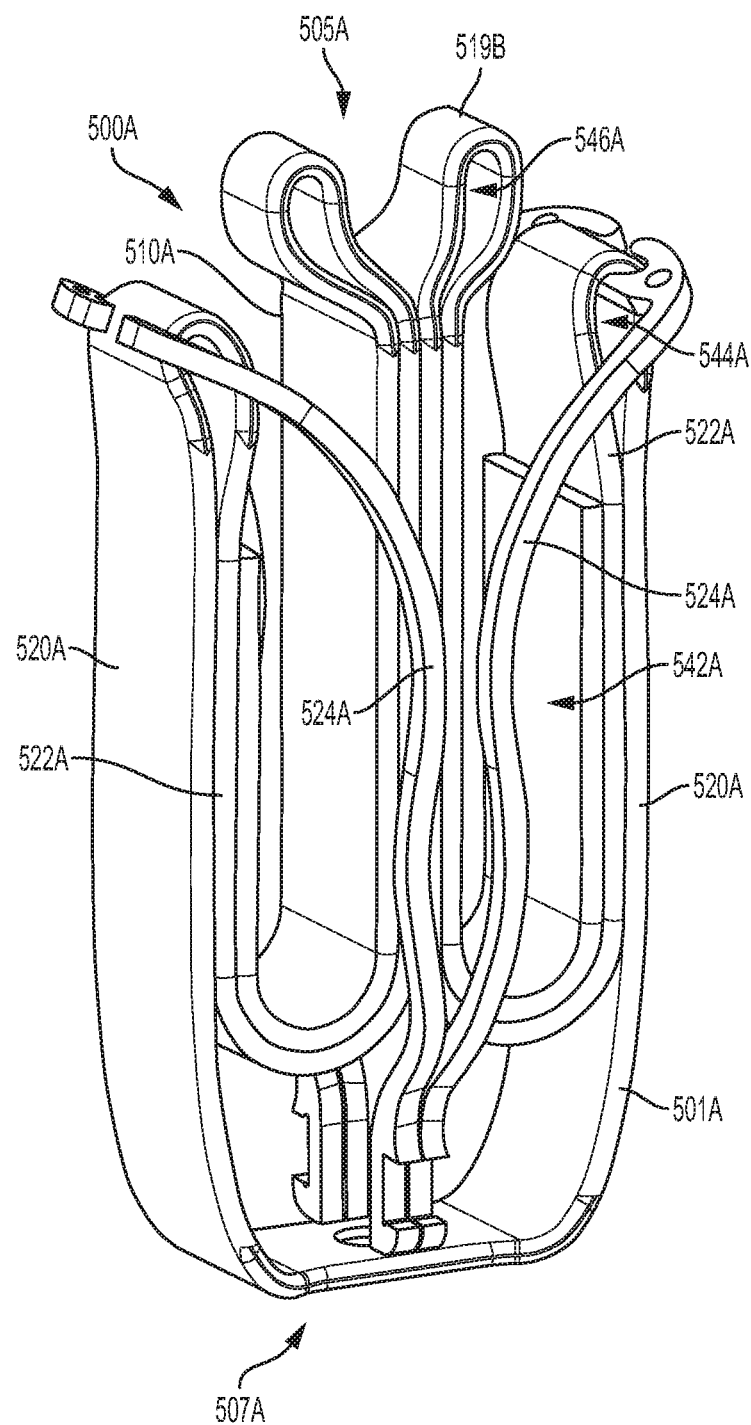
FIG. 65A shows a perspective view of an exemplary implantable prosthetic device in a closed position.
Figure 97A:
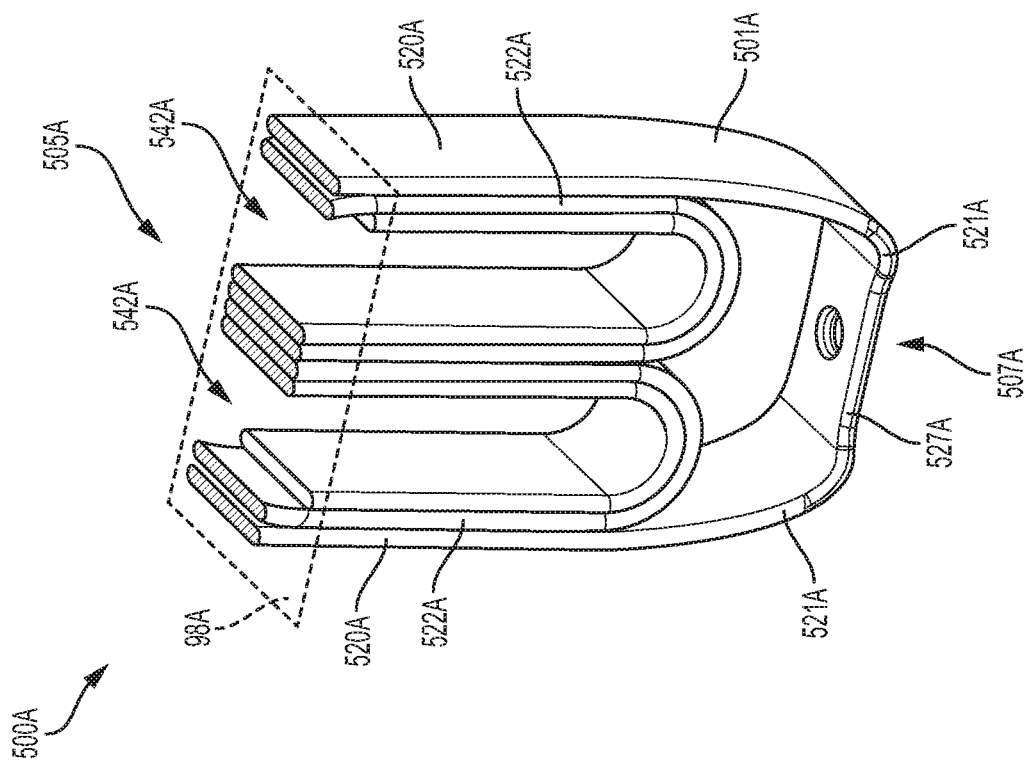
Figure 97:
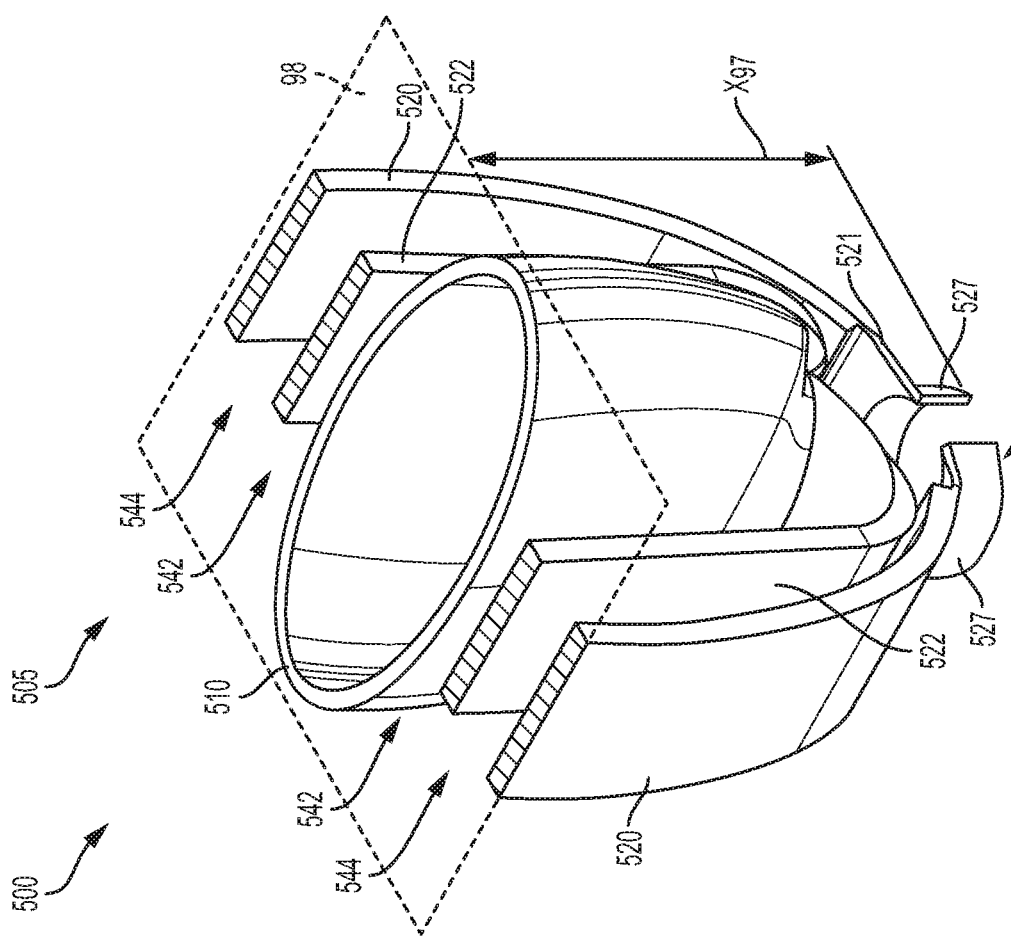
Figure 99A:
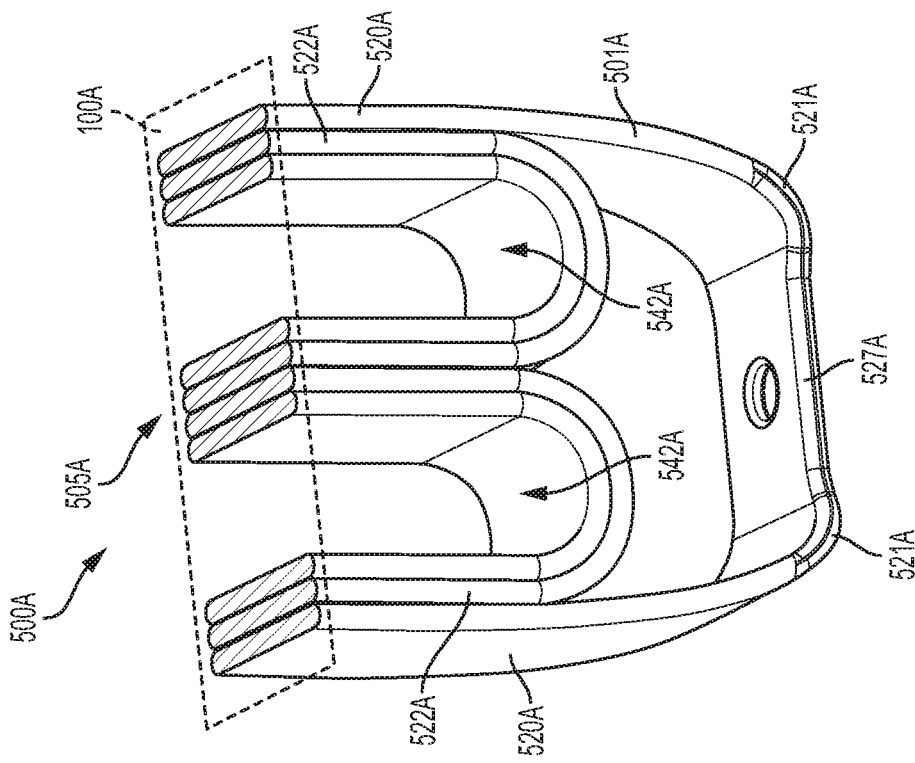
Figure 99:
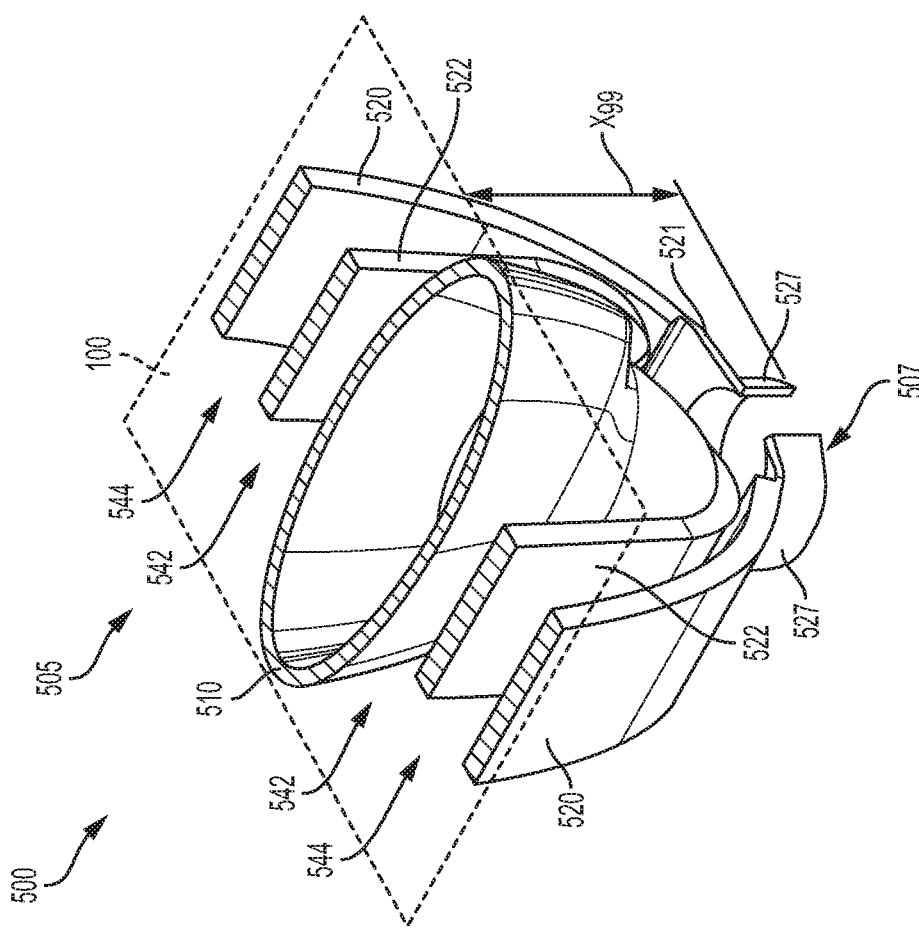
Figure 101:
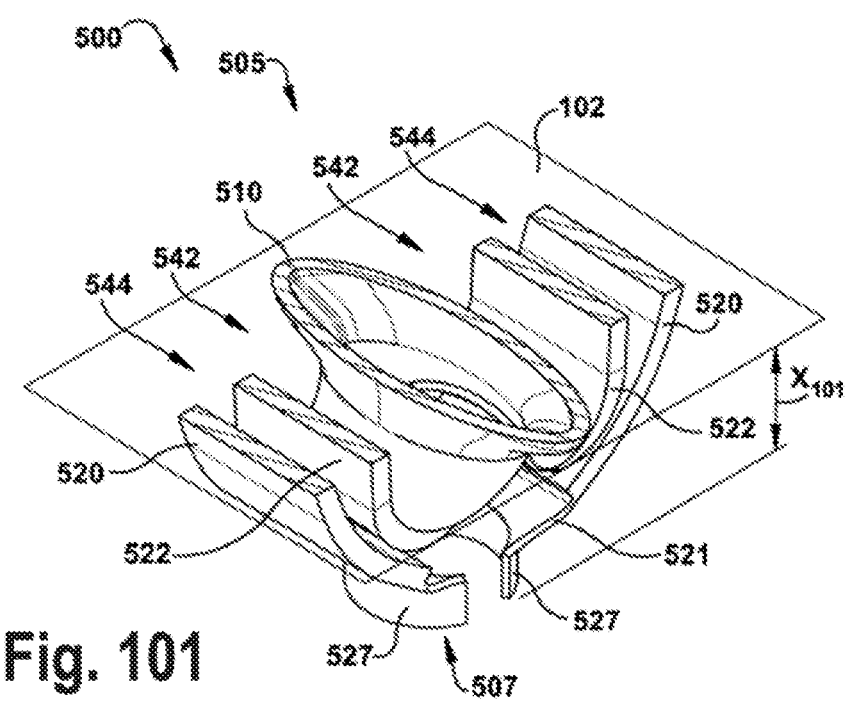
Figure 101A:
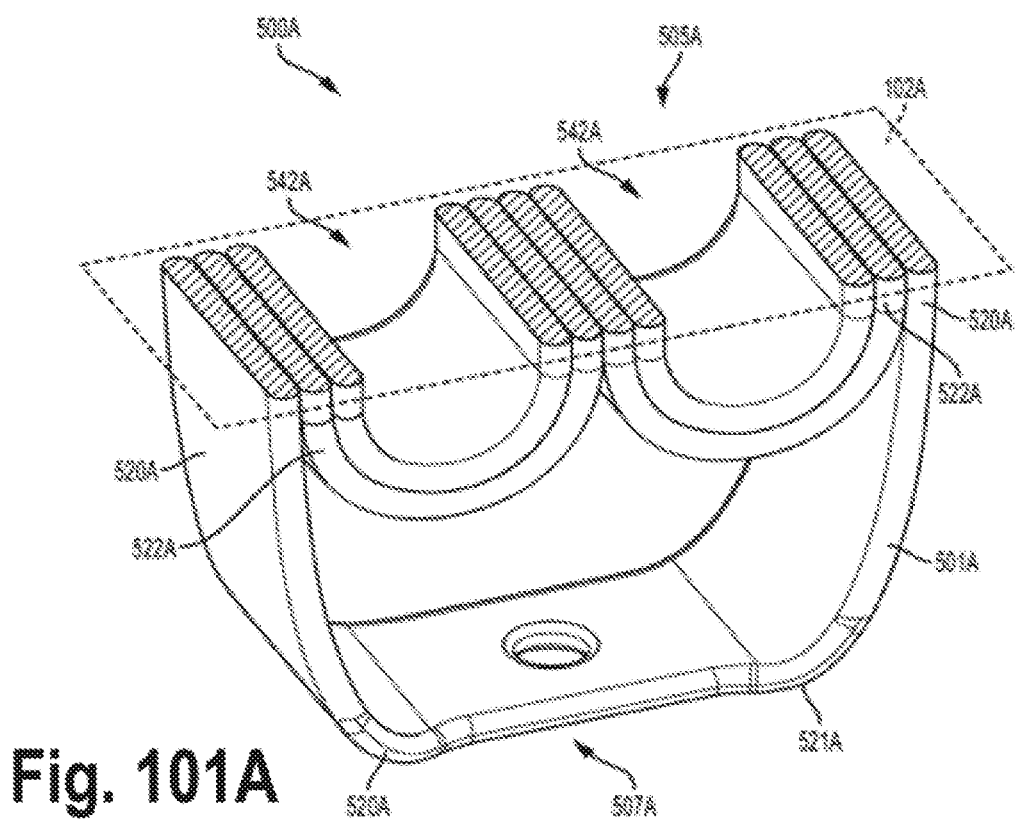
Figure 102:
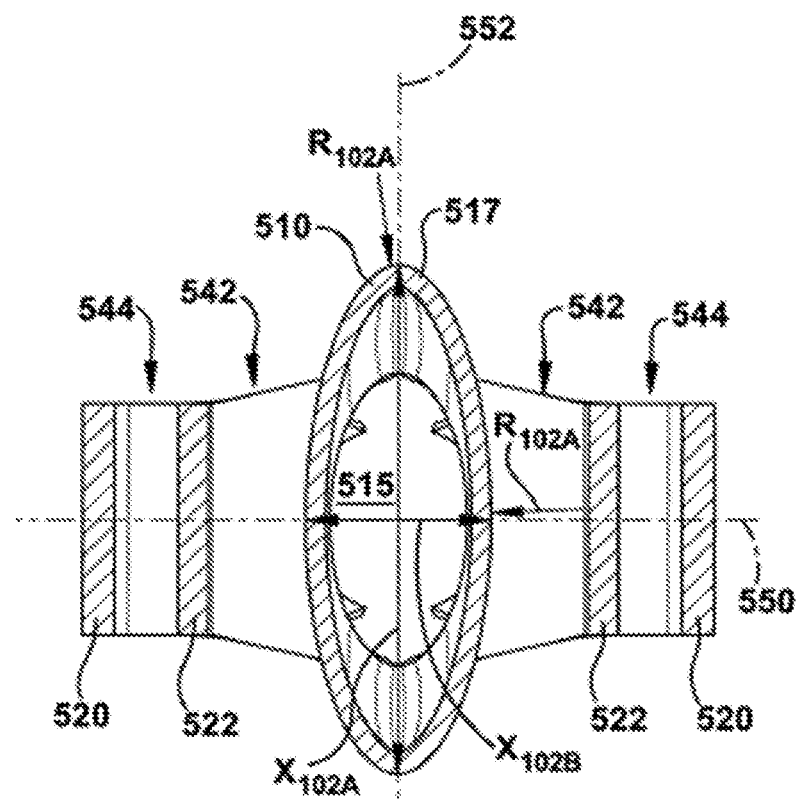
Figure 102A:
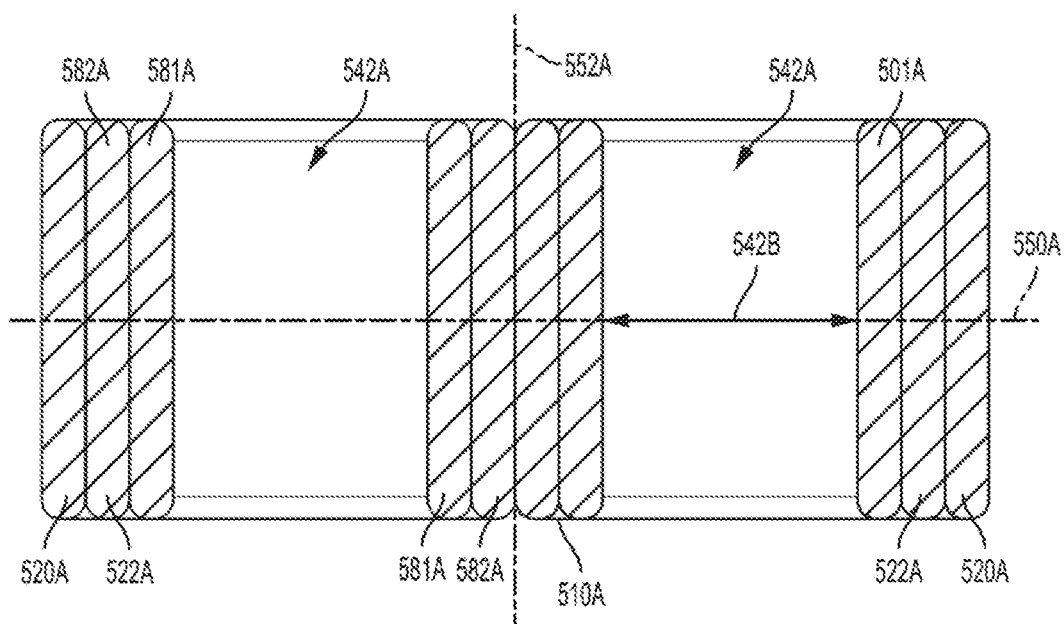
Figure 106:
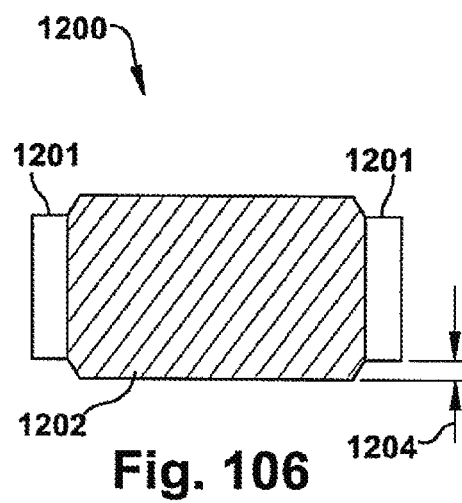
Figure 106A:
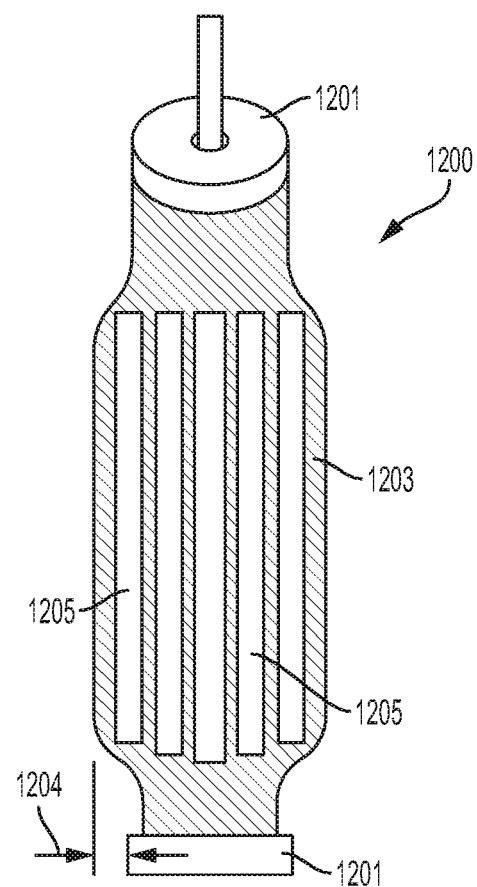
Figure 106C:
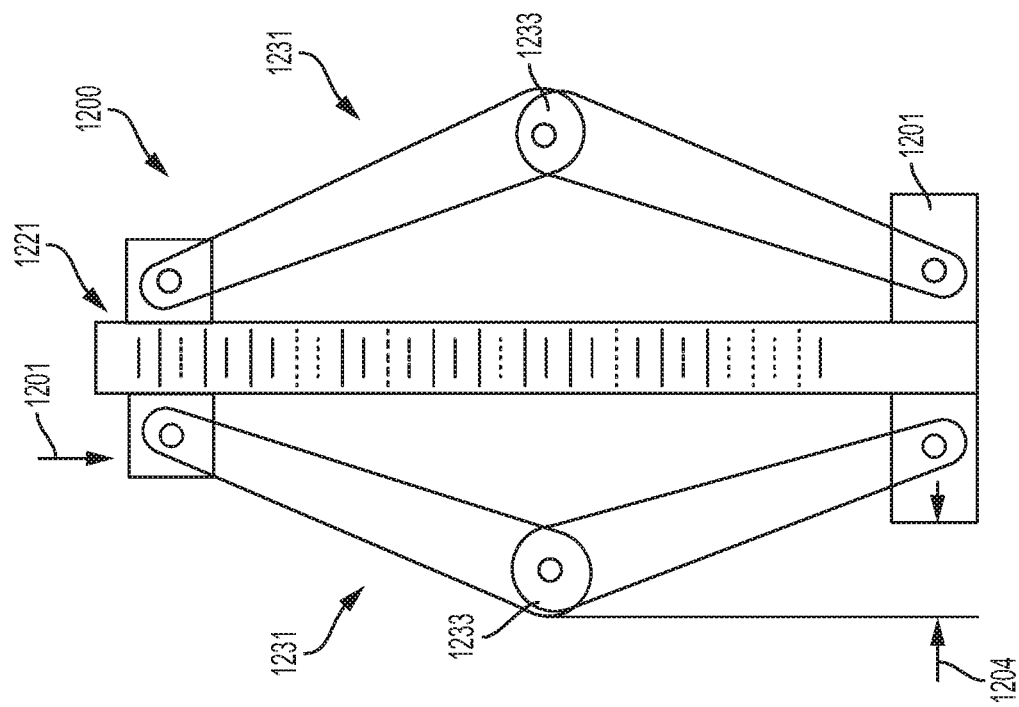
Figure 106B:
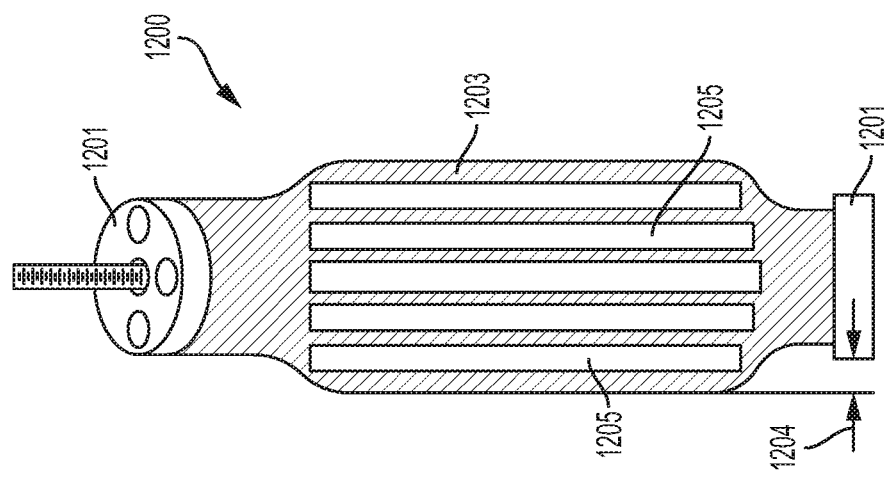
Figure 106F:
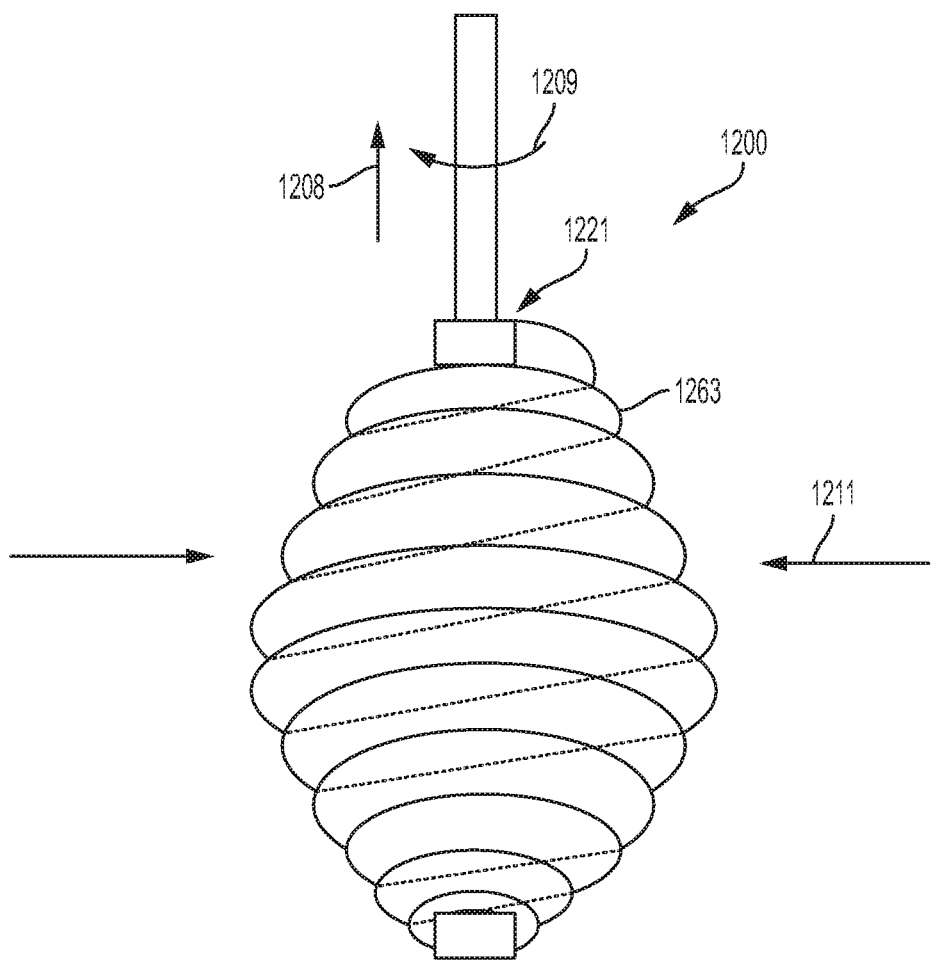
Figure 106G:
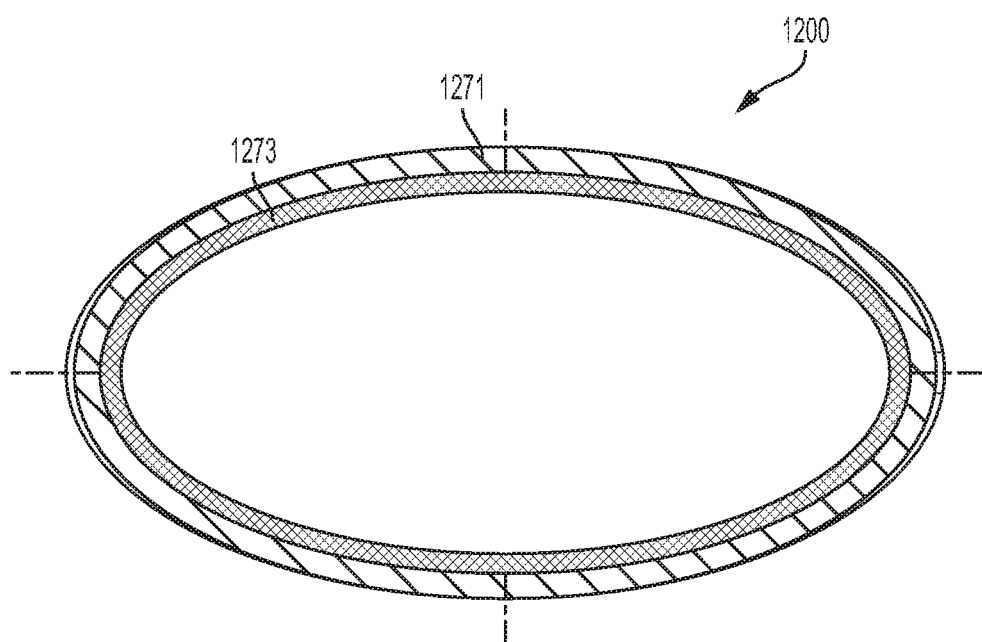
Figure 106H:
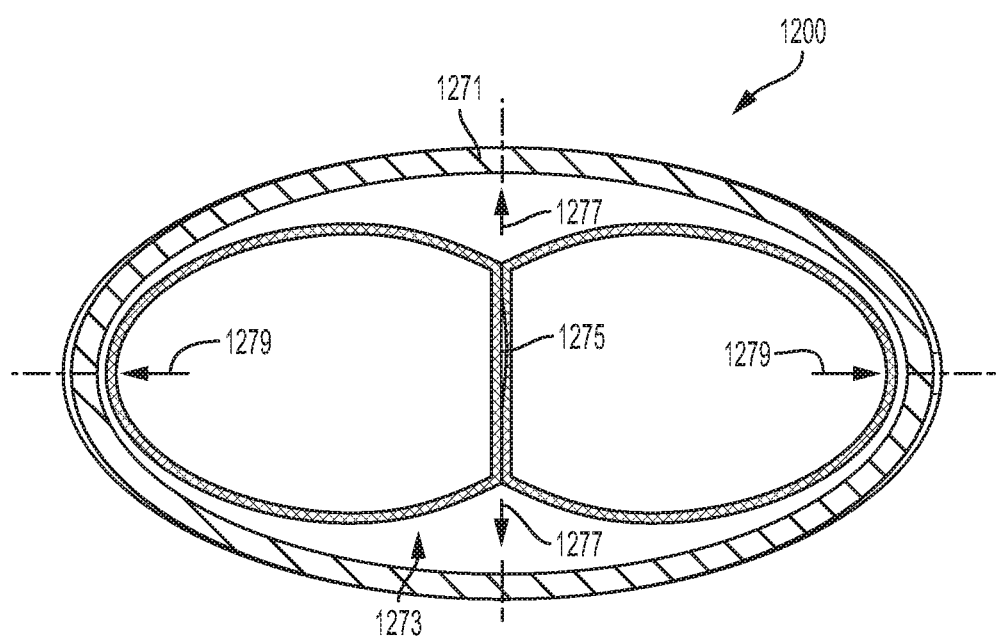
Figure 106I:
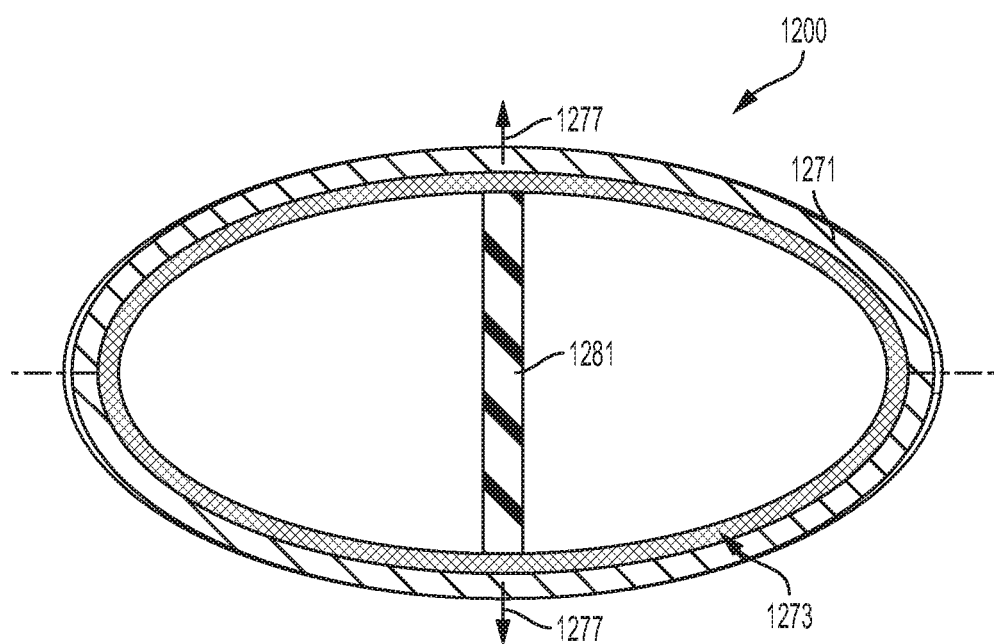
Figure 107:
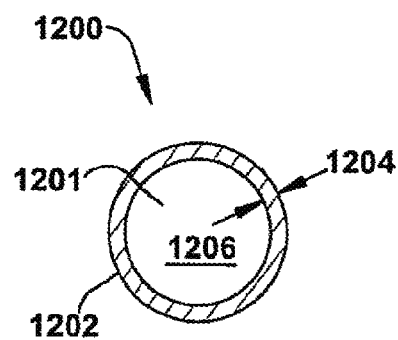
Figure 108:
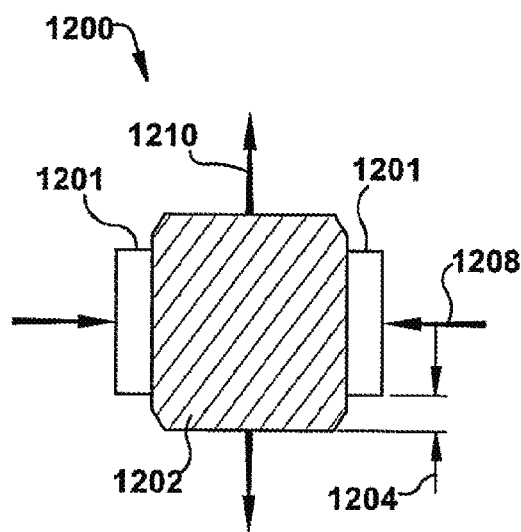
Figure 108E:
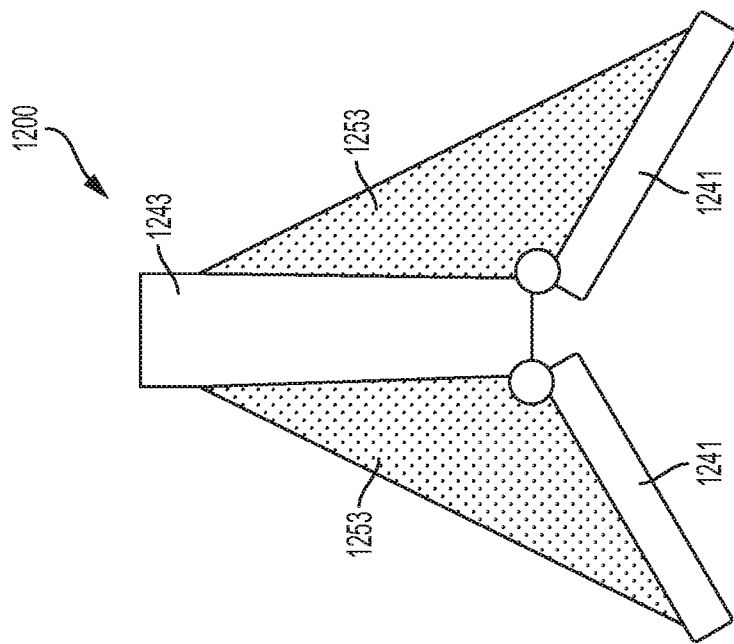
Figure 108D:
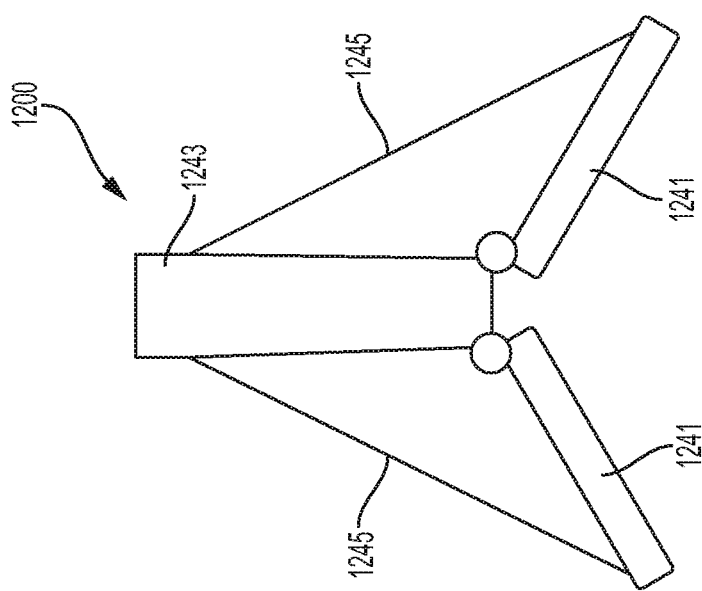
Figure 111:
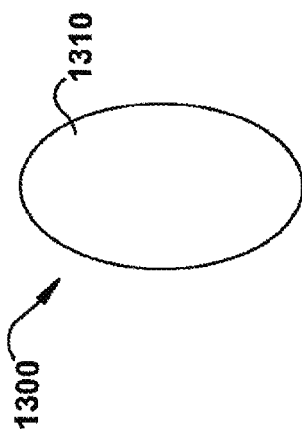
Figure 110:
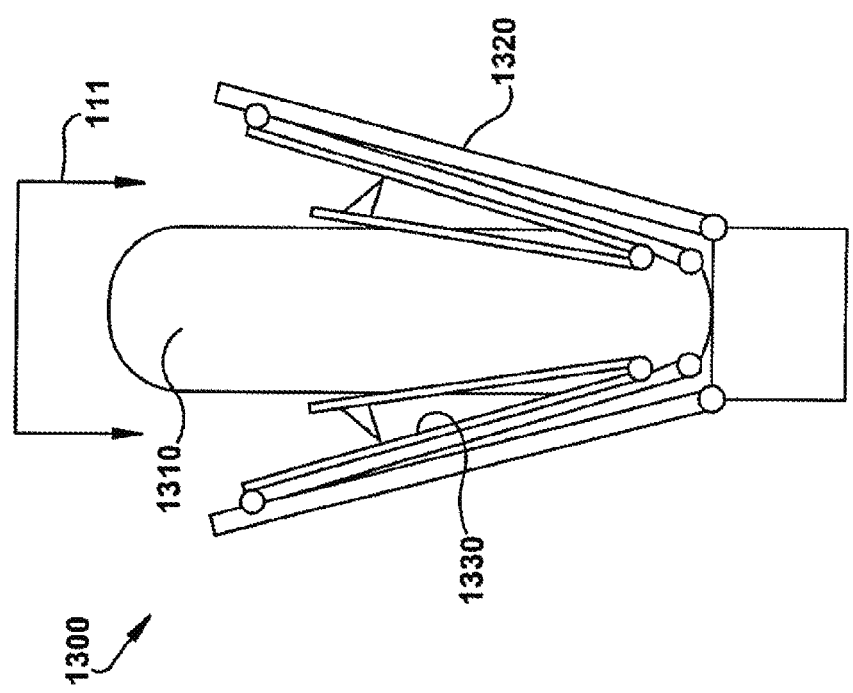
Figure 109:
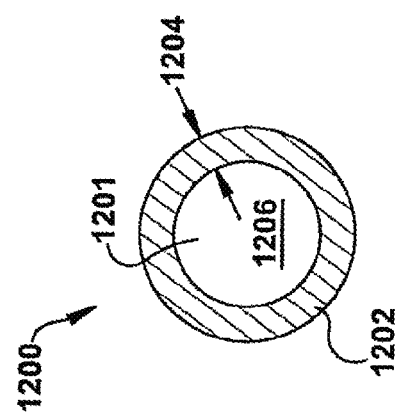

FIG. 96 shows a cross-section view of the coapting portion and paddle portions of FIG. 95;

FIG. 96A shows a cross-section view of the coapting portion and paddle portions of FIG. 95A;

FIG. 97 shows a sectioned perspective view of a coapting portion and paddle portions of the implantable prosthetic device illustrated by FIG. 65 with the section taken across plane 98;

FIG. 97A shows a sectioned perspective view of a coapting portion and paddle portions of the implantable prosthetic device illustrated by FIG. 65A with the section taken across plane 98A;

FIG. 98 shows a cross-section view of the coapting portion and paddle portions of FIG. 97;

FIG. 98A shows a cross-section view of the coapting portion and paddle portions of FIG. 97A;

FIG. 99 shows a sectioned perspective view of a coapting portion and paddle portions of the implantable prosthetic device illustrated by FIG. 65 with the section taken across plane 100;

FIG. 99A shows a sectioned perspective view of a coapting portion and paddle portions of the implantable prosthetic device illustrated by FIG. 65A with the section taken across plane 100A;

FIG. 100 shows a cross-section view of the coapting portion and paddle portions of FIG. 99;

FIG. 100A shows a cross-section view of the coapting portion and paddle portions of FIG. 99A;

FIG. 101 shows a sectioned perspective view of a coapting portion and paddle portions of the implantable prosthetic device illustrated by FIG. 65 with the section taken across plane 102;

FIG. 101A shows a sectioned perspective view of a coapting portion and paddle portions of the implantable prosthetic device illustrated by FIG. 65A with the section taken across plane 102A;

FIG. 102 shows a cross-section view of the coapting portion and paddle portions of FIG. 101;

FIG. 102A shows a cross-section view of the coapting portion and paddle portions of FIG. 101A;

FIG. 103 shows an exemplary embodiment of an implantable prosthetic device;

FIG. 104 shows an exemplary embodiment of an implantable prosthetic device;

FIG. 105 shows an exemplary embodiment of an implantable prosthetic device;

FIG. 106 shows a side view of an exemplary embodiment of an expandable coaption element in an unexpanded condition;

FIG. 106A shows a side view of an exemplary embodiment of an expandable coaption element in an unexpanded condition;

FIG. 106B shows a side view of an exemplary embodiment of an expandable coaption element in an unexpanded condition;

FIG. 106C shows a side view of an exemplary embodiment of an expandable coaption element in an unexpanded condition;

FIG. 106D shows a side view of an exemplary embodiment of an expandable coaption element in an unexpanded condition;

FIG. 106E shows a side view of an exemplary embodiment of an expandable coaption element in an unexpanded condition;

FIG. 106F shows an exemplary embodiment of an expandable coaption element;

FIG. 106G shows an exemplary embodiment of an expandable coaption element;

FIG. 106H shows an exemplary embodiment of an expandable coaption element;

FIG. 106I shows an exemplary embodiment of an expandable coaption element;

FIG. 107 shows an end view of the expandable coaption element of FIG. 106;

FIG. 108 shows the expandable coaption element of FIG. 106 in an expanded condition;

FIG. 108A shows the expandable coaption element of FIG. 106A in an expanded condition;

FIG. 108B shows the expandable coaption element of FIG. 106B in an expanded condition;

FIG. 108C shows the expandable coaption element of FIG. 106C in an expanded condition;

FIG. 108D shows the expandable coaption element of FIG. 106D in an expanded condition;

FIG. 108E shows the expandable coaption element of FIG. 106E in an expanded condition;

FIG. 109 shows an end view of the coaption element of FIG. 108;

FIG. 108 shows a side view of the coaption element for an exemplary prosthetic device of FIG. 106 in a compressed condition;

FIG. 109 shows an end view of the coaption element of FIG. 108;

FIG. 110 shows a side view of an exemplary embodiment of an implantable prosthetic device;

FIG. 111 shows an end view of a coaption element of the exemplary prosthetic device of FIG. 110, taken along lines 111.

Figure 112:
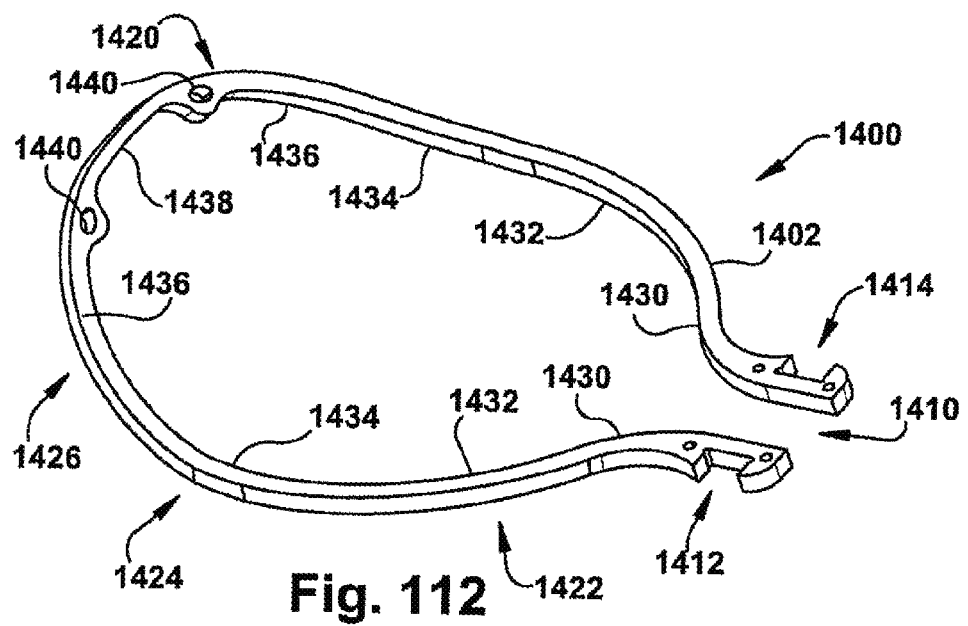
Figure 112A:
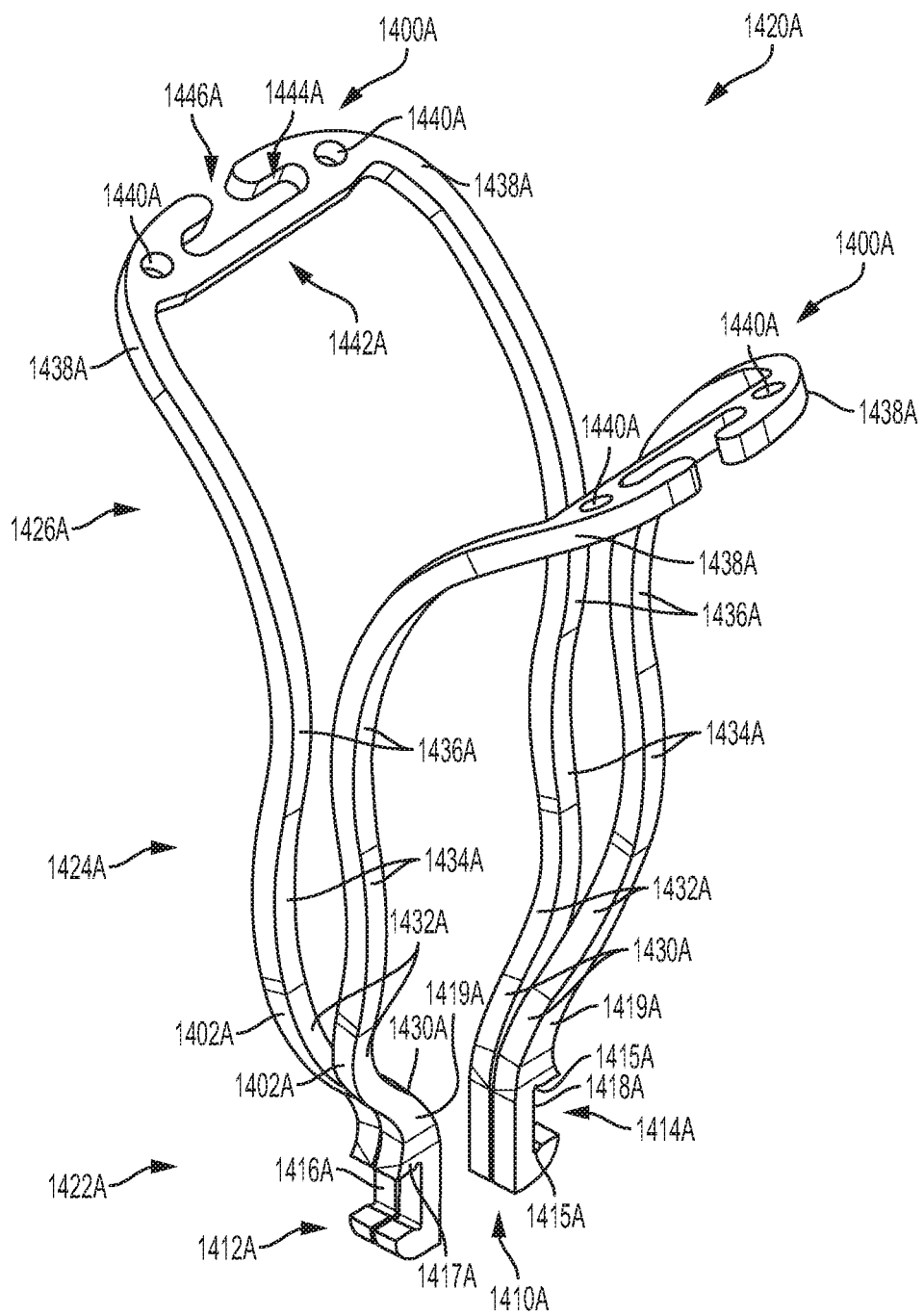
Figure 114:
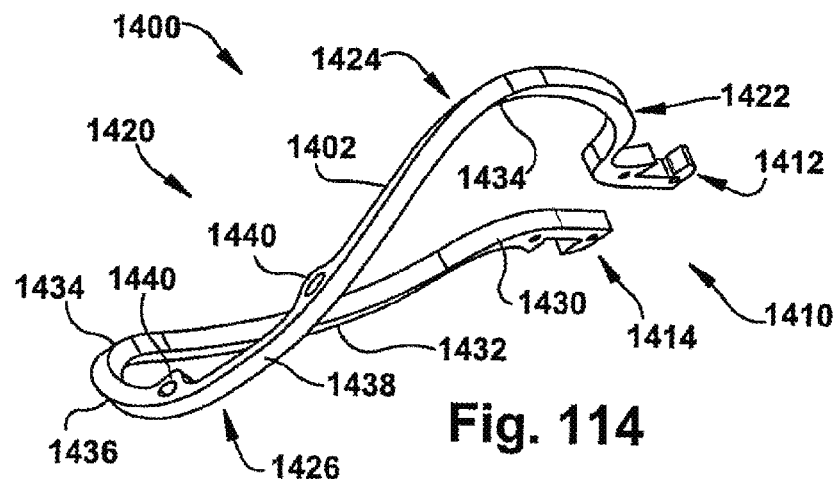
Figure 114A:
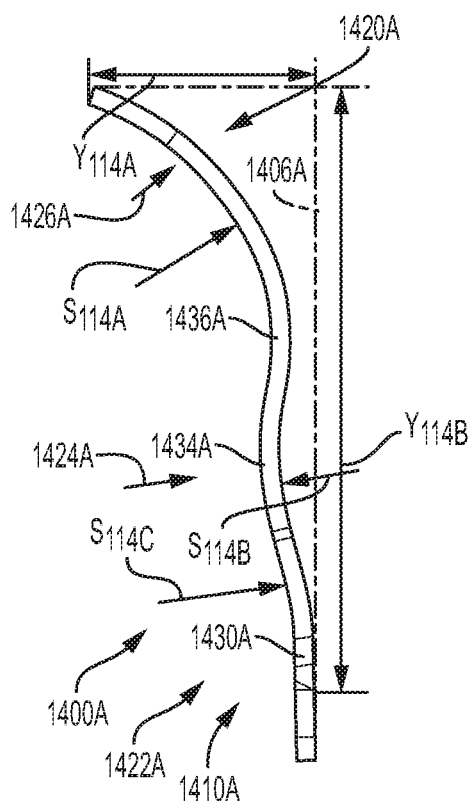
Figure 116:
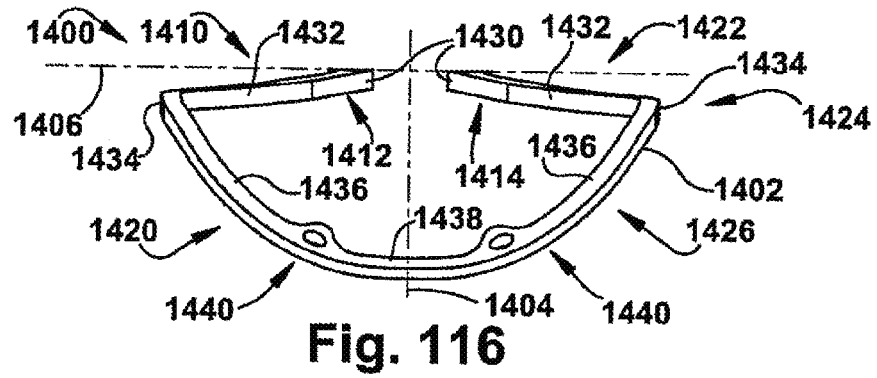
Figure 116A:
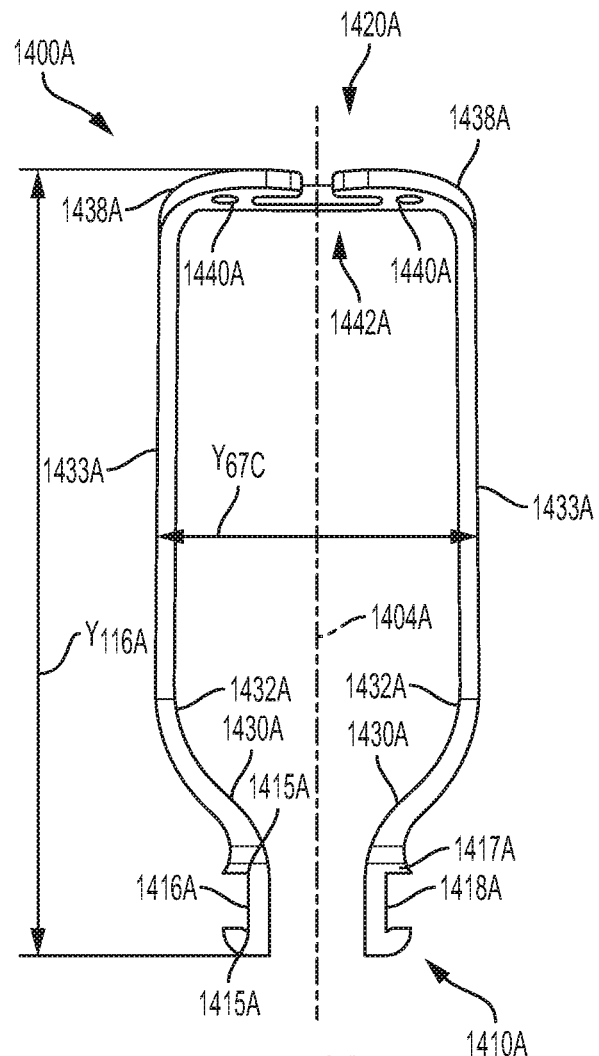
Figure 117A:
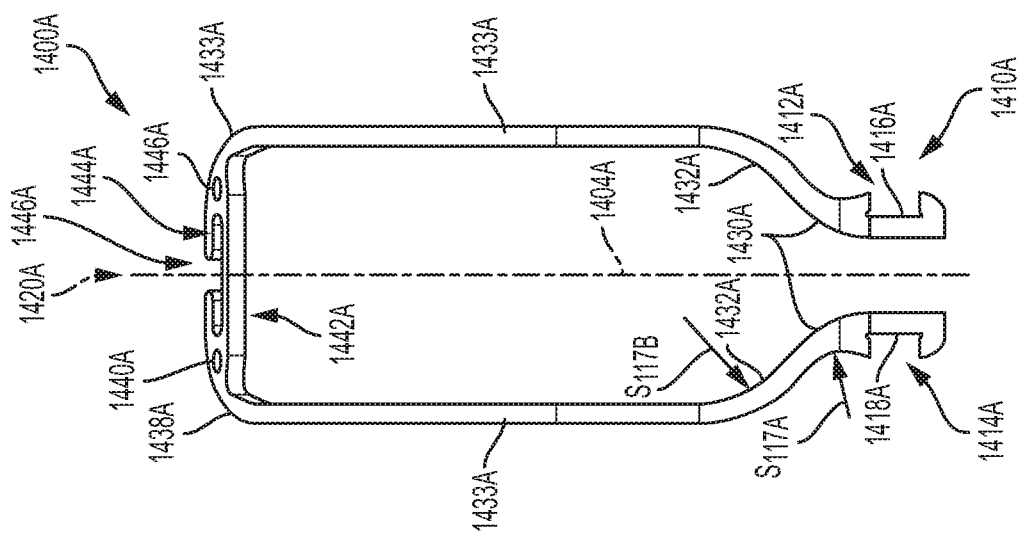
Figure 117:
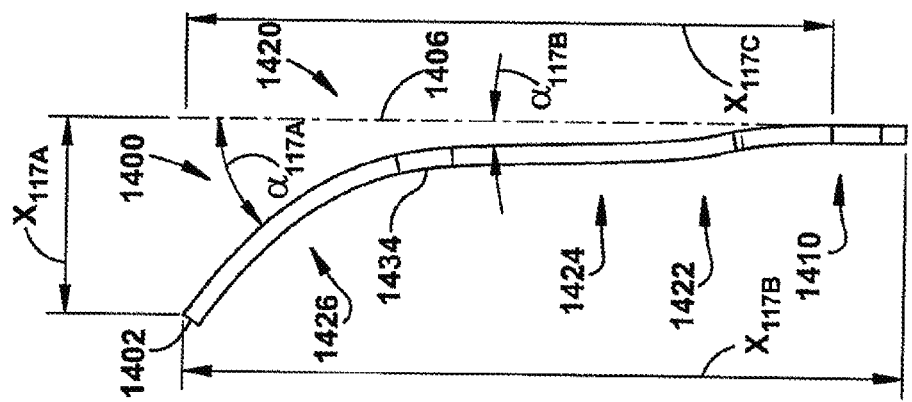
Figure 118:
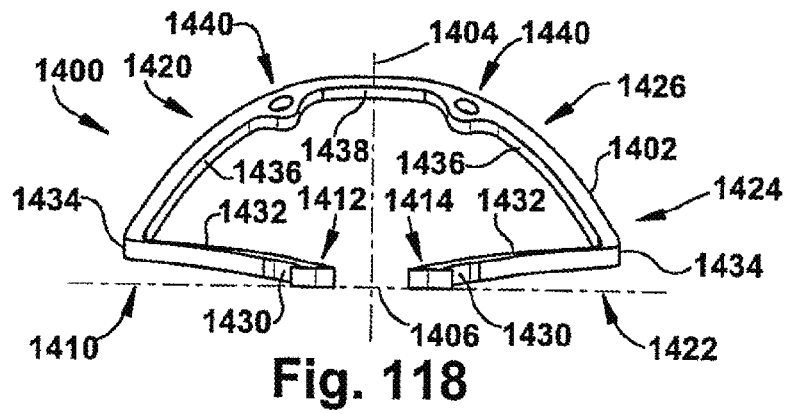
Figure 118A:
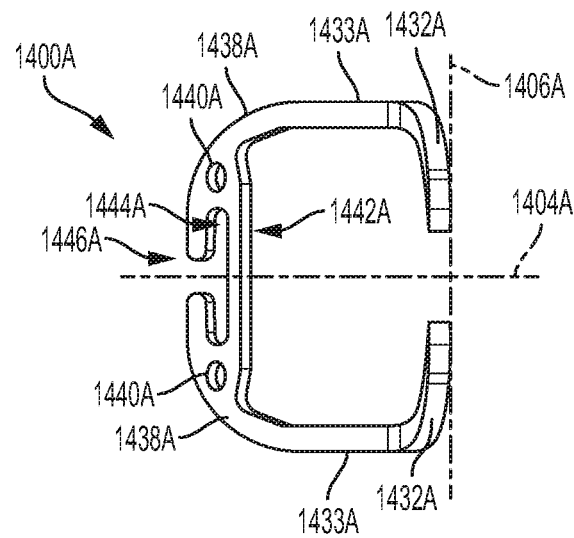
Figure 119:
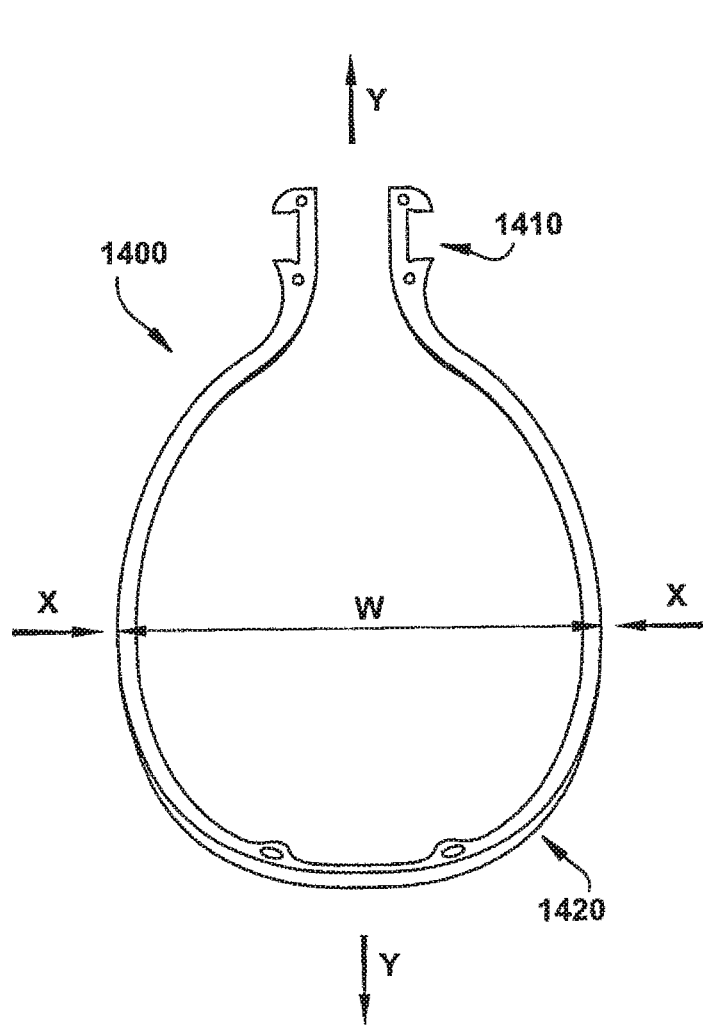
Figure 120:
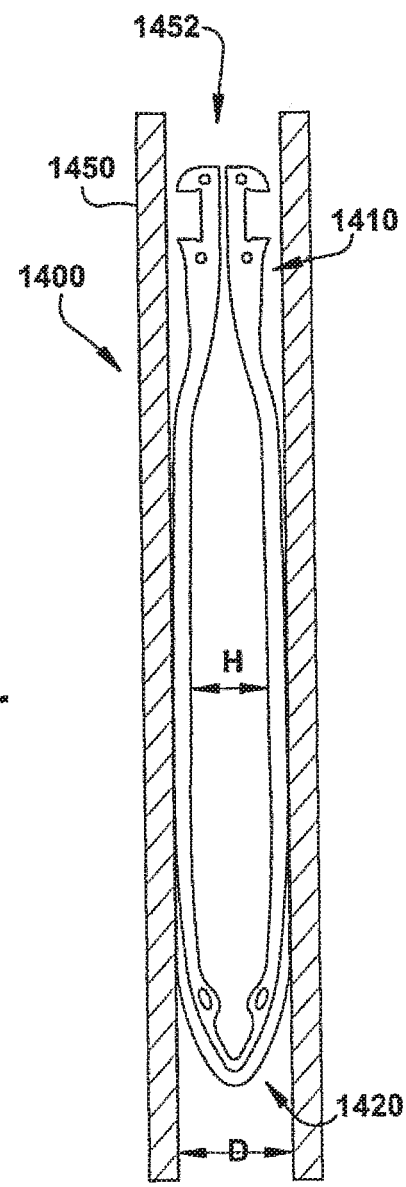
Figure 121:
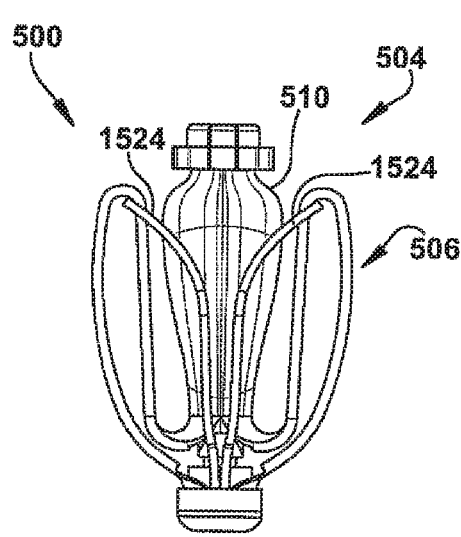
Figure 122:
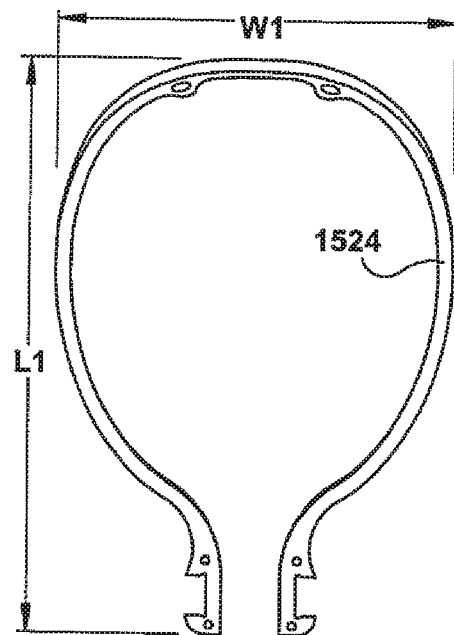
Figure 123:
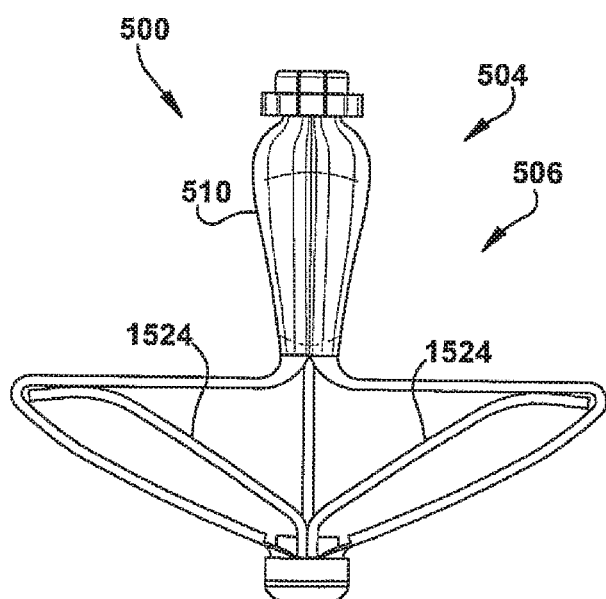
Figure 124:
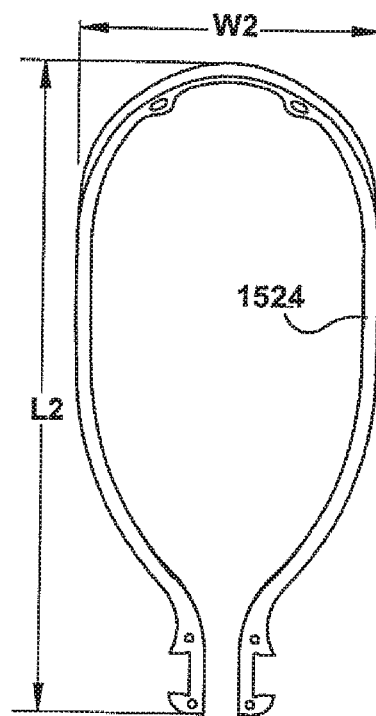
Figure 125:
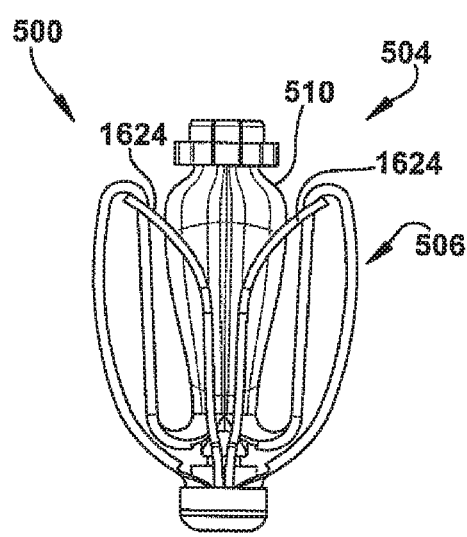
Figure 126:
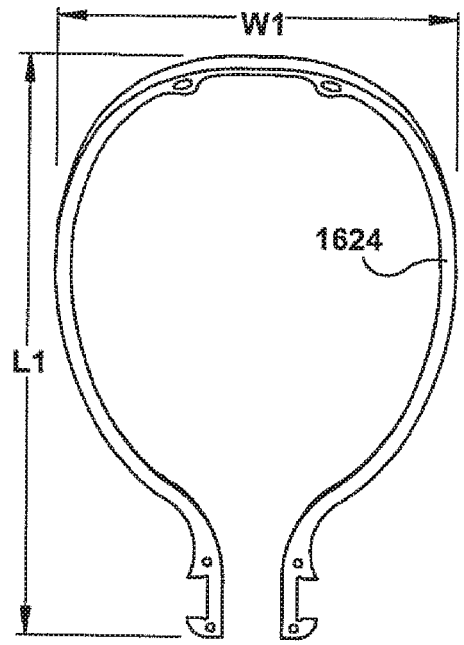
Figure 127:
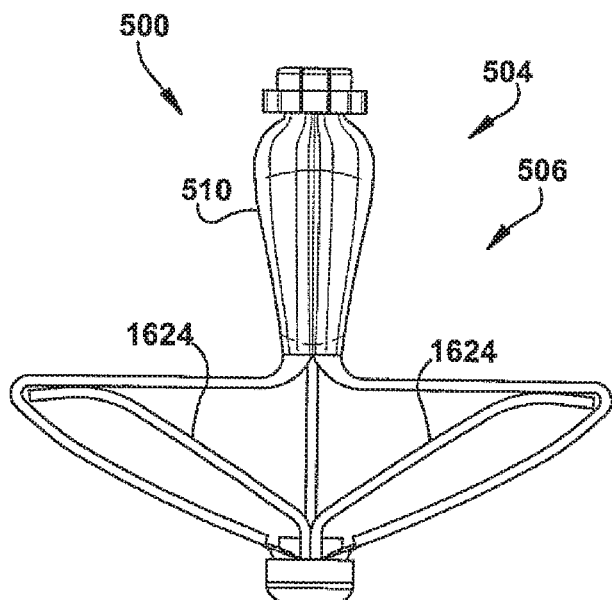
Figure 128:
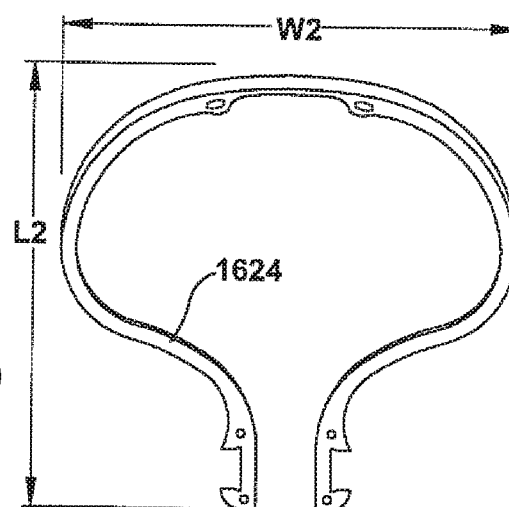
Figure 129:
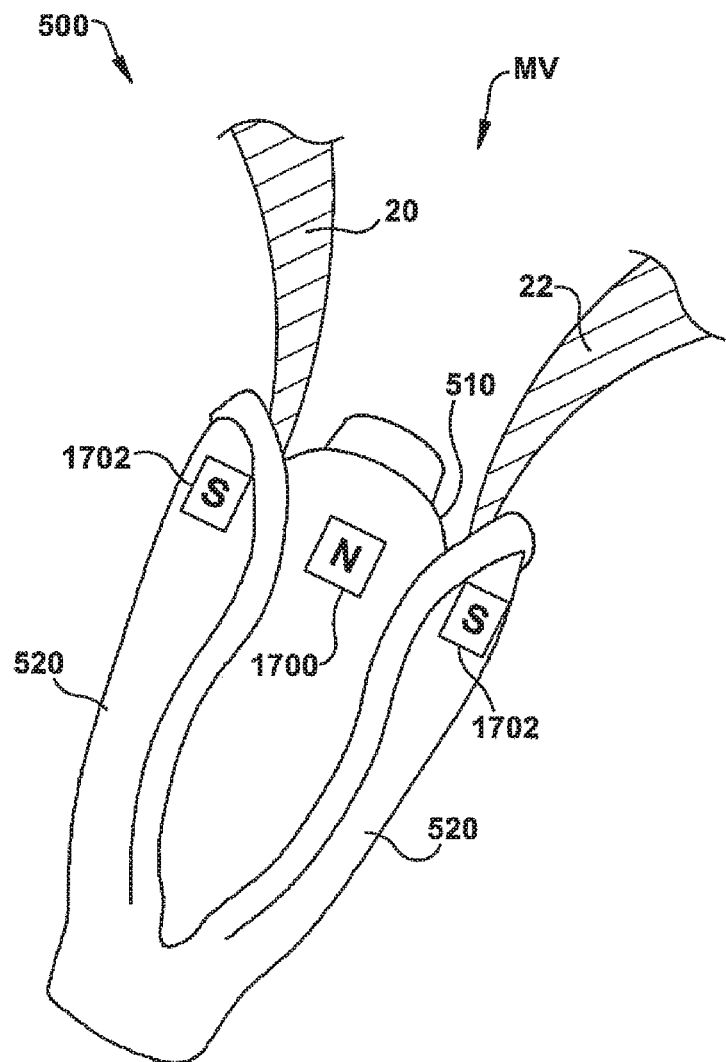
Figure 131:
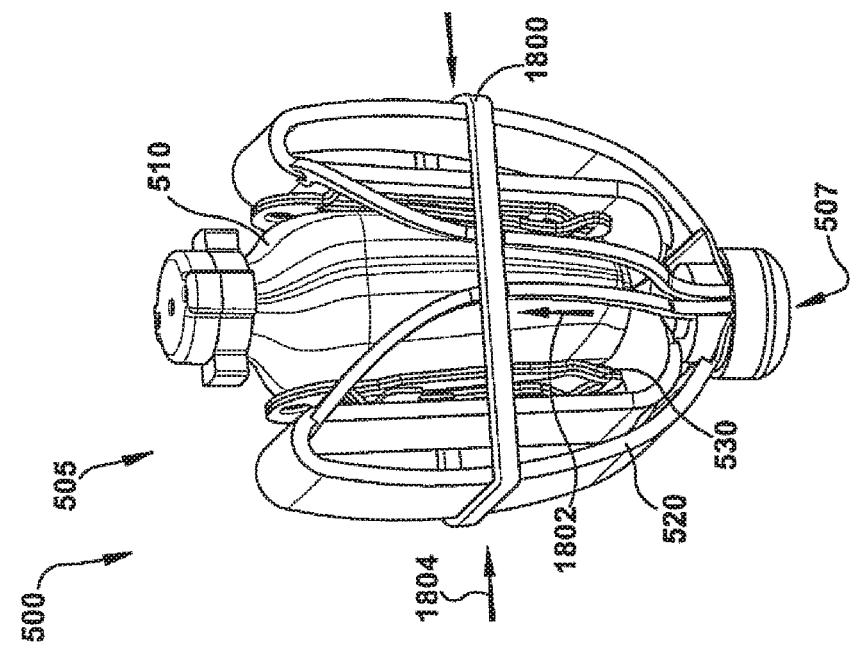
Figure 130:
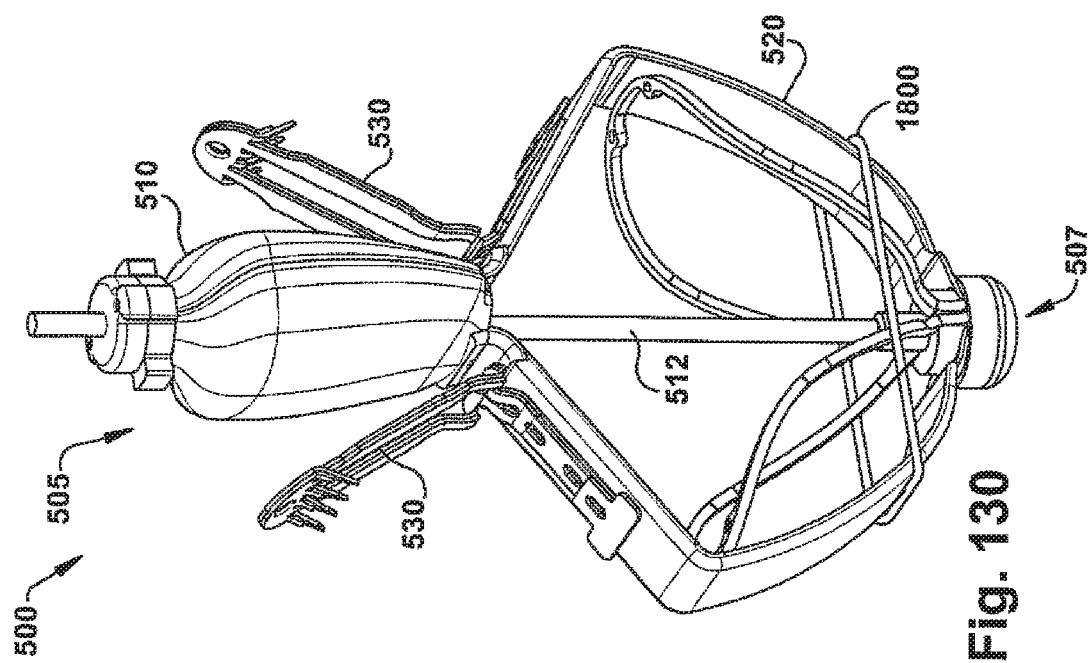
Figure 132:
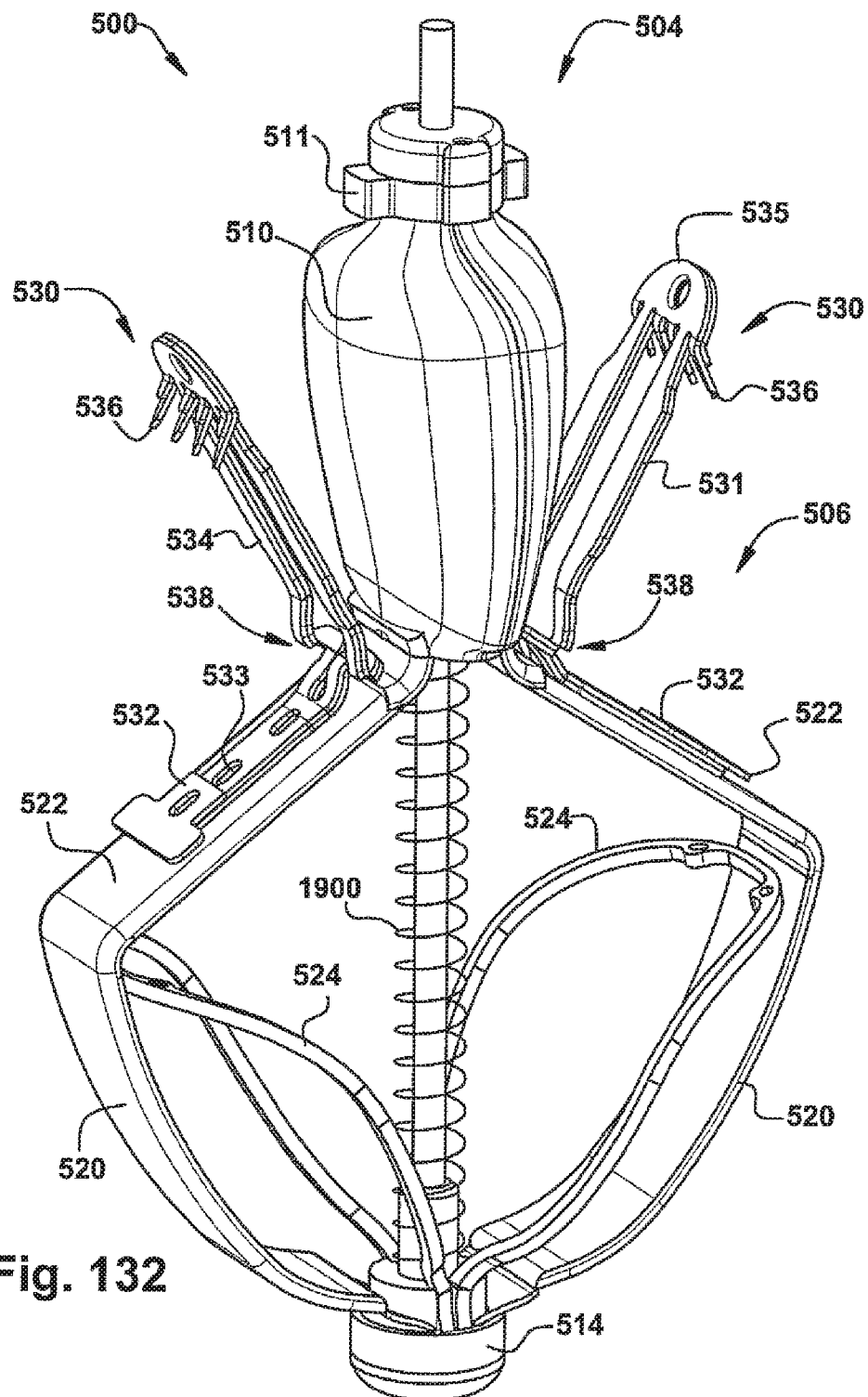
Figure 133:
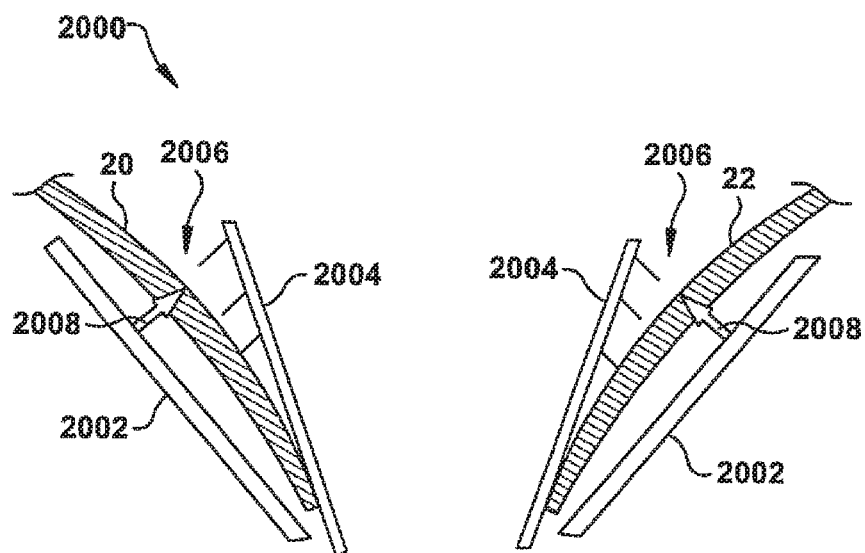
Figure 134:
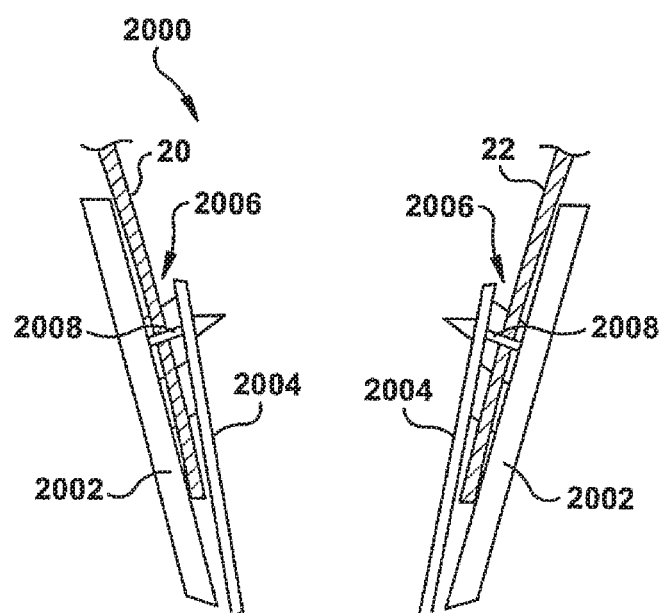
Figure 135:
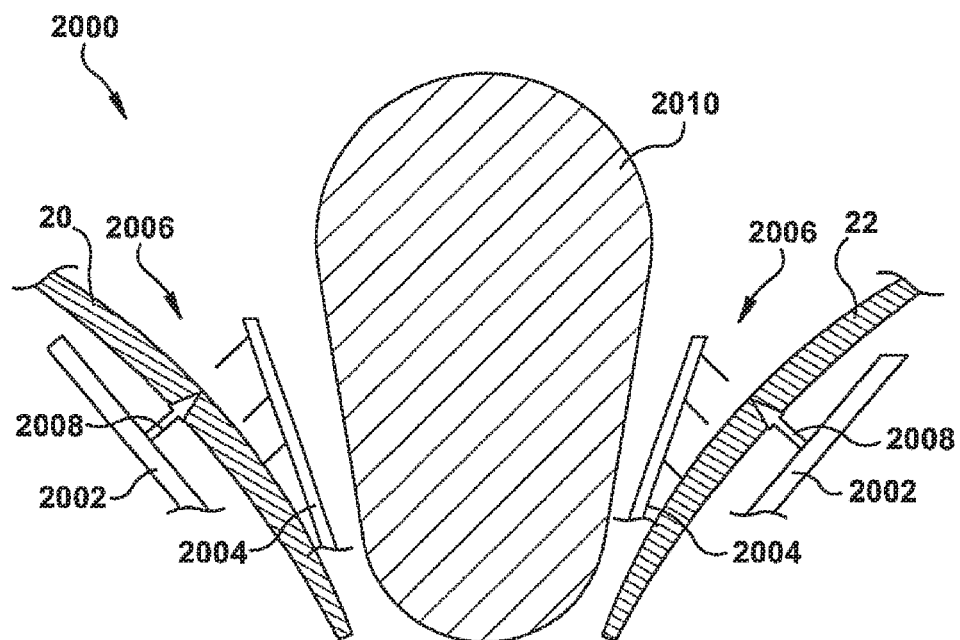
Figure 136:
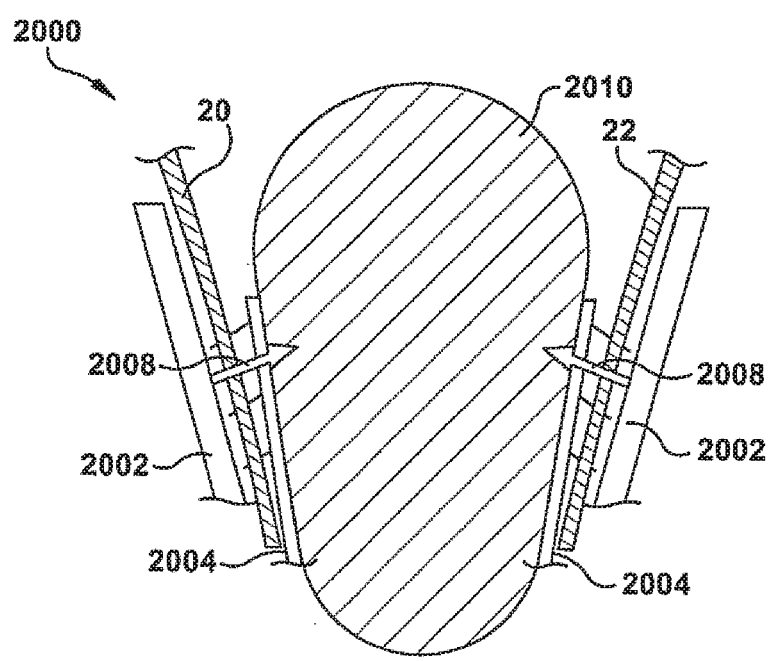
Figure 137:
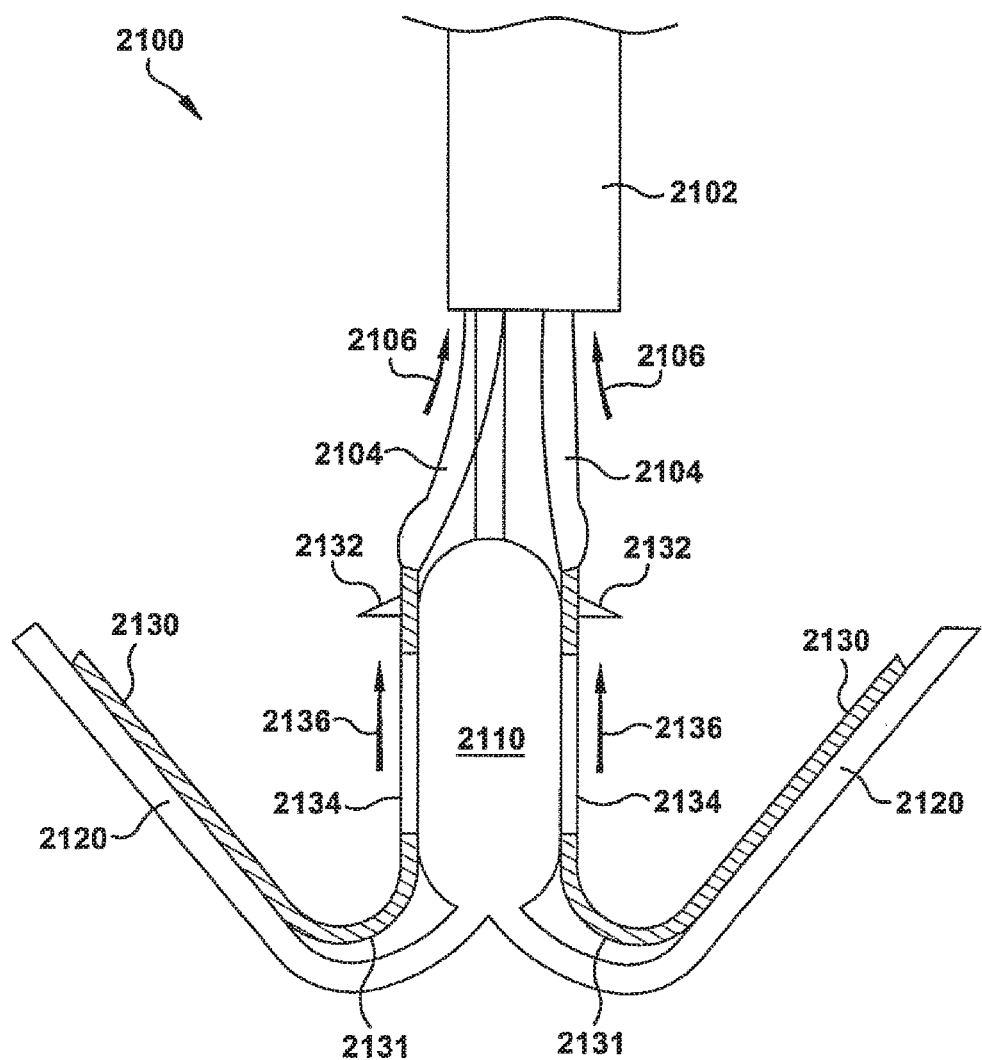
Figure 144:
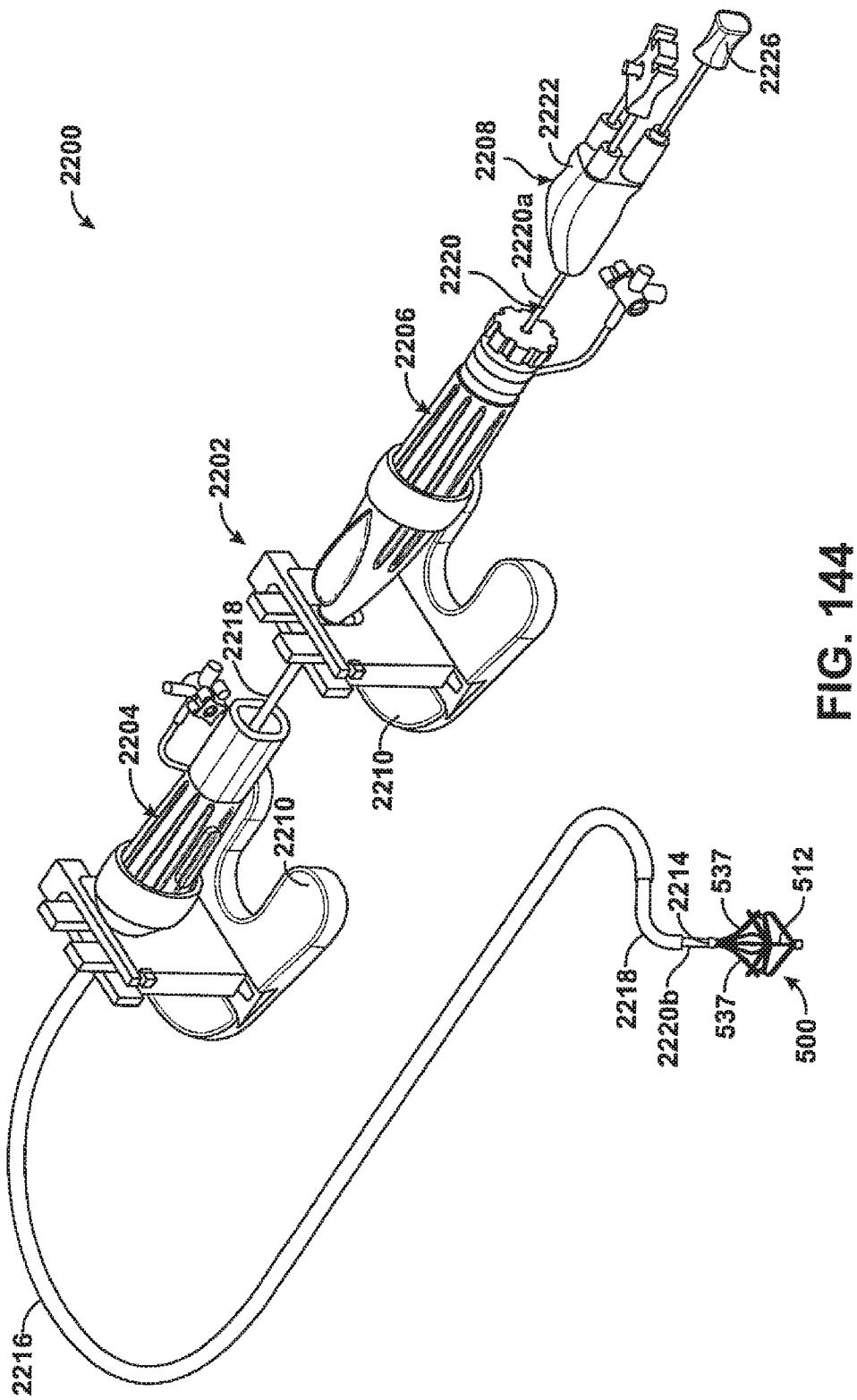
Figure 145:
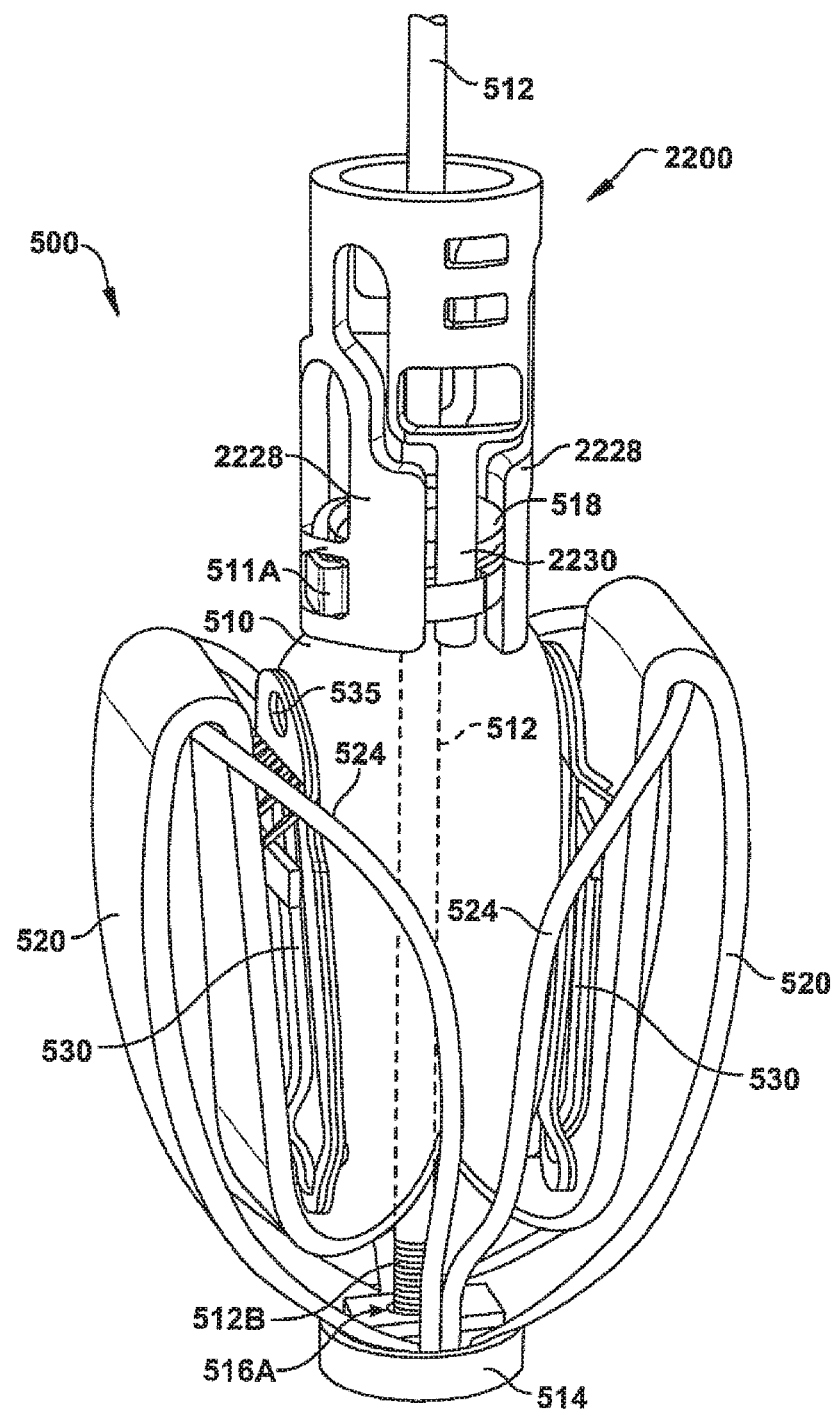
Figure 146:
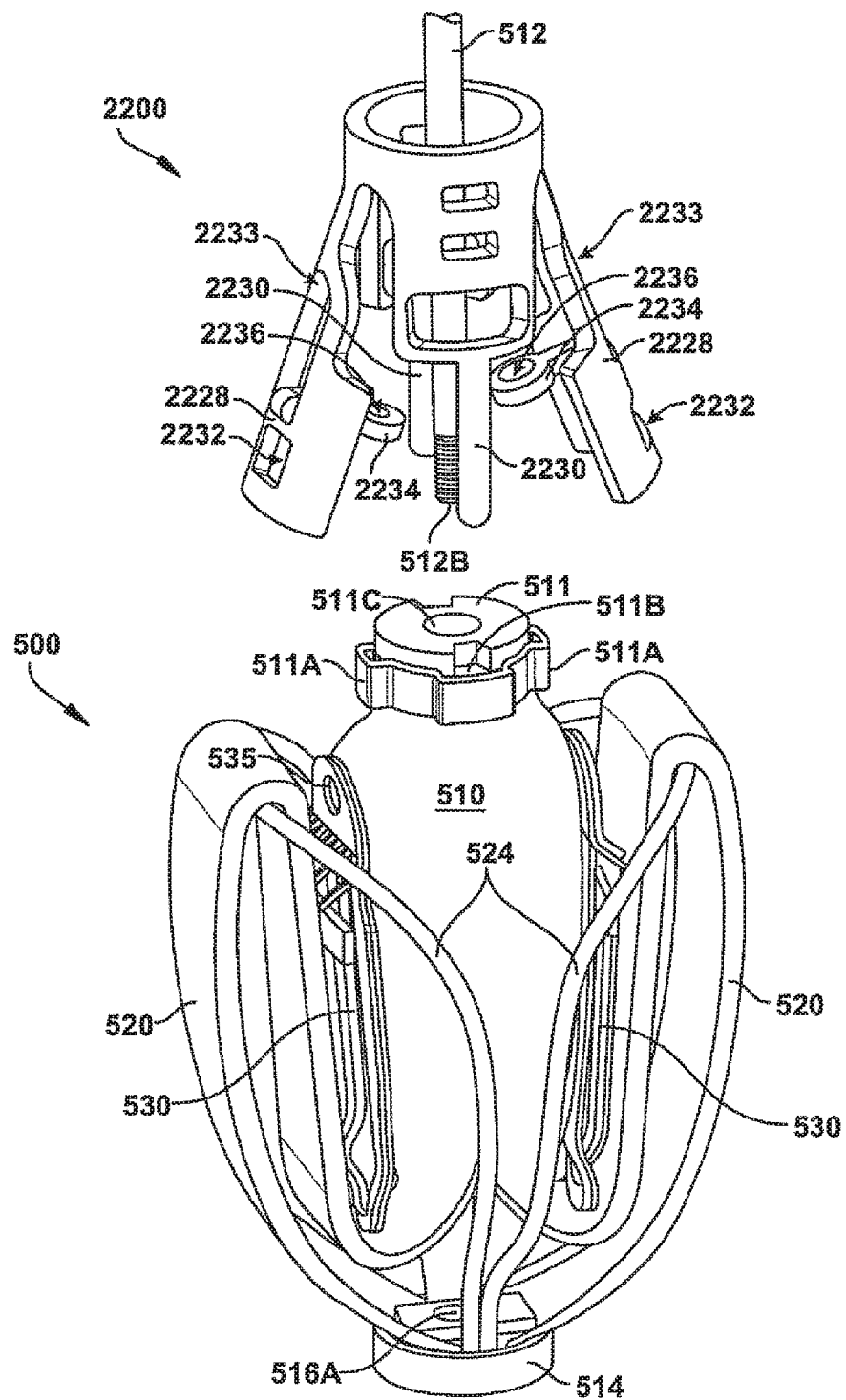
Figure 147:
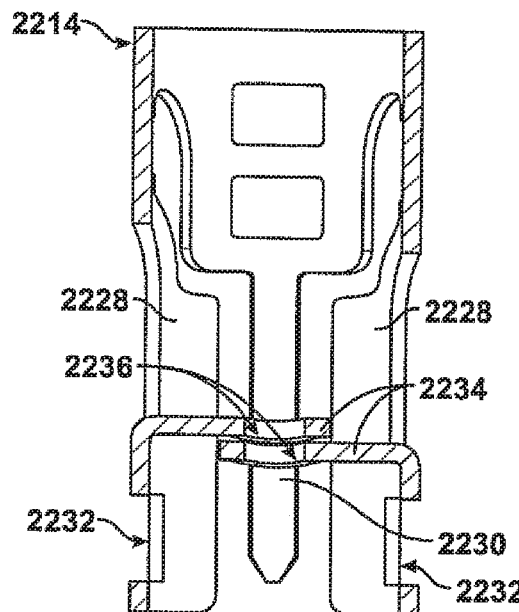
Figure 148:
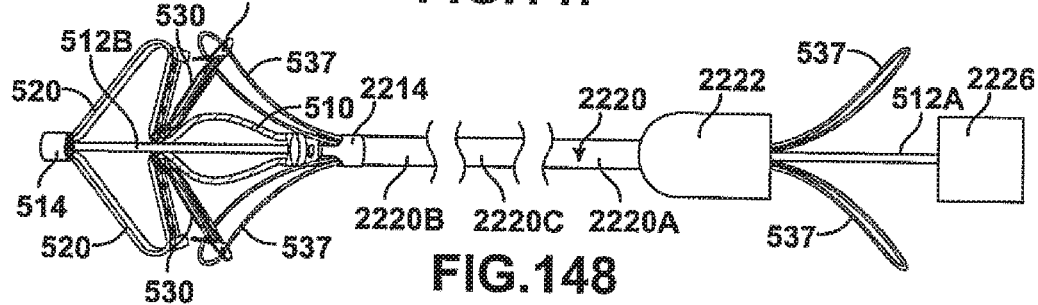
Figure 149:
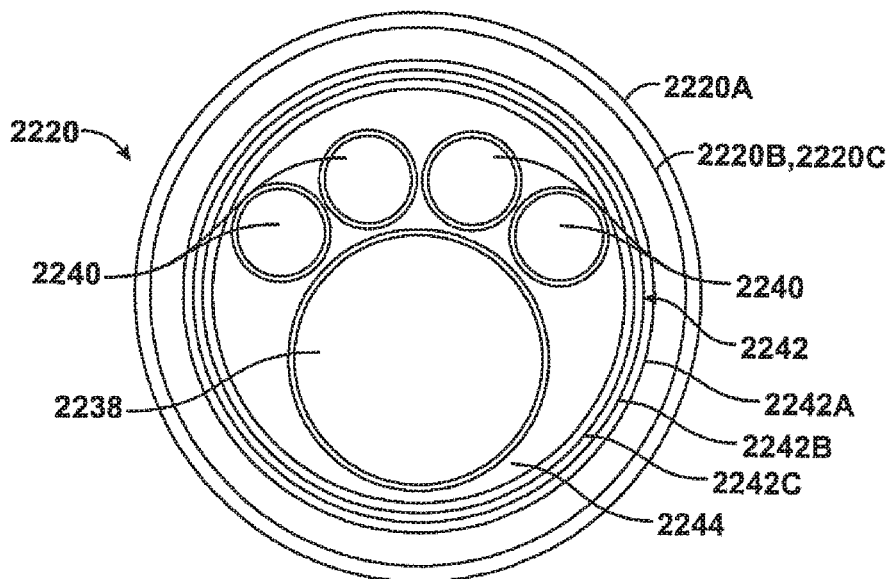
Figure 150:
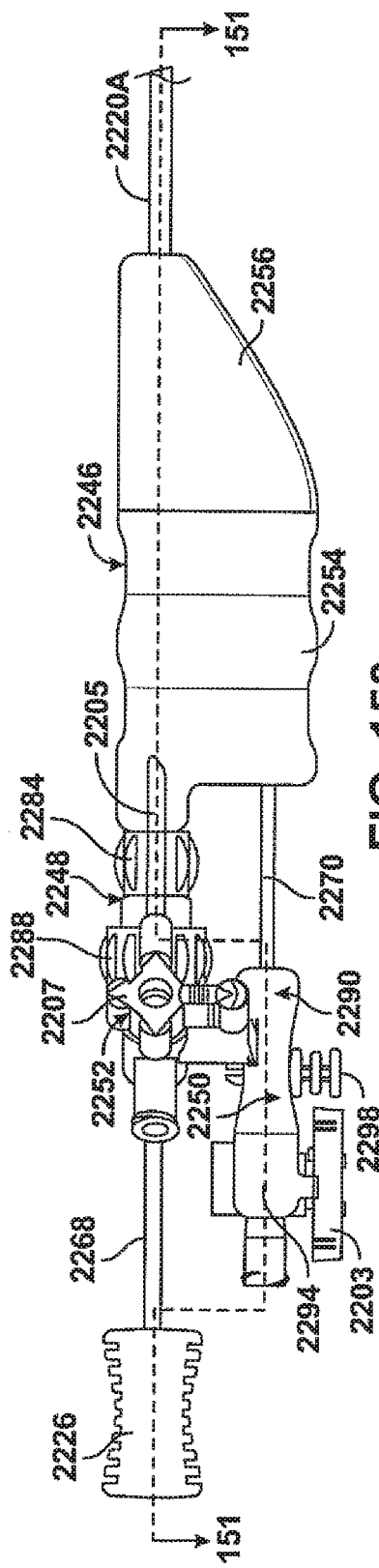
Figure 151:
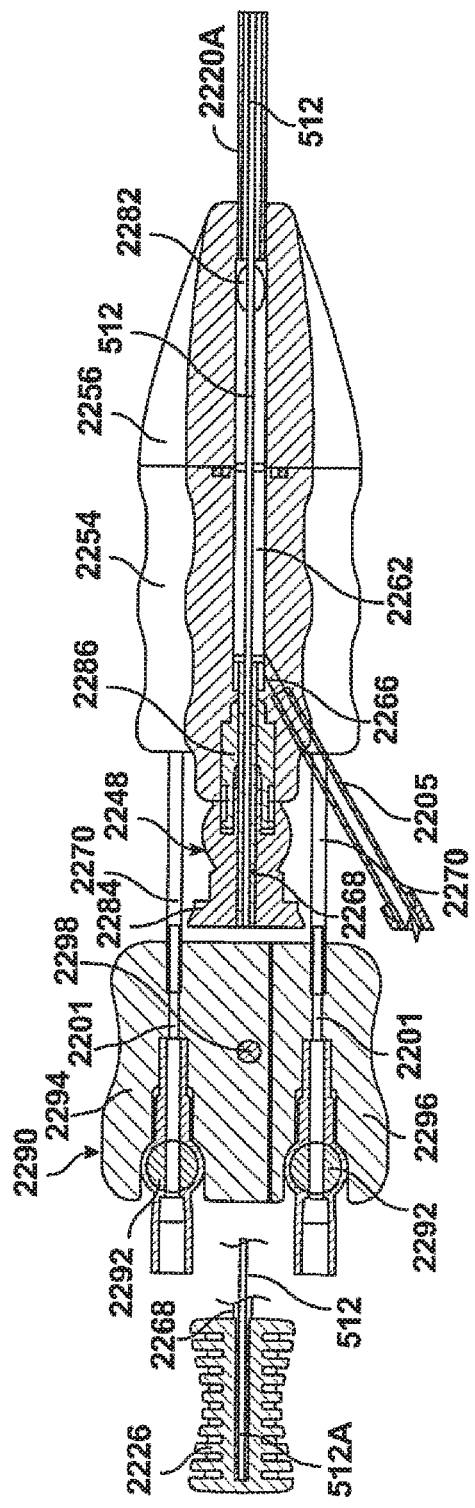
Figure 152:
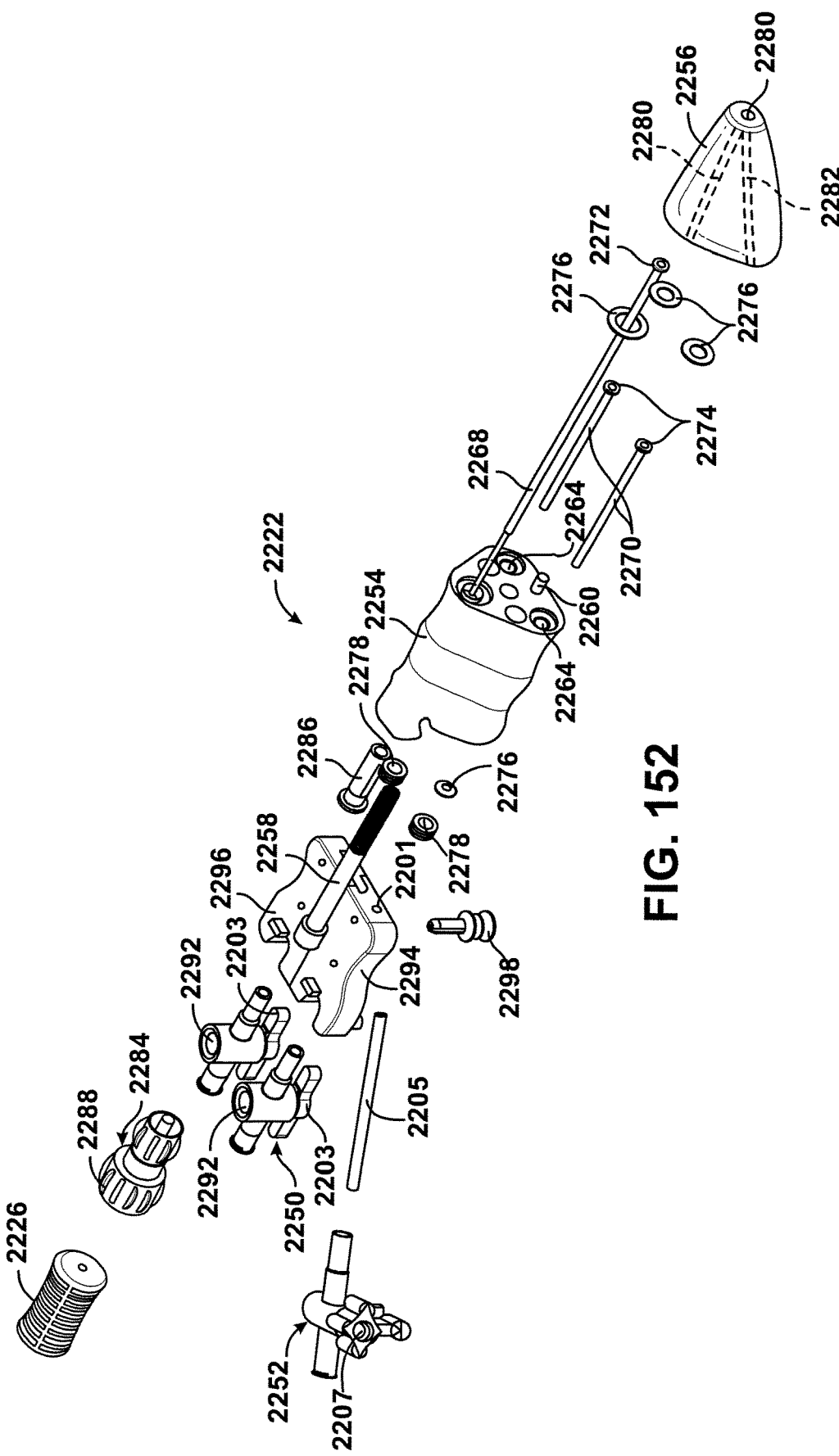
Figure 161:
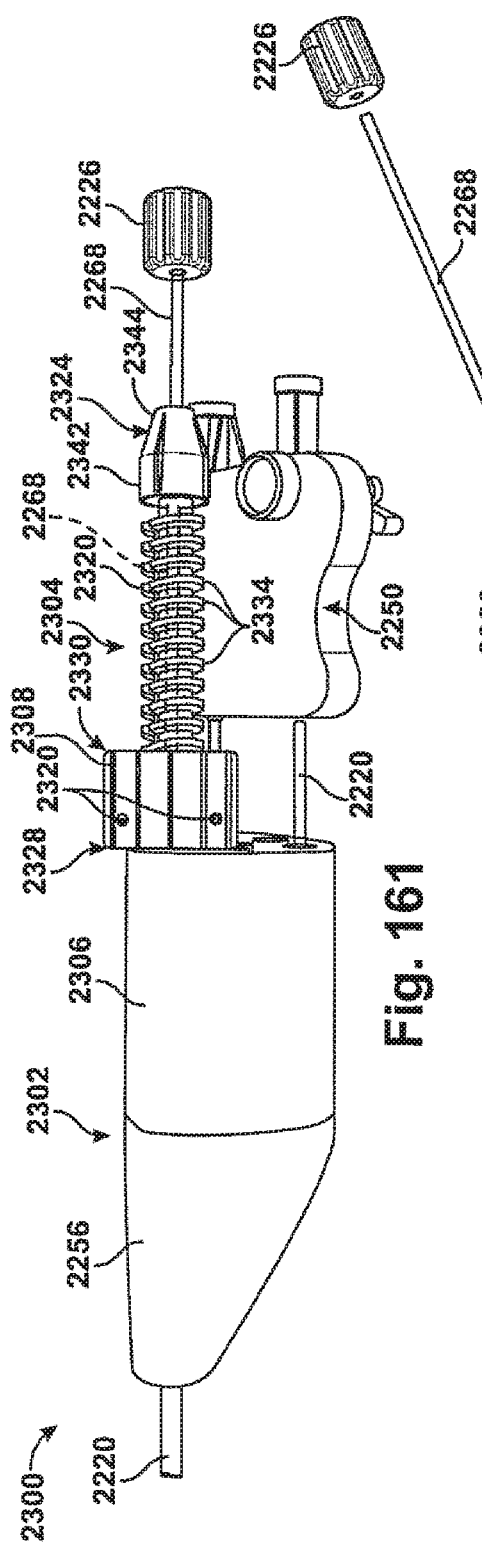
Figure 162:
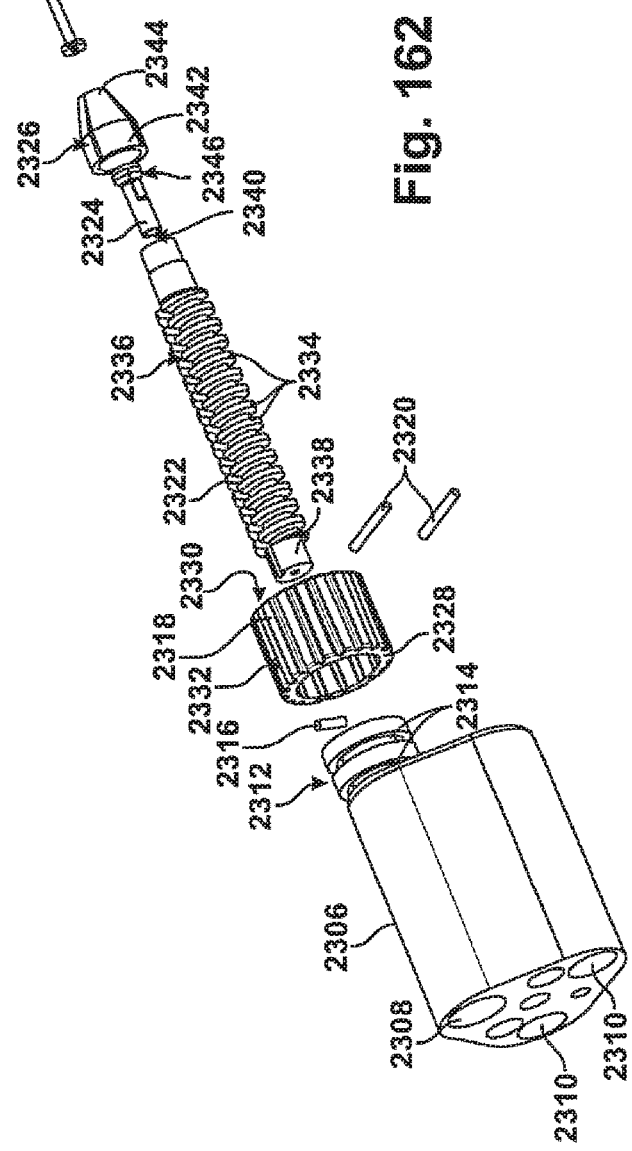
Figure 163:
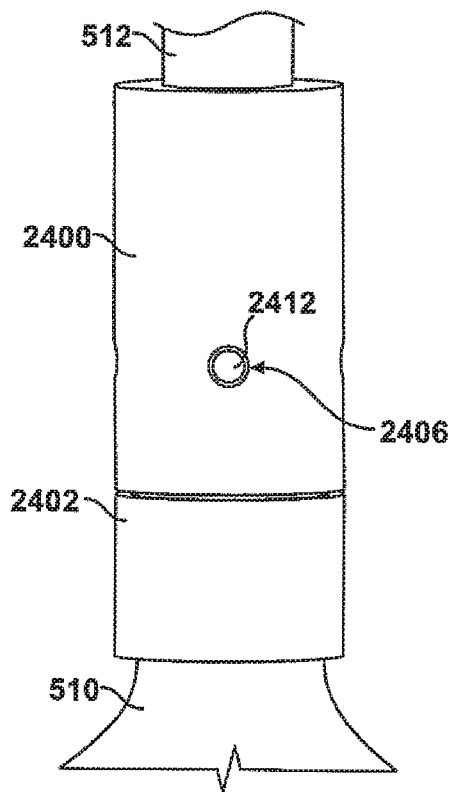
Figure 164:
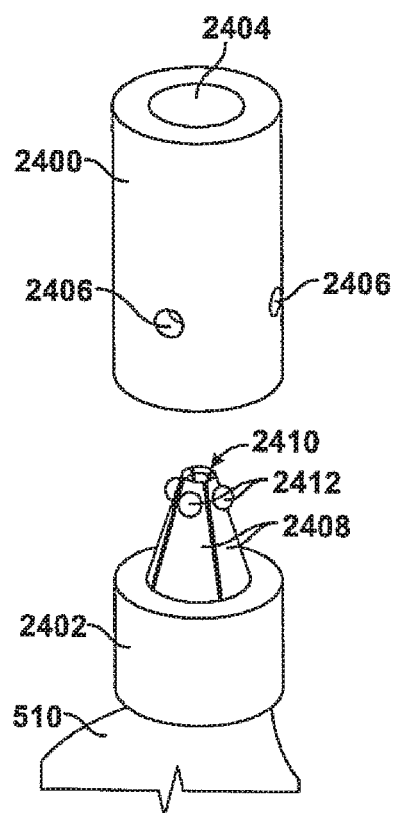
Figure 165:
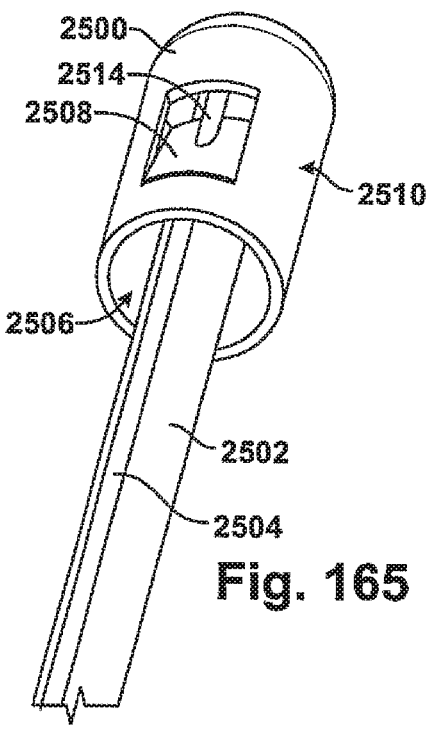

FIGS. 112-114 show perspective views of an exemplary embodiment of a paddle frame for the implantable prosthetic device of FIG. 65;

FIG. 112A shows a perspective view of an exemplary embodiment of a paddle frame for the implantable prosthetic device of FIG. 65A;

FIG. 114A shows a side view of the paddle frame of FIG. 112A;

FIG. 115 shows a front view of the paddle frame of FIGS. 112-114;

FIG. 115A shows a top view of the paddle frame of FIG. 112A;

FIG. 116 shows a top view of the paddle frame of FIGS. 112-114;

FIG. 116A shows a front view of the paddle frame of FIG. 112A;

FIG. 117 shows a side view of the paddle frame of FIGS. 112-114;

FIG. 117A shows a rear view of the paddle frame of FIG. 112A;

FIG. 118 shows a bottom view of the paddle frame of FIGS. 112-114;

FIG. 118A shows a bottom view of the paddle frame of FIG. 112A;

FIG. 119 shows a front view of the paddle frame of FIGS. 112-114;

FIG. 120 shows a front view of the paddle frame of FIGS. 112-114 in a compressed condition inside a delivery device;

FIG. 121 shows a side view of an exemplary embodiment of an implantable prosthetic device in a closed condition;

FIG. 122 shows a front view of a paddle frame of the exemplary prosthetic device of FIG. 121;

FIG. 123 shows a side view of the implantable prosthetic device of FIG. 121 in a closed condition;

FIG. 124 shows a front view of the paddle frame of the open prosthetic device of FIG. 123;

FIG. 125 shows a side view of an exemplary embodiment of an implantable prosthetic device in a closed condition;

FIG. 126 shows a front view of a paddle frame of the exemplary prosthetic device of FIG. 125;

FIG. 127 shows a side view of the implantable prosthetic device of FIG. 125 in a closed condition;

FIG. 128 shows a front view of the paddle frame of the open prosthetic device of FIG. 127;

FIG. 129 shows an exemplary embodiment of an implantable prosthetic device;

FIGS. 130-131 show an exemplary embodiment of an implantable prosthetic device;

FIG. 132 shows an exemplary embodiment of an implantable prosthetic device;

FIGS. 133-134 show an exemplary embodiment of an implantable prosthetic device;

FIGS. 135-136 show an exemplary embodiment of an implantable prosthetic device;

FIG. 137 shows an exemplary embodiment of an implantable prosthetic device;

FIGS. 138-143 show use of an exemplary embodiment of an implantable prosthetic device;

FIG. 144 shows an exemplary embodiment of a delivery assembly including a delivery device and an exemplary prosthetic device;

FIG. 145 shows a perspective view of an exemplary embodiment of an implantable prosthetic device releasably coupled to a delivery device;

FIG. 146 shows the embodiment of FIG. 145 with the implantable prosthetic device released from to the delivery device;

FIG. 147 shows a cross-sectional view of the coupler of FIG. 145;

FIG. 148 shows a perspective view of the delivery assembly of FIG. 144 with the prosthetic device shown in partial cross-section and some components of the delivery apparatus shown schematically;

FIG. 149 shows a plan view of a shaft of the delivery device of FIG. 144;

FIG. 150 shows a side elevation view of a proximal end portion of the delivery device of FIG. 144;

FIG. 151 shows a cross-sectional view of the proximal end portion of the delivery device of FIG. 144, taken along the line 150-150 shown in FIG. 150;

FIG. 152 shows an exploded view of the proximal end portion of the delivery device of FIG. 144;

FIGS. 153-160 show an exemplary procedure used to repair a native mitral valve of a heart, which is partially shown;

FIG. 161 shows an exemplary embodiment of a handle for the delivery apparatus of FIG. 144;

FIG. 162 is an exploded view of the handle of FIG. 161;

FIG. 163 shows an exemplary embodiment of a coupler and a proximal collar for the delivery assembly of FIG. 144, showing the coupler releasably coupled to the proximal collar;

FIG. 164 shows a perspective view of the coupler and proximal collar of FIG. 163, showing the coupler released from the proximal collar;

FIG. 165 shows other exemplary embodiments of a cap, actuation shaft or means of actuating, and release wire for the delivery assembly of FIG. 144, showing the cap releasably coupled to the actuation shaft or means of actuating by the release wire.

Figure 60:
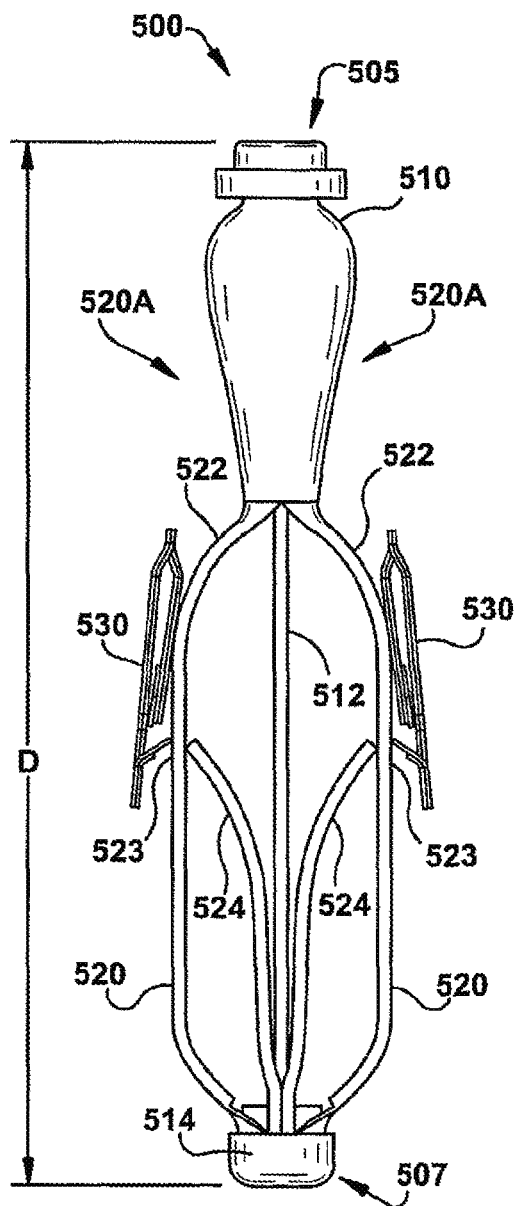
FIG. 60 shows a side view of an exemplary implantable in a full bailout position with barbed clasps in a closed position.
Figure 60A:
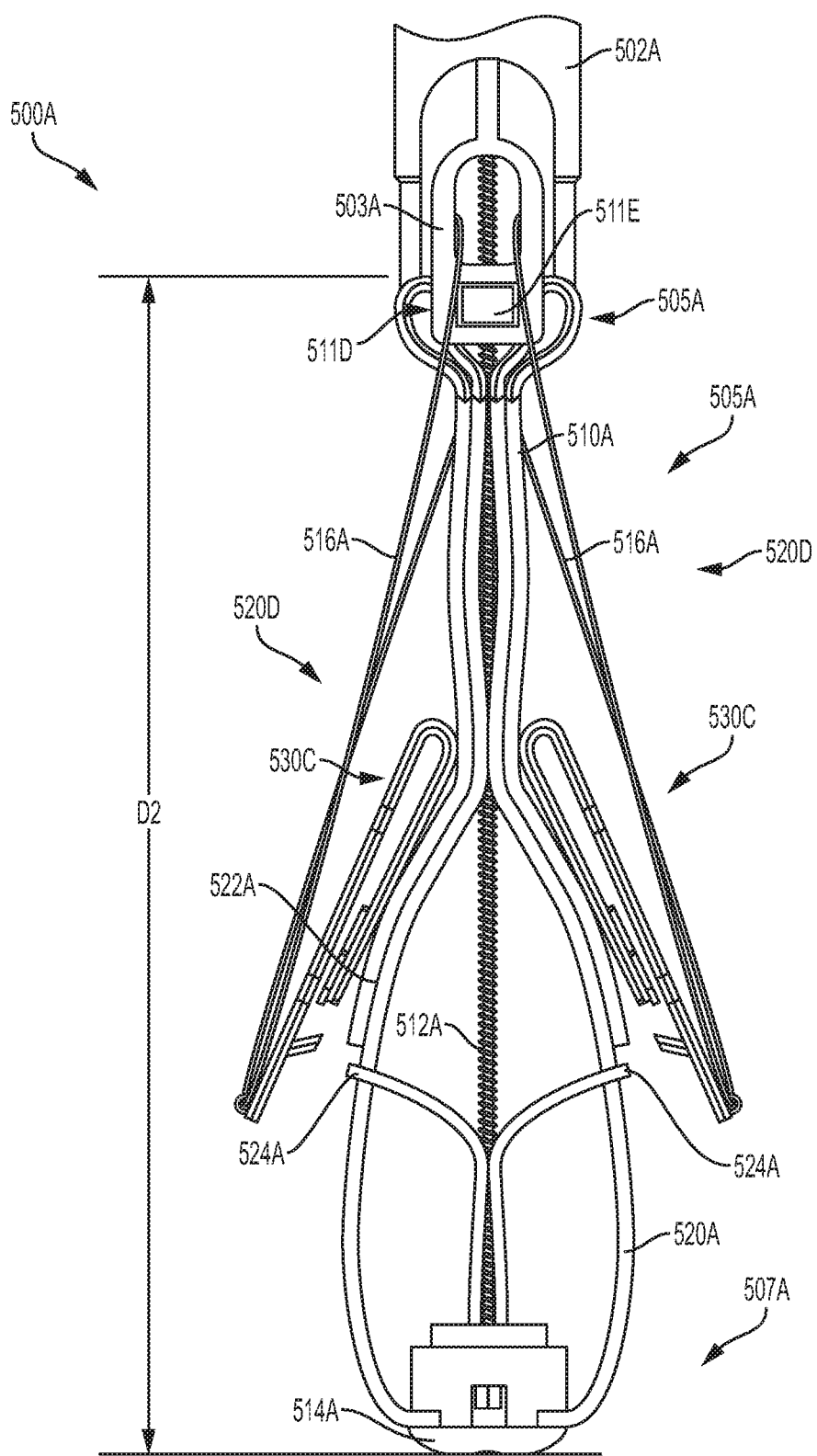
FIG. 60A shows a side view of an exemplary implantable in a full bailout position with barbed clasps in a closed position.
Figure 60B:
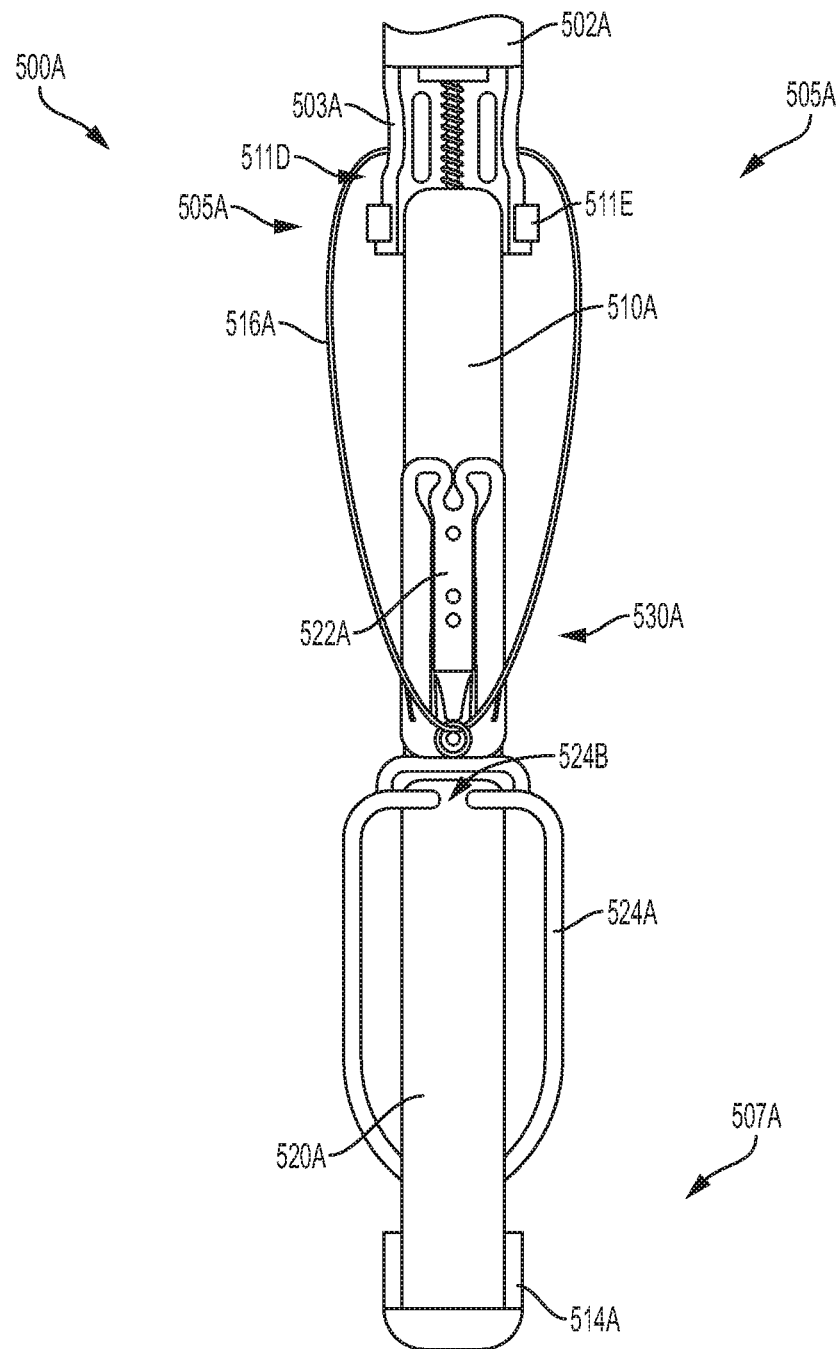
FIG. 60B shows a front view of the exemplary implantable prosthetic device according to FIG. 60A.
Figure 60C:
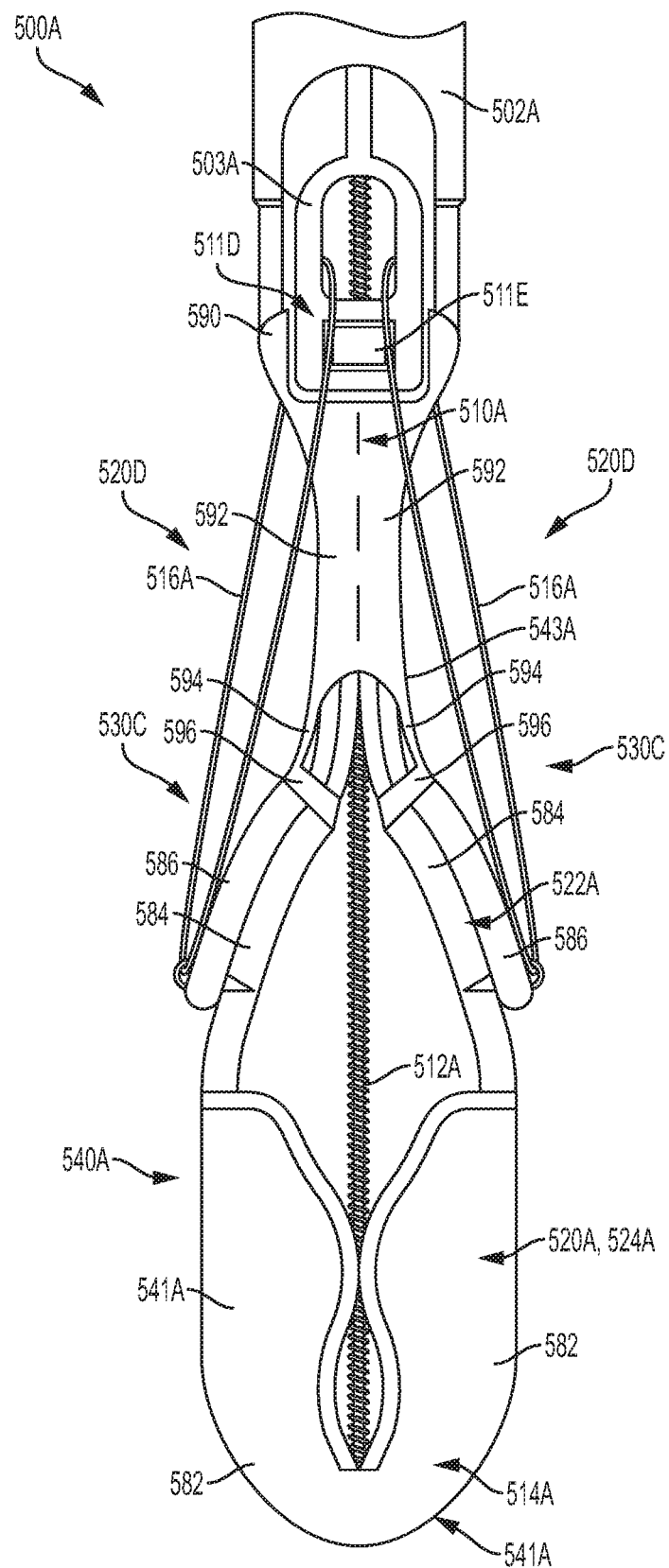
FIG. 60C shows a side view the exemplary implantable prosthetic device according to FIG. 60A, the device being provided with a cover.
Figure 60D:
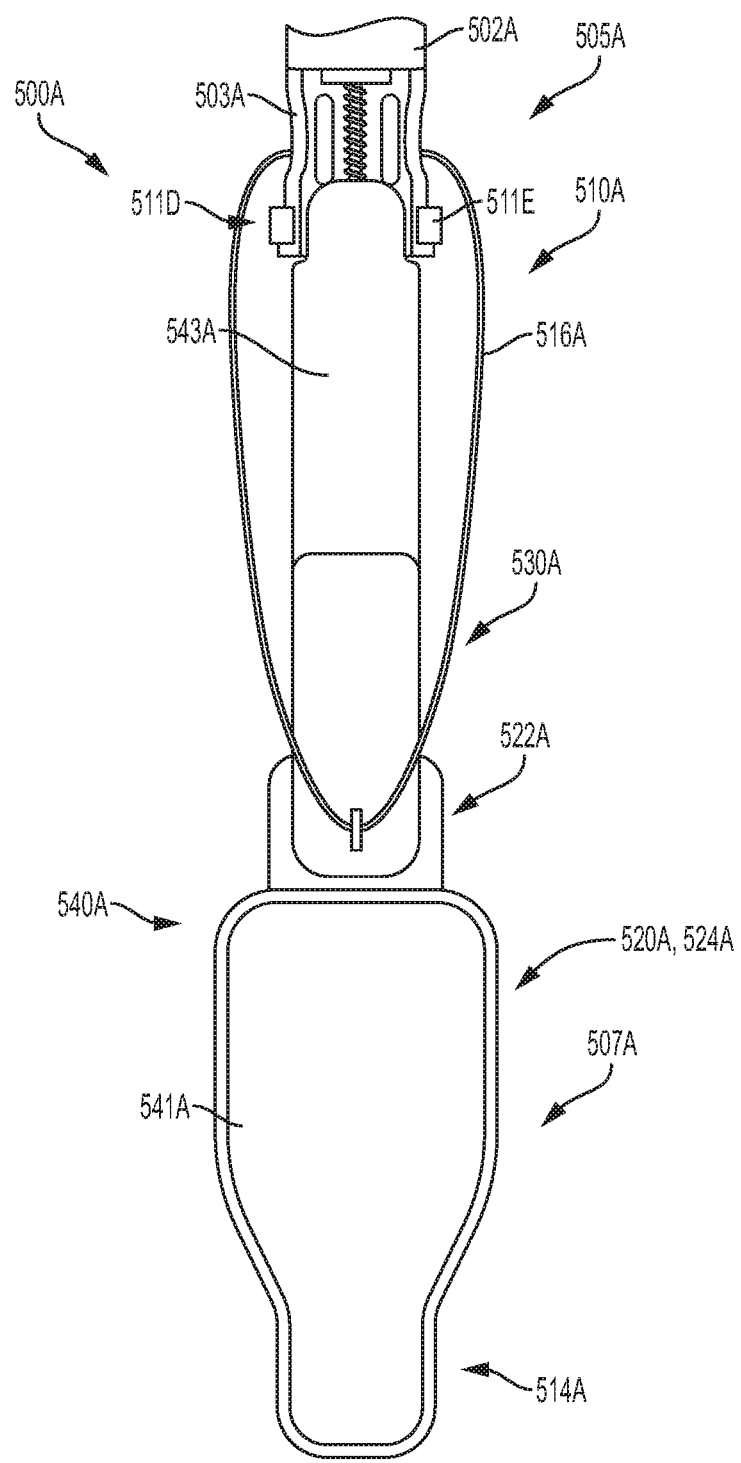
FIG. 60D shows a front view the exemplary implantable prosthetic device according to FIG. 60A, the device being provided with a cover.
Figure 166:
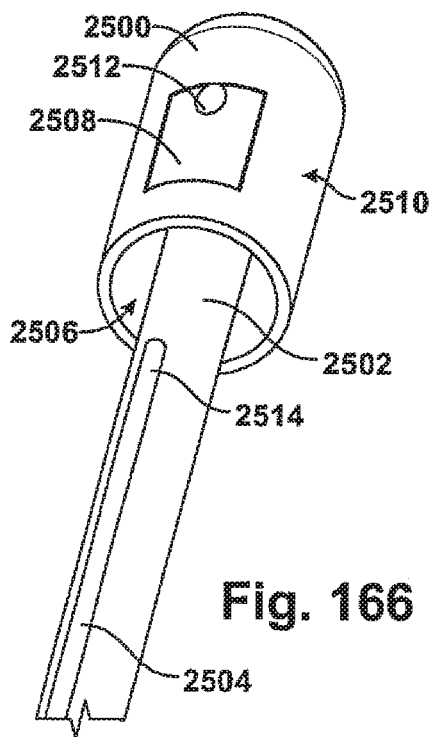
Figure 167:
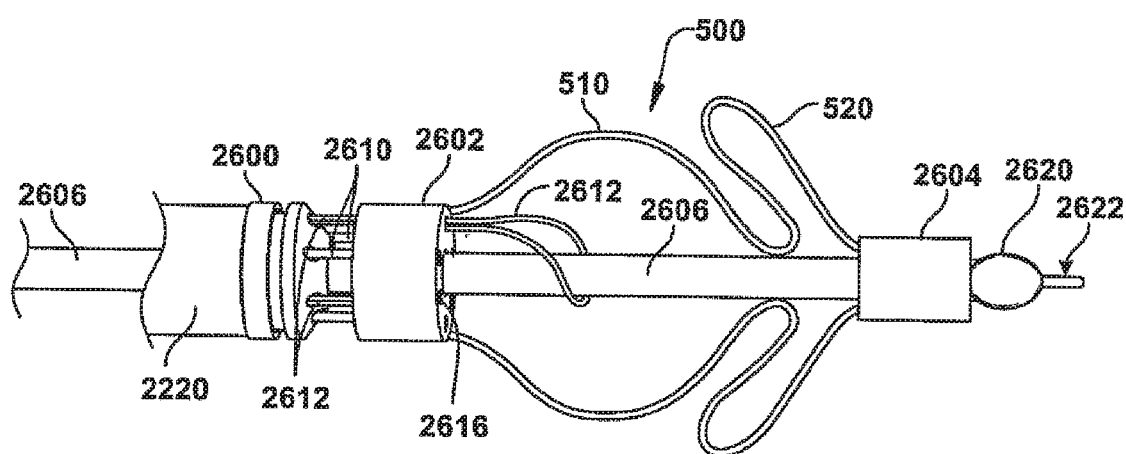
Figure 168:
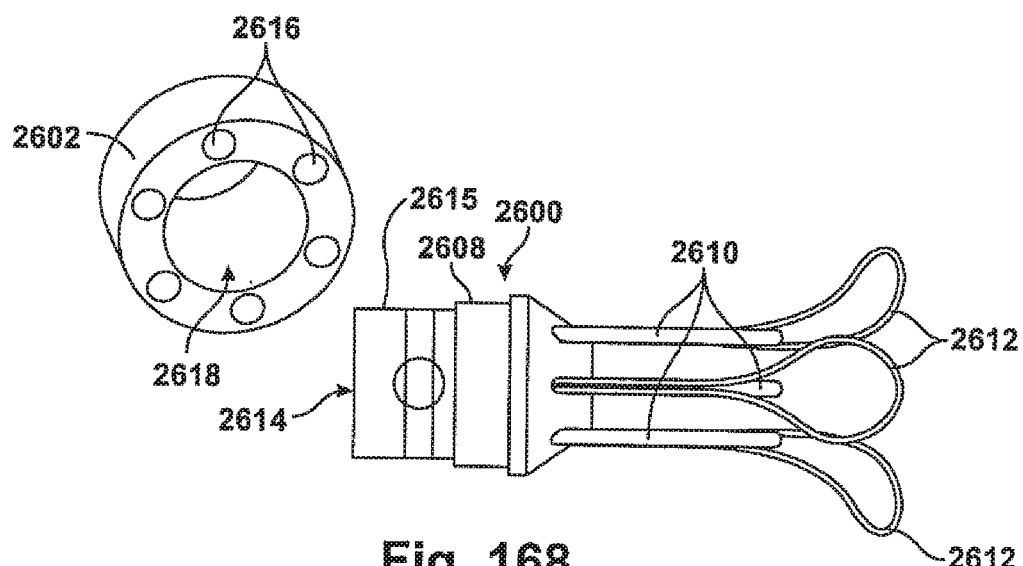
Figure 169:
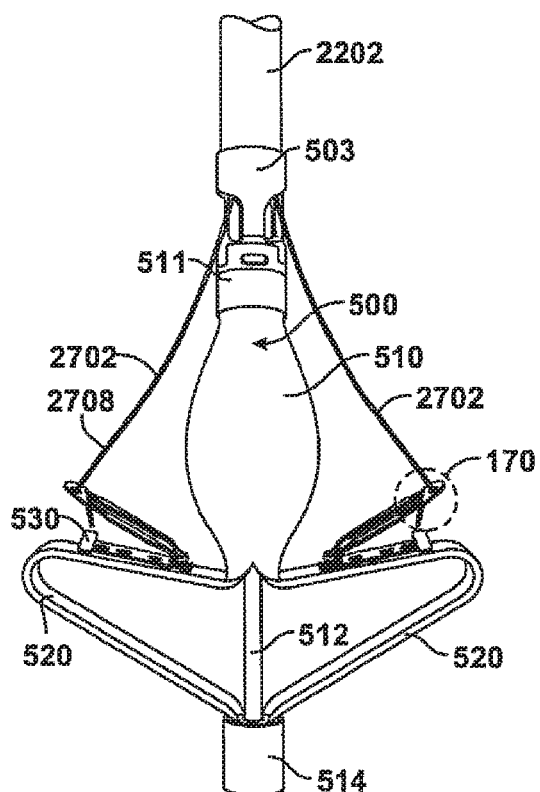
Figure 170:
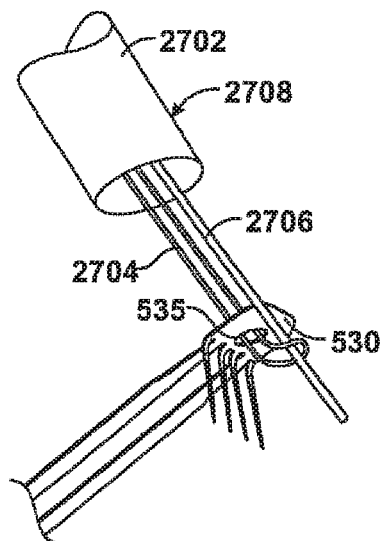
Figure 171:
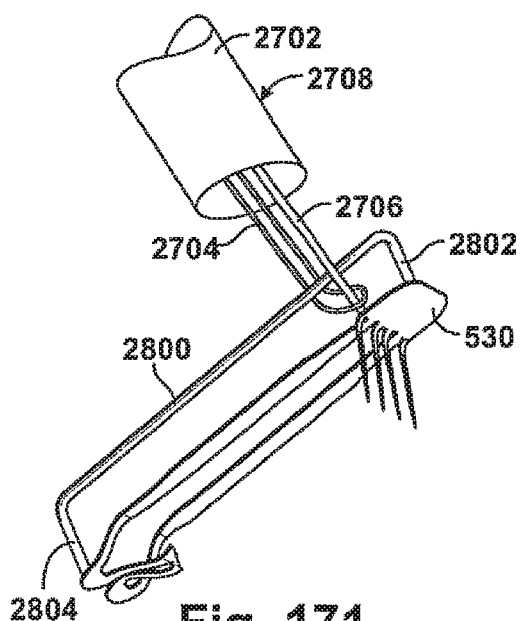
Figure 172:
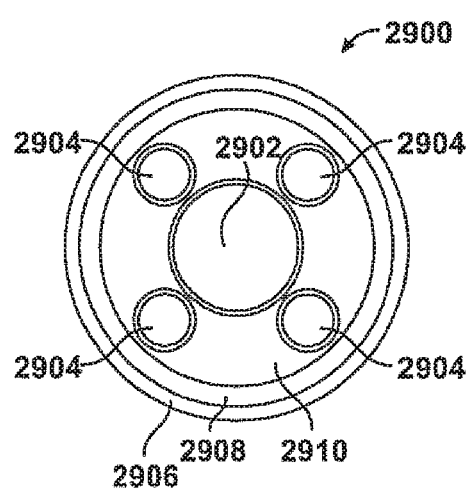
Figure 173:
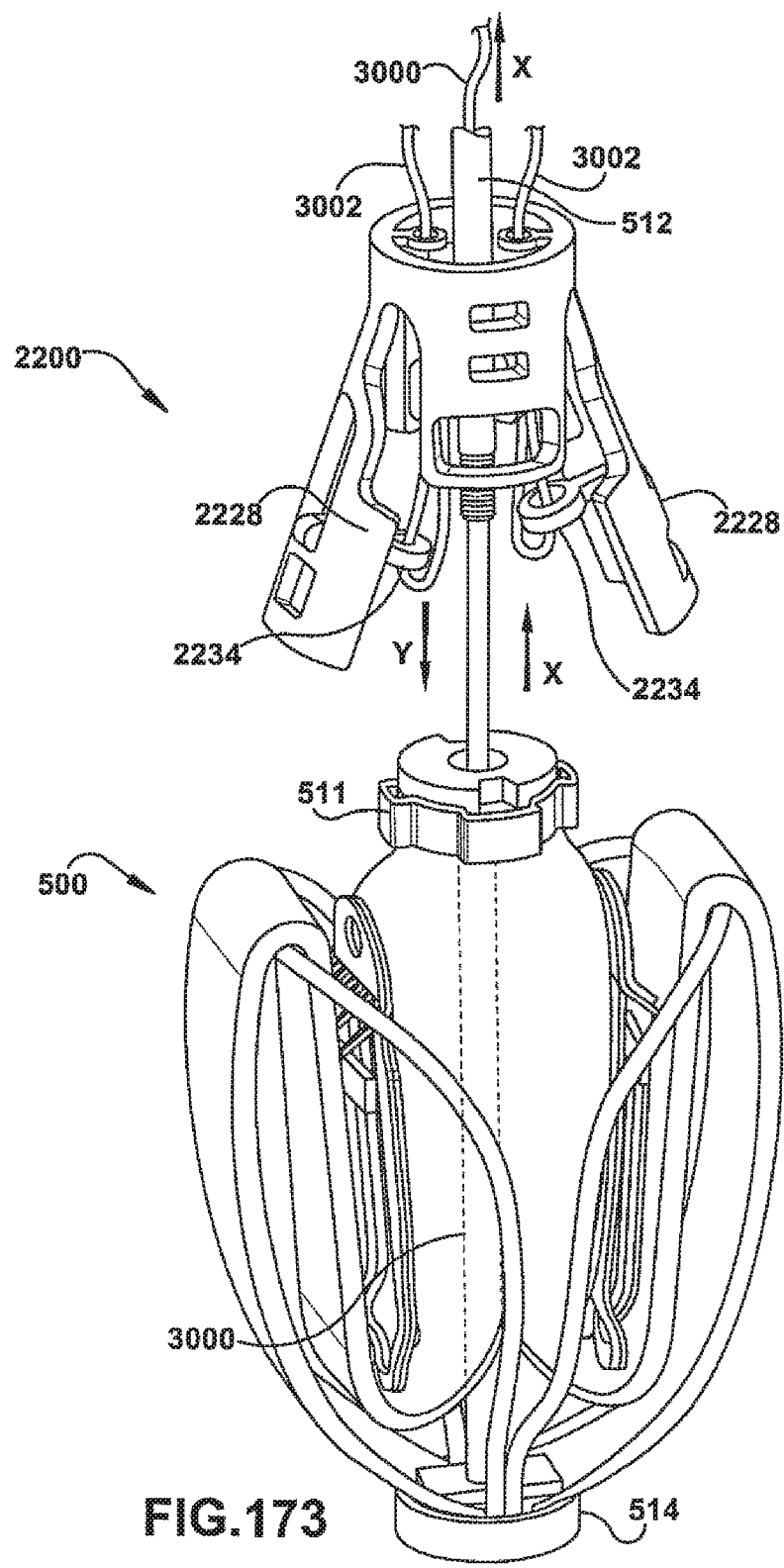
Figure 174:
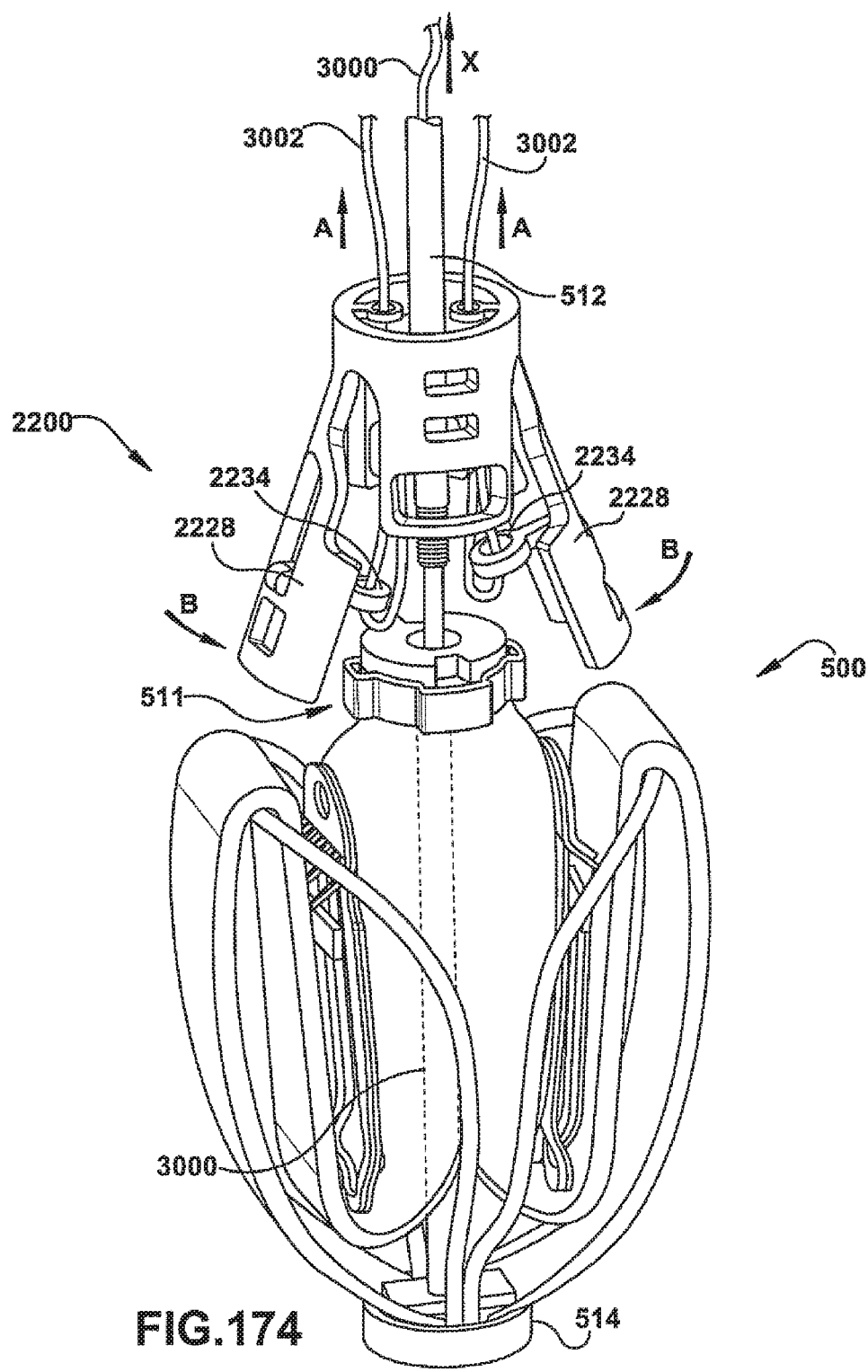
Figure 174A:
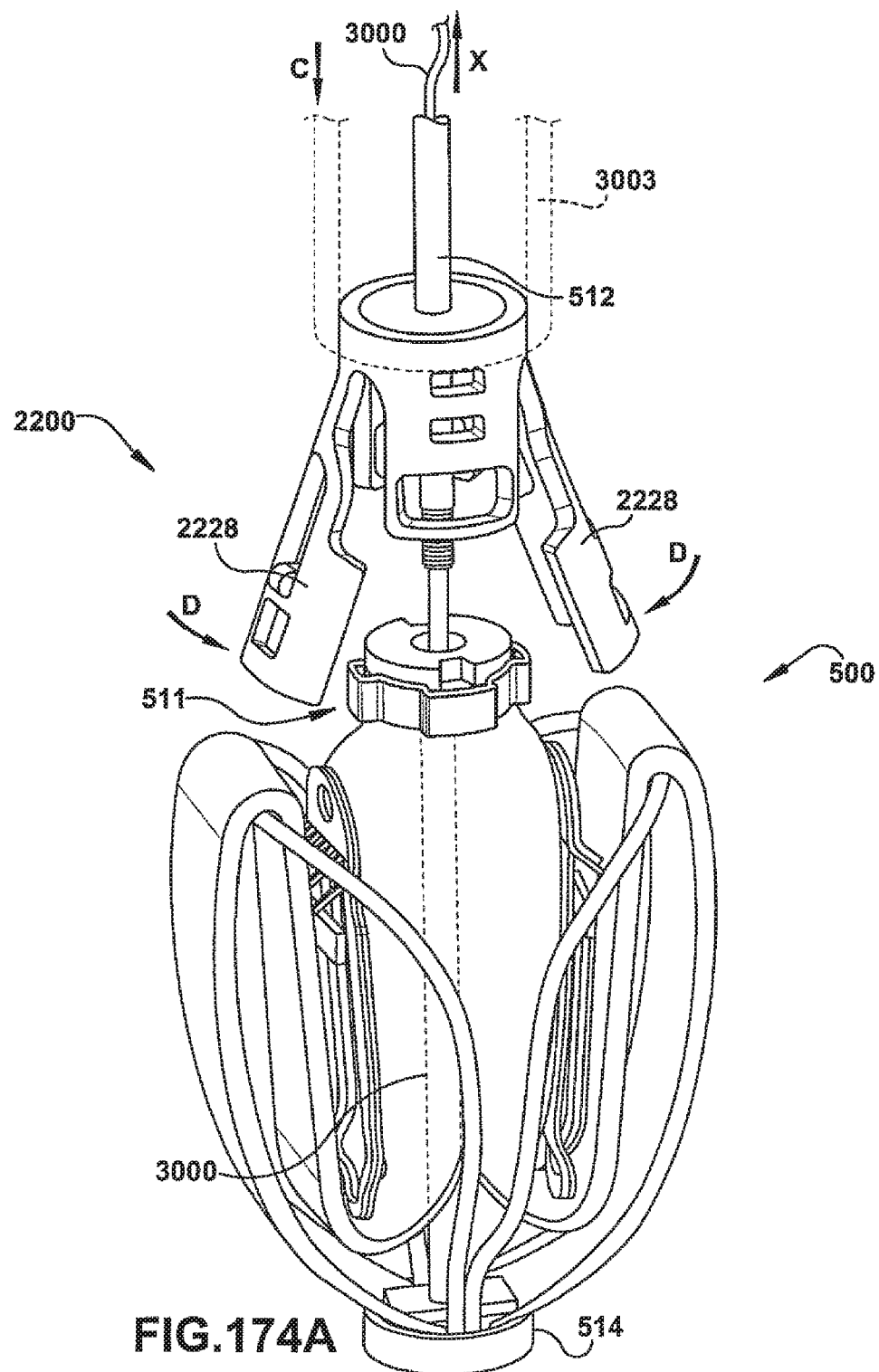
Figure 175:
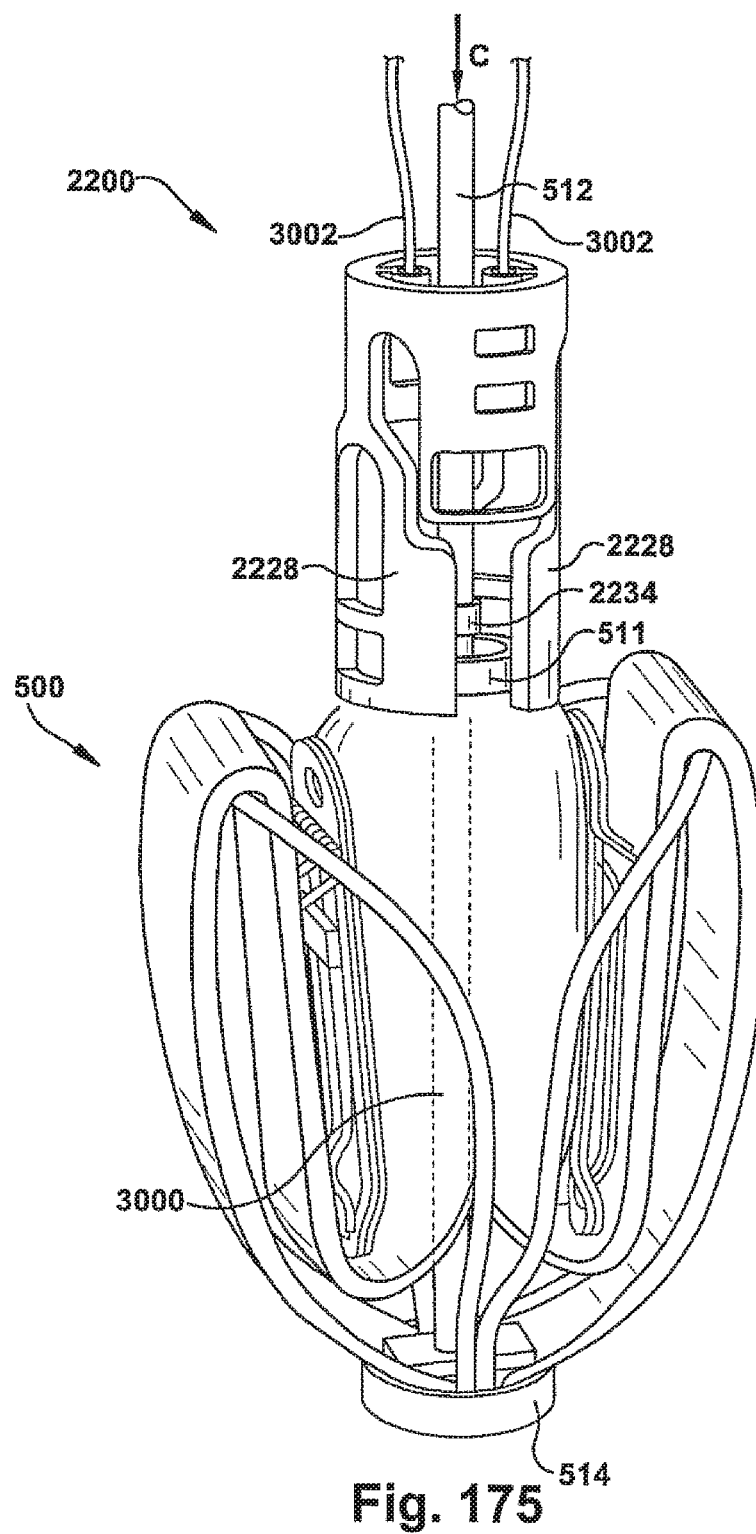
Figure 175A:
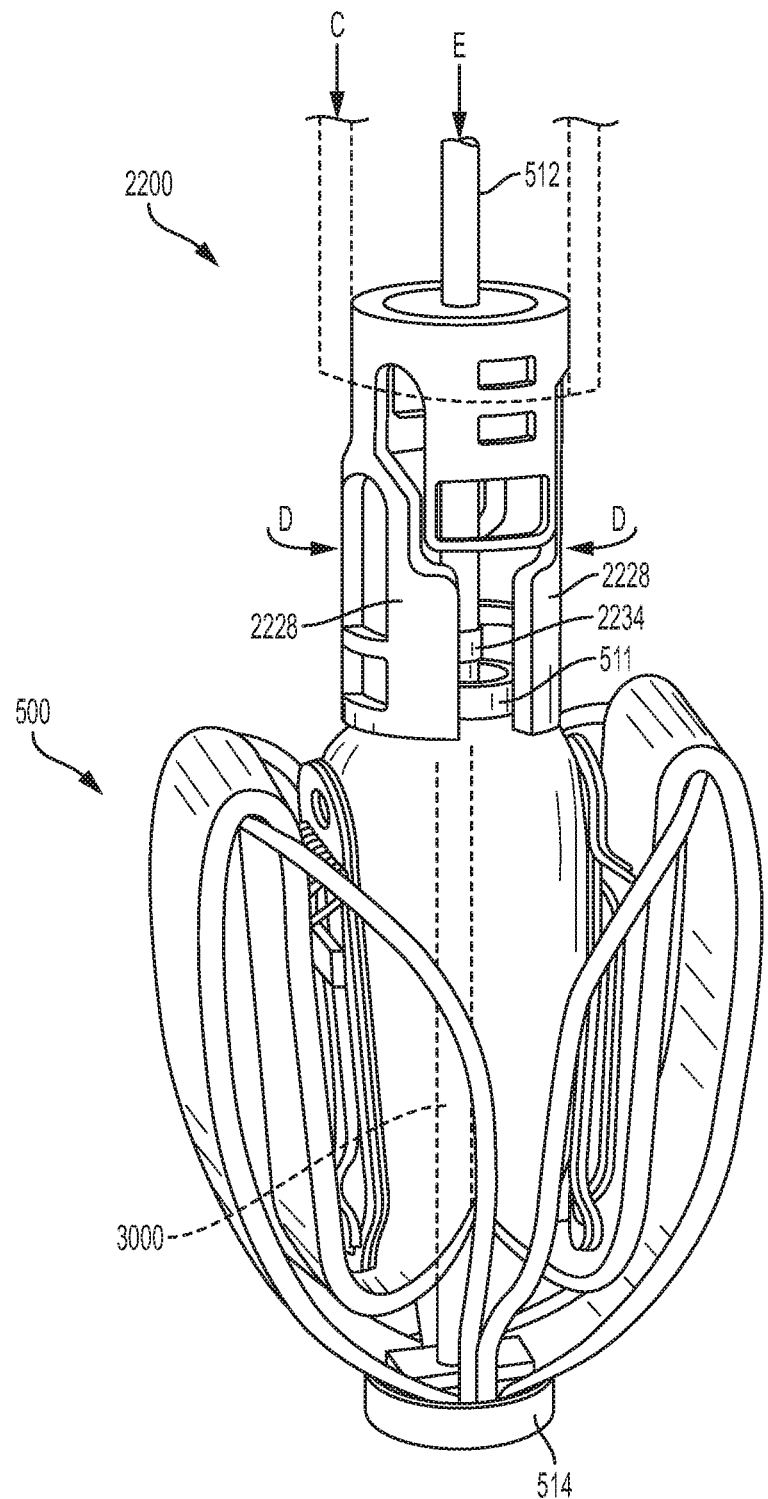
Figure 176:
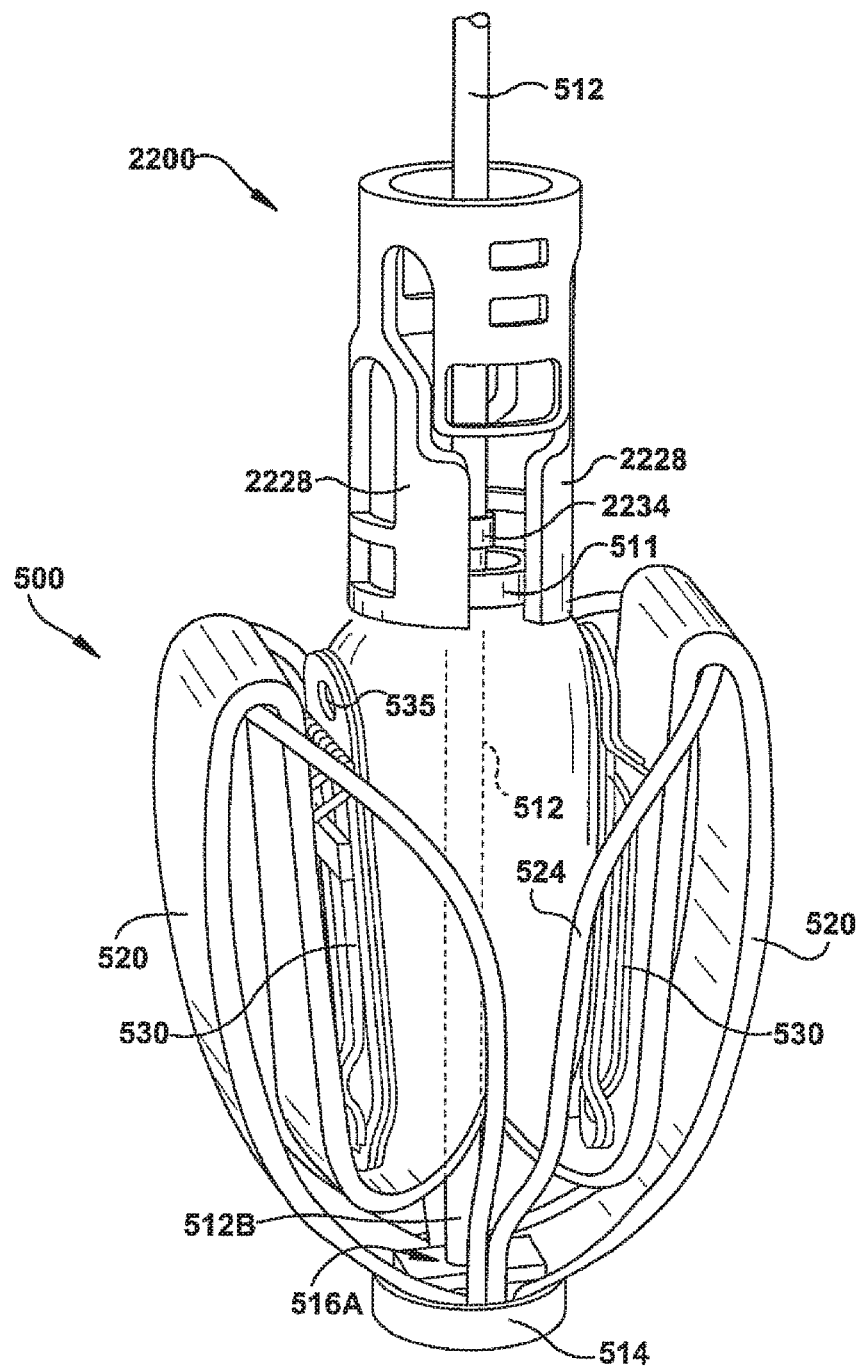
Figure 177:
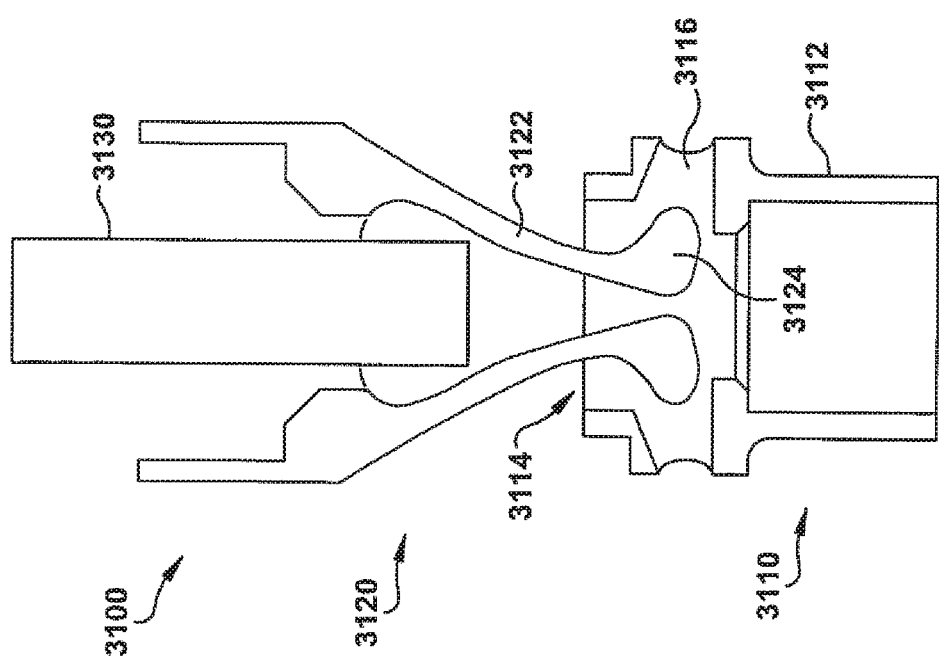
Figure 178:
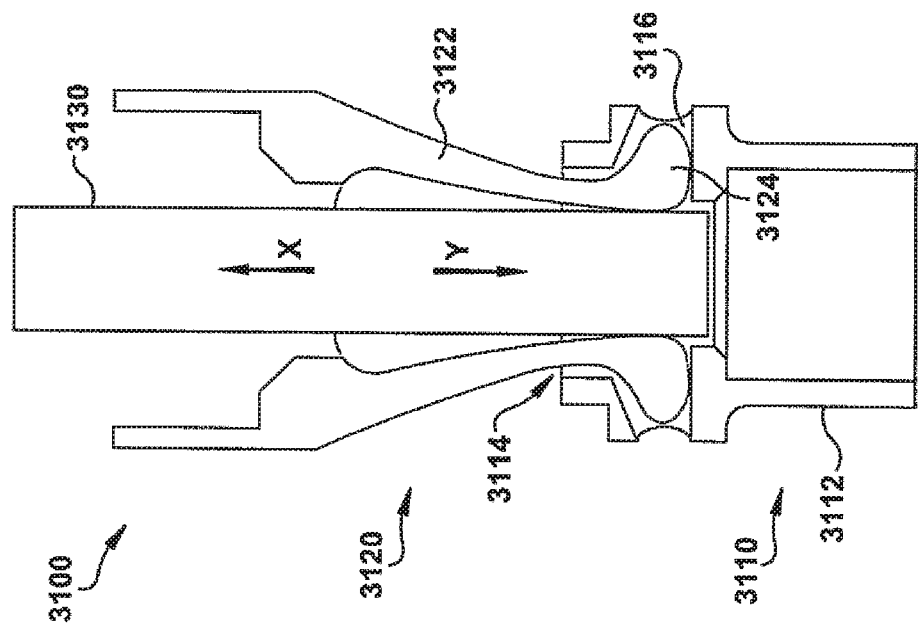
Figure 179:
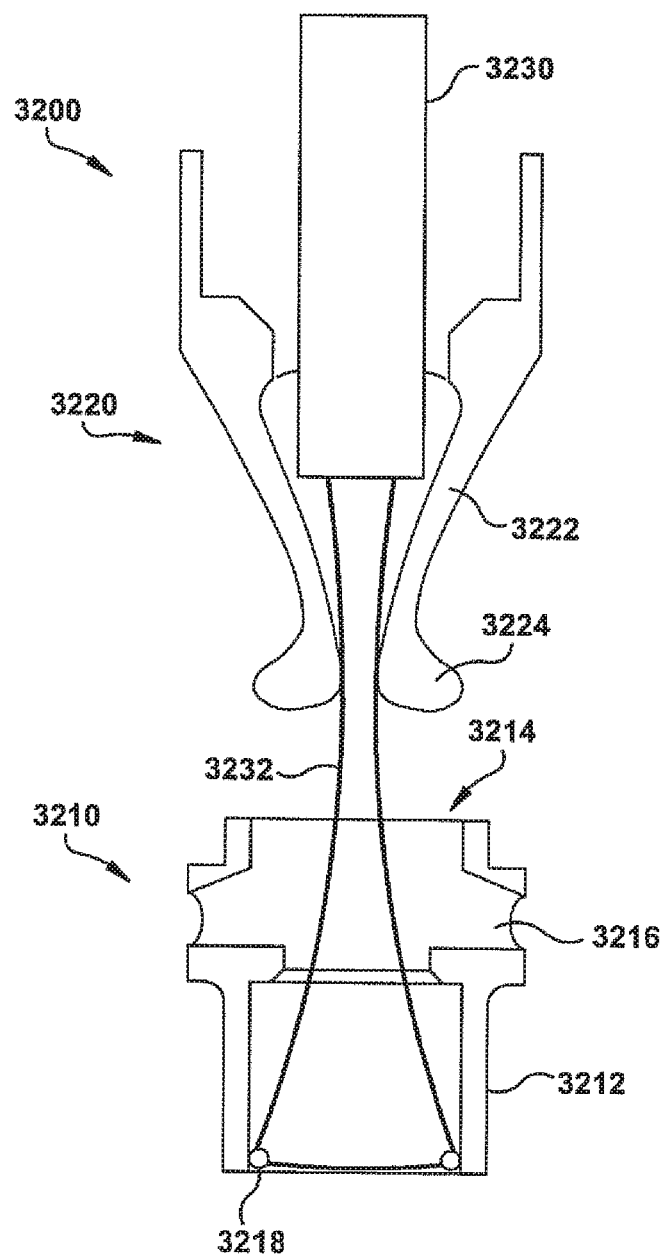
Figure 180:
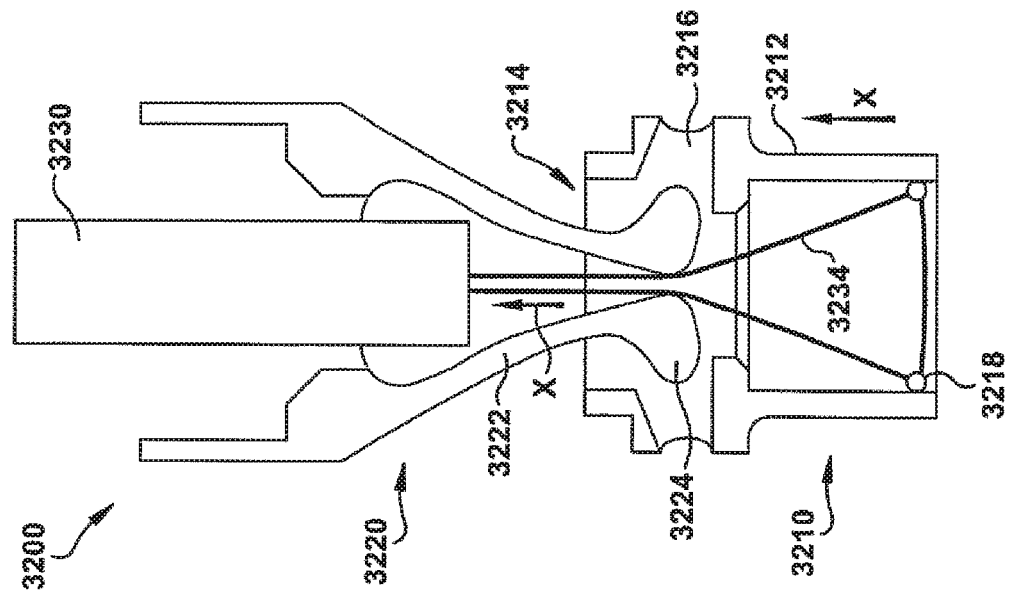
Figure 181:
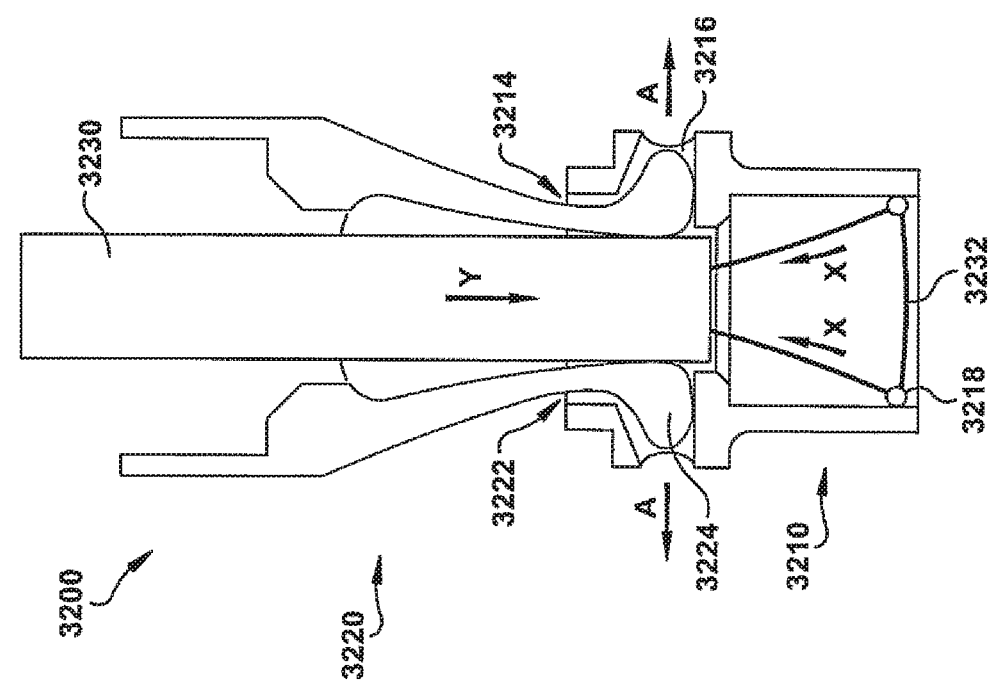
Figure 186:
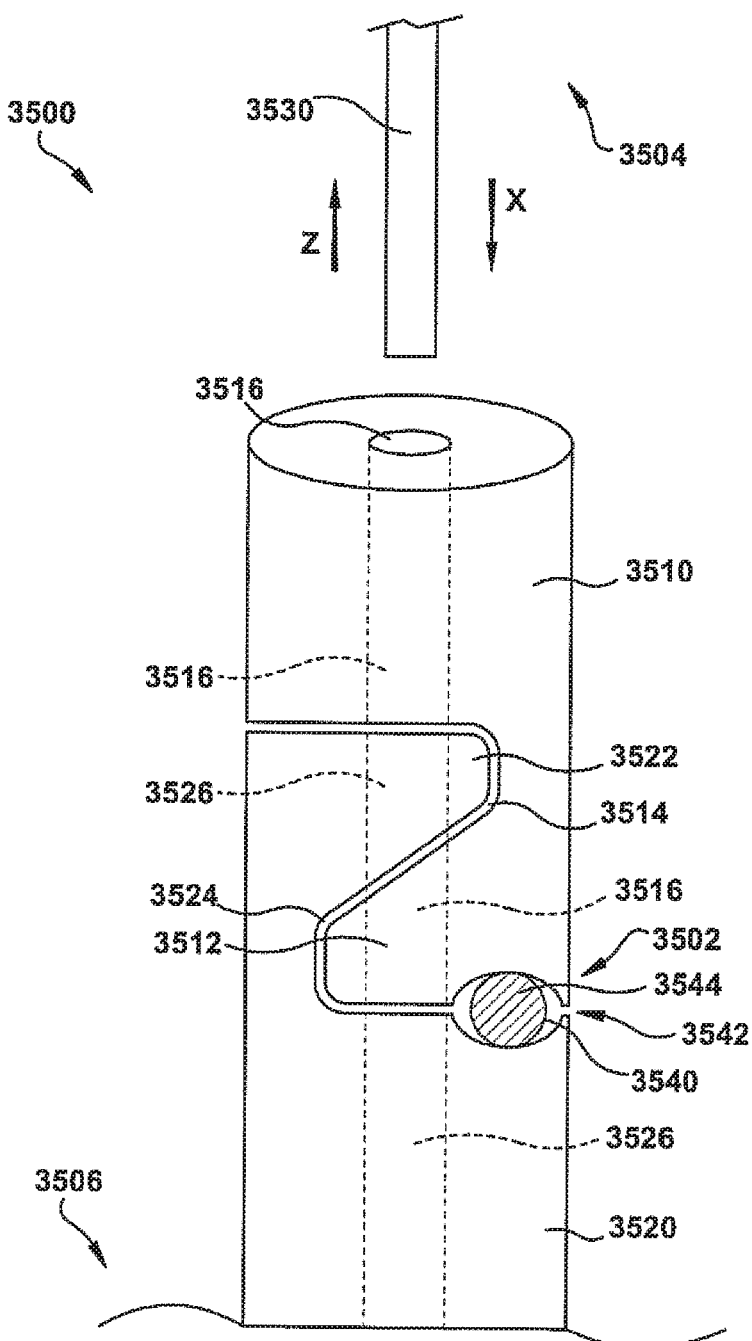
Figure 187:
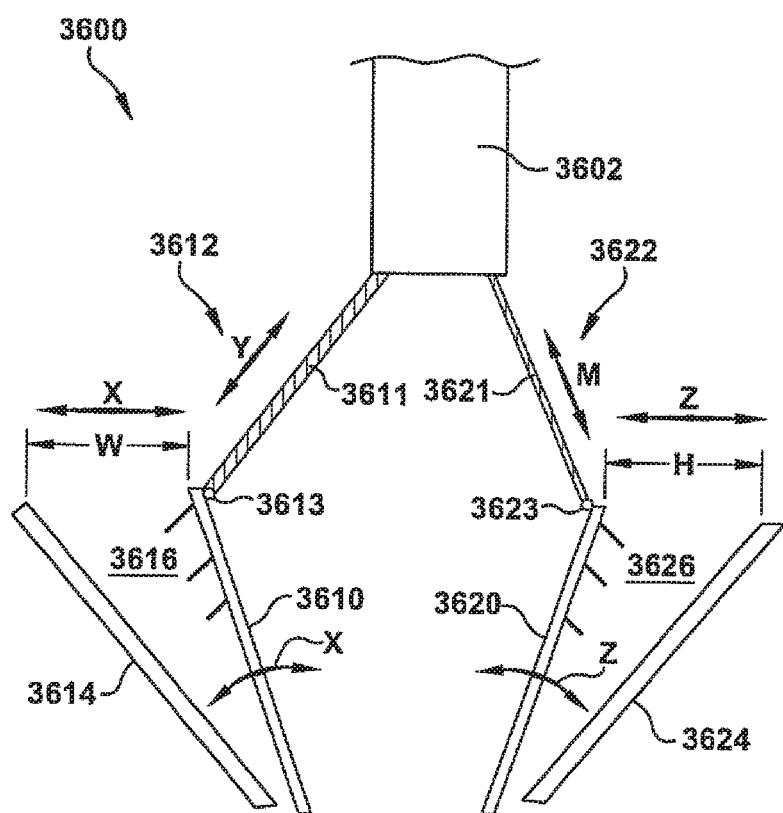
Figure 188:
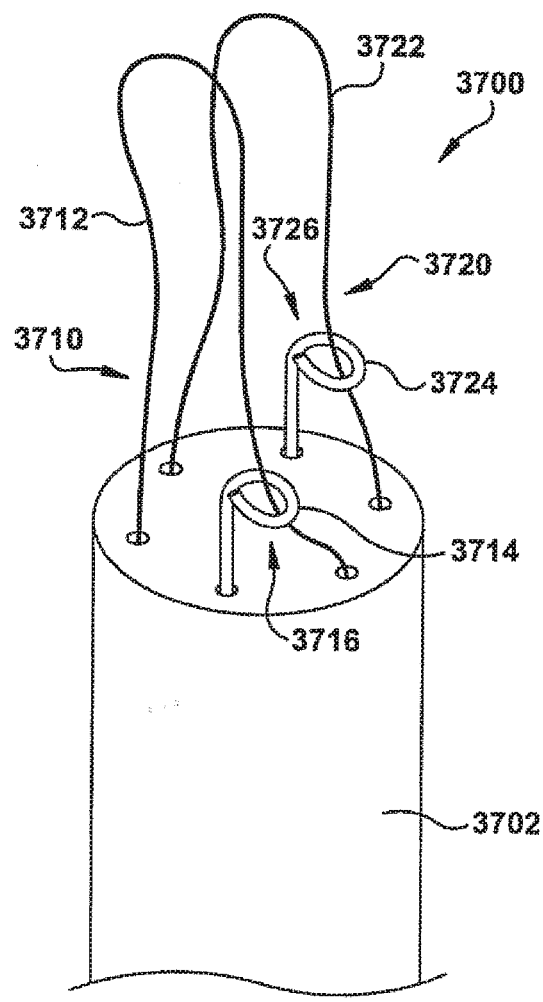
Figure 188A:
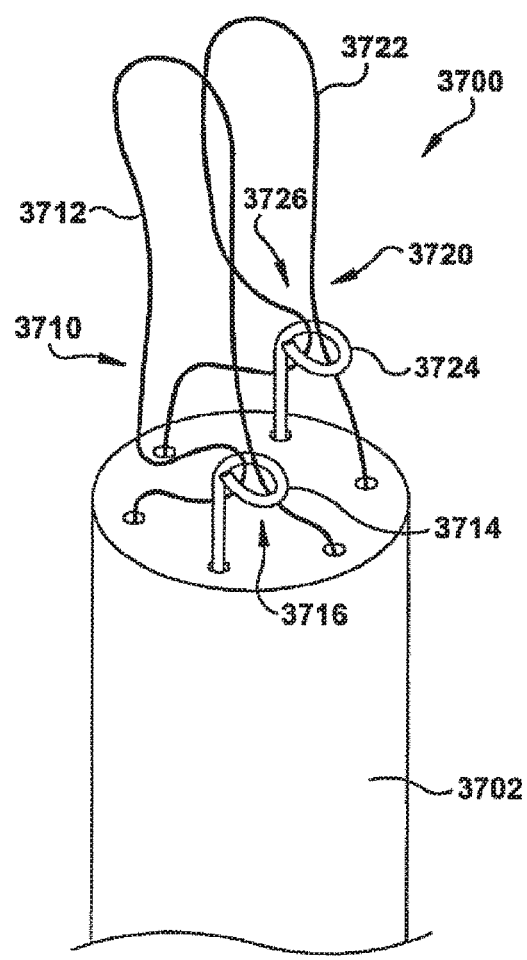
Figure 189:
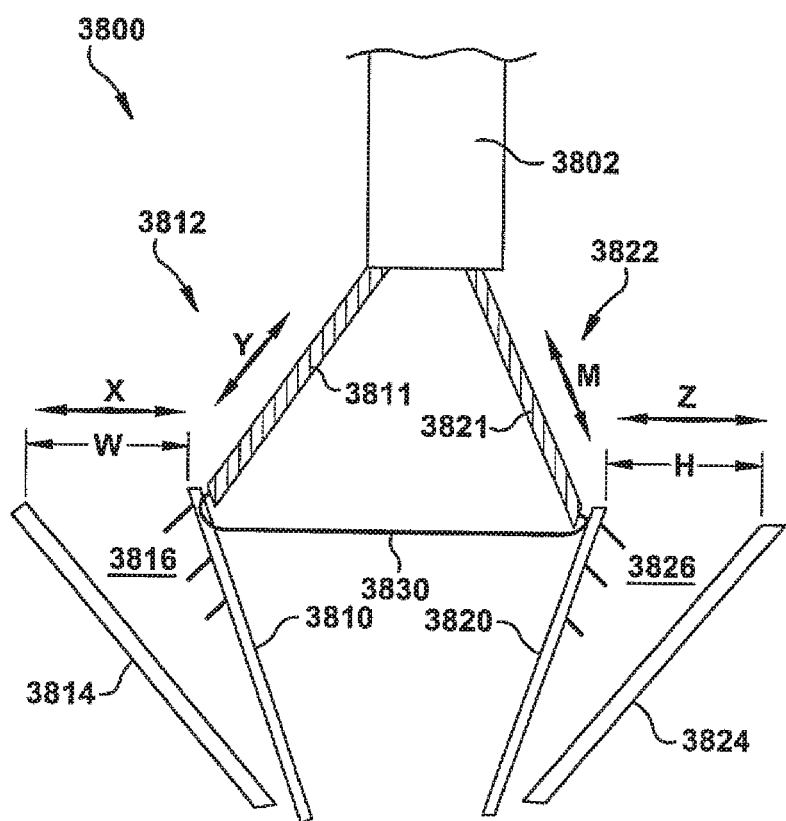
Figure 190:
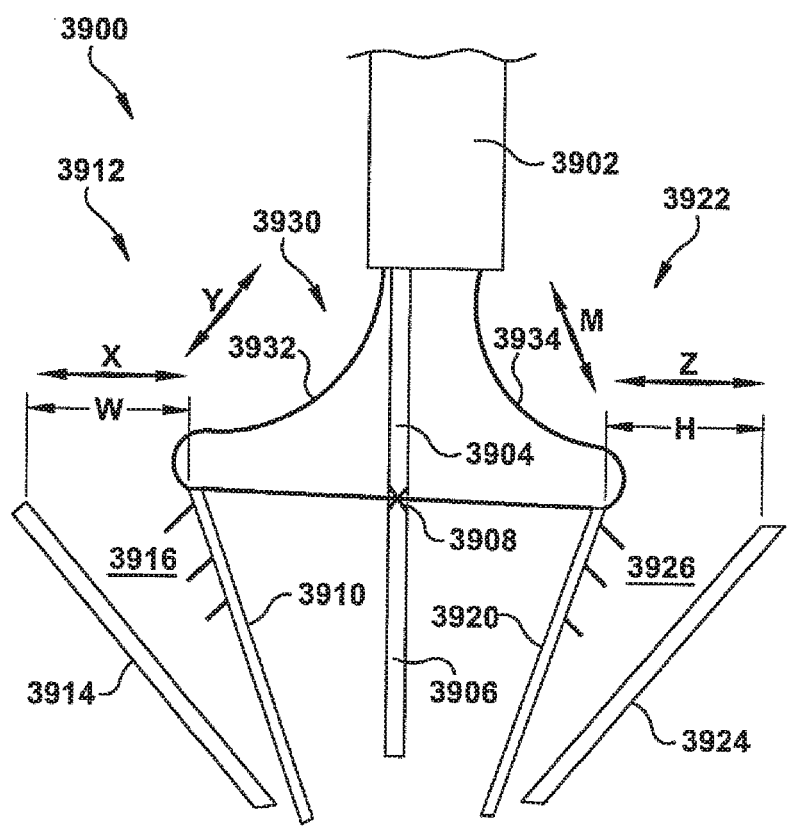
Figure 193:
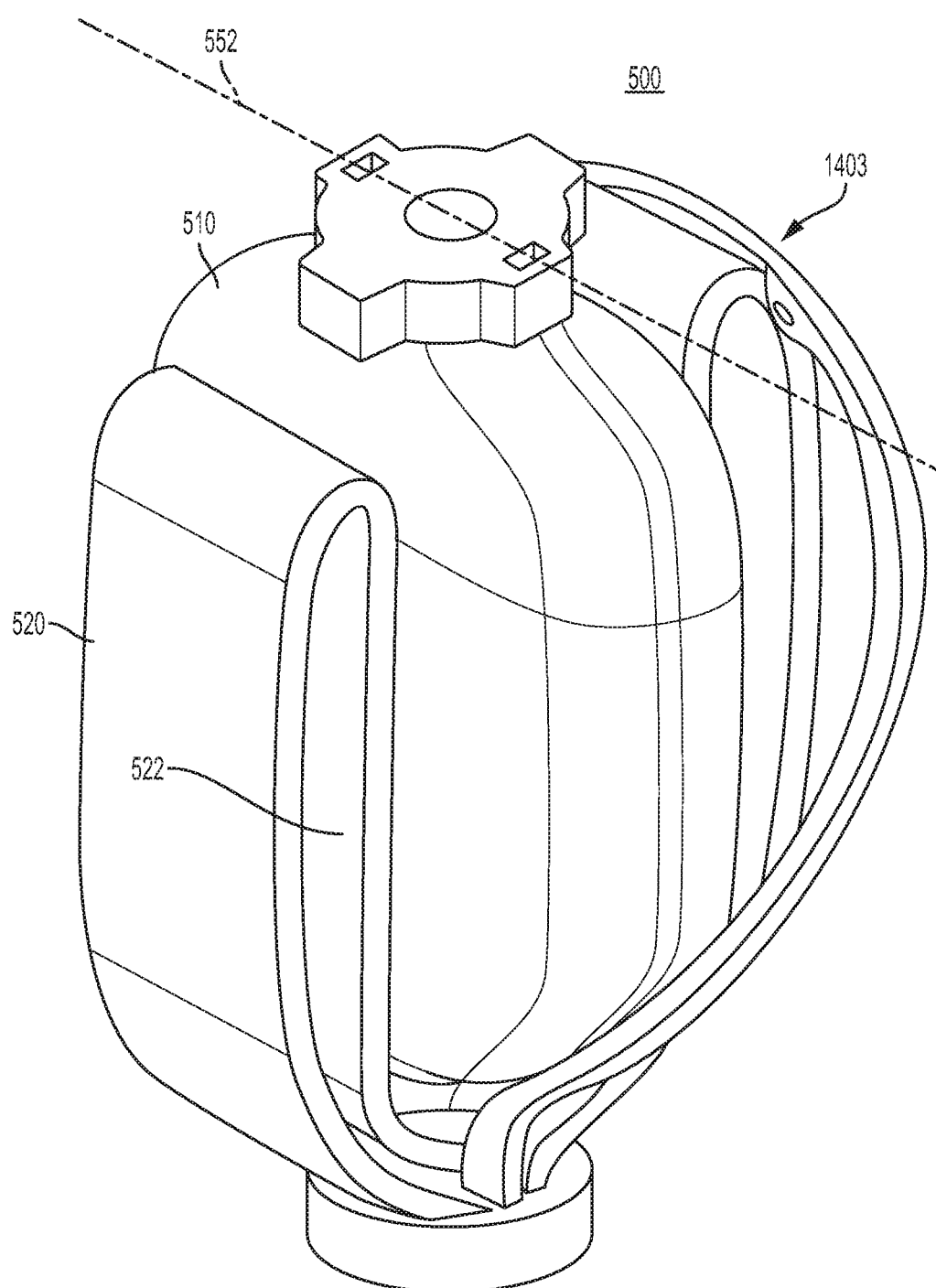
Figure 194:
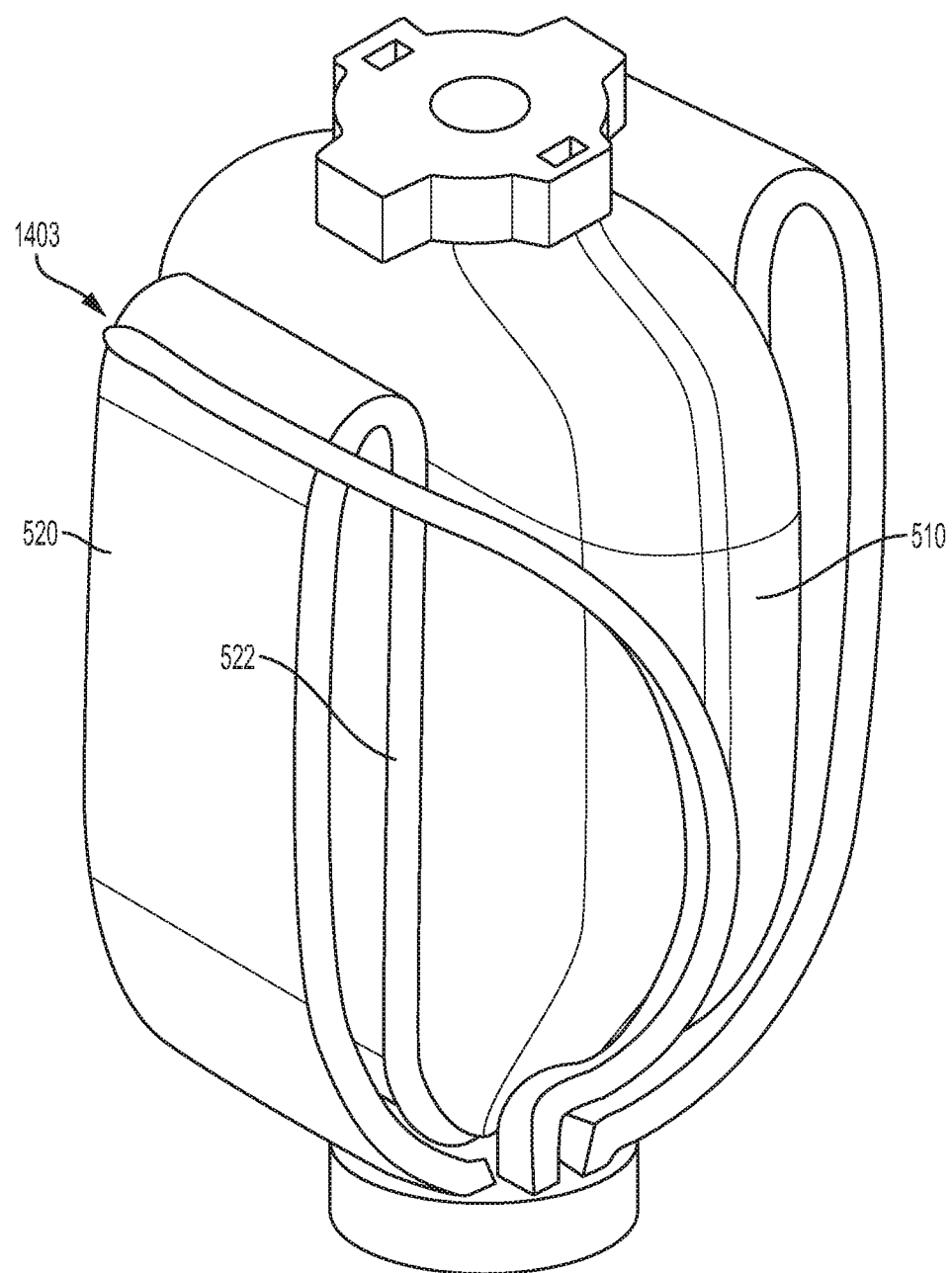
Figure 195:
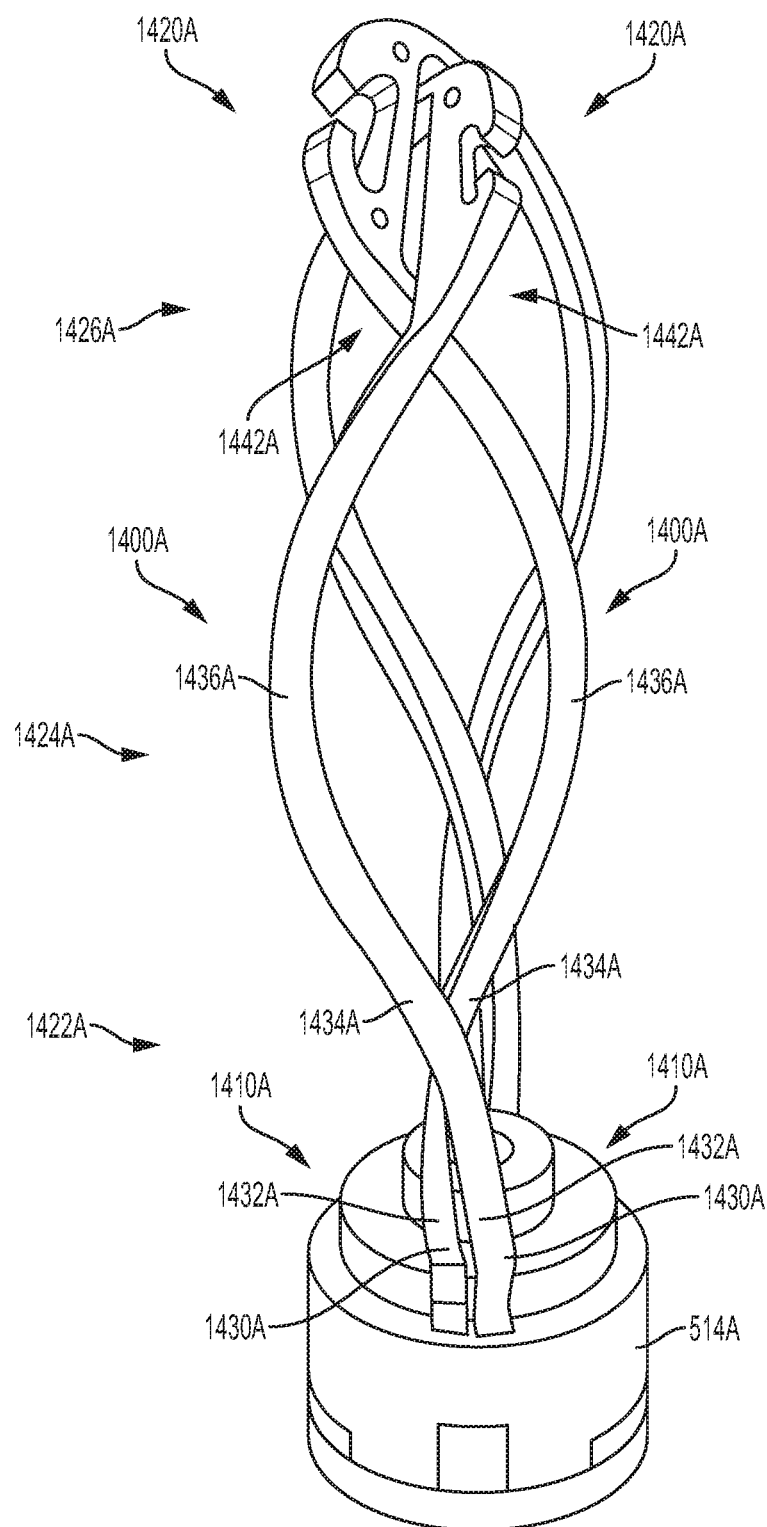
Figure 196:
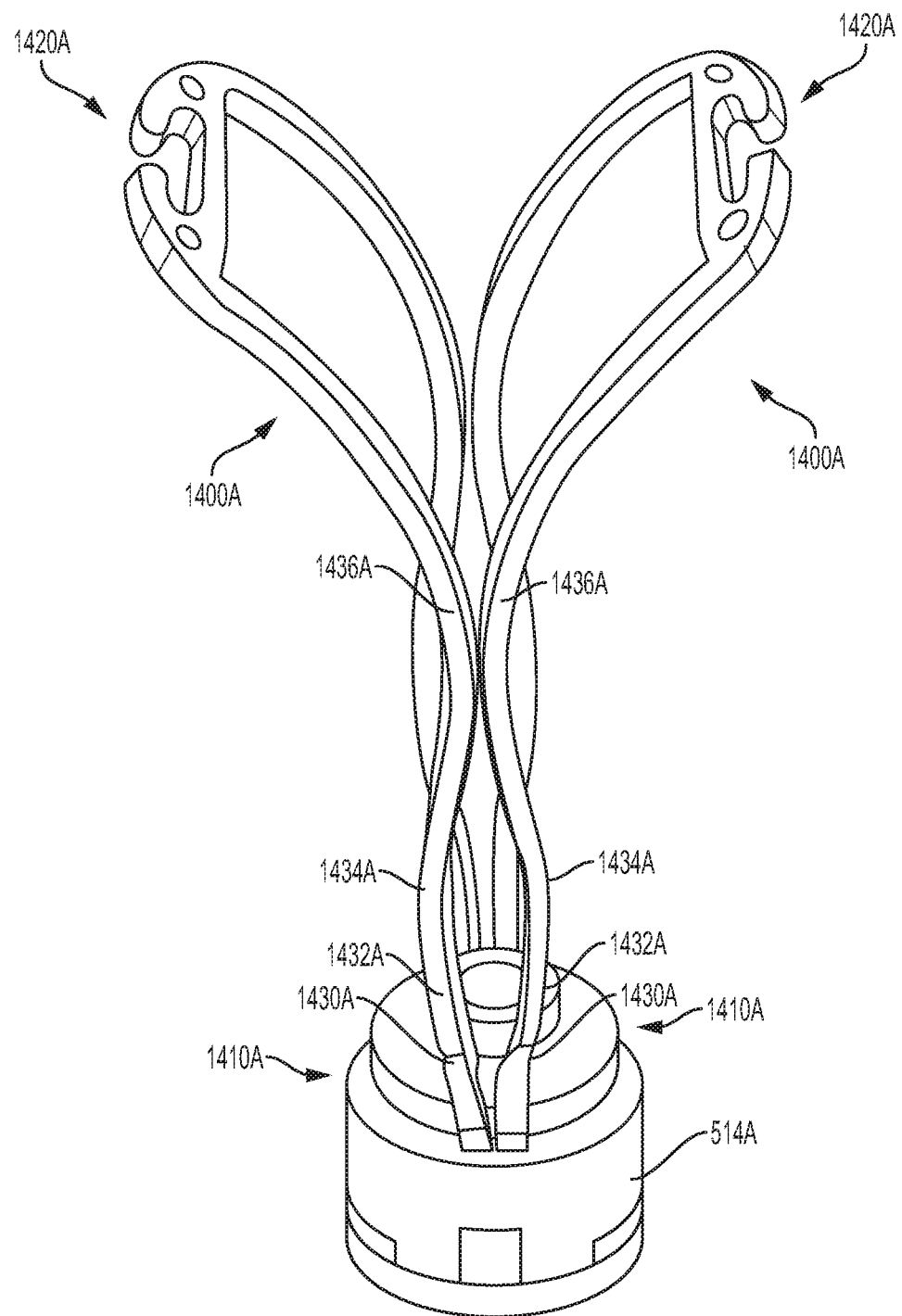
Figure 197:
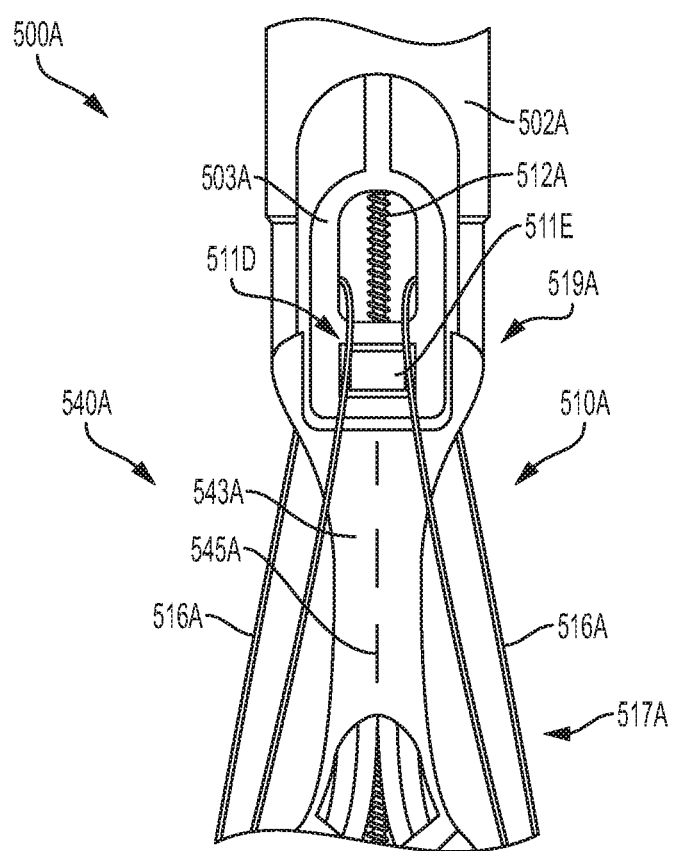
Figure 198:
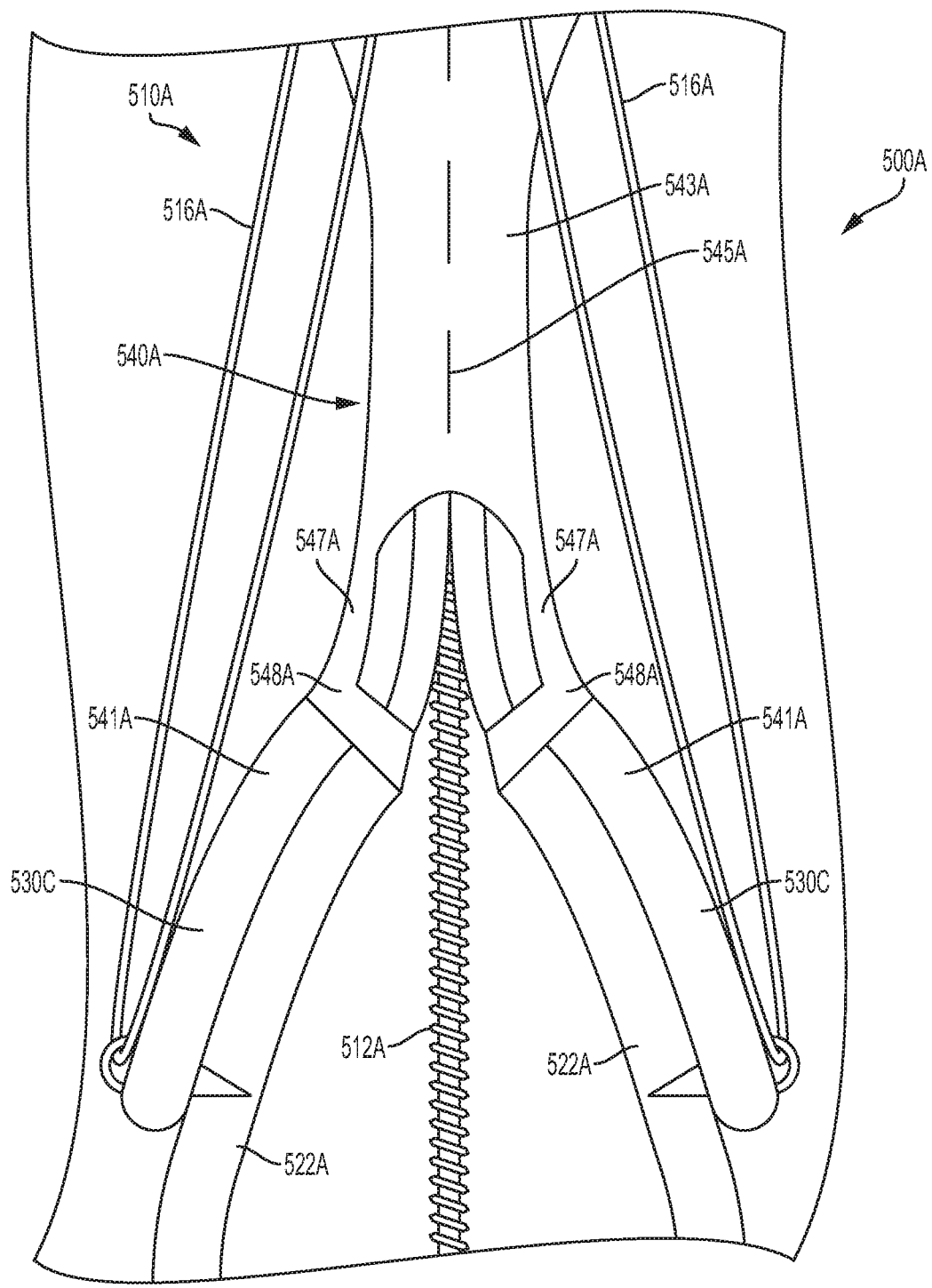
Figure 199:
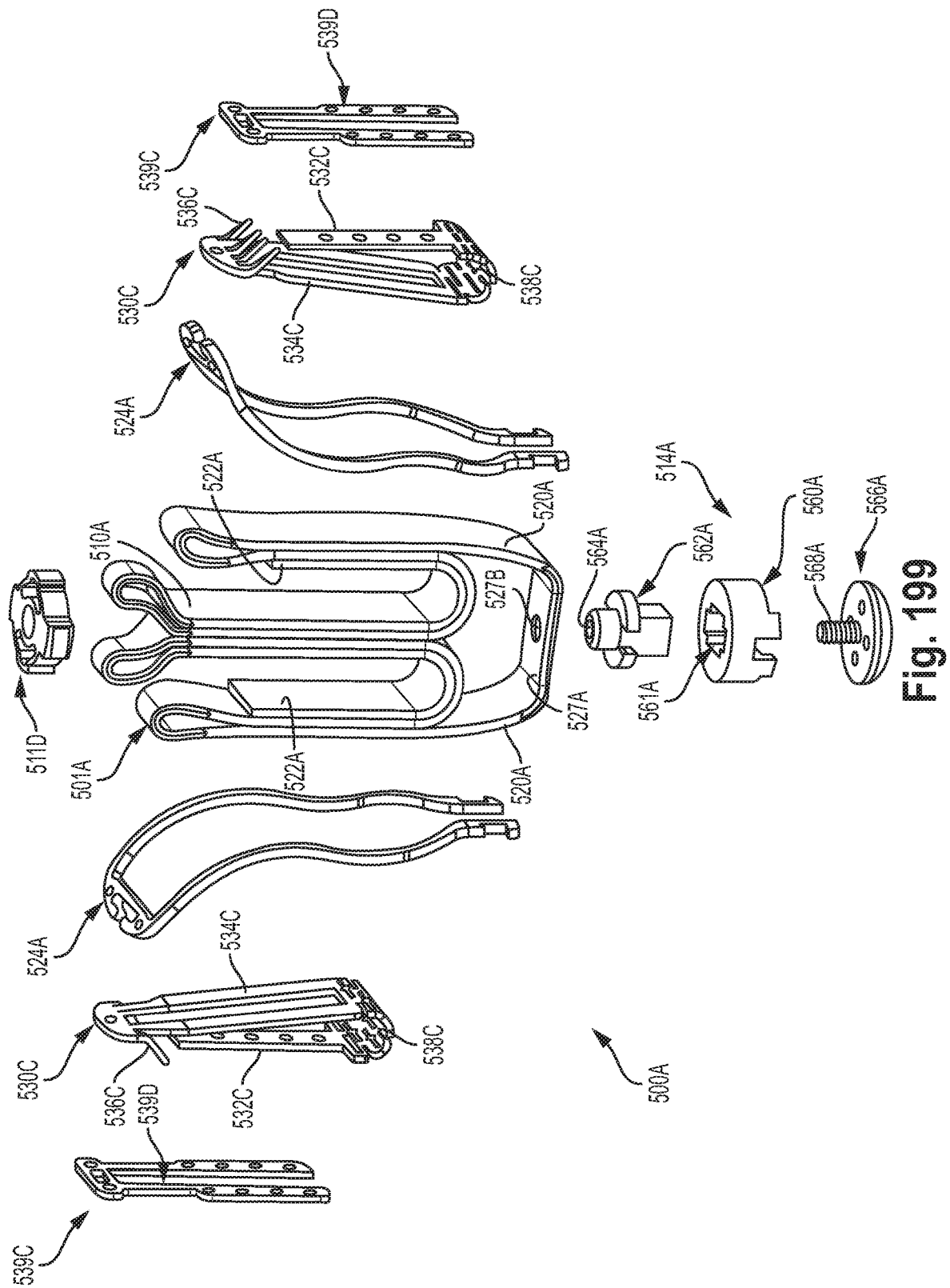
Figure 200:
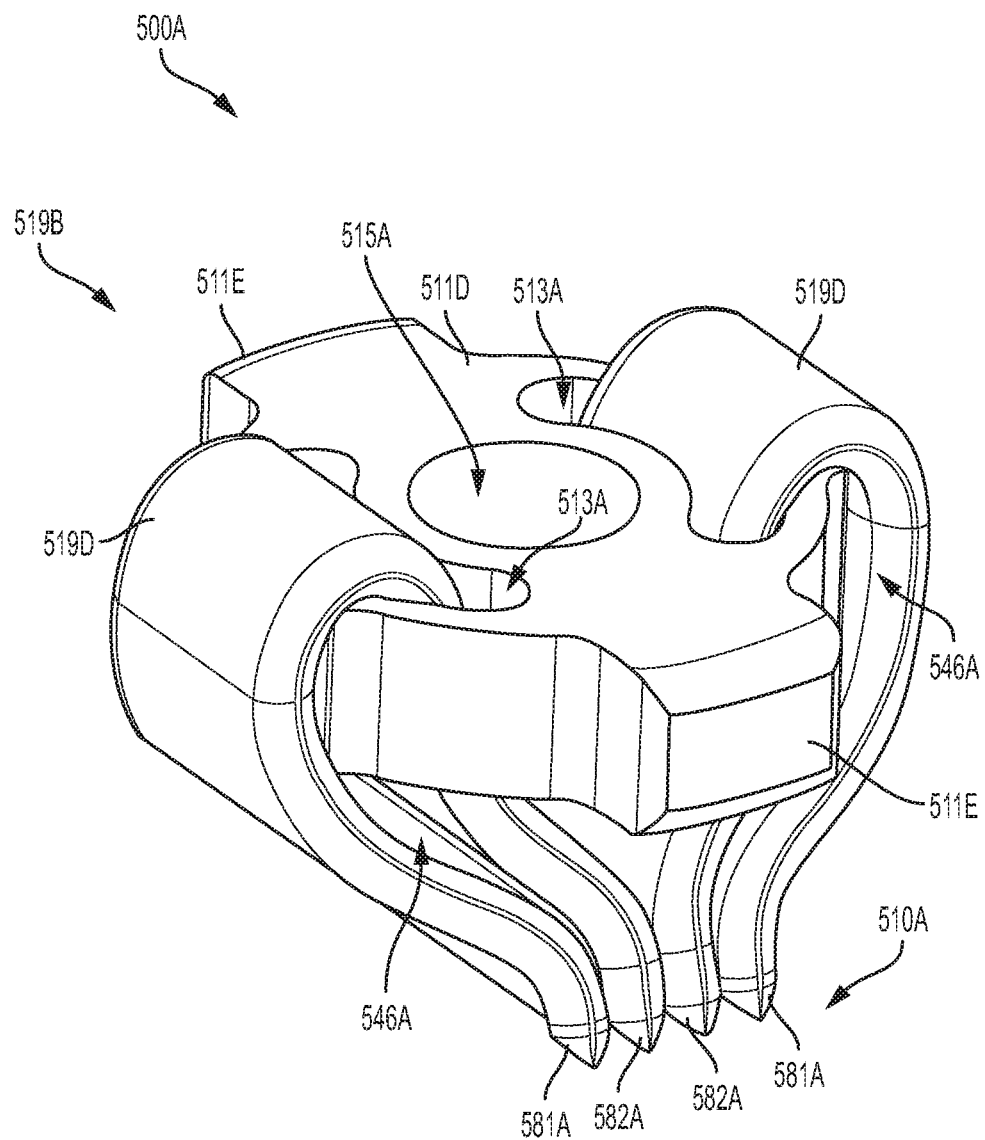
Figure 201:
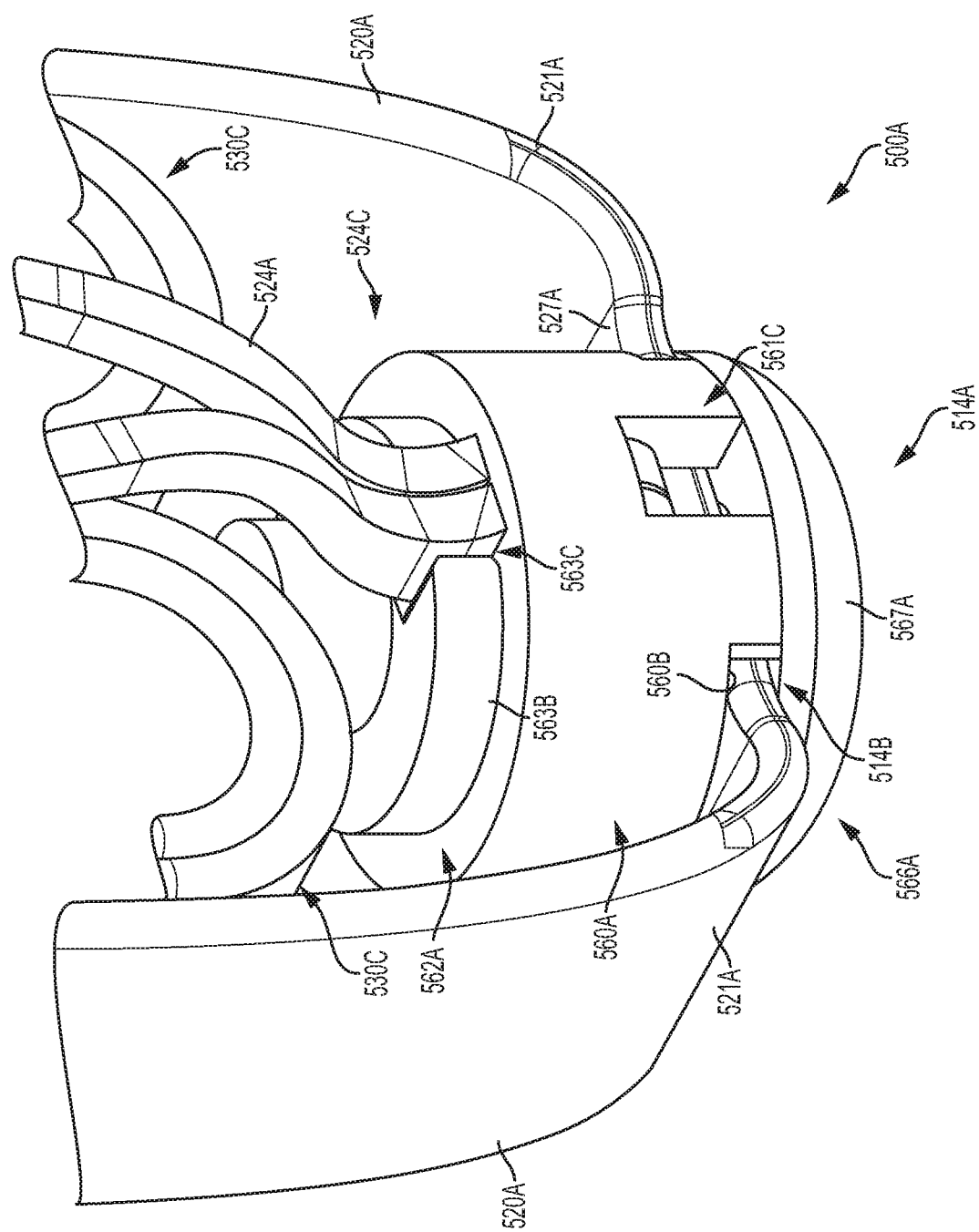
Figure 202:
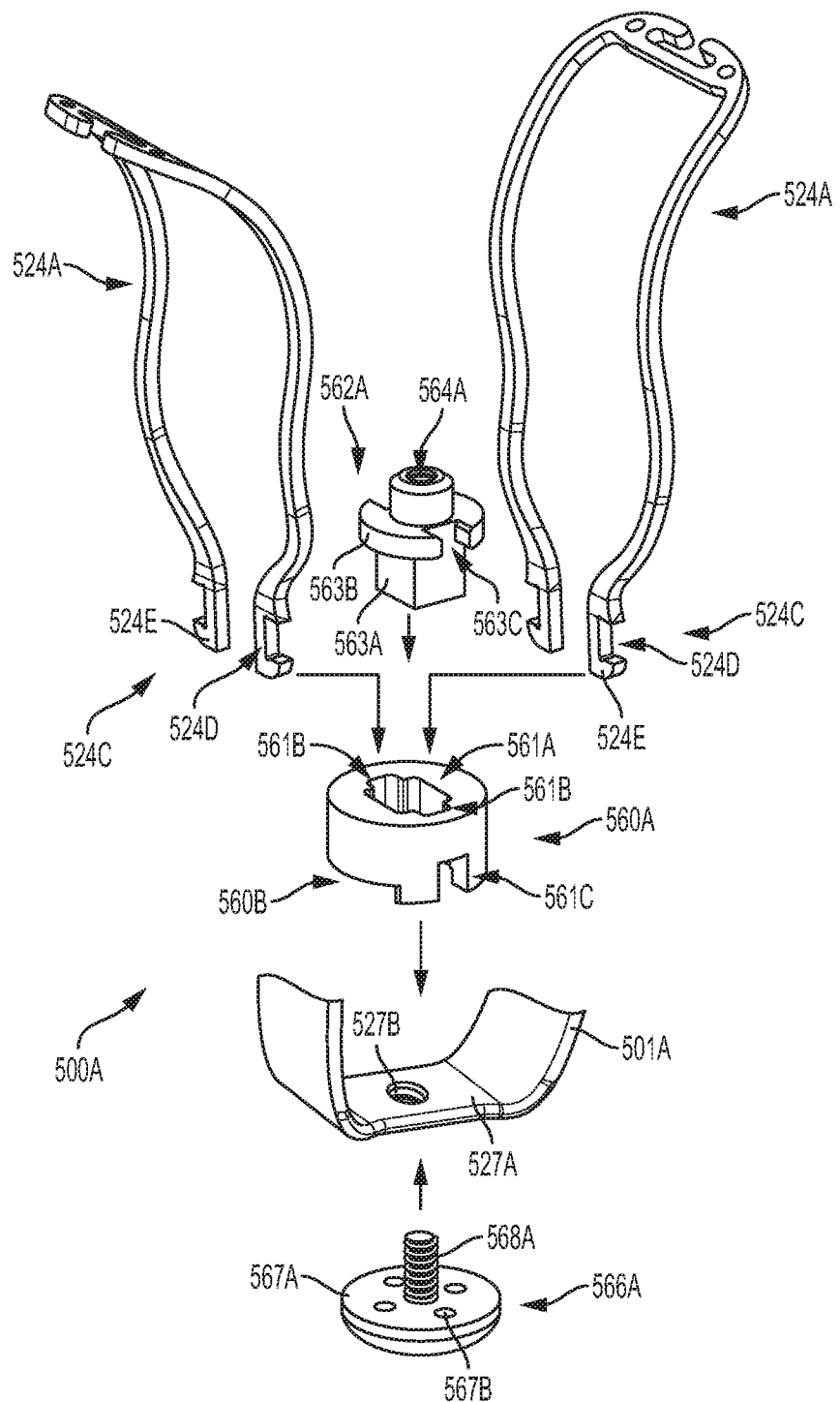
Figure 203:
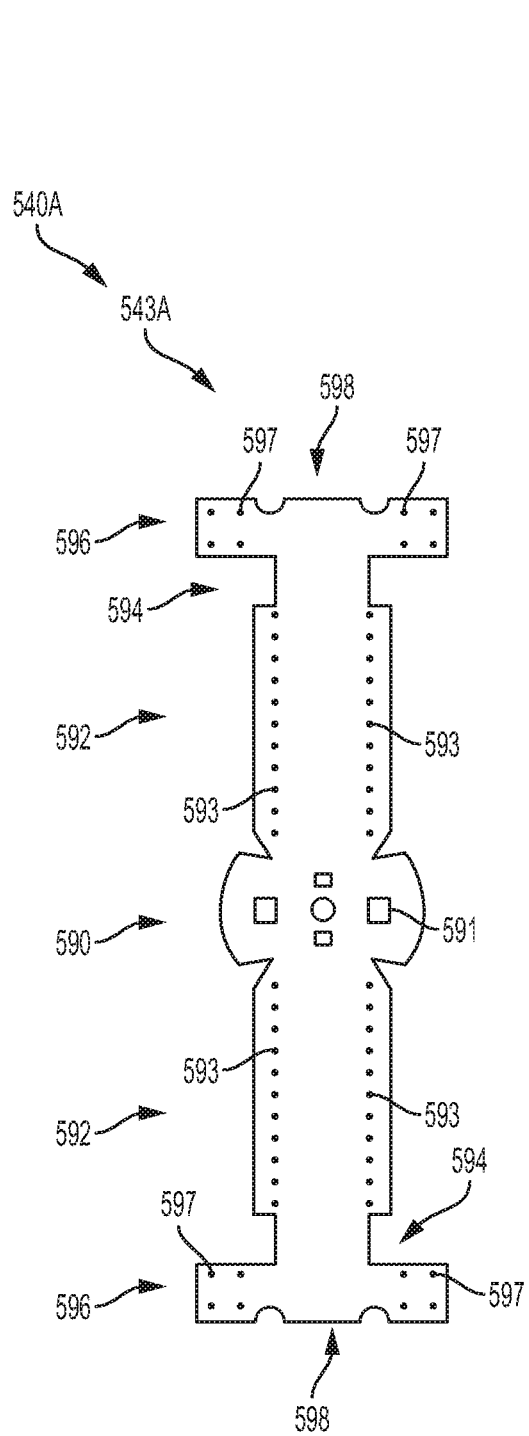
Figure 204:
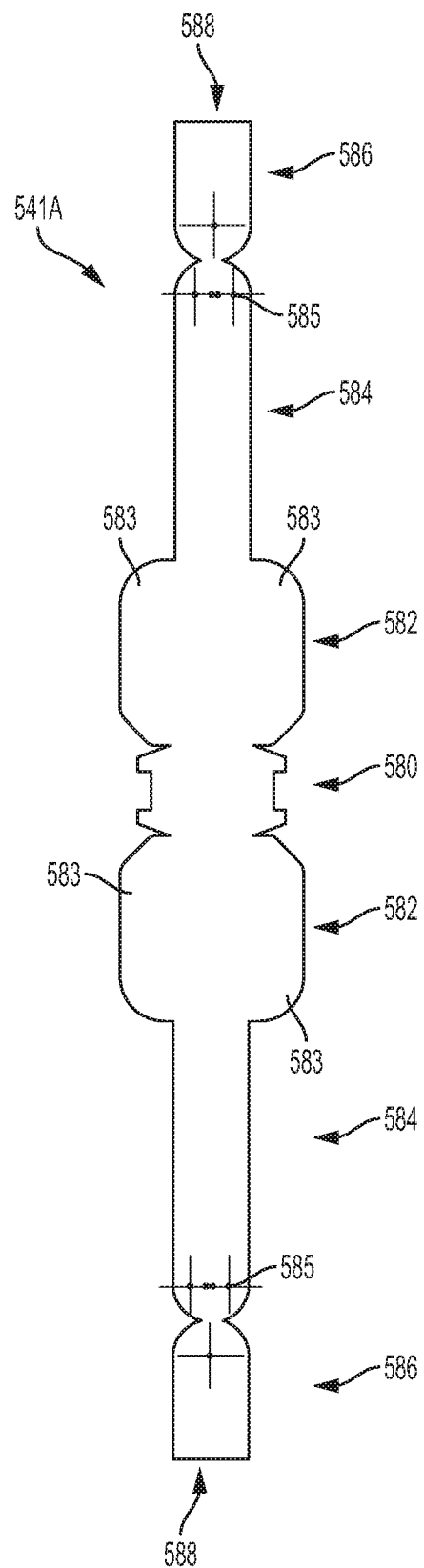
Figure 206:
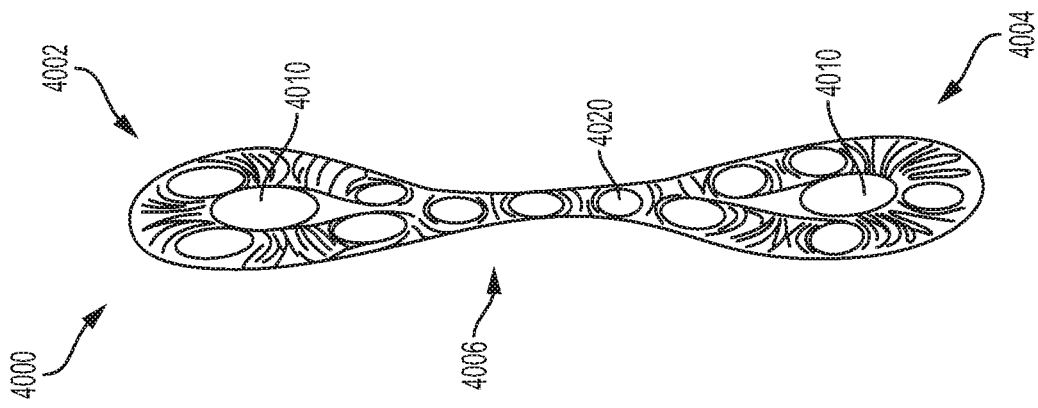
Figure 205:
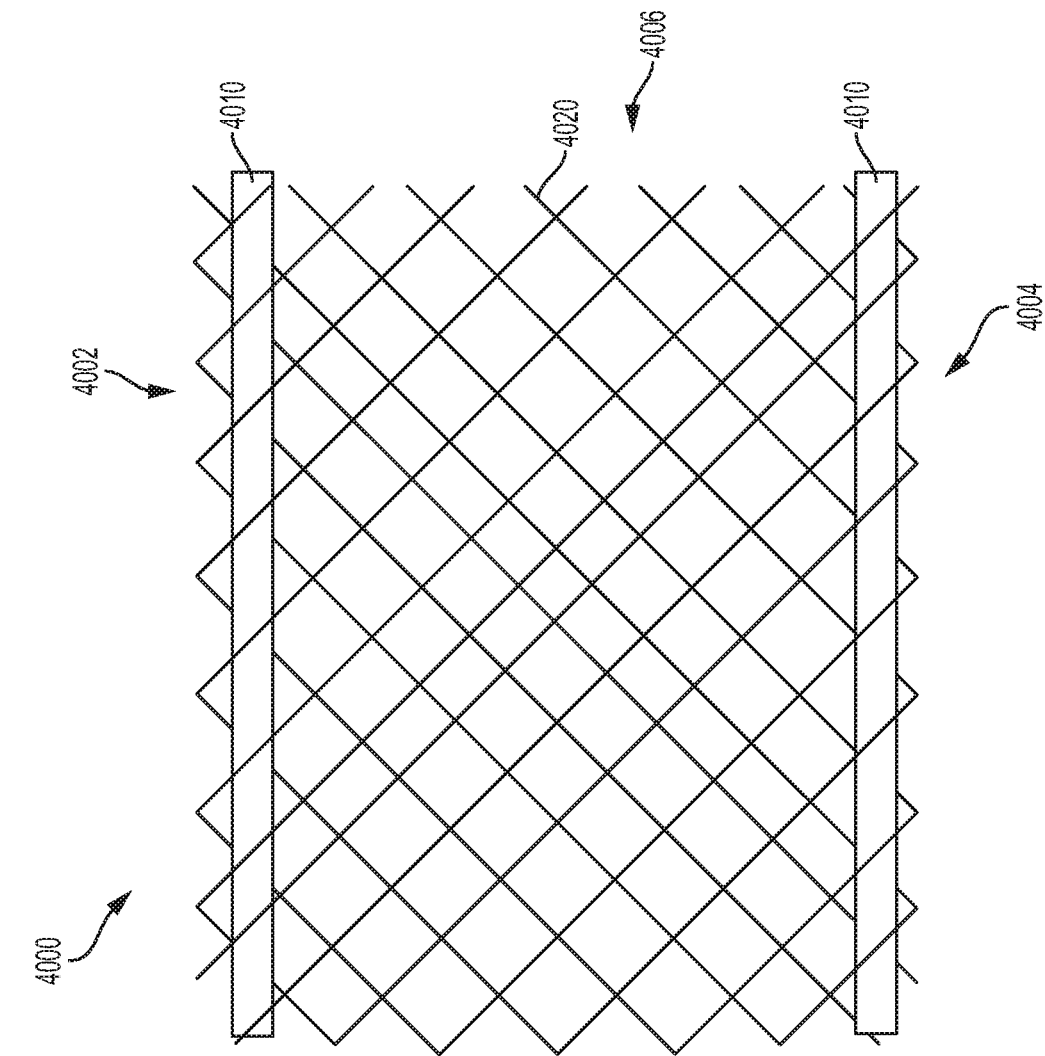
Figure 207:
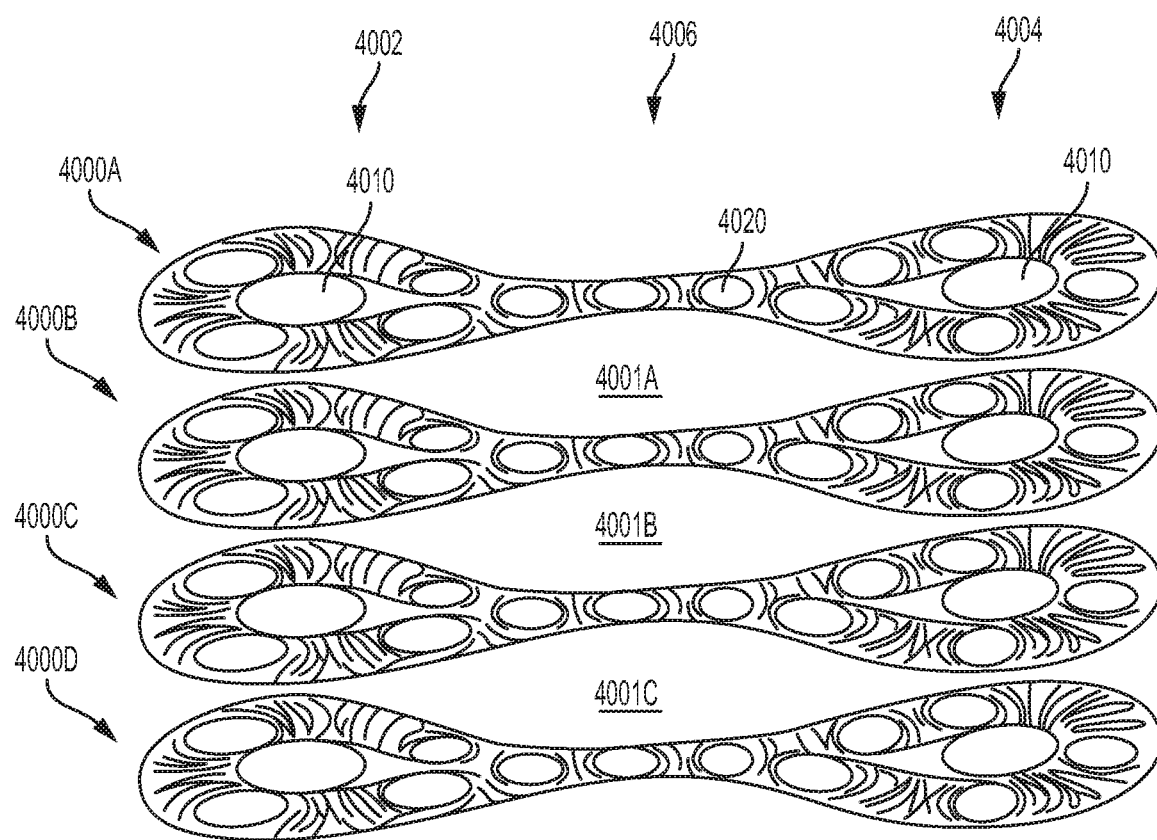
Figure 209B:
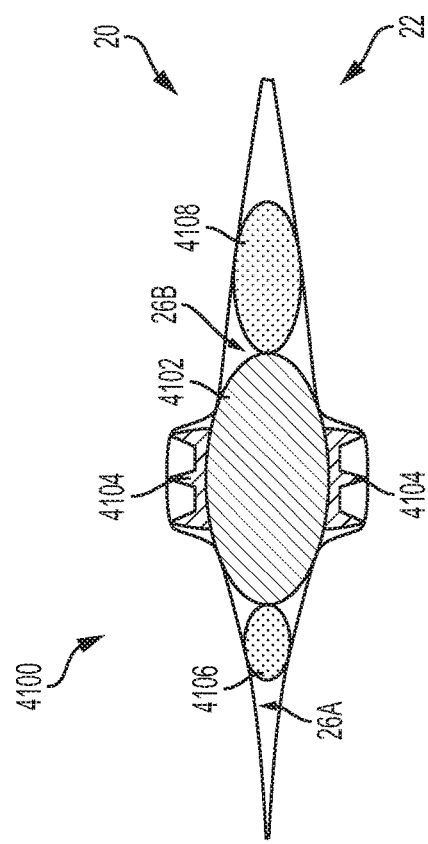
Figure 209A:
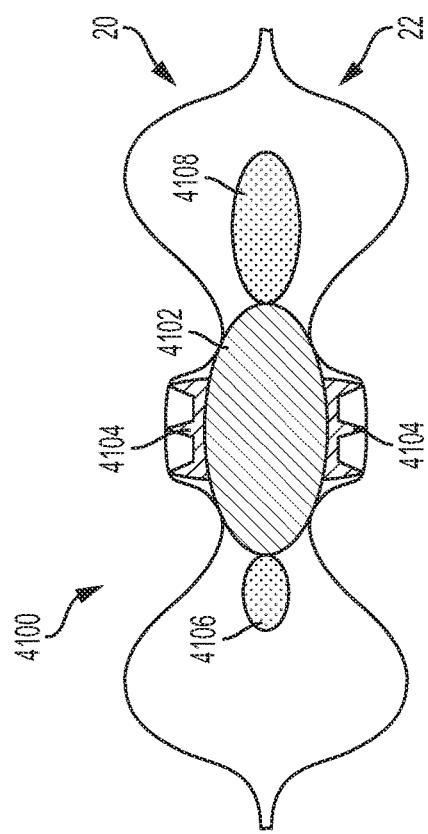
Figure 210B:
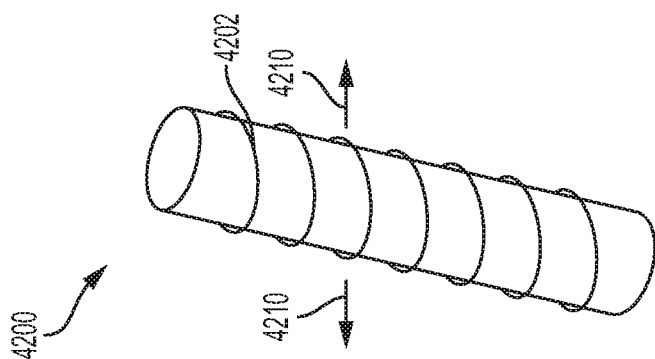
Figure 210A:
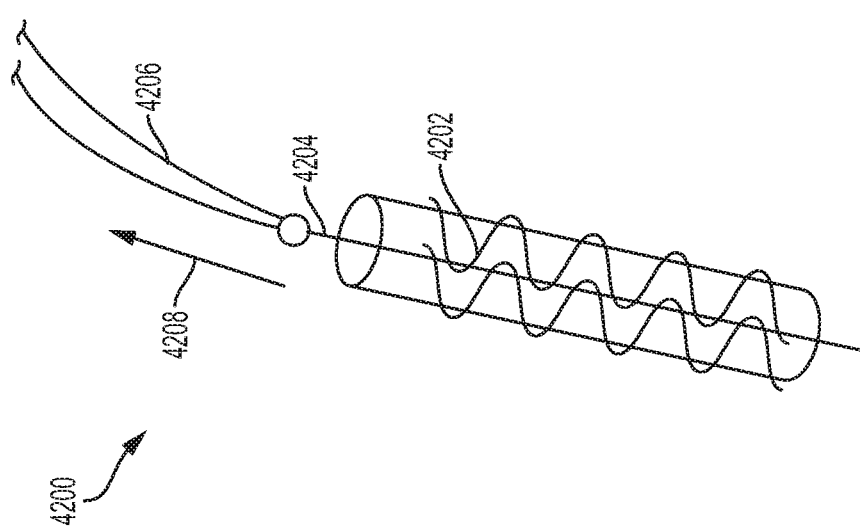
Figure 211B:
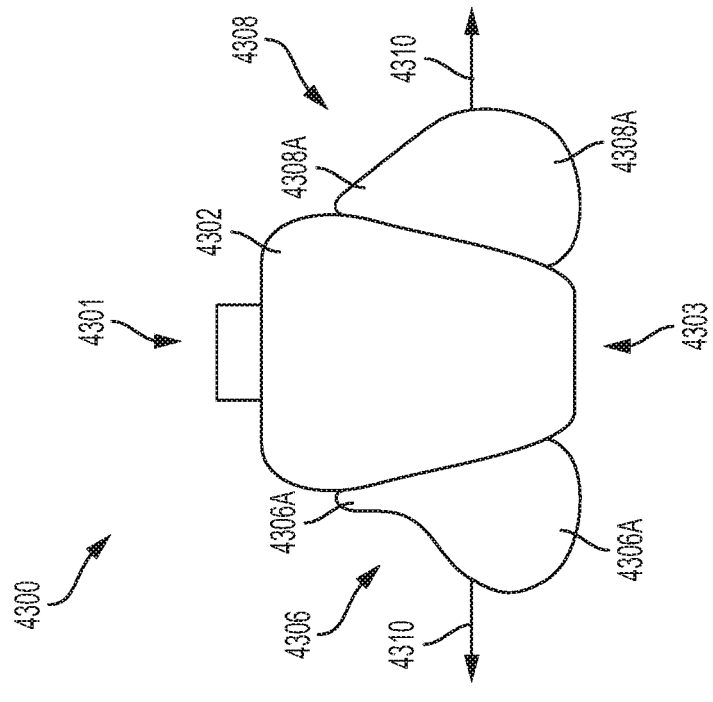
Figure 211A:
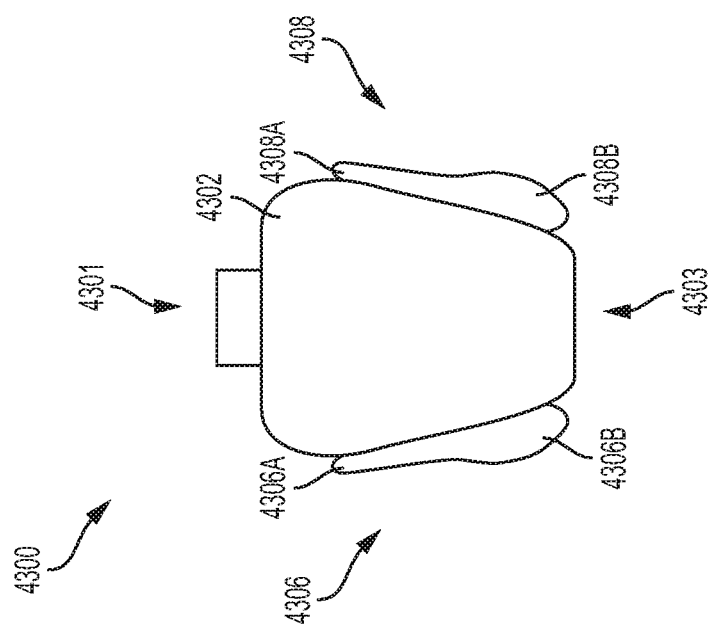
Figure 215A:
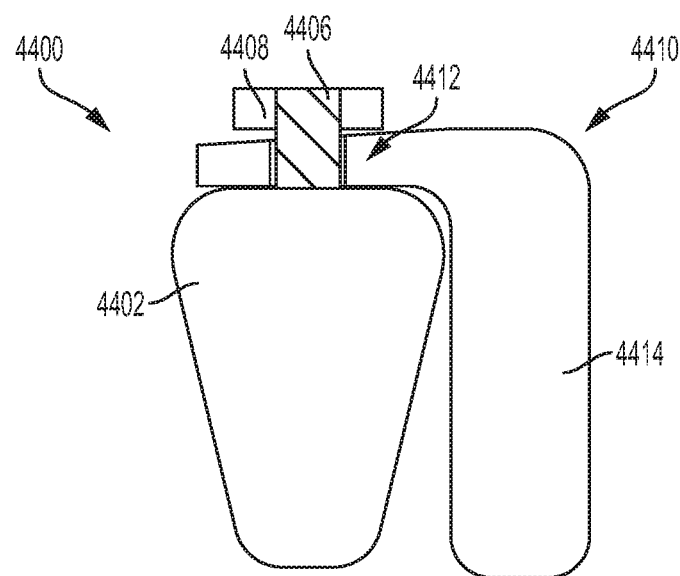
Figure 215B:
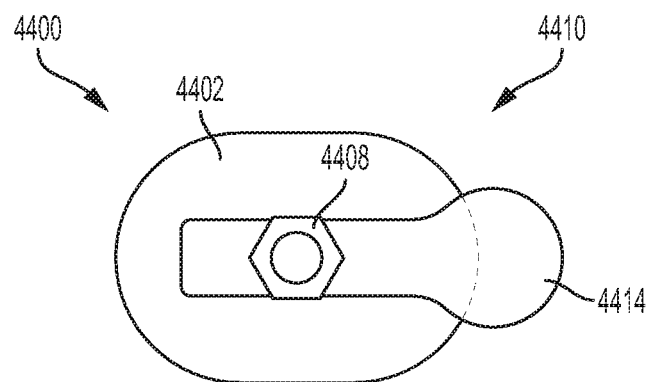
Figure 216B:
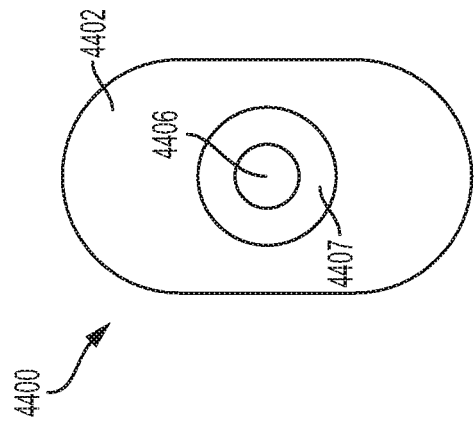
Figure 217B:
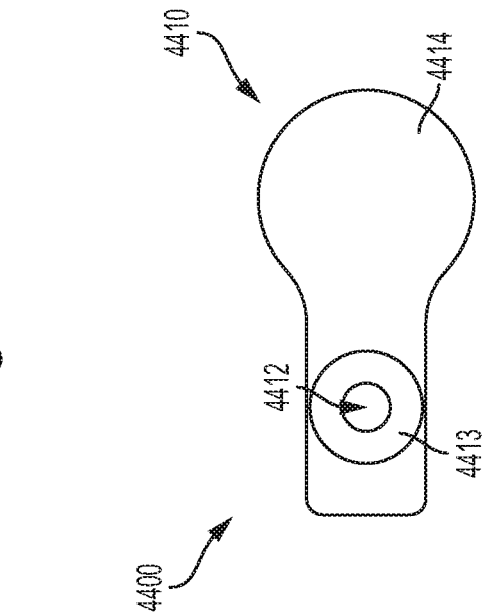
Figure 216A:
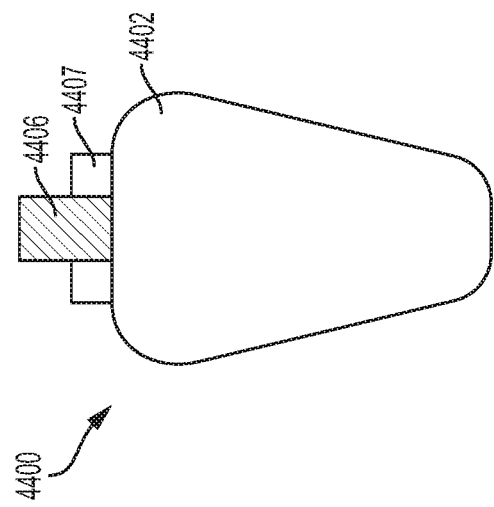
Figure 217A:
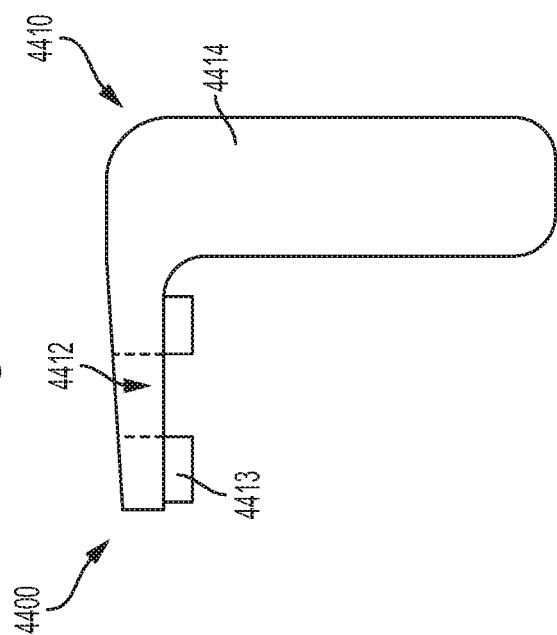
Figure 218:
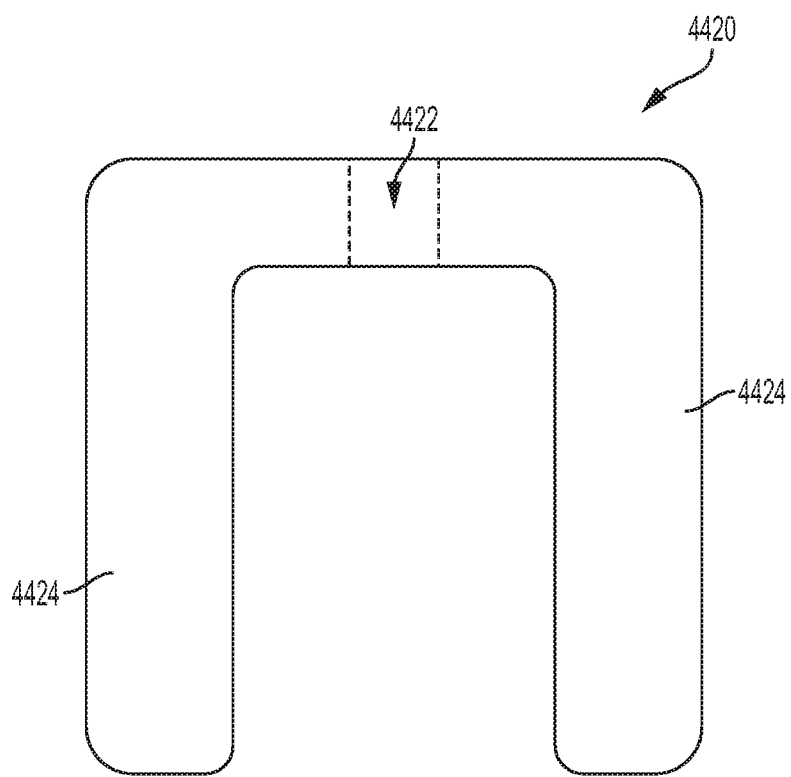
Figure 219A:
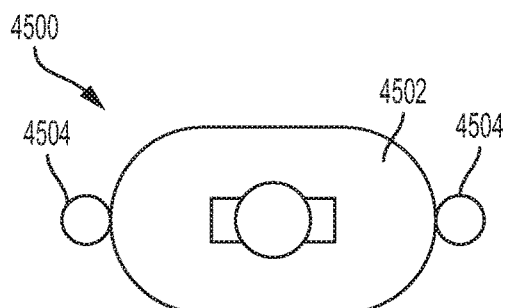
Figure 220A:
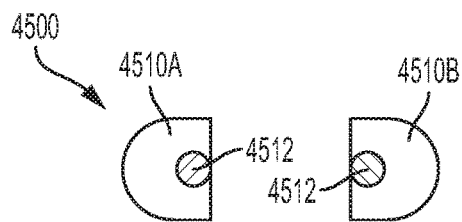
Figure 220B:
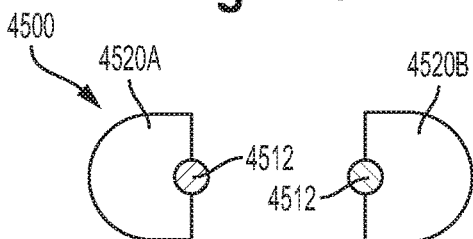
Figure 219B:
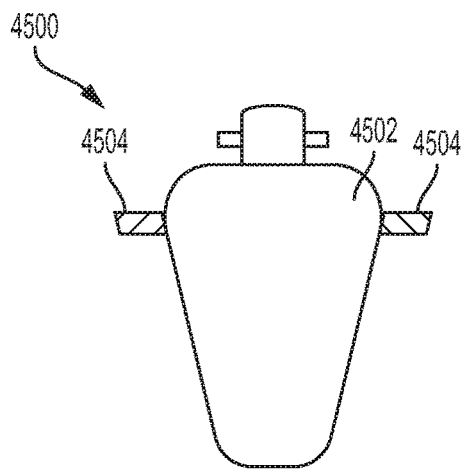
Figure 220C:
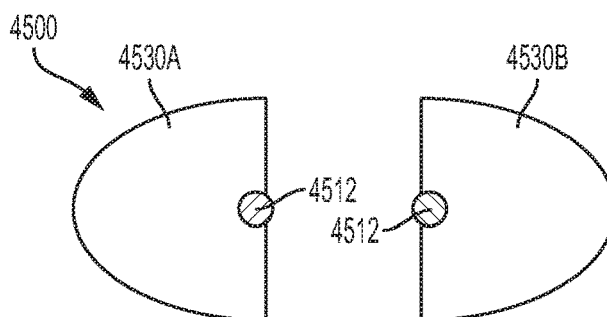
Figure 220D:
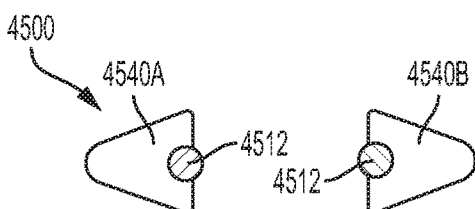
Figure 220E:
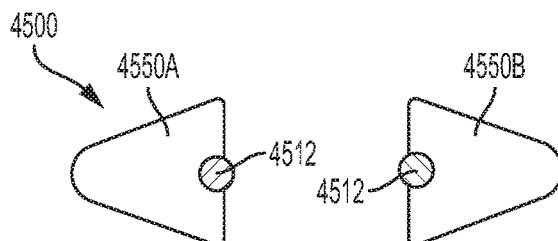
Figure 221:
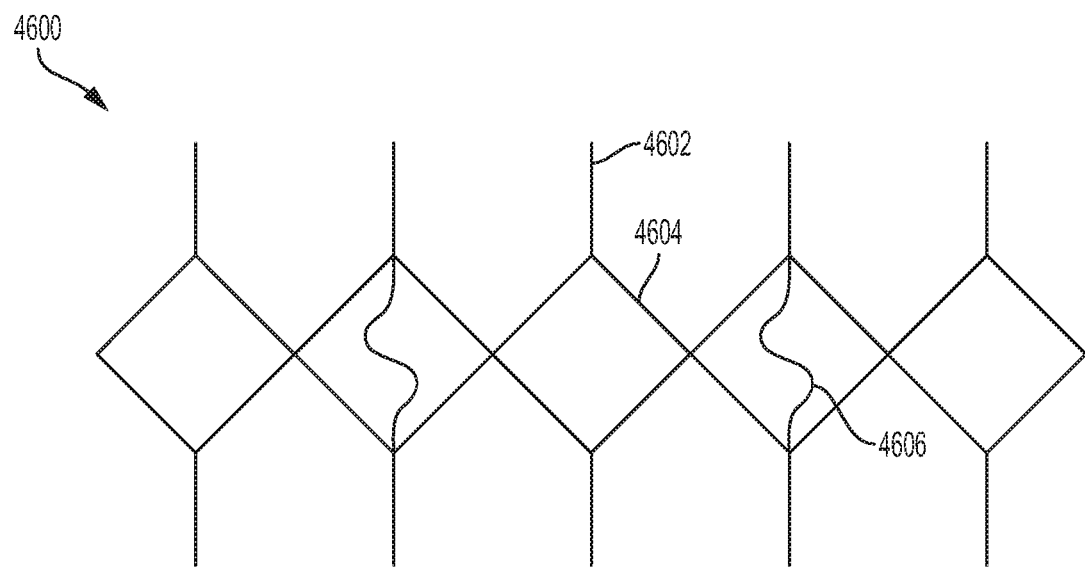
Figure 222:
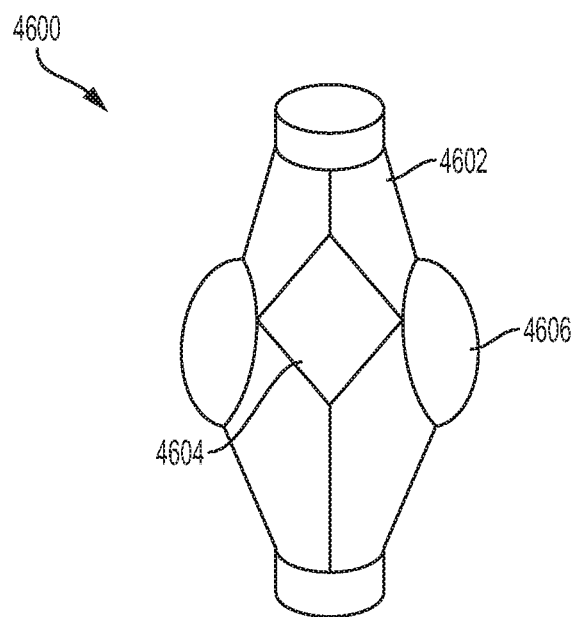
Figure 223:
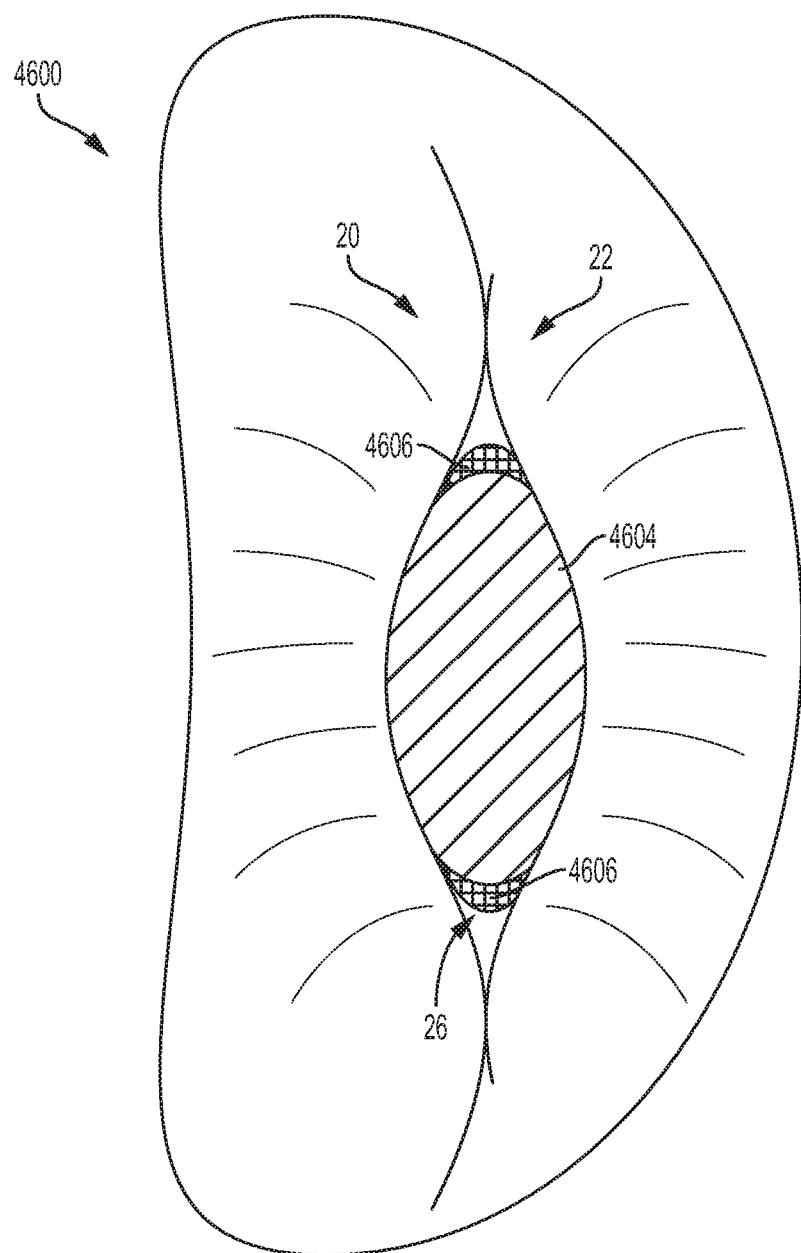
Figure 224:
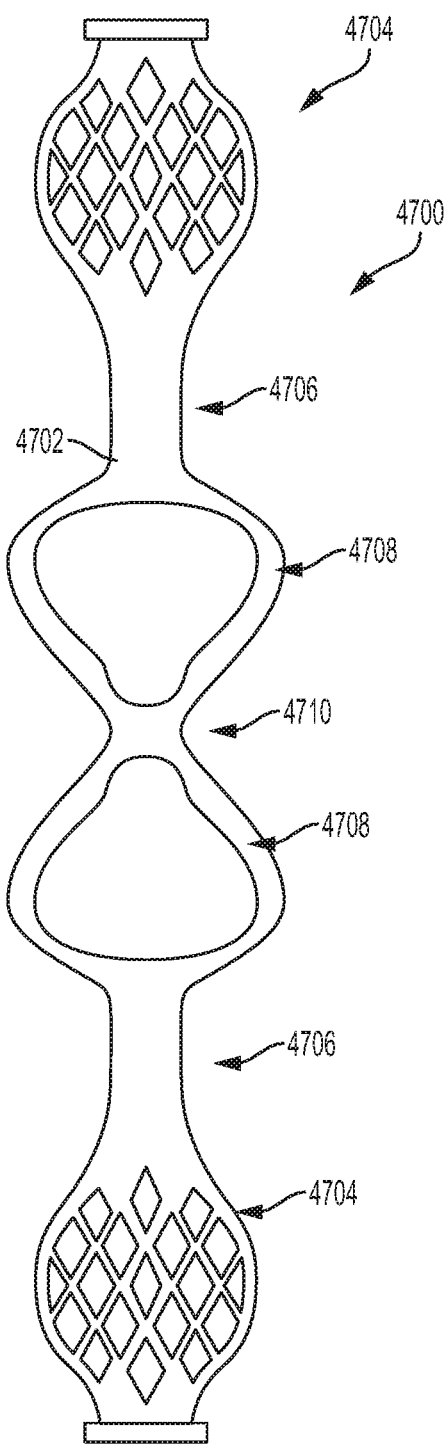
Figure 225:
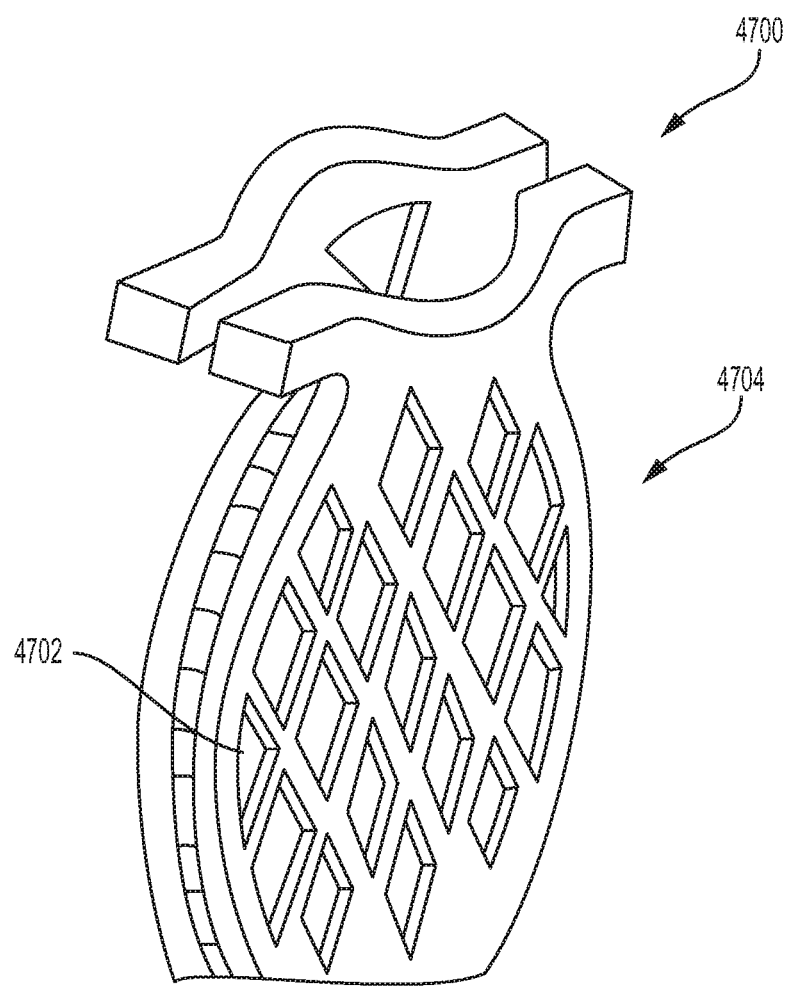
Figure 226:
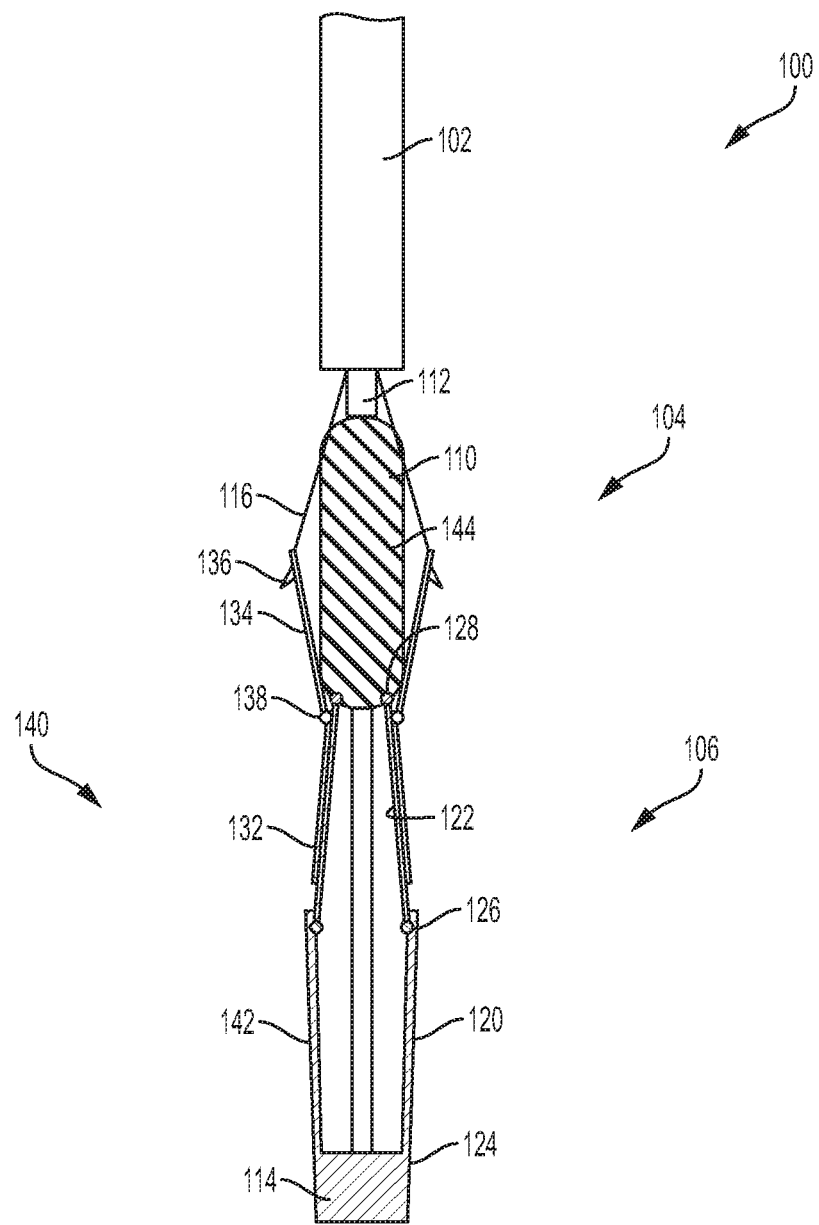
Figure 227:
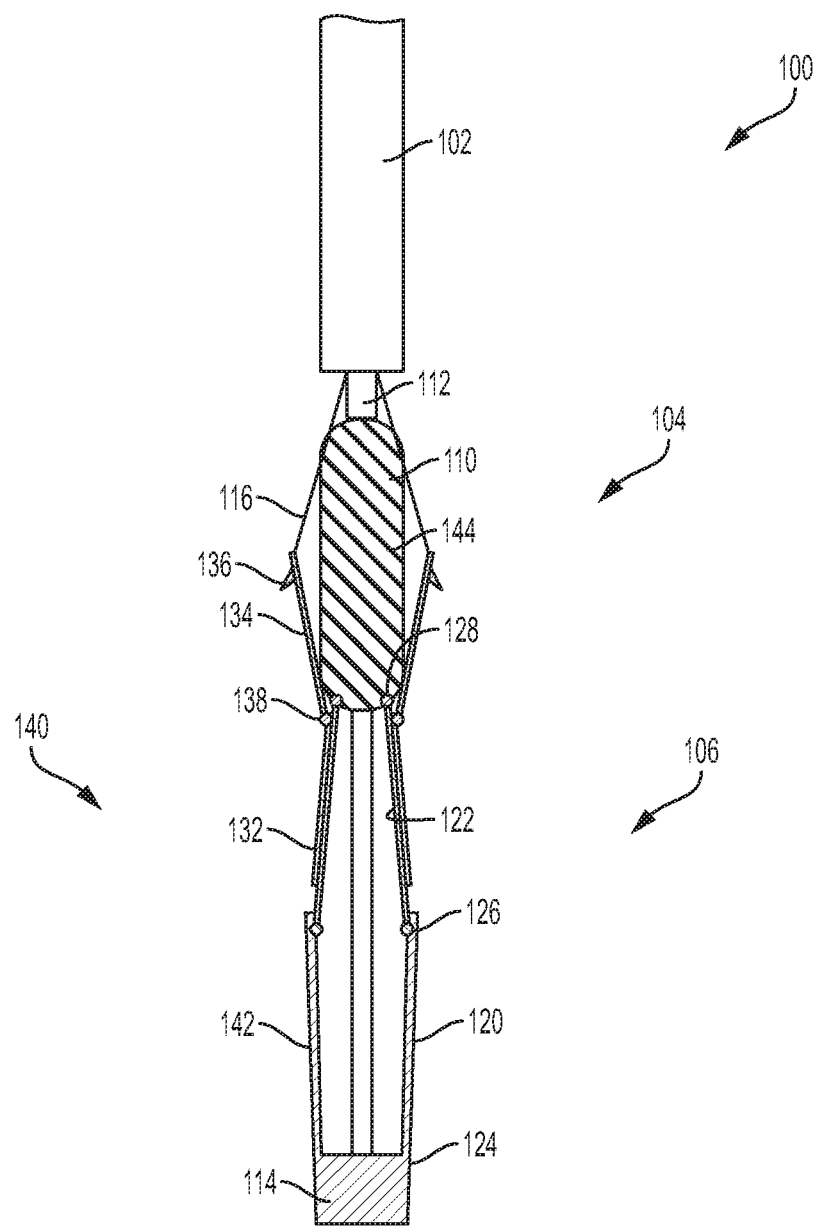
Figure 228:
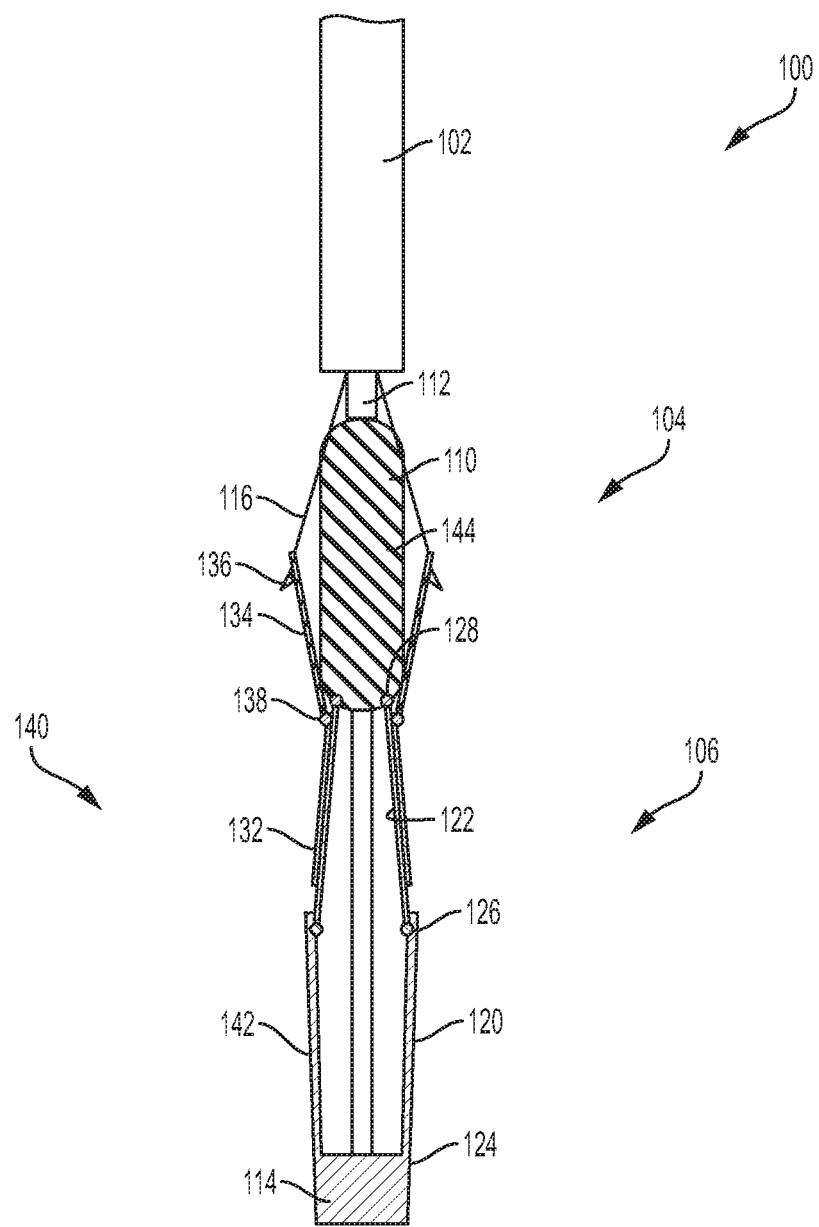
Figure 229:
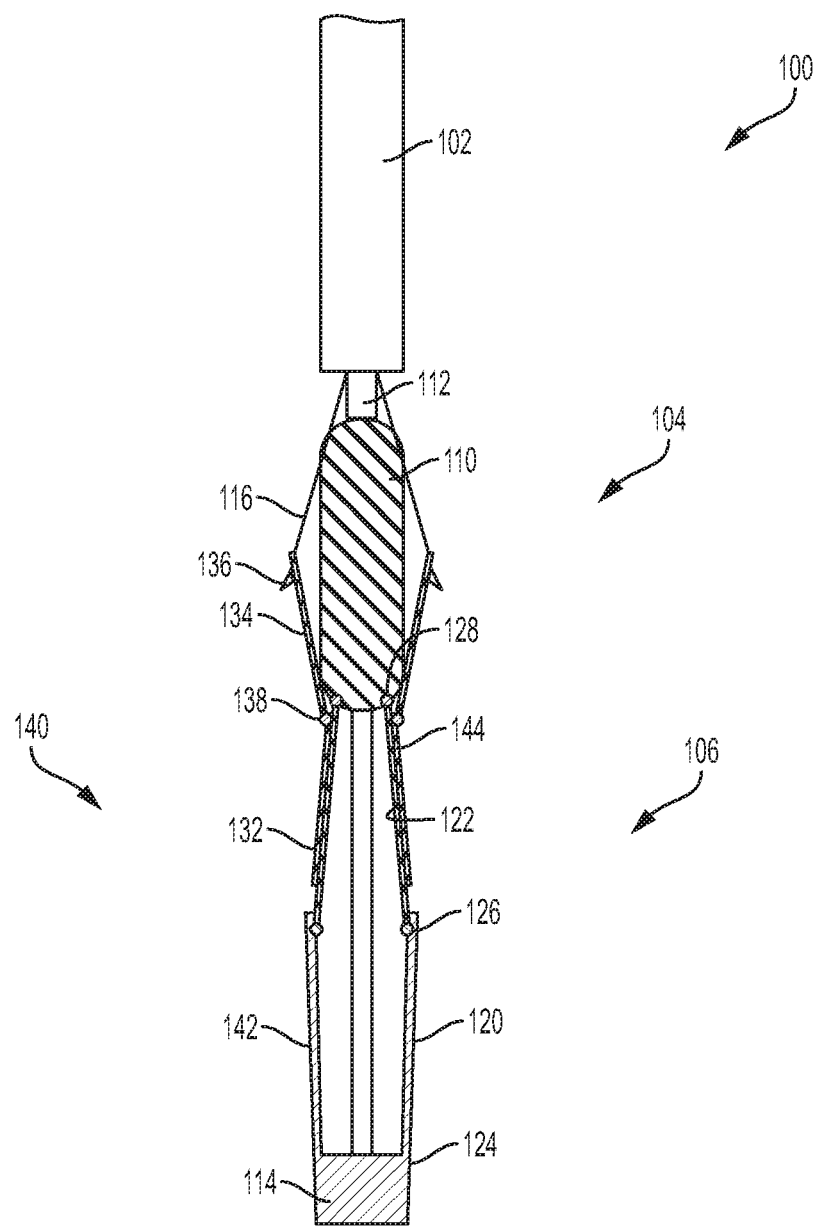
Figure 230:
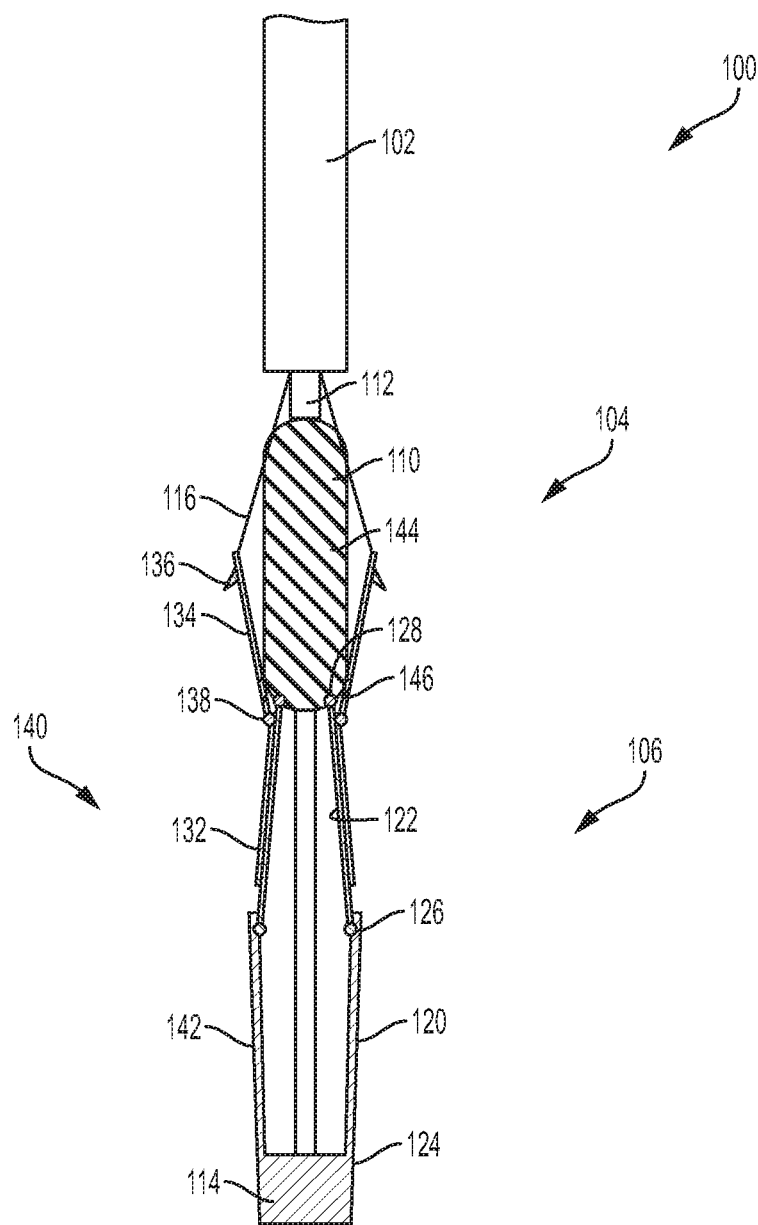
Figure 231:
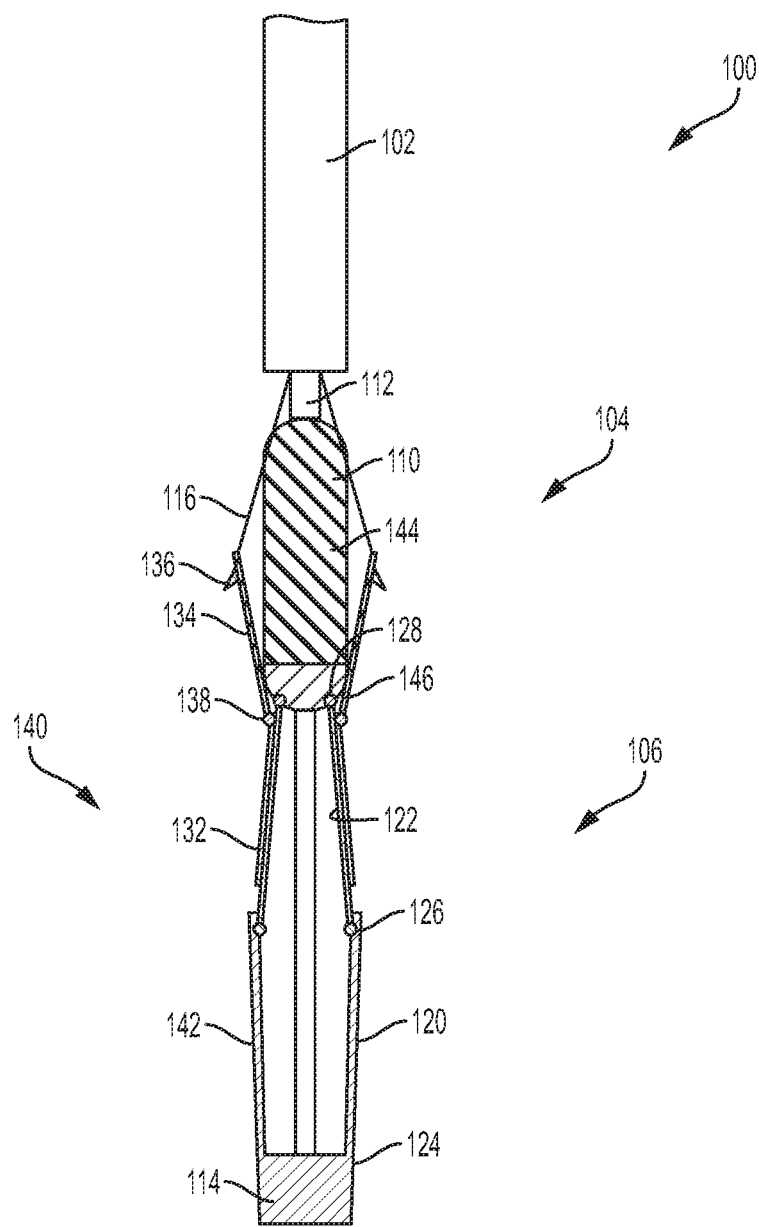

FIG. 166 shows a perspective view of the cap, actuation shaft or means of actuating, and the release wire of FIG. 163, showing the cap released from the actuation shaft or means of actuating and the release wire;

FIG. 167 shows other exemplary embodiments of a coupler, a proximal collar, a cap, and an actuation shaft or means of actuating of the delivery assembly of FIG. 144;

FIG. 168 shows a perspective view of the coupler and proximal collar of FIG. 167;

FIG. 169 shows an exemplary embodiment of a clasp control member of the delivery apparatus of FIG. 144;

FIG. 170 shows a detail view of the clasp control member of FIG. 169, taken from the perspective 170 shown in FIG. 169;

FIG. 171 shows an exemplary embodiment of a guide rail for the clasp control member of FIG. 169;

FIG. 172 shows an exemplary embodiment of a shaft of the delivery device of FIG. 144;

FIG. 173 shows an exemplary embodiment of an implantable prosthetic device and delivery device for releasing and recapturing the prosthetic device;

FIG. 174 shows an exemplary embodiment of an implantable prosthetic device and delivery device for releasing and recapturing the prosthetic device;

FIG. 174A shows an exemplary embodiment of an implantable prosthetic device and delivery device for releasing and recapturing the prosthetic device;

FIG. 175 shows an exemplary embodiment of an implantable prosthetic device and delivery device for releasing and recapturing the prosthetic device;

FIG. 175A shows an exemplary embodiment of an implantable prosthetic device and delivery device for releasing and recapturing the prosthetic device;

FIG. 176 shows an exemplary embodiment of an implantable prosthetic device and delivery device for releasing and recapturing the prosthetic device;

FIGS. 177-178 show an exemplary embodiment of a coupler for an exemplary implantable prosthetic device;

FIGS. 179-181 show an exemplary embodiment of a coupler for an exemplary implantable prosthetic device;

FIGS. 182-183 show an exemplary embodiment of a coupler for an exemplary implantable prosthetic device;

FIGS. 184-185 show an exemplary embodiment of a coupler for an exemplary implantable prosthetic device;

FIG. 186 shows an exemplary embodiment of an actuation shaft or means of actuating for an exemplary prosthetic device;

FIG. 187 shows an actuation mechanism for an exemplary prosthetic device;

FIG. 188 shows an actuation mechanism for an exemplary prosthetic device;

FIG. 188A shows an actuation mechanism for an exemplary prosthetic device;

FIG. 189 shows an actuation mechanism for an exemplary prosthetic device;

FIG. 190 shows an actuation mechanism for an exemplary prosthetic device;

FIG. 191 is a perspective view of a blank used to make a paddle frame;

FIG. 192 is a perspective view of the blank of FIG. 191 bent to make a paddle frame;

FIG. 193 is a perspective view of a shape-set paddle frame attached to a cap of a valve repair device;

FIG. 194 is a perspective view of the paddle frame of FIG. 193 flexed and attached to inner and outer paddles at a closed position;

FIG. 195 is a perspective view of two of the paddles frames of FIG. 112A showing the paddle frames in a shape-set position;

FIG. 196 is a perspective view of the paddle frames of FIG. 195 showing the paddle frames in a loaded position;

FIG. 197 is an enlarged side view of device of FIG. 60C showing the cover;

FIG. 198 is an enlarged side view of the device of FIG. 60C showing the cover;

FIG. 199 shows an exploded view of an exemplary prosthetic device;

FIG. 200 shows an enlarged perspective view of the collar of an exemplary prosthetic device;

FIG. 201 shows an enlarged perspective view of the cap of an exemplary prosthetic device;

FIG. 202 shows an exploded view of the cap of FIG. 206;

FIG. 203 shows a plan view of an inner cover for an exemplary prosthetic device;

FIG. 204 shows a plan view of an outer cover for an exemplary prosthetic device;

FIG. 205 shows an enlarged view of a strip of material for an exemplary prosthetic device;

FIG. 206 shows an end view of the material of FIG. 205;

FIG. 207 shows an end view of the material of FIG. 205 arranged in a plurality of layers;

FIG. 208A shows an exemplary implantable prosthetic device in the gap of the mitral valve as viewed from an atrial side of the mitral valve during diastole, with exemplary inflatable spacers in a deflated condition;

FIG. 208B shows the device of FIG. 208A during systole, with exemplary inflatable spacers in a deflated condition;

FIG. 209A shows the device of FIG. 208A during diastole, with exemplary inflatable spacers in an inflated condition;

FIG. 209B shows the device of FIG. 208A during systole, with exemplary inflatable spacers in an inflated condition;

FIG. 210A shows an exemplary expandable spacer in a compressed condition;

FIG. 210B shows the expandable spacer of FIG. 210A in an expanded condition;

FIG. 211A shows an exemplary implantable prosthetic device, with exemplary inflatable spacers in a deflated condition;

FIG. 211B shows the device of FIG. 211B, with exemplary inflatable spacers in an inflated condition;

FIG. 212A is a side view of an exemplary implantable prosthetic device;

FIG. 212B is a front/back view of the device of FIG. 212A;

FIG. 213A is a top view of an exemplary auxiliary spacer for attaching to the device of FIG. 212A;

FIG. 213B is a side view of the spacer of FIG. 213A;

FIG. 214 is a side view of the spacer of FIGS. 213A, 213B being assembled to the device of FIGS. 212A, 212B;

FIG. 215A is a side view of the spacer of FIGS. 213A, 213B assembled to the device of FIGS. 212A, 212B;

FIG. 215B is a top view of the assembly of FIG. 215A;

FIG. 216A is a side view of an exemplary implantable prosthetic device;

FIG. 216B is a front/back view of the device of FIG. 216A;

FIG. 217A is a top view of an exemplary auxiliary spacer for attaching to the device of FIG. 216A;

FIG. 217B is a side view of the spacer of FIG. 217A;

FIG. 218 is an exemplary auxiliary spacer;

FIG. 219A is a top view of an exemplary implantable prosthetic device;

FIG. 219B is a side view of an exemplary implantable prosthetic device;

FIG. 220A is a top view of exemplary auxiliary spacers;

FIG. 220B is a top view of exemplary auxiliary spacers;

FIG. 220C is a top view of exemplary auxiliary spacers;

FIG. 220D is a top view of exemplary auxiliary spacers;

FIG. 220E is a top view of exemplary auxiliary spacers;

FIG. 221 is a plan view of an exemplary implantable prosthetic device cut from a flat sheet of material;

FIG. 222 is a perspective view of the device of FIG. 221;

FIG. 223 shows the device of FIGS. 221-222 in the gap of the mitral valve as viewed from an atrial side of the mitral valve;

FIG. 224 is a plan view of an exemplary implantable prosthetic device cut from a flat sheet of material;

FIG. 225 is a perspective view of the device of FIG. 224;

FIG. 226 shows an exemplary embodiment of an implantable prosthetic device with a two-piece cover;

FIG. 227 shows an exemplary embodiment of an implantable prosthetic device with a two-piece cover;

FIG. 228 shows an exemplary embodiment of an implantable prosthetic device with a two-piece cover;

FIG. 229 shows an exemplary embodiment of an implantable prosthetic device with a two-piece cover;

FIG. 230 shows an exemplary embodiment of an implantable prosthetic device with a two-piece cover; and FIG. 231 shows an exemplary embodiment of an implantable prosthetic device with a two-piece cover.

DETAILED DESCRIPTION

The following description refers to the accompanying drawings, which illustrate specific embodiments of the present disclosure. Other embodiments having different structures and operation do not depart from the scope of the present disclosure.

Exemplary embodiments of the present disclosure are directed to devices and methods for repairing a defective heart valve. It should be noted that various embodiments of native valve reparation devices and systems for delivery are disclosed herein, and any combination of these options can be made unless specifically excluded. In other words, individual components of the disclosed devices and systems can be combined unless mutually exclusive or otherwise physically impossible.

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 1% of, and most preferably within 0.1% of).

Figure 1:
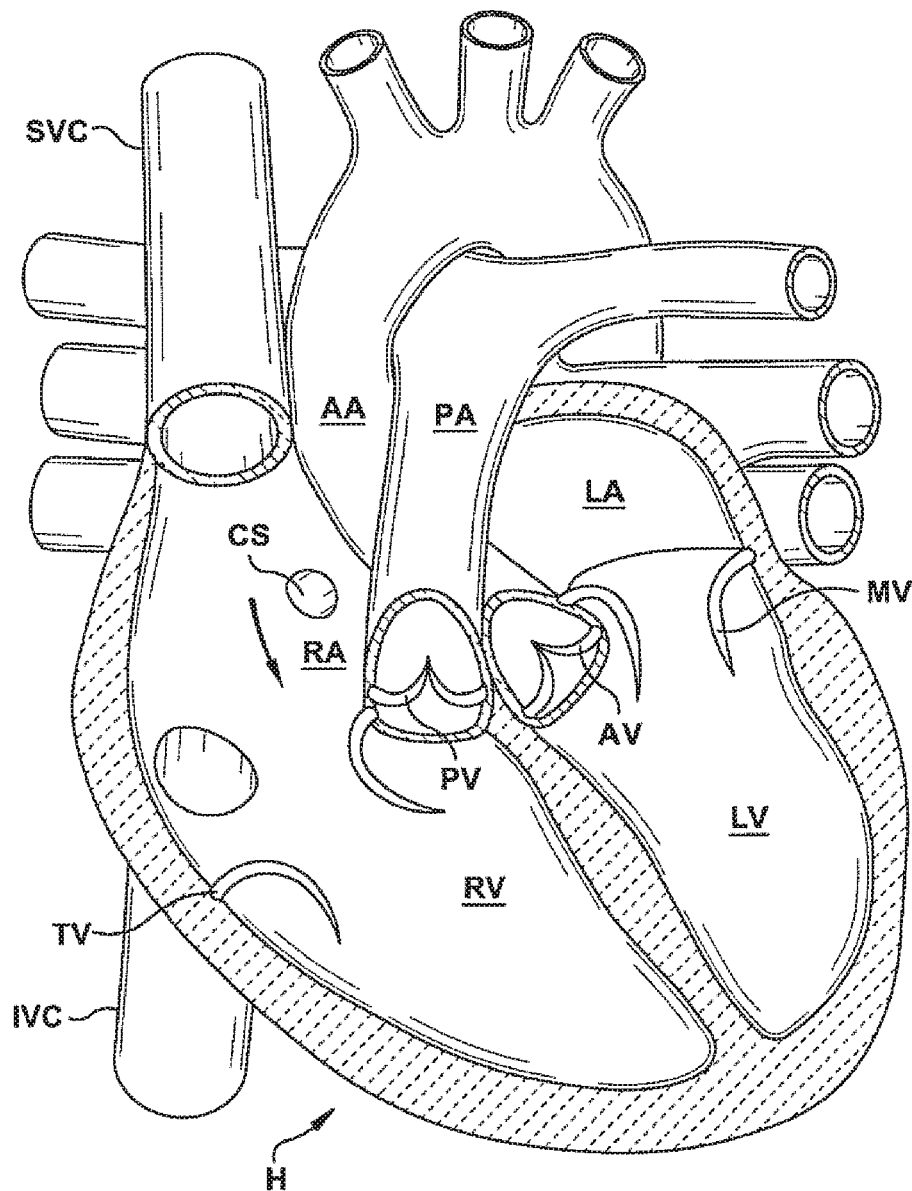
FIG. 1 illustrates a cutaway view of the human heart in a diastolic phase.
Figure 2:
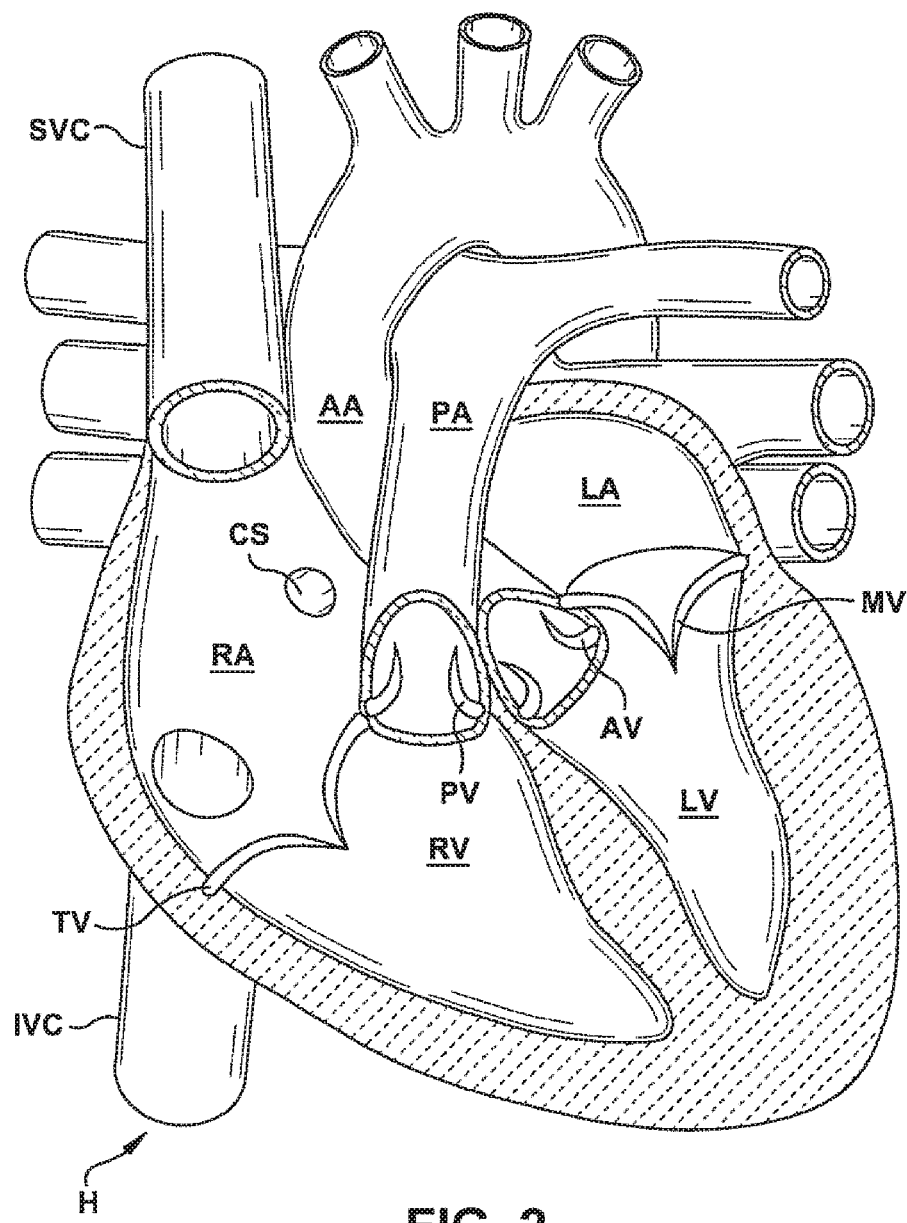
FIG. 2 illustrates a cutaway view of the human heart in a systolic phase.

FIGS. 1 and 2 are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta AA, and the pulmonary valve PV separates the right ventricle from the pulmonary artery PA. Each of these valves has flexible leaflets (e.g., leaflets 20, 22 shown in FIGS. 4 and 5) extending inward across the respective orifices that come together or "coapt" in the flowstream to form the one-way, fluid-occluding surfaces. The native valve repair systems of the present application are described primarily with respect to the mitral valve MV. Therefore, anatomical structures of the left atrium LA and left ventricle LV will be explained in greater detail. It should be understood that the devices described herein may also be used in repairing other native valves, e.g., the devices can be used in repairing the tricuspid valve TV, the aortic valve AV, and the pulmonary valve PV.

The left atrium LA receives oxygenated blood from the lungs. During the diastolic phase, or diastole, seen in FIG. 1, the blood that was previously collected in the left atrium LA (during the systolic phase) moves through the mitral valve MV and into the left ventricle LV by expansion of the left ventricle LV. In the systolic phase, or systole, seen in FIG. 2, the left ventricle LV contracts to force the blood through the aortic valve AV and ascending aorta AA into the body. During systole, the leaflets of the mitral valve MV close to prevent the blood from regurgitating from the left ventricle LV and back into the left atrium LA, and blood is collected in the left atrium from the pulmonary vein. In one exemplary embodiment, the devices described by the present application are used to repair the function of a defective mitral valve MV. That is, the devices are configured to help close the leaflets of the mitral valve to prevent blood from regurgitating from the left ventricle LV and back into the left atrium LA. Unlike the prior art that describes using sutures or clips often require multiple sutures or clips and additional supports to treat large regurgitant, the devices described in the present application are designed to easily grasp and secure the native leaflets around a coaption element that acts as a filler in the regurgitant orifice.

Figure 3:
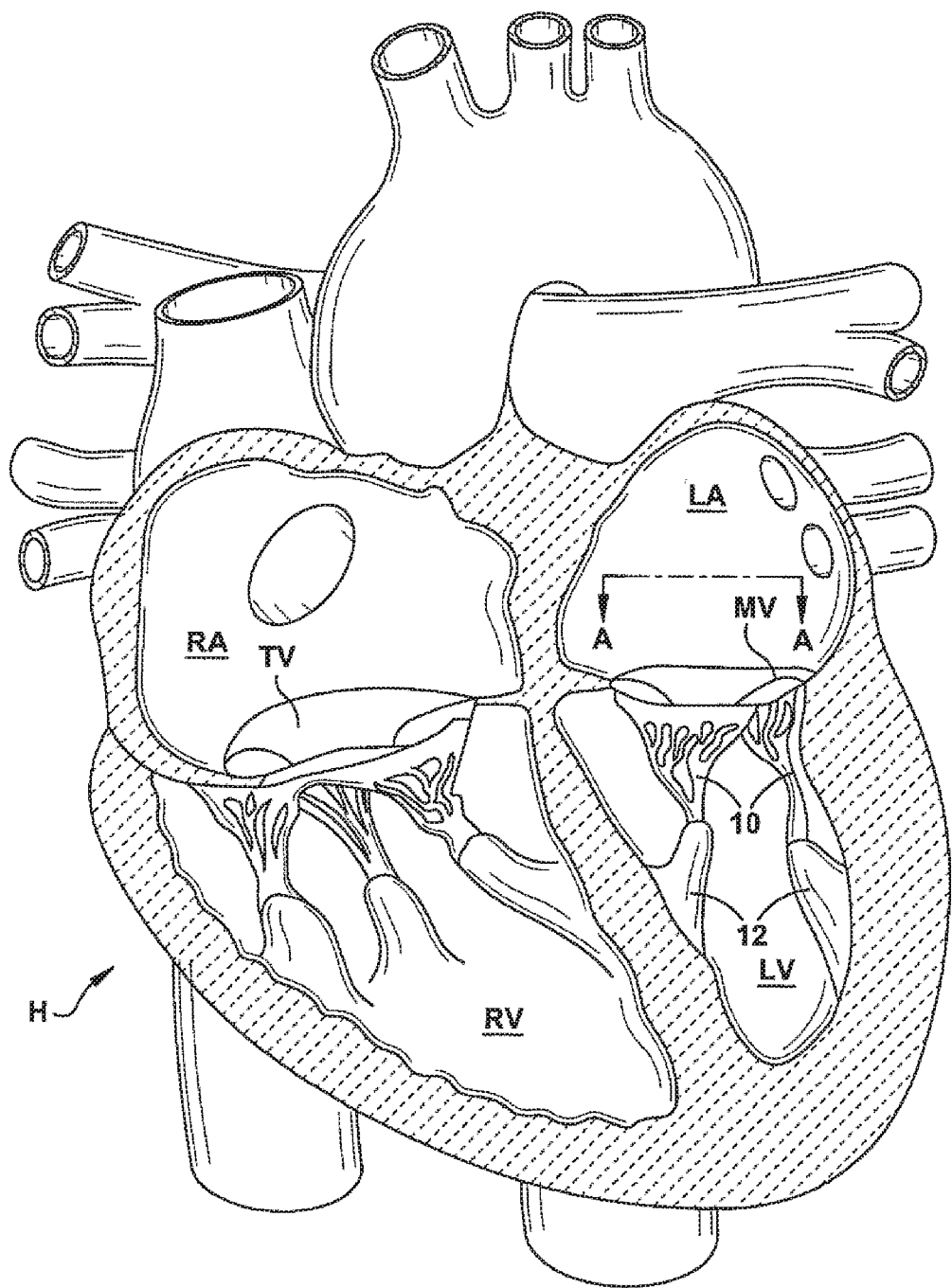
FIG. 3 illustrates a cutaway view of the human heart in a diastolic phase, in which the chordae tendineae are shown attaching the leaflets of the mitral and tricuspid valves to ventricle walls.

Referring now to FIGS. 1-7, the mitral valve MV includes two leaflets, the anterior leaflet 20 and the posterior leaflet 22. The mitral valve MV also includes an annulus 24, which is a variably dense fibrous ring of tissues that encircles the leaflets 20, 22. Referring to FIG. 3, the mitral valve MV is anchored to the wall of the left ventricle LV by chordae tendineae 10. The chordae tendineae 10 are cord-like tendons that connect the papillary muscles 12 (i.e., the muscles located at the base of the chordae tendineae and within the walls of the left ventricle) to the leaflets 20, 22 of the mitral valve MV. The papillary muscles 12 serve to limit the movements of the mitral valve MV and prevent the mitral valve from being reverted. The mitral valve MV opens and closes in response to pressure changes in the left atrium LA and the left ventricle LV. The papillary muscles do not open or close the mitral valve MV. Rather, the papillary muscles brace the mitral valve MV against the high pressure needed to circulate blood throughout the body. Together the papillary muscles and the chordae tendineae are known as the subvalvular apparatus, which functions to keep the mitral valve MV from prolapsing into the left atrium LA when the mitral valve closes.

Various disease processes can impair proper function of one or more of the native valves of the heart H. These disease processes include degenerative processes (e.g., Barlow's Disease, fibroelastic deficiency), inflammatory processes (e.g., Rheumatic Heart Disease), and infectious processes (e.g., endocarditis). In addition, damage to the left ventricle LV or the right ventricle RV from prior heart attacks (i.e., myocardial infarction secondary to coronary artery disease) or other heart diseases (e.g., cardiomyopathy) can distort a native valve's geometry, which can cause the native valve to dysfunction. However, the vast majority of patients undergoing valve surgery, such as surgery to the mitral valve MV, suffer from a degenerative disease that causes a malfunction in a leaflet (e.g., leaflets 20, 22) of a native valve (e.g., the mitral valve MV), which results in prolapse and regurgitation.

Generally, a native valve may malfunction in two different ways: (1) valve stenosis; and (2) valve regurgitation. Valve stenosis occurs when a native valve does not open completely and thereby causes an obstruction of blood flow. Typically, valve stenosis results from buildup of calcified material on the leaflets of a valve, which causes the leaflets to thicken and impairs the ability of the valve to fully open to permit forward blood flow.

The second type of valve malfunction, valve regurgitation, occurs when the leaflets of the valve do not close completely thereby causing blood to leak back into the prior chamber (e.g., causing blood to leak from the left ventricle to the left atrium). There are three mechanisms by which a native valve becomes regurgitant—or incompetent—which include Carpentier's type I, type II, and type III malfunctions. A Carpentier type I malfunction involves the dilation of the annulus such that normally functioning leaflets are distracted from each other and fail to form a tight seal (i.e., the leaflets do not coapt properly). Included in a type I mechanism malfunction are perforations of the leaflets, as are present in endocarditis. A Carpentier's type II malfunction involves prolapse of one or more leaflets of a native valve above a plane of coaption. A Carpentier's type III malfunction involves restriction of the motion of one or more leaflets of a native valve such that the leaflets are abnormally constrained below the plane of the annulus. Leaflet restriction can be caused by rheumatic disease (Ma) or dilation of a ventricle (Mb).

Figure 4:
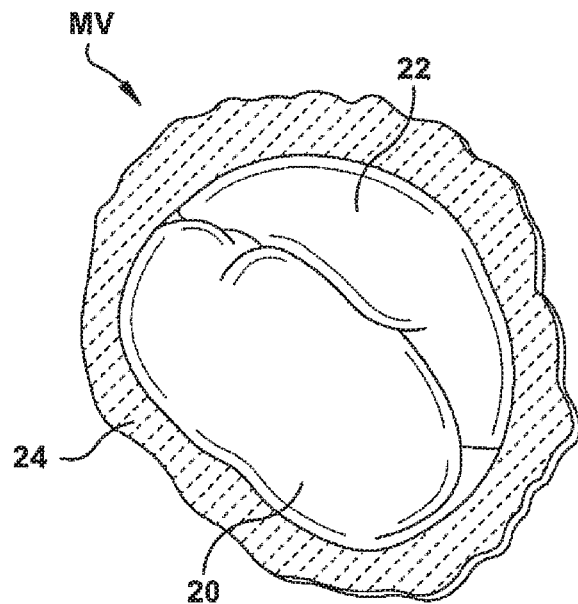
FIG. 4 illustrates a healthy mitral valve with the leaflets closed as viewed from an atrial side of the mitral valve.
Figure 5:
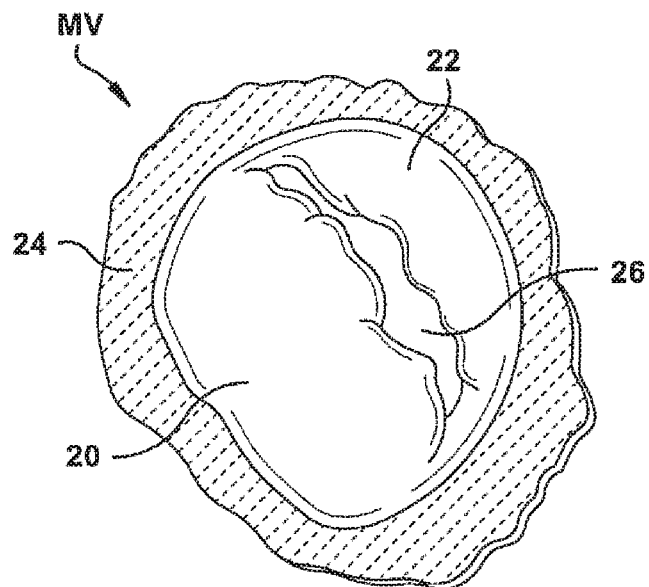
FIG. 5 illustrates a dysfunctional mitral valve with a visible gap between the leaflets as viewed from an atrial side of the mitral valve.

Referring to FIG. 4, when a healthy mitral valve MV is in a closed position, the anterior leaflet 20 and the posterior leaflet 22 coapt, which prevents blood from leaking from the left ventricle LV to the left atrium LA. Referring to FIG. 5, regurgitation occurs when the anterior leaflet 20 and/or the posterior leaflet 22 of the mitral valve MV is displaced into the left atrium LA during systole. This failure to coapt causes a gap 26 between the anterior leaflet 20 and the posterior leaflet 22, which allows blood to flow back into the left atrium LA from the left ventricle LV during systole. As set forth above, there are several different ways that a leaflet (e.g. leaflets 20, 22 of mitral valve MV) may malfunction, which can thereby lead to regurgitation.

Figure 6:
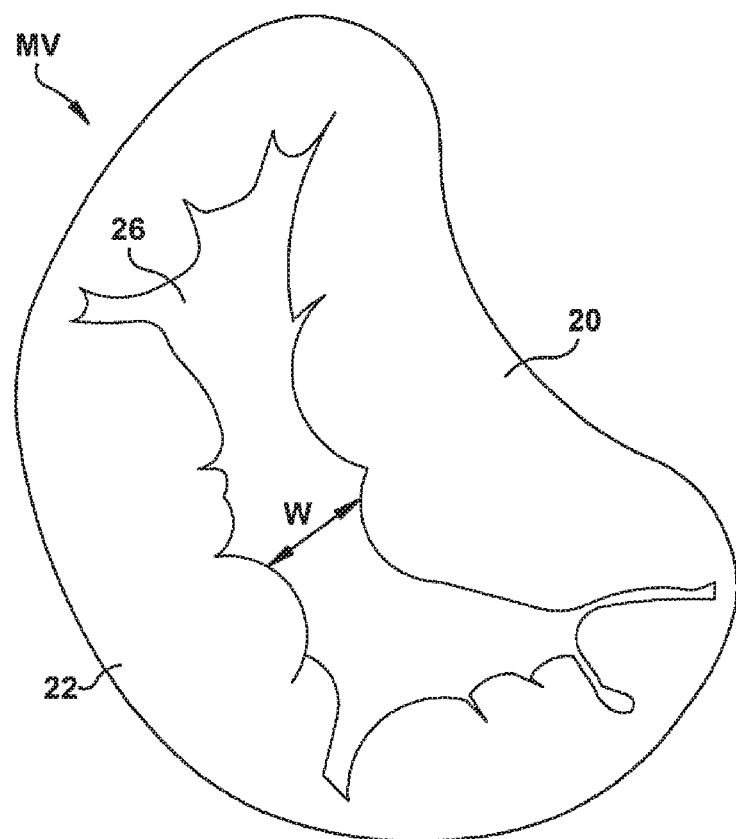
FIG. 6 illustrates a mitral valve having a wide gap between the posterior leaflet and the anterior leaflet.

Referring to FIG. 6, in certain situations, the mitral valve MV of a patient can have a wide gap 26 between the anterior leaflet 20 and the posterior leaflet 22 when the mitral valve is in a closed position (i.e., during the systolic phase). For example, the gap 26 can have a width W between about 2.5 mm and about 17.5 mm, such as between about 5 mm and about 15 mm, such as between about 7.5 mm and about 12.5 mm, such as about 10 mm. In some situations, the gap 3002 can have a width W greater than 15 mm. In any of the above-mentioned situations, a valve repair device is desired that is capable of engaging the anterior leaflet 20 and the posterior leaflet 22 to close the gap 26 and prevent regurgitation of blood through the mitral valve MV.

Although stenosis or regurgitation can affect any valve, stenosis is predominantly found to affect either the aortic valve AV or the pulmonary valve PV, and regurgitation is predominantly found to affect either the mitral valve MV or the tricuspid valve TV. Both valve stenosis and valve regurgitation increase the workload of the heart H and may lead to very serious conditions if left un-treated; such as endocarditis, congestive heart failure, permanent heart damage, cardiac arrest, and ultimately death. Because the left side of the heart (i.e., the left atrium LA, the left ventricle LV, the mitral valve MV, and the aortic valve AV) is primarily responsible for circulating the flow of blood throughout the body, malfunction of the mitral valve MV or the aortic valve AV is particularly problematic and often life threatening. Accordingly, because of the substantially higher pressures on the left side of the heart, dysfunction of the mitral valve MV or the aortic valve AV is much more problematic.

Malfunctioning native heart valves may either be repaired or replaced. Repair typically involves the preservation and correction of the patient's native valve. Replacement typically involves replacing the patient's native valve with a biological or mechanical substitute. Typically, the aortic valve AV and pulmonary valve PV are more prone to stenosis. Because stenotic damage sustained by the leaflets is irreversible, the most conventional treatments for a stenotic aortic valve or stenotic pulmonary valve are removal and replacement of the valve with a surgically implanted heart valve, or displacement of the valve with a transcatheter heart valve. The mitral valve MV and the tricuspid valve TV are more prone to deformation of leaflets, which, as described above, prevents the mitral valve or tricuspid valve from closing properly and allows for regurgitation or back flow of blood from the ventricle into the atrium (e.g., a deformed mitral valve MV may allow for regurgitation or back flow from the left ventricle LV to the left atrium LA). The regurgitation or back flow of blood from the ventricle to the atrium results in valvular insufficiency. Deformations in the structure or shape of the mitral valve MV or the tricuspid valve TV are often repairable. In addition, regurgitation can occur due to the chordae tendineae 10 becoming dysfunctional (e.g., the chordae tendineae may stretch or rupture), which allows the anterior leaflet 20 and the posterior leaflet 22 to be reverted such that blood is regurgitated into the left atrium LA. The problems occurring due to dysfunctional chordae tendineae 10 can be repaired by repairing the chordae tendineae or the structure of the mitral valve (e.g., by securing the leaflets 20, 22 at the affected portion of the mitral valve).

Figure 7:
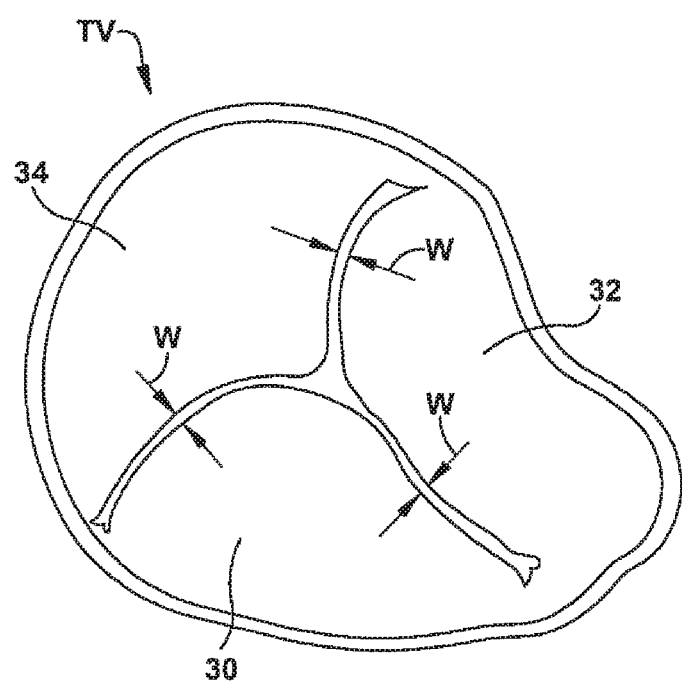
FIG. 7 illustrates a tricuspid valve viewed from an atrial side of the tricuspid valve.

The devices and procedures disclosed herein make reference to repairing the structure of a mitral valve. However, it should be understood that the devices and concepts provided herein can be used to repair any native valve, as well as any component of a native valve. Referring now to FIG. 7, any of the devices and concepts provided herein can be used to repair the tricuspid valve TV. For example, any of the devices and concepts provided herein can be used between any two of the anterior leaflet 30, septal leaflet 32, and posterior leaflet 34 to prevent regurgitation of blood from the right ventricle into the right atrium. In addition, any of the devices and concepts provided herein can be used on all three of the leaflets 30, 32, 34 together to prevent regurgitation of blood from the right ventricle to the right atrium. That is, the valve repair devices provided herein can be centrally located between the three leaflets 30, 32, 34.

An exemplary implantable prosthetic device has a coaption element and at least one anchor. The coaption element is configured to be positioned within the native heart valve orifice to help fill the space and form a more effective seal, thereby reducing or preventing regurgitation described above. The coaption element can have a structure that is impervious to blood and that allows the native leaflets to close around the coaption element during ventricular systole to block blood from flowing from the left or right ventricle back into the left or right atrium, respectively. The prosthetic device can be configured to seal against two or three native valve leaflets; that is, the device may be used in the native mitral (bicuspid) and tricuspid valves. The coaption element is sometimes referred to herein as a spacer because the coaption element can fill a space between improperly functioning native mitral or tricuspid leaflets that do not close completely.

The coaption element can have various shapes. In some embodiments, the coaption element can have an elongated cylindrical shape having a round cross-sectional shape. In other embodiments, the coaption element can have an oval cross-sectional shape, a crescent cross-sectional shape, or various other non-cylindrical shapes. The coaption element can have an atrial portion positioned in or adjacent to the left atrium, a ventricular or lower portion positioned in or adjacent to the left ventricle, and a side surface that extends between the native mitral leaflets. In embodiments configured for use in the tricuspid valve, the atrial or upper portion is positioned in or adjacent to the right atrium, and the ventricular or lower portion is positioned in or adjacent to the right ventricle, and the side surface that extends between the native tricuspid leaflets.

The anchor can be configured to secure the device to one or both of the native mitral leaflets such that the coaption element is positioned between the two native leaflets. In embodiments configured for use in the tricuspid valve, the anchor is configured to secure the device to one, two, or three of the tricuspid leaflets such that the coaption element is positioned between the three native leaflets. In some embodiments, the anchor can attach to the coaption element at a location adjacent the ventricular portion of the coaption element. In some embodiments, the anchor can attach to a shaft or actuation wire, to which the coaption element is also attached. In some embodiments, the anchor and the coaption element can be positioned independently with respect to each other by separately moving each of the anchor and the coaption element along the longitudinal axis of the shaft or actuation wire. In some embodiments, the anchor and the coaption element can be positioned simultaneously by moving the anchor and the coaption element together along the longitudinal axis of the shaft or actuation wire. The anchor can be configured to be positioned behind a native leaflet when implanted such that the leaflet is grasped by the anchor.

The prosthetic device can be configured to be implanted via a delivery sheath. The coaption element and the anchor can be compressible to a radially compressed state and can be self-expandable to a radially expanded state when compressive pressure is released. The device can be configured for the anchor to be expanded radially away from the still-compressed coaption element initially in order to create a gap between the coaption element and the anchor. A native leaflet can then be positioned in the gap. The coaption element can be expanded radially, closing the gap between the coaption element and the anchor and capturing the leaflet between the coaption element and the anchor. In some embodiments, the anchor and coaption element are optionally configured to self-expand. The implantation methods for various embodiments can be different and are more fully discussed below with respect to each embodiment. Additional information regarding these and other delivery methods can be found in U.S. Pat. No. 8,449,599 and U.S. Patent Application Publication Nos. 2014/0222136, and 2014/0067052, 2016/0331523 each of which is incorporated herein by reference in its entirety.

The disclosed prosthetic devices can be configured such that the anchor is connected to a leaflet, taking advantage of the tension from native chordae tendineae to resist high systolic pressure urging the device toward the left atrium. During diastole, the devices can rely on the compressive and retention forces exerted on the leaflet that is grasped by the anchor.

Referring now to FIGS. 8-14, a schematically illustrated implantable prosthetic device 100 is shown in various stages of deployment. The device 100 can include any other features for an implantable prosthetic device discussed in the present application, and the device 100 can be positioned to engage valve tissue 20, 22 as part of any suitable valve repair system (e.g., any valve repair system disclosed in the present application).

The device 100 is deployed from a delivery sheath or means for delivery 102 and includes a coaption portion 104 and an anchor portion 106. The coaption portion 104 of the device 100 includes a coaption element or means for coapting 110 that is adapted to be implanted between the leaflets of the native mitral valve and is slidably attached to an actuation wire or shaft 112. The anchor portion 106 is actuatable between open and closed conditions and can take a wide variety of forms, such as, for example, paddles, gripping elements, or the like. Actuation of the actuation wire or means for actuating 112 opens and closes the anchor portion 106 of the device 100 to grasp the mitral valve leaflets during implantation. The actuation wire or shaft 112 may take a wide variety of different forms. For example, the actuation wire or shaft may be threaded such that rotation of the actuation wire or shaft moves the anchor portion 106 relative to the coaption portion 104. Or, the actuation wire or shaft may be unthreaded, such that pushing or pulling the actuation wire or shaft 112 moves the anchor portion 106 relative to the coaption portion 104.

The anchor portion 106 of the device 100 includes outer paddles 120 and inner paddles 122 that are connected between a cap 114 and the coaption element or means for coapting 110 by portions 124, 126, 128. The portions 124, 126, 128 may be jointed and/or flexible to move between all of the positions described below. The interconnection of the outer paddles 120, the inner paddles 122, the coaption element or means for coapting 110, and the cap 114 by the portions 124, 126, and 128 can constrain the device to the positions and movements illustrated herein.

The actuation wire or means for actuating 112 extends through the delivery sheath and the coaption element or means for coapting 110 to the cap 114 at the distal connection of the anchor portion 106. Extending and retracting the actuation wire or means for actuating 112 increases and decreases the spacing between the coaption element or means for coapting 110 and the cap 114, respectively. A collar removably attaches the coaption element or means for coapting 110 to the delivery sheath or means for delivery 102 so that the actuation wire or means for actuating 112 slides through the collar and coaption element or means for coapting 110 during actuation to open and close the paddles 120, 122 of the anchor portion 106.

Figures 11, 11A:
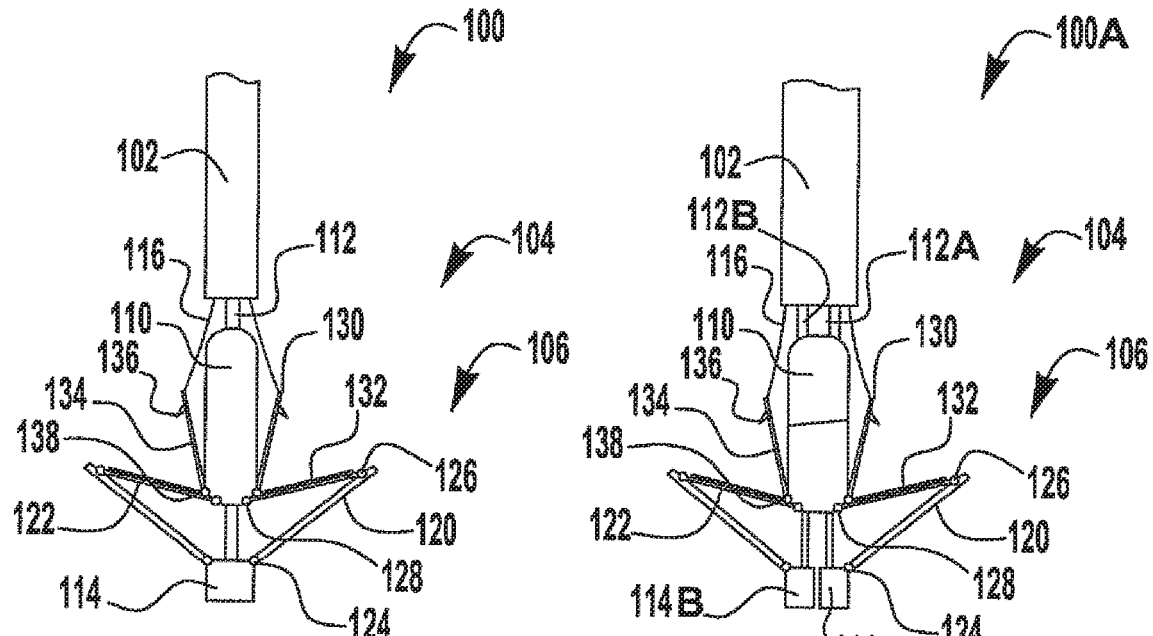
FIG. 11A shows an exemplary embodiment of an implantable prosthetic device that is similar to the device illustrated by FIG. 11, but where the paddles are independently controllable.

Referring now to FIG. 11, the anchor portion 106 includes attachment portions or gripping members. The illustrated gripping members are barbed clasps 130 that include a base or fixed arm 132, a moveable arm 134, barbs or means for securing 136, and a joint portion 138. The fixed arms 132 are attached to the inner paddles 122, with the joint portion 138 disposed proximate the coaption element or means for coapting 110. The barbed clasps have flat surfaces and do not fit in a recess of the paddle. Rather, the flat portions of the barbed clasps are disposed against the surface of the inner paddle 122. The joint portion 138 provides a spring force between the fixed and moveable arms 132, 134 of the barbed clasp 130. The joint portion 138 can be any suitable joint, such as a flexible joint, a spring joint, a pivot joint, or the like. In certain embodiments, the joint portion 138 is a flexible piece of material integrally formed with the fixed and moveable arms 132, 134. The fixed arms 132 are attached to the inner paddles 122 and remain stationary relative to the inner paddles 122 when the moveable arms 134 are opened to open the barbed clasps 130 and expose the barbs or means for securing 136. The barbed clasps 130 are opened by applying tension to actuation lines 116 attached to the moveable arms 134, thereby causing the moveable arms 134 to pivot on the joint portions 138.

During implantation, the paddles 120, 122 are opened and closed to grasp the native mitral valve leaflets between the paddles 120, 122 and the coaption element or means for coapting 110. The barbed clasps 130 further secure the native leaflets by engaging the leaflets with barbs or means for securing 136 and pinching the leaflets between the moveable and fixed arms 134, 132. The barbs or means for securing 136 of the barbed clasps 130 increase friction with the leaflets or may partially or completely puncture the leaflets. The actuation lines 116 can be actuated separately so that each barbed clasp 130 can be opened and closed separately. Separate operation allows one leaflet to be grasped at a time, or for the repositioning of a clasp 130 on a leaflet that was insufficiently grasped, without altering a successful grasp on the other leaflet. The barbed clasps 130 can be opened and closed relative to the position of the inner paddle 122 (as long as the inner paddle is in an open position), thereby allowing leaflets to be grasped in a variety of positions as the particular situation requires.

The barbed clasps 130 can be opened separately by pulling on an attached actuation line 116 that extends through the delivery sheath or means for delivery 102 to the barbed clasp 130. The actuation line 116 can take a wide variety of forms, such as, for example, a line, a suture, a wire, a rod, a catheter, or the like. The barbed clasps 130 can be spring loaded so that in the closed position the barbed clasps 130 continue to provide a pinching force on the grasped native leaflet. This pinching force remains constant regardless of the position of the inner paddles 122. Barbs or means for securing 136 of the barbed clasps 130 can pierce the native leaflets to further secure the native leaflets.

Figure 8:
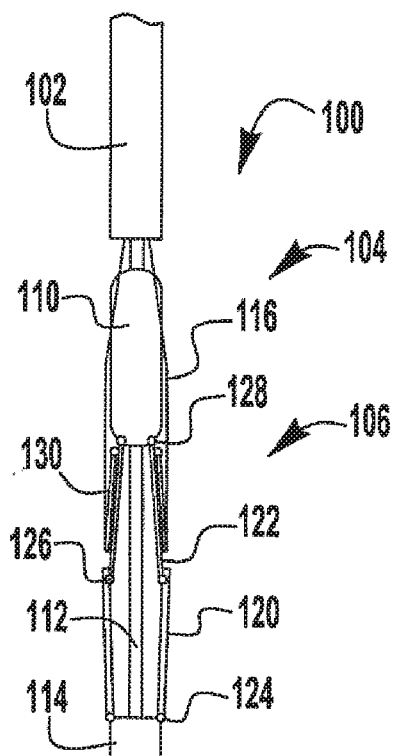
FIGS. 8-14 show an exemplary embodiment of an implantable prosthetic device, in various stages of deployment.

Referring now to FIG. 8, the device 100 is shown in an elongated or fully open condition for deployment from the delivery sheath. The device 100 is loaded in the delivery sheath in the fully open position, because the fully open position takes up the least space and allows the smallest catheter to be used (or the largest device 100 to be used for a given catheter size). In the elongated condition the cap 114 is spaced apart from the coaption element or means for coapting 110 such that the paddles 120, 122 of the anchor portion 106 are fully extended. In some embodiments, an angle formed between the interior of the outer and inner paddles 120, 122 is approximately 180 degrees. The barbed clasps 130 are kept in a closed condition during deployment through the delivery sheath or means for delivery 102 so that the barbs or means for securing 136 (FIG. 11) do not catch or damage the sheath or tissue in the patient's heart.

Figure 9:
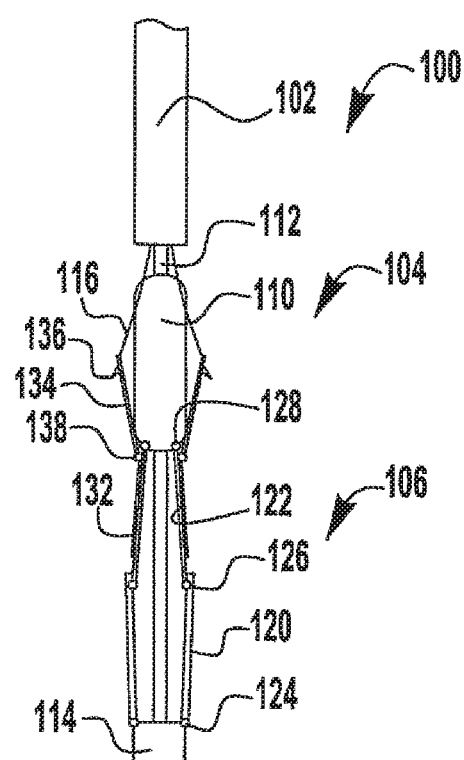

Referring now to FIG. 9, the device 100 is shown in an elongated detangling condition, similar to FIG. 8, but with the barbed clasps 130 in a fully open position, ranging from about 140 degrees to about 200 degrees, to about 170 degrees to about 190 degrees, or about 180 degrees between fixed and moveable portions of the barbed clasps 130. Fully opening the paddles 120, 122 and the clasps 130 has been found to improve ease of detanglement from anatomy of the patient during implantation of the device 100.

Figure 10:
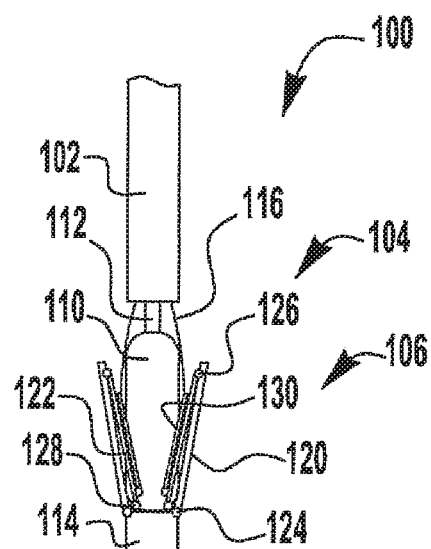

Referring now to FIG. 10, the device 100 is shown in a shortened or fully closed condition. The compact size of the device 100 in the shortened condition allows for easier maneuvering and placement within the heart. To move the device 100 from the elongated condition to the shortened condition, the actuation wire or means for actuating 112 is retracted to pull the cap 114 towards the coaption element or means for coapting 110. The joints or flexible connections 126 between the outer paddle 120 and inner paddle 122 are constrained in movement such that compression forces acting on the outer paddle 120 from the cap 114 being retracted towards the coaption element or means for coapting 110 cause the paddles or gripping elements 120, 122 to move radially outward. During movement from the open to closed position, the outer paddles 120 maintain an acute angle with the actuation wire or means for actuating 112. The outer paddles 120 can optionally be biased toward a closed position. The inner paddles 122 during the same motion move through a considerably larger angle as they are oriented away from the coaption element or means for coapting 110 in the open condition and collapse along the sides of the coaption element or means for coapting 110 in the closed condition. In certain embodiments, the inner paddles 122 are thinner and/or narrower than the outer paddles 120, and the joint or flexible portions 126, 128 connected to the inner paddles 122 can be thinner and/or more flexible. For example, this increased flexibility can allow more movement than the joint or flexible portion 124 connecting the outer paddle 124 to the cap 114. In certain other embodiments, the outer paddles 120 are narrower than the inner paddles 122. The joint or flexible portions 126, 128 connected to the inner paddles 122 can be more flexible, for example, to allow more movement than the joint or flexible portion 124 connecting the outer paddle 124 to the cap 114. In yet another embodiment, the inner paddles 122 can be the same or substantially the same width as the outer paddles (See for example, FIG. 65A).

Figure 12:
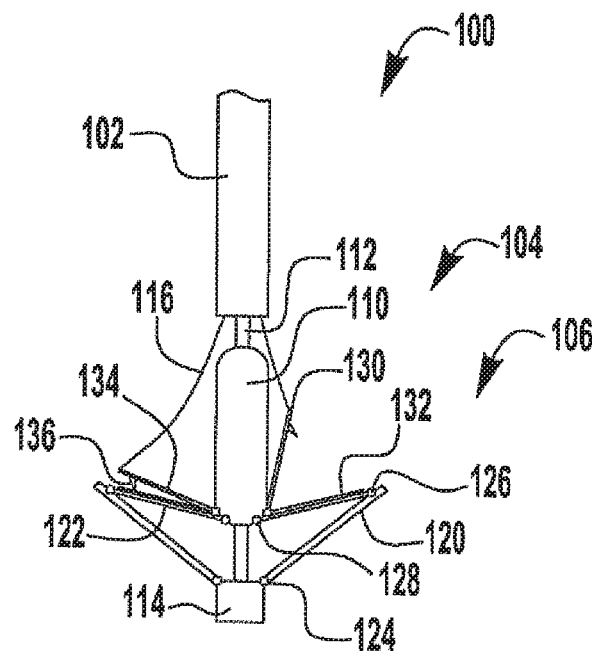
Figure 13:
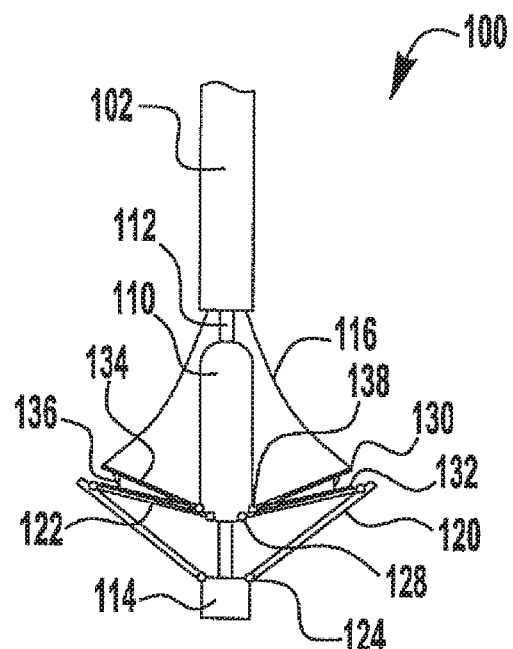

Referring now to FIGS. 11-13, the device 100 is shown in a partially open, grasp-ready condition. To transition from the fully closed to the partially open condition, the actuation wire or means for actuating 112 is extended to push the cap 114 away from the coaption element or means for coapting 110, thereby pulling on the outer paddles 120, which in turn pulls on the inner paddles 122, causing the anchor portion 106 to partially unfold. The actuation lines 116 are also retracted to open the clasps 130 so that the leaflets can be grasped. In the example illustrated by FIG. 11, the pair of inner and outer paddles 122, 120 are moved in unison, rather than independently, by a single actuation wire or means for actuating 112. Also, the positions of the clasps 130 are dependent on the positions of the paddles 122, 120. For example, referring to FIG. 10 closing the paddles 122, 120 also closes the clasps.

FIG. 11A illustrates an exemplary embodiment where the paddles 120, 122 are independently controllable. The device 100A illustrated by FIG. 11A is similar to the device illustrated by FIG. 11, except the device 100A includes two independent actuation wires 112A, 112B that are coupled to two independent caps 114A, 114B. To transition a first inner paddle and a first outer paddle from the fully closed to the partially open condition, the actuation wire or means for actuating 112A is extended to push the cap 114A away from the coaption element or means for coapting 110, thereby pulling on the outer paddle 120, which in turn pulls on the inner paddle 122, causing the first anchor portion 106 to partially unfold. To transition a second inner paddle and a second outer paddle from the fully closed to the partially open condition, the actuation wire or means for actuating 112B is extended to push the cap 114 away from the coaption element or means for coapting 110, thereby pulling on the outer paddle 120, which in turn pulls on the inner paddle 122, causing the second anchor portion 106 to partially unfold. The independent paddle control illustrated by FIG. 11A can be implemented on any of the devices disclosed by the present application.

Referring now to FIG. 12, one of the actuation lines 116 is extended to allow one of the clasps 130 to close. Referring now to FIG. 13, the other actuation line 116 is extended to allow the other clasp 130 to close. Either or both of the actuation lines 116 may be repeatedly actuated to repeatedly open and close the barbed clasps 130.

Figure 14:
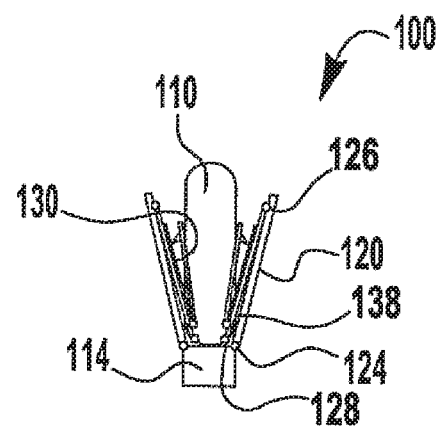

Referring now to FIG. 14, the device 100 is shown in a fully closed and deployed condition. The delivery sheath or means for delivery 102 and actuation wire or means for actuating 112 are retracted and the paddles 120, 122 and clasps 130 remain in a fully closed position. Once deployed, the device 100 may be maintained in the fully closed position with a mechanical latch or may be biased to remain closed through the use of spring materials, such as steel, other metals, plastics, composites, etc. or shape-memory alloys such as Nitinol. For example, the jointed or flexible portions 124, 126, 128, 138, and/or the inner and outer paddles 122, and/or an additional biasing component (see component 524 in FIG. 28) may be formed of metals such as steel or shape-memory alloy, such as Nitinol—produced in a wire, sheet, tubing, or laser sintered powder—and are biased to hold the outer paddles 120 closed around the coaption element or means for coapting 110 and the barbed clasps 130 pinched around native leaflets. Similarly, the fixed and moveable arms 132, 134 of the barbed clasps 130 are biased to pinch the leaflets. In certain embodiments, the joint portions 124, 126, 128, 138, and/or the inner and outer paddles 122, and/or an additional biasing component (see component 524 in FIG. 28) may be formed of any other suitably elastic material, such as a metal or polymer material, to maintain the device in the closed condition after implantation.

Referring now to FIGS. 226-231, the implantable device 100 is shown provided with a cover 140. The cover 140 can be a cloth material such as polyethylene cloth of a fine mesh. The cloth cover can provide a blood seal on the surface of the spacer, and/or promote rapid tissue ingrowth. The cover 140 includes first and second cover portions 142, 144 that each cover different portions of the device 100. In some embodiments, a portion of one of the first and second cover portions 142, 144 overlaps a portion of the other of the first and second cover portion 142, 144. The first and second cover portions 142, 144 can be arranged in various ways, and in some embodiments, can include an overlapping portion 146 that overlaps one of the first and second cover portions 142, 144.

Referring now to FIGS. 226-229, various arrangements of the first and second cover portions 142, 144 are shown without overlapping portions 146. Referring now to FIG. 226, the first cover portion 142 extends from the cap 114 to cover the cap 114, outer paddles 120, inner paddles 122, and the fixed arms 132 of the clasps 130. The second cover 144 covers the coaption element or means for coapting 110. Referring now to FIG. 227, the first cover portion 142 extends from the cap 114 to cover the cap 114, outer paddles 120, inner paddles 122, and the fixed arms 132 and moveable arms 134 of the clasps 130. As with the cover 140 of FIG. 226, the second cover 144 covers the coaption element or means for coapting 110. Referring now to FIG. 228, the first cover portion 142 extends from the cap 114 to cover the cap 114, outer paddles 120, inner paddles 122, and the fixed arms 132 of the clasps 130. The second cover 144 covers the coaption element or means for coapting 110 and extends from the coaption element or means for coapting 110 to cover the moveable arms 134 of the clasps 130. Referring now to FIG. 229, the first cover portion 142 extends from the cap 114 to cover the cap 114 and outer paddles 120. The second cover 144 covers the coaption element or means for coapting 110 and extends from the coaption element or means for coapting 110 to cover the inner paddles 122, and the fixed arms 132 and moveable arms 134 of the clasps 130.

Referring now to FIGS. 230-231, arrangements of the first and second cover portions 142, 144 are shown that include an overlapping portion 146. Referring now to FIG. 230, the first cover portion 142 extends from the cap 114 to cover the cap 114, outer paddles 120, inner paddles 122, and the fixed arms 132 and moveable arms 134 of the clasps 130. The second cover 144 covers the coaption element or means for coapting 110 and includes overlapping portions 146 that extend from the coaption element or means for coapting 110 to overlap a portion of the moveable arms 134 that are covered by the first cover 142. Referring now to FIG. 231, the first cover portion 142 extends from the cap 114 to cover the cap 114, outer paddles 120, inner paddles 122, and the fixed arms 132 of the clasps 130. The second cover 144 covers the coaption element or means for coapting 110 and moveable arms 134 of the clasps 130. The first cover 142 also includes overlapping portions 146 that extend from the fixed arms 132 and inner paddles 122 to overlap a portion of the moveable arms 134 and coaption element or means for coapting 110 that are covered by the second cover 144.

Figure 15:
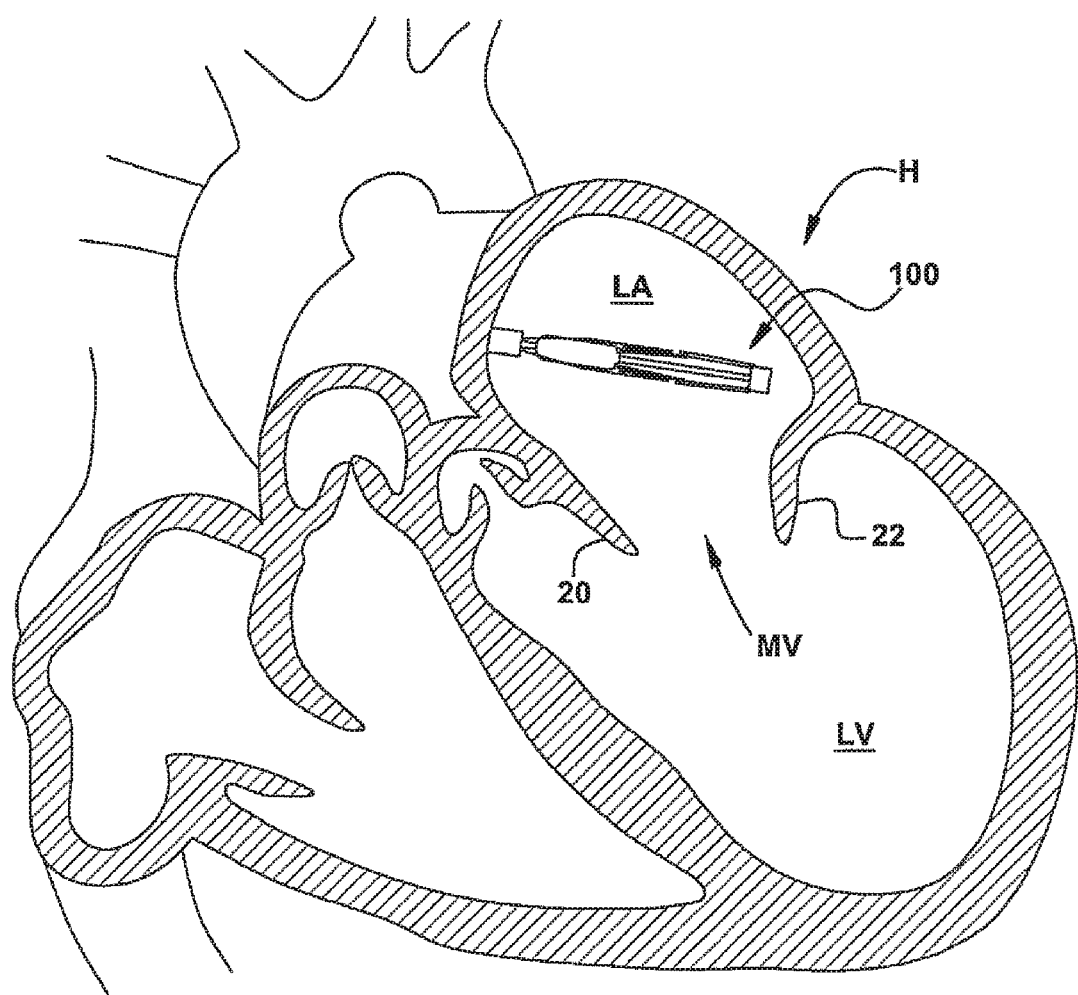
FIGS. 15-20 show the implantable prosthetic device of FIGS. 8-14 being delivered and implanted within the native mitral valve.
Figure 16:
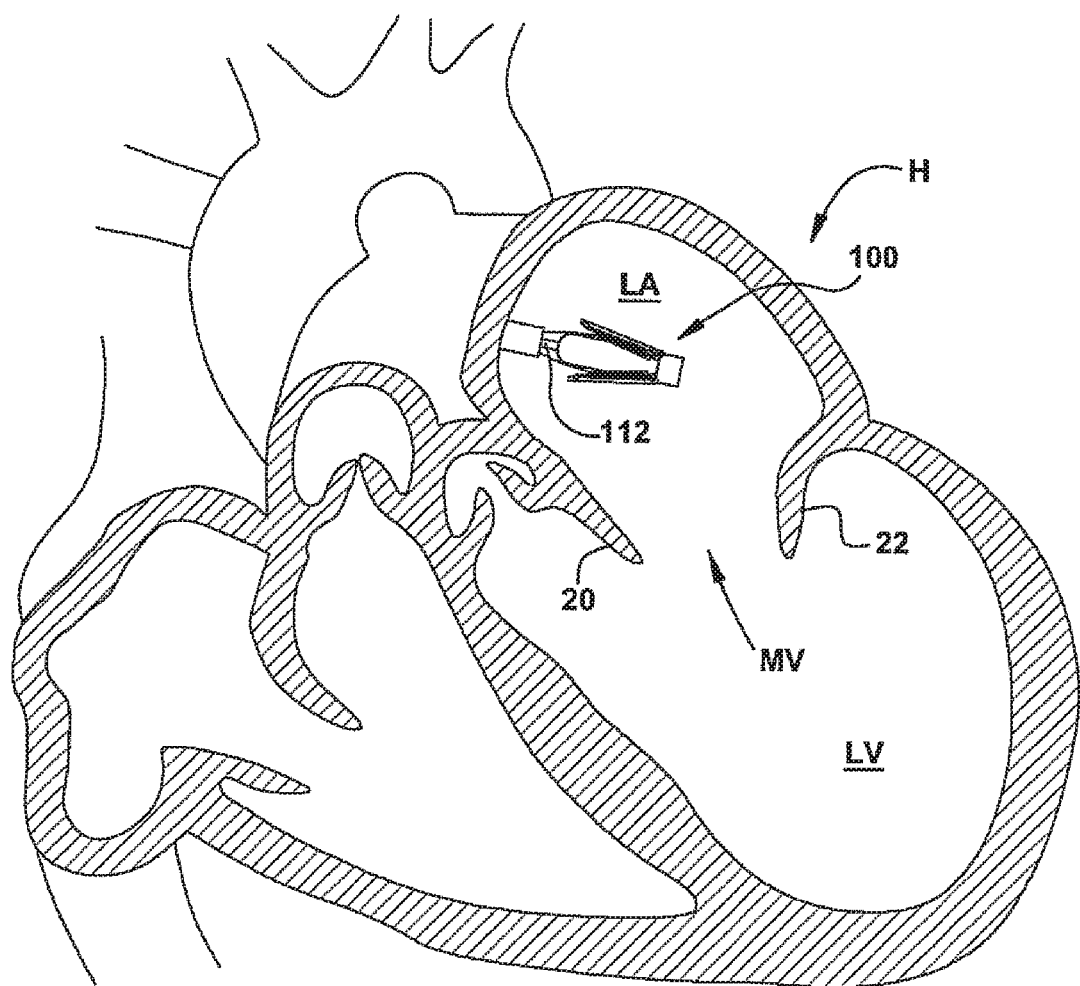
Figure 17:
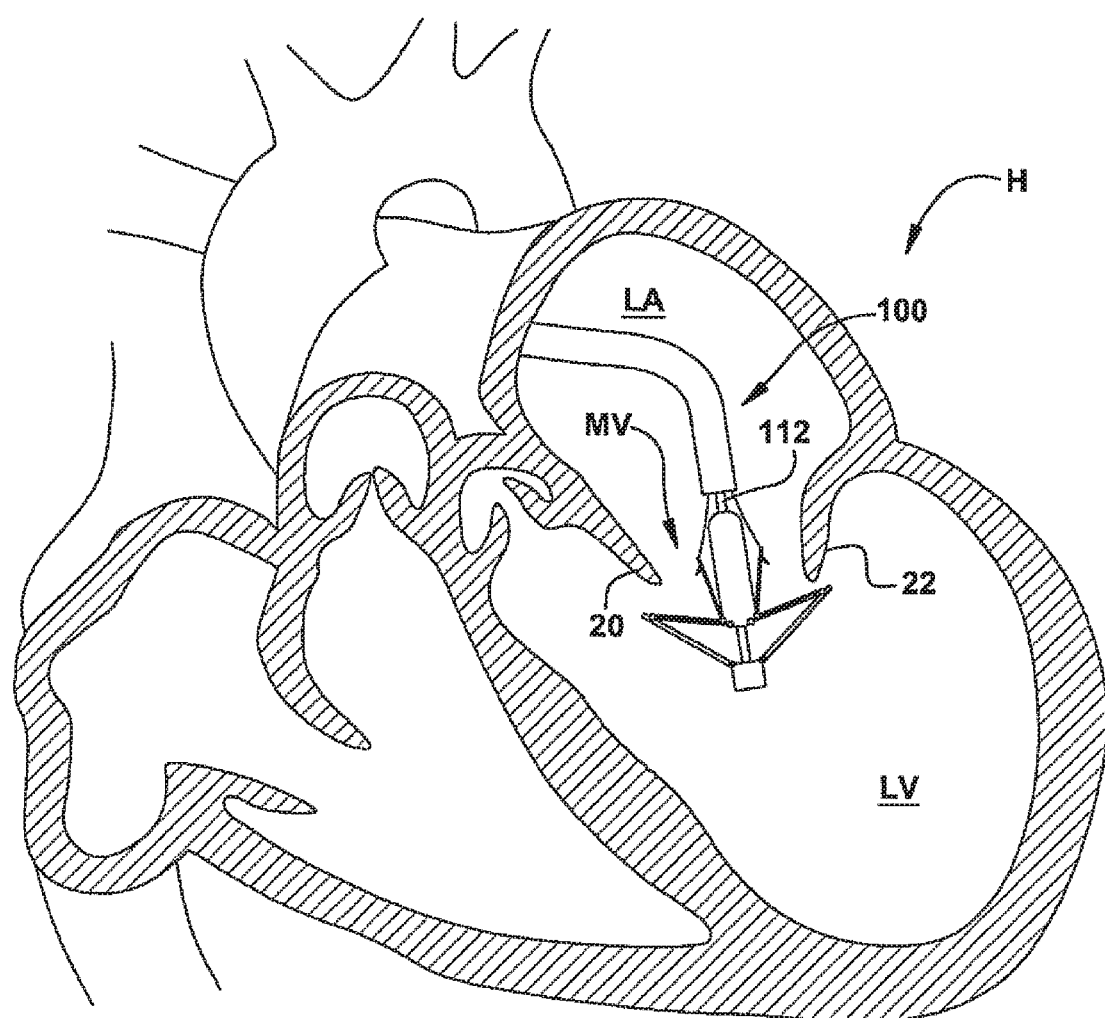
Figure 18:
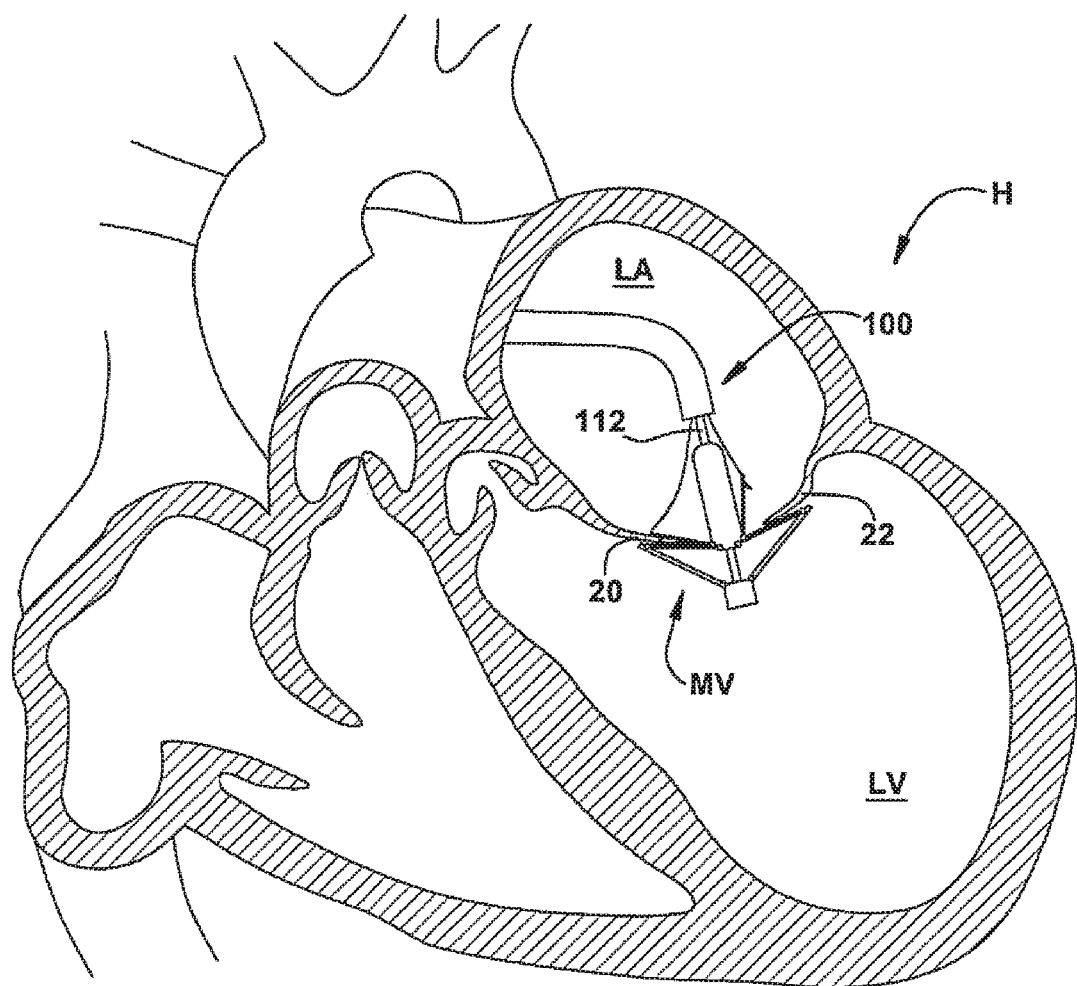
Figure 19:
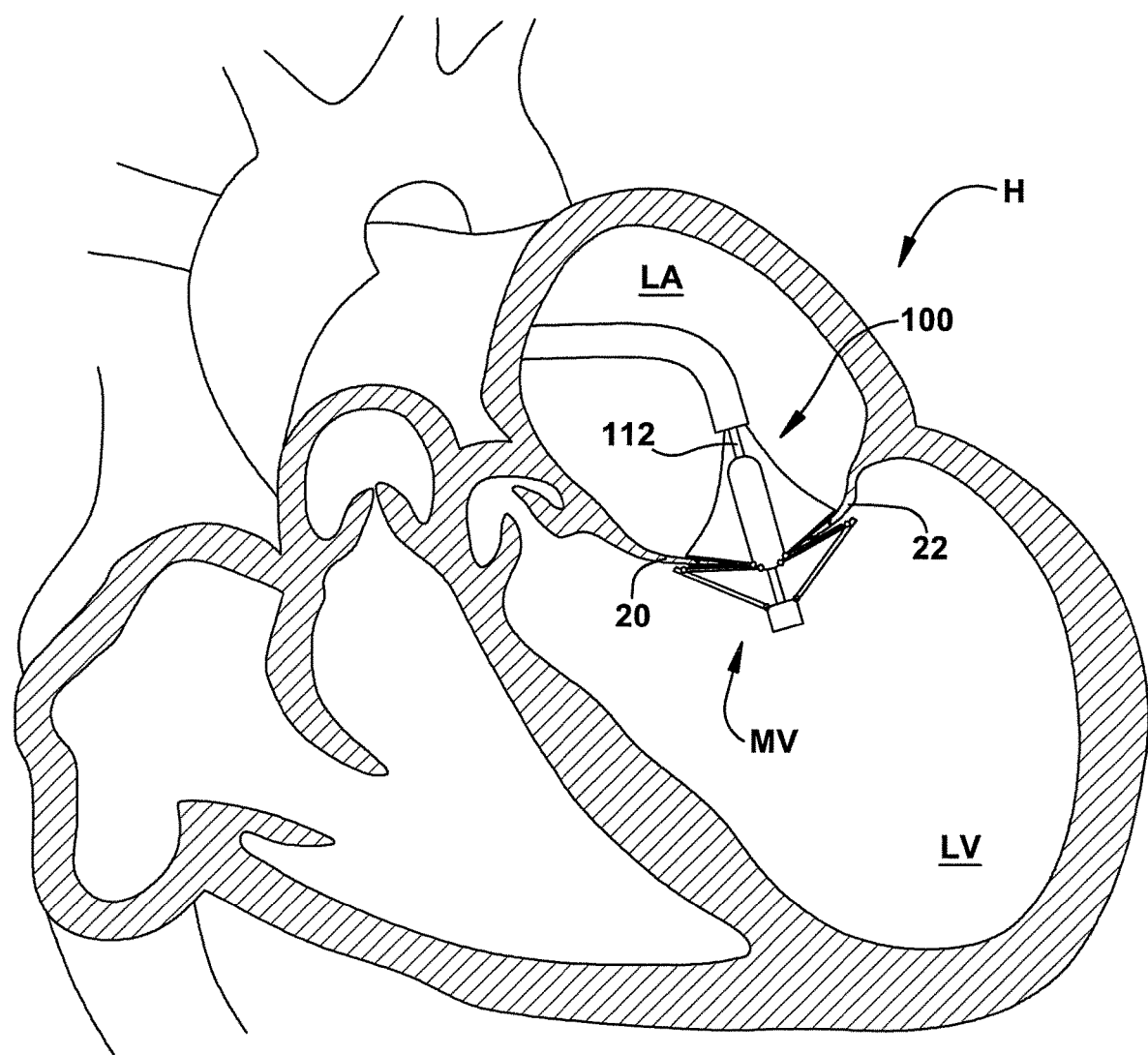
Figure 20:
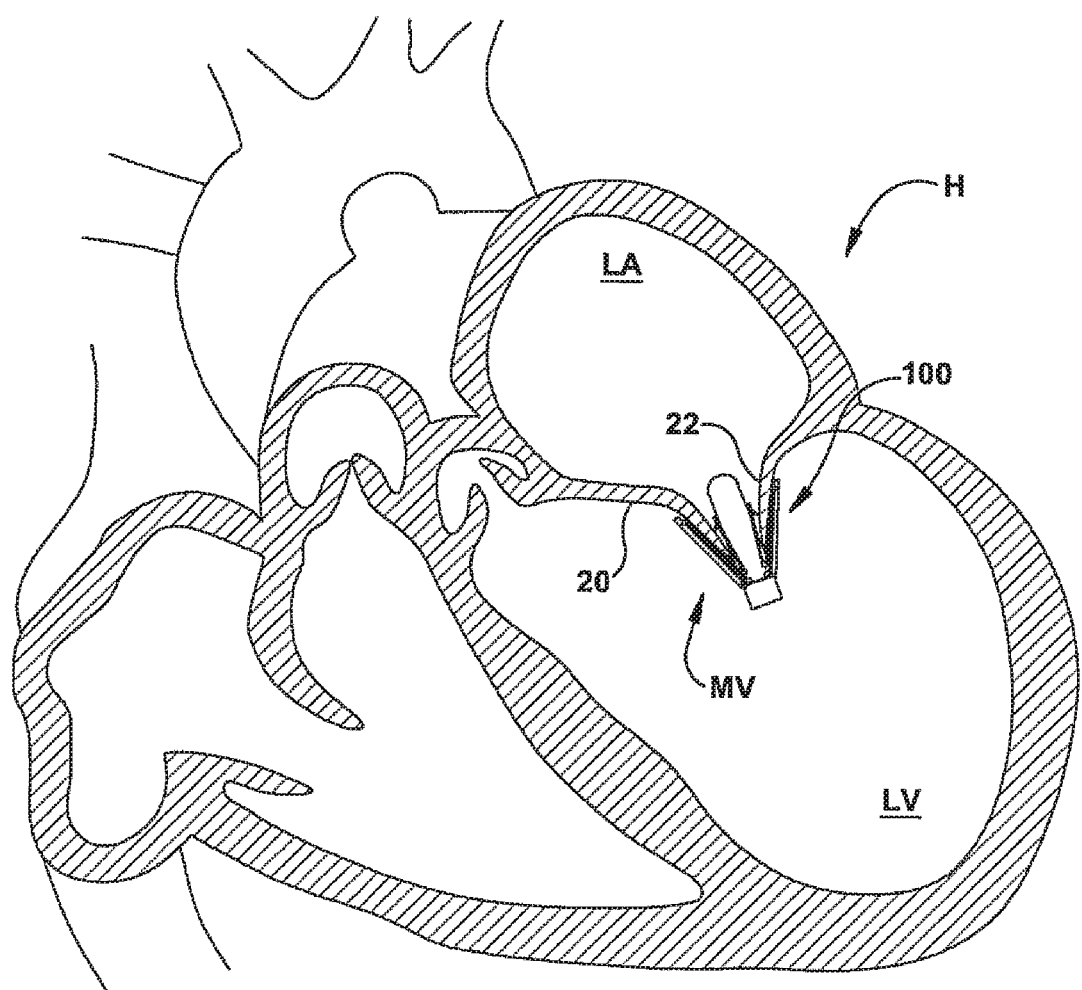

Referring now to FIGS. 15-20, the implantable device 100 of FIGS. 8-14 is shown being delivered and implanted within the native mitral valve MV of the heart H. Referring now to FIG. 15, the delivery sheath is inserted into the left atrium LA through the septum and the device 100 is deployed from the delivery sheath in the fully open condition. The actuation wire or means for actuating 112 is then retracted to move the device 100 into the fully closed condition shown in FIG. 16. As can be seen in FIG. 17, the device 100 is moved into position within the mitral valve MV into the ventricle LV and partially opened so that the leaflets 20, 22 can be grasped. Referring now to FIG. 18, an actuation line 116 is extended to close one of the clasps 130, capturing a leaflet 20. FIG. 19 shows the other actuation line 116 being then extended to close the other clasp 130, capturing the remaining leaflet 22. Lastly, as can be seen in FIG. 20, the delivery sheath or means for delivery 102 and actuation wire or means for actuating 112 and actuation lines 116 are then retracted and the device 100 is fully closed and deployed in the native mitral valve MV.

Figure 21:
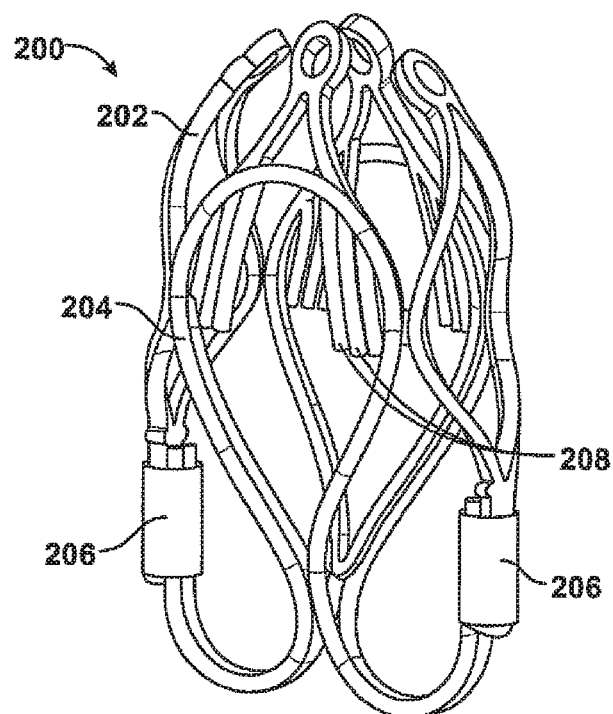
FIG. 21 shows an exemplary embodiment of an implantable prosthetic device.

Referring now to FIG. 21, an implantable prosthetic device 200 is shown. The device 200 includes an annular spacer member 202, a fabric cover (not shown), and anchors 204 extending from the spacer member 202. The ends of each anchor 204 can be coupled to respective struts of the spacer member 202 by respective sleeves 206 that can be crimped or welded around the connection portions of the anchors 206 and the struts of the spacer member 202. In another exemplary embodiment, a latching mechanism can bind the spacer member 202 to the anchor 204 within the sleeve 206. For example, the sleeve can be machined to have an interior shape that matches or is slightly smaller than the exterior shape of the ends of the spacer member 202 and the anchor 204, so that the sleeve can be friction fit on the connection portions. One or more barbs or projections 208 can be mounted on the frame of the spacer member 202. The free ends of the barbs or projections 208 can comprise various shapes including rounded, pointed, barbed, or the like. The projections 208 can exert a retaining force against native leaflets by virtue of the anchors 204, which are shaped to force the native leaflets inwardly into the spacer member 202.

Figure 22:
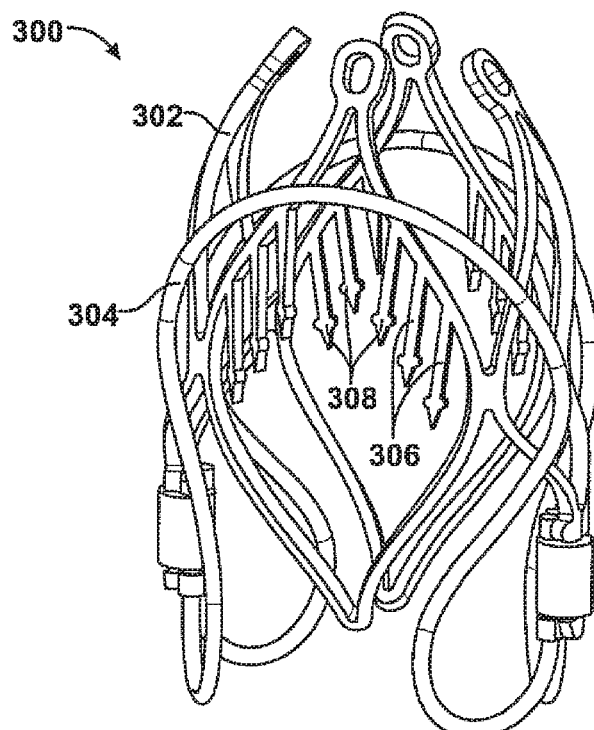
FIG. 22 shows an exemplary embodiment of an implantable prosthetic device.

Referring now to FIG. 22, an implantable prosthetic device 300 is shown. The prosthetic spacer device 300 includes an annular spacer member 302, a fabric cover (not shown), and anchors 304 extending from the spacer member 302 and can be configured similar to the prosthetic spacer device 200. One or more barbs or projections 306 can be mounted on the frame of the spacer member 302. The ends of the projections 306 can comprise stoppers 308. The stoppers 308 of the projections can be configured in a wide variety of different ways. For example, the stoppers 308 can be configured to limit the extent of the projections 306 that can engage and/or penetrate the native leaflets and/or the stoppers can be configured to prevent removal of the projections 306 from the tissue after the projections 306 have penetrated the tissue.

The anchors 304 of the prosthetic spacer device 300 can be configured similar to the anchors 204 of the prosthetic spacer device 200 except that the curve of each anchor 304 comprises a larger radius than the anchors 204. As such, the anchors 304 cover a relatively larger portion of the spacer member 302 than the anchors 204. This can, for example, distribute the clamping force of the anchors 304 against the native leaflets over a relatively larger surface of the native leaflets in order to further protect the native leaflet tissue.

Additional details regarding the prosthetic spacer devices can be found, for example, in U.S. Patent Application Publication No. 2016/0331523 and U.S. Provisional Application No. 62/161,688, which applications are incorporated by reference herein. The devices 200, 300 can include any other features for an implantable prosthetic device discussed in the present application, and the device 200, 300 can be positioned to engage valve tissue 20, 22 as part of any suitable valve repair system (e.g., any valve repair system disclosed in the present application).

Referring now to FIGS. 23-27, an exemplary embodiment of an implantable prosthetic spacer device 400 is shown. The device 400 can include any other features for an implantable prosthetic device discussed in the present application, and the device 400 can be positioned to engage valve tissue 20, 22 as part of any suitable valve repair system (e.g., any valve repair system disclosed in the present application).

Figure 23:
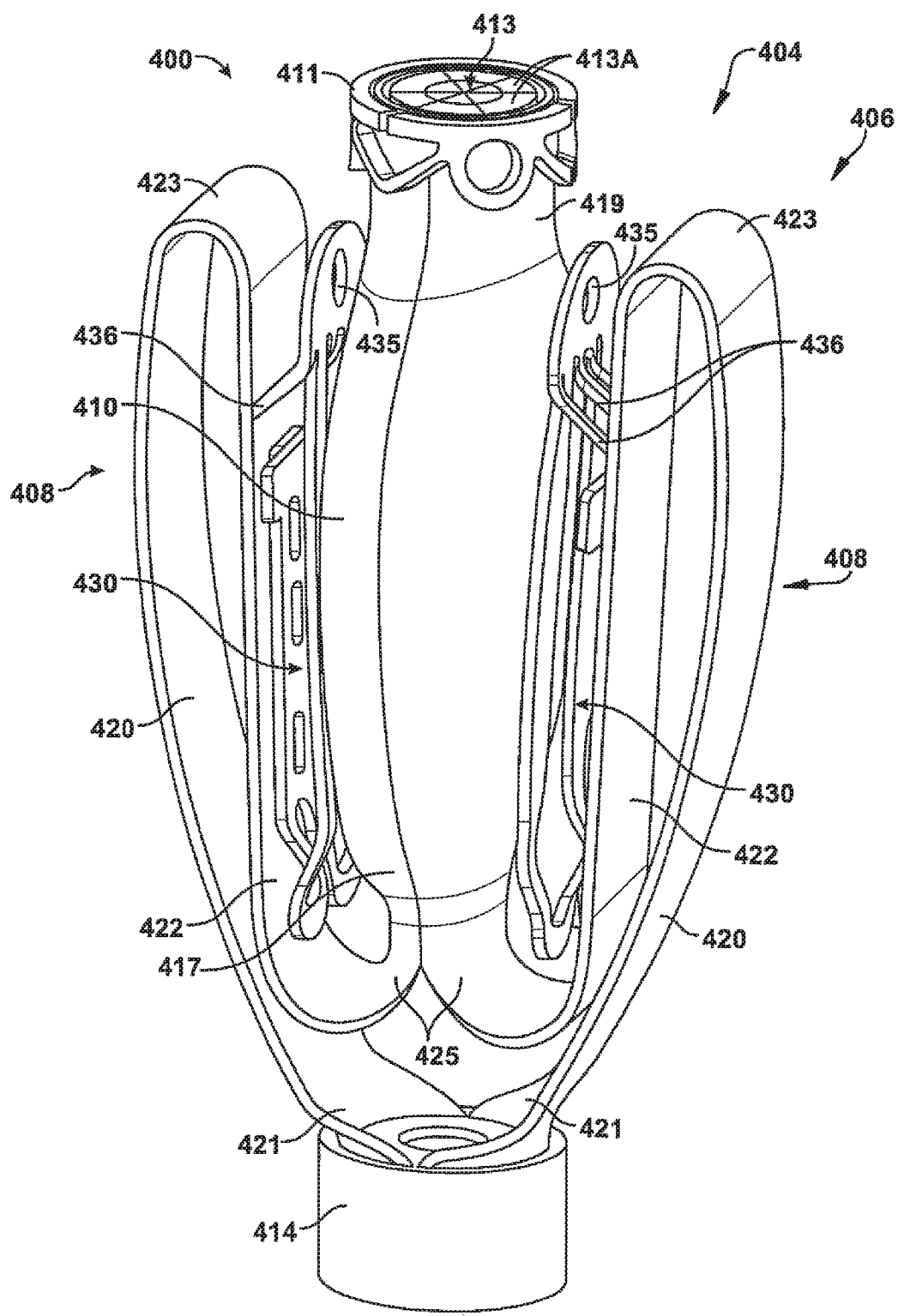
FIGS. 23-25 show an exemplary embodiment of an implantable prosthetic device.

Referring now to FIG. 23, the prosthetic spacer or coaption device 400 can include a coaption portion 404 and an anchor portion 406, the anchor portion 406 including a plurality of anchors 408. The coaption portion 404 includes a coaption or spacer member 410. The anchor portion 406 includes a plurality of paddles 420 (e.g., two in the illustrated embodiment), and a plurality of clasps 430 (e.g., two in the illustrated embodiment). A first or proximal collar 411, and a second collar or cap 414 are used to move the coaption portion 404 and the anchor portion 406 relative to one another.

Figure 25:
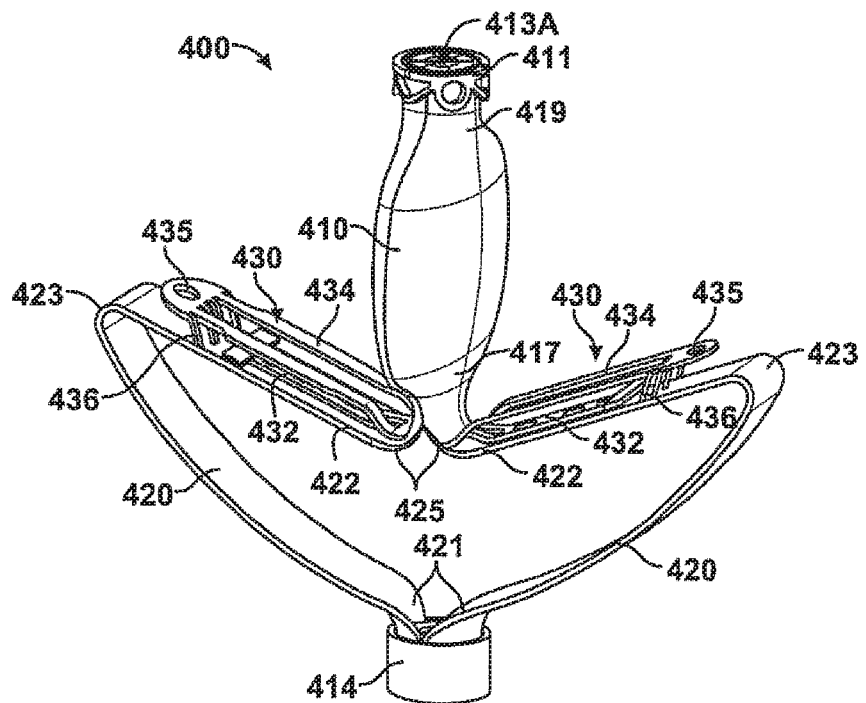

As shown in FIG. 25, first connection portions 425 of the anchors 408 can be coupled to and extend from a first portion 417 of the coaption or spacer member 410, and second connection portions 421 of the anchors 408 can be coupled to the first collar 414. The proximal collar 411 can be coupled to a second portion 419 of the coaption member 410.

The coaption member 410 and the anchors 408 can be coupled together in various ways. For example, as shown in the illustrated embodiment, the coaption member 410 and the anchors 408 can be coupled together by integrally forming the coaption member 410 and the anchors 408 as a single, unitary component. This can be accomplished, for example, by forming the coaption member 410 and the anchors 408 from a braided or woven material, such as braided or woven nitinol wire. In other embodiments, the coaption member 410 and the anchors 408 can be coupled together by welding, fasteners, adhesive, joint connections, sutures, friction fittings, swaging, and/or other means for coupling.

Figure 24:
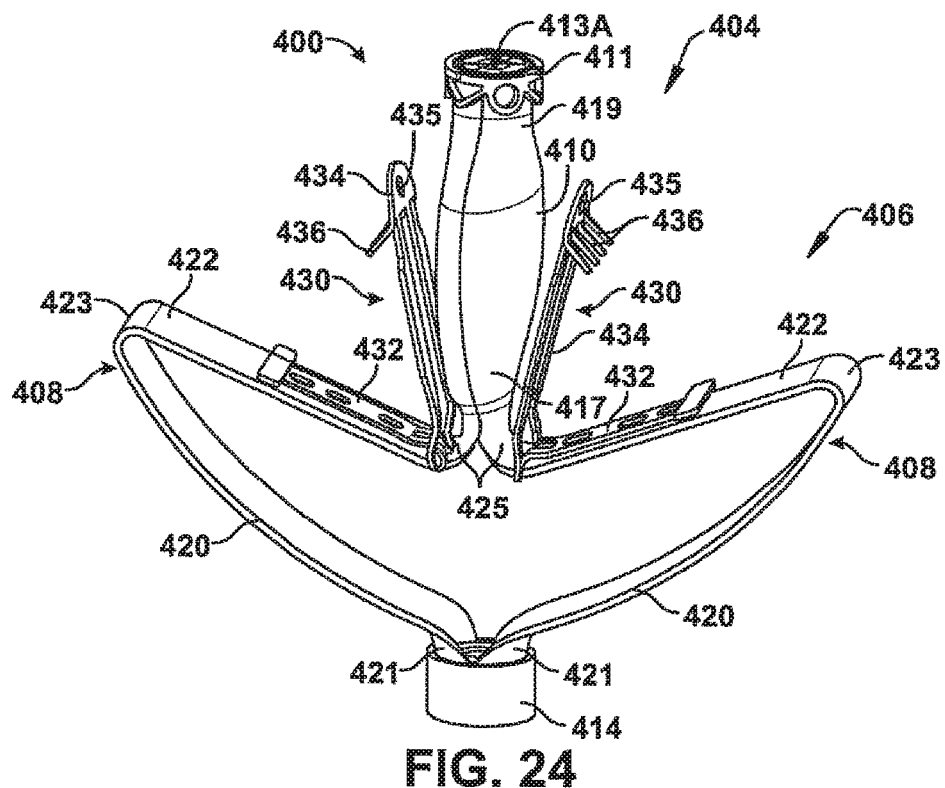

Referring now to FIG. 24, the anchors 408 can comprise first portions or outer paddles 420 and second portions or inner paddles 422 separated by joint portions 423. In this manner, the anchors 408 are configured similar to legs in that the inner paddles 422 are like upper portions of the legs, the outer paddles 420 are like lower portions of the legs, and the joint portions 423 are like knee portions of the legs. In the illustrated example, the inner paddle portion 422, the outer paddle portion 420, and the joint portion 423 are formed from a continuous strip of fabric, such as a metal fabric.

The anchors 408 can be configured to move between various configurations by axially moving the cap 414 relative to the proximal collar 411 and thus the anchors 408 relative to the coaption member 410 along a longitudinal axis extending between the first or distal and second or proximal portions 417, 419 of the coaption member 410. For example, the anchors 408 can be positioned in a straight configuration by moving the cap 414 away from the coaption member 410. In the straight configuration, the paddle portions are aligned or straight in the direction of the longitudinal axis of the device and the joint portions 423 of the anchors 408 are adjacent the longitudinal axis of the coaption member 410 (e.g., similar to the configuration shown in FIG. 59). From the straight configuration, the anchors 408 can be moved to a fully folded configuration (e.g., FIG. 23) by moving the toward the coaption member 410. Initially as the cap 414 moves toward the coaption member 410, the anchors 408 bend at the joint portions 423, 425, 421 and the joint portions 423 move radially outwardly relative to the longitudinal axis of the coaption member 410 and axially toward the first portion 414 of the coaption member 410, as shown in FIGS. 24-25. As the cap 414 continues to move toward the coaption member 410, the joint portions 423 move radially inwardly relative to the longitudinal axis of the coaption member 410 and axially toward the proximal portion 419 of the coaption member 410, as shown in FIG. 23.

In some embodiments, an angle between the inner paddles 422 of the anchors 408 and the coaption member 410 can be approximately 180 degrees when the anchors 408 are in the straight configuration (see, e.g., FIG. 59), and the angle between the inner paddles 422 of the anchors 408 and the coaption member 410 can be approximately 0 degrees when the anchors 408 are in the fully folded configuration (See FIG. 23). The anchors 408 can be positioned in various partially folded configurations such that the angle between the inner paddles 422 of the anchors 408 and the coaption member 410 can be approximately 10-170 degrees or approximately 45-135 degrees.

Configuring the prosthetic spacer device 400 such that the anchors 408 can extend to a straight or approximately straight configuration (e.g. approximately 120-180 degrees relative to the coaption member 410) can provide several advantages. For example, this can reduce the radial crimp profile of the prosthetic spacer device 400. It can also make it easier to grasp the native leaflets by providing a larger opening in which to grasp the native leaflets. Additionally, the relatively narrow, straight configuration can prevent or reduce the likelihood that the prosthetic spacer device 400 will become entangled in native anatomy (e.g., chordae tendineae) when positioning and/or retrieving the prosthetic spacer device 400 into the delivery apparatus.

Referring again to FIG. 24, the clasps 430 can comprise attachment or fixed portions 432 and arm or moveable portions 434. The attachment or fixed portions 432 can be coupled to the inner paddles 422 of the anchors 408 in various ways such as with sutures, adhesive, fasteners, welding, stitching, swaging, friction fit and/or other means for coupling.

The moveable portions 434 can pivot relative to the fixed portions 432 between an open configuration (e.g., FIG. 24) and a closed configuration (FIGS. 23 and 25). In some embodiments, the clasps 430 can be biased to the closed configuration. In the open configuration, the fixed portions 432 and the moveable portions 434 pivot away from each other such that native leaflets can be positioned between the fixed portions 432 and the moveable portions 434. In the closed configuration, the fixed portions 432 and the moveable portions 434 pivot toward each other, thereby clamping the native leaflets between the fixed portions 432 and the moveable portions 434.

Figure 26:
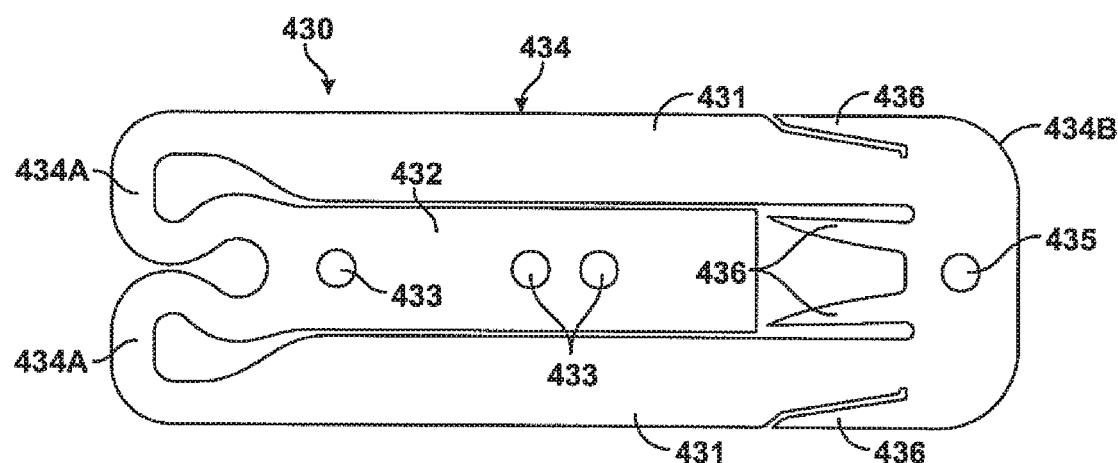
FIGS. 26 and 27 show an exemplary embodiment of a barbed clasp for use in an implantable prosthetic device.
Figure 27:
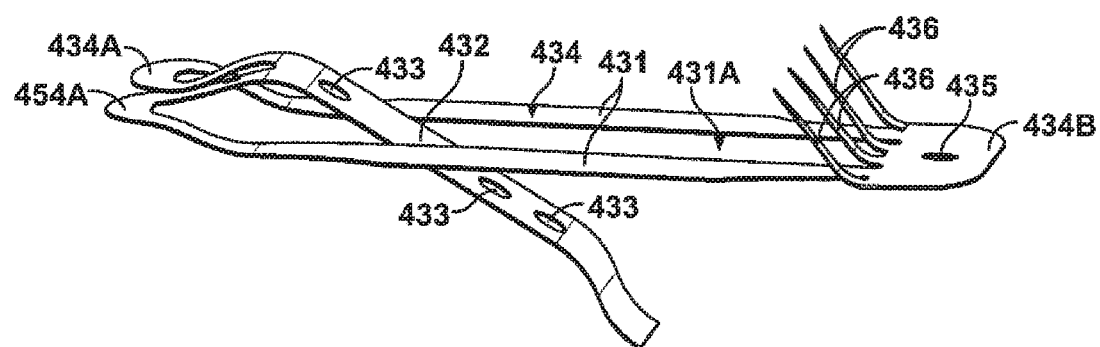

Referring to FIGS. 26-27, clasps 430 are shown in top and perspective views. The fixed portions 432 (only one shown in FIGS. 26-27) can comprise one or more openings 433 (e.g., three in the illustrated embodiment). At least some of the openings 433 can be used to couple the fixed portions 432 to the anchors 408. For example, sutures and/or fasteners can extend through the openings 433 to couple the fixed portions 432 to the anchors 408 or other attachments, such as welding, adhesives, etc. can be used.

The moveable portions 434 can comprise one or more side beams 431. When two side beams are included as illustrated, the side beams can be spaced apart to form slots 431A. The slots 431A can be configured to receive the fixed portions 432. The moveable portions 434 can also include spring portions 434A that are coupled to the fixed portions 432 and barb support portions 434B disposed opposite the spring portions 434A.

The barb support portions 434B can comprise gripper or attachment elements such as barbs 436 and/or other means for frictionally engaging native leaflet tissue. The gripper elements can be configured to engage and/or penetrate the native leaflet tissue to help retain the native leaflets between the fixed portions 432 and moveable portions 434 of the clasps 430.

The barb support portions 434B can also comprise eyelets 435, which can be used to couple the barb support portions 434B to an actuation mechanism configured to pivot the moveable portions 434 relative to the fixed portions 432. Additional details regarding coupling the clasps 430 to the actuation mechanism are provided below.

In some embodiments, the clasps 430 can be formed from a shape memory material such as nitinol, stainless steel, and/or shape memory polymers. In certain embodiments, the clasps 430 can be formed by laser-cutting a piece of flat sheet material (e.g., nitinol) or a tube in the configuration shown in FIG. 26 or a similar or different configuration and then shape-setting the clasp 430 in the configuration shown in FIG. 27.

Shape-setting the clasps 430 in this manner can provide several advantages. For example, the clasps 430 can optionally be compressed from the shape-set configuration (e.g., FIG. 27) to the flat configuration (e.g., FIG. 26), or another configuration which reduces the radial crimp profile of the clasps 430. For example, the barbs can optionally be compressed to a flat configuration. Reducing the radial crimp profile can improve trackability and retrievability of the prosthetic spacer device 400 relative to a catheter shaft of a delivery apparatus because barbs 440 are pointing radially inwardly toward the anchors 408 when the prosthetic spacer device 400 is advanced through or retrieved into the catheter shaft (see, e.g., FIG. 33). This can prevent or reduce the likelihood that the clasps 430 may snag or skive the catheter shaft.

In addition, shape-setting the clasps 430 in the configuration shown in FIG. 27 can increase the clamping force of the clasps 430 when the clasps 430 are in the closed configuration. This is because the moveable portions 434 are shape-set relative to the fixed portions 432 to a first position (e.g., FIG. 27) which is beyond the position the moveable portions 434 can achieve when the clasps 430 are attached to the anchors 408 (e.g., FIG. 25) because the anchors 408 prevent the moveable portions 434 from further movement toward the shape-set configuration. This results in moveable portions 434 having a preload (i.e., the clamping force is greater than zero) when the clasps 430 are attached to the anchors 408 and in the closed configuration. Thus, shape-setting the clasps 430 in the FIG. 27 configuration can increase the clamping force of the clasps 430 compared to clasps that are shape-set in the closed configuration.

The magnitude of the preload of the clasps 430 can be altered by adjusting the angle in which the moveable portions 434 are shape-set relative to the fixed portions 432. For example, increasing the relative angle between the moveable portions 434 and the fixed portions 432 increases the preload, and decreasing the relative angle between the moveable portions 434 and the fixed portions 432 decreases the preload.

In some embodiments, the proximal collar 411 and/or the coaption member 410 can comprise a hemostatic seal 413 configured to reduce or prevent blood from flowing through the proximal collar 411 and/or the coaption member 410. For example, in some embodiments, the hemostatic seal 413 can comprise a plurality of flexible flaps 413A, as shown in FIG. 23. The flaps 413A can be configured to pivot from a sealed configuration to an open configuration to allow a shaft of a delivery apparatus to extend through the second collar 410. In one exemplary embodiment, the flaps 413A form a seal around the shaft of the delivery apparatus. When the shaft of the delivery apparatus is removed, the flaps 413A can be configured to return to the sealed configuration from the open configuration.

Figure 23A:
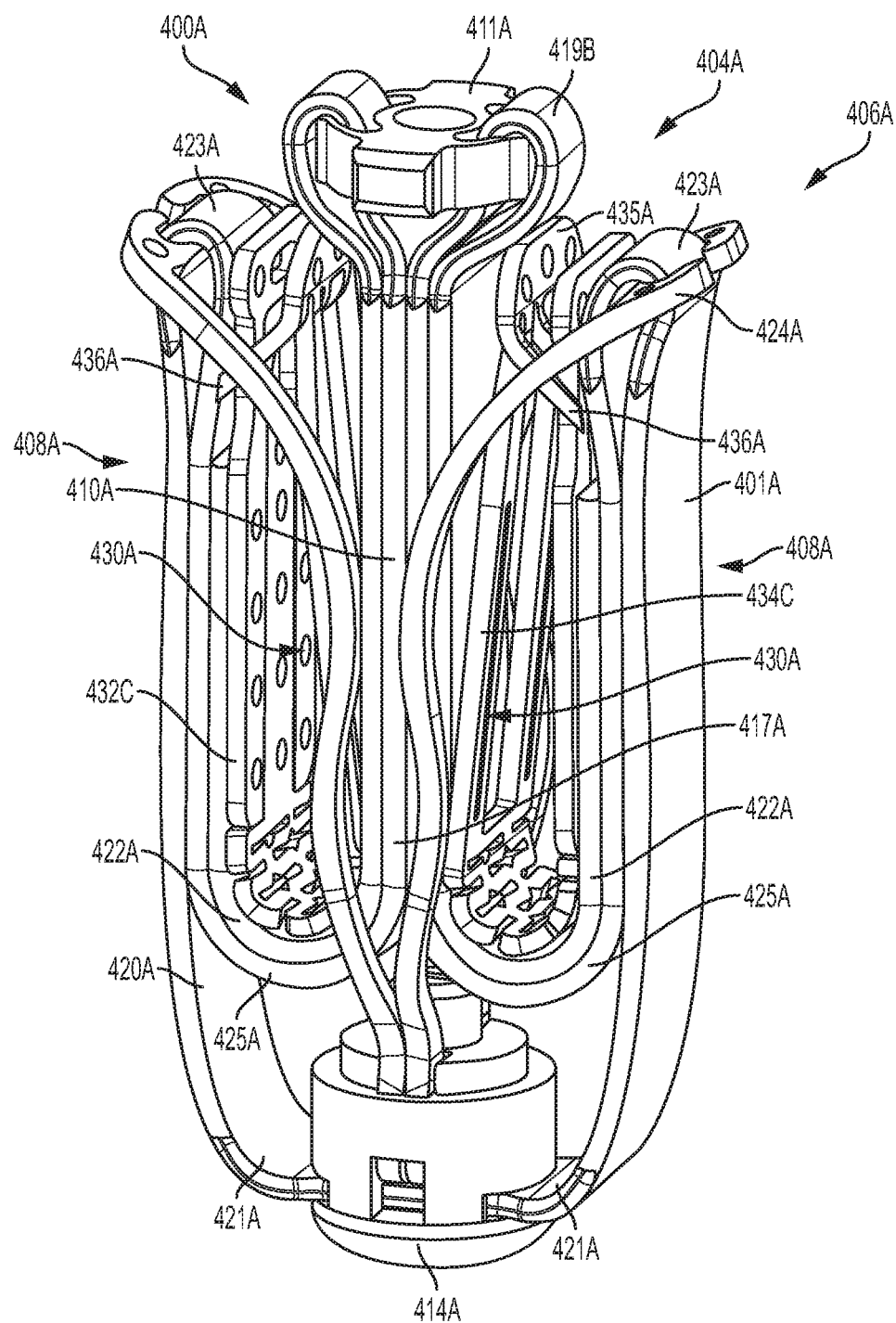
FIG. 23A shows an exemplary embodiment of an implantable prosthetic device.

Referring now to FIG. 23A, an exemplary embodiment of an implantable prosthetic spacer device 400A is shown. The device 400A can include any other features for an implantable prosthetic device discussed in the present application, and the device 400A can be positioned to engage valve tissue 20, 22 as part of any suitable valve repair system (e.g., any valve repair system disclosed in the present application).

The prosthetic spacer or coaption device 400A can include a coaption portion 404A and an anchor portion 406A, the anchor portion 406A including a plurality of anchors 408A. The coaption portion 404A includes a coaption member or spacer 410A. The anchor portion 406A includes a plurality of paddles 420A (e.g., two in the illustrated embodiment), and a plurality of clasps 430A (e.g., two in the illustrated embodiment). A first or proximal collar 411A, and a second collar or cap 414A are used to move the coaption portion 404A and the anchor portion 406A relative to one another.

The coaption member 410A extends from a proximal portion 419A assembled to the collar 411A to a distal portion 417A that connects to the anchors 408A. The coaption member 410A and the anchors 408A can be coupled together in various ways. For example, as shown in the illustrated embodiment, the coaption member 410A and the anchors 408A can be coupled together by integrally forming the coaption member 410A and the anchors 408A as a single, unitary component. This can be accomplished, for example, by forming the coaption member 410A and the anchors 408A from a continuous strip 401A of a braided or woven material, such as braided or woven nitinol wire.

The anchors 408A are attached to the coaption member 410A by hinge portions 425A and to the cap 414A by hinge portions 421A. The anchors 408A can comprise first portions or outer paddles 420A and second portions or inner paddles 422A separated by joint portions 423A. The joint portions 423A are attached to paddle frames 424A that are hingeably attached to the cap 414A. In this manner, the anchors 408A are configured similar to legs in that the inner paddles 422A are like upper portions of the legs, the outer paddles 420A are like lower portions of the legs, and the joint portions 423A are like knee portions of the legs. In the illustrated example, the inner paddle portion 422A, the outer paddle portion 420A, and the joint portion 423A are formed from the continuous strip of fabric 401A, such as a metal fabric.

The anchors 408A can be configured to move between various configurations by axially moving the cap 414A relative to the proximal collar 411A and thus the anchors 408A relative to the coaption member 410A along a longitudinal axis extending between the cap 414A and the proximal collar 411A. For example, the anchors 408 can be positioned in a straight configuration (see FIG. 60A) by moving the cap 414A away from the coaption member 410A. In the straight configuration, the paddle portions 420A, 422A are aligned or straight in the direction of the longitudinal axis of the device and the joint portions 423A of the anchors 408A are adjacent the longitudinal axis of the coaption member 410A (e.g., similar to the configuration shown in FIG. 60A). From the straight configuration, the anchors 408 can be moved to a fully folded configuration (e.g., FIG. 23A) by moving the cap 414A toward the coaption member 410A. Initially, as the cap 414A moves toward the coaption member 410A, the anchors 408A bend at joint portions 421A, 423A, 425A, and the joint portions 423A move radially outwardly relative to the longitudinal axis of the device 400A and axially toward the distal portion 417A of the coaption member 410A, as shown in FIGS. 53A and 54A. As the cap 414A continues to move toward the coaption member 410A, the joint portions 423A move radially inwardly relative to the longitudinal axis of the device 400A and axially toward the proximal portion 419A of the coaption member 410A, as shown in FIG. 23A.

In some embodiments, an angle between the inner paddles 422A of the anchors 408A and the coaption member 410A can be approximately 180 degrees when the anchors 408A are in the straight configuration (see, e.g., FIG. 60A), and the angle between the inner paddles 422A of the anchors 408A and the coaption member 410A can be approximately 0 degrees when the anchors 408A are in the fully folded configuration (see FIG. 23A). The anchors 408A can be positioned in various partially folded configurations such that the angle between the inner paddles 422A of the anchors 408A and the coaption member 410A can be approximately 10-170 degrees or approximately 45-135 degrees.

Configuring the prosthetic spacer device 400A such that the anchors 408A can extend to a straight or approximately straight configuration (e.g. approximately 120-180 degrees relative to the coaption member 410A) can provide several advantages. For example, this can reduce the radial crimp profile of the prosthetic spacer device 400A. It can also make it easier to grasp the native leaflets by providing a larger opening in which to grasp the native leaflets. Additionally, the relatively narrow, straight configuration can prevent or reduce the likelihood that the prosthetic spacer device 400A will become entangled in native anatomy (e.g., chordae tendineae) when positioning and/or retrieving the prosthetic spacer device 400A into the delivery apparatus.

The clasps 430A can comprise attachment or fixed portions 432C and arm or moveable portions 434C. The attachment or fixed portions 432C can be coupled to the inner paddles 422A of the anchors 408A in various ways such as with sutures, adhesive, fasteners, welding, stitching, swaging, friction fit and/or other means for coupling. The clasps 430A are similar to the clasps 430.

The moveable portions 434C can pivot relative to the fixed portions 432C between an open configuration (e.g., FIG. 54A) and a closed configuration (FIG. 53A). In some embodiments, the clasps 430A can be biased to the closed configuration. In the open configuration, the fixed portions 432C and the moveable portions 434C pivot or flex away from each other such that native leaflets can be positioned between the fixed portions 432C and the moveable portions 434C. In the closed configuration, the fixed portions 432C and the moveable portions 434C pivot or flex toward each other, thereby clamping the native leaflets between the fixed portions 432C and the moveable portions 434C.

The strip 401A is attached the collar 411A, cap 414A, paddle frames 424A, clasps 430A to form both the coaption portion 404A and the anchor portion 406A of the device 400A. In the illustrated embodiment, the coaption member 410A, hinge portions 421A, 423A, 425A, outer paddles 420A, and inner paddles 422A are formed from the continuous strip 401A. The continuous strip 401A may be a single layer of material or may include two or more layers. In certain embodiments, portions of the device 400A have a single layer of the strip of material 401A and other portions are formed from multiple overlapping or overlying layers of the strip of material 401A. For example, FIG. 23A shows the coaption member 410A and inner paddles 422A formed from multiple overlapping layers of the strip of material 401A. The single continuous strip of material 401A can start and end in various locations of the device 400A. The ends of the strip of material 401A can be in the same location or different locations of the device 400A. For example, in the illustrated embodiment of FIG. 23A, the strip of material begins and ends in the location of the inner paddles 422A.

Figure 30:
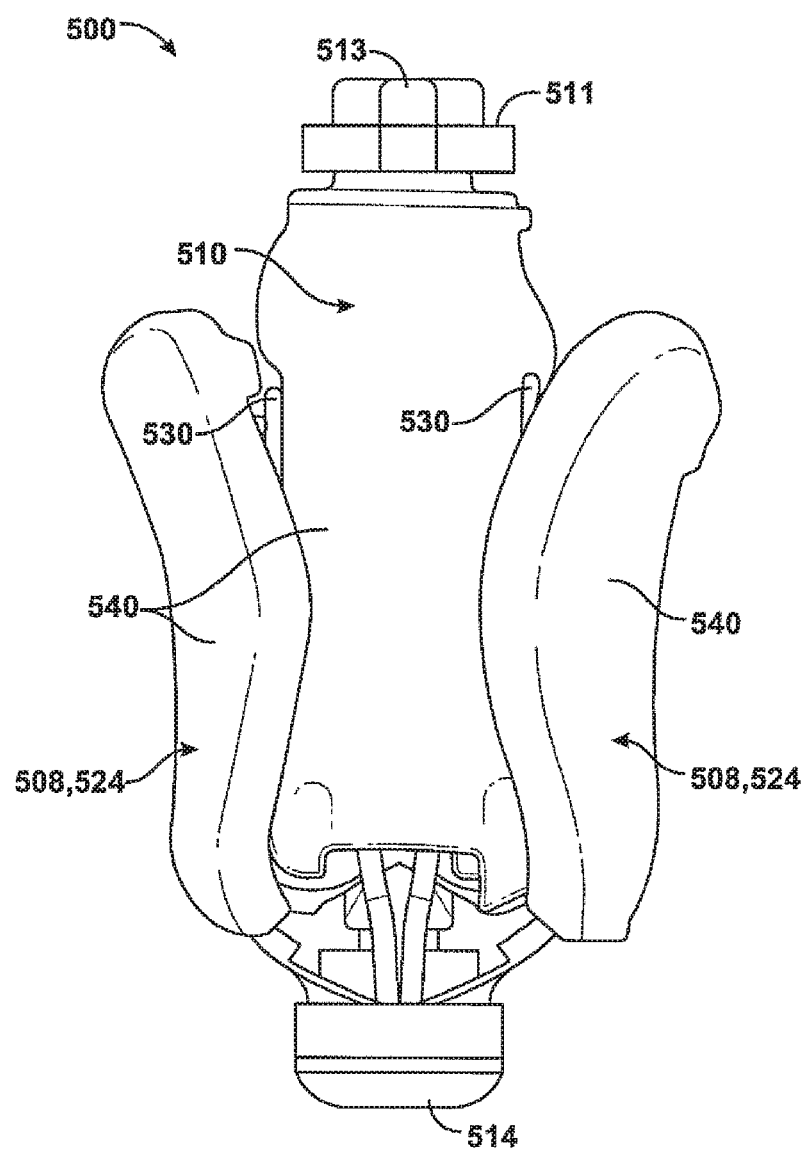
Figure 30A:
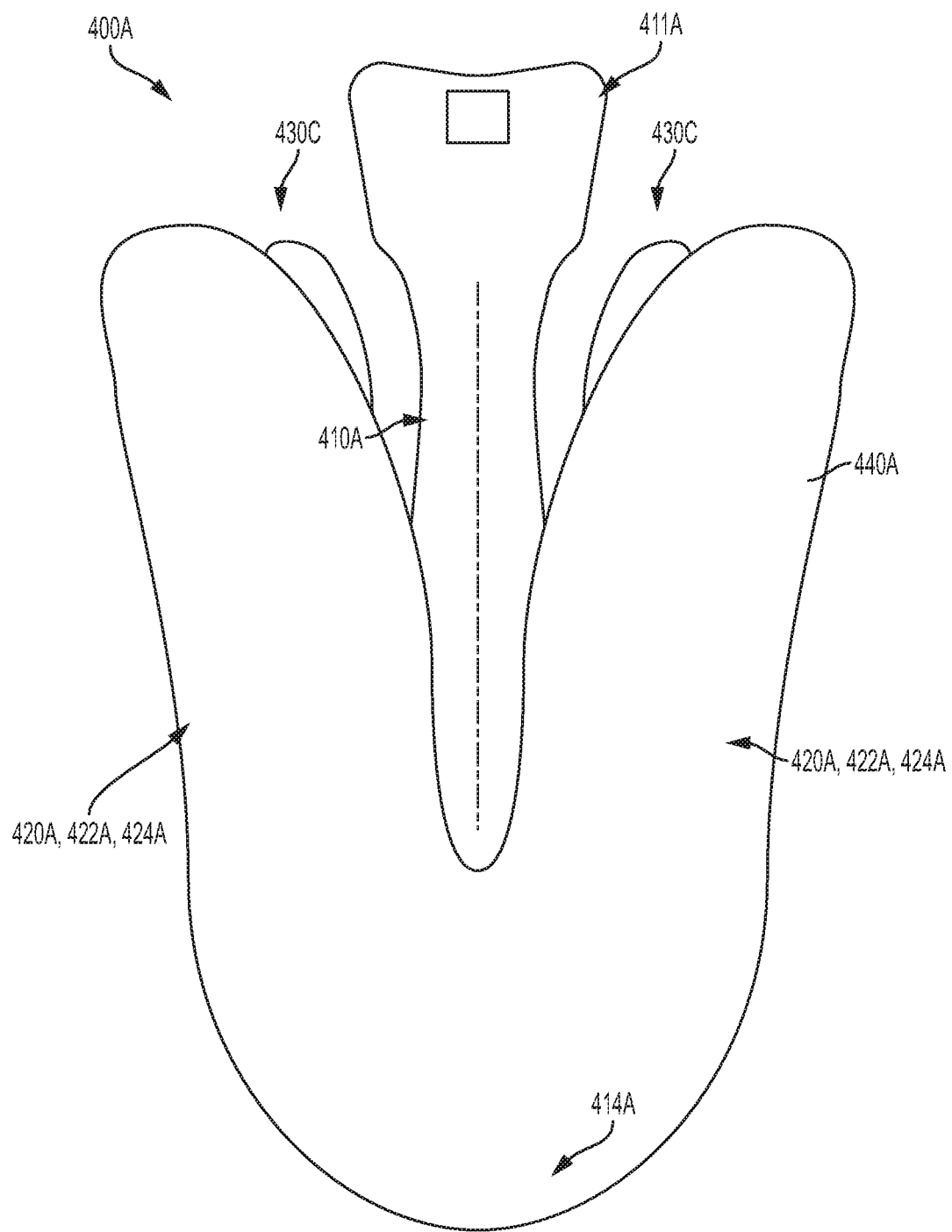
FIG. 30A shows an exemplary embodiment of an implantable prosthetic device.

Referring now to FIG. 30A, the exemplary implantable prosthetic device 400A is shown covered with a cover 440A. The cover 440A is disposed on the coaption member 410A, the collar 411A, the cap 414A, the paddles 420A, 422A, the paddle frames 424A, and the clasps 430A. The cover 440A can be configured to prevent or reduce blood-flow through the prosthetic spacer device 400A and/or to promote native tissue ingrowth. In some embodiments, the cover 440A can be a cloth or fabric such as PET, velour, or other suitable fabric. In other embodiments, in lieu of or in addition to a fabric, the cover 440A can include a coating (e.g., polymeric material) that is applied to the prosthetic spacer device 400A.

Figure 28:
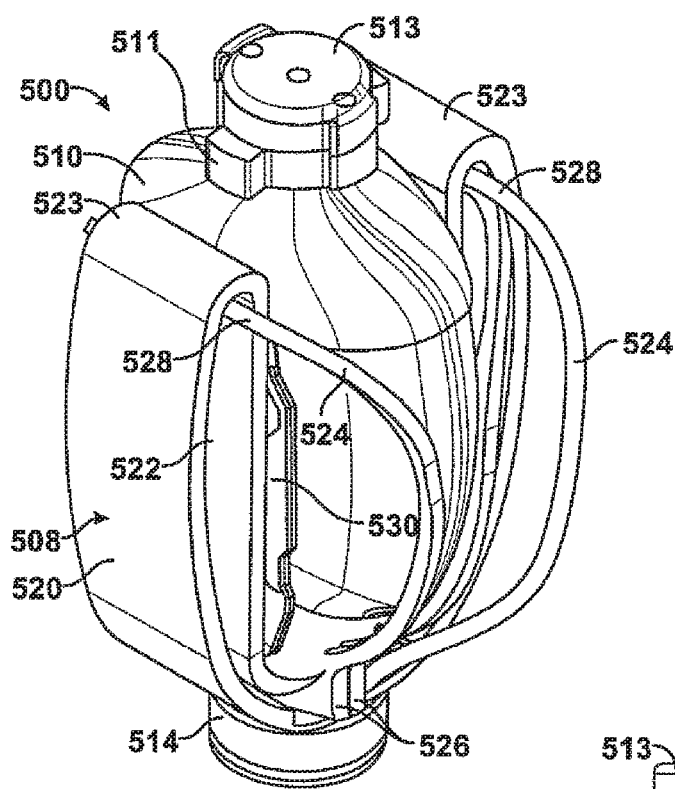
FIGS. 28-32 show an exemplary embodiment of an implantable prosthetic device.
Figure 29:
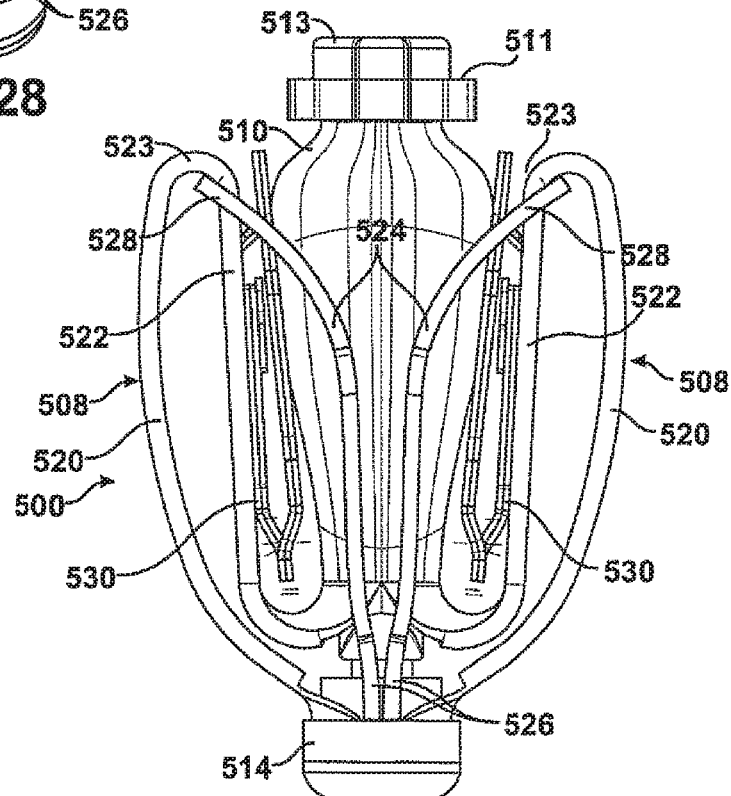

Referring now to FIGS. 28-30, an exemplary embodiment of an implantable prosthetic spacer device 500 is shown. The implantable device 500 is one of the many different configurations that the device 100 that is schematically illustrated in FIGS. 8-20 can take. The device 500 can include any other features for an implantable prosthetic device discussed in the present application, and the device 500 can be positioned to engage valve tissue 20, 22 as part of any suitable valve repair system (e.g., any valve repair system disclosed in the present application).

The prosthetic spacer device 500 can comprise a coaption element or spacer member 510, a plurality of anchors 508 that include outer paddles 520, inner paddles 522, clasps 530, a first or proximal collar 511, and a second collar or cap 514. These components of the prosthetic spacer device 500 can be configured substantially similar to the corresponding components of the prosthetic spacer device 400.

The prosthetic spacer device 500 can also include a plurality of paddle extension members or paddle frames 524. The paddle frames 524 can be configured with a round three-dimensional shape with first connection portions 526 coupled to and extending from the cap 514 and second connection portions 528 disposed opposite the first connection portions 526. The paddle frames 524 can be configured to extend circumferentially farther around the coaption member 510 than the outer paddles 520. For example, in some embodiments, each of the paddle frames 524 can extend around approximately half of the circumference of the coaption member 510 (as shown in FIG. 29), and the outer paddles 520 can extend around less than half of the circumference of the coaption member 510 (as shown in FIG. 28). The paddle frames 524 can also be configured to extend laterally (i.e., perpendicular to a longitudinal axis of the coaption member 510) beyond an outer diameter of the coaption member 510. In the illustrated example, the inner paddle portions 522 and the outer paddle portions 520 are formed from a continuous strip of fabric that are connected to the paddle frames 524. For example, the inner paddle portions and the outer paddle portions can be connected to the connection portion of the paddle frame at the flexible connection between the inner paddle portion and the outer paddle portion.

The paddle frames 524 can further be configured such that connection portions 528 of the paddle frames 524 are connected to or axially adjacent a joint portion 523. The connection portions of the paddle frames 534 can be positioned between outer and inner paddles 520, 522, on the outside of the paddle portion 520, on the inside of the inner paddle portion, or on top of the joint portion 523 when the prosthetic spacer device 500 is in a folded configuration (e.g., FIGS. 28-30). The connections between the paddle frames 524, the single strip that forms the outer and inner paddles 520, 522, the cap 514, and the coaption element can constrain each of these parts to the movements and positions described herein. In particular the joint portion 523 is constrained by its connection between the outer and inner paddles 520, 522 and by its connection to the paddle frame. Similarly, the paddle frame 524 is constrained by its attachment to the joint portion 523 (and thus the inner and outer paddles) and to the cap.

Configuring the paddle frames 524 in this manner provides increased surface area compared to the outer paddles 520 alone. This can, for example, make it easier to grasp and secure the native leaflets. The increased surface area can also distribute the clamping force of the paddles 520 and paddle frames 524 against the native leaflets over a relatively larger surface of the native leaflets in order to further protect the native leaflet tissue.

The increased surface area of the paddle frames 524 can also allow the native leaflets to be clamped to the prosthetic spacer device 500, such that the native leaflets coapt entirely around the coaption member 510. This can, for example, improve sealing of the native leaflet and thus prevent or further reduce mitral regurgitation.

Referring to FIG. 30, the prosthetic spacer device 500 can also include a cover 540. In some embodiments, the cover 540 can be disposed on the coaption member 510, the paddles 520, 522, and/or the paddle frames 524. The cover 540 can be configured to prevent or reduce blood-flow through the prosthetic spacer device 500 and/or to promote native tissue ingrowth. In some embodiments, the cover 540 can be a cloth or fabric such as PET, velour, or other suitable fabric. In other embodiments, in lieu of or in addition to a fabric, the cover 540 can include a coating (e.g., polymeric) that is applied to the prosthetic spacer device 500.

Figure 31:
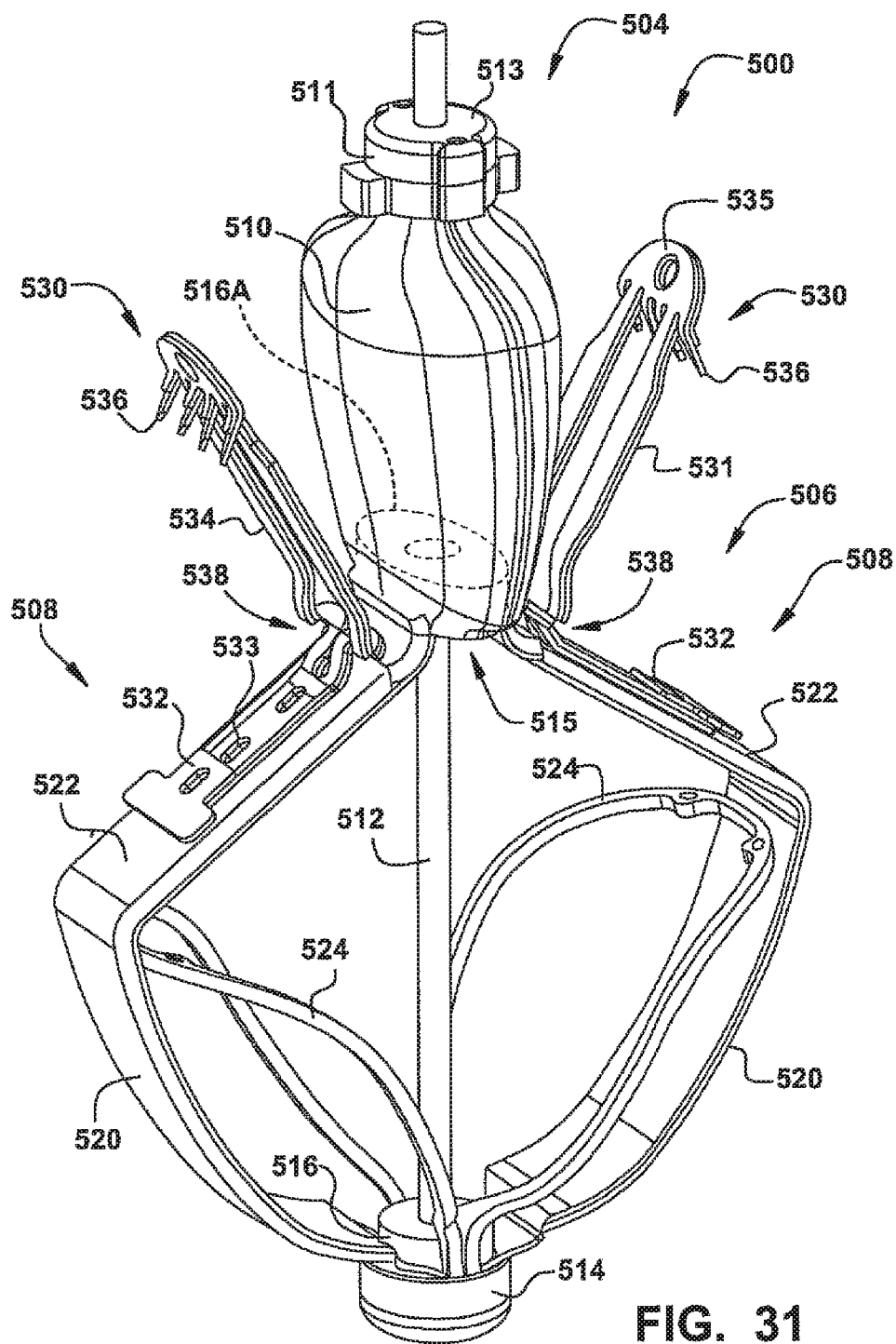
Figure 32:
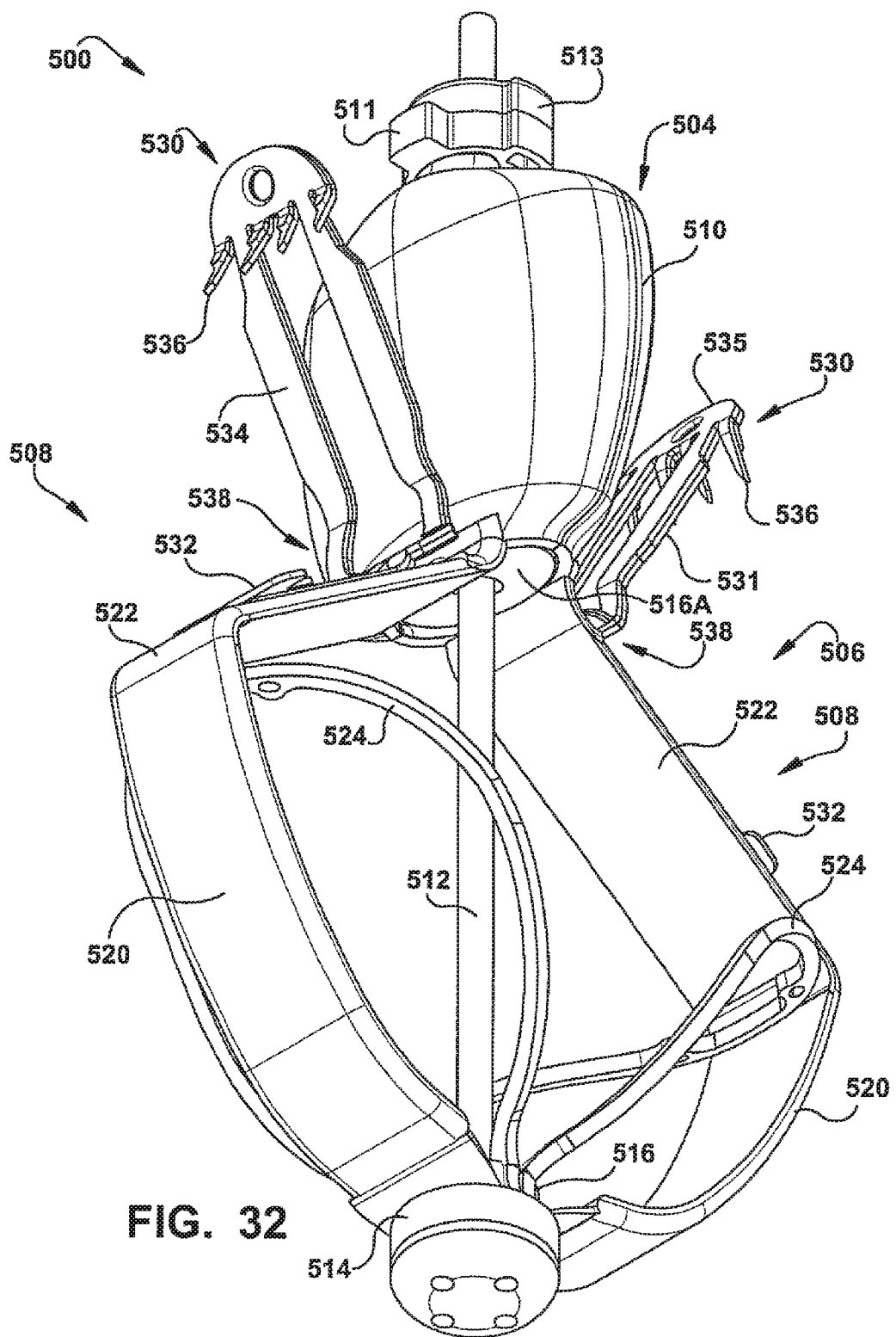

FIGS. 31-32 illustrate the implantable prosthetic device 500 of FIGS. 28 and 29 with anchors 508 of an anchor portion 506 and clasps 530 in open positions. The device 500 is deployed from a delivery sheath (not shown) and includes a coaption portion 504 and the anchor portion 506. The device 500 is loaded in the delivery sheath in the fully extended or bailout position, because the fully extended or bailout position takes up the least space and allows the smallest catheter to be used (See FIG. 35). Or, the fully extended position allows the largest device 500 to be used for a given catheter size. The coaption portion 504 of the device includes a coaption element 510 for implantation between the leaflets of the native mitral valve. An insert 516A is disposed inside the coaption element 510. The insert 516A and the coaption element 510 are slidably attached to an actuation wire or shaft 512. The anchors 508 of the device 500 include outer paddles 520 and inner paddles 522 that are flexibly connected to the cap 514 and the coaption element 510. Actuation of the actuation wire or shaft 512 opens and closes the anchors 508 of the device 500 to grasp the mitral valve leaflets during implantation.

The actuation wire 512 extends through the delivery sheath (not shown), the proximal collar 511, the coaption element 510, the insert 516A, and extends to the cap 514. Extending and retracting the actuation wire 512 increases and decreases the spacing between the coaption element 510 and the cap 514, respectively. This changing of the spacing between the coaption element 510 and the cap 514 causes the anchor portion 506 of the device to move between different positions.

The proximal collar 511 optionally includes a collar seal 513 that forms a seal around the actuation wire or shaft 512 during implantation of the device 500, and that seals shut when the actuation wire 512 is removed to substantially close the proximal end of the device 500 to blood flow through the interior of the coaption element 510 after implantation. In some embodiments, a coupler or means for coupling 2214 (see FIG. 145) removably engages and attaches the proximal collar 511 and the coaption element 500 to the delivery sheath. In some embodiments, coupler or means for coupling 2214 is held closed around the proximal collar 511 by the actuation wire 512, such that removal of the actuation wire 512 allows fingers (see FIG. 145) of the coupler or means for coupling 2214 to open, releasing the proximal collar 511.

Figure 32A:
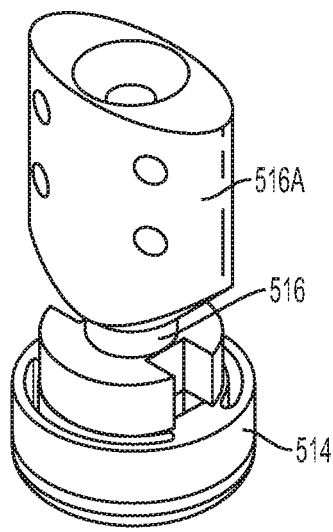
FIGS. 32A and 32B are perspective views of a cap and a coaption element insert of the implantable prosthetic device of FIGS. 28-32 in sealed and spaced apart positions, respectively.
Figure 32B:
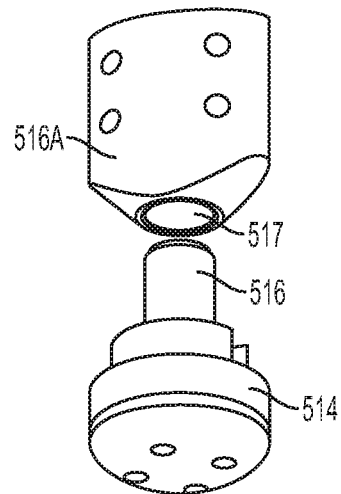

The proximal collar 511 and the insert 516A in the coaption element 510 slide along the actuation wire 512 during actuation to open and close the paddles 520, 522 of the anchors 508. Referring to FIGS. 32A and 32B, in some embodiments the cap 514 optionally includes a sealing projection 516 that sealingly fits within a sealing opening 517 of the insert 516A. In another exemplary embodiment, the cap 514 includes a sealing opening and the insert 516A includes a sealing projection. The insert 516A can sealingly fit inside a distal opening 515 of the coaption element 510, the coaption element 510 having a hollow interior. Referring to FIG. 32A, the sealing projection 516 of the cap 514 sealingly engages the opening 517 in the insert 516A to maintain the distal end of the coaption element 510 substantially closed to blood flow when the device 500 is implanted and/or in the closed position.

In another exemplary embodiment, instead of the sealing engagement between the cap 514 and the insert 516A, the insert 516A can optionally include a seal, like the collar seal 513 of the proximal collar, that forms a seal around the actuation wire or shaft 512 during implantation of the device 500, and that seals shut when the actuation wire 512 is removed. Such a seal can substantially close the distal end of the coaption element 510 to blood flow after implantation.

The coaption element 510 and paddles 520, 522 are formed from a flexible material that may be a metal fabric, such as a mesh, woven, braided, or formed in any other suitable way or a laser cut or otherwise cut flexible material. The material may be cloth, shape-memory alloy wire—such as Nitinol—to provide shape-setting capability, or any other flexible material suitable for implantation in the human body. Paddle frames 524 provide additional pinching force between the inner paddles 522 and the coaption element 510 and assist in wrapping the leaflets around the sides of the coaption element 510 for a better seal between the coaption element 510 and the leaflets. In some embodiments, the covering 540 illustrated by FIG. 30 extends around the paddle frames 524.

The clasps 530 include a base or fixed arm 532, a moveable arm 534, barbs 536, and a joint portion 538. The fixed arms 532 are attached to the inner paddles 522, with the joint portion 538 disposed proximate the coaption element 510. The barbed clasps have flat surfaces and do not fit in a recess of the paddle. Rather, the flat portion of the barbed clasps are disposed against the surface of the inner paddle 522. For example, the fixed arms 532 are attached to the inner paddles 522 through holes or slots 533 with sutures (not shown). The fixed arms 532 may be attached to the inner paddles 522 with any suitable means, such as screws or other fasteners, crimped sleeves, mechanical latches or snaps, welding, adhesive, or the like. The fixed arms 532 remain substantially stationary relative to the inner paddles 522 when the moveable arms 534 are opened to open the barbed clasps 530 and expose the barbs 536. The barbed clasps 530 are opened by applying tension to actuation lines (not shown) attached to holes 535 in the moveable arms 534, thereby causing the moveable arms 534 to pivot or flex on the joint portions 538.

During implantation, the anchors 508 are opened and closed to grasp the native mitral valve leaflets between the paddles 520, 522 and the coaption element 510. The barbed clasps 530 further secure the native leaflets by engaging the leaflets with barbs 536 and pinching the leaflets between the moveable and fixed arms 534, 532. The barbs 536 of the barbed clasps 530 increase friction with the leaflets or may partially or completely puncture the leaflets. The actuation lines can be actuated separately so that each barbed clasp 530 can be opened and closed separately. Separate operation allows one leaflet to be grasped at a time, or for the repositioning of a clasp 530 on a leaflet that was insufficiently grasped, without altering a successful grasp on the other leaflet. The barbed clasps 530 can open and close when the inner paddle 522 is not closed, thereby allowing leaflets to be grasped in a variety of positions as the particular situation requires.

Figure 33:
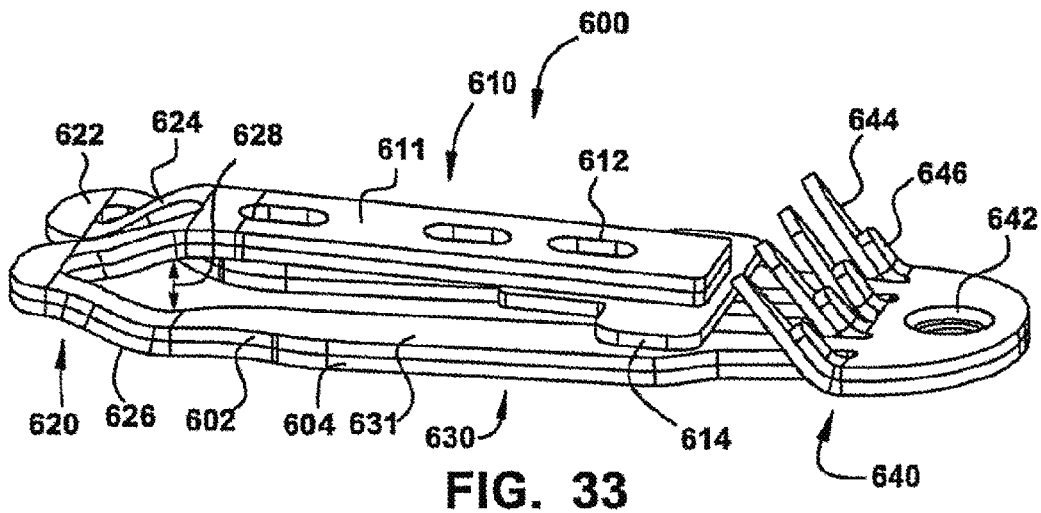
FIG. 33 shows a barbed clasp for use in an implantable prosthetic device.

Referring now to FIG. 33, an exemplary barbed clasp 600 for use in implantable prosthetic devices, such as the devices described above, is shown. However, a wide variety of different barbed clasps can be used. Examples of barbed clasps that can be used include, but are not limited to any of the barbed clasps disclosed in the present application and any of the applications that are incorporated herein by reference and/or that the present application claims priority to. In the illustrated example, the barbed clasp 600 is formed from a top layer 602 and a bottom layer 604. The two-layer design of the clasp 600 allow thinner sheets of material to be used, thereby improving the flexibility of the clasp 600 over a clasp formed from a single thicker sheet, while maintaining the strength of the clasp 600 needed to successfully retain a native valve leaflet.

The barbed clasp 600 includes a fixed arm 610, a jointed portion 620, and a movable arm 630 having a barbed portion 640. The top and bottom layers 602, 604 have a similar shape and in certain embodiments are attached to each other at the barbed portion 640. However, the top and bottom layers 602, 604 can be attached to one another at other or additional locations. The jointed portion 620 is spring-loaded so that the fixed and moveable arms 610, 630 are biased toward each other when the barbed clasp 600 is in a closed condition. When assembled to an implantable prosthetic device, the fixed arm 610 is attached to a portion of the prosthetic device. The clasp 600 is opened by pulling on an actuation line attached to the moveable arm 630 until the spring force of the joint portion 620 is overcome.

The fixed arm 610 is formed from a tongue 611 of material extending from the jointed portion 620 between two side beams 631 of the moveable arm 630. The tongue 611 is biased between the side beams 631 by the joint portion 620 such that force must be applied to move the tongue 611 from a neutral position located beyond the side beams 631 to a preloaded position substantially parallel with the side beams 631. The tongue 611 is held in the preloaded position by an optional T-shaped cross-bar 614 that is attached to the tongue 611 and extends outward to engage the side beams 631. In another exemplary embodiment, the cross-bar is omitted and the tongue 611 is attached to the inner paddle 522, and the inner paddle 522 maintains the clasp in the preloaded position. In the two-layer clasp application, the top and bottom layers 602, 604 or just the top layer can be attached to the inner paddle. In some embodiments, the angle between the fixed and moveable arms 610, 630 when the tongue is in the neutral position is about 30 to about 100 degrees, 30 to about 90 degrees, or about 30 to about 60 degrees, or about 40 to about 50 degrees, or about 45 degrees.

The tongue 611 includes holes 612 for receiving sutures (not shown) that attach the fixed arm 610 to an implantable device. The fixed arm 610 may be attached to an implantable device, such as with screws or other fasteners, crimped sleeves, mechanical latches or snaps, welding, adhesive, or the like. In certain embodiments, the holes 612 are elongated slots or oval-shaped holes to accommodate sliding of the layers 602, 604 without damaging the sutures attaching the clasp 600 to an implantable device.

The joint portion 620 is formed by two beam loops 622 that extend from the tongue 611 of the fixed arm 610 to the side beams 631 of the moveable arm 630. In certain embodiments, the beam loops 622 are narrower than the tongue 611 and side beam 631 to provide additional flexibility. The beam loops 622 each include a center portion 624 extending from the tongue 611 and an outer portion 626 extending to the side beams 631. The beam loops 622 are bent into a somewhat spiral or helical shape by bending the center and outer portions 624, 626 in opposite directions, thereby forming an offset or step distance 628 between the tongue 611 and side beams 631. The step distance 628 provides space between the arms 610, 630 to accommodate the native leaflet of the mitral valve after it is grasped. In certain embodiments, the step distance 628 is about 0.5 millimeter to about 1 millimeters, or about 0.75 millimeters.

When viewed in a top plan view, the beam loops have an "omega-like" shape. This shape of the beam loops 622 allows the fixed and moveable arms 610, 630 to move considerably relative to each other without plastically deforming the clasp material. For example, in certain embodiments, the tongue 611 can be pivoted from a neutral position that is approximately 45 degrees beyond the moveable arm 630 to a fully open position that ranges from about 140 degrees to about 200 degrees, to about 170 degrees to about 190 degrees, or about 180 degrees from the moveable arm 630 without plastically deforming the clasp material. In certain embodiments, the clasp material plastically deforms during opening without reducing or without substantially reducing the pinch force exerted between the fixed and moveable arms in the closed position.

Preloading the tongue 611 enables the clasp 600 to maintain a pinching or clipping force on the native leaflet when closed. The preloading of the tongue 611 provides a significant advantage over prior art clips that provide little or no pinching force when closed. Additionally, closing the clasp 600 with spring force is a significant improvement over clips that use a one-time locking closure mechanism, as the clasp 600 can be repeatedly opened and closed for repositioning on the leaflet while still maintaining sufficient pinching force when closed. In addition, the spring-loaded clasps also allow for easier removal of the device over time as compared to a device that locks in a closed position (after tissue ingrowth). In one exemplary embodiment, both the clasps and the paddles are spring biased to their closed positions (as opposed to being locked in the closed position), which can allow for easier removal of the device after tissue ingrowth.

The barbed portion 640 of the moveable arm 630 includes an eyelet 642, barbs 644, and barb supports 646. Positioning the barbed portion of the clasp 600 toward an end of the moveable arm 630 increases the space between the barbs 644 and the fixed arm 610 when the clasp 600 is opened, thereby improving the ability of the clasp 600 to successfully grasp a leaflet during implantation. This distance also allows the barbs 644 to more reliably disengage from the leaflet for repositioning. In certain embodiments, the barbs of the clasps may be staggered longitudinally to further distribute pinch forces and local leaflet stress.

The barbs 644 are laterally spaced apart at the same distance from the joint portion 620, providing a superior distribution of pinching forces on the leaflet tissue while also making the clasp more robust to leaflet grasp than barbs arranged in a longitudinal row. In some embodiments, the barbs 644 can be staggered to further distribute pinch forces and local leaflet stress.

The barbs 644 are formed from the bottom layer 604 and the barb supports 646 are formed from the top layer. In certain embodiments, the barbs are formed from the top layer 602 and the barb supports are formed from the bottom layer 604. Forming the barbs 644 only in one of the two layers 602, 604 allows the barbs to be thinner and therefore effectively sharper than a barb formed from the same material that is twice as thick. The barb supports 646 extend along a lower portion of the barbs 644 to stiffen the barbs 644, further improving penetration and retention of the leaflet tissue. In certain embodiments, the ends of the barbs 644 are further sharpened using any suitable sharpening means.

The barbs 644 are angled away from the moveable arm 630 such that they easily penetrate tissue of the native leaflets with minimal pinching or clipping force. The barbs 644 extend from the moveable arm at an angle of about 45 degrees to about 75 degrees, or about 45 degrees to about 60 degrees, or about 48 to about 56 degrees, or about 52 degrees. The angle of the barbs 644 provides further benefits, in that force pulling the implant off the native leaflet will encourage the barbs 644 to further engage the tissue, thereby ensuring better retention. Retention of the leaflet in the clasp 600 can be further improved by the position of the T-shaped cross bar 614 near the barbs 644 when the clasp 600 is closed. In this arrangement, the tissue pierced by the barbs 644 is pinched against the moveable arm 630 at the cross bar 614 location, thereby forming the tissue into an S-shaped torturous path as it passes over the barbs 644. Thus, forces pulling the leaflet away from the clasp 600 will encourage the tissue to further engage the barbs 644 before the leaflets can escape. For example, leaflet tension during diastole can encourage the barbs to pull toward the end portion of the leaflet. The S-shaped path can utilize the leaflet tension during diastole to more tightly engage the leaflets with the barbs.

Each layer 602, 604 of the clasp 600 is laser cut from a sheet of shape-memory alloy, such as Nitinol. The top layer 602 is aligned and attached to the bottom layer 604. In certain embodiments, the layers 602, 604 are attached at the barbed portion 640 of the moveable arm 630. For example, the layers 602, 604 may be attached only at the barbed portion 640, to allow the remainder of the layers to slide relative to one another. Portions of the combined layers 602, 604, such as a fixed arm 610, barbs 644 and barb supports 646, and beam loops 622 are bent into a desired position. The layers 602, 604 may be bent and shape-set together or may be bent and shape-set separately and then joined together. The clasp 600 is then subjected to a shape-setting process so that internal forces of the material will tend to return to the set shape after being subjected to deformation by external forces. After shape-setting, the tongue 611 is moved to its preloaded position so that the cross-bar 614 can be attached. In one exemplary embodiment, the clasp 600 can optionally be completely flattened for delivery through a delivery sheath and allowed to expand once deployed within the heart. The clasp 600 is opened and closed by applying and releasing tension on an actuation line, suture, wire, rod, catheter, or the like (not shown) attached to the moveable arm 630. The suture is inserted through an eyelet 642 near the barbed portion 640 of the moveable arm 630 and wraps around the moveable arm 630 before returning to the delivery sheath. In certain embodiments, an intermediate suture loop is made through the eyelet and the suture is inserted through the intermediate loop. An alternate embodiment of the intermediate loop can be composed of fabric or another material attached to the movable arm, instead of a suture loop.

An intermediate loop of suture material reduces friction experienced by the actuation suture relative to the friction between the actuation suture and the clasp material. When the suture is looped through the eyelet 642 or intermediate loop, both ends of the actuation suture extend back into and through a delivery sheath (e.g., FIG. 8). The suture can be removed by pulling one end of the suture proximally until the other end of the suture pulls through the eyelet or intermediate loop and back into the delivery sheath.

Figure 34:
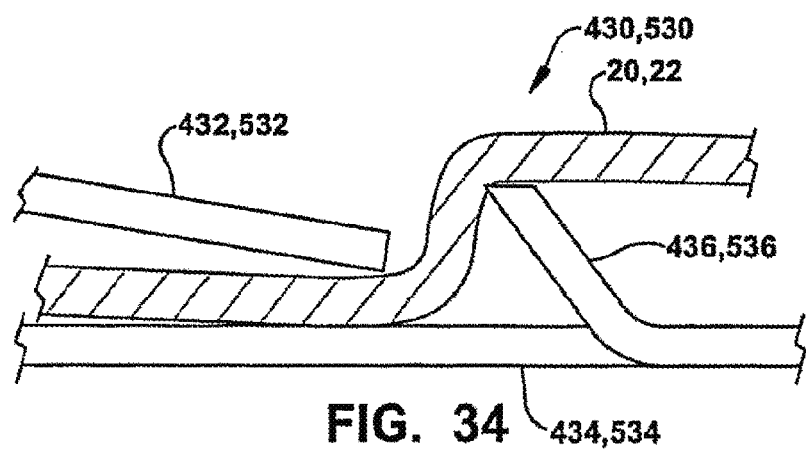
FIG. 34 shows a portion of mitral valve tissue grasped by a barbed clasp.

Referring now to FIG. 34, a close-up view of one of the leaflets 20, 22 grasped by a barbed clasp such as clasps 430, 530 is shown. The leaflet 20, 22 is grasped between the moveable and fixed arms 434, 534 of the clasp 430, 530. As shown in FIG. 34, the tissue of the leaflet 20, 22 is not pierced by the barbs 436, 536, though in some embodiments the barbs 436, 536 may partially or fully pierce through the leaflet 20, 22. The angle and height of the barbs 436, 536 relative to the moveable arm 434, 534 helps to secure the leaflet 20, 22 within the clasp 430, 530. In particular, a force pulling the implant off of the native leaflet will encourage the barbs 436, 536 to further engage the tissue, thereby ensuring better retention. Retention of the leaflet 20, 22 in the clasp 430, 530 is further improved by the position of fixed arm 432, 532 near the barbs 436, 536 when the clasp 430, 530 is closed. In this arrangement, the tissue is formed by the fixed arms 432, 532 and the moveable arms 434, 534 and the barbs 436, 536 into an S-shaped torturous path. Thus, forces pulling the leaflet away from the clasp 430, 530 will encourage the tissue to further engage the barbs 436, 536 before the leaflets can escape. For example, as mentioned above, leaflet tension during diastole can encourage the barbs to pull toward the end portion of the leaflet. The S-shaped path can utilize the leaflet tension during diastole to more tightly engage the leaflets with the barbs.

Referring now to FIGS. 35-46, the implantable device 500 is shown being delivered and implanted within the native mitral valve MV of the heart H. As described above, the device 500 has a covering 540 (see FIG. 30) over the coaption element 510, clasps 530, inner paddles 522 and/or the outer paddles 520. The device 500 is deployed from a delivery sheath 502 and includes a coaption portion 504 and an anchor portion 506 including a plurality of anchors 508 (i.e., two in the illustrated embodiment). The coaption portion 504 of the device includes a coaption element 510 for implantation between the leaflets 20, 22 of the native mitral valve MV that is slidably attached to an actuation wire or shaft 512. Actuation of the actuation wire or shaft 512 opens and closes the anchors 508 of the device 500 to grasp the mitral valve leaflets 20, 22 during implantation.

The anchors 508 of the device 500 include outer paddles 520 and inner paddles 522 that are flexibly connected to the cap 514 and the coaption element 510. The actuation wire 512 extends through a capture mechanism 503 (see FIG. 41), delivery sheath 502, and the coaption element 510 to the cap 514 connected to the anchor portion 506. Extending and retracting the actuation wire 512 increases and decreases the spacing between the coaption element 510 and the cap 514, respectively. In the example illustrated by FIGS. 35-46, the pair of inner and outer paddles 522, 520 are moved in unison, rather than independently, by a single actuation wire 512. Also, the positions of the clasps 530 are dependent on the positions of the paddles 522, 520. For example, referring to FIG. 45 closing the paddles 522, 520 also closes the clasps. In one exemplary embodiment, the device 500 can be made to have the paddles 520, 522 be independently controllable in the same manner as the FIG. 11A embodiment.

Fingers of the capture mechanism 503 removably attach the collar 511 to the delivery sheath 502. The collar 511 and the coaption element 510 slide along the actuation wire 512 during actuation to open and close the anchors 508 of the anchor portion 506. In some embodiments, the capture mechanism 503 is held closed around the collar 511 by the actuation wire 512, such that removal of the actuation wire 512 allows the fingers of the capture mechanism 503 to open, releasing the collar 511, and thus the coaption element 510.

The coaption element 510 and paddles 520, 522 can be formed from a flexible material that may be a metal fabric, such as a mesh, woven, braided, or formed in any other suitable way or a laser cut or otherwise cut flexible material. The flexible material may be cloth, shape-memory alloy wire—such as Nitinol—to provide shape-setting capability, or any other flexible material suitable for implantation in the human body.

The barbed clasps 530 include a base or fixed arm 532, a moveable arm 534, barbs 536 (see FIG. 41), and a joint portion 538. The fixed arms 532 are attached to the inner paddles 522, with the joint portions 538 disposed proximate the coaption element 510. Sutures (not shown) attach the fixed arms 532 to the inner paddles 522. The fixed arms 532 may be attached to the inner paddles 522 with any suitable means, such as screws or other fasteners, crimped sleeves, mechanical latches or snaps, welding, adhesive, or the like. The fixed arms 532 remain substantially stationary when the moveable arms 534 are opened to open the barbed clasps 530 and expose the barbs 536. The barbed clasps 530 are opened by applying tension to actuation lines 537 attached to the moveable arms 534, thereby causing the moveable arms 534 to pivot or flex on the joint portions 538.

During implantation, the anchors 508 are opened and closed to grasp the native mitral valve leaflets between the paddles 520, 522 and the coaption element 510. The outer paddles 520 have a wide curved shape that fits around the curved shape of the coaption element 510 to more securely grip the leaflets 20, 22. The curved shape and rounded edges of the outer paddle 520 also prohibits tearing of the leaflet tissue. The barbed clasps 530 further secure the native leaflets by engaging the leaflets with barbs 536 and pinching the leaflets between the moveable and fixed arms 534, 532. The barbs 536 of the barbed clasps 530 increase friction with the leaflets or may partially or completely puncture the leaflets. The actuation lines can be actuated separately so that each barbed clasp 530 can be opened and closed separately. Separate operation allows one leaflet to be grasped at a time, or for the repositioning of a clasp 530 on a leaflet that was insufficiently grasped, without altering a successful grasp on the other leaflet. The barbed clasps 530 can be fully opened and closed when the inner paddle 522 is not closed, thereby allowing leaflets to be grasped in a variety of positions as the particular situation requires.

Figure 35:
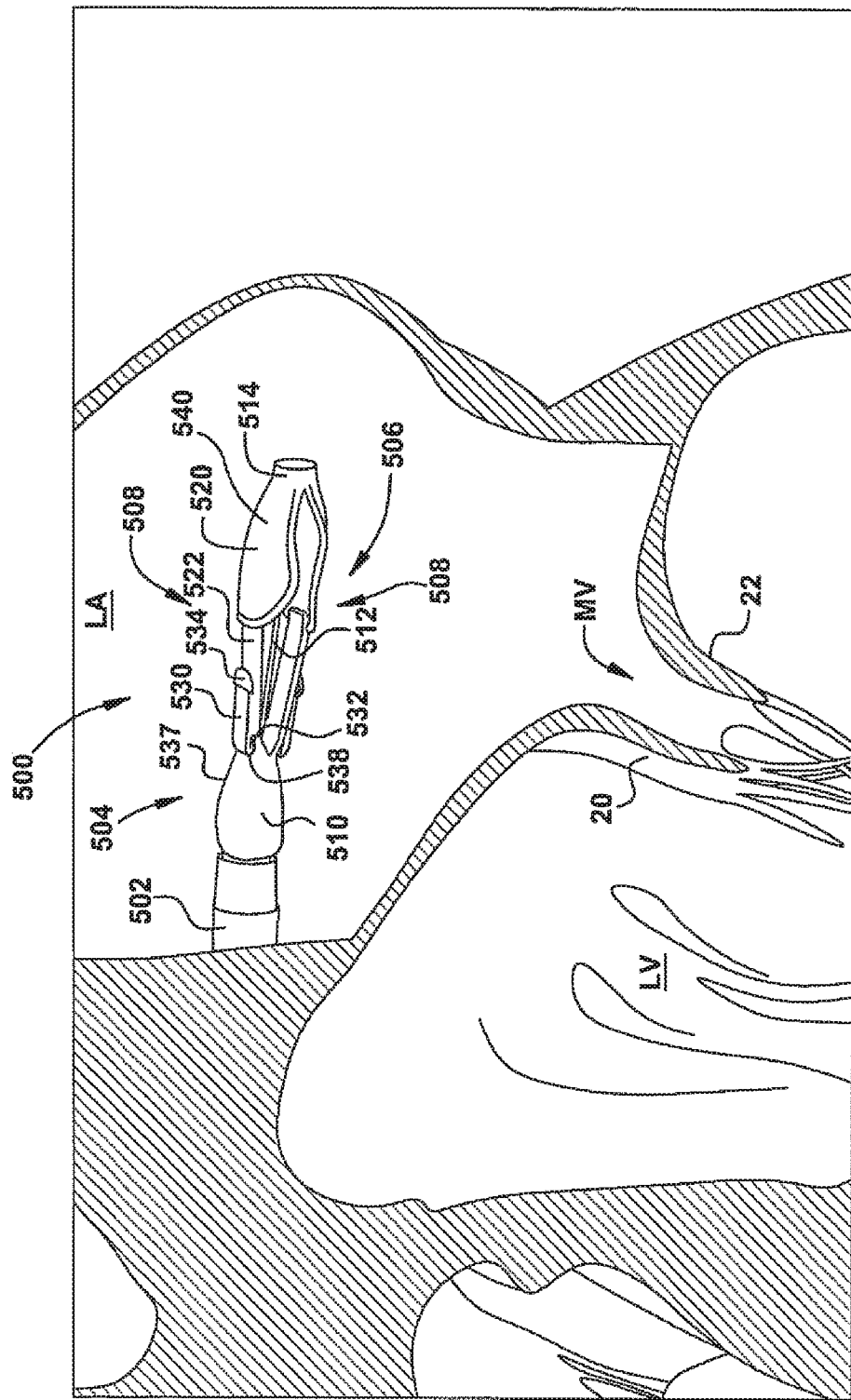
FIGS. 35-46 show an exemplary embodiment of an implantable prosthetic device being delivered and implanted within the native mitral valve.
Figure 36:
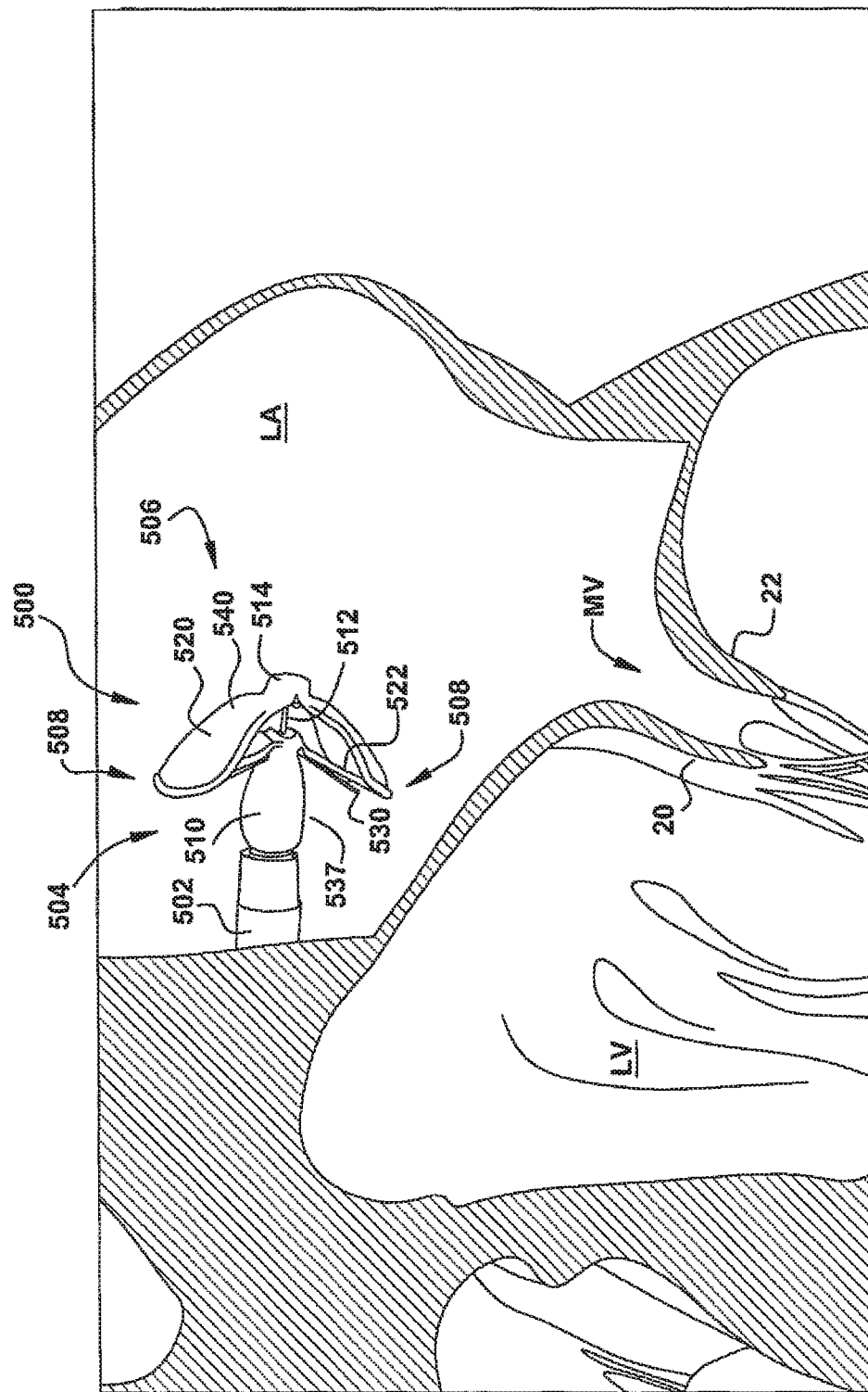
Figure 37:
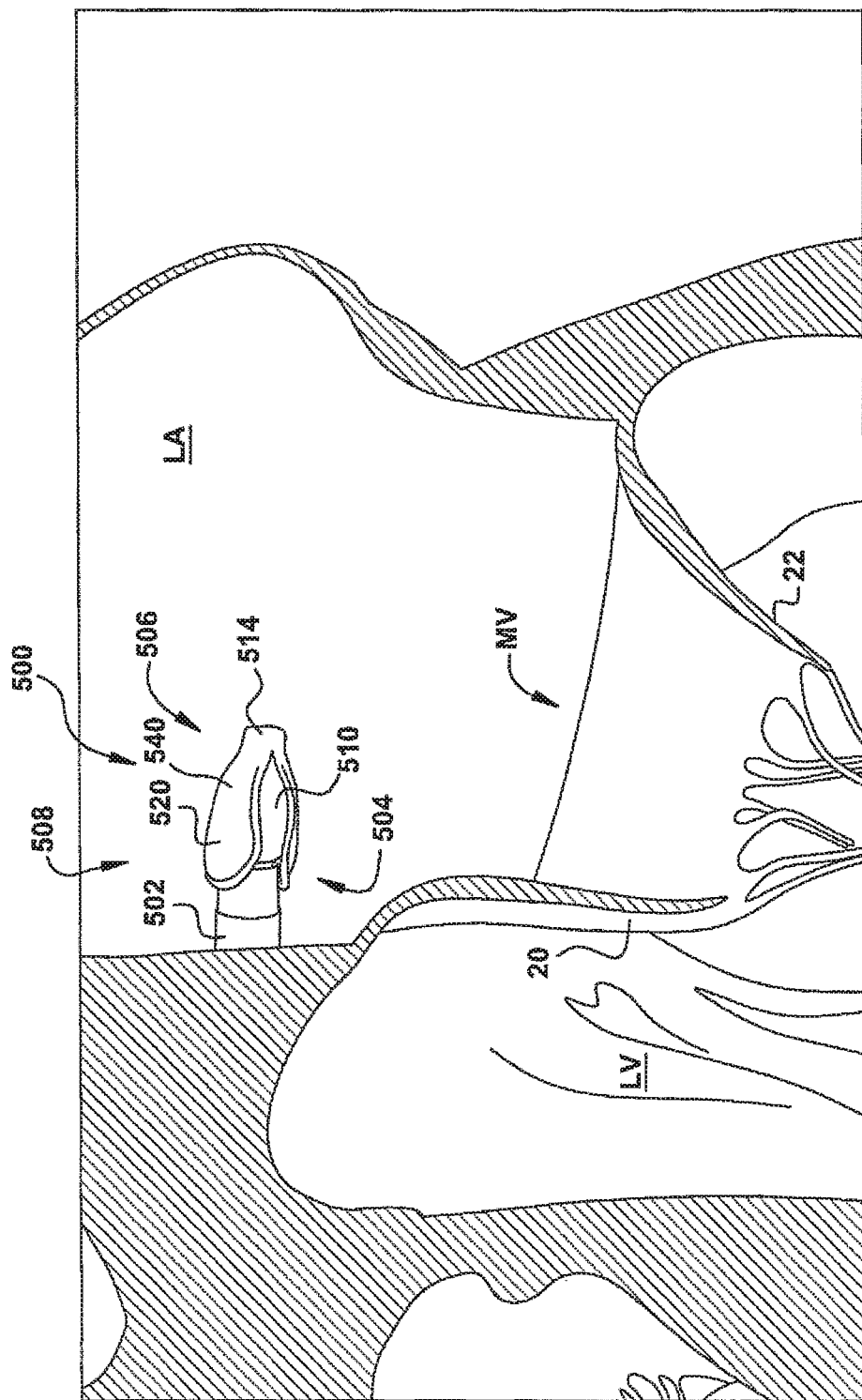
Figure 38:
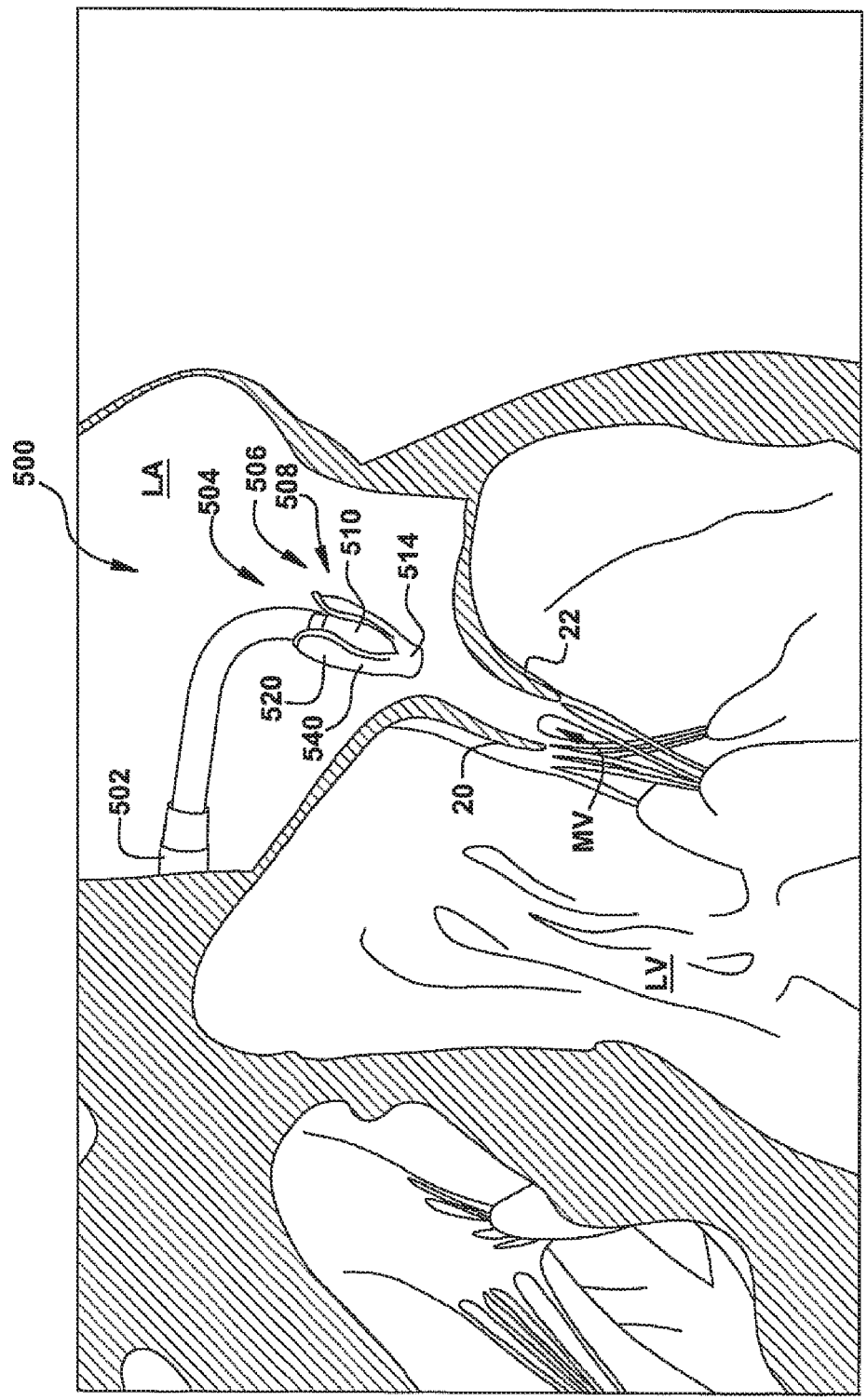
Figure 39:
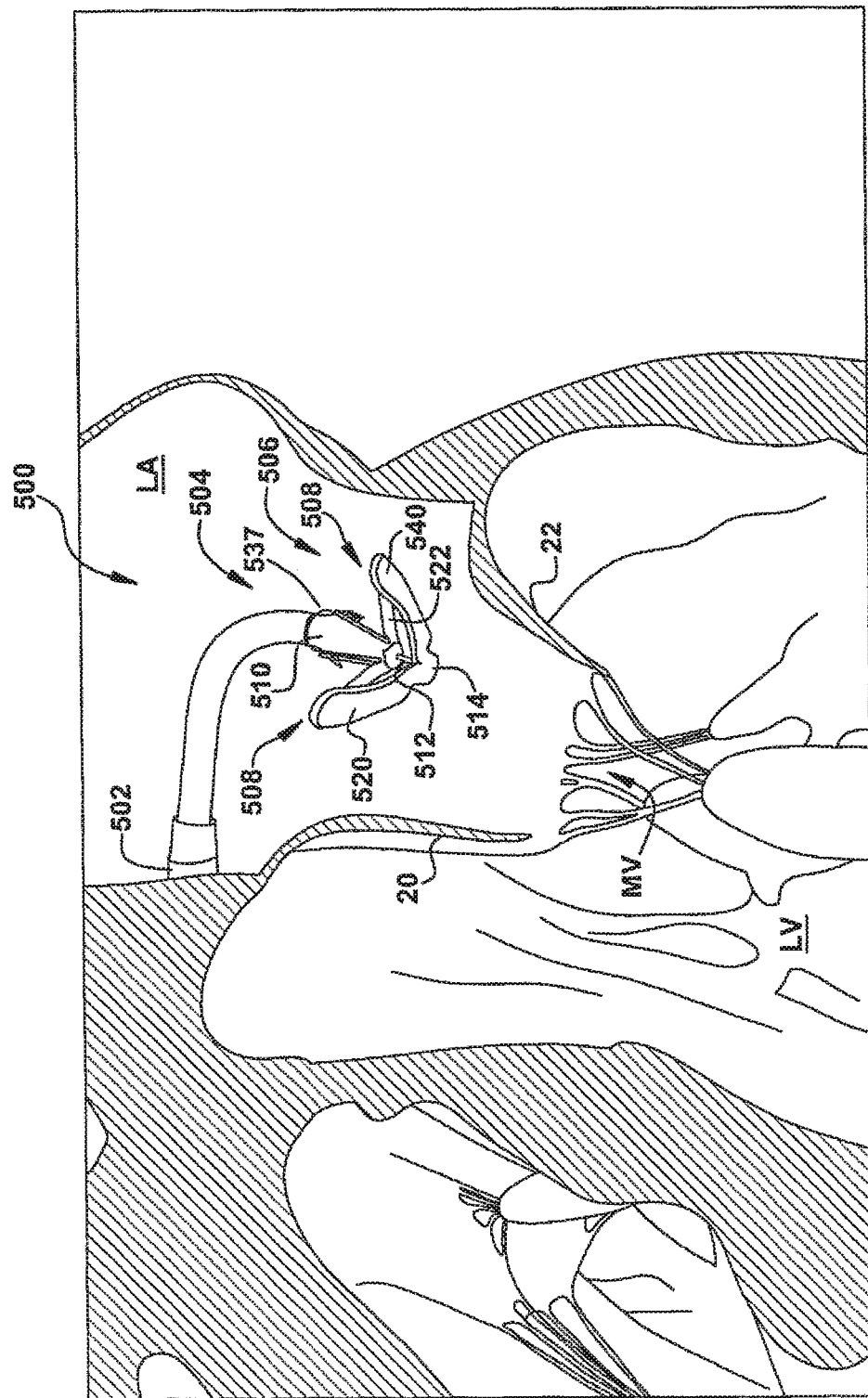
Figure 40:
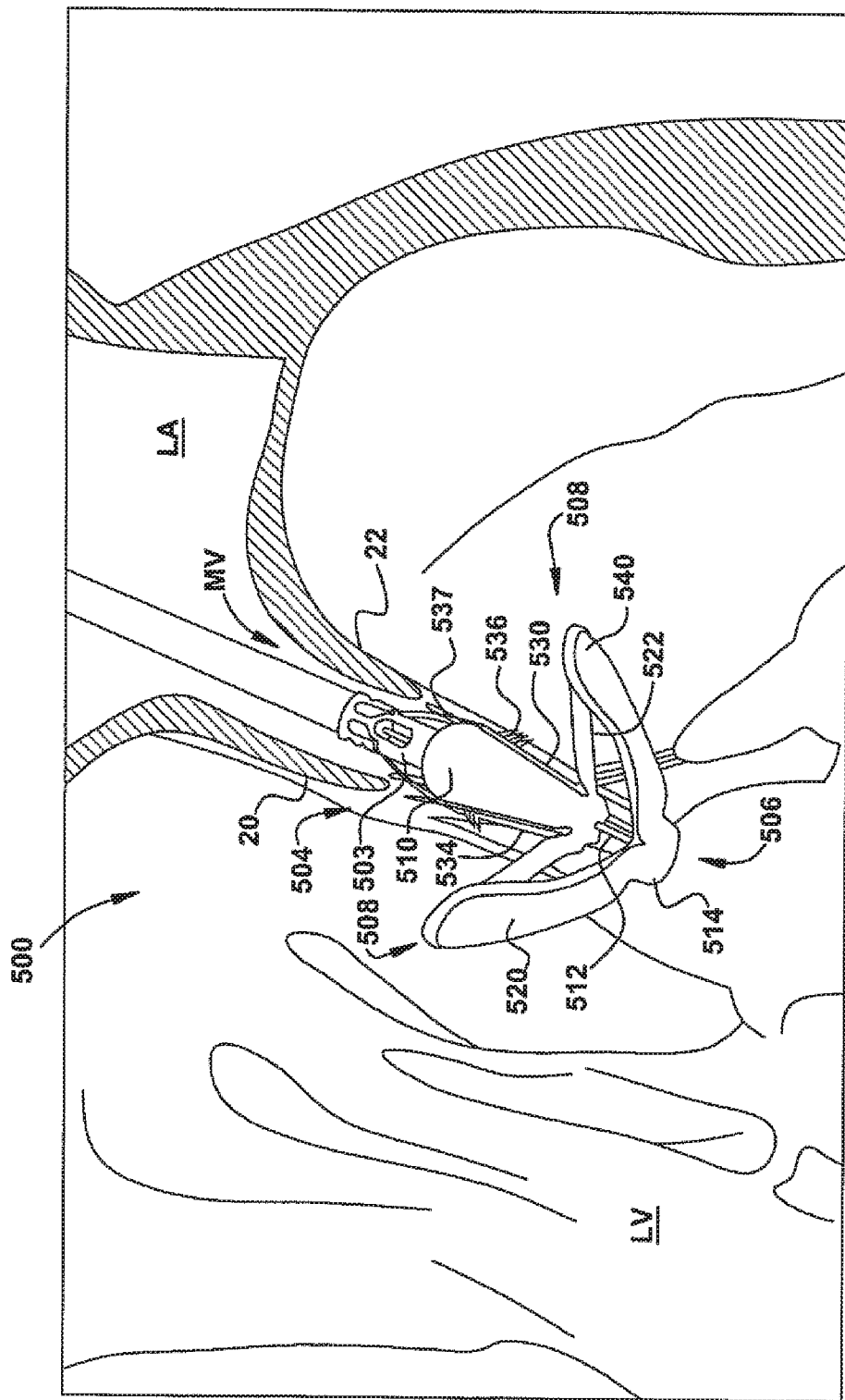
Figure 41:
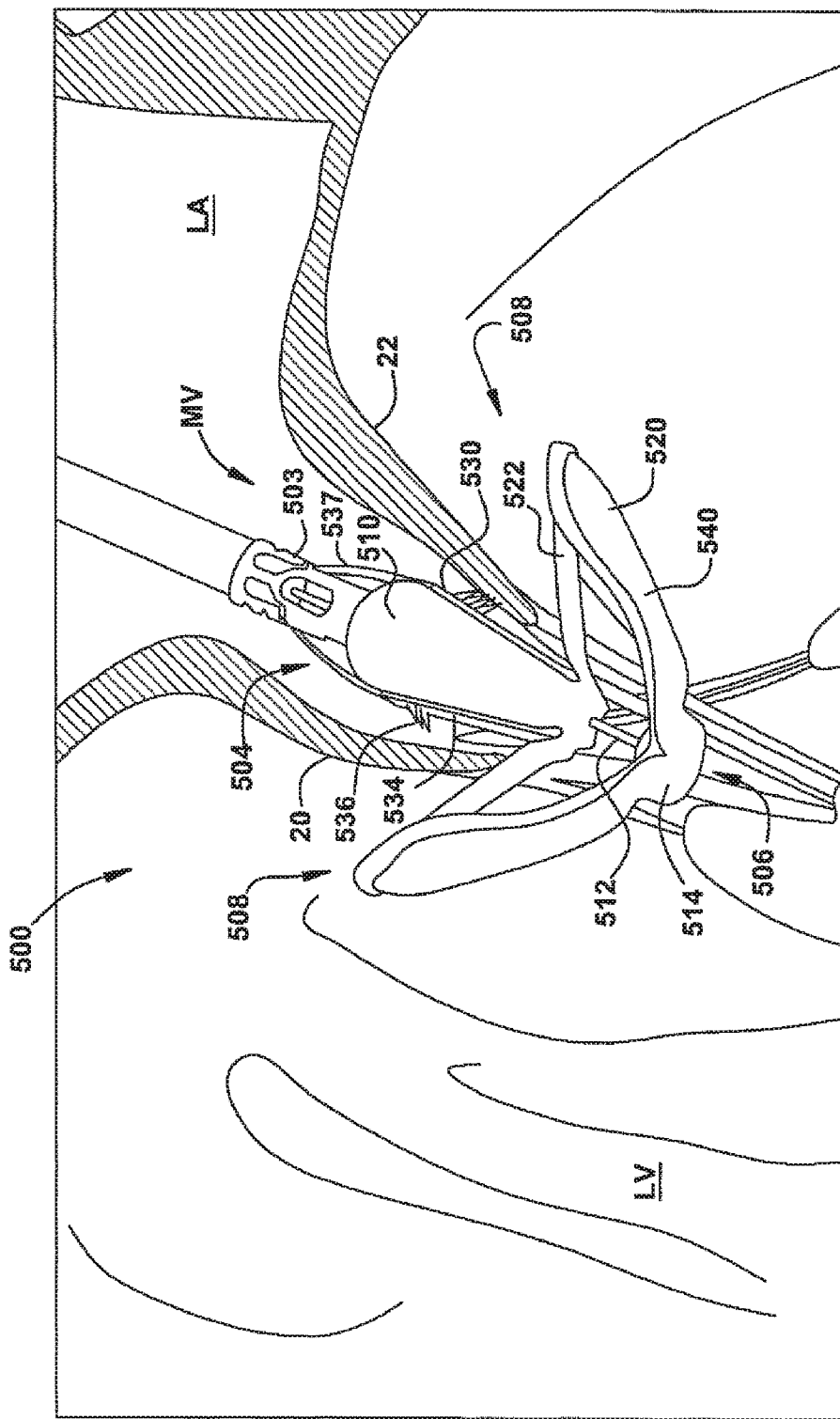
Figure 42:
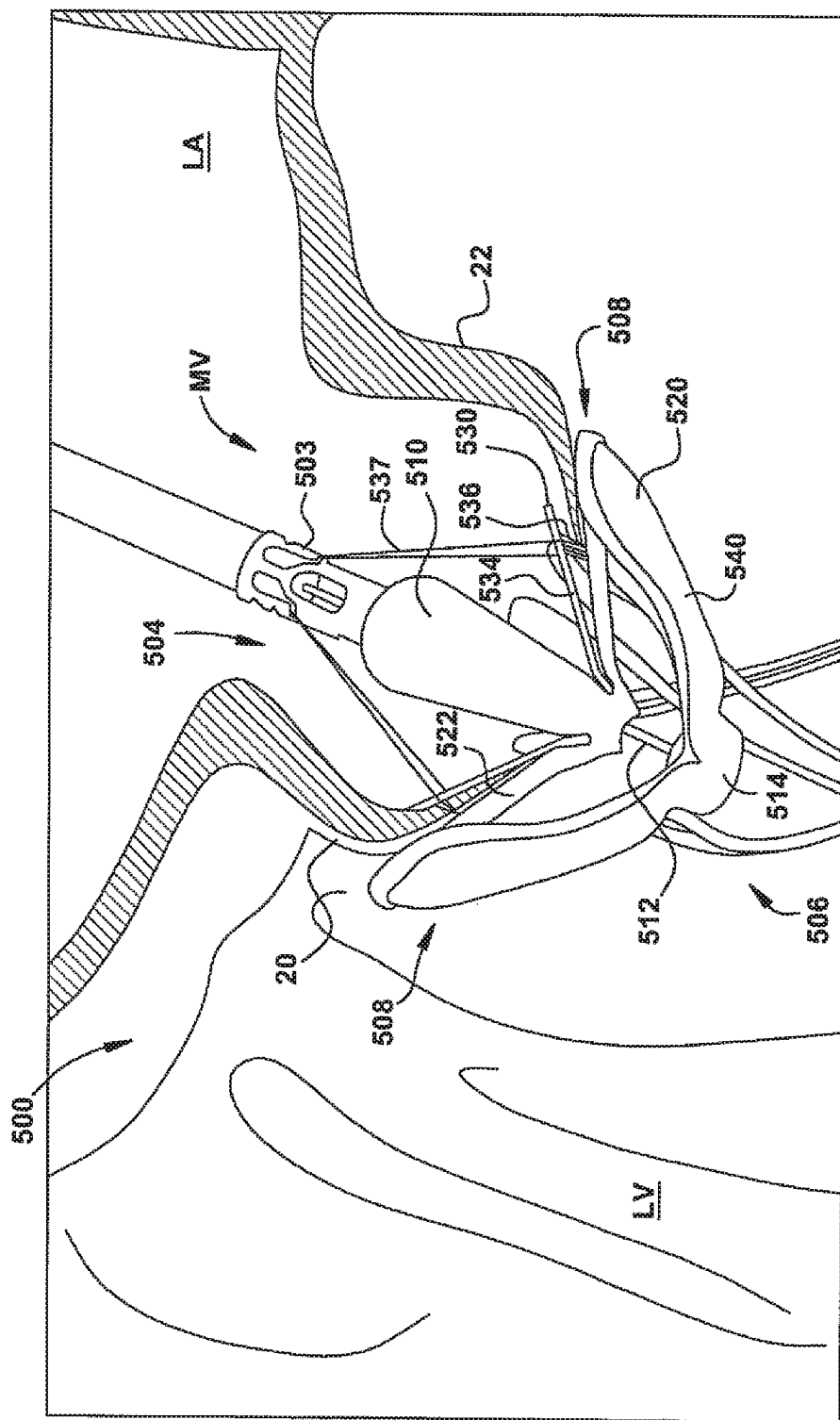
Figure 43:
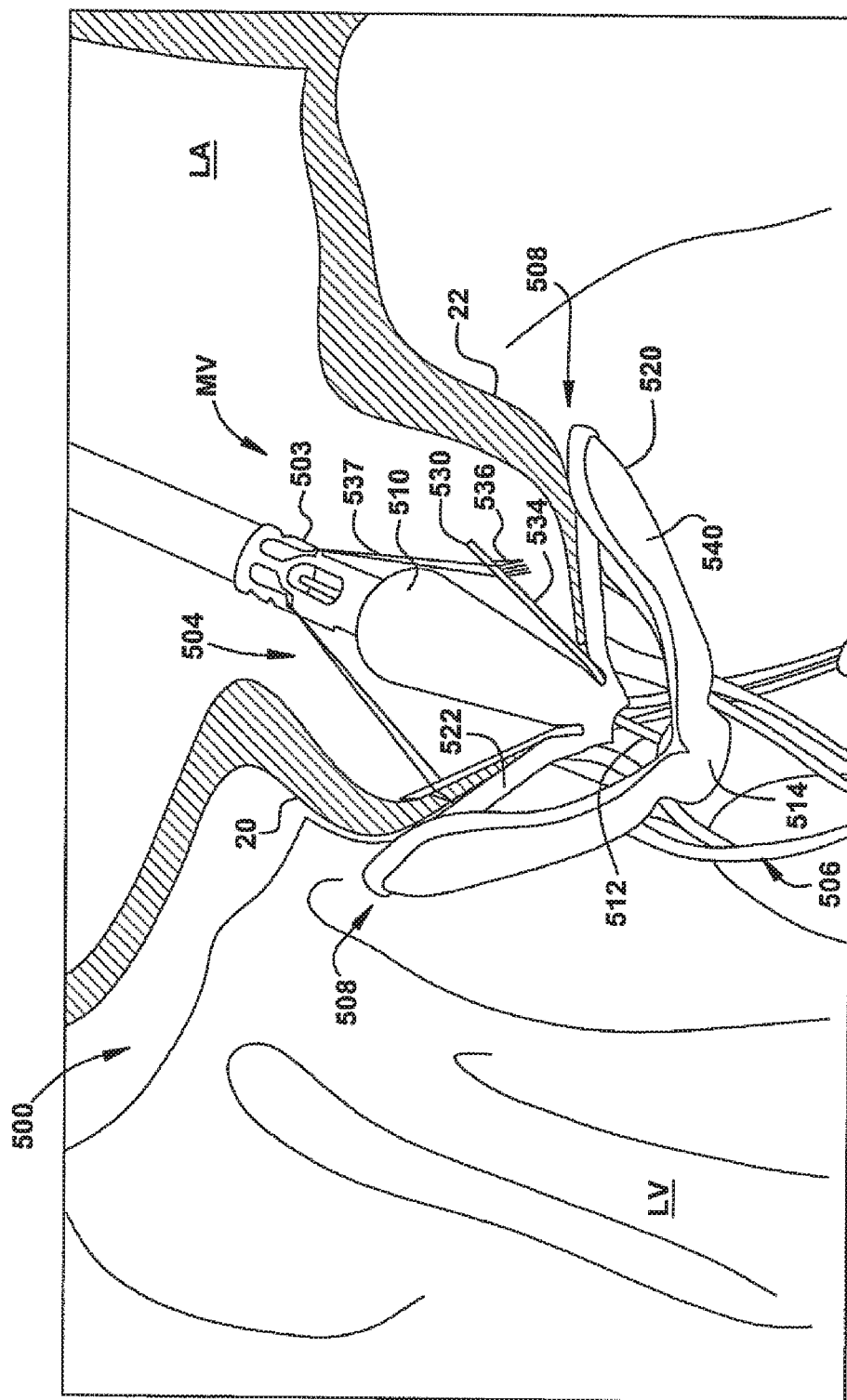
Figure 44:
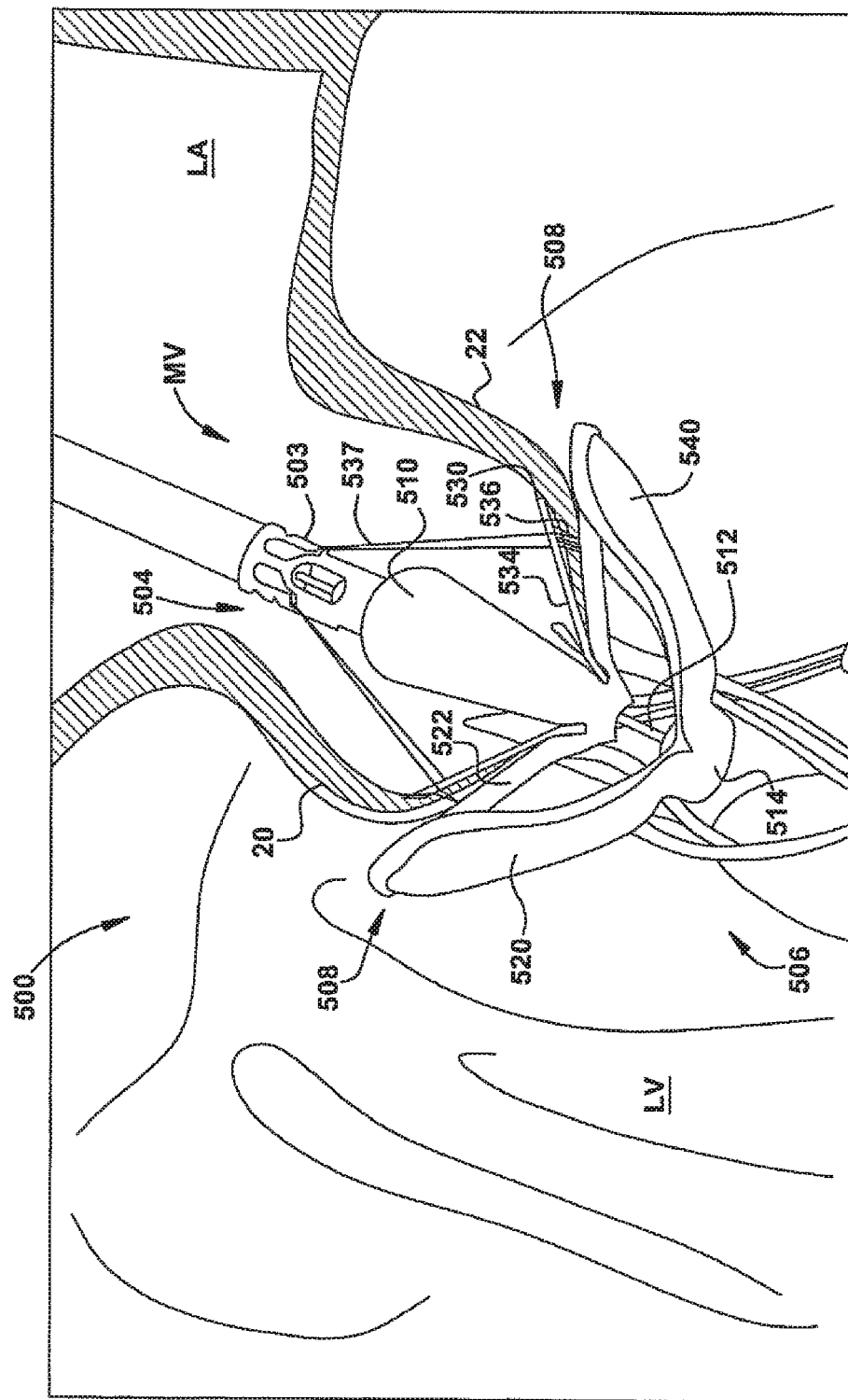
Figure 45:
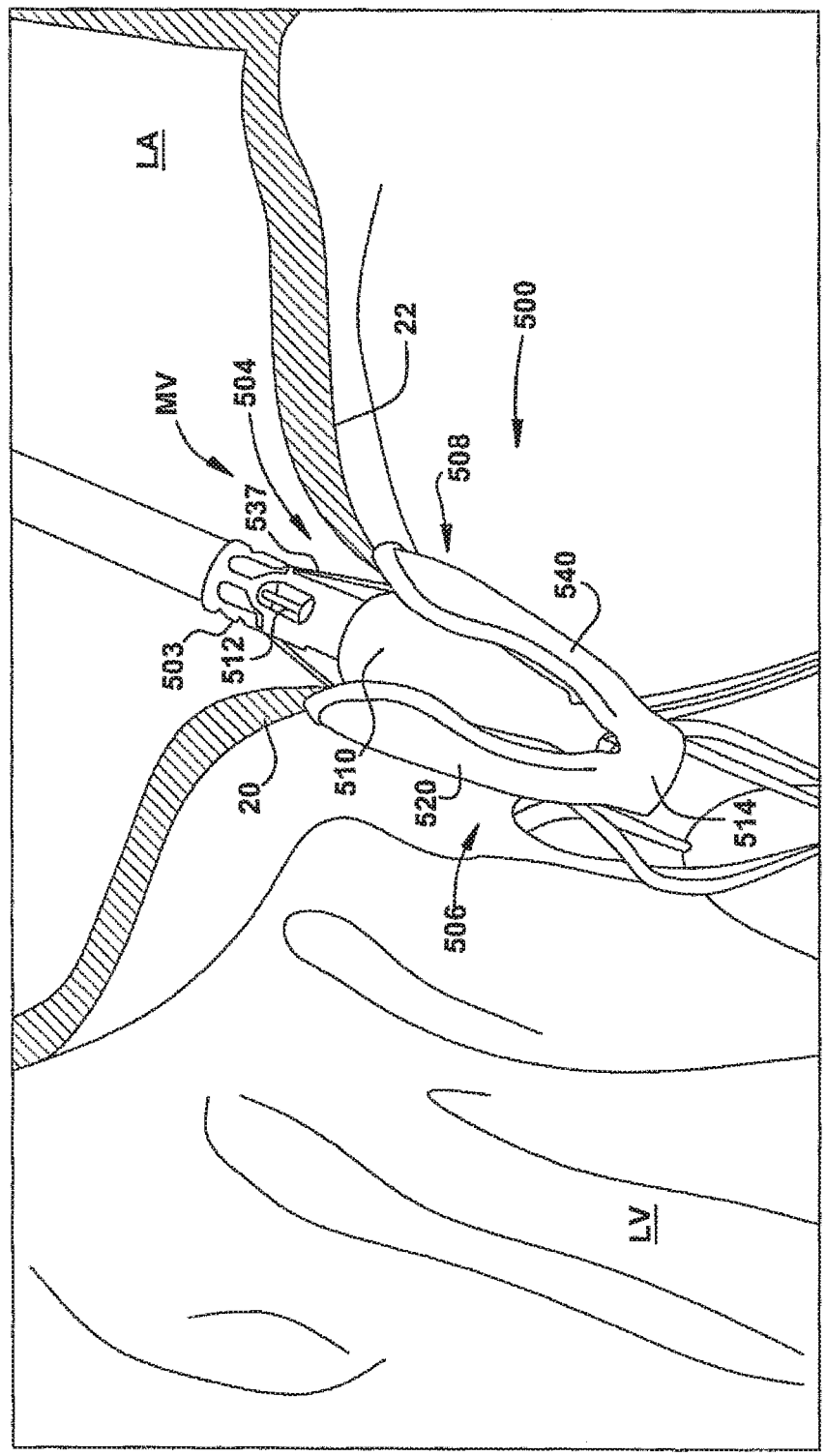
Figure 46:
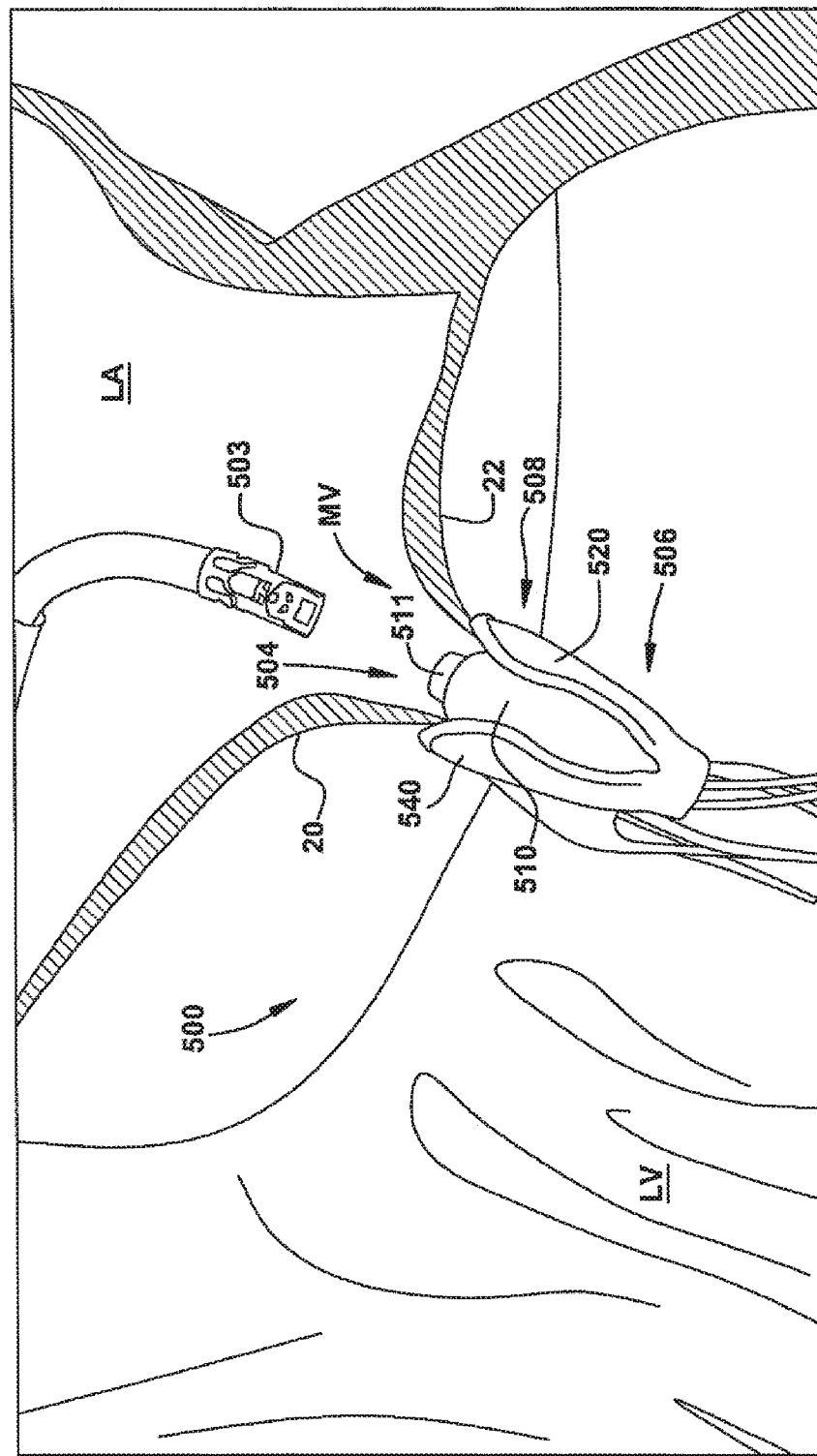

The device 500 is loaded in the delivery sheath in the fully open position, because the fully open position takes up the least space and allows the smallest catheter to be used (or the largest device 500 to be used for a given catheter size). Referring now to FIG. 35, the delivery sheath is inserted into the left atrium LA through the septum and the device 500 is deployed from the delivery sheath 502 in the fully open condition. The actuation wire 512 is then retracted to move the device 500 into the fully closed condition shown in FIGS. 36-37 and then maneuvered towards the mitral valve MV as shown in FIG. 38. Referring now to FIG. 39, when the device 500 is aligned with the mitral valve MV, the actuation wire 512 is extended to open the paddles 520, 522 into the partially opened position and the actuation lines 537 are retracted to open the barbed clasps 530 to prepare for leaflet grasp. Next, as shown in FIGS. 40-41, the partially open device 500 is inserted through the mitral valve MV until leaflets 20, 22 are properly positioned in between the inner paddles 522 and the coaption element 510 and inside the open barbed clasps 530. FIG. 42 shows the device 500 with both clasps 530 closed, though the barbs 536 of one clasp 530 missed one of the leaflets 22. As can be seen in FIGS. 42-44, the out of position clasp 530 is opened and closed again to properly grasp the missed leaflet 22. When both leaflets 20, 22 are grasped properly, the actuation wire 512 is retracted to move the device 500 into the fully closed position shown in FIG. 45. With the device 500 fully implanted in the native mitral valve MV, the actuation wire 512 is withdrawn to release the capture mechanism 503 from the proximal collar 511. Once deployed, the device 500 may be maintained in the fully closed position with a mechanical means such as a latch or may be biased to remain closed through the use of spring material, such as steel, and/or shape-memory alloys such as Nitinol. For example, the paddles 520, 522 may be formed of steel or Nitinol shape-memory alloy—produced in a wire, sheet, tubing, or laser sintered powder—and are biased to hold the outer paddles 520 closed around the inner paddles 522, coaption element 510, and the barbed clasps 530 pinched around native leaflets 20, 22.

Figure 6B:
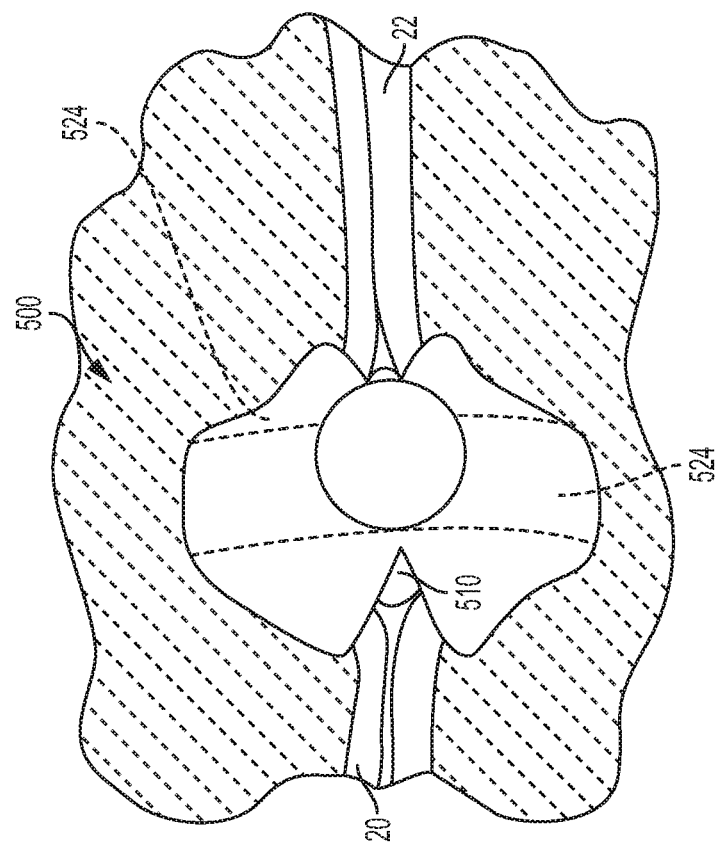
FIG. 6B illustrates a valve repair device attached to mitral valve leaflets with the coaption element in the gap of the mitral valve as viewed from a ventricular side of the mitral valve.
Figure 6A:
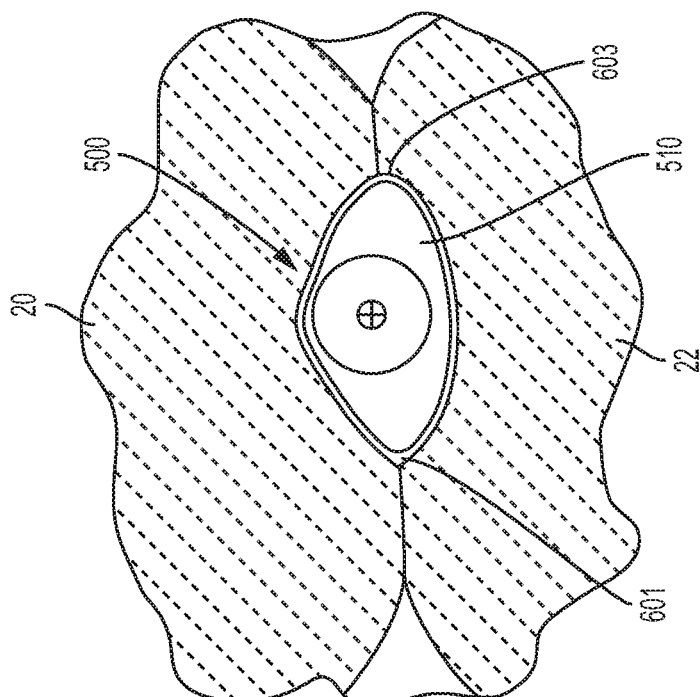
FIG. 6A illustrates a coaption element in the gap of the mitral valve as viewed from an atrial side of the mitral valve.

The device 500 can have a wide variety of different shapes and sizes. Referring to FIGS. 6 and 6A-6E, in an exemplary embodiment, the coaption element 510 functions as a gap filler in the valve regurgitant orifice, such as the gap 26 in the mitral valve MV illustrated by FIG. 6. Referring to FIG. 6A, since the coaption element 510 is deployed between two opposing valve leaflets 20, 22, the leaflets will not coapt against each other in the area of the coaption element 510, but coapt against the coaption element 510 instead. This reduces the distance the leaflets 20, 22 need to be approximated. A reduction in leaflet approximation distance can result in several advantages. For example, the coaption element and resulting reduced approximation can facilitate repair of severe mitral valve anatomies, such as large gaps in functional valve disease (See for example, FIG. 6). Since the coaption element 510 reduces the distance the native valves have to be approximated, the stress in the native valves can be reduced or minimized Shorter approximation distance of the valve leaflets 20, 22 can require less approximation forces which can result in less tension of the leaflets and less diameter reduction of the valve annulus. The smaller reduction of the valve annulus (or no reduction of the valve annulus) can result in less reduction in valve orifice area as compared to a device without a spacer. As a result, the coaption element 510 can reduce the transvalvular gradients.

Figure 6D:
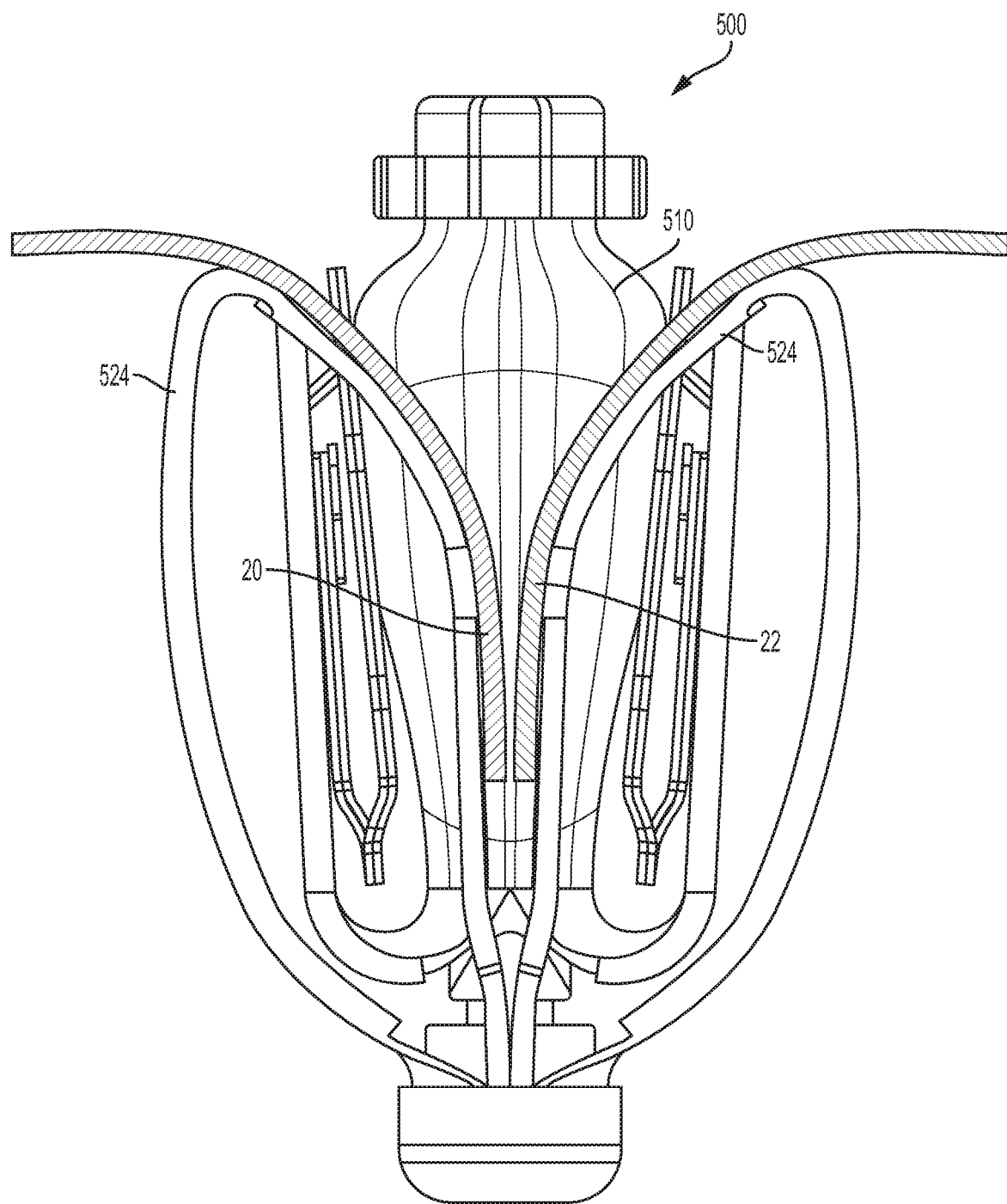
FIG. 6D is a schematic view illustrating a path of mitral valve leaflets along each side of a coaption element of mitral valve repair device.
Figure 6E:
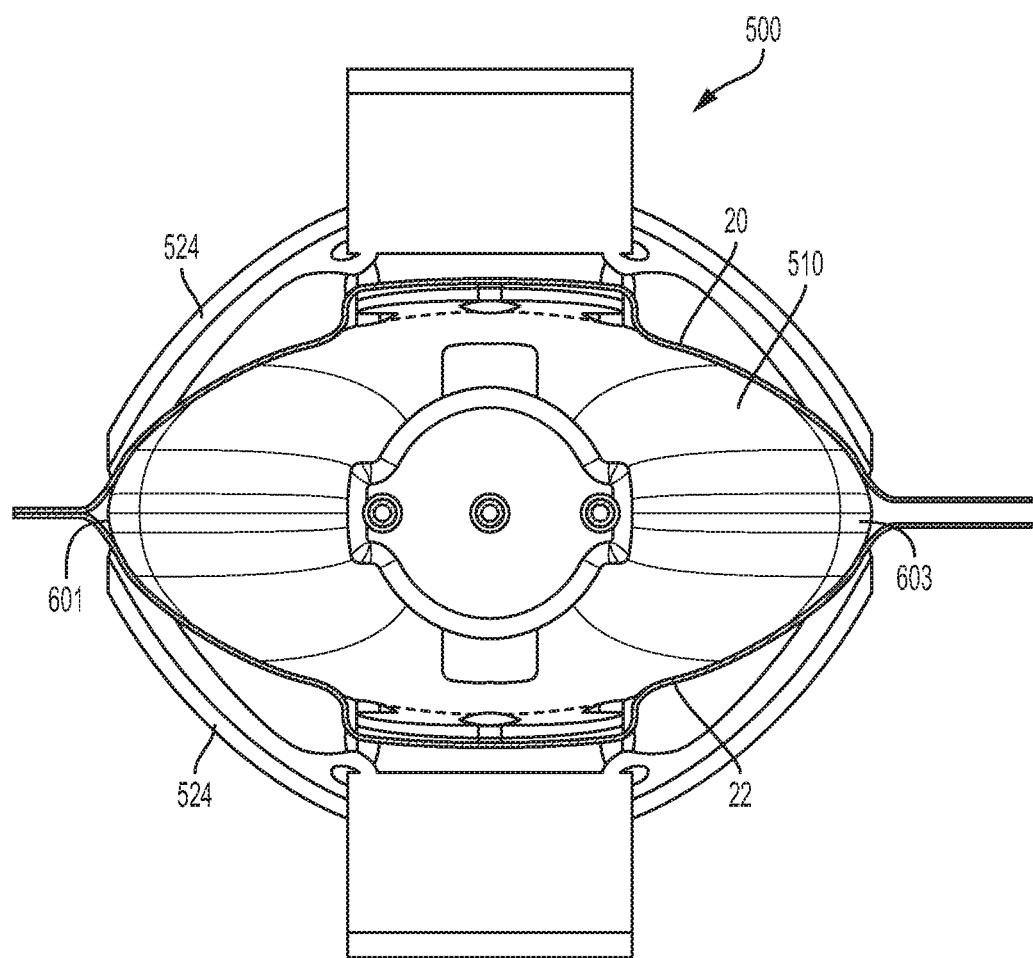
FIG. 6E is a top schematic view illustrating a path of mitral valve leaflets around a coaption element of a mitral valve repair device.

In one exemplary embodiments, the paddle frames 524 conform to the shape of the coaption element 510. In one example, if the coaption element 510 is wider than the paddle frames 524, a distance (gap) between the opposing leaflets 20, 22 can be created by the device 500. Referring to FIGS. 6A-6E, in one exemplary embodiment the paddles are configured to conform to the shape or geometry of the coaption element 510. As a result, the paddles can mate with both the coaption element 510 and the native valve. Referring to FIGS. 6D and 6E, in one exemplary embodiment the paddles 524 surround the coaption element 510. Thus, when the leaflets 20, 22 are coapted against the coaption element 510, the leaflets 20, 22 fully surround or "hug" the coaption element 510 in its entirety, and small leaks on the medial and lateral aspects of the coaption element 510 can thus be prevented. FIGS. 6B and 6C illustrate the valve repair device 500 attached to mitral valve leaflets 20, 22 from the ventricular side of the mitral valve. FIG. 6A illustrates the valve repair device 500 attached to mitral valve leaflets 20, 22 from the atrial side of the mitral valve. Referring to FIGS. 6A and 6B, when the paddles have a geometry that conforms to the geometry of the coaption element 510, the leaflets 20, 22 can coapt around the coaption element and/or along the length of the spacer. Referring to FIG. 6E, a schematic atrial view/surgeons view depicts the paddle frames (which would not actually be visible from a true atrial view), conforming to the spacer geometry. The opposing leaflets 20, 22 (the ends of which would also not be visible in the true atrial view) being approximated by the paddles, to fully surround or "hug" the coaption element 510.

Referring to FIGS. 6B-6E, because the paddle frames 524 conform to the shape of the coaption element 510, the valve leaflets 20, 22 can be coapted completely around the coaption element by the paddle frames 524, including on the lateral and medial aspects 601, 603 of the coaption element 510. This coaption of the leaflets 20, 22 against the lateral and medial aspects of the coaption element 510 would seem to contradict the statement above that the presence of a coaption element 510 minimizes the distance the leaflets need to be approximated. However, the distance the leaflets 20, 22 need to be approximated is still minimized if the coaption element 510 is placed precisely at a regurgitant gap and the regurgitant gap is less than the width (medial—lateral) of the coaption element 510.

Referring to FIGS. 6A and 6E, the coaption element 510 can take a wide variety of different shapes. In one exemplary embodiment, when viewed from the top (and/or sectional views from the top; see FIGS. 95-102), the coaption element has an oval shape or an elliptical shape. The oval or elliptical shape can allow the paddle frames 524 co conform to the shape of the coaption element and/or can reduce lateral leaks (See FIGS. 65-83).

Figure 2A:
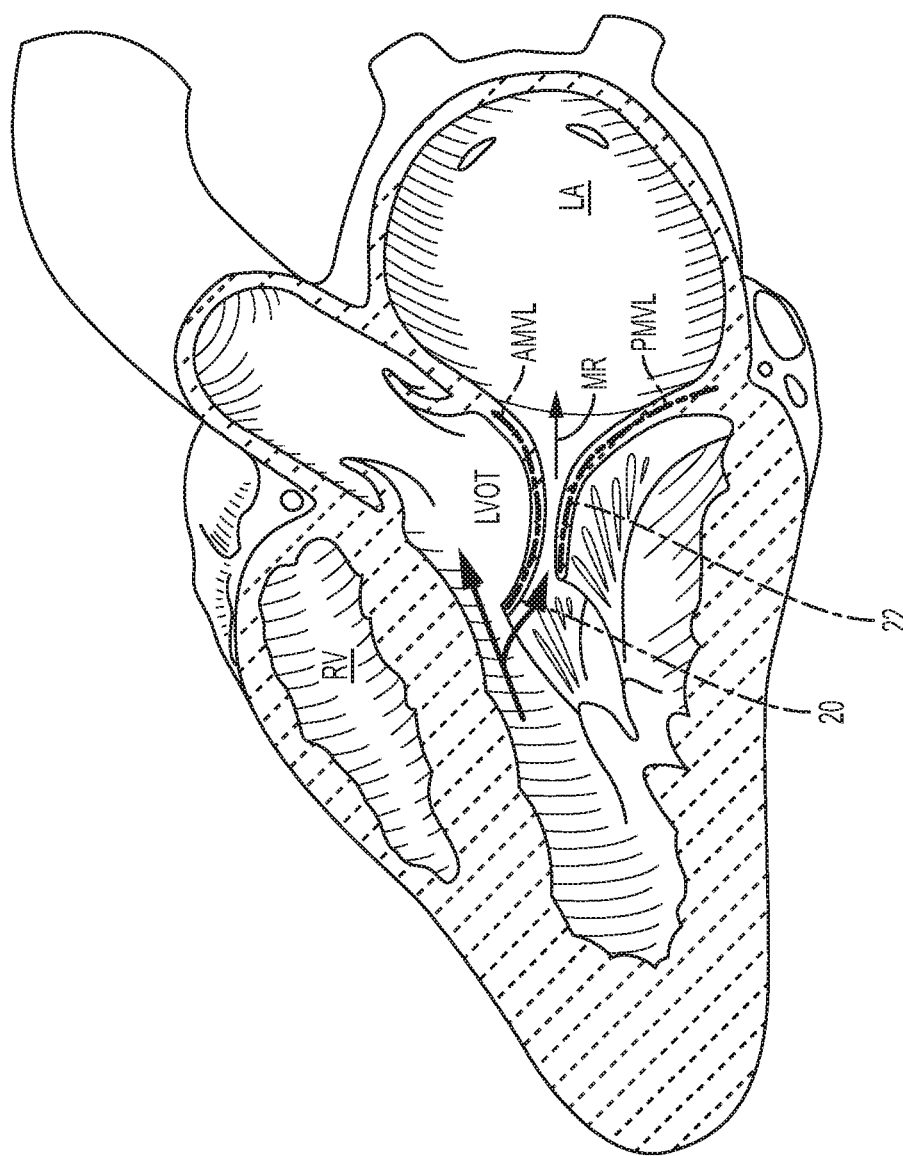
FIG. 2A is another cutaway view of the human heart in a systolic phase.

As mentioned above, the coaption element 510 can reduce tension of the opposing leaflets by reducing the distance the leaflets need to be approximated to the coaption element 510 at the positions 601, 603. The reduction of the distance of leaflet approximation at the positions 601, 603 can result in the reduction of leaflet stresses and gradients. In addition, as is also explained above, the native valve leaflets 20, 22 can surround or "hug" the coaption element in order to prevent lateral leaks. In one exemplary embodiment, the geometrical characteristics of the coaption element can be designed to preserve and augment these two characteristics of the device 500. Referring to FIG. 2A, as seen from a Left Ventricular Outflow Tract (LVOT) view, the anatomy of the leaflets 20, 22 is such that the inner sides of the leaflets coapt at the free end portions and the leaflets 20, 22 start receding or spreading apart from each other. The leaflets 20, 22 spread apart in the atrial direction, until each leaflet meets with the mitral annulus.

Figure 2B:
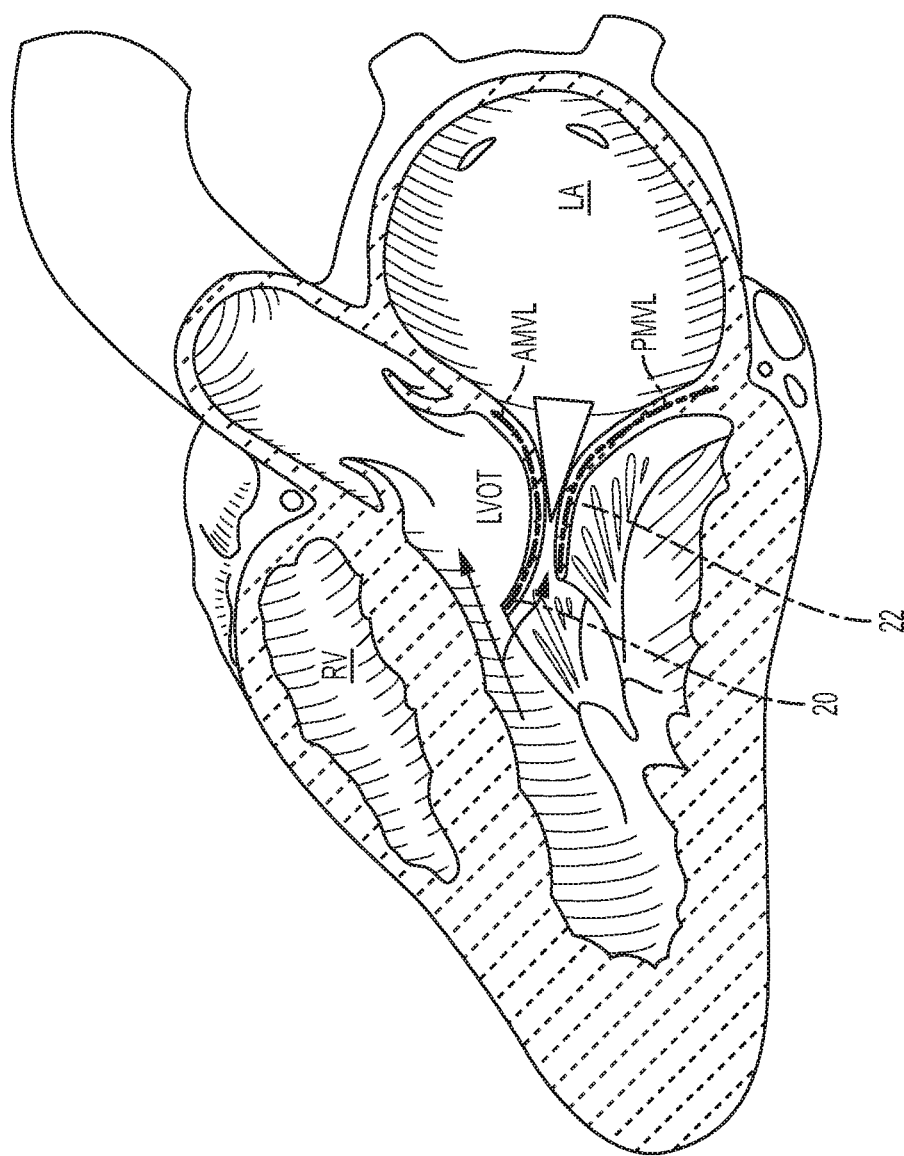
FIG. 2B is the cutaway view of FIG. 2A annotated to illustrate a natural shape of mitral valve leaflets in the systolic phase.

In one exemplary embodiment, the valve repair device 500 and its coaption element 510 are designed to conform to the geometrical anatomy of the valve leaflets 20, 22. To achieve valve sealing, the valve repair device 500 can be designed to coapt the native leaflets to the coaption element, completely around the coaption element, including at the medial 601 and lateral 603 positions of the coaption element 510. Additionally, a reduction on forces required to bring the leaflets into contact with the coaption element 510 at the positions 601, 603 can minimize leaflet stress and gradients. FIG. 2B shows how a tapered or triangular shape of a coaption element 510 will naturally adapt to the native valve geometry and to its expanding leaflet nature (toward the annulus).

FIG. 6D illustrates the geometry of the coaption element 510 and the paddle frame 524 from an LVOT perspective. As can be seen in this view, the coaption element 510 has a tapered shape being smaller in dimension in the area closer to where the inside surfaces of the leaflets 20, 22 are required to coapt and increase in dimension as the coaption element extends toward the atrium. The depicted native valve geometry is accommodated by a tapered coaption element geometry. Still referring to FIG. 6D, the tapered coaption element geometry, in conjunction with the illustrated expanding paddle frame 524 shape (toward the valve annulus) can help to achieve coaptation on the lower end of the leaflets, reduce stress, and minimize transvalvular gradients.

Figure 67:
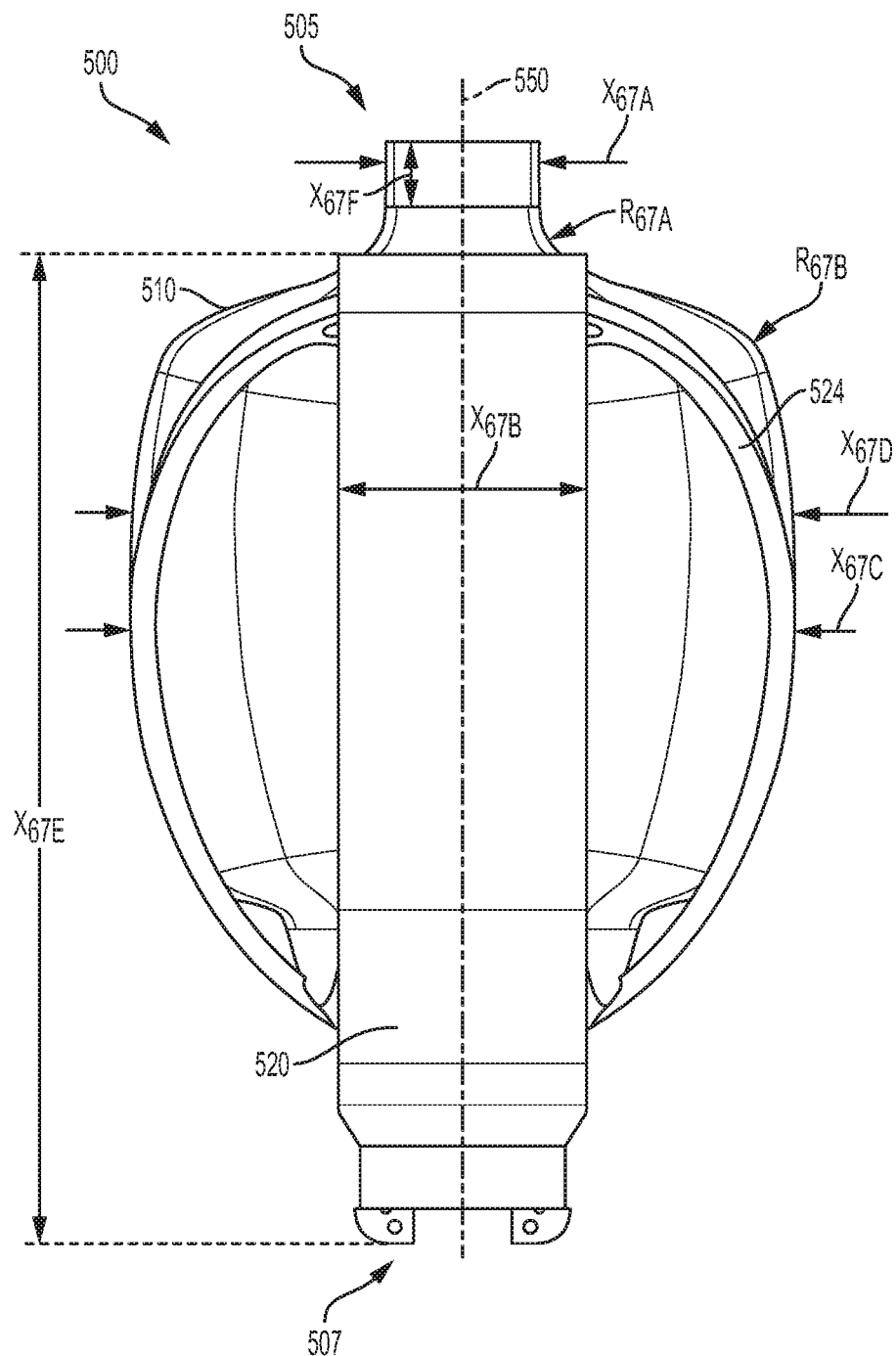
FIG. 67 shows a front view of the implantable prosthetic device of FIG. 65.

Referring to FIG. 6C, in one exemplary embodiment remaining shapes of the coaption element 510 and the paddle frames 524 can be defined based on an Intra-Commissural view of the native valve and the device 510. Two factors of these shapes are leaflet coaptation against the coaption element 510 and reduction of stress on the leaflets due to the coaption. Referring to FIGS. 6C and 67, to both coapt the valve leaflets 20, 22 against the coaption element 510 and reduce the stress applied to the valve leaflets 20, 22 by the coaption element 510 and/or the paddles 524, the coaption element 510 can have a round or rounded shape and the paddle frame 524 can have a full radius that spans from one leg of the paddles to the other leg of the paddles. The round shape of the coaption element and/or the illustrated fully rounded shape of the paddle frame will distribute the stresses on the leaflets 20, 22 across a large, curved engagement area 607. For example, in FIG. 6C, the force on the leaflets 20, 22 by the paddle frames is spread along the entire rounded length of the paddle frame 524, as the leaflets 20 try to open during the diastole cycle.

Referring to FIG. 67, in one exemplary embodiment, to cooperate with the full rounded shape of the paddle frames 524, and/or in order to maximize leaflet coaptation against the coaption element 510 and leaflet-to-leaflet coaptation at the sides 601, 603 of the coaption element 510, the shape of the coaption element in the intra-commissural view follows a round shape. Referring to FIG. 67, the round shape of the coaption element in this view substantially follows or is close to the shape of the paddle frames 524.

Figure 68:
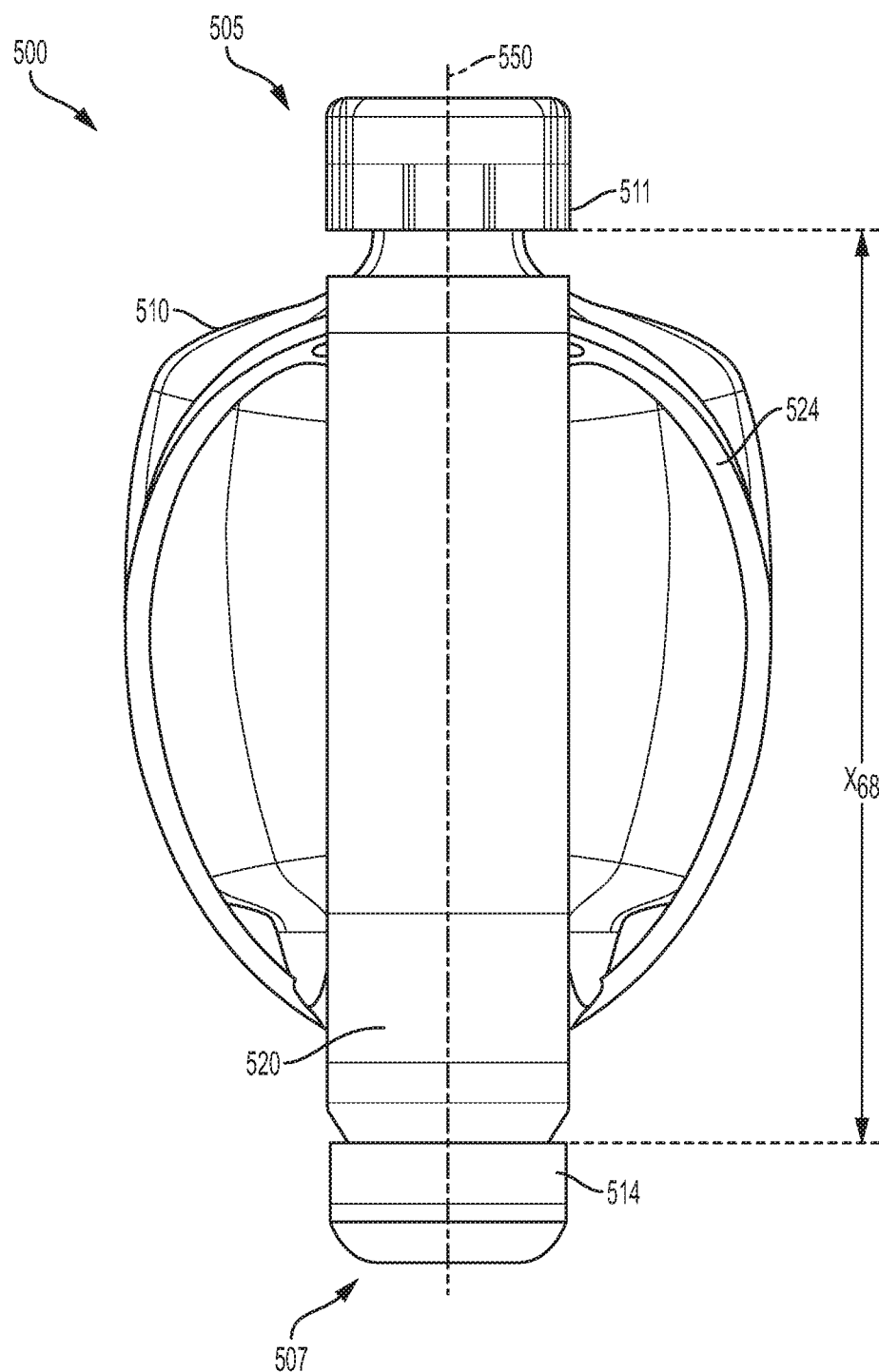
FIG. 68 shows a front view of the implantable prosthetic device of FIG. 65 with additional components.

In one exemplary embodiment, the overall shape of the coaption element 510 is an elliptical or oval cross section when seen from the surgeon's view (top view—See FIG. 70), a tapered shape or cross section when seen from an LVOT view (side view—See FIG. 69), and a substantially round shape or rounded shape when seen from an intra-commissural view (See FIG. 68). In one exemplary embodiment, a blend of these three geometries can result in the three-dimensional shape of the illustrated coaption element 510 that achieves the benefits described above.

In one exemplary embodiment, the dimensions of the coaption element are selected to minimize the number of implants that a single patient will require (preferably one), while at the same time maintaining low transvalvular gradients. In one exemplary embodiment, the anterior-posterior distance $X_{47B}$ at the top of the spacer is about 5 mm, and the medial-lateral distance $X_{67D}$ of the spacer at its widest is about 10 mm. In one exemplary embodiment, the overall geometry of the device 510 can be based on these two dimensions and the overall shape strategy described above. It should be readily apparent that the use of other anterior-posterior distance anterior-posterior distance $X_{47B}$ and medial-lateral distance $X_{67D}$ as starting points for the device will result in a device having different dimensions. Further, using other dimensions and the shape strategy described above will also result in a device having different dimensions.

Tables A, B, and C provide examples of values and ranges for dimensions of the device and components of the device for some exemplary embodiments. However, the device can have a wide variety of different shapes and sizes and need not have all or any of the dimensional values or dimensional ranges provided in Tables A, B, and C. Table A provides examples of linear dimensions X in millimeters and ranges of linear dimensions in millimeters for the device and components of the device. Table B provides examples of radius dimensions R in millimeters and ranges of radius dimensions in millimeters for the device and components of the device. Table C provides examples of angular dimensions a in degrees and ranges of angular dimensions in degrees for the device and components of the device. The subscripts for each of the dimensions indicates the drawing in which the dimension first appears.

TABLE A

| | | Linear Dimensions (mm) | | | | | | | |
| --- | --- | --- | --- | --- | --- | --- | --- | --- | --- |
| | | Range A | | Range B | | Range C | | Range C | |
| | Example | (min) | (max) | (min) | (max) | (min) | (max) | (min) | (max) |
| $X_{47A}$ | 2.8 | 1.4 | 4.2 | 2.1 | 3.5 | 2.52 | 3.08 | 2.66 | 2.94 |
| $X_{47B}$ | 5.3 | 2.65 | 7.95 | 3.975 | 6.625 | 4.77 | 5.83 | 5.035 | 5.565 |
| $X_{47C}$ | 2.8 | 1.4 | 4.2 | 2.1 | 3.5 | 2.52 | 3.08 | 2.66 | 2.94 |
| $X_{47D}$ | 3.3 | 1.65 | 4.95 | 2.475 | 4.125 | 2.97 | 3.63 | 3.135 | 3.465 |
| $X_{47E}$ | 5.4 | 2.7 | 8.1 | 4.05 | 6.75 | 4.86 | 5.94 | 5.13 | 5.67 |
| $X_{47F}$ | 8 | 4 | 12 | 6 | 10 | 7.2 | 8.8 | 7.6 | 8.4 |
| $X_{47G}$ | 1 | 0.5 | 1.5 | 0.75 | 1.25 | 0.9 | 1.1 | 0.95 | 1.05 |

TABLE A-continued

| | | Range A | | Range B | | Range C | | Range C | |
|---|---|---|---|---|---|---|---|---|---|
| | Example | (min) | (max) | (min) | (max) | (min) | (max) | (min) | (max) |
| $X_{52A}$ | 12 | 6 | 18 | 9 | 15 | 10.8 | 13.2 | 11.4 | 12.6 |
| $X_{58A}$ | 11 | 5.5 | 16.5 | 8.25 | 13.75 | 9.9 | 12.1 | 10.45 | 11.55 |
| $X_{59A}$ | 27 | 13.5 | 40.5 | 20.25 | 33.75 | 24.3 | 29.7 | 25.65 | 28.35 |
| $X_{59B}$ | 8 | 4 | 12 | 6 | 10 | 7.2 | 8.8 | 7.6 | 8.4 |
| $X_{59C}$ | 7 | 3.5 | 10.5 | 5.25 | 8.75 | 6.3 | 7.7 | 6.65 | 7.35 |
| $X_{67A}$ | 2.4 | 1.2 | 3.6 | 1.8 | 3 | 2.16 | 2.64 | 2.28 | 2.52 |
| $X_{67B}$ | 3.7 | 1.85 | 5.55 | 2.775 | 4.625 | 3.33 | 4.07 | 3.515 | 3.885 |
| $X_{67C}$ | 10 | 5 | 15 | 7.5 | 12.5 | 9 | 11 | 9.5 | 10.5 |
| $X_{67D}$ | 10 | 5 | 15 | 7.5 | 12.5 | 9 | 11 | 9.5 | 10.5 |
| $X_{67E}$ | 15 | 7.5 | 22.5 | 11.25 | 18.75 | 13.5 | 16.5 | 14.25 | 15.75 |
| $X_{67F}$ | 1 | 0.5 | 1.5 | 0.75 | 1.25 | 0.9 | 1.1 | 0.95 | 1.05 |
| $X_{68}$ | 14.2 | 7.1 | 21.3 | 10.65 | 17.75 | 12.78 | 15.62 | 13.49 | 14.91 |
| $X_{70A}$ | 1.7 | 0.85 | 2.55 | 1.275 | 2.125 | 1.53 | 1.87 | 1.615 | 1.785 |
| $X_{70B}$ | 2.8 | 1.4 | 4.2 | 2.1 | 3.5 | 2.52 | 3.08 | 2.66 | 2.94 |
| $X_{71A}$ | 6.2 | 3.1 | 9.3 | 4.65 | 7.75 | 5.58 | 6.82 | 5.89 | 6.51 |
| $X_{71B}$ | 5.4 | 2.7 | 8.1 | 4.05 | 6.75 | 4.86 | 5.94 | 5.13 | 5.67 |
| $X_{71C}$ | 0.9 | 0.45 | 1.35 | 0.675 | 1.125 | 0.81 | 0.99 | 0.855 | 0.945 |
| $X_{71D}$ | 3.75 | 1.875 | 5.625 | 2.8125 | 4.6875 | 3.375 | 4.125 | 3.5625 | 3.9375 |
| $X_{71E}$ | 4.5 | 2.25 | 6.75 | 3.375 | 5.625 | 4.05 | 4.95 | 4.275 | 4.725 |
| $X_{72A}$ | 10.4 | 5.2 | 15.6 | 7.8 | 13 | 9.36 | 11.44 | 9.88 | 10.92 |
| $X_{91A}$ | 8.8 | 4.4 | 13.2 | 6.6 | 11 | 7.92 | 9.68 | 8.36 | 9.24 |
| $X_{91B}$ | 7.8 | 3.9 | 11.7 | 5.85 | 9.75 | 7.02 | 8.58 | 7.41 | 8.19 |
| $X_{91C}$ | 8.1 | 4.05 | 12.15 | 6.075 | 10.125 | 7.29 | 8.91 | 7.695 | 8.505 |
| $X_{91D}$ | 13.6 | 6.8 | 20.4 | 10.2 | 17 | 12.24 | 14.96 | 12.92 | 14.28 |
| $X_{92A}$ | 0.05 | 0.025 | 0.075 | 0.0375 | 0.0625 | 0.045 | 0.055 | 0.0475 | 0.0525 |
| $X_{92B}$ | 1.5 | 0.75 | 2.25 | 1.125 | 1.875 | 1.35 | 1.65 | 1.425 | 1.575 |
| $X_{92C}$ | 10.8 | 5.4 | 16.2 | 8.1 | 13.5 | 9.72 | 11.88 | 10.26 | 11.34 |
| $X_{95A}$ | 13.8 | 6.9 | 20.7 | 10.35 | 17.25 | 12.42 | 15.18 | 13.11 | 14.49 |
| $X_{96A}$ | 8.2 | 4.1 | 12.3 | 6.15 | 10.25 | 7.38 | 9.02 | 7.79 | 8.61 |
| $X_{96B}$ | 5.1 | 2.55 | 7.65 | 3.825 | 6.375 | 4.59 | 5.61 | 4.845 | 5.355 |
| $X_{96C}$ | 0.5 | 0.25 | 0.75 | 0.375 | 0.625 | 0.45 | 0.55 | 0.475 | 0.525 |
| $X_{97}$ | 10.8 | 5.4 | 16.2 | 8.1 | 13.5 | 9.72 | 11.88 | 10.26 | 11.34 |
| $X_{98A}$ | 9.8 | 4.9 | 14.7 | 7.35 | 12.25 | 8.82 | 10.78 | 9.31 | 10.29 |
| $X_{98B}$ | 5 | 2.5 | 7.5 | 3.75 | 6.25 | 4.5 | 5.5 | 4.75 | 5.25 |
| $X_{99}$ | 8 | 4 | 12 | 6 | 10 | 7.2 | 8.8 | 7.6 | 8.4 |
| $X_{100A}$ | 9.7 | 4.85 | 14.55 | 7.275 | 12.125 | 8.73 | 10.67 | 9.215 | 10.185 |
| $X_{100B}$ | 4 | 2 | 6 | 3 | 5 | 3.6 | 4.4 | 3.8 | 4.2 |
| $X_{101}$ | 5.2 | 2.6 | 7.8 | 3.9 | 6.5 | 4.68 | 5.72 | 4.94 | 5.46 |
| $X_{102A}$ | 8 | 4 | 12 | 6 | 10 | 7.2 | 8.8 | 7.6 | 8.4 |
| $X_{102B}$ | 2.9 | 1.45 | 4.35 | 2.175 | 3.625 | 2.61 | 3.19 | 2.755 | 3.045 |
| $X_{117A}$ | 4.2 | 2.1 | 6.3 | 3.15 | 5.25 | 3.78 | 4.62 | 3.99 | 4.41 |
| $X_{117B}$ | 14.5 | 7.25 | 21.75 | 10.875 | 18.125 | 13.05 | 15.95 | 13.775 | 15.225 |
| $X_{117C}$ | 13 | 6.5 | 19.5 | 9.75 | 16.25 | 11.7 | 14.3 | 12.35 | 13.65 |

TABLE B

Radius Dimensions (mm)

| | | Range A | | Range B | | Range C | | Range C | |
|---|---|---|---|---|---|---|---|---|---|
| | Example | (min) | (max) | (min) | (max) | (min) | (max) | (min) | (max) |
| $R_{47A}$ | 1.3 | 0.65 | 1.95 | 0.975 | 1.625 | 1.17 | 1.43 | 1.235 | 1.365 |
| $R_{47B}$ | 1 | 0.5 | 1.5 | 0.75 | 1.25 | 0.9 | 1.1 | 0.95 | 1.05 |
| $R_{47C}$ | 0.6 | 0.3 | 0.9 | 0.45 | 0.75 | 0.54 | 0.66 | 0.57 | 0.63 |
| $R_{47D}$ | 5 | 2.5 | 7.5 | 3.75 | 6.25 | 4.5 | 5.5 | 4.75 | 5.25 |
| $R_{47E}$ | 0.75 | 0.375 | 1.125 | 0.5625 | 0.9375 | 0.675 | 0.825 | 0.7125 | 0.7875 |
| $R_{67A}$ | 0.75 | 0.375 | 1.125 | 0.5625 | 0.9375 | 0.675 | 0.825 | 0.7125 | 0.7875 |
| $R_{67B}$ | 0.9 | 0.45 | 1.35 | 0.675 | 1.125 | 0.81 | 0.99 | 0.855 | 0.945 |
| $R_{70A}$ | 1.4 | 0.7 | 2.1 | 1.05 | 1.75 | 1.26 | 1.54 | 1.33 | 1.47 |
| $R_{70B}$ | 0.4 | 0.2 | 0.6 | 0.3 | 0.5 | 0.36 | 0.44 | 0.38 | 0.42 |
| $R_{70C}$ | 0.6 | 0.3 | 0.9 | 0.45 | 0.75 | 0.54 | 0.66 | 0.57 | 0.63 |
| $R_{70D}$ | 7 | 3.5 | 10.5 | 5.25 | 8.75 | 6.3 | 7.7 | 6.65 | 7.35 |
| $R_{71A}$ | 1.6 | 0.8 | 2.4 | 1.2 | 2 | 1.44 | 1.76 | 1.52 | 1.68 |
| $R_{72A}$ | 1.85 | 0.925 | 2.775 | 1.3875 | 2.3125 | 1.665 | 2.035 | 1.7575 | 1.9425 |
| $R_{73A}$ | 1.9 | 0.95 | 2.85 | 1.425 | 2.375 | 1.71 | 2.09 | 1.805 | 1.995 |
| $R_{91A}$ | 9.2 | 4.6 | 13.8 | 6.9 | 11.5 | 8.28 | 10.12 | 8.74 | 9.66 |
| $R_{91B}$ | 0.3 | 0.15 | 0.45 | 0.225 | 0.375 | 0.27 | 0.33 | 0.285 | 0.315 |
| $R_{91C}$ | 0.3 | 0.15 | 0.45 | 0.225 | 0.375 | 0.27 | 0.33 | 0.285 | 0.315 |
| $R_{92A}$ | 0.75 | 0.375 | 1.125 | 0.5625 | 0.9375 | 0.675 | 0.825 | 0.7125 | 0.7875 |
| $R_{94A}$ | 1.65 | 0.825 | 2.475 | 1.2375 | 2.0625 | 1.485 | 1.815 | 1.5675 | 1.7325 |

TABLE B-continued

Radius Dimensions (mm)

| Example | Range A (min) | Range A (max) | Range B (min) | Range B (max) | Range C (min) | Range C (max) | Range C (min) | Range C (max) |
|---|---|---|---|---|---|---|---|---|
| $R_{96A}$ | 1.7 | 0.85 | 2.55 | 1.275 | 2.125 | 1.53 | 1.87 | 1.615 | 1.785 |
| $R_{96B}$ | 4.7 | 2.35 | 7.05 | 3.525 | 5.875 | 4.23 | 5.17 | 4.465 | 4.935 |
| $R_{98A}$ | 1.3 | 0.65 | 1.95 | 0.975 | 1.625 | 1.17 | 1.43 | 1.235 | 1.365 |
| $R_{98B}$ | 7.6 | 3.8 | 11.4 | 5.7 | 9.5 | 6.84 | 8.36 | 7.22 | 7.98 |
| $R_{100A}$ | 0.9 | 0.45 | 1.35 | 0.675 | 1.125 | 0.81 | 0.99 | 0.855 | 0.945 |
| $R_{100B}$ | 9.6 | 4.8 | 14.4 | 7.2 | 12 | 8.64 | 10.56 | 9.12 | 10.08 |
| $R_{102A}$ | 0.45 | 0.225 | 0.675 | 0.3375 | 0.5625 | 0.405 | 0.495 | 0.4275 | 0.4725 |
| $R_{102B}$ | 8.5 | 4.25 | 12.75 | 6.375 | 10.625 | 7.65 | 9.35 | 8.075 | 8.925 |
| $R_{115A}$ | 9.3 | 4.65 | 13.95 | 6.975 | 11.625 | 8.37 | 10.23 | 8.835 | 9.765 |
| $R_{115B}$ | 7.8 | 3.9 | 11.7 | 5.85 | 9.75 | 7.02 | 8.58 | 7.41 | 8.19 |
| $R_{115C}$ | 7.8 | 3.9 | 11.7 | 5.85 | 9.75 | 7.02 | 8.58 | 7.41 | 8.19 |
| $R_{115D}$ | 6.7 | 3.35 | 10.05 | 5.025 | 8.375 | 6.03 | 7.37 | 6.365 | 7.035 |
| $R_{115E}$ | 1.5 | 0.75 | 2.25 | 1.125 | 1.875 | 1.35 | 1.65 | 1.425 | 1.575 |

TABLE C

Angular Dimensions (degrees)

| Example | Range A (min) | Range A (max) | Range B (min) | Range B (max) | Range C (min) | Range C (max) | Range C (min) | Range C (max) |
|---|---|---|---|---|---|---|---|---|
| $\alpha_{47}$ | 12 | 6 | 18 | 9 | 15 | 10.8 | 13.2 | 11.4 | 12.6 |
| $\alpha_{91A}$ | 9 | 4.5 | 13.5 | 6.75 | 11.25 | 8.1 | 9.9 | 8.55 | 9.45 |
| $\alpha_{91B}$ | 14 | 7 | 21 | 10.5 | 17.5 | 12.6 | 15.4 | 13.3 | 14.7 |
| $\alpha_{91C}$ | 20 | 10 | 30 | 15 | 25 | 18 | 22 | 19 | 21 |
| $\alpha_{117A}$ | 39 | 19.5 | 58.5 | 29.25 | 48.75 | 35.1 | 42.9 | 37.05 | 40.95 |
| $\alpha_{117B}$ | 3 | 1.5 | 4.5 | 2.25 | 3.75 | 2.7 | 3.3 | 2.85 | 3.15 |

Referring now to FIGS. 47-61, an implantable device 500 is shown in various positions and configurations. The implantable device 500 can include any other features for an implantable prosthetic device discussed in the present application, and the device 500 can be positioned to engage valve tissue 20, 22 as part of any suitable valve repair system (e.g., any valve repair system disclosed in the present application).

The implantable device 500 has a proximal or attachment portion 505, a coaption element 510, inner anchor portions or inner paddles 522, outer anchor portions or outer paddles 520, anchor extension members or paddle frames 524, and a distal portion 507. The inner paddles 522 are jointably attached between the coaption element 510 and the outer paddles 520. The outer paddles 520 are jointably attached between the inner paddles 522 and the distal portion 507. The paddle frames 524 are attached to the cap 514 at the distal portion 507 and extend to the joint portion 523 between the inner and outer paddles 522, 520. In some embodiments, the paddle frames 524 are formed of a material that is more rigid and stiff than the material forming the paddles 522, 520 so that the paddle frames 524 provide support for the paddles 522, 520. In one exemplary embodiment, the inner paddles 522 are stiff, relatively stiff, rigid, have rigid portions and/or are stiffened by a stiffening member or the fixed portion of the clasps 530. The stiffening of the inner paddle allows the device to move to the various different positions shown and described herein. The inner paddle 522, the outer paddle 520, the coaption can all be interconnected as described herein, such that the device 500 is constrained to the movements and positions shown and described herein.

Figure 47:
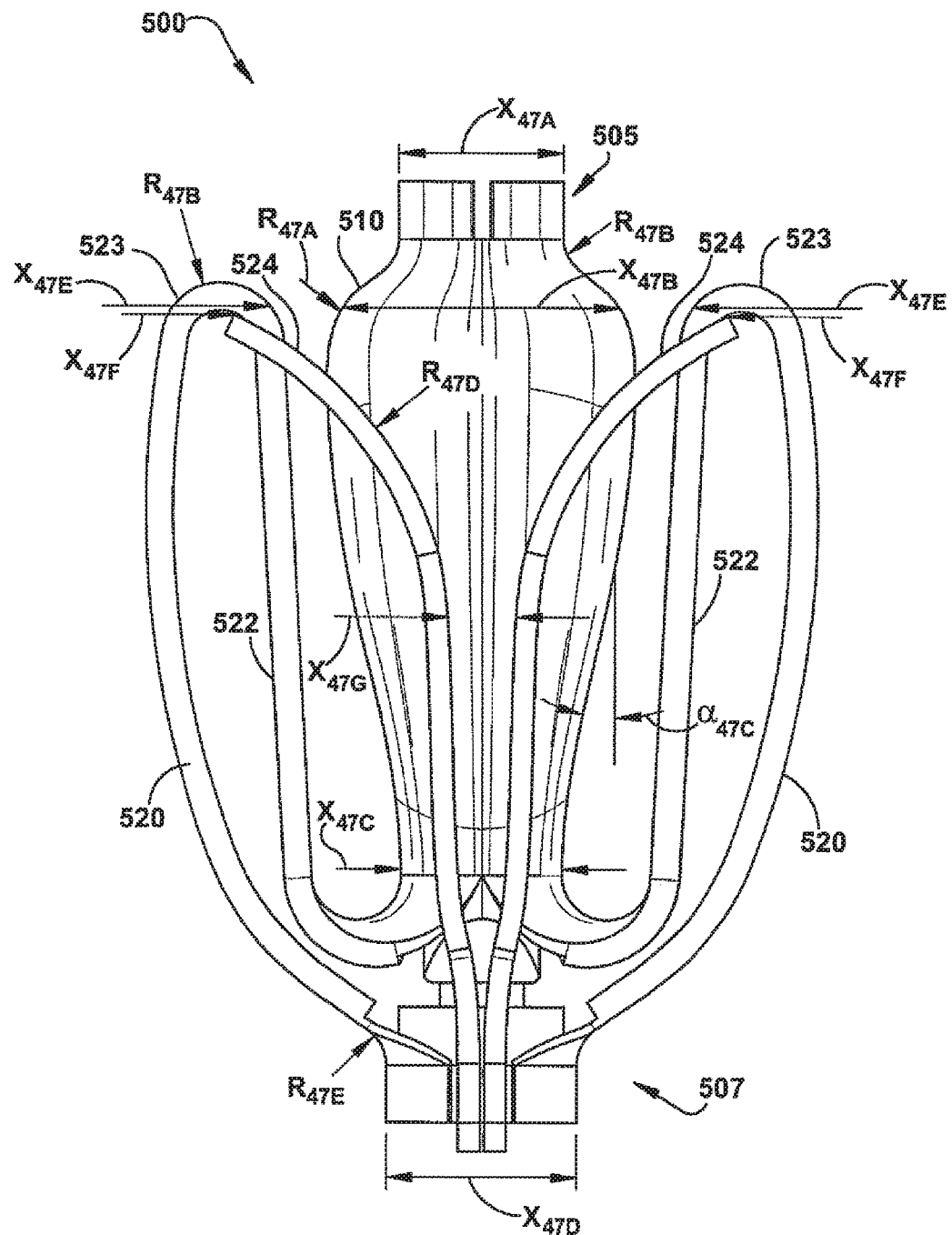
FIG. 47 shows a side view of an exemplary implantable prosthetic device without barbed clasps in a closed position.
Figure 48:
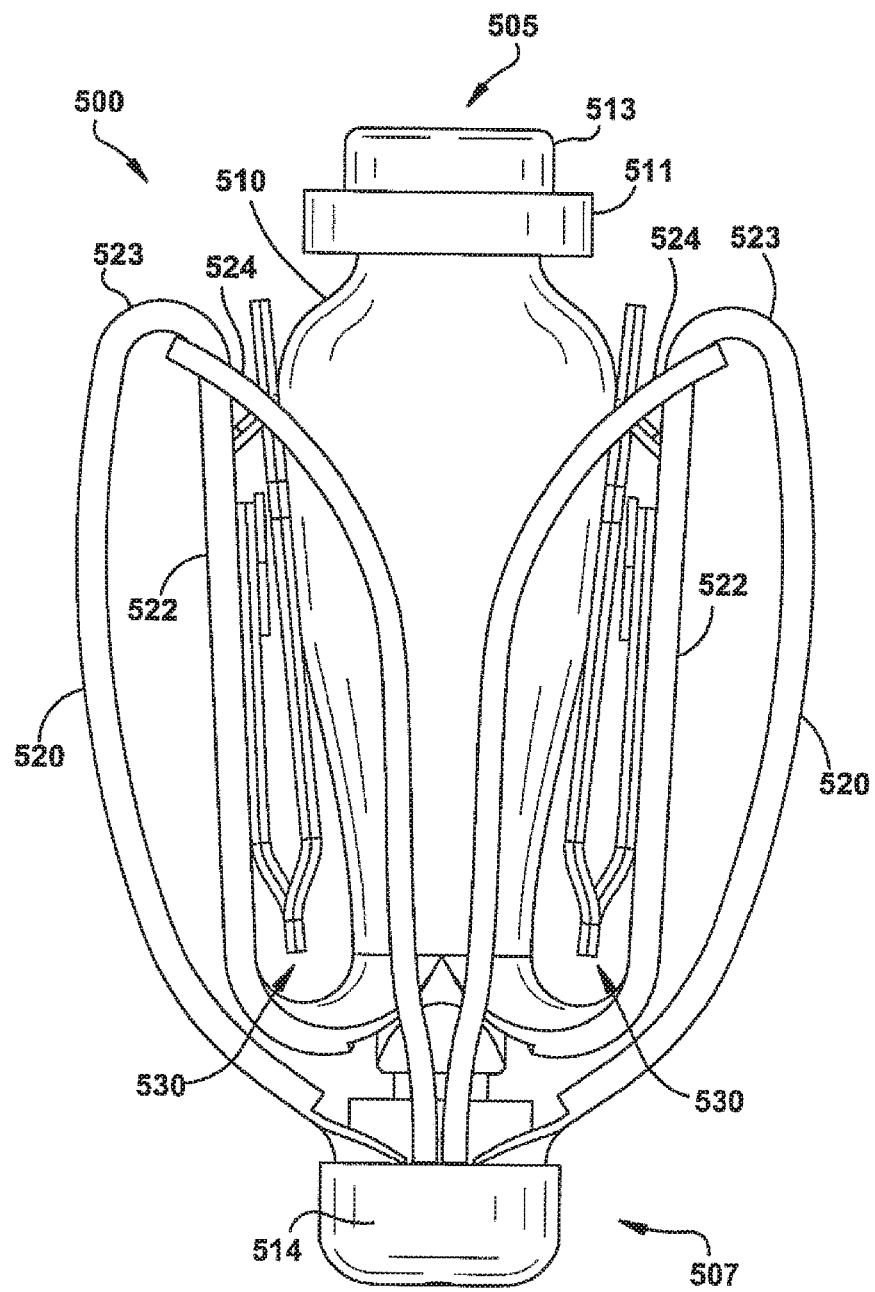
FIG. 48 shows a side view of an exemplary implantable prosthetic device with barbed clasps in a closed position.

Referring now to FIGS. 47-48, the device 500 is shown in a closed position. When closed, the inner paddles 522 are disposed between the outer paddles 520 and the coaption element 510. In some embodiments, the device 500 includes clasps or gripping members 530 (FIG. 48) that can be opened and closed to grasp the native leaflets 20, 22 of the mitral valve MV. The clasps 530 are attached to and move with the inner paddles 522 and are disposed between the inner paddles 522 and the coaption element 510.

Figure 49:
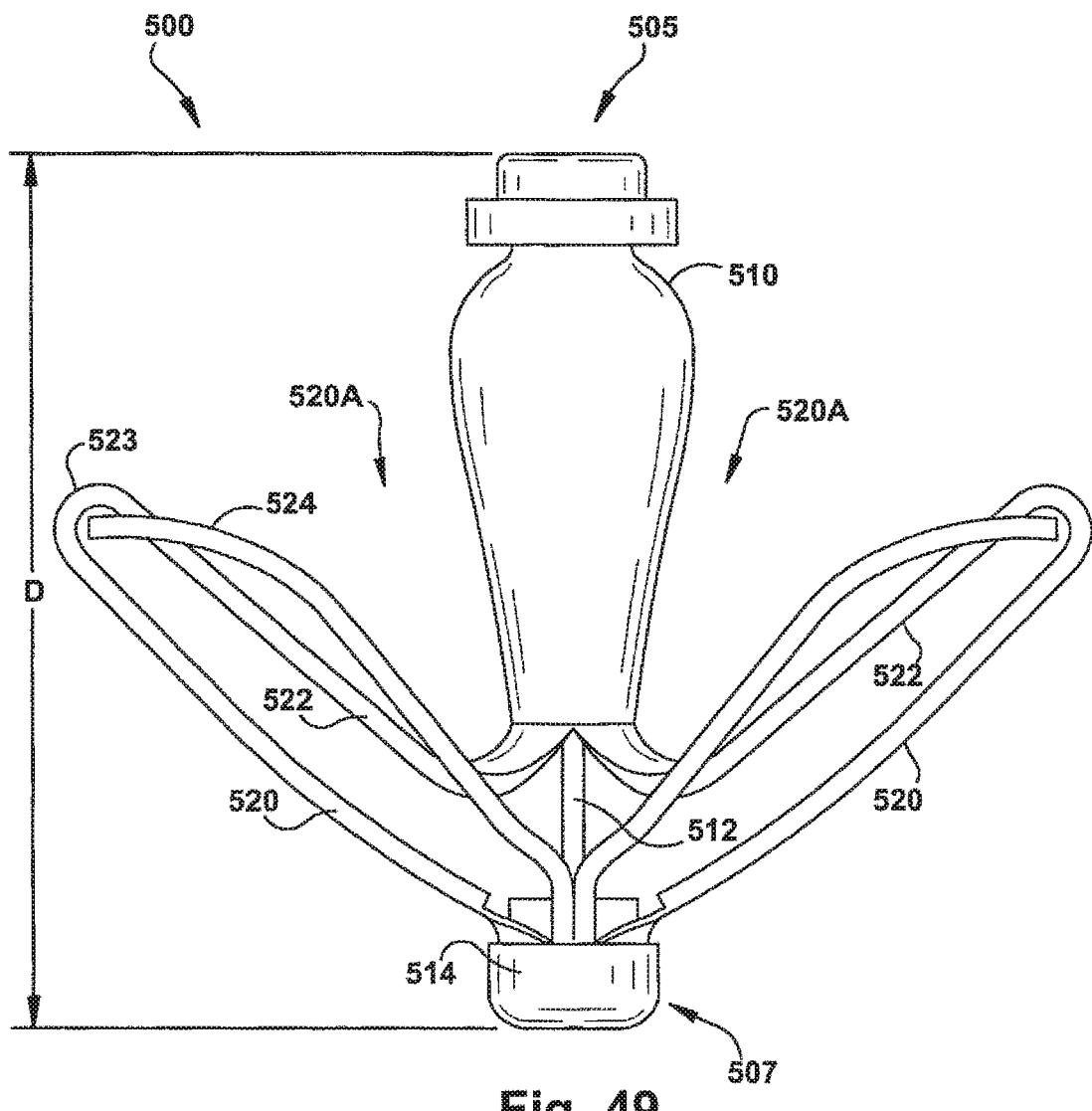
FIG. 49 shows a side view of an exemplary implantable prosthetic device without barbed clasps in a partially-open position.
Figure 50:
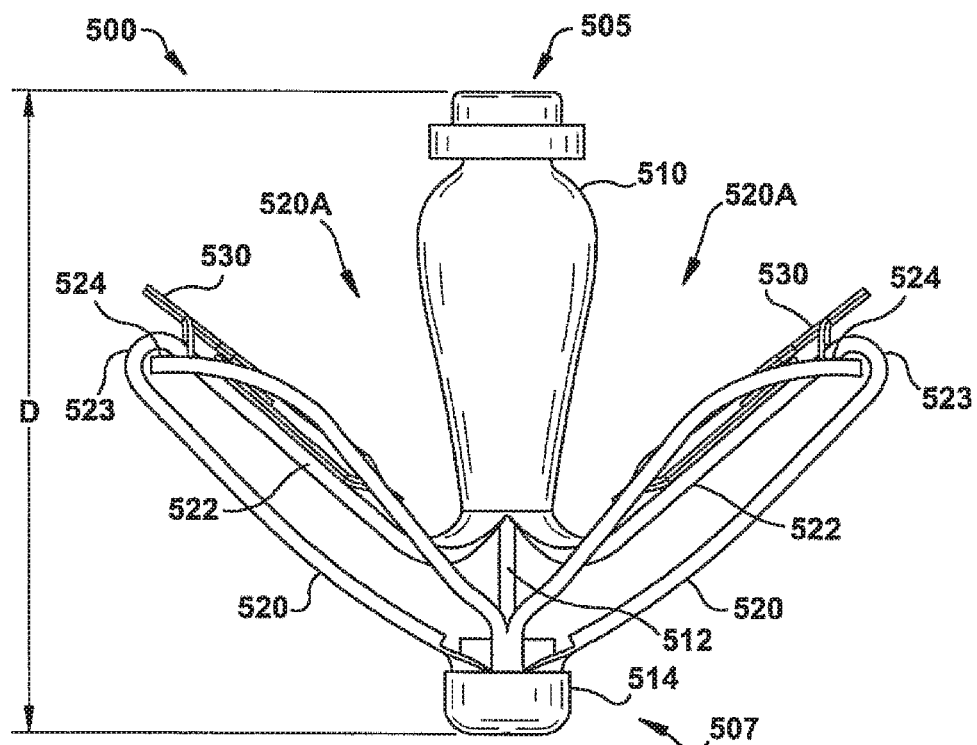
FIG. 50 shows a side view of an exemplary implantable prosthetic device in a partially-open position with barbed clasps in an open position.
Figure 51:
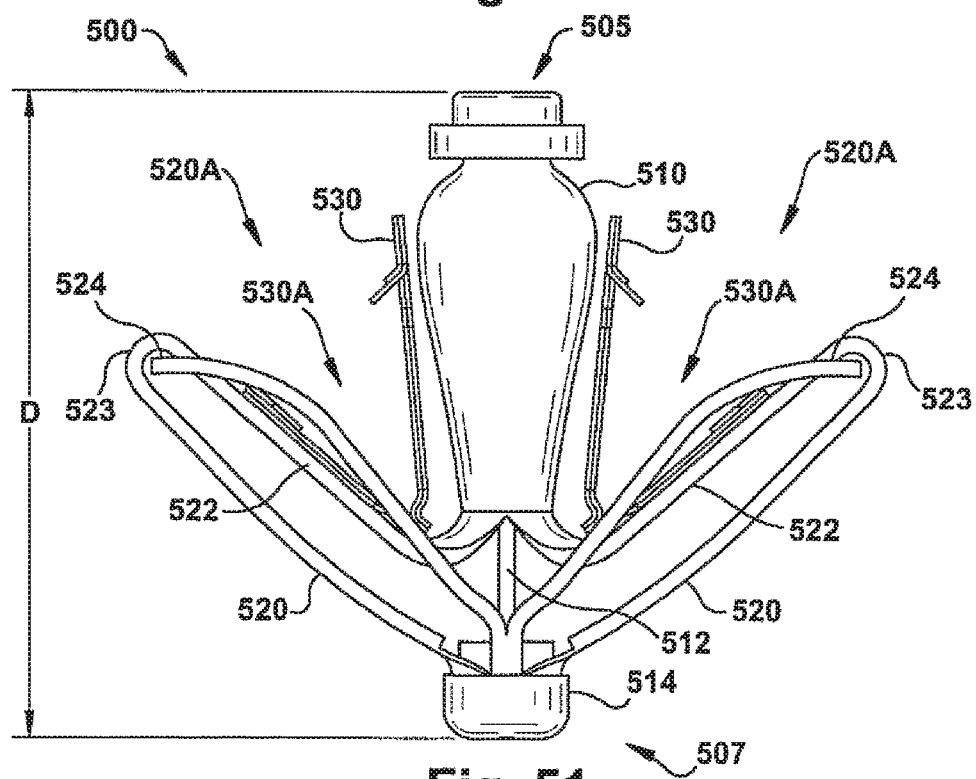
FIG. 51 shows a side view of an exemplary implantable prosthetic device in a partially-open position with barbed clasps in a closed position.

Referring now to FIGS. 49-51, the device 500 is shown in a partially open position. The device 500 is moved into the partially open position by an actuation wire or shaft 512 that passes through the attachment portion 505 and coaption element 510 and can removably engage the distal portion 507. The actuation wire 512 is extended through the attachment portion 505 such that a distance D between the attachment portion 505 and distal portion 507 increases as the actuation wire 512 is extended. In the example illustrated by FIGS. 49-51, the pair of inner and outer paddles 522, 520 are moved in unison, rather than independently, by a single actuation wire 512. Also, the positions of the clasps 530 are dependent on the positions of the paddles 522, 520. For example, referring to FIG. 48 closing the paddles 522, 520 also closes the clasps. In one exemplary embodiment, the device 500 can be made to have the paddles 520, 522 be independently controllable in the same manner as the FIG. 11A embodiment.

Extending the actuation wire 512 pulls down on the bottom portions of the outer paddles 520 and paddle frames 524. The outer paddles 520 and paddle frames 524 pull down on the inner paddles 522, where the inner paddles 522 are connected to the outer paddles 520 and the paddle frames 524. Because the attachment portion 505 and coaption element 510 are held in place, the inner paddles 522 are caused to pivot or flex in an opening direction. The inner paddles 522, the outer paddles 520, and the paddle frames all flex to the position shown in FIG. 49. Opening the paddles 522, 520 and frames 524 forms a gap 520A between the coaption element 510 and the inner paddle 522 that can receive and grasp the native leaflets 20.

As is described above, some embodiments of the device 500 include clasps or gripping members 530. When the device 500 is partially opened the clasps 530 are exposed. In some embodiments, the closed clasps 530 (FIG. 50) can be opened (FIG. 51), thereby creating a second opening or gap 530A for receiving and capturing the native leaflets 20, 22. The extent of the gap 530A in the clasps 530 is limited to the extent that the inner paddle 522 has spread away from the coaption element 510.

Figure 52:
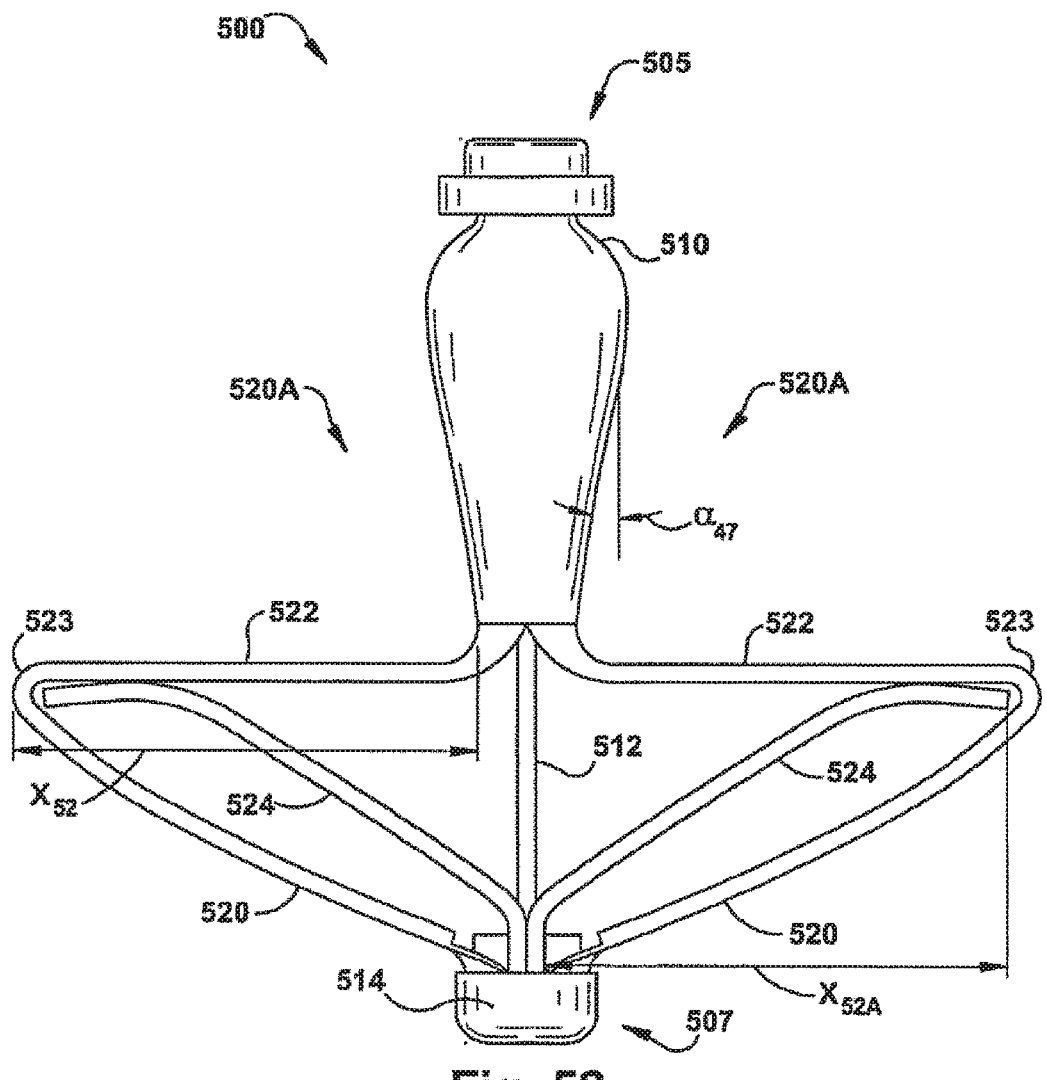
FIG. 52 shows a side view of an exemplary implantable prosthetic device without barbed clasps in a half-open position.
Figure 53:
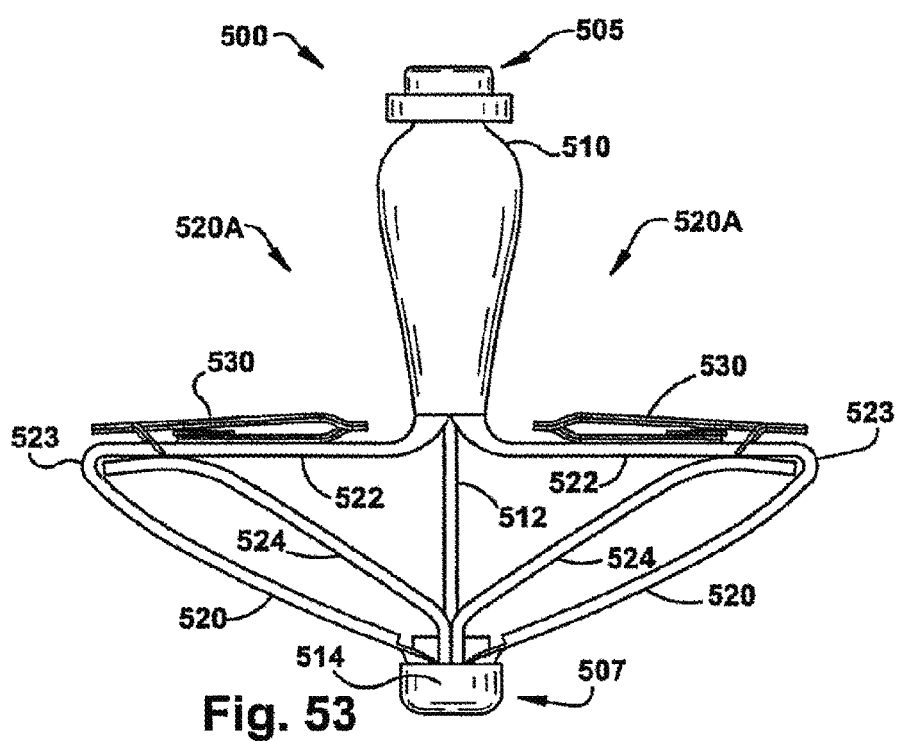
FIG. 53 shows a side view of an exemplary implantable prosthetic device in a half-open position with barbed clasps in a closed position.
Figure 53A:
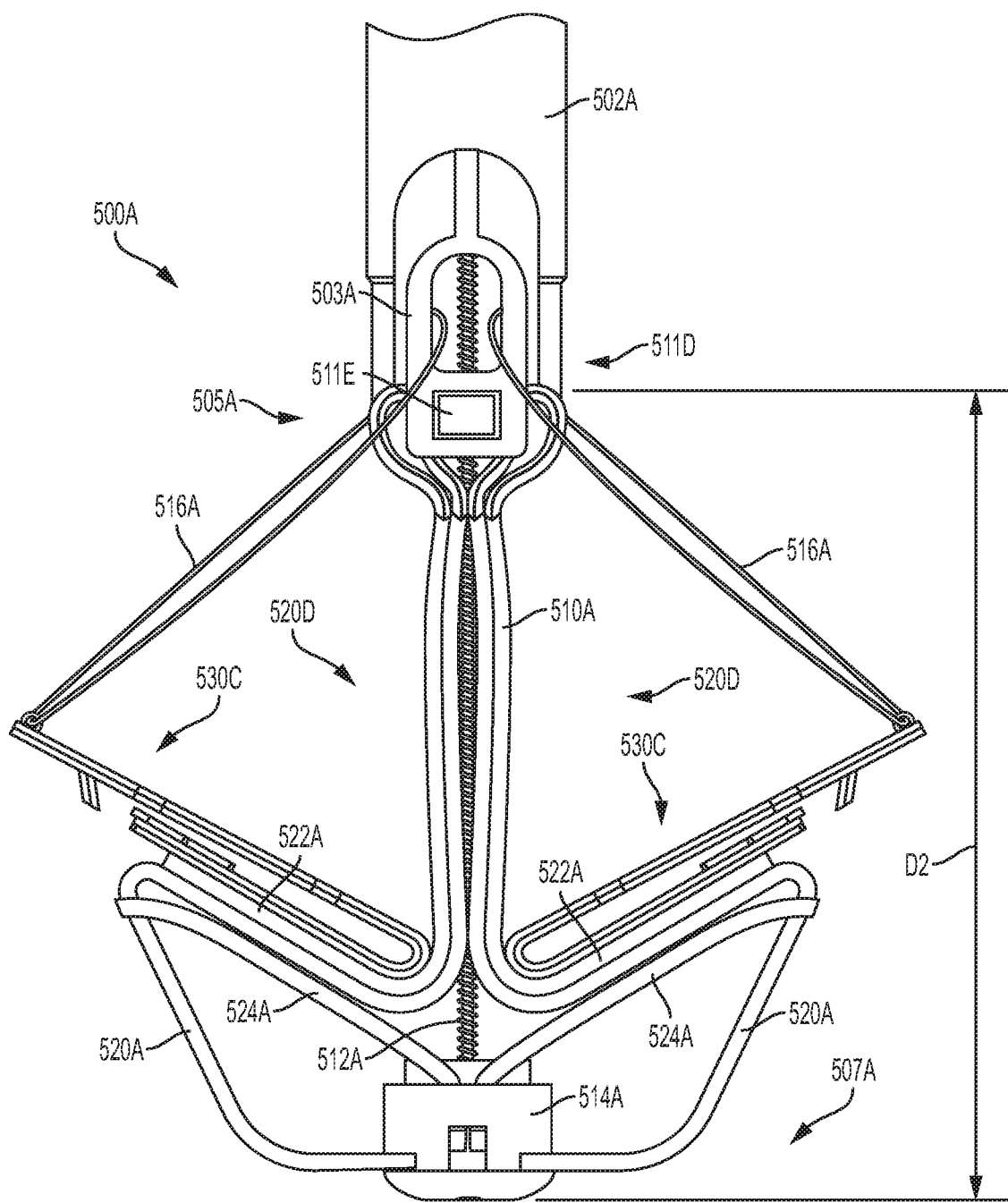
FIG. 53A shows a side view of an exemplary implantable prosthetic device in a half-open position with barbed clasps in a closed position.
Figure 53B:
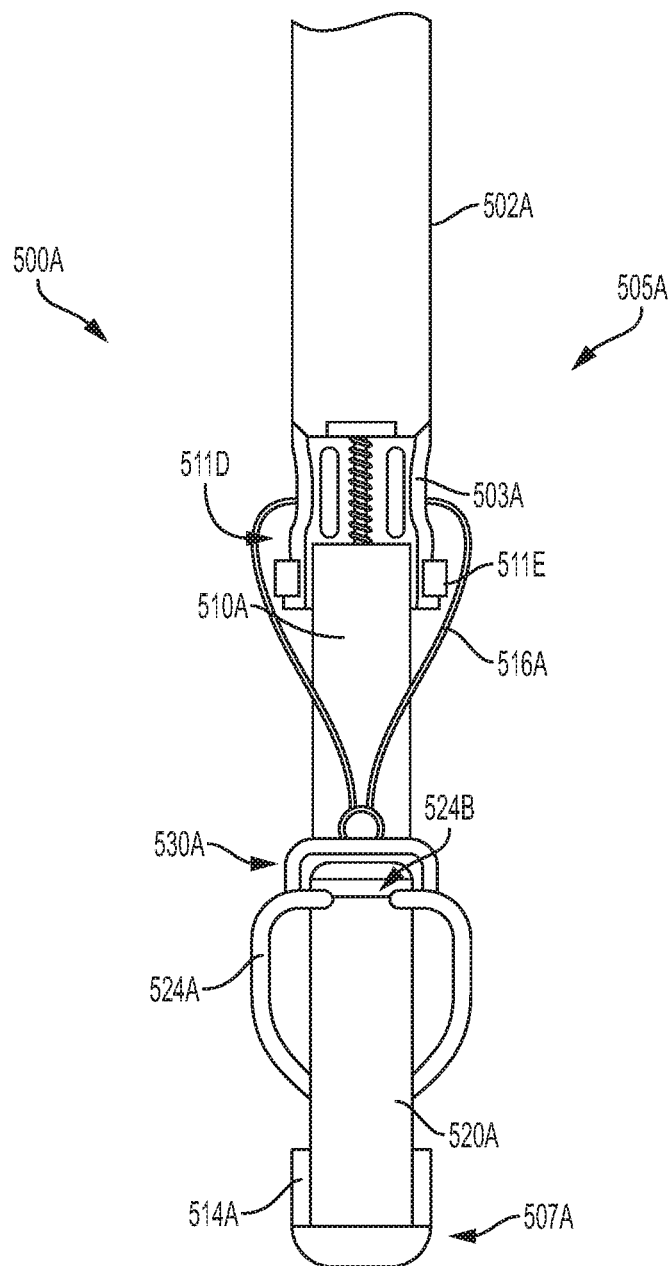
FIG. 53B shows a front view of the exemplary implantable prosthetic device according to FIG. 53A.
Figure 53C:
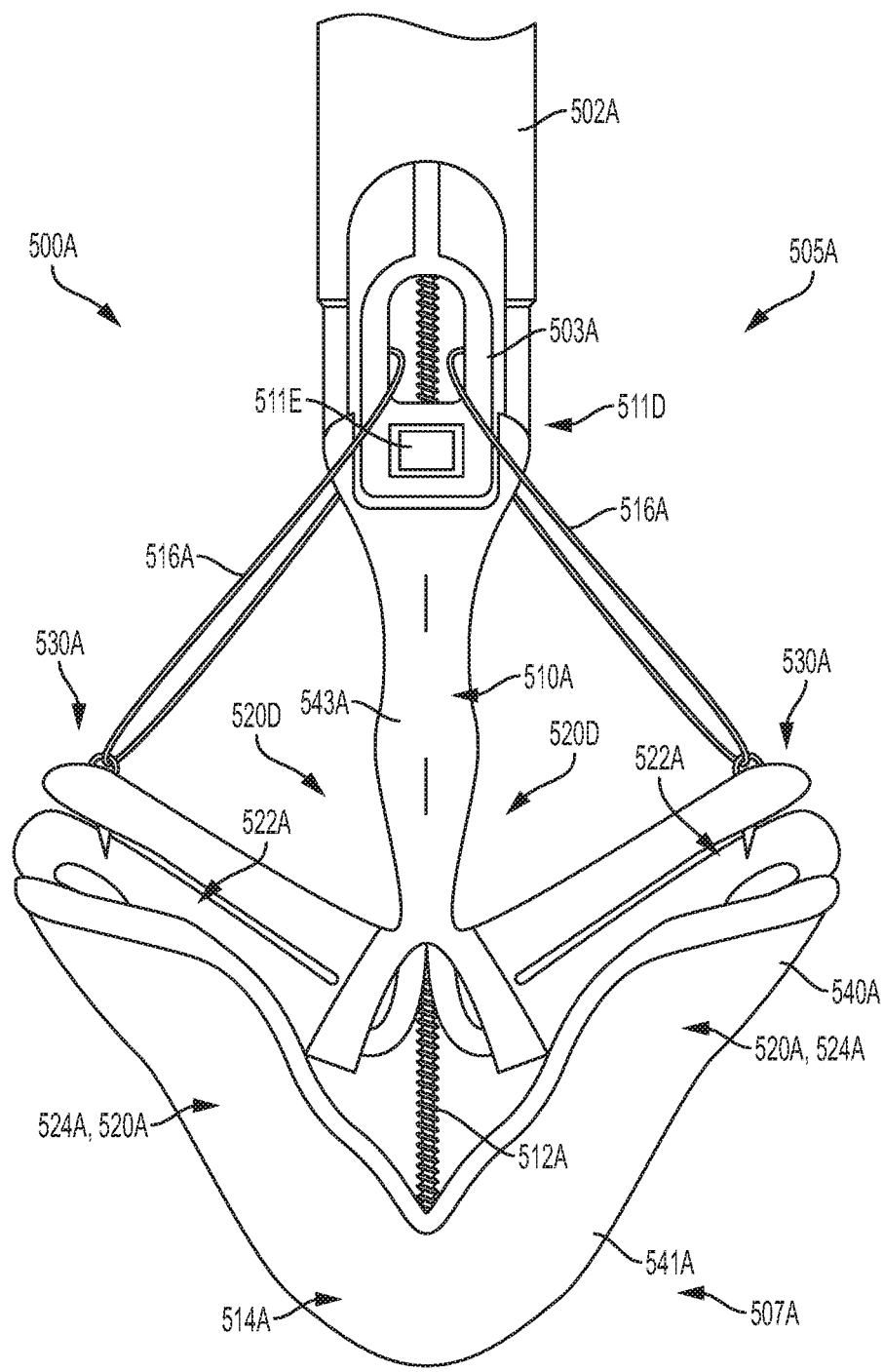
FIG. 53C shows a side view the exemplary implantable prosthetic device according to FIG. 53A, the device being provided with a cover.
Figure 53D:
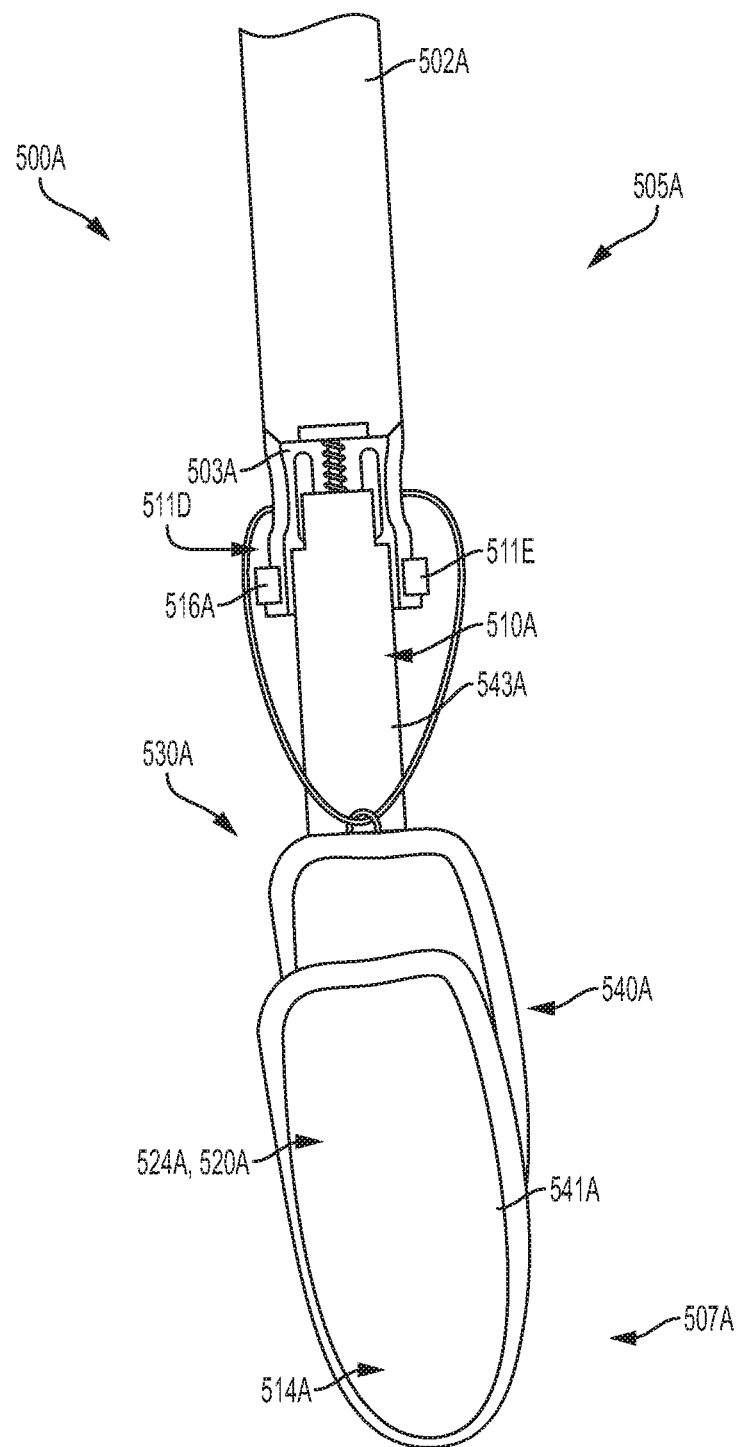
FIG. 53D shows a front view the exemplary implantable prosthetic device according to FIG. 53A, the device being provided with a cover.
Figure 54:
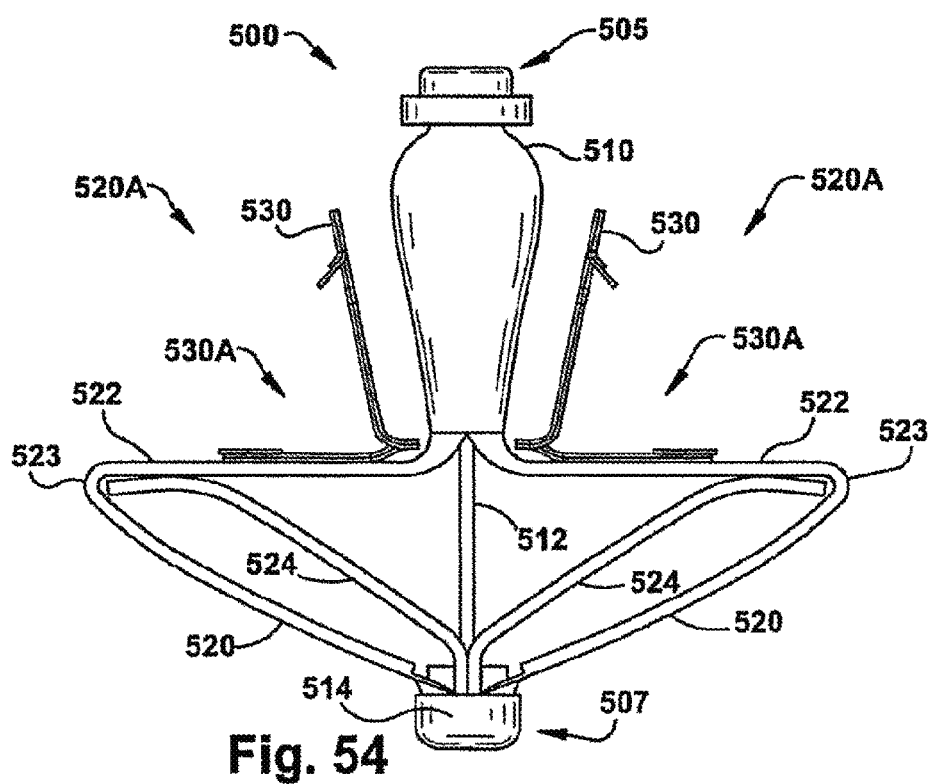
FIG. 54 shows a side view of an exemplary implantable prosthetic device in a half-open position with barbed clasps in an open position.
Figure 54A:
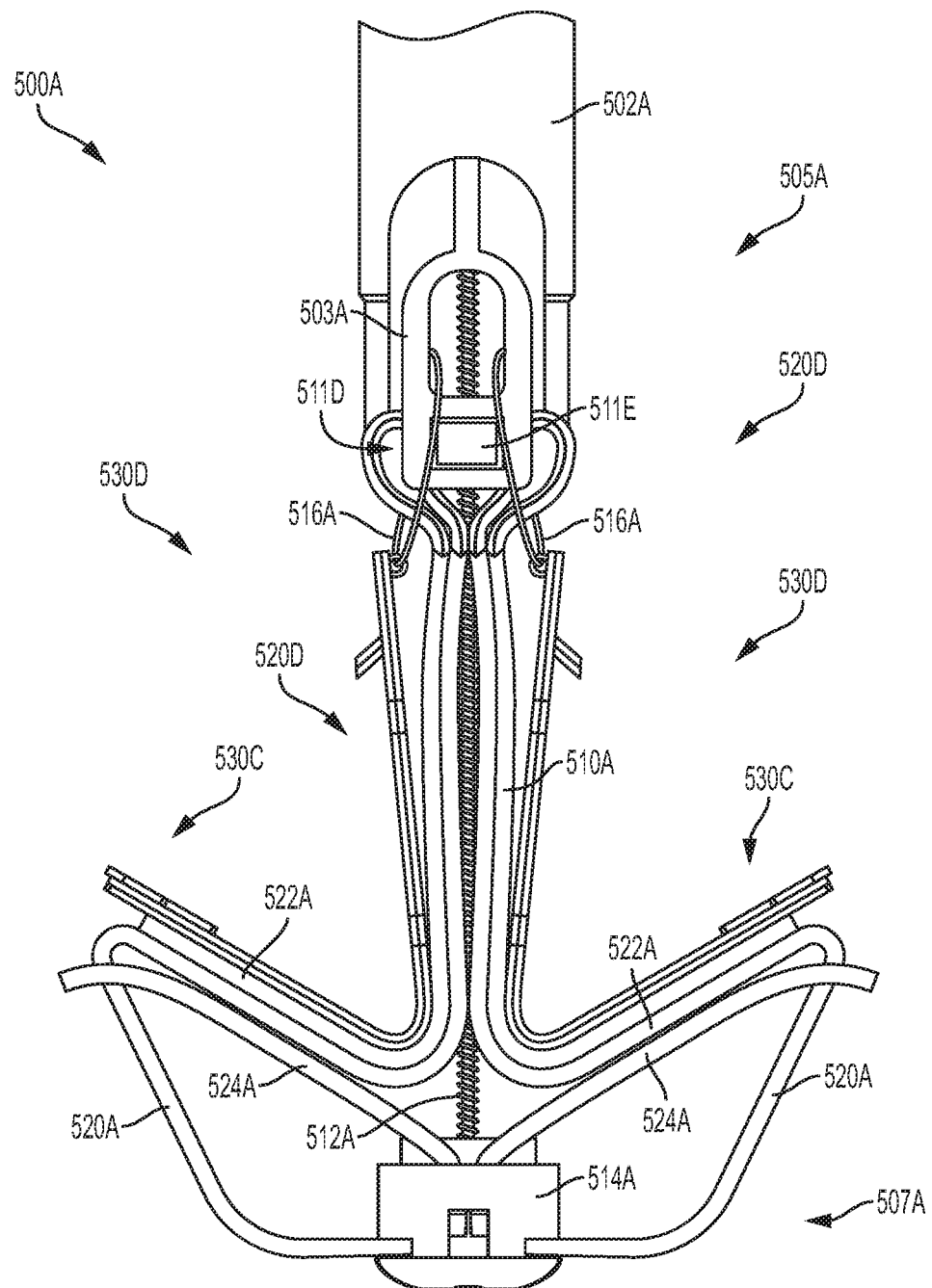
FIG. 54A shows a side view of an exemplary implantable prosthetic device in a half-open position with barbed clasps in an open position.
Figure 54B:
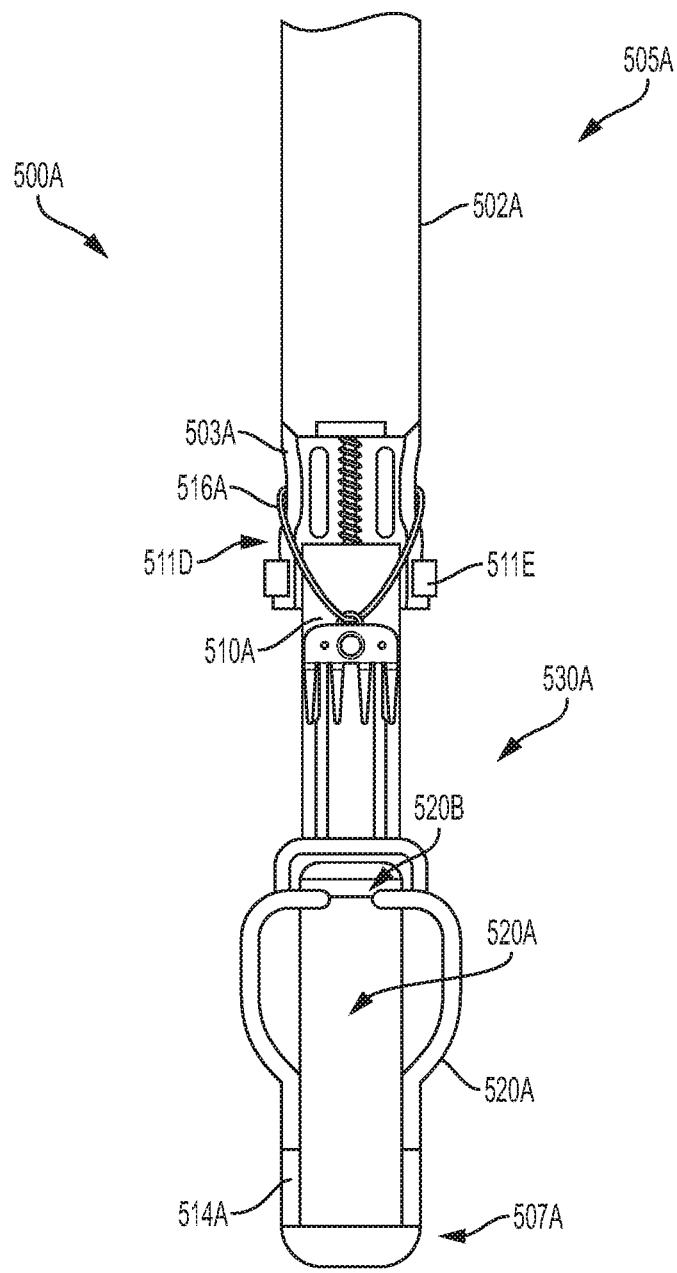
FIG. 54B shows a front view of the exemplary implantable prosthetic device according to FIG. 54A.
Figure 54C:
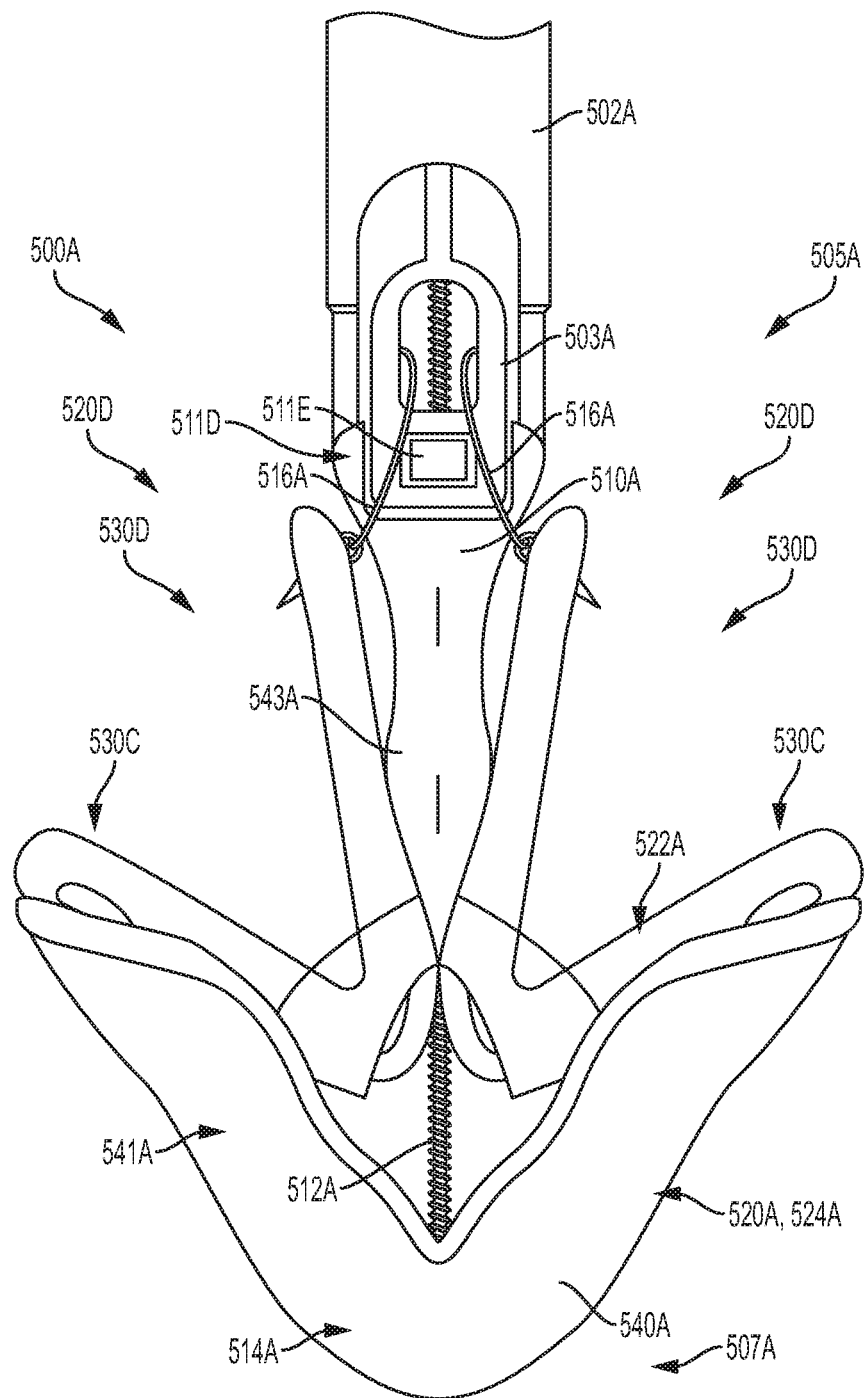
FIG. 54C shows a side view the exemplary implantable prosthetic device according to FIG. 54A, the device being provided with a cover.
Figure 54D:
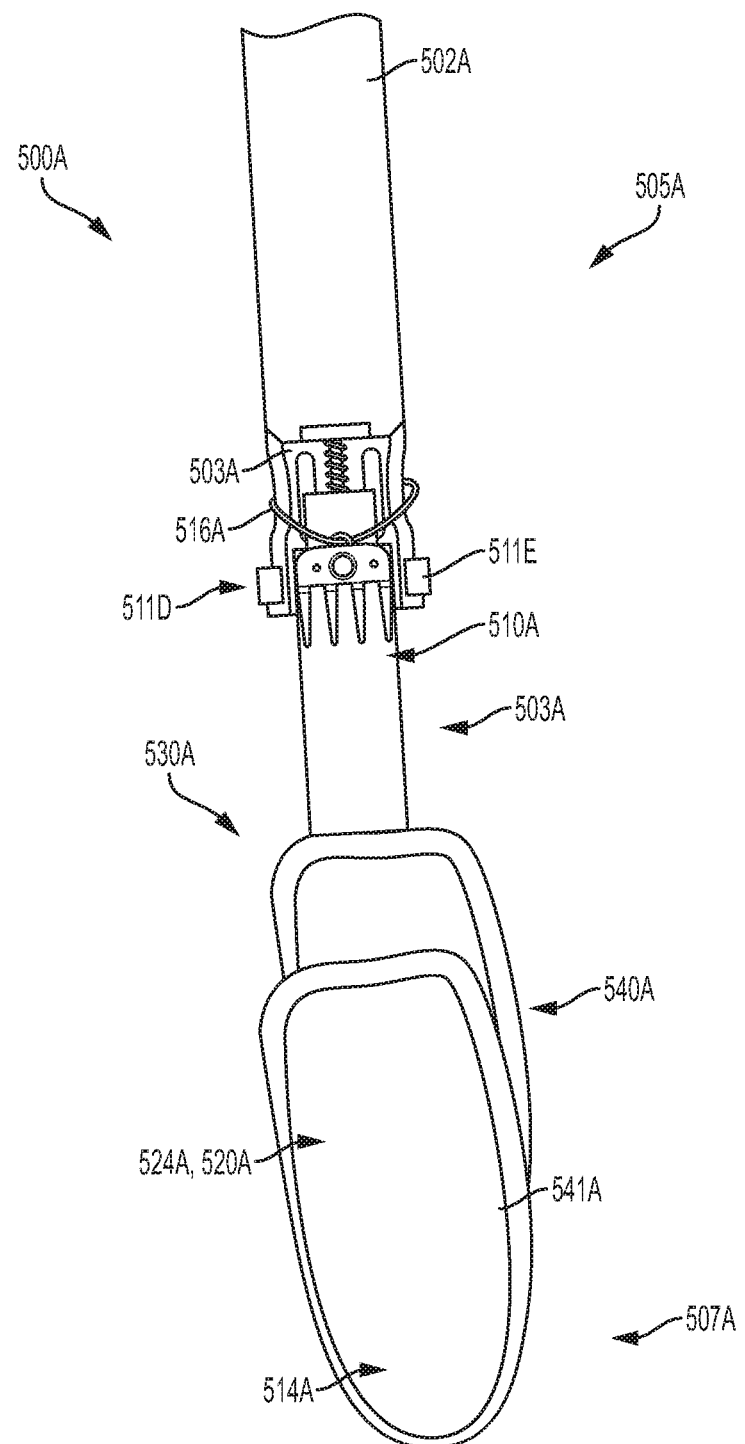
FIG. 54D shows a front view the exemplary implantable prosthetic device according to FIG. 54A, the device being provided with a cover.

Referring now to FIGS. 52-54, the device 500 is shown in a laterally extended or open position. The device 500 is moved into the laterally extended or open position by continuing to extend the actuation wire 512 described above, thereby increasing the distance D between the attachment portion 505 and distal portion 507. Continuing to extend the actuation wire 512 pulls down on the outer paddles 520 and paddle frames 524, thereby causing the inner paddles 522 to spread apart further from the coaption element 510. In the laterally extended or open position, the inner paddles 522 extend horizontally more than in other positions of the device 500 and form an approximately 90-degree angle with the coaption element 510. Similarly, the paddle frames 524 are at their maximum spread position when the device 500 is in the laterally extended or open position. The increased gap 520A formed in the laterally extended or open position allows clasps 530 to open further (FIG. 54) before engaging the coaption element 510, thereby increasing the size of the gap 530A.

Figure 55:
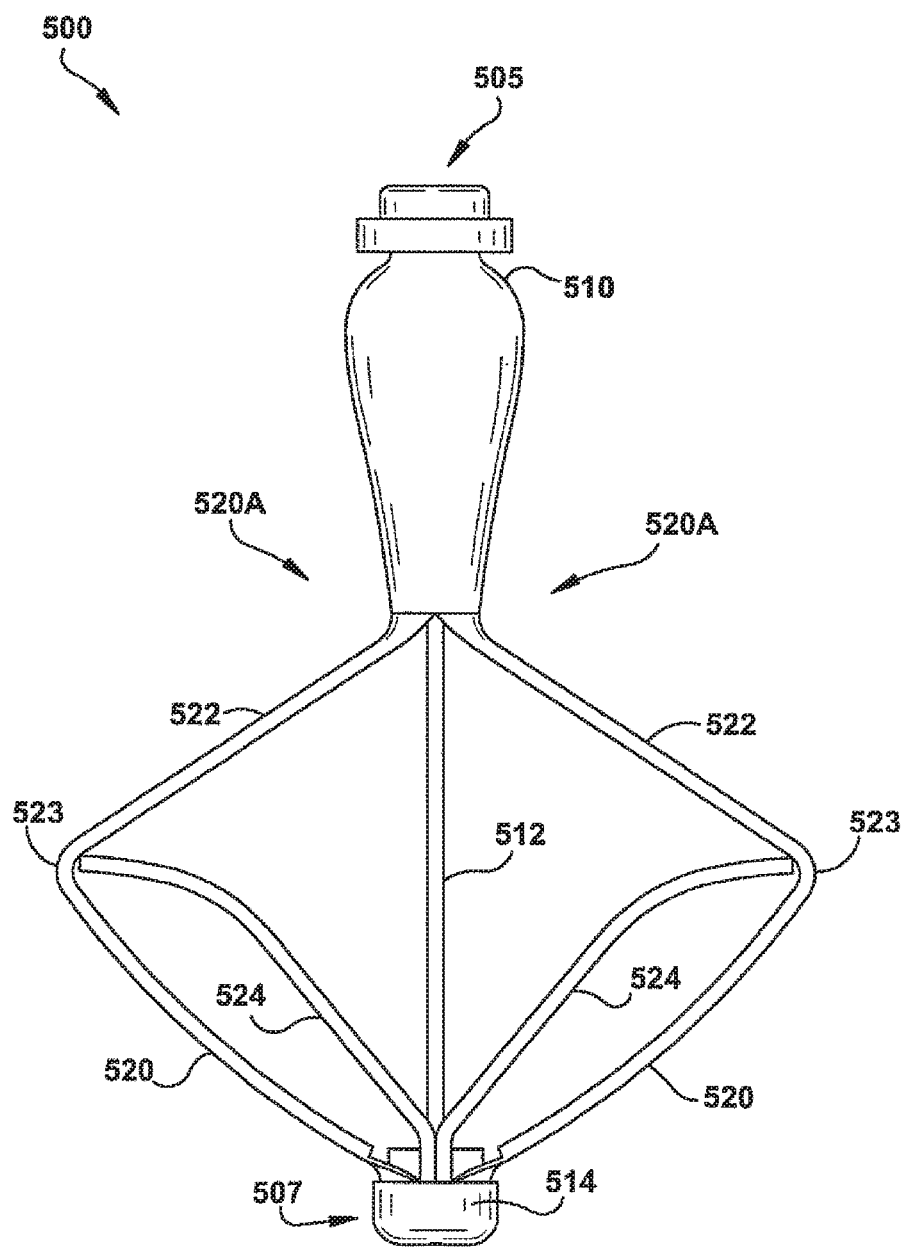
FIG. 55 shows a side view of an exemplary implantable prosthetic device without barbed clasps in a three-quarters-open position.
Figure 57:
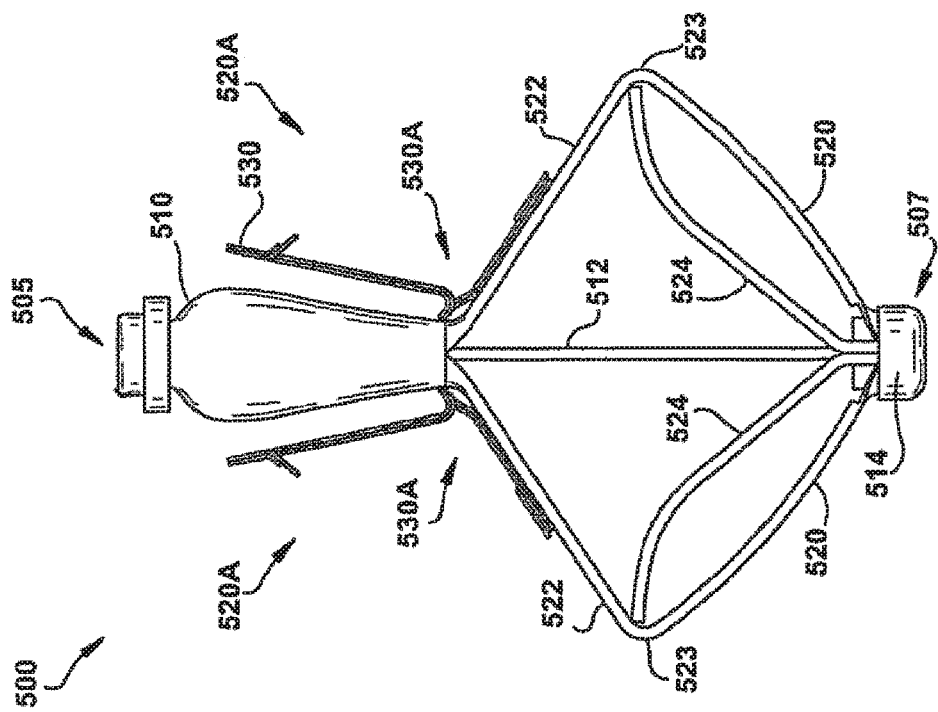
FIG. 57 shows a side view of an exemplary implantable prosthetic device in a three-quarters-open position with barbed clasps in an open position.
Figure 56:
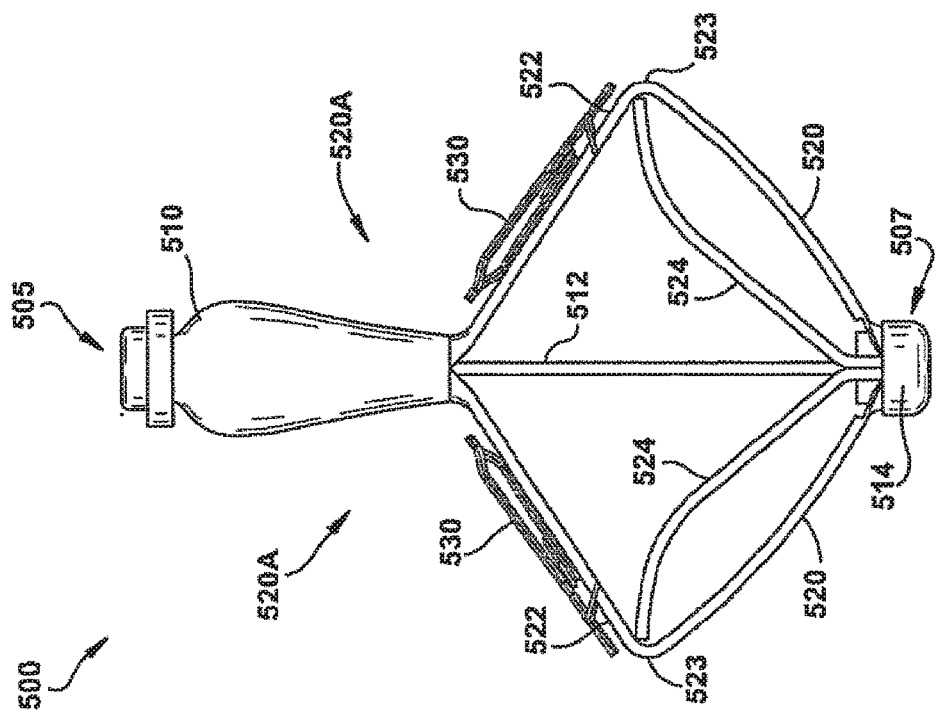
FIG. 56 shows a side view of an exemplary implantable prosthetic device in a three-quarters-open position with barbed clasps in a closed position.

Referring now to FIGS. 55-57, the device 500 is shown in a three-quarters extended position. The device 500 is moved into the three-quarters extended position by continuing to extend the actuation wire 512 described above, thereby increasing the distance D between the attachment portion 505 and distal portion 507. Continuing to extend the actuation wire 512 pulls down on the outer paddles 520 and paddle frames 524, thereby causing the inner paddles 522 to spread apart further from the coaption element 510. In the three-quarters extended position, the inner paddles 522 are open beyond 90 degrees to an approximately 135-degree angle with the coaption element 510. The paddle frames 524 are less spread than in the laterally extended or open position and begin to move inward toward the actuation wire 512 as the actuation wire 512 extends further. The outer paddles 520 also flex back toward the actuation wire 512. As with the laterally extended or open position, the increased gap 520A formed in the laterally extended or open position allows clasps 530 to open even further (FIG. 57), thereby increasing the size of the gap 530A.

Figure 58:
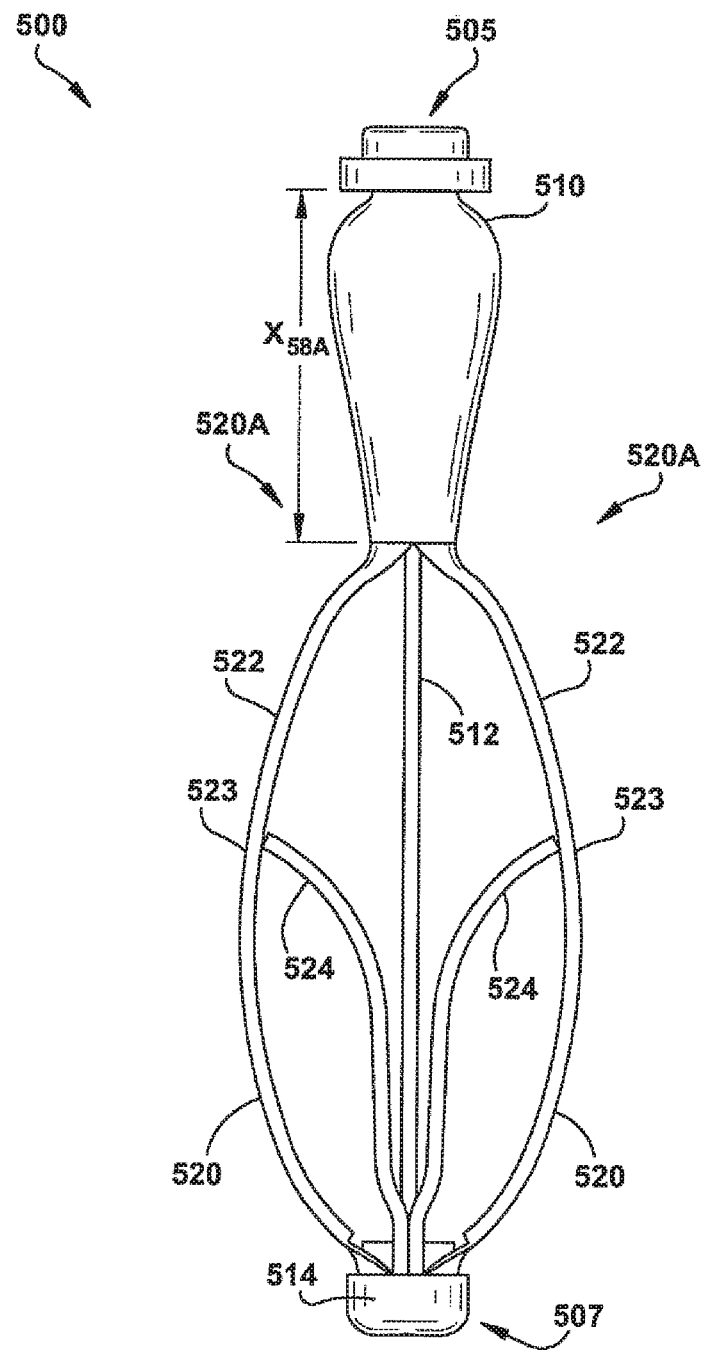
FIG. 58 shows a side view of an exemplary implantable prosthetic device without barbed clasps near a full bailout position.

Referring now to FIG. 58, the device 500 is shown in an almost fully extended position. The device 500 is moved into the almost fully extended position by continuing to extend the actuation wire 512 described above, thereby increasing the distance D between the attachment portion 505 and distal portion 507. Continuing to extend the actuation wire 512 pulls down on the outer paddles 520 and paddle frames 524, thereby causing the inner paddles 522 to spread apart further from the coaption element 510. In the almost fully extended position the inner paddles 522 begin to approach an approximately 180-degree angle with the coaption element 510. Although the inner paddles move to this position, the outer paddles 520 and the paddle frames 522 never move or flex to or past a ninety-degree angle with respect to the coaption element 510. In the almost fully extended position the inner and outer paddles 522, 520 can have a somewhat curved shape.

Figure 59:
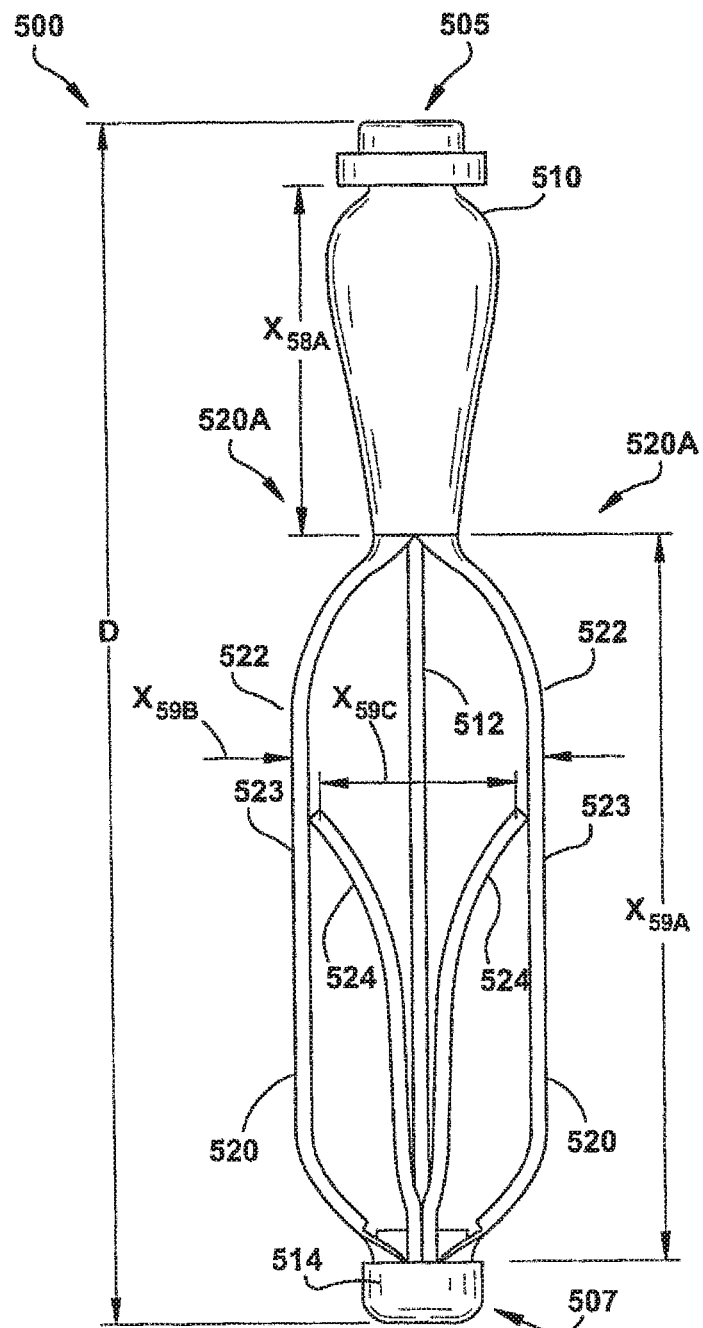
FIG. 59 shows a side view of an exemplary implantable prosthetic device without barbed clasps in a full bailout position.
Figure 61:
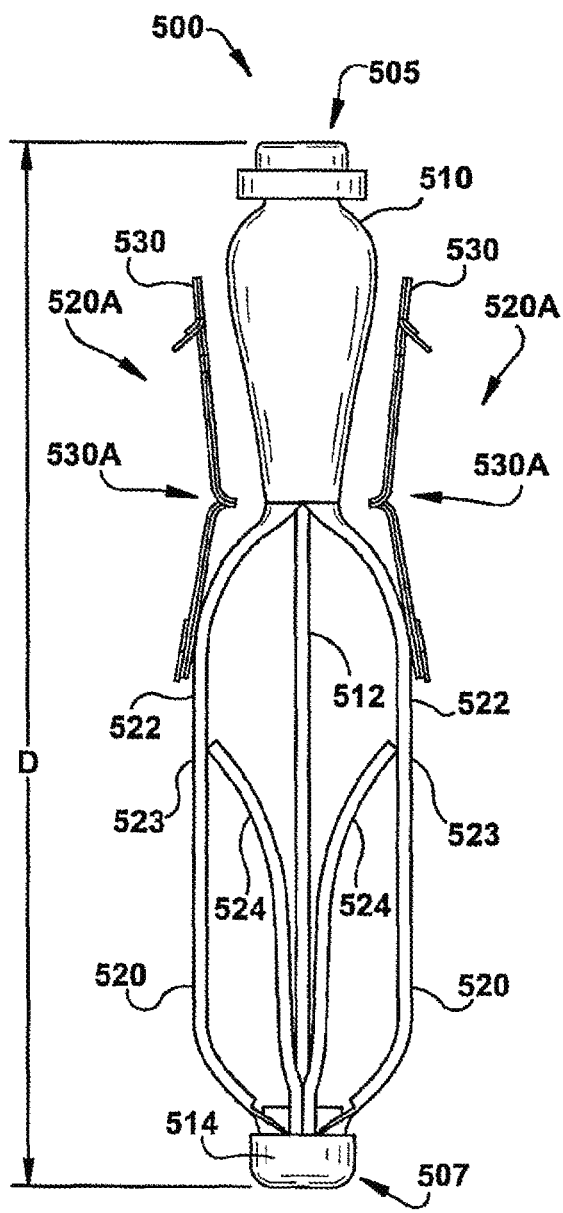
FIG. 61 shows a side view of an exemplary implantable in a full bailout position with barbed clasps in an open position.
Figure 61A:
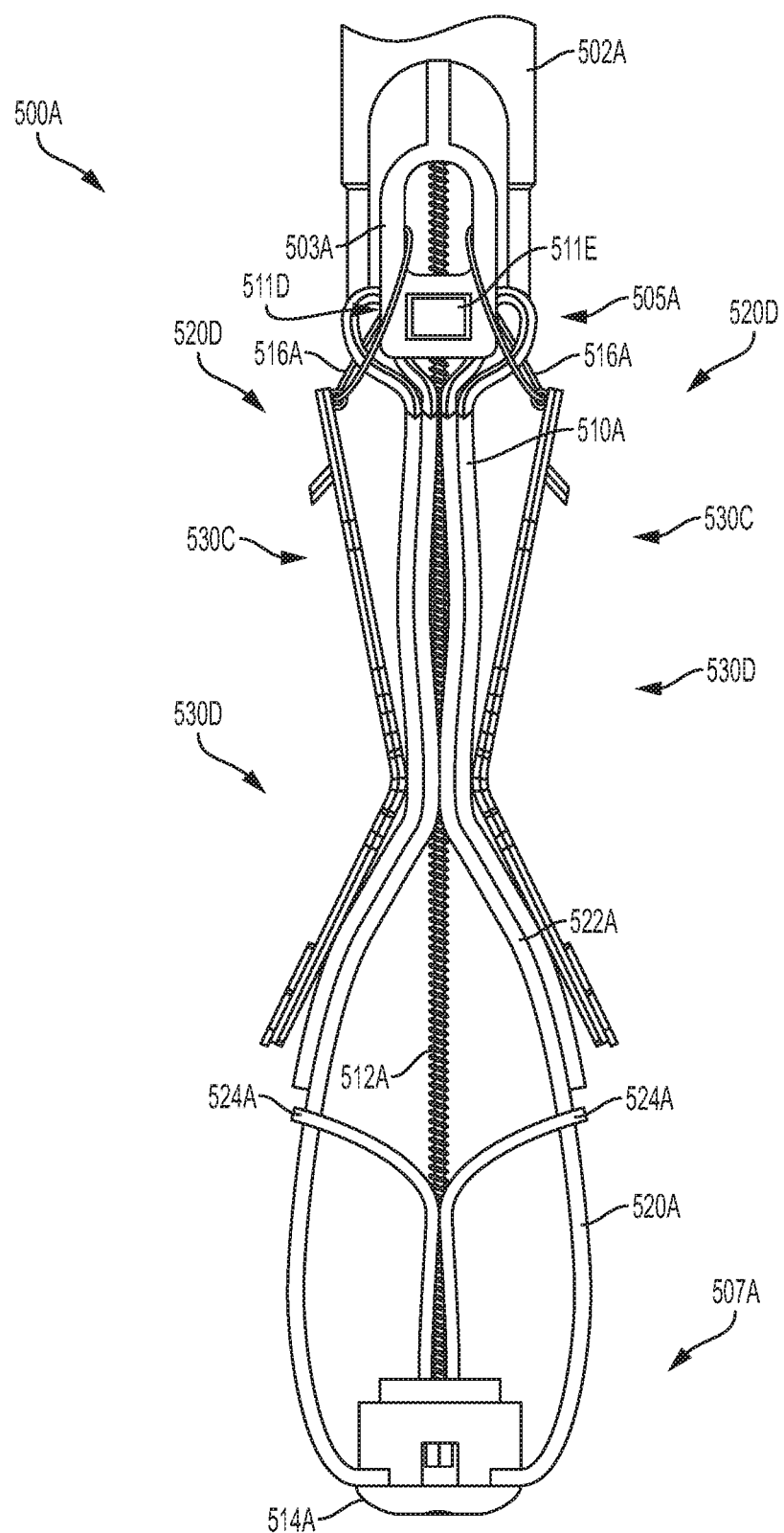
FIG. 61A shows a side view of an exemplary implantable in a full bailout position with barbed clasps in an open position.
Figure 61B:
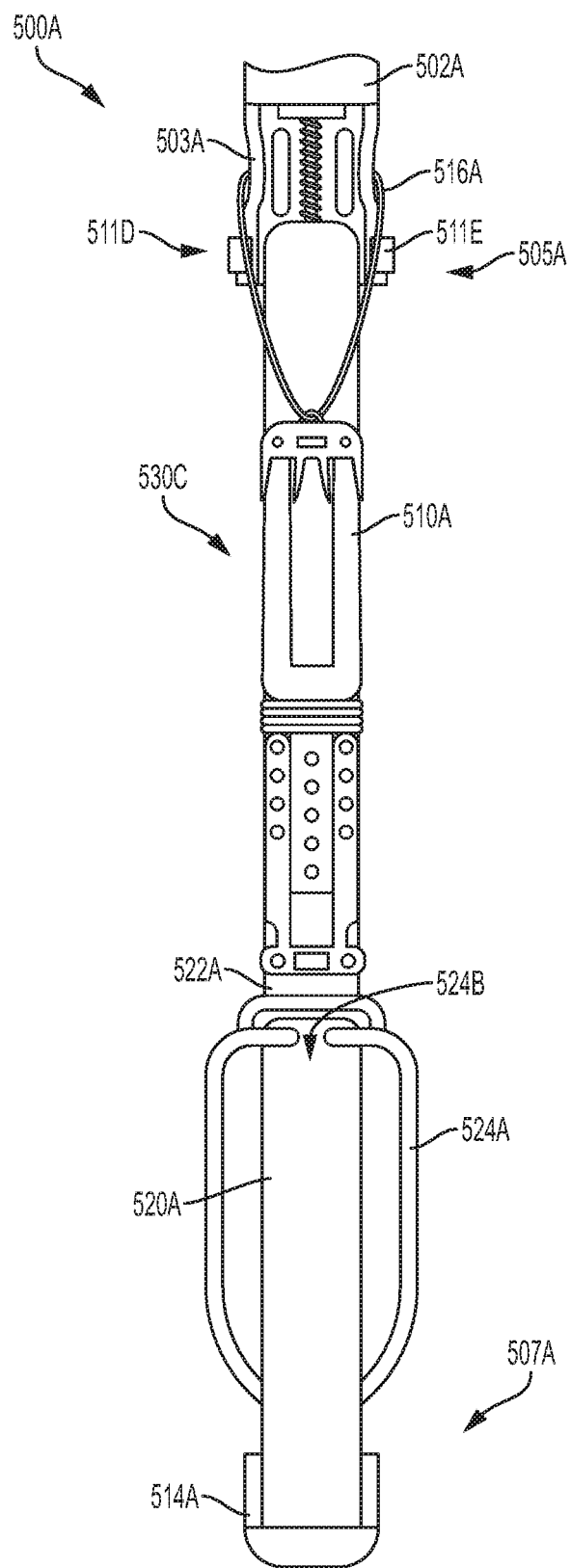
FIG. 61B shows a front view of the exemplary implantable prosthetic device according to FIG. 61A.
Figure 61C:
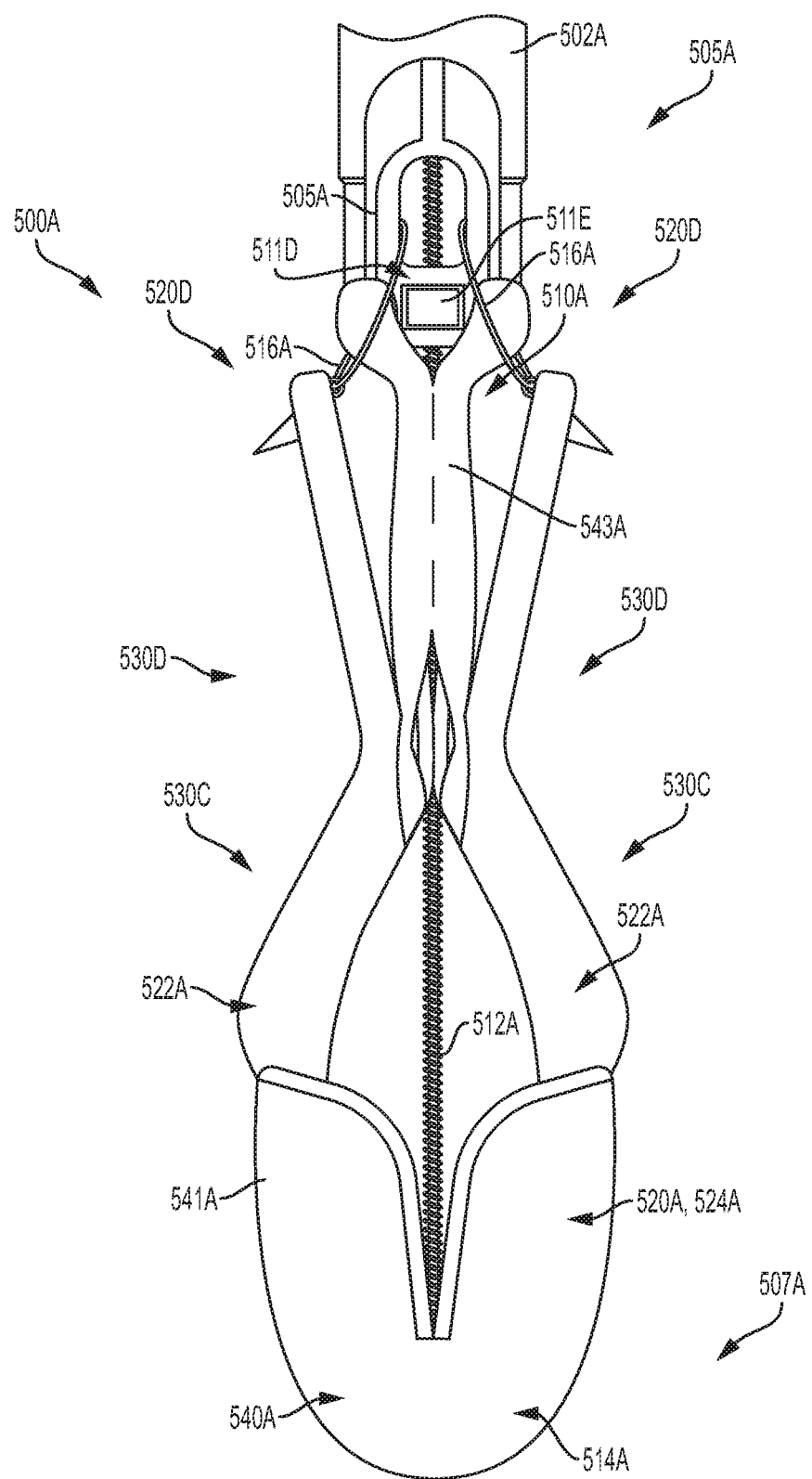
FIG. 61C shows a side view the exemplary implantable prosthetic device according to FIG. 61A, the device being provided with a cover.
Figure 61D:
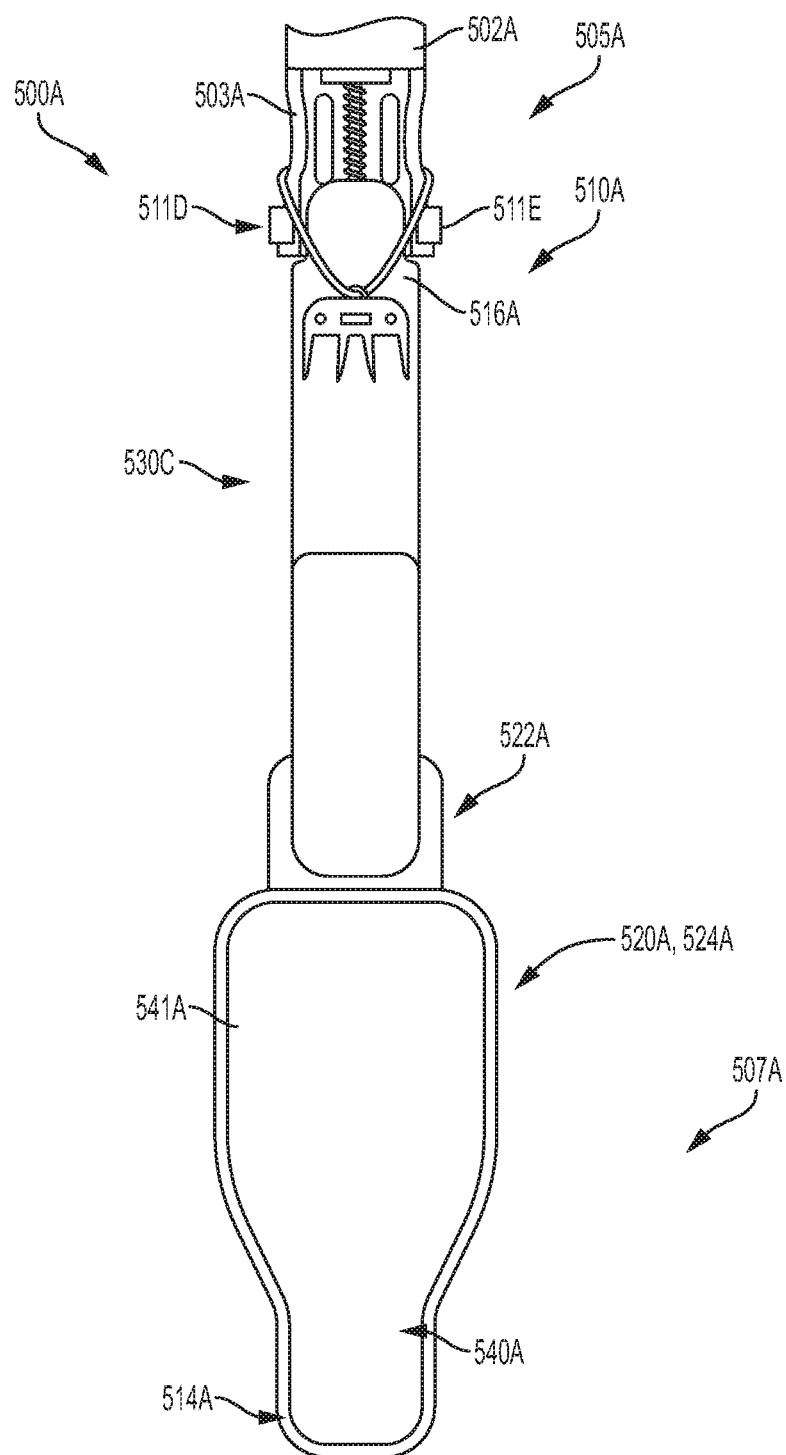
FIG. 61D shows a front view the exemplary implantable prosthetic device according to FIG. 61A, the device being provided with a cover.

Referring now to FIGS. 59-61, the device 500 is shown in a fully extended position. The device 500 is moved into the fully extended position by continuing to extend the actuation wire 512 described above, thereby increasing the distance D between the attachment portion 505 and distal portion 507 to a maximum distance allowable by the device 500. Continuing to extend the actuation wire 512 pulls down on the outer paddles 520 and paddle frames 524, thereby causing the inner paddles 522 to spread apart further from the coaption element 510. The outer paddles 520 and paddle frames 524 move to a position where they are close to the actuation wire. In the fully extended position, the inner paddles 522 are open to an approximately 180-degree angle with the coaption element 510. The inner and outer paddles 522, 520 are stretched straight in the fully extended position to form an approximately 180-degree angle between the paddles 522, 520. The fully extended position of the device 500 provides the maximum size of the gap 520A between the paddles, and, in some embodiments, allows clasps 530 to also open fully to approximately 180 degrees (FIG. 61) between portions of the clasp 530. The position of the device 500 is the narrowest configuration. Thus, the fully extended position of the device 500 may be a desirable position for bailout of the device 500 from an attempted implantation or may be a desired position for placement of the device in a delivery catheter, or the like.

Referring now to FIGS. 47A, 48A-48H, 53A-53C, 54A-54D, 60A-60D, and 61A-61D, an implantable device 500A is shown in various positions and configurations. The implantable device 500A can include any other features for an implantable prosthetic device discussed in the present application, and the device 500A can be positioned to engage valve tissue 20, 22 as part of any suitable valve repair system (e.g., any valve repair system disclosed in the present application).

The implantable device 500A has a proximal or attachment portion 505A, a coaption element 510A, inner anchor portions or inner paddles 522A, outer anchor portions or outer paddles 520A, anchor extension members or paddle frames 524A, and a distal portion 507A. The inner paddles 522A are jointably attached between the coaption element 510A by joint portions 525A and the outer paddles 520A by joint portions 523A. The outer paddles 520A are jointably attached between the inner paddles 522A by joint portions 523A and the distal portion 507A by joint portions 521A. The paddle frames 524A are attached to the cap 514A (FIG. 48A) at the distal portion 507A and extend to the joint portion 523A between the inner and outer paddles 522A, 520A. In some embodiments, the paddle frames 524A are formed of a material that is more rigid and stiff than the material forming the paddles 522A, 520A so that the paddle frames 524A provide support for the paddles 522A, 520A. The paddle frames 524A include an opening or slot 524B for receiving the joint portions 523A (FIG. 65A). In some embodiments, the inner paddles 522A are stiff, relatively stiff, rigid, have rigid portions and/or are stiffened by a stiffening member or the fixed portion of the clasps 530C. The stiffening of the inner paddle allows the device to move to the various different positions shown and described herein. The inner paddle 522A, the outer paddle 520A, and the coaption element can all be interconnected as described herein, such that the device 500A is constrained to the movements and positions shown and described herein.

The coaption element 510A, inner paddles 522A, outer paddles 520A can be attached together by integrally forming the coaption element 510A and the paddles 520A, 522A as a single, unitary component. This can be accomplished, for example, by forming the coaption element 510A and the paddles 520A, 522A from a continuous strip 501A of a braided or woven material, such as braided or woven nitinol wire.

Figure 47A:
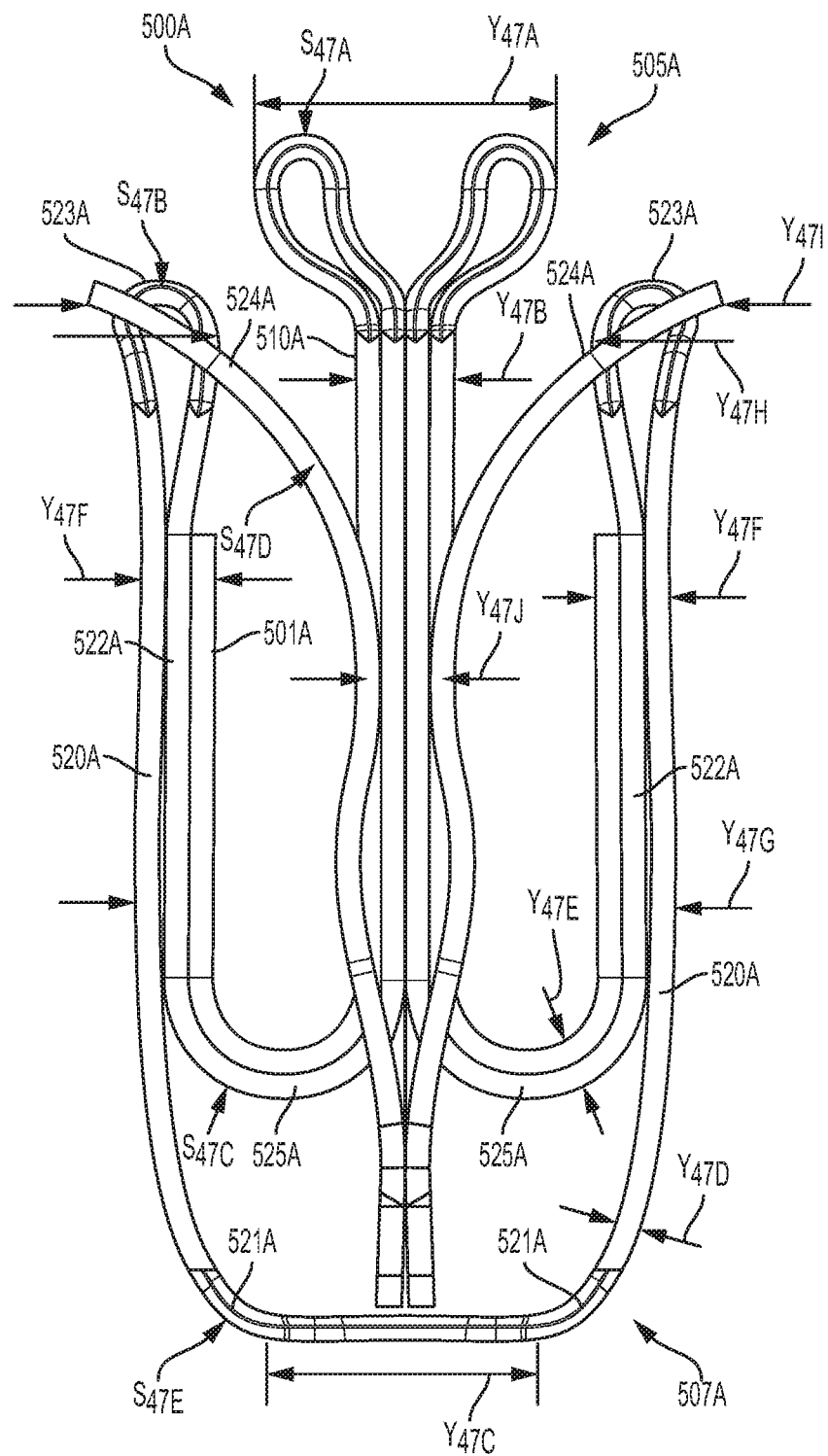
FIG. 47A shows a side view of an exemplary implantable prosthetic device without barbed clasps in a closed position.

The continuous strip 501A is attached a collar 511D, a cap 514A, paddle frames 524A, clasps 530C. In the illustrated embodiment, the coaption element 510A, hinge portions 521A, 523A, 525A, outer paddles 520A, and inner paddles 522A are formed from the continuous strip 501A. The continuous strip 501A may be a single layer of material or may include two or more layers. In certain embodiments, portions of the device 500A have a single layer of the strip of material 501A and other portions are formed from multiple overlapping or overlying layers of the strip of material 501A. For example, FIG. 47A shows the coaption element 510A and inner paddles 522A formed from multiple overlapping or overlying layers of the strip of material 501A. Consequently, the coaption element 510A and inner paddle 522A have an increased stiffness relative to the outer paddles 520A that are formed from a single layer of material 501A. The single continuous strip of material 501A can start and end in various locations of the device 500A. The ends of the strip of material 501A can be in the same location or different locations of the device 500A. For example, in the illustrated embodiment of FIG. 47A, the strip of material begins and ends in the location of the inner paddles 522.

Figure 48A:
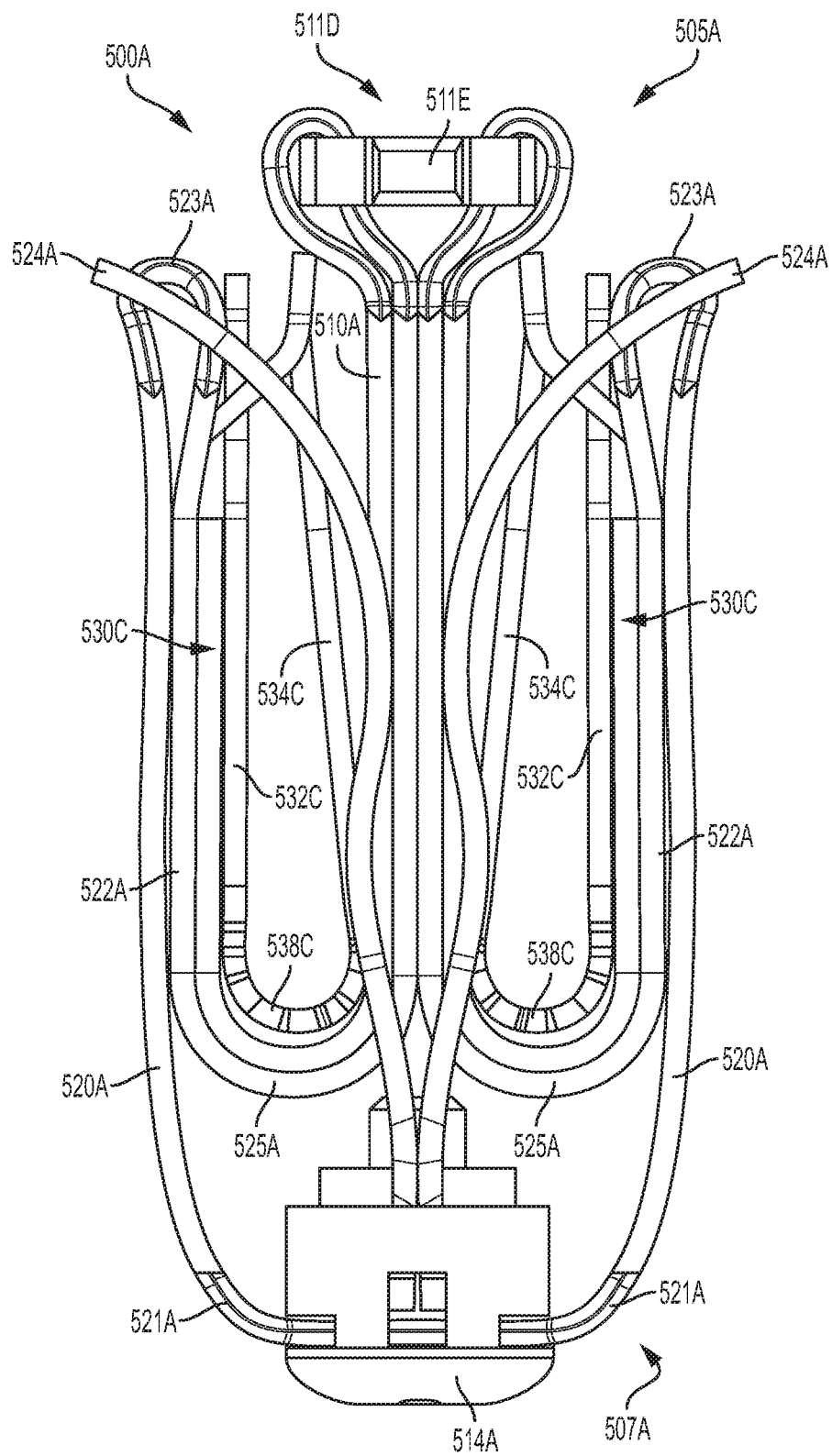
FIG. 48A shows a side view of an exemplary implantable prosthetic device with barbed clasps in a closed position.

The clasps 530C can comprise attachment or fixed portions 532C, arm or moveable portions 534C, barbs 536C, and joint portions 538C. The attachment or fixed portions 532C can be coupled to the inner paddles 522A in various ways such as with sutures, adhesive, fasteners, welding, stitching, swaging, friction fit and/or other means for coupling with the joint portions 538C disposed proximate the coaption element 510A. The clasps 530C can be similar to clasps 430, The moveable portions 534C can pivot or flex relative to the fixed portions 532C between an open configuration (e.g., FIG. 54A) and a closed configuration (FIG. 48A). In some embodiments, the clasps 530C can be biased to the closed configuration. In the open configuration, the fixed portions 532C and the moveable portions 534C pivot or flex away from each other such that native leaflets can be positioned between the fixed portions 532C and the moveable portions 534C. In the closed configuration, the fixed portions 532C and the moveable portions 534C pivot or flex toward each other, thereby clamping the native leaflets between the fixed portions 532C and the moveable portions 534C. The fixed arms 532C remain substantially stationary when the moveable arms 534C are opened to open the barbed clasps 530C and expose the barbs 536C. The barbed clasps 530C are opened by applying tension to actuation lines 516A attached to the moveable arms 534C, thereby causing the moveable arms 534C to pivot or flex on the joint portions 538C.

Figure 48B:
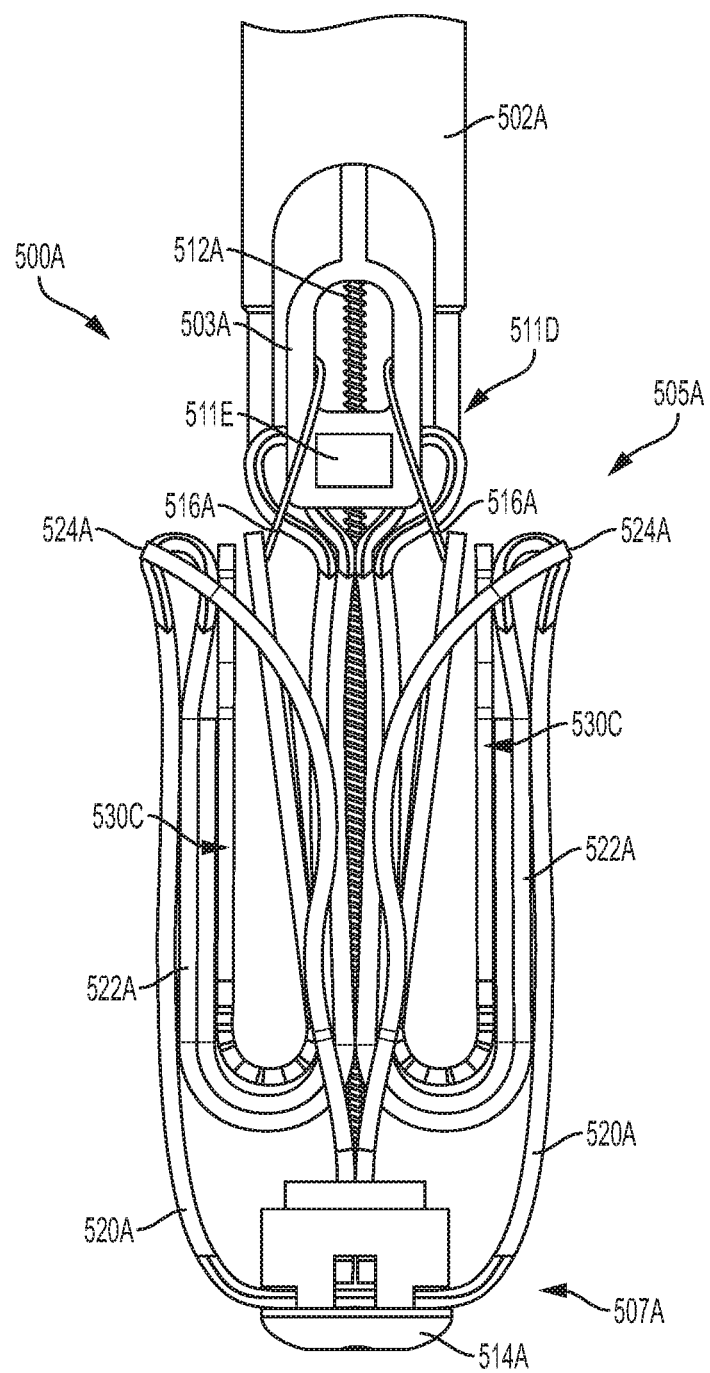
FIG. 48B shows a side view of an exemplary implantable prosthetic device with barbed clasps in a closed position, the device being attached to a deployment device.
Figure 48C:
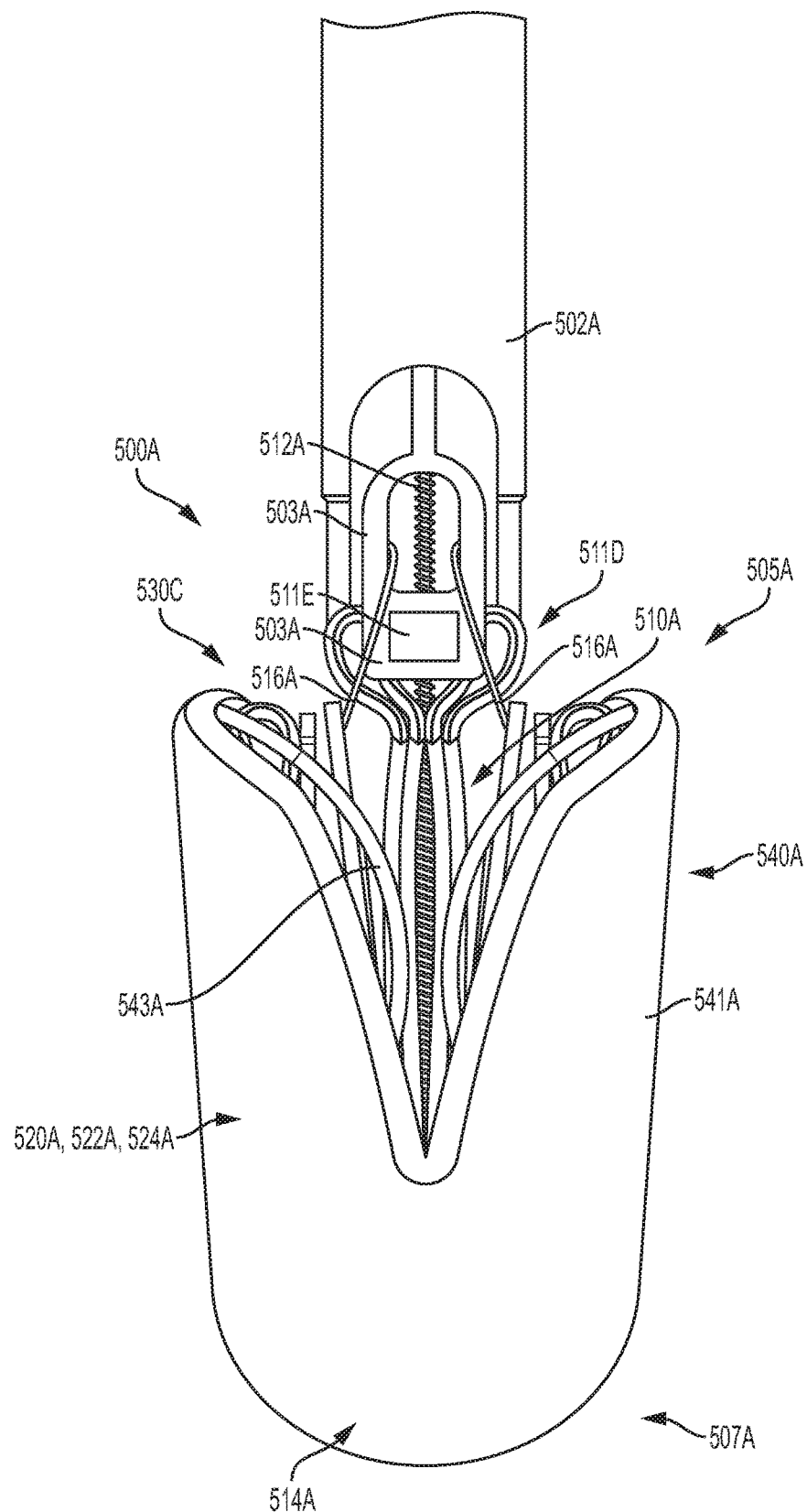
FIG. 48C shows a side view of the exemplary implantable prosthetic device according to FIG. 48B, the device being provided with a cover.
Figure 48D:
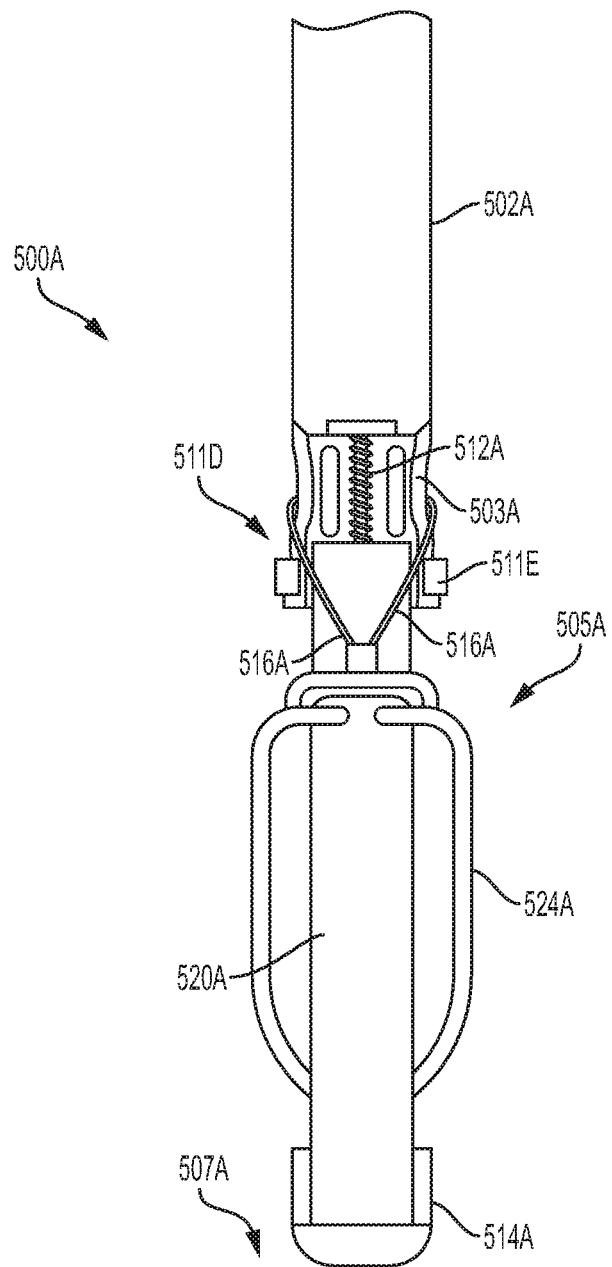
FIG. 48D shows a front view of the exemplary implantable prosthetic device according to FIG. 48B, the device being attached to a deployment device.
Figure 48E:
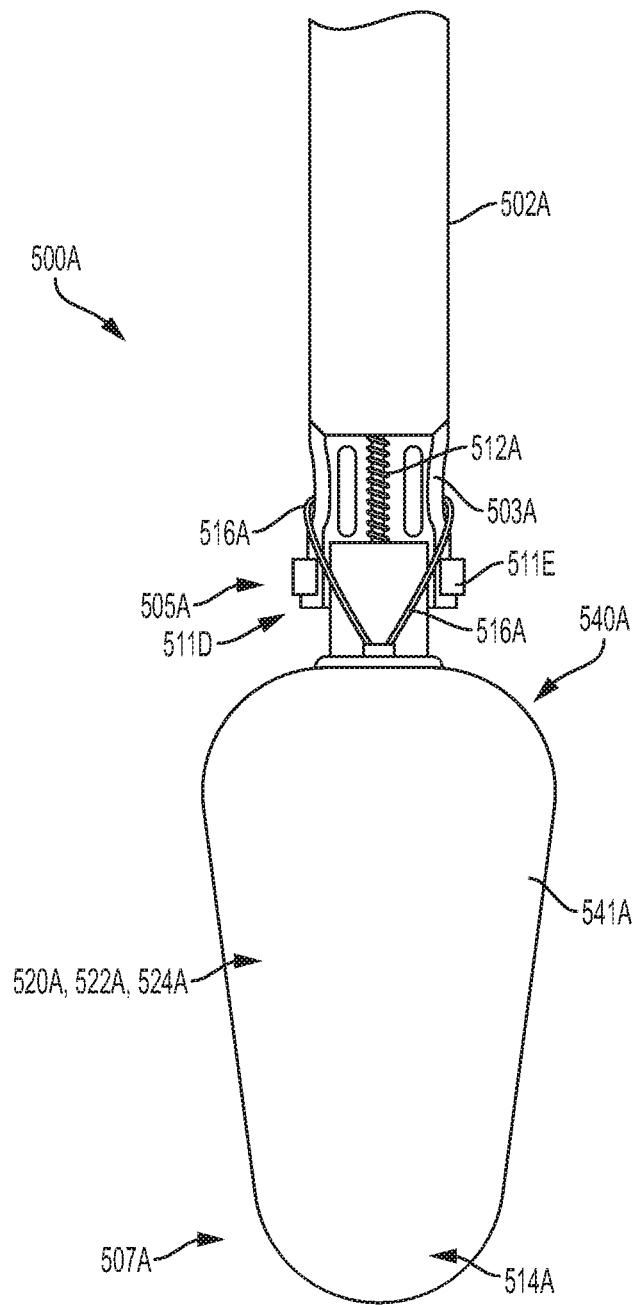
FIG. 48E shows a front view of the exemplary implantable prosthetic device according to FIG. 48D, the device being provided with a cover.
Figure 48F:
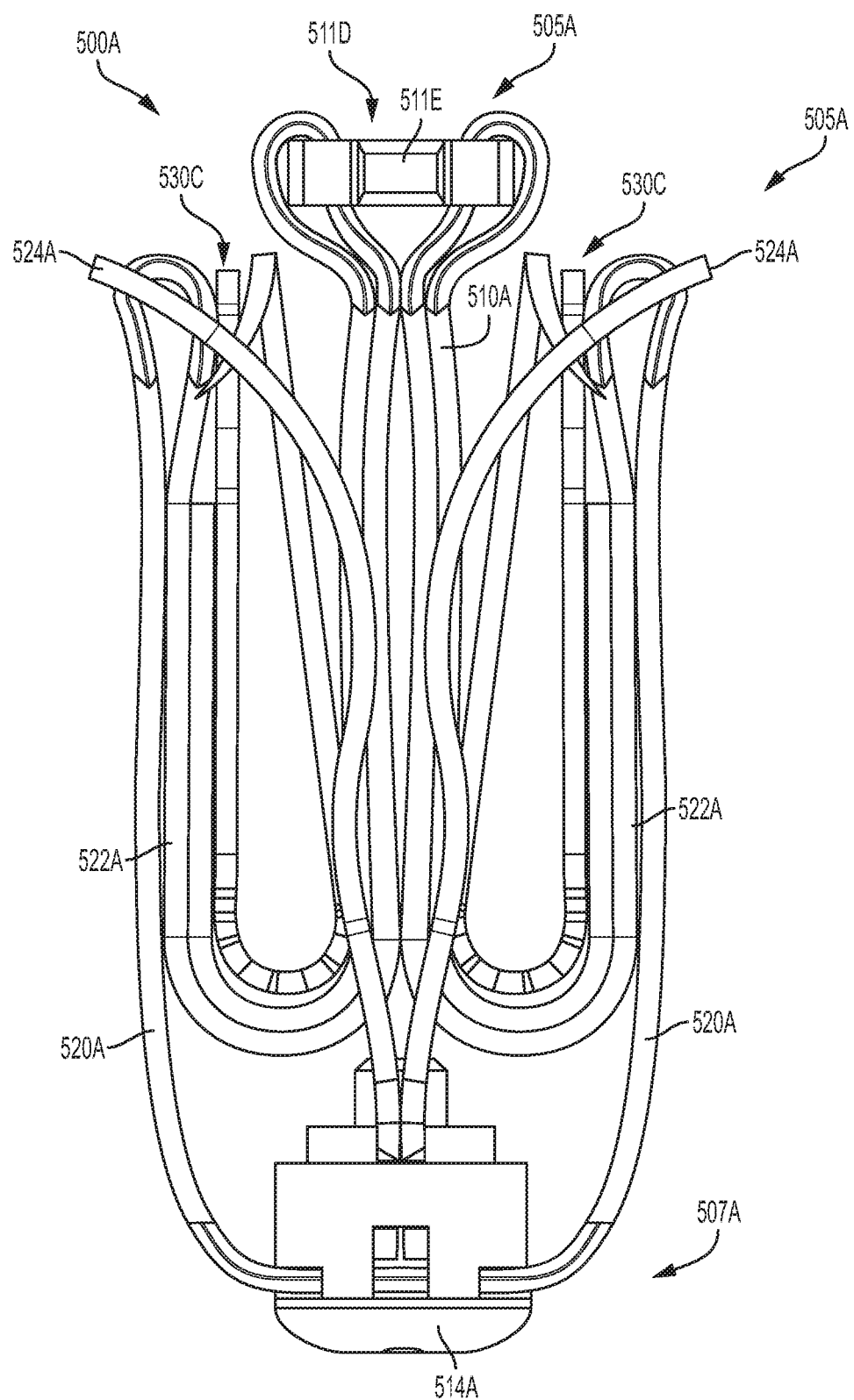
FIG. 48F shows a side view of the exemplary implantable prosthetic device according to FIG. 48B with barbed clasps in the closed position.
Figure 48G:
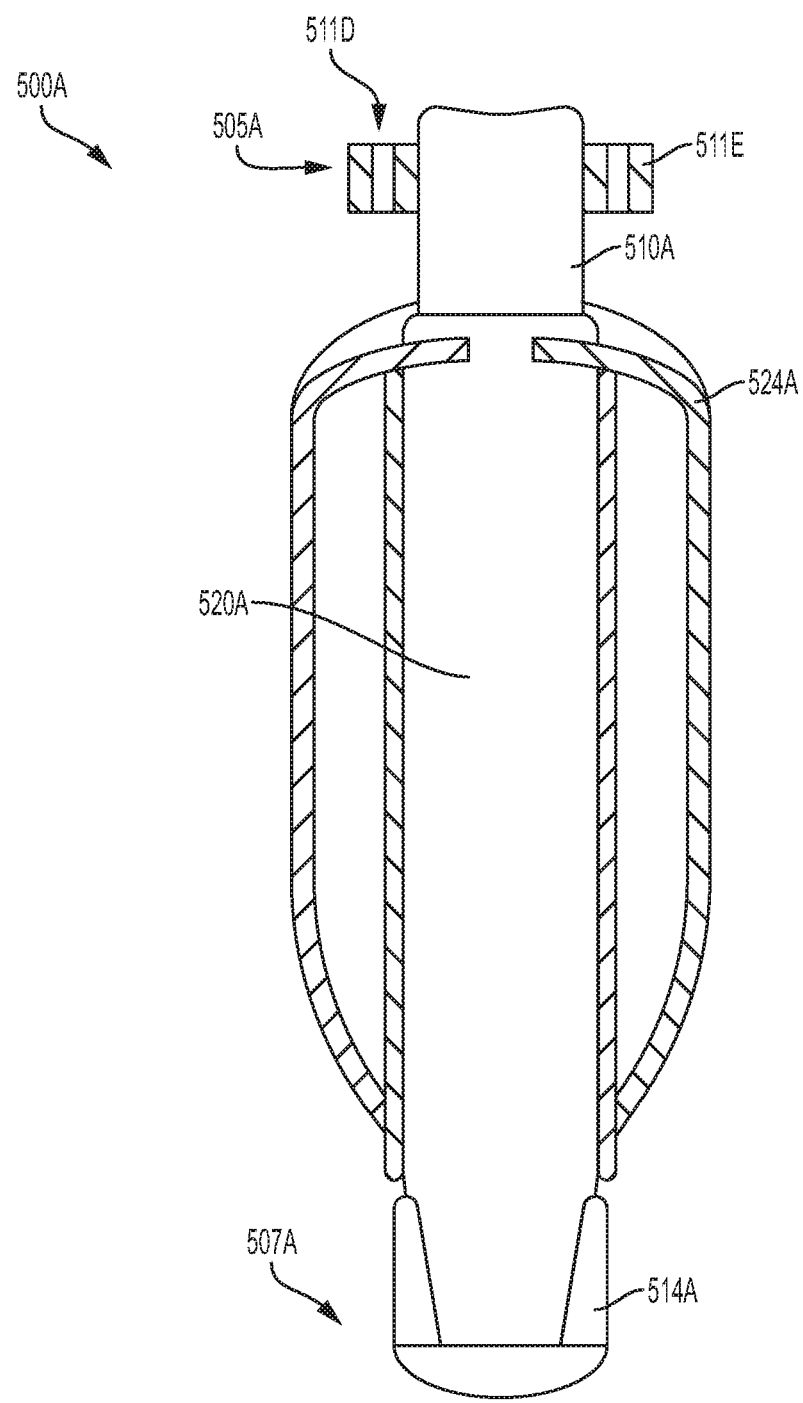
FIG. 48G shows a front view of the exemplary implantable prosthetic device according to FIG. 48F.
Figure 48H:
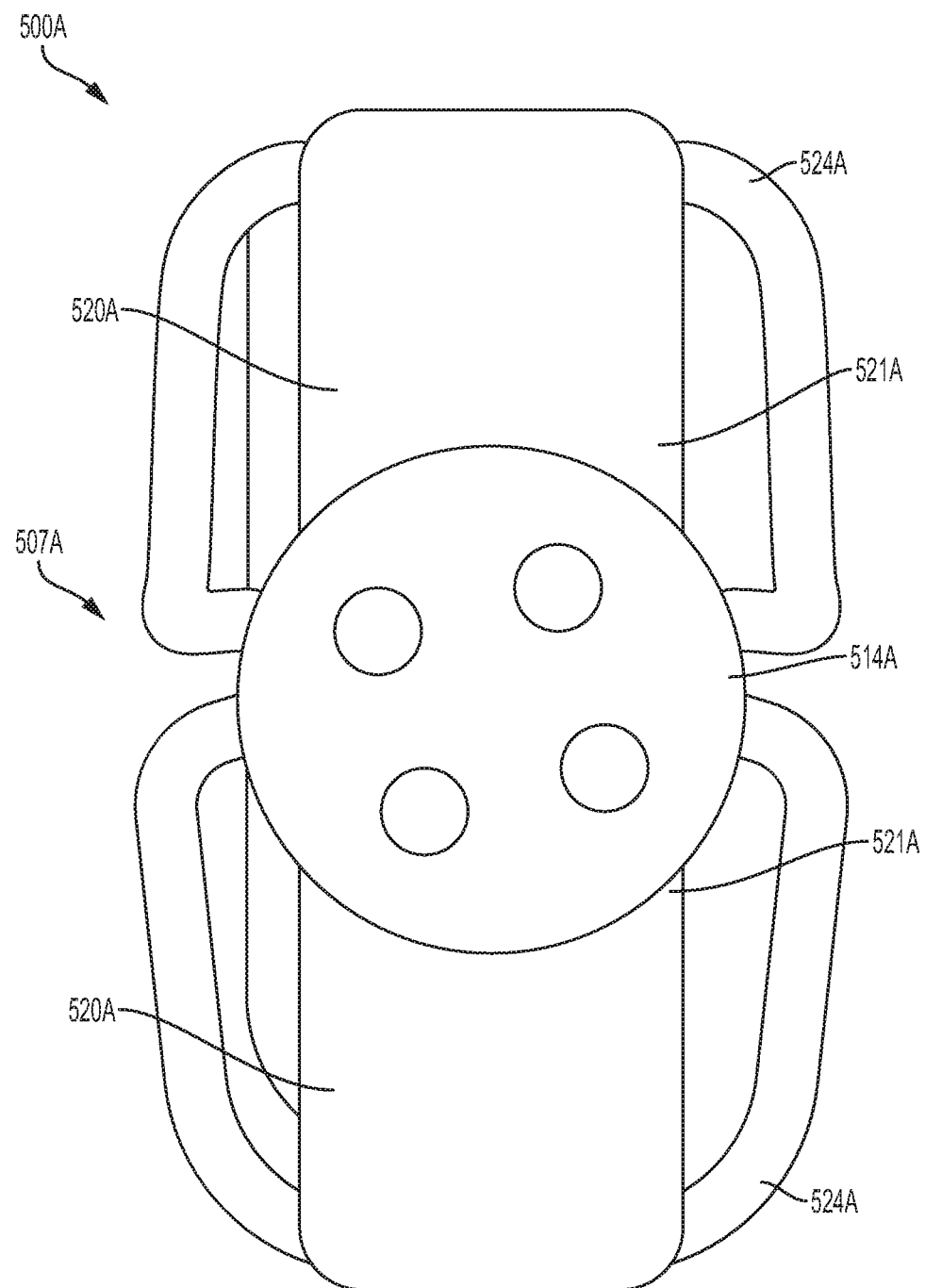
FIG. 48H shows a top view of the exemplary implantable prosthetic device according to FIG. 48F.

Referring now to FIGS. 47A, and 48A-48H, the device 500A is shown in a closed position. A side view of the device 500A is shown in FIGS. 48B, 48C, and 48F, from a front view in Figures FIGS. 48D, 48E, and 48G, and from a bottom view in FIG. 48H. The device 500A is narrower when viewed from the front than the side. From the side, the device 500A has a generally inverted trapezoidal shape that is rounded and tapers toward the distal portion 507A of the device 500A. From the front, the device 500A has a generally rounded rectangle shape that tapers somewhat toward the distal portion 507A. As can be seen from the bottom view of the device 500A shown in FIG. 48H, the device 500A has a generally rounded rectangle shape when viewed from below (and when viewed from above as can be seen in, for example, FIG. 70A).

In the closed configuration of the device 500A, the inner paddles 522A are disposed between the outer paddles 520A and the coaption element 510A. In some embodiments, the device 500A includes clasps or gripping members 530C (FIG. 48A) that can be opened and closed to grasp the native leaflets 20, 22 of the mitral valve MV. The clasps 530C are attached to and move with the inner paddles 522A and are disposed between the inner paddles 522A and the coaption element 510A.

Referring now to FIGS. 48B-48D, the device 500A is shown attached to a delivery device 502A. The delivery device 502A has actuatable members or fingers 503A that releasably engage the attachment portion 505A. An actuation wire 512A extends from the delivery device 502A to the cap 514A through the attachment portion 505A and coaption element 510A of the prosthetic device 500A. Extending and retracting the actuation wire 512A causes the device 500A to open and close, as is described below. Actuation sutures 516A extend from the delivery device 502A to attach to the clasps 530C. Tension can be applied to the sutures 516A to open the clasps 530C and released to allow the clasps 530C to close. The device 500A is shown separated from the delivery device 502A in a deployed condition in FIGS. 48F-48G.

Referring now to FIGS. 48C and 48E, the device 500A is shown with a cover 540A. The cover 540A can be formed from a single piece of material, or from multiple segments abutting or joined to each other. In the illustrated embodiment, the cover 540A has an outer or lower cover 541A and an inner or upper cover 543A. The outer cover 541A covers the cap 514A, outer paddles 520A, inner paddles 522A, and clasps 530C. The inner cover 543A covers the coaption element 510A and the proximal ends of the inner paddles 522A and clasps 530C where the coaption element 510A meets the inner paddles 522A and clasps 530C. The cover 540A can be a cloth material such as polyethylene cloth of a fine mesh. The cloth cover can provide a blood seal on the surface of the spacer, and/or promote rapid tissue ingrowth.

Referring now to FIGS. 53A-53D and 54A-54D, the device 500A is shown in a laterally extended or open position. The device 500A is moved into the open position by the actuation wire or shaft 512A that passes through the attachment portion 505A and coaption element 510A and can removably engage the distal portion 507A. The actuation wire 512A is extended through the attachment portion 505A such that a distance D2 between the attachment portion 505A and distal portion 507A increases as the actuation wire 512A is extended. In the example illustrated by FIGS. 53A-53D and 54A-54D, the pair of inner and outer paddles 520A, 522A are moved in unison, rather than independently, by a single actuation wire 512A. Also, the positions of the clasps 530C are dependent on the positions of the paddles 520A, 522A. For example, referring to FIG. 48A closing the paddles 520A, 522A also closes the clasps 530C. In one exemplary embodiment, the device 500A can be made to have the paddles 520A, 522A be independently controllable in the same manner as the FIG. 11A embodiment.

Extending the actuation wire 512A pulls down on the bottom portions of the outer paddles 520A and paddle frames 524A to transition the device 500A from a closed to partially open position. The outer paddles 520A and paddle frames 524A pull down on the inner paddles 522A where the inner paddles 522A are connected to the outer paddles 520A and the paddle frames 524A. Because the attachment portion 505A and coaption element 510A are held in place, the inner paddles 522A are caused to pivot or flex in an opening direction. The inner paddles 522A, the outer paddles 520A, and the paddle frames all flex to the position shown in FIG. 53A. Opening the paddles 522A, 520A and frames 524 forms a gap 520D between the coaption element 510A and the inner paddle 522A that can receive and grasp the native leaflets 20.

Continuing to extend the actuation wire 512A pulls down on the outer paddles 520A and paddle frames 524A, thereby causing the inner paddles 522A to spread apart further from the coaption element 510A. In the laterally extended or open position, the inner paddles 522A extend horizontally more than in other positions of the device 500A and form an approximately 90-degree angle with the coaption element 510A. Similarly, the paddle frames 524A are at their maximum spread position when the device 500A is in the laterally extended or open position. The increased gap 520D formed in the laterally extended or open position allows clasps 530C to open further (FIG. 54A) before engaging the coaption element 510A, thereby increasing the size of the gap 530D as compared to the partially open position.

As is described above, some embodiments of the device 500A include clasps or gripping members 530A. When the device 500A is opened the clasps 530C are exposed. In some embodiments, the closed clasps 530C (FIGS. 53A-53D) can be opened (FIGS. 54A-54D), thereby creating a second opening or gap 530D for receiving and capturing the native leaflets 20, 22. The extent of the gap 530D in the clasps 530C is limited to the extent that the inner paddle 522A has spread away from the coaption element 510A.

Referring now to FIGS. 60A-60D and 61A-61D, the device 500A is shown in a fully extended position. The device 500A is moved into the fully extended position by continuing to extend the actuation wire 512A described above, thereby increasing the distance D2 between the attachment portion 505A and distal portion 507A to a maximum distance allowable by the device 500A. Continuing to extend the actuation wire 512A pulls down on the outer paddles 520A and paddle frames 524A, thereby causing the inner paddles 522A to extend further away from the coaption element 510A. The outer paddles 520A and paddle frames 524A move to a position where they are close to the actuation wire. In the fully extended position, the inner paddles 522A are open to an approximately 180-degree angle with the coaption element 510A. The inner and outer paddles 522A, 520A are stretched substantially straight in the fully extended position to form an approximately 180-degree angle between the paddles 522A, 520A. The fully extended position of the device 500A provides the maximum size of the gap 520D between the paddles, and, in some embodiments, allows clasps 530C to also open fully to approximately 180 degrees (FIG. 61A) between portions of the clasp 530A. The position of the device 500A is the narrowest configuration. Thus, the fully extended position of the device 500A may be a desirable position for bailout of the device 500A from an attempted implantation or may be a desired position for placement of the device in a delivery catheter, or the like.

Referring now to FIGS. 197-198, enlarged views of portions of FIG. 60C are shown. Referring now to FIG. 197, the inner cover 543A can be seen covering the coaption element 510A from the proximal portion 519B to the distal portion 517A. The inner cover 543A is formed from a flat sheet (see FIG. 201) of a cloth material such as polyethylene cloth of a fine mesh and is folded around the coaption element 510A and held in place by stitches 545A. Referring now to FIG. 198, the outer cover 541A can be seen covering the clasps 530C and inner paddles 522A. Collar portions 548A of inner cover 543A cover the portion of the clasps 530C and inner paddles 522A closest to the coaption element 510A. Transition portions 547A of the inner cover 543A extend from the coaption element 510A to the collar portions 548A to provide a smooth transition between the coaption element 510A and the clasps 530C and inner paddles 522A so that native tissue is not caught on the device 500A during implantation.

Referring now to FIG. 199, an exploded view of the device 500A is shown. The coaption element 510A, outer paddles 520A, and inner paddles 522A are formed from a single strip of material 501A, as described above. The collar 511D, cap 514A, paddle frames 524A, and clasps 530C are assembled to the strip of material 501A to form the device 500A. The cap 514A includes a retention body 560A with a locking aperture 561A for receiving a retaining nut 562A having a threaded bore 564A that engages a threaded portion 568A of a retaining bolt 566A. The threaded portion 568A of the retaining bolt 566A is inserted through the opening 527B to engage the retention body and nut 560A, 562A to attach the cap 514A to the strip of material 501A.

In some embodiments, a stiffening member 539C is attached to the inner paddle 522A to stiffen the inner paddle 522A to maintain the inner paddle in a straight or substantially straight configuration as the inner paddle is moved between the various positions. A cutout 539D in the stiffening member 539C is shaped to receive the fixed arm 532C of the clasp 530C so that the stiffening member 539C can fit around the fixed arm 532C when both the stiffening member 539C and clasp 530C are attached to the inner paddle 522A. Like the fixed arm 532C, the stiffening member 539C may be coupled to the inner paddles 522A in various ways such as with sutures, adhesive, fasteners, welding, stitching, swaging, friction fit and/or other means for coupling.

Referring now to FIG. 200, an enlarged view of the collar 511A attached to the proximal portion 519B of the coaption element 510A is shown. The collar 511A includes protrusions 511B for releasably engaging the fingers 503A of the delivery device 502A. An aperture 515A in the collar 511A receives the actuation wire 512A. The proximal portion 519B of the coaption element 510A flares outward to form two loops 519D that are inserted through the arcuate openings 513A of the collar 511D to attach the collar 511D to the proximal portion 519B of the coaption element 510A. The loops 519D are formed by folding the strip of material 501A to form first and second layers 581A, 582A. In some embodiments, the arcuate openings 513A include an opening (not shown) similar to the Referring now to FIGS. 201-202, enlarged and exploded views of the cap 514A are shown, respectively. FIG. 201 shows an enlarged view of the cap 514A attached to the distal portion 527A of the strip of material 501A is shown. The retention body 560A, retaining nut 562A, and retaining bolt 566A cooperate to attach the paddle frames 524A to the distal portion 527A of the strip of material 501A. In particular, the retaining bolt 566A is inserted through the opening 527B of the distal portion 527A (FIG. 202) to prohibit movement of the cap 514A along the strip of material 501A. A channel 560B in the retention body 560A and a flange 567A of the bolt 566A form a passageway 514B through the cap 514A for the distal portion 527A.

Referring now to FIG. 202, the components of the cap 514A are shown in an exploded view to better illustrate the features of the components of the cap 514A and paddle frames 524A and to show how those features interlock during assembly of the cap 514A to the distal portion 527A. Forming the cap 514A from multiple components that can be assembled around the strip of material 501A allows the cap 514A to be attached after the strip of material 501A has been folded to form the coaption element 510A and paddles 520A, 522A and been woven through the collar 511D and paddle frames 524A.

The retention body 560A includes a locking aperture 561A for receiving the retaining nut 562A. The locking aperture 561A has a generally rectangular shape and includes two opposing locking channels 561B that receive the attachment portions 524C of the paddle frames 524A. A transverse locking channel 561C formed in the bottom of the retention body 560A has the same width as the locking channels 561B. The paddle frames 524A include notches 524D in the attachment portions 524C that form hook portions 524E that engage the transverse locking channel 561A to secure the paddle frames 524A to the cap 514A.

The retaining nut 562A includes a rectangular locking body 563A extending distally from a flange 563B. The locking body 563A is configured to slidably engage the locking aperture 561A of the retention body 560A while leaving the locking channels 561B unobstructed. Thus, the locking body 563A can be inserted into the locking aperture 561A to lock the attachment portions 524C of the paddle frames 524A within the locking channels 561B. Notches 563C in the flange 563B accommodate the attachment portions 524C of the paddle frames 524A. The threaded bore 564A is formed through the retaining nut 562A to receive the retaining bolt 566A. d The retaining bolt 566A includes a threaded portion 568A extending from the flange 567A. The threaded portion 568A is inserted through the opening 527B in the distal portion 527A to threadably engage the threaded bore 564A of the retaining nut 562A. The flange 567A has a rounded shape that provides a rounded end to the distal portion 505A of the device 500A. The flange 567A includes openings 567B for receiving a tool (not shown) that engages the bolt 566A so that the bolt 566A can be turned during assembly to couple the components of the cap 514A together.

To assemble the paddle frames 524A and cap 514A to the distal portion 527A, the paddle frames 524A are squeezed to narrow the width of the attachment portion 524C so that the attachment portions 524C can be inserted into the locking channels 561B of the locking aperture 561A. When the paddle frames 524A are allowed to expand, the attachment portions 524C expand outward so that the notches 524D engage the retention body 560A and the hook portions 524E engage the transverse locking channel 561C. The retaining nut 562A is then inserted into the locking aperture 561A with the locking portion 563A arranged between the two attachment portions 524C of each paddle frame 524A, thereby locking the paddle frames 524A in engagement with the retention body 560A. The assembled paddle frames 524A, retention body 560A, and retaining nut 562A are placed on the distal portion 527A so that the threaded bore 564A aligns with the opening 527B and the threaded portion 568A of the bolt 566A is inserted through the opening 527B to threadably engage the threaded bore 564A. The bolt 566A is then tightened until the flange 567A engages the retention body 560A and the cap 514A is securely assembled to the distal portion 527A.

Referring now to FIGS. 203 and 204, portions of the cover 540A are shown cut from flat sheets of material. The cover 540A includes the outer cover 541A and the inner cover 543A. Each of the covers 541A, 543A include different shaped segments or portions to attach to different portions of the device 500A. In particular, the covers 541A, 543A are shaped to smooth transitions between portions of the device 500A to reduce catch points and provide a smoother exterior to the device 500.

The various segments of the covers 541A, 543A extend from a middle portion that is shaped to attach to an end of the device 500A. In other embodiments, the portion of the cover 541A, 543A that attaches to an end of the device 500A is located at an end of the covers 541A, 543A or may be located anywhere between the middle and ends of the covers 541A, 543A. Various portions of the covers 541A, 543A may be shaped to wrap around portions of the device 500A. The cover 540A can be made of any suitable material, such as a polyethylene cloth of a fine mesh. In certain embodiments, the cover is formed out of a single piece of material. In other embodiments, the cover may be formed of any number of pieces of material that are attached to the device and/or joined together by any suitable means, such as by stitching, adhesives, welding, or the like.

Referring to FIGS. 60C and 204, the outer cover 541A extends outward from a middle portion 580 to end portions 588. The middle portion 580 is shaped to be attached to the cap 514A of the device 500A. Outer paddle portions 582 extend from the middle portion 580 to inner paddle and inside clasp portions 584. The inner paddle and inside clasp portions 584 extend from the outer paddle portions 582 to outside moveable clasp portions 586. The outside moveable clasp portions 586 extend from the inner paddle portions 584 to the end portions 588.

The outer paddle portions 582 include wing portions 583 that extend laterally to a width that is wider than the other portions of the outer cover 541A so that the outer paddle portions 582 can attach to the outer paddles 520A and paddle frames 524A of the device 500A. The inner paddle portions 584 attach to the inner paddles 522A, stationary arms 532C, and the inside surface (the side with the barbs) of the moveable arms 534C. The outside clasp portions 586 attach to the outside surface (the side without the barbs) of the moveable arms 534C of the clasps 530C. The ends 588 of the outer cover 541A terminate near the joint portion 538C of the clasp 530C on the outside of the clasps 530C. The inner paddle and inside clasp portions 584 include openings 585 that allow the barbs 536C of the clasps 530C to protrude through the outer cover 541A to engage tissue of the native heart valve.

Referring to FIGS. 60C and 203, the inner cover 543A extends outward from a middle portion 590 to end portions 598. The middle portion 590 is configured to be attached to the collar 511D of the device 500A. Openings 591 in the middle portion 590 expose the protrusions 511E from the collar 511D when the middle portion 590 is attached to the collar 511D so that the protrusions 511E can be engaged by the delivery device 502A. Coaption portions 592 extend from the middle portion 590 to flexible hinge portions 594. Holes 593 along the edges of the coaption portions 592 allow each of the coaption portions 592 to be joined together after being folded around the coaption element 510A, such as, for example, by stitches 545A. The flexible hinge portions 594 extend from the coaption portions 592 to transition portions 596. The transition portions 596 extend from the flexible hinge portions 594 to the end portions 598. Holes 597 along the edges of the transition portions 596 allow each of the transition portions 596 to be wrapped around the inner paddle 522A and ends of the clasp 536C and secured to itself by stitches or other suitable securing means. The flexible hinge portions 594 bridge the gaps between the coaption element 510A and the clasps 530C when the device 500A is opened, as can be seen in FIG. 198.

Referring now to FIGS. 62A-64C, an implantable device 700 is shown. The implantable device 700 has paddles 702 that open and close to grasp leaflets 20, 22 against barbed clasps or gripping devices 704. The paddles 702 move to create an opening 706 between the paddles 702 and gripping devices 704 in which the leaflets 20, 22 can be grasped. The device 700 can be configured to close a wide gap 26 (FIG. 6) in the native heart valve MV, TV. In addition, the implantable device 700 can include any other features for a device discussed in the present application, and the device 700 can be positioned to engage valve leaflets 20, 22 as part of any suitable valve repair system (e.g., any valve repair system disclosed in the present application). The device 700 can include any other features for an implantable prosthetic device discussed in the present application, and the device 700 can be positioned to engage valve tissue 20, 22 as part of any suitable valve repair system (e.g., any valve repair system disclosed in the present application).

Figure 62A:
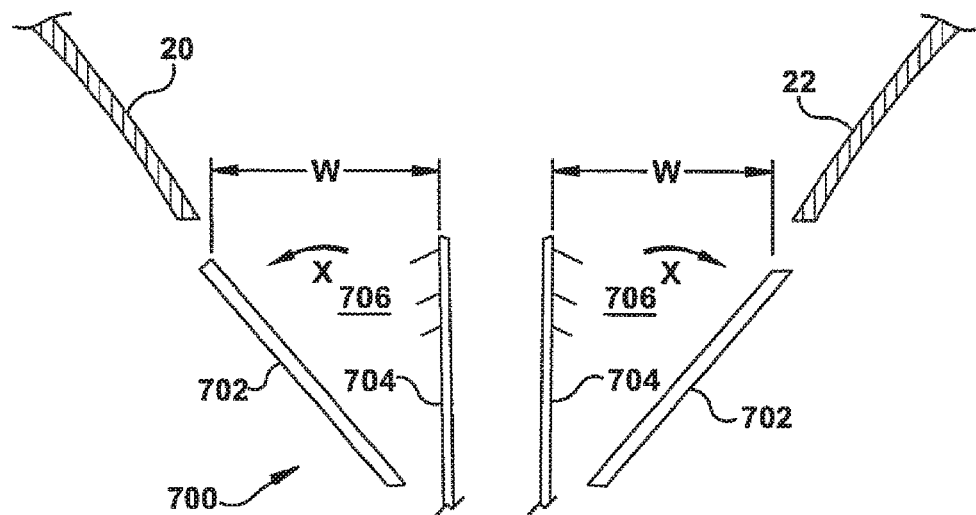
FIGS. 62A-62B illustrate the movement of the paddles of an exemplary embodiment of an implantable prosthetic device.

Referring to FIG. 62A, the paddles 702 of the device 700 are pivoted outward in the direction X to create an opening 706 between the paddles 702 and the gripping members 704 having a width W. The width W can be, for example, between about 5 mm and about 15 mm, such as between 7.5 mm and about 12.5 mm, such as about 10 mm. In alternative embodiments, the width W can be less than 5 mm or greater than 15 mm.

Figure 62B:
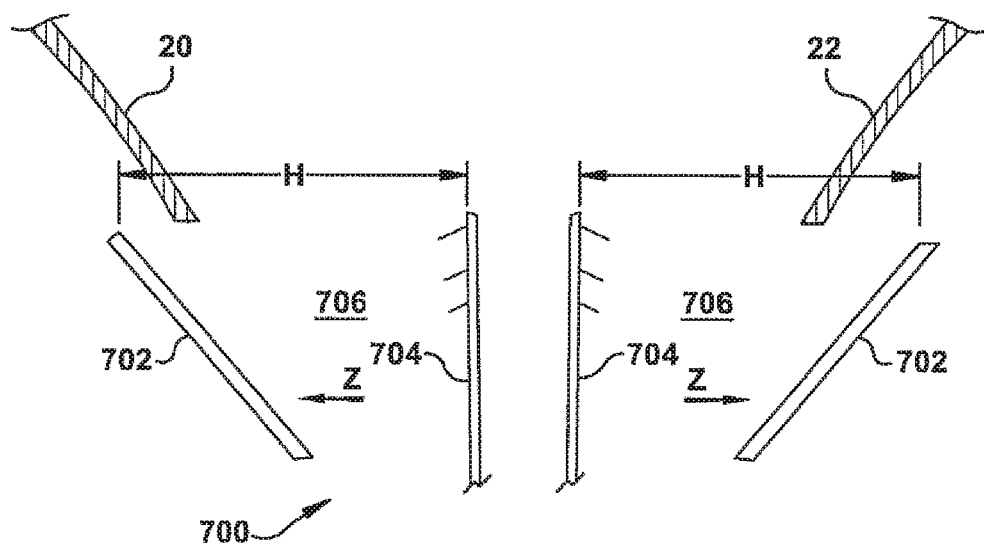

Referring to FIG. 62B, the paddles 702 of the device 700 are moved outward in the direction Z such that the opening 706 has a width H. The width H can be, for example, between about 10 mm and about 25 mm, such as between about 10 mm and about 20 mm, such as between about 12.5 mm and about 17.5 mm, such as about 15 mm. In alternative embodiments, the width H can be less than 10 mm or more than 25 mm. In certain embodiments, the ratio between the width H and the width W can be about 5 to 1 or less, such as about 4 to 1 or less such as about 3 to 1 or less, such as about 2 to 1 or less, such as about 1.5 to 1 or less, such as about 1.25 to 1 or less, such as about 1 to 1. The device 700 can be configured such that the paddles 702 are pivoted outward in the direction X and then moved outward in the direction Z to create the opening 706 having a width H between the paddles 702 and the gripping members 704. Alternatively, the device 700 can be configured such that the paddles are moved outward in the direction Z and then pivoted outward in the direction X to create width H between the paddles 702 and gripping members 704. In addition, the device 700 can be configured such that the paddles 702 are pivoted outward in the direction X and moved outward in the direction Z simultaneously to create the width H between the paddles 702 and the gripping members 704.

Figures 63A, 63B, 63C:
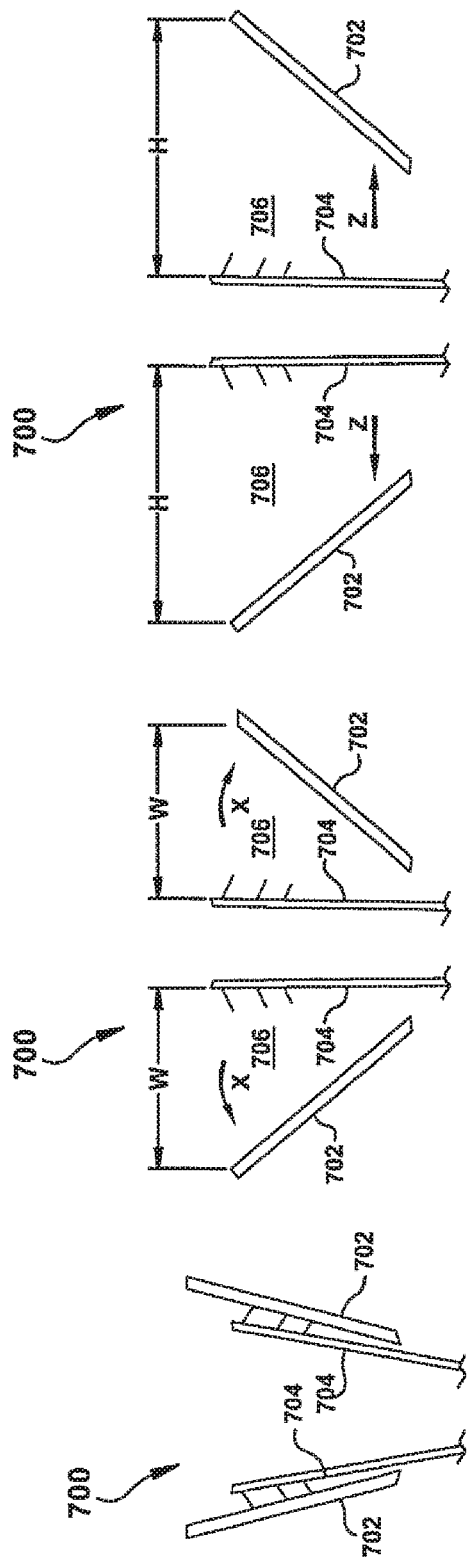
FIGS. 63A-63C illustrate the movement of the paddles of an exemplary embodiment of an implantable prosthetic device.

FIGS. 63A-63C illustrate an implantable device 700 in which the paddles 702 are pivoted outward in the direction X, and, subsequently, moved outward in the direction Z to create a wider opening 706. FIG. 63A illustrates the implantable device 700 in a closed position, such that the paddles 702 are engaging the gripping members 704. Referring to FIG. 63B, the paddles 702 are pivoted outward in the direction X to create an opening 706 having a width W for receiving valve tissue. Referring to FIG. 63C, after the paddles 702 are pivoted outward in the direction X, the paddles 702 are moved outward in the direction Z such that the opening 706 has a width H. After valve tissue is received in the openings 706 between the paddles 702 and the gripping members 704, the valve repair device is moved back to the closed position (as shown in FIG. 63A) to secure the valve repair device 700 to the valve tissue. The implantable device 700 can include any other features for an implantable device discussed in the present application, and the implantable device 700 can be positioned to engage valve tissue 20, 22 as part of any suitable valve repair system (e.g., any valve repair system disclosed in the present application).

Figures 64A, 64B, 64C:
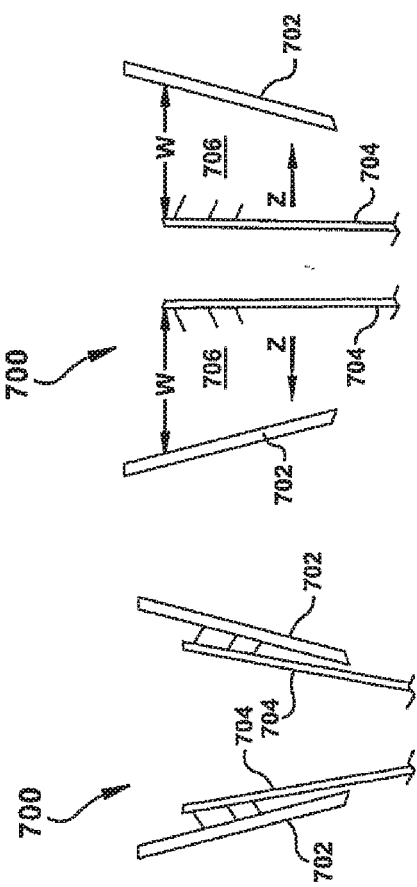
FIGS. 64A-64C illustrate the movement of the paddles of an exemplary embodiment of an implantable prosthetic device.

FIGS. 64A-64C illustrate an implantable device 700 in which the paddles 702 are moved outward in the direction Z, and, subsequently, pivoted outward in the direction X to create a wider opening 706. FIG. 64A illustrates the implantable device 700 in a closed position, such that the paddles 702 are engaging the gripping members 704. Referring to FIG. 64B, the paddles 702 are moved outward in the direction Z to create an opening 706 having a width W for receiving valve tissue. Referring to FIG. 64C, after the paddles 702 are moved outward in the direction Z, the paddles 702 are pivoted outward in the direction X such that the opening 706 has a width H. After valve tissue is received in the openings 706 between the paddles 702 and the gripping members 704, the implantable device 700 is moved back to the closed position (as shown in FIG. 64A) to secure the implantable device 700 to the valve tissue. The implantable device 700 can include any other features for an implantable device discussed in the present application, and the implantable device 700 can be positioned to engage valve tissue 20, 22 as part of any suitable valve repair system (e.g., any valve repair system disclosed in the present application).

While FIGS. 63A-63C illustrate a device 700 in which the paddles 702 are pivoted and then spread apart, and FIGS. 64A-64C illustrate a device 700 in which the paddles 702 are spread apart and then pivoted, in alternative embodiments, a device 700 can include paddles 702 that can be spread apart and pivoted simultaneously. In addition, in certain embodiments, the paddles 702 can be spread apart and pivoted independently of each other. That is, in the embodiments for the valve repair device 700 shown in FIGS. 63A-63C and 64A-64C, as well as the embodiment in which the spreading apart and pivoting of each paddle 702 is completed simultaneously, the paddles 702 can be controlled independently of each other.

Figure 66:
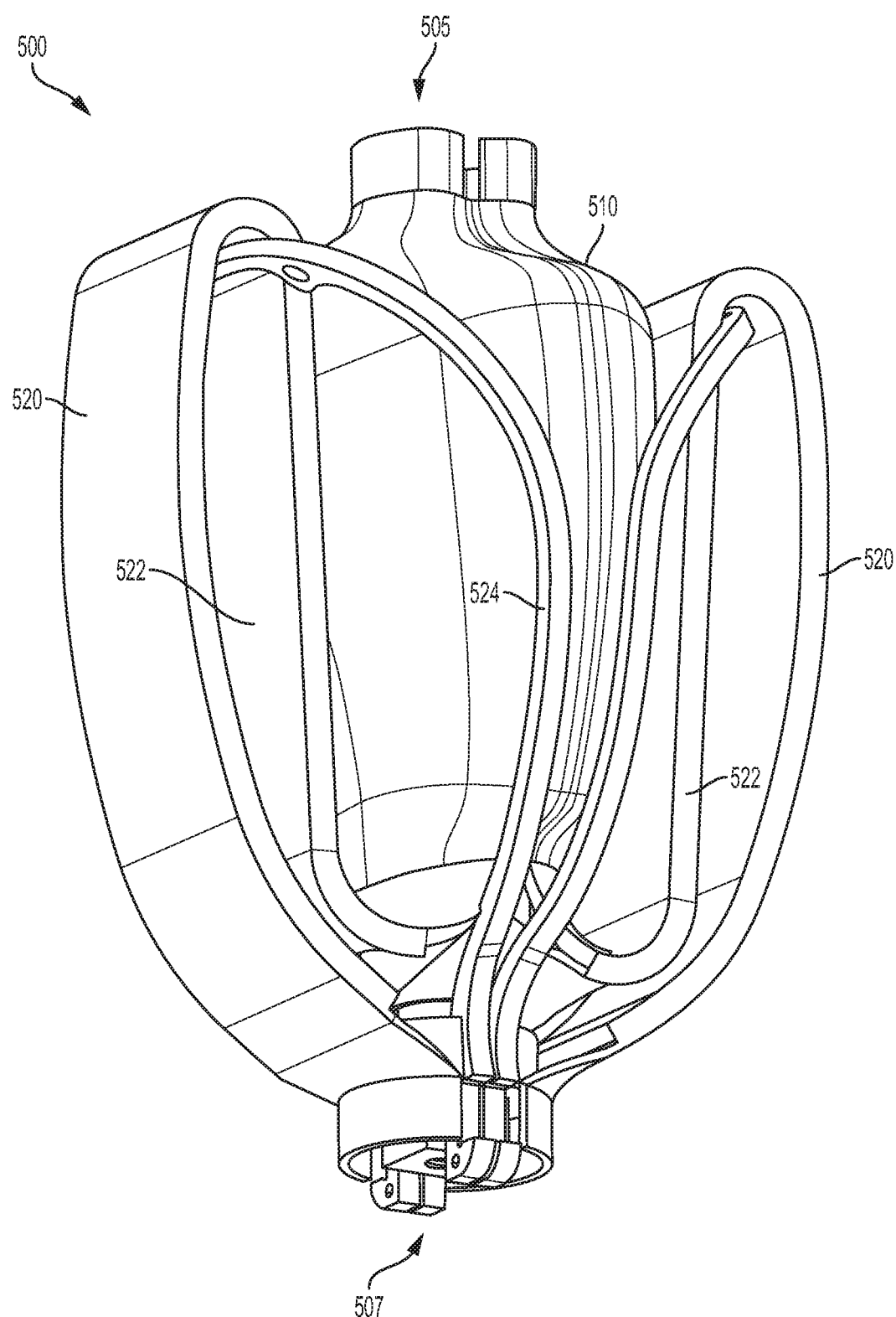
FIG. 66 shows a perspective view of the implantable prosthetic device of FIG. 65.

Referring now to FIGS. 65-83, the exemplary implantable device 500 is shown in the closed condition. Referring now to FIGS. 65-66, the device 500 extends from a proximal portion 505 to a distal portion 507 and includes a coaption portion 510, inner paddles 522, outer paddles 520, and paddle frames 524. In some embodiments, the outer paddles 520 extend to and/or around the paddle frames 524 and can have more than one layer to surround the paddle frames 524. The proximal portion 505 can include a collar 511 for attaching a delivery device (not shown). The distal portion 507 can include a cap 514 that is jointably attached to the outer paddles 520 and is engaged by an actuation wire (not shown) to open and close the device 500 to facilitate implantation in the mitral valve as described in the present application.

Referring now to FIGS. 67-68, a front view of the device 500 is shown. The device 500 has a shape that is substantially symmetrical around a vertical front-to-back plane 550 and is generally narrower at the distal portion 507 than the proximal portion 505. The shape of the coaption element 510 and paddle frames 524 is generally rounded to prevent the device 500 from catching or snagging on structures of the heart, such as the chordae tendineae, during implantation. For this reason, the proximal collar 511 (FIG. 68) and cap 514 (FIG. 68) also have round edges. When viewed from the front or back, the paddle frames 524 can be seen to have a generally rounded shape, extending upwards and outwards from the distal portion 507 to approximately coincide with the shape of the coaption element 510 when viewed from the front or back. Thus, the coaption element 510 and paddle frames 524 generally define the shape of the device 500 when viewed from the front or back. In addition, the rounded shape of the paddle frames 524 and the corresponding rounded shape of the coaption element can distribute leaflet stress across a wider surface. In other exemplary embodiment, the paddle frames 524 and/or the coaption element 510 can have other shapes.

Figure 69:
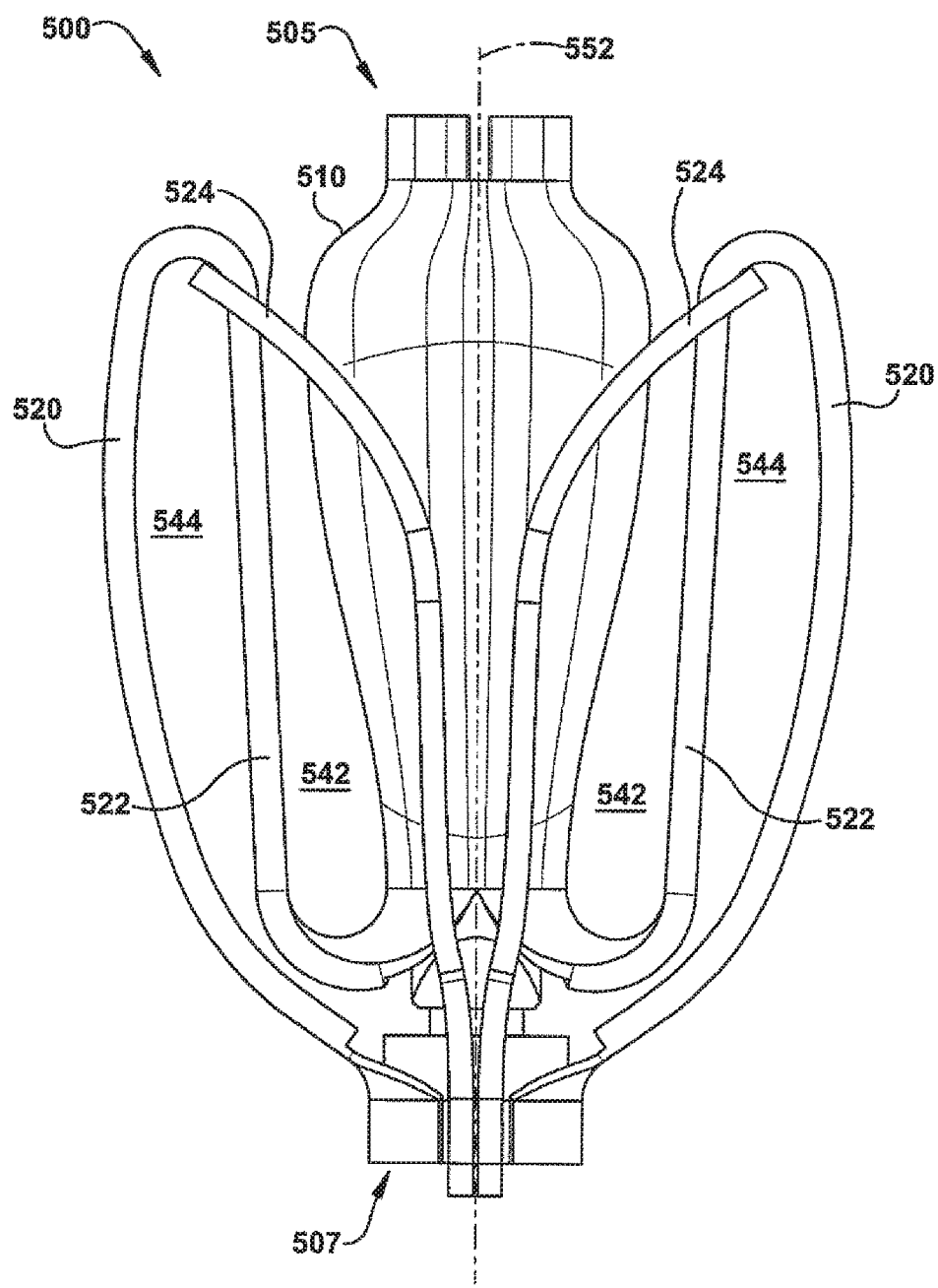
FIG. 69 shows a side view of the implantable prosthetic device of FIG. 65.

Referring now to FIG. 69, a side view of the device 500 is shown. As with the front and back views (FIGS. 67-68), the device 500 has a shape that is substantially symmetrical around a vertical side-to-side plane 552 when viewed from the side. The distal portion 507 is also generally narrower than the proximal portion 505 when the device 500 is viewed from the side. The coaption element 510 optionally also has a generally tapering shape that narrows toward the distal portion 507 of the device 500. However, in other exemplary embodiments, the coaption element does not taper as it extends from the proximal portion of the device to the distal portion of the device.

The generally rounded features of the device 500 are further demonstrated by the round shape of the paddles 520, 522 where the inner and outer paddles 520, 522 are joined together and the round shape of the paddle frames 524. However, the paddles 520, 522 and paddle frames 524 can take a wide variety of different forms. For example, the paddles 520, 522 and the paddle frames 524 can be rounded along the top edges, but be flat or substantially flat on the sides of the paddles 520, 522 and/or the paddle frames. By making the paddles 520, 522 flat or substantially flat on the sides, two devices can be implanted side-by-side on the mitral valve leaflet, with the two devices sitting substantially flush against each other.

The closed paddles 520, 522 form gaps 542 between the inner paddles 522 and the coaption element 510 that are configured to receive native tissue. As can be seen in FIG. 69, the narrowing of the coaption element 510 gives the gaps 542 a somewhat teardrop shape that increases in width as the gaps 542 approach the distal portion 507 of the device. The widening of the gaps 542 toward the distal portion 507 allows the paddles 520, 522 to contact tissue grasped in the gaps 542 nearer to the proximal portion 505.

The paddle frames 524 extend vertically from the distal portion 507 toward the proximal portion 505 until approximately a middle third of the device 500 before bending or flaring outward so that the connection portion of the frames 524 passes through gaps 544 formed by the inner paddles 522 folded inside of the outer paddles 520. However, in other embodiments the connection of the frames are positioned inside the inner paddles 522 or outside the outer paddles 520. The outer paddles 520 have a rounded shape that is similar to that of the coaption element 510 when viewed from the front or back (FIGS. 67-68). Thus, the device 500 has a substantially round shape. The round shape of the device 500 is particularly visible when the device 500 is viewed from the top (FIGS. 70-71) or bottom (FIGS. 72-73).

Figure 70:
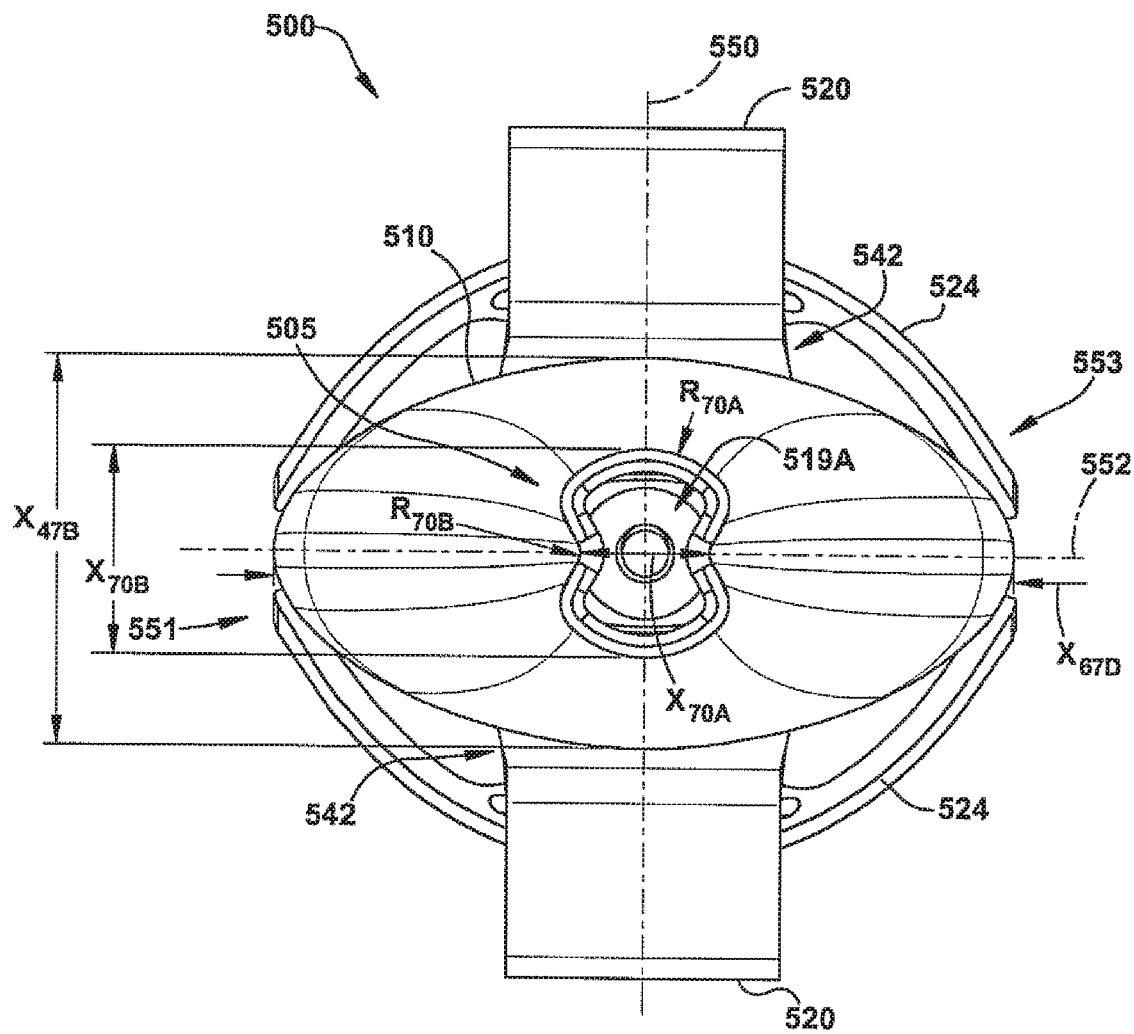
FIG. 70 shows a top view of the implantable prosthetic device of FIG. 65.
Figure 71:
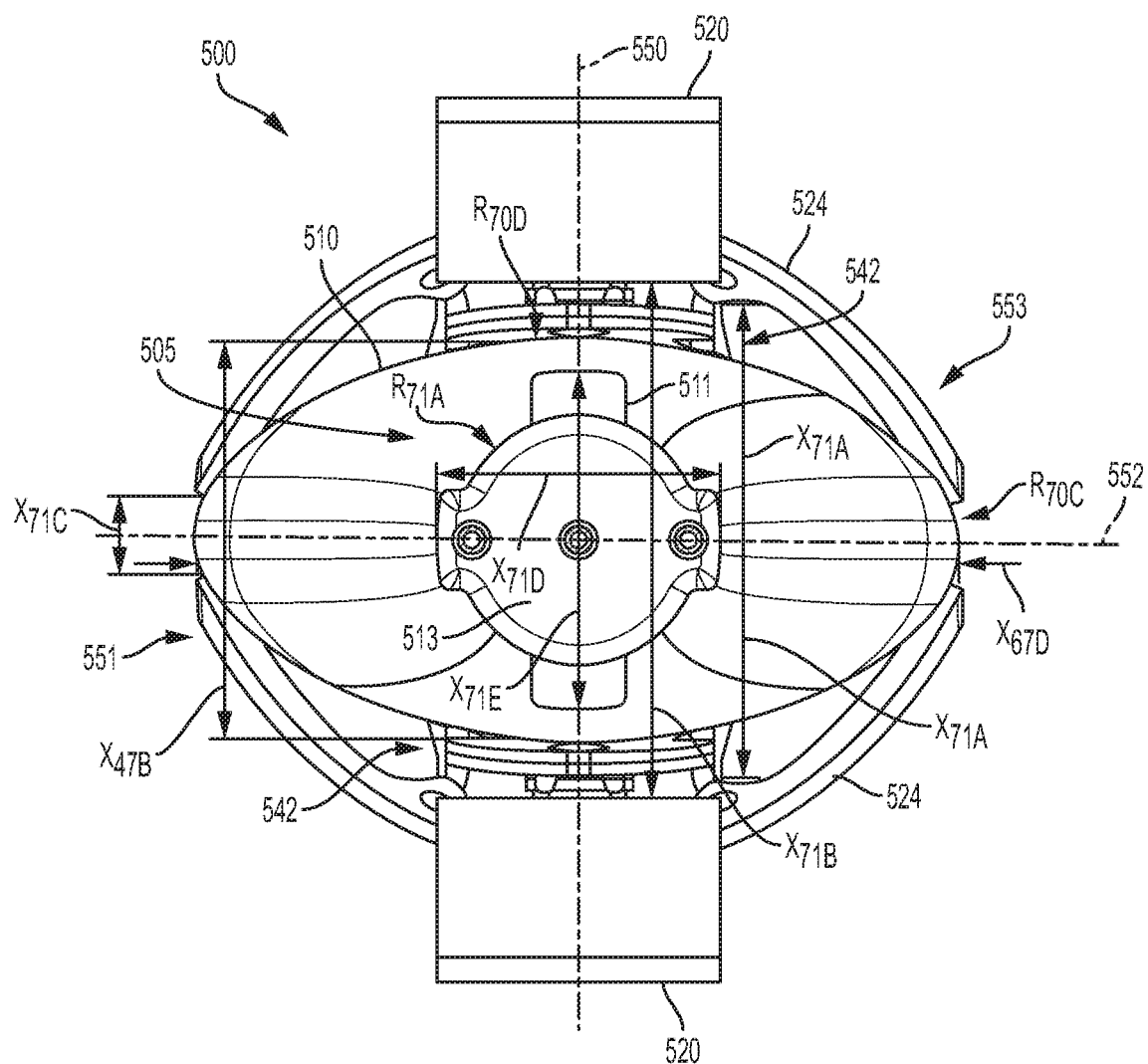
FIG. 71 shows a top view of the implantable prosthetic device of FIG. 65 with a collar component.

Referring now to FIGS. 70-71, top views of the device 500 are shown. The device 500 has a shape that is substantially symmetrical around a front-to-back plane 550 and is also substantially symmetrical around a side-to-side plane 552 when viewed from the top. An opening 519A in the coaption element 510 is visible at the proximal portion 505 of the device 500. As can be seen in FIG. 70, the coaption element 510 can be hollow inside. The proximal collar 511 shown in FIG. 71 can be secured to the coaption element 510 to close off the coaption element 510.

In one exemplary embodiment, the coaption element is not planar and has all curved surfaces. For example, the coaption elements 510 illustrated herein can be formed of a series of blended surfaces have a variety of different radii of curvature. The coaption element 510 has a generally oval-shape when viewed from the top. However, in other exemplary embodiments, the coaption element 510 can have other shapes when viewed from the top. For example, the coaption element can have a rectangular, square, diamond, elliptical, or any other shape. The paddle frames 224 each have an arcuate shape with a smaller radius than the coaption element 510 so that the gaps 542 formed between the inner paddles 522 and paddle frames 524 and the coaption element 510 taper as they approach left 551 and right 553 sides of the device 500. Thus, native tissue, such as the leaflets 20, 22 tend to be pinched between the paddle frames 524 and the coaption element 510 towards the left and right sides 551, 553 of the device 500.

Figure 72:
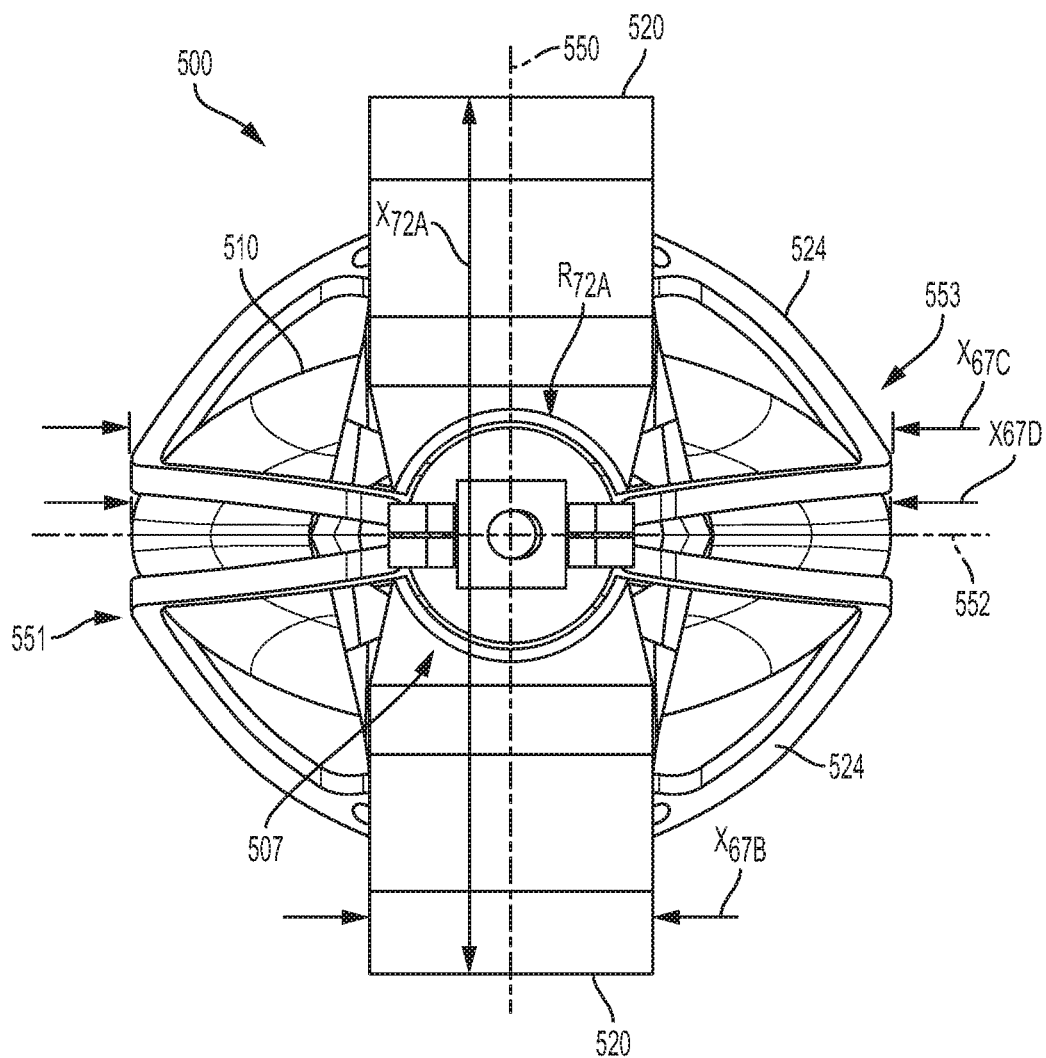
FIG. 72 shows a bottom view of the implantable prosthetic device of FIG. 65.
Figure 73:
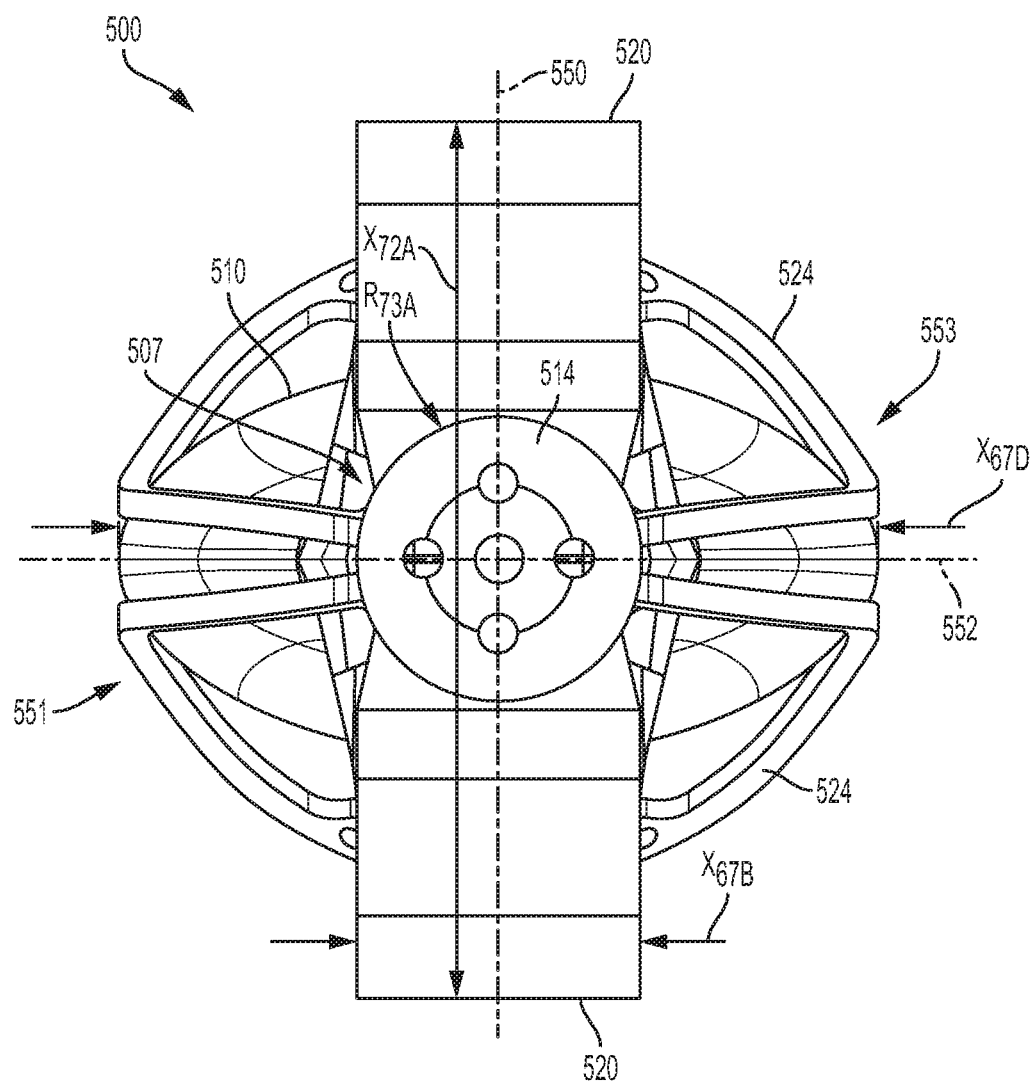
FIG. 73 shows a bottom view of the implantable prosthetic device of FIG. 65 with a cap component.

Referring now to FIGS. 72-73, bottom views of the device 500 are shown. As with the top views (FIGS. 70-71), the device 500 has a shape that is substantially symmetrical around the front-to-back plane 550 and is also substantially symmetrical around the side-to-side plane 552 when viewed from the bottom. The cap 514 is shown in FIG. 73 and can jointably attach to the outer paddles 520 and the paddle frames 524.

The paddle frames 524 extend outward from the distal portion 507 of the device 500 to the left and right sides 551, 553 at a narrow or slight angle from the side-to-side plane 552. The paddle frames 524 extend further away from the side-to-side plane 552 as the paddle frames 524 extend toward the proximal portion of the device 500 (FIG. 69) to ultimately form the arcuate shape seen in FIGS. 70-71.

Figure 74A:
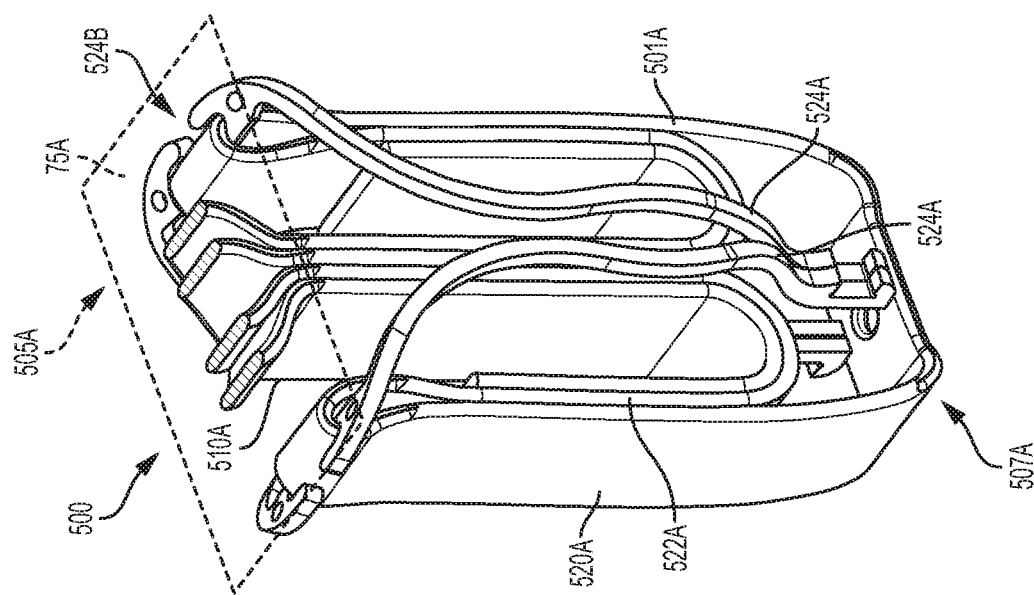
FIG. 74A shows a sectioned perspective view of the implantable prosthetic device of FIG. 65A sectioned by cross-section plane 75A.
Figure 74:
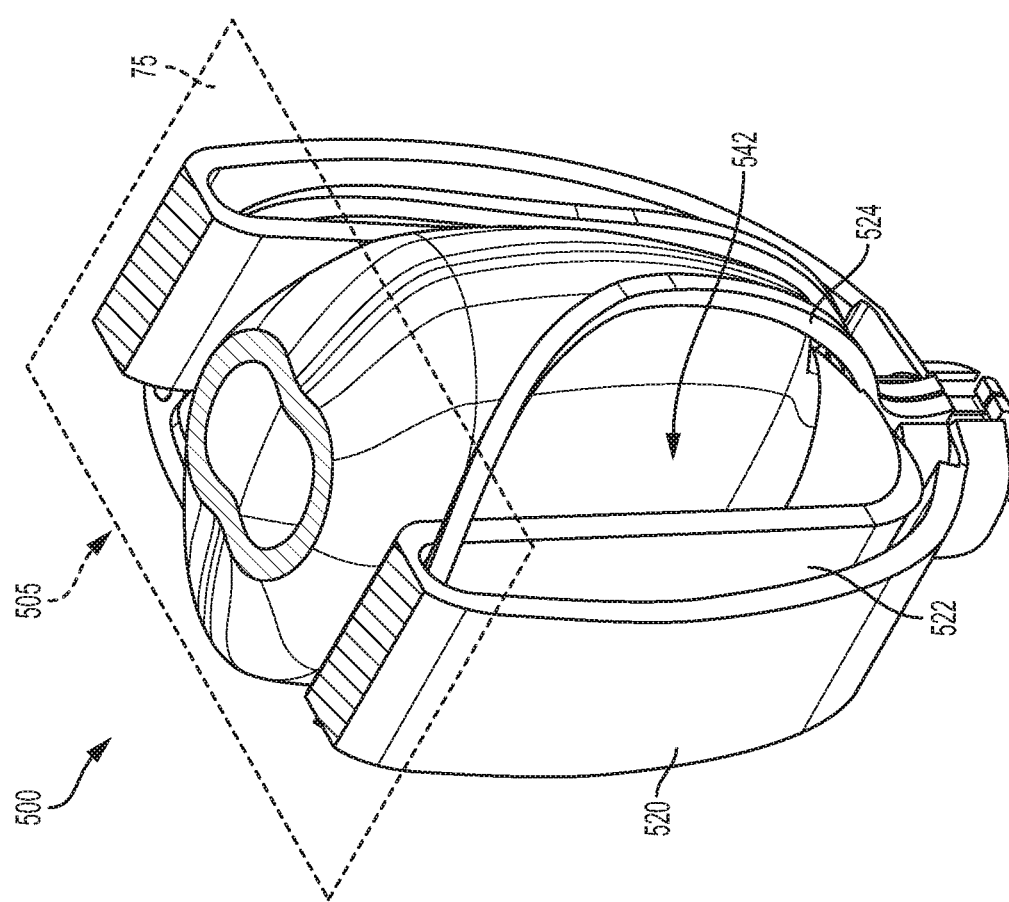
FIG. 74 shows a sectioned perspective view of the implantable prosthetic device of FIG. 65 sectioned by cross-section plane 75.

Referring now to FIGS. 74-83, perspective and cross-sectional views of the device 500 are shown. Referring now to FIG. 74, the device 500 is shown sliced by cross-section plane 75 near the proximal portion of the coaption element 510. Referring now to FIG. 75, a cross-sectional view of the device 500 is shown as viewed from cross-section plane 75 in FIG. 74. At the location of the plane 75, the coaption element 510 has a generally round shape with lobes arranged along the front-to-back plane 550. The gaps 542 between the paddle frames 524 and coaption element 510 form a crescent-like shape with a central width 543. As noted above, the gaps 542 narrow as the gaps 542 approach the left and right sides 551, 553.

Figure 76A:
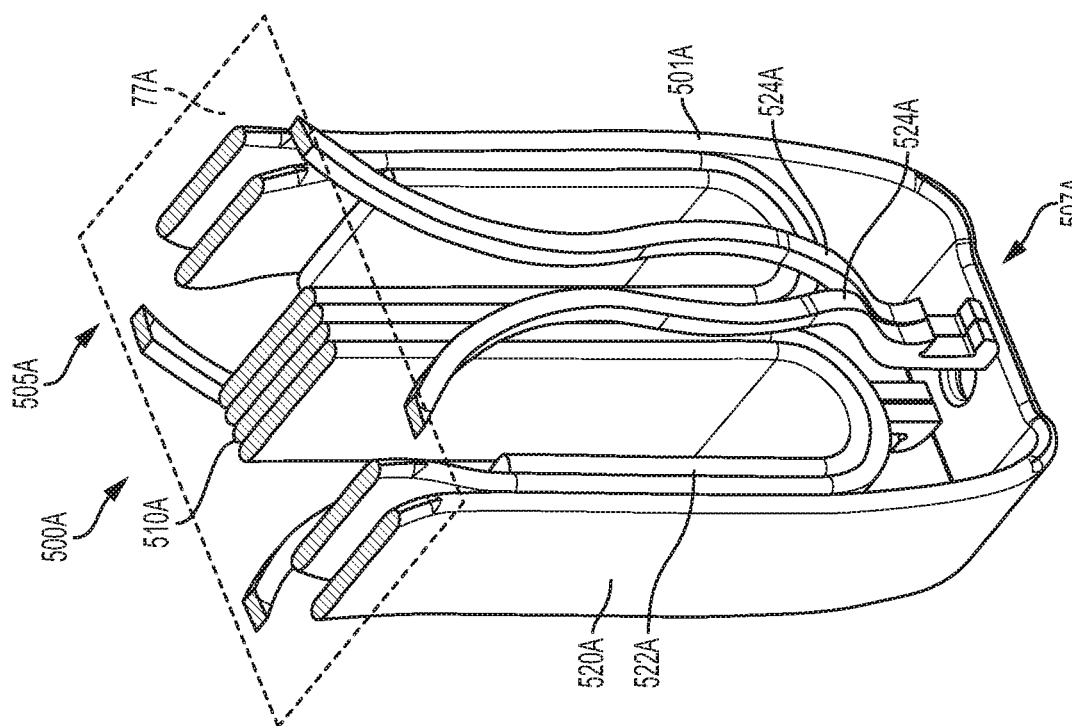
FIG. 76A shows a sectioned perspective view of the implantable prosthetic device of FIG. 65A sectioned by cross-section plane 77A.
Figure 76:
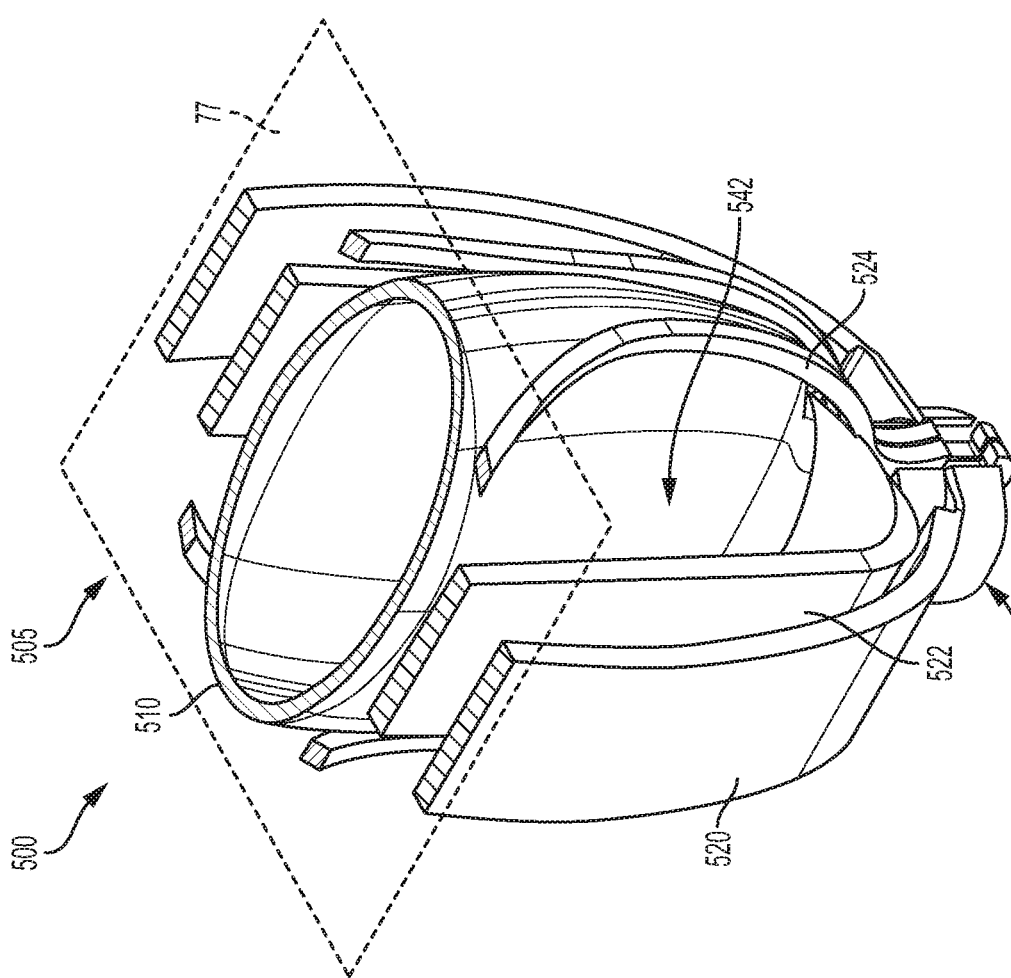
FIG. 76 shows a sectioned perspective view of the implantable prosthetic device of FIG. 65 sectioned by cross-section plane 77.
Figure 77A:
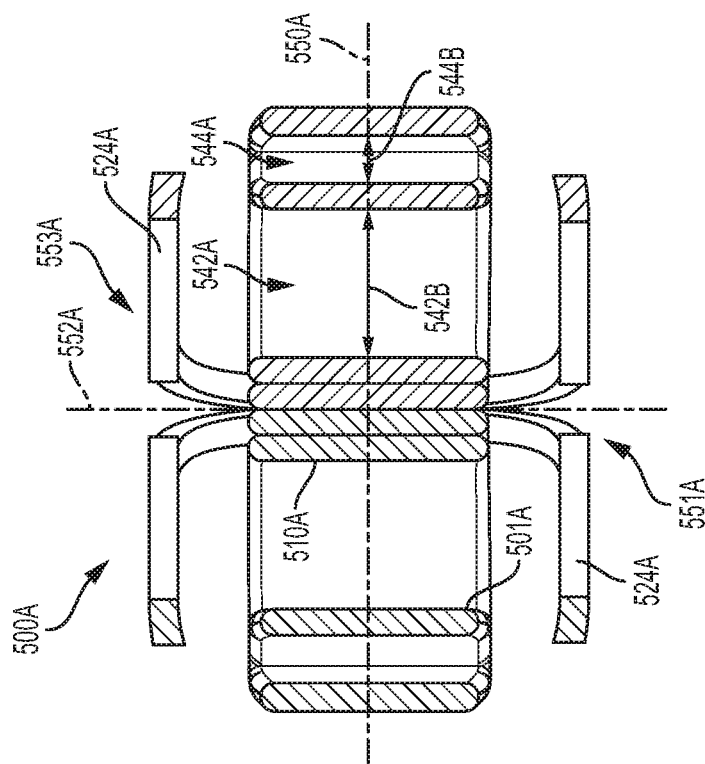
FIG. 77A shows a top cross-section view of the exemplary prosthetic device illustrated by FIG. 76A.
Figure 77:
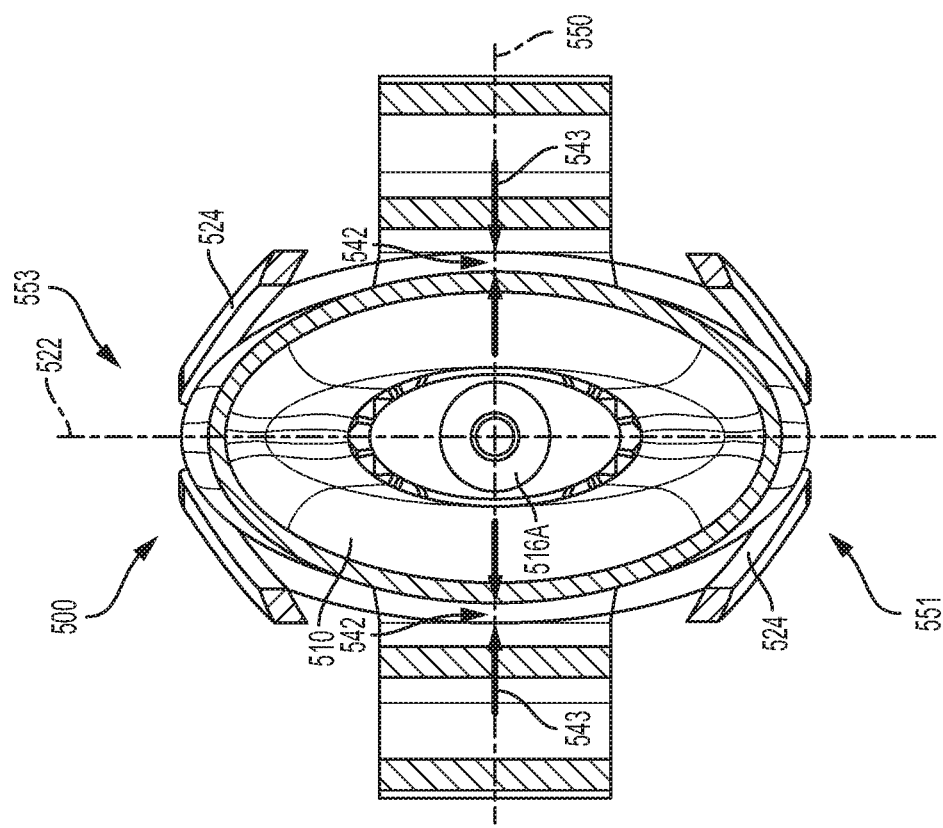
FIG. 77 shows a top cross-section view of the exemplary prosthetic device illustrated by FIG. 76.

Referring now to FIG. 76, the device 500 is shown sliced by cross-section plane 77 positioned about three-quarters of the way between the distal portion 507 and the proximal portion 505 of the coaption element 510. Referring now to FIG. 77, a cross-sectional view of the device 500 is shown as viewed from cross-section plane 77 in FIG. 76. At the location of the plane 75, the coaption element 510 has a generally oval shape oriented along the side-to-side plane 552. The gaps 542 between the paddle frames 524 and coaption element 510 form a crescent-like shape with a central width 543 that is less than the central width 543 seen in FIG. 75. At the location of the plane 77, the width 543 of the gaps 542 is narrower towards the center of the device, widens somewhat as the gaps 542 approach the left and right sides 551, 553 before narrowing again. Thus, the native tissue is pinched in the center of the gaps 542 about three-quarters of the way up the coaption element 510.

Figure 79A:
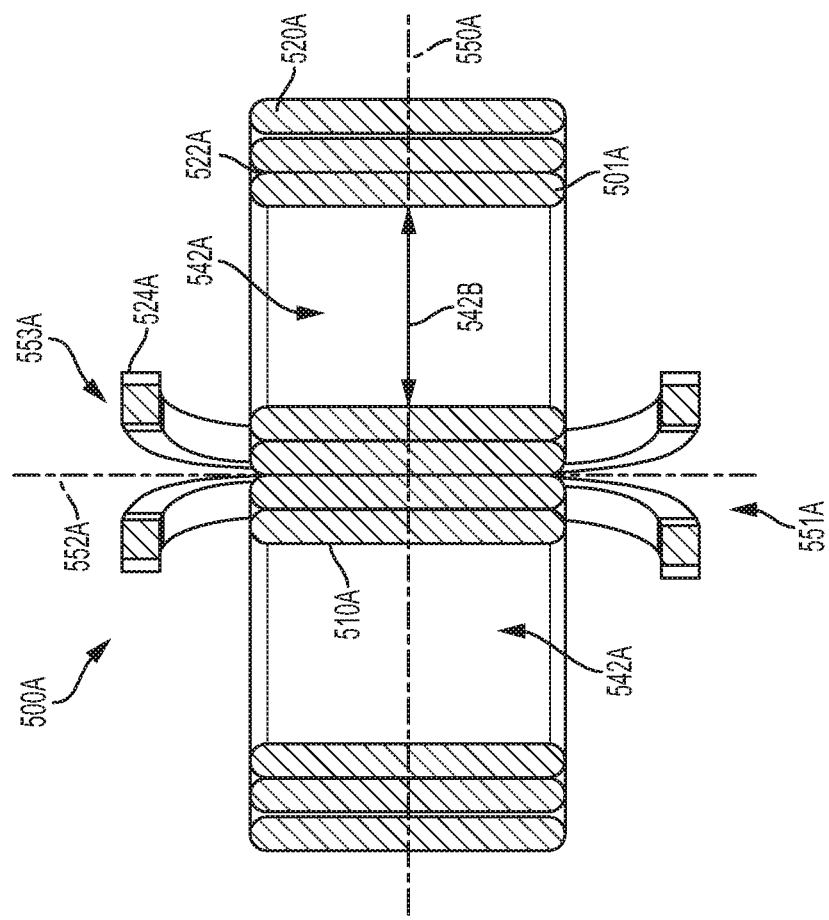
FIG. 79A shows a top cross-section view of the exemplary prosthetic device illustrated by FIG. 78A.
Figure 79:
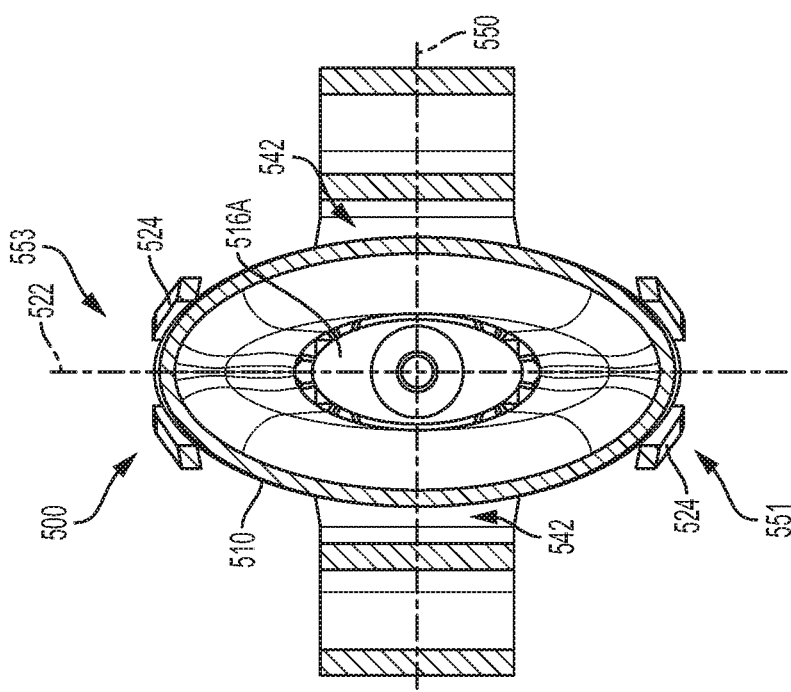
FIG. 79 shows a top cross-section view of the exemplary prosthetic device illustrated by FIG. 78.

Referring now to FIG. 78, the device 500 is shown sliced by cross-section plane 79 positioned about half of the way between the distal portion 507 and the proximal portion 505 of the coaption element 510. Referring now to FIG. 79, a cross-sectional view of the device 500 is shown as viewed from cross-section plane 79 in FIG. 78. At the location of the plane 79, the coaption element 510 has a generally oval shape oriented along the side-to-side plane 552. The paddle frames 524 can be seen near the left and right sides 551, 553 very close to or in contact with the coaption element 510. The gaps 542 are generally crescent shaped and are wider than the gaps 542 viewed along the plane 77 (FIG. 77.)

Figure 80A:
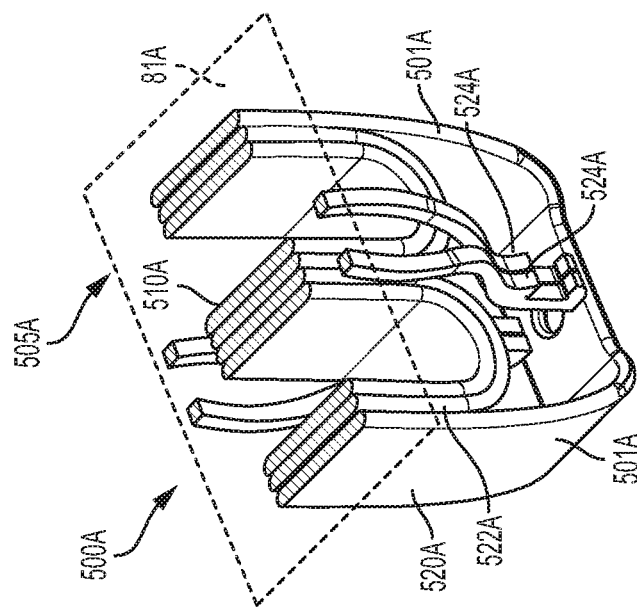
FIG. 80A shows a sectioned perspective view of the implantable prosthetic device of FIG. 65A sectioned by cross-section plane 81A.
Figure 80:
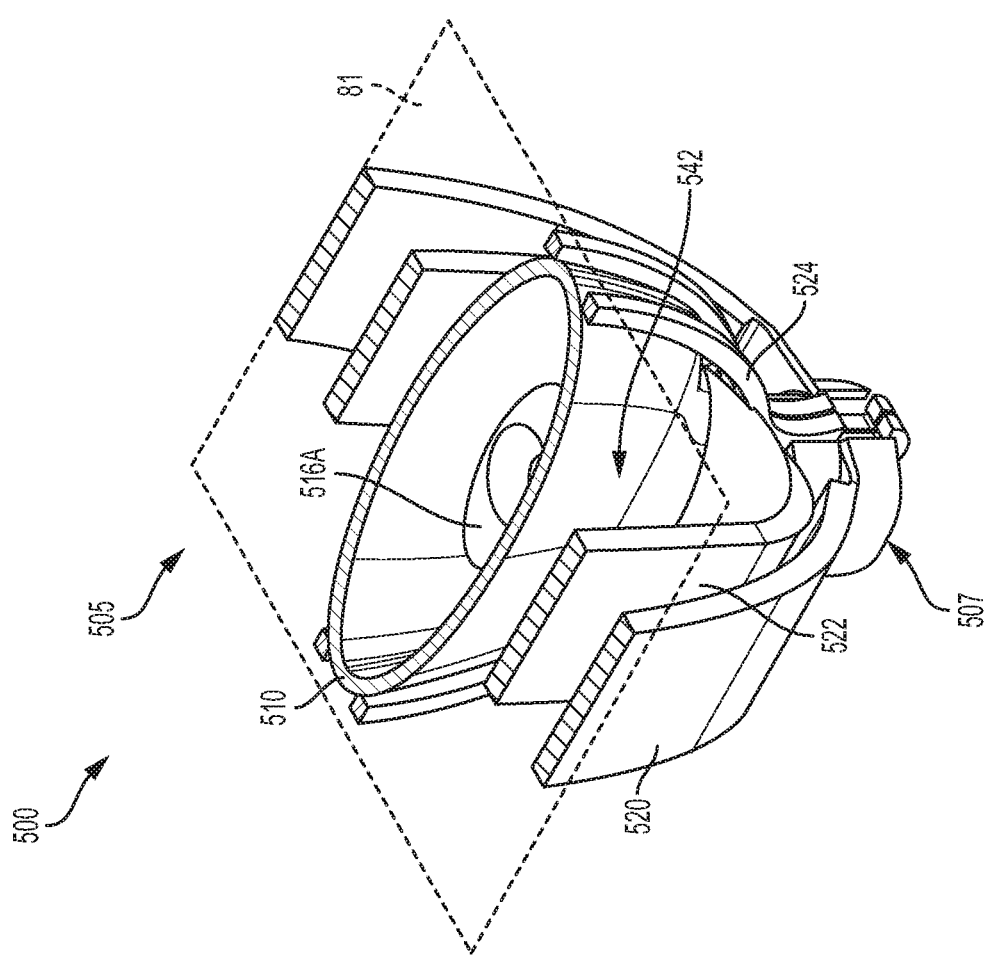
FIG. 80 shows a sectioned perspective view of the implantable prosthetic device of FIG. 65 sectioned by cross-section plane 81.
Figure 81A:
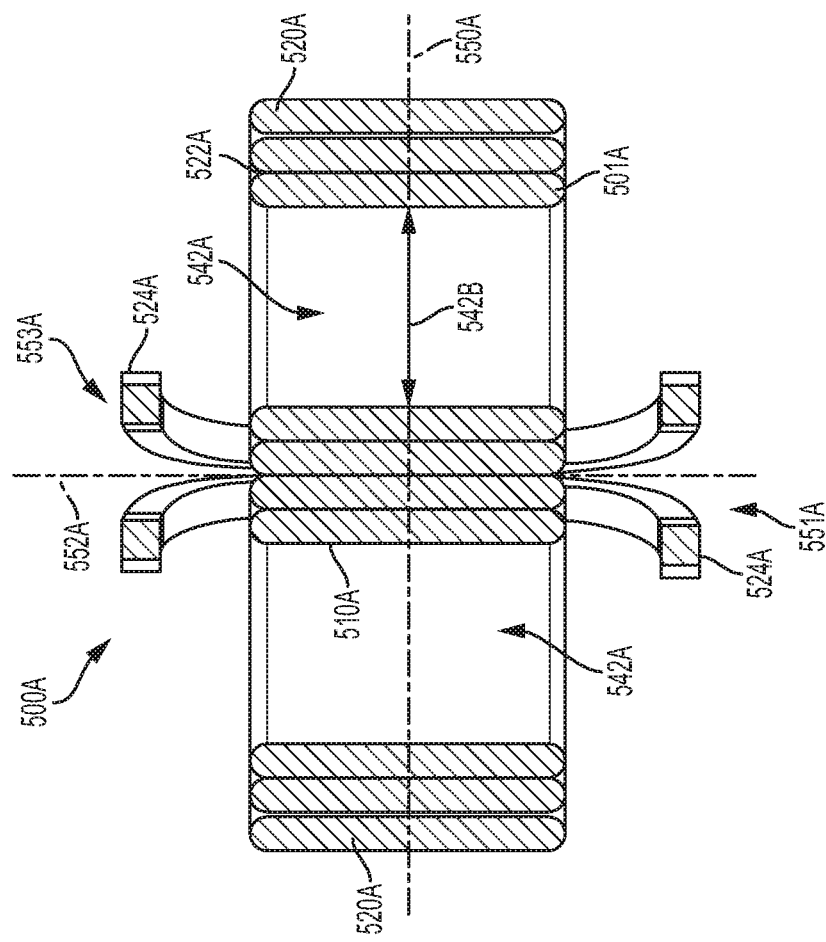
FIG. 81A shows a top cross-section view of the exemplary prosthetic device illustrated by FIG. 80A.
Figure 81:
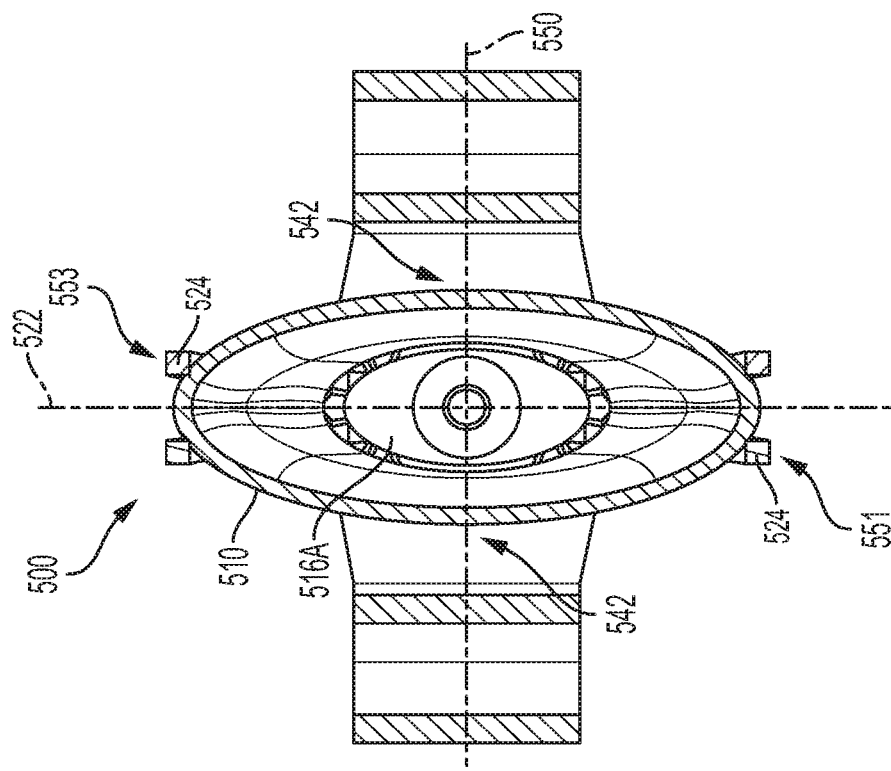
FIG. 81 shows a top cross-section view of the exemplary prosthetic device illustrated by FIG. 80.

Referring now to FIG. 80, the device 500 is shown sliced by cross-section plane 81 positioned about one-quarter of the way between the distal portion 507 and the proximal portion 505 of the coaption element 510. Referring now to FIG. 81, a cross-sectional view of the device 500 is shown as viewed from cross-section plane 81 in FIG. 80. At the location of the plane 81, the coaption element 510 has a generally oval shape oriented along the side-to-side plane 552 that is narrower than the oval shape seen in FIG. 77. The paddle frames 524 can be seen near the left and right sides 551, 553 very close to or in contact with the coaption element 510. The gaps 542 are generally crescent shaped and are wider than the gaps 542 viewed along the plane 79 (FIG. 79.)

Figure 82A:
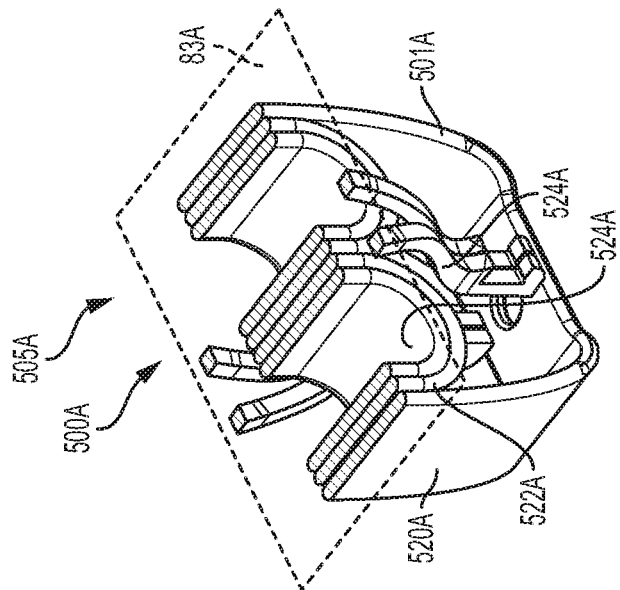
FIG. 82A shows a sectioned perspective view of the implantable prosthetic device of FIG. 65A sectioned by cross-section plane 83A.
Figure 82:
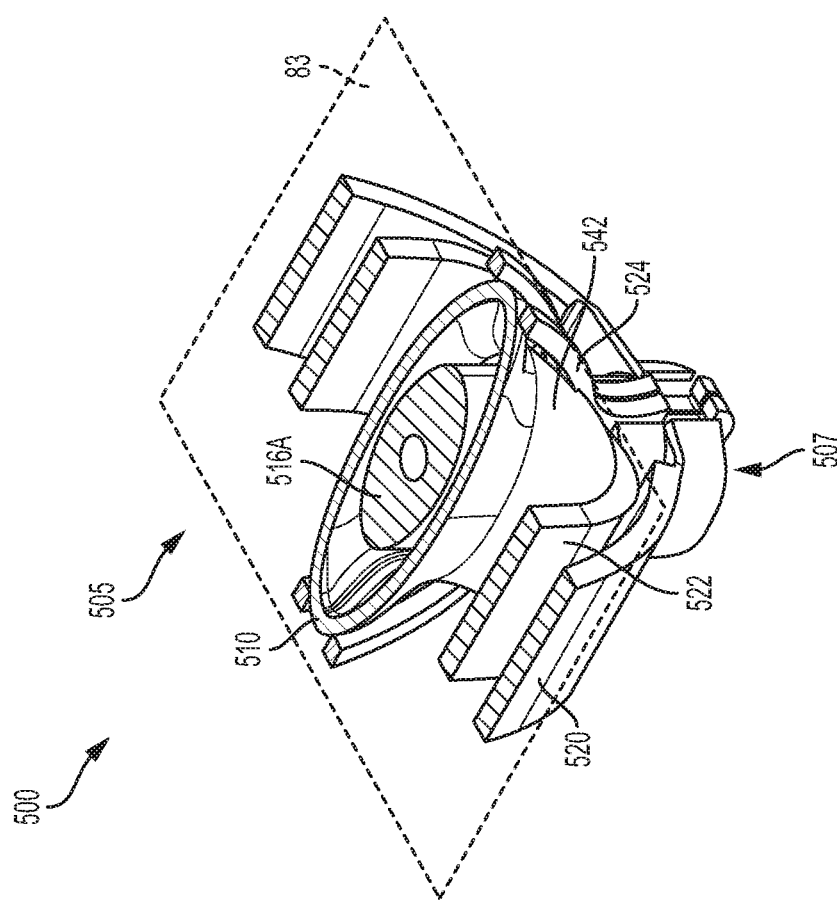
FIG. 82 shows a sectioned perspective view of the implantable prosthetic device of FIG. 65 sectioned by cross-section plane 83.
Figure 83A:
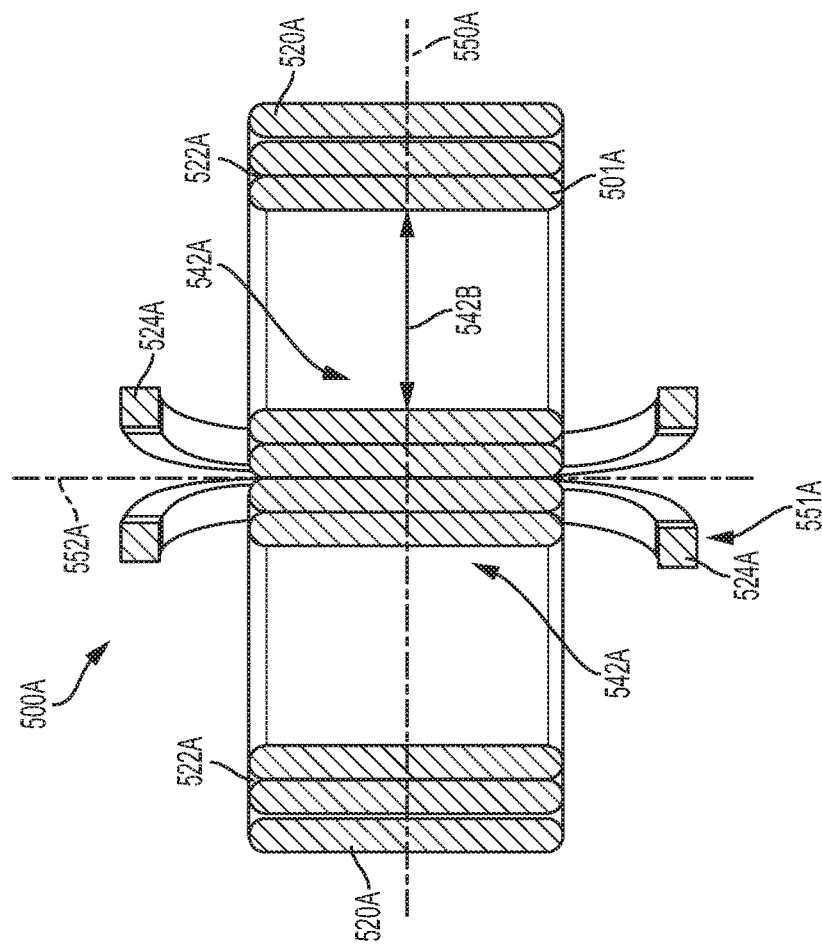
FIG. 83A shows a top cross-section view of the exemplary prosthetic device illustrated by FIG. 82A.
Figure 83:
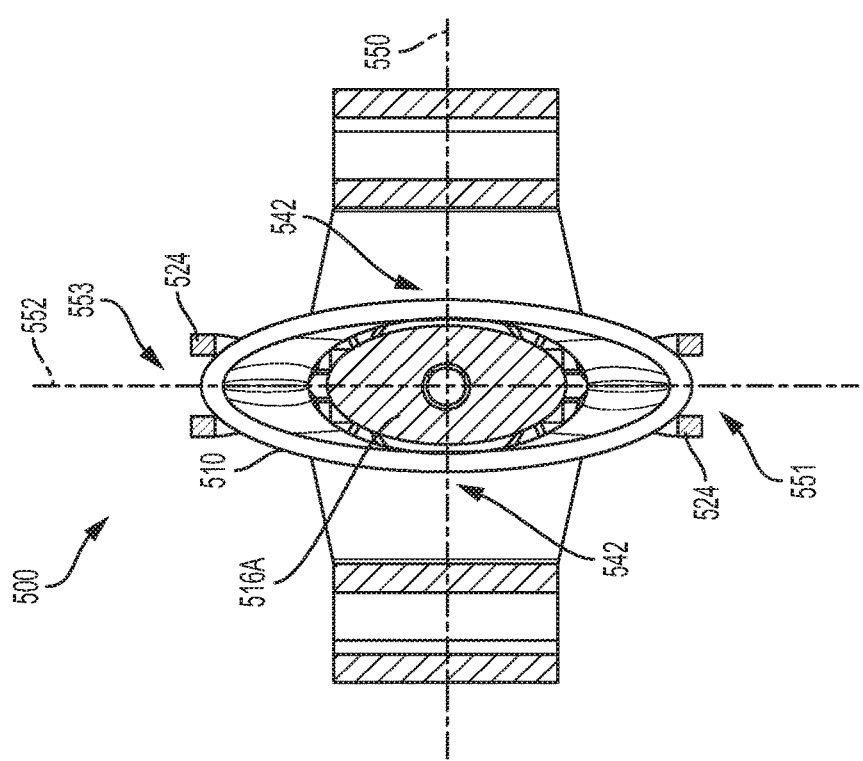
FIG. 83 shows a top cross-section view of the exemplary prosthetic device illustrated by FIG. 82.

Referring now to FIG. 82, the device 500 is shown sliced by cross-section plane 83 positioned near the distal portion 507 of the coaption element 510. Referring now to FIG. 83, a cross-sectional view of the device 500 is shown as viewed from cross-section plane 83 in FIG. 82. At the location of the plane 83, the coaption element 510 has a generally oval shape oriented along the side-to-side plane 552 that is narrower than the oval shape seen in FIG. 79 as the coaption element 510 tapers toward the distal portion 507 of the device 500. The paddle frames 524 can be seen near the left and right sides 551, 553 very close to or in contact with the coaption element 510. While the inner paddles 522 are not visible in FIG. 81, the gaps 542 are generally crescent shaped and are wider than the gaps 542 viewed along the plane 81 (FIG. 81.)

Figure 66A:
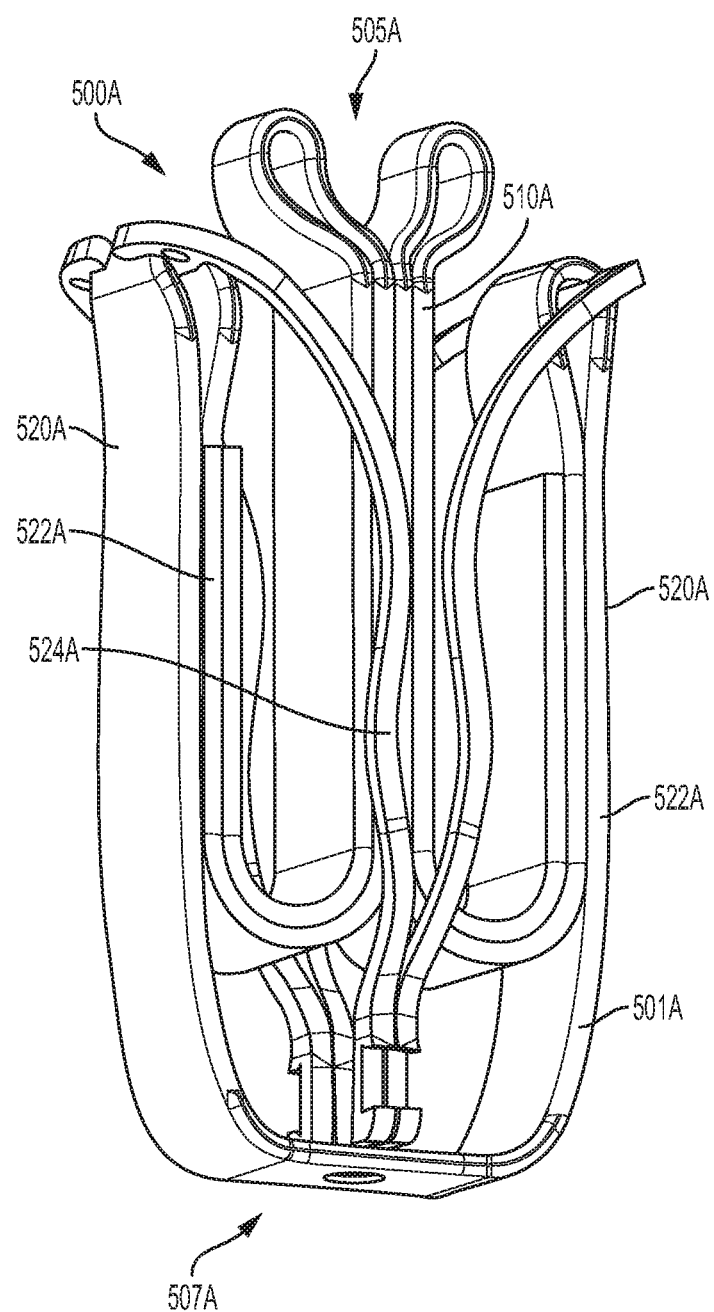
FIG. 66A shows a perspective view of the implantable prosthetic device of FIG. 65A.

Referring now to FIGS. 65A, 66A, 67A, 68A, 70A, 71A, 72A, 73A, 74A, 75A, 76A, 77A, 78A, 79A, 80A, 81A, 82A, and 83A, the exemplary implantable device 500A is shown in the closed condition. Referring now to FIGS. 65A and 66A, the device 500A extends from a proximal portion 505A to a distal portion 507A and includes a coaption portion 510A, inner paddles 522A, outer paddles 520A, and paddle frames 524A. The proximal portion 505A can include a collar 511D for attaching a delivery device (not shown). The distal portion 507A can include a cap 514A that is jointably attached to the outer paddles 520A and is engaged by an actuation wire (not shown) to open and close the device 500A to facilitate implantation in the mitral valve as described in the present application.

Figure 67A:
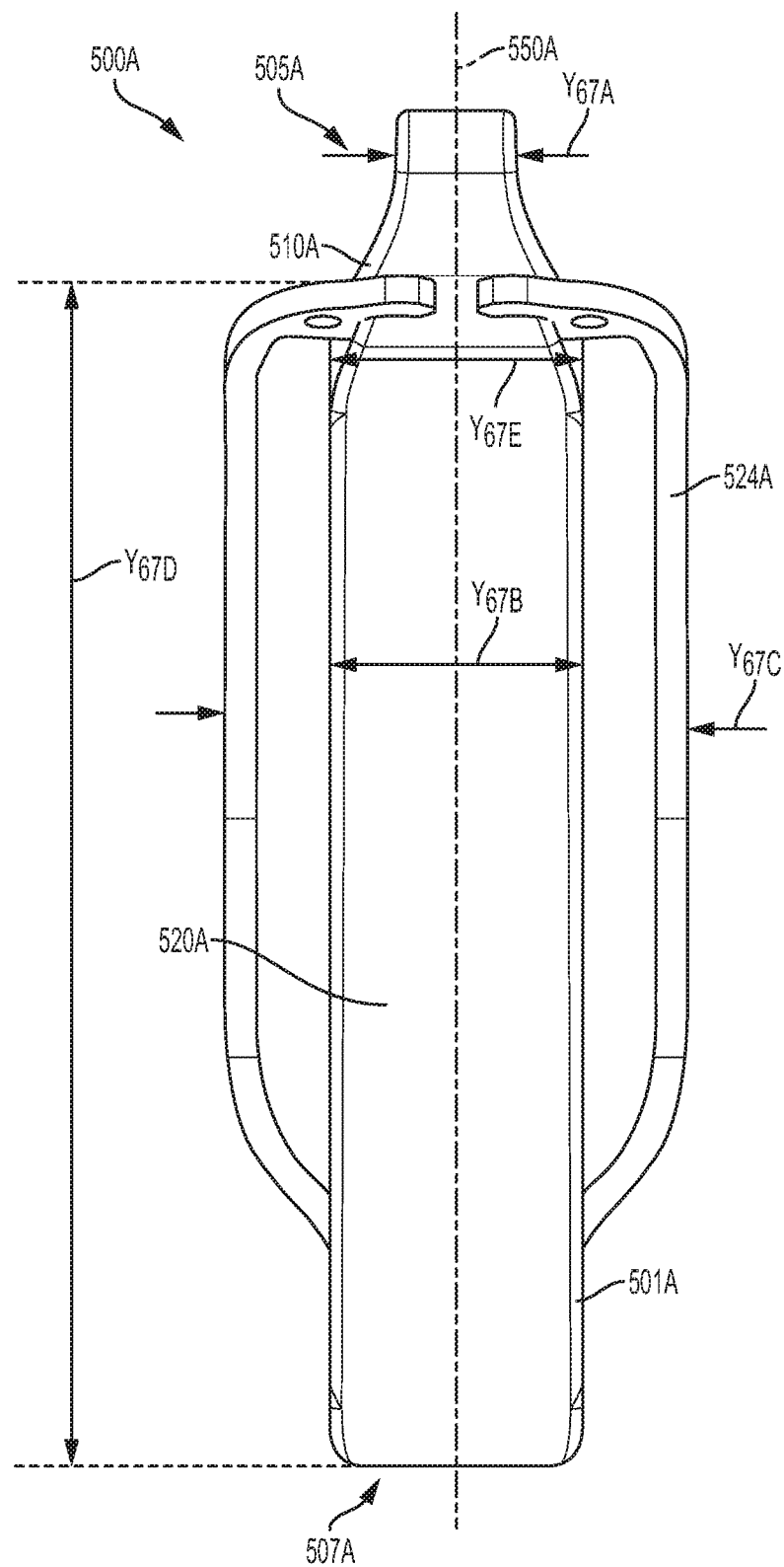
FIG. 67A shows a front view of the implantable prosthetic device of FIG. 65A.
Figure 68A:
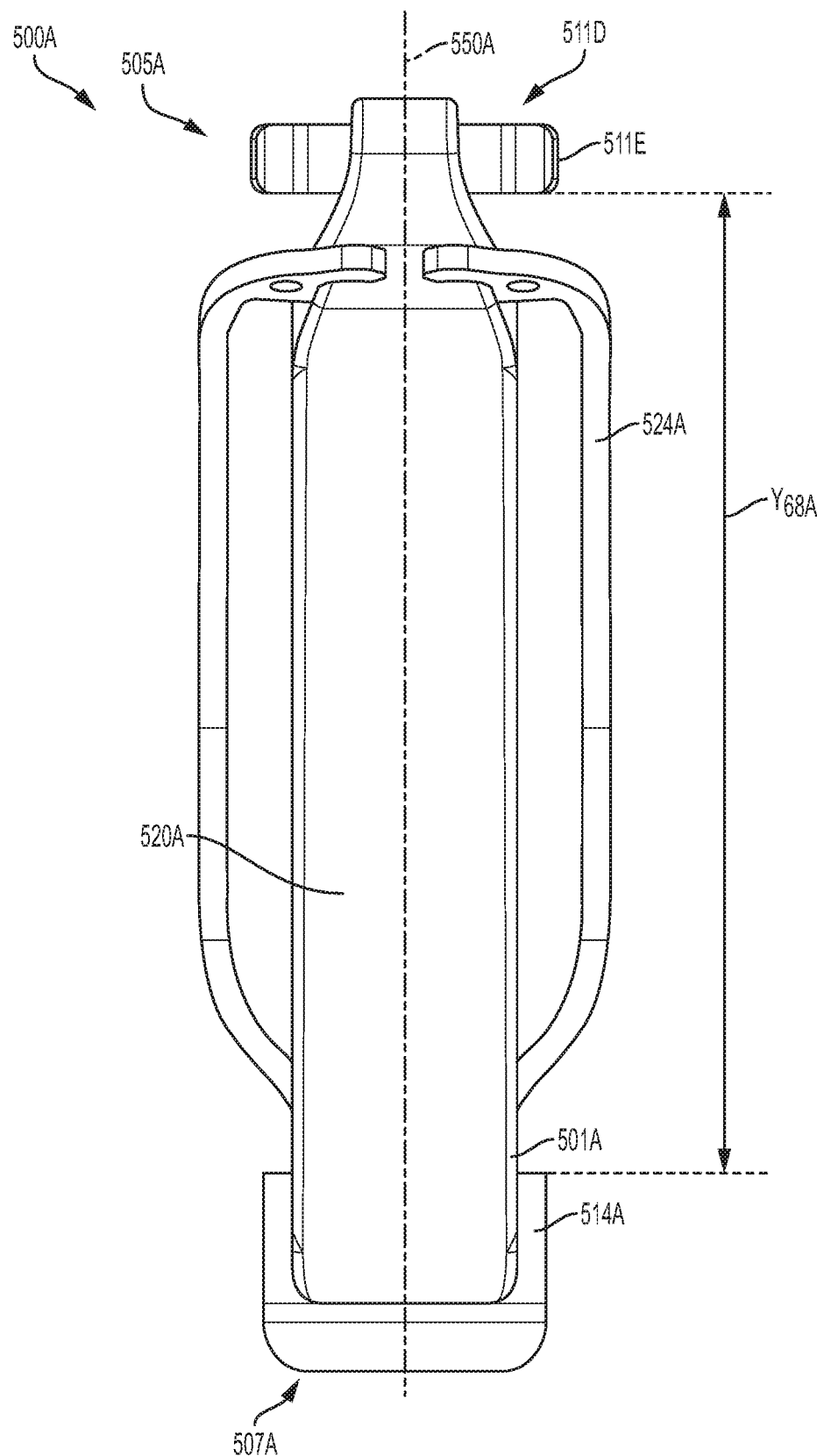
FIG. 68A shows a front view of the implantable prosthetic device of FIG. 65A with additional components.

Referring now to FIGS. 67A and 68A, front views of the device 500A are shown. The device 500A has a shape that is substantially symmetrical around a vertical front-to-back plane 550A and that is generally narrower at the distal portion 507A than it is along the paddle frames 524A. The shape of the coaption element 510A and paddle frames 524A is a generally rounded rectangular shape to prevent the device 500A from catching or snagging on structures of the heart, such as the chordae tendineae, during implantation. For this reason, the proximal collar 511D (FIG. 68A) and cap 514A (FIG. 68A) can also have round edges. When viewed from the front or back, the paddle frames 524A can be seen to have a generally rounded rectangular shape, extending upwards and outwards from the distal portion 507A to a shape that has sides that are wider than and approximately parallel to the coaption element 510A when viewed from the front or back. Thus, the paddle frames 524A generally define the shape of the device 500A when viewed from the front or back. In addition, the rounded rectangular shape of the paddle frames 524A can distribute leaflet stress across a wider surface. In other exemplary embodiment, the paddle frames 524A and/or the coaption element 510A can have other shapes.

As with the front and back views (FIGS. 67A and 68A), the device 500A has a shape that is substantially symmetrical around a vertical side-to-side plane 552A (FIG. 70A) when viewed from the side (e.g., FIG. 47A). The distal portion 507A is also generally narrower than the proximal portion 505A when the device 500A is viewed from the side. In the embodiment illustrated in FIG. 48B, the coaption element 510A does not taper as it extends from the proximal portion 505A of the device 500A to the distal portion 507A of the device 500A. However, in other exemplary embodiments, the coaption element does taper as it extends from the proximal portion of the device to the distal portion of the device (e.g., FIG. 47).

The generally rounded features of the device 500A are further demonstrated by the rounded shape of the paddles 520A, 522A where the inner and outer paddles 520A, 522A are joined together. However, the paddles 520A, 522A and paddle frames 524A can take a wide variety of different forms. For example, the paddles 520A, 522A and the paddle frames 524A can be rounded along the top edges and be flat or substantially flat on the sides (e.g., the sides of the paddle frames 524A arranged at the front and back sides of the device 500A). By making the paddles 520A, 522A flat or substantially flat on the sides, two devices can be implanted side-by-side on the mitral valve leaflet, with the two devices sitting substantially flush against each other.

The closed paddles 520A, 522A form gaps 542A between the inner paddles 522A and the coaption element 510A that are configured to receive native tissue. As can be seen in FIGS. 48B and 48F, the proximal end of the coaption element 510A has an approximately dog-bone shape so that the gaps 542A are narrower toward the proximal portion 505A than as the gaps 542A approach the distal portion 507A of the device. The narrowing of the gaps 542A toward the attachment portion 507A allows the paddles 520A, 522A to contact tissue grasped in the gaps 542A nearer to the proximal portion 505A.

The paddle frames 524A extend vertically from the distal portion 507A toward the proximal portion 505A until approximately a middle third of the device 500A before bending or flaring outward so that a connection portion 524B of the frames 524A passes through gaps 544A formed by the inner paddles 522A folded inside of the outer paddles 520A. However, in other embodiments the connections of the frames are positioned inside the inner paddles 522A or outside the outer paddles 520A. The outer paddles 520A have a rounded rectangular shape that is similar to that of the coaption element 510A when viewed from the front or back (FIGS. 67A and 68A). Thus, the device 500A has a substantially rounded rectangular shape. The rounded rectangular shape of the device 500A is particularly visible when the device 500A is viewed from the top (FIGS. 70A and 71A) or bottom (FIGS. 72A and 73A).

Figure 70A:
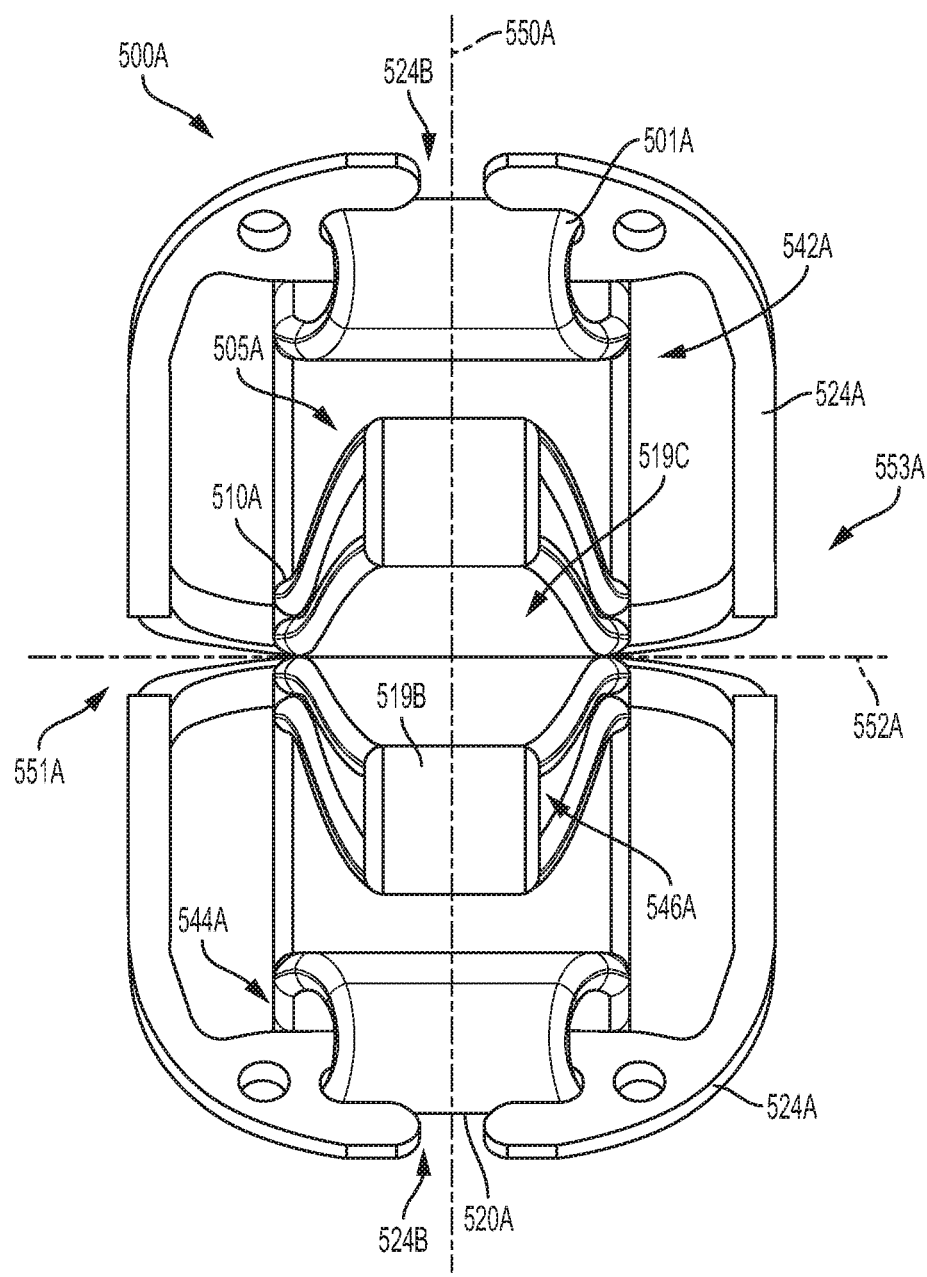
FIG. 70A shows a top view of the implantable prosthetic device of FIG. 65A.
Figure 71A:
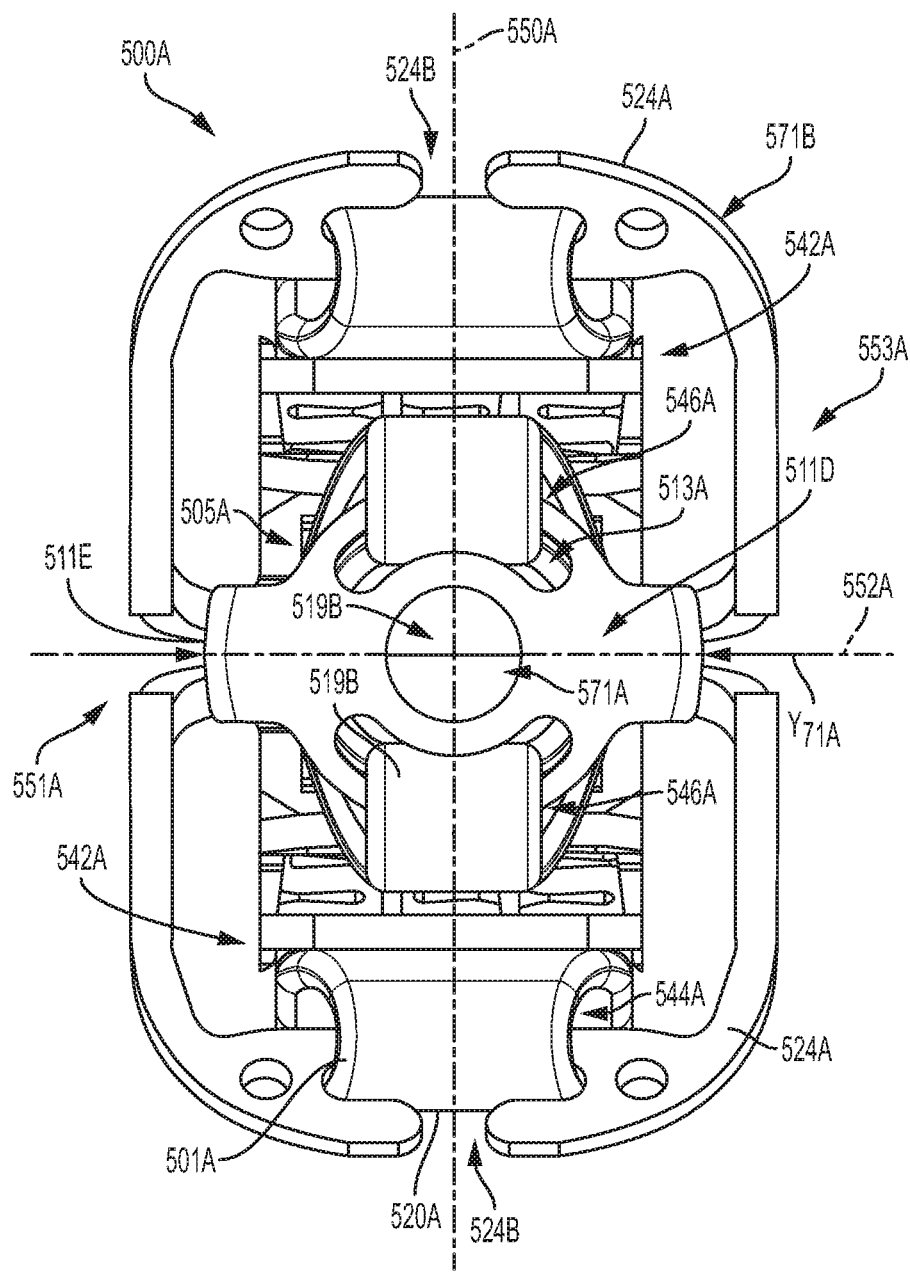
FIG. 71A shows a top view of the implantable prosthetic device of FIG. 65A with a collar component.

Referring now to FIGS. 70A and 71A, top views of the device 500A are shown. The device 500A has a shape that is substantially symmetrical around a front-to-back plane 550A and is also substantially symmetrical around a side-to-side plane 552A when viewed from the top. A proximal opening 519C in the coaption element 510A is visible at the proximal portion 505A of the device 500A. The actuation wire 512A is received through the opening 519C so that the coaption element 510A wraps around the actuation wire 512A. In some embodiments, the opening 519C is formed by inserting the actuation wire 512A between the folded and overlapping layers of the strip of material 501A (described in detail below). In other embodiments, the opening 519C is formed by shape-setting the folded layers of the strip of material 501A forming the coaption element 510A around a blank or jig to give the coaption element 510A a generally rounded shape. The proximal collar 511D shown in FIG. 71A can be secured to the coaption element 510A to close off the coaption element 510A. The proximal collar 511D includes attachment portions 513A that engage with openings 546A formed by the folded layers of the strip of material 501A that form the coaption element 510A. In some embodiments, the attachment portions 513A are holes in the collar 511D so that the strip of material 501A must be inserted through the collar 511D before folding the strip of material 501A during assembly of the device 500A. In some embodiments, the attachment portions 513A are open slots (e.g., the attachment portions 524B of the paddle frames 524A) that receive the strip of material 501A before or after folding the strip of material 501A.

As is noted above, the coaption element 510A has a generally rectangular shape when viewed from the top. In other exemplary embodiments, the coaption element 510A can have other shapes when viewed from the top. For example, the coaption element can have a round, square, diamond, elliptical, or any other shape. The paddle frames 224A each have a rounded rectangular shape when viewed from the top so that the paddle frames 224A surround the rectangular coaption element 510A. Thus, native tissue, such as the leaflets 20, 22 tend to be pinched or compressed evenly in the gaps 542A formed between the inner paddles 522A and paddle frames 524A and the coaption element 510A.

Figure 72A:
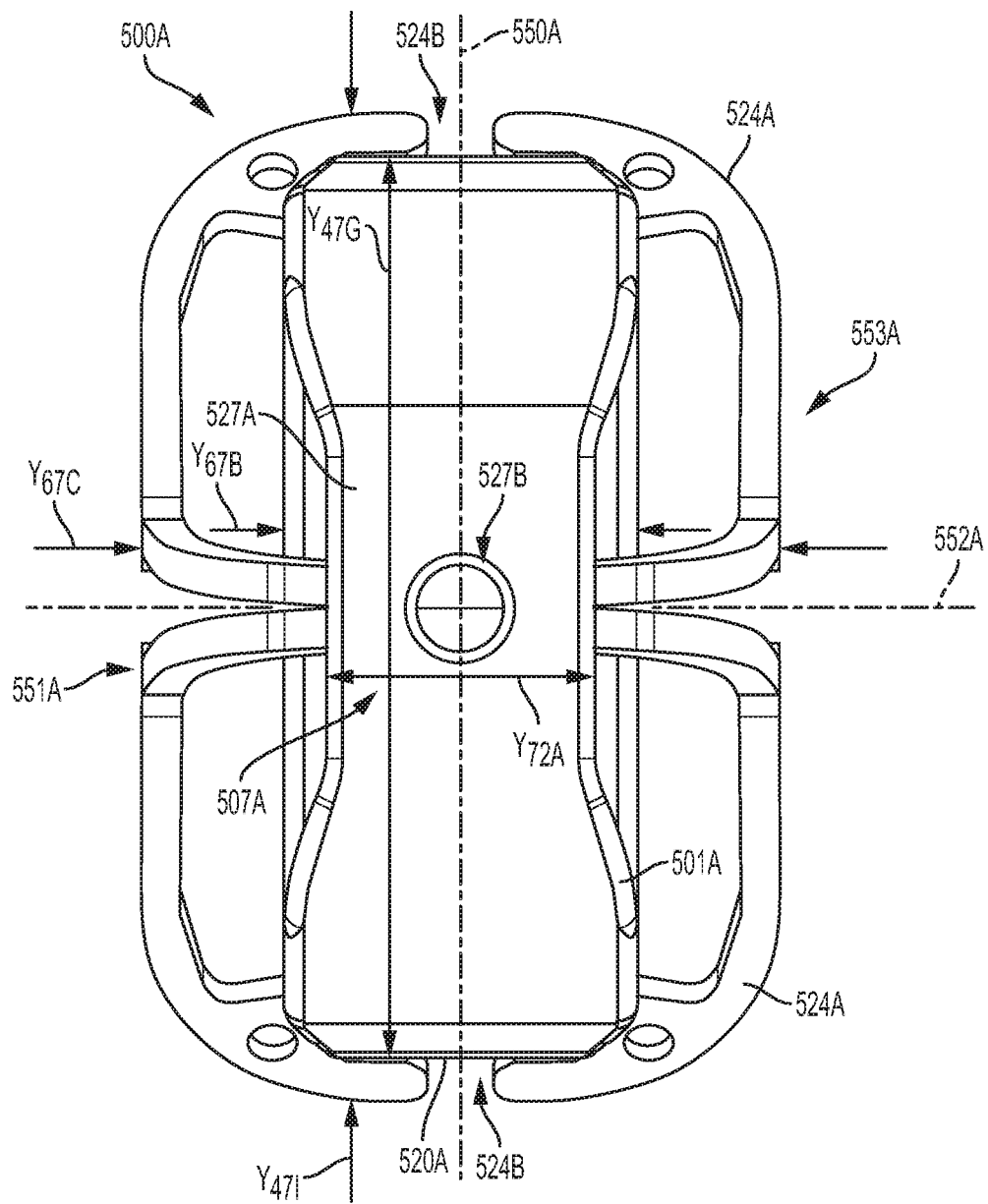
FIG. 72A shows a bottom view of the implantable prosthetic device of FIG. 65A.
Figure 73A:
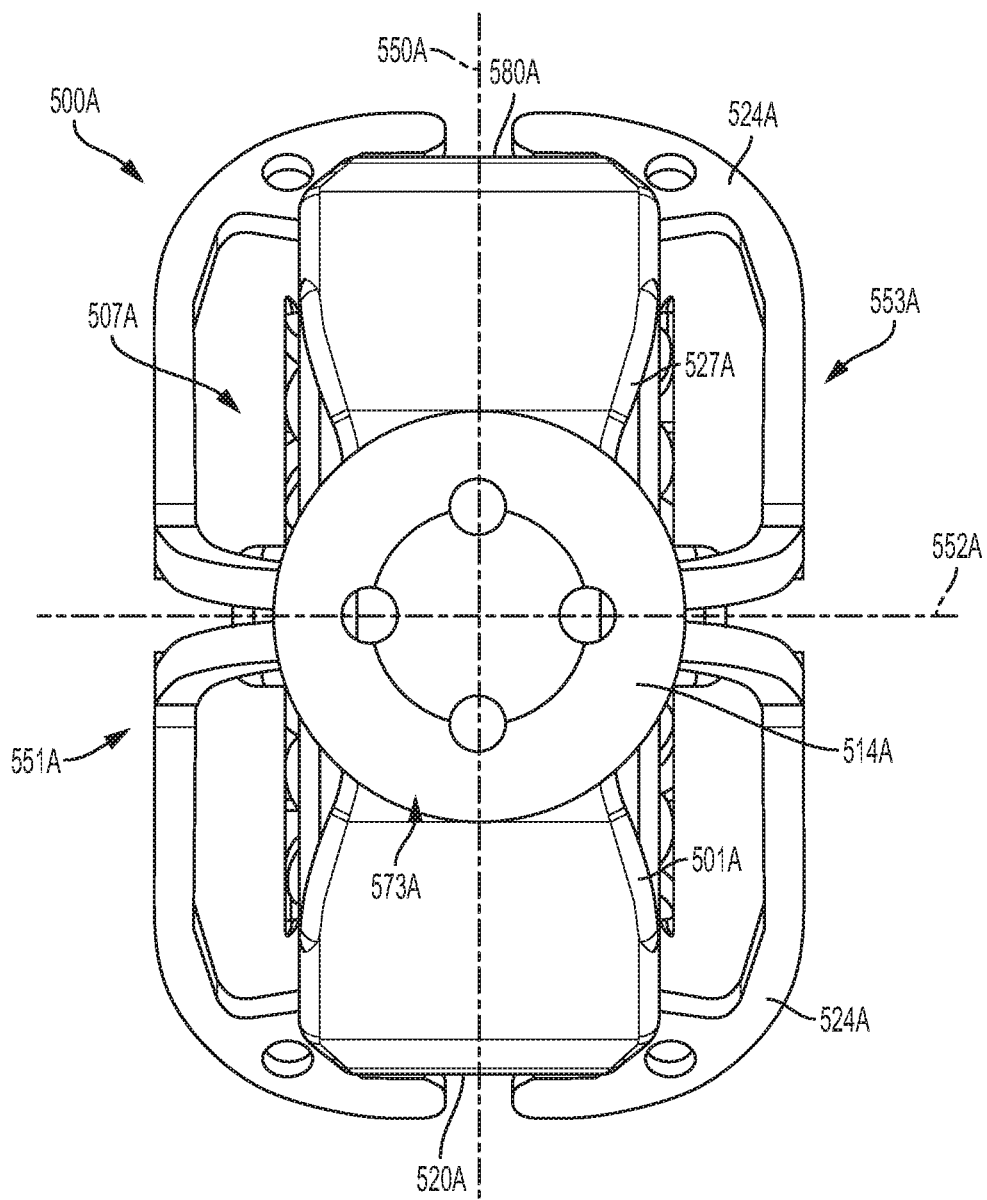
FIG. 73A shows a bottom view of the implantable prosthetic device of FIG. 65A with a cap component.

Referring now to FIGS. 72A and 73A, bottom views of the device 500A are shown. As with the top views (FIGS. 70A and 71A), the device 500A has a shape that is substantially symmetrical around the front-to-back plane 550A and is also substantially symmetrical around the side-to-side plane 552A when viewed from the bottom. A distal portion 527A of the strip of material 501A includes an aperture 527B for receiving the cap 514A shown in FIG. 73A.

The paddle frames 524A extend outward from the distal portion 507A of the device 500A to the left and right sides 551A, 553A at a narrow or slight angle from the side-to-side plane 552A. The paddle frames 524A extend further away from the side-to-side plane 552A while maintaining a generally constant distance relative to the front-to-back plane 550A as the paddle frames 524A extend toward the proximal portion 505A of the device 500A (FIG. 65A) to ultimately form the rounded rectangle shape seen in FIGS. 70A and 71A.

In one exemplary embodiment, the dimensions of the device 500A are selected to minimize the number of implants that a single patient will require (preferably one), while at the same time maintaining low transvalvular gradients. In one exemplary embodiment, the anterior-posterior distance $Y_{47I}$ of the device 500A at the widest is less than 10 mm, and the medial-lateral distance $Y_{67C}$ of the spacer at its widest is less than 6 mm. In one exemplary embodiment, the overall geometry of the device 500A can be based on these two dimensions and the overall shape strategy described above. It should be readily apparent that the use of other anterior-posterior distance $Y_{47I}$ and medial-lateral distance $Y_{67C}$ as starting points for the device 500A will result in a device having different dimensions. Further, using other dimensions and the shape strategy described above will also result in a device having different dimensions.

Tables D and E provide examples of values and ranges for dimensions of the device 500A and components of the device 500A for some exemplary embodiments. However, the device 500A can have a wide variety of different shapes and sizes and need not have all or any of the dimensional values or dimensional ranges provided in Tables D and E. Table D provides examples of linear dimensions Y in millimeters and ranges of linear dimensions in millimeters for the device 500A and components of the device 500A. Table B provides examples of radius dimensions S in millimeters and ranges of radius dimensions in millimeters for the device 500A and components of the device 500A. The subscripts for each of the dimensions indicates the drawing in which the dimension first appears.

TABLE D

| | | Angular Dimensions (degrees) | | | | | | |
| | | Range A | | Range B | | Range C | | Range C |
| | Example | (min) | (max) | (min) | (max) | (min) | (max) | (min) | (max) |
|---|---|---|---|---|---|---|---|---|---|
| $Y_{47A}$ | 2.58 | 1.29 | 3.87 | 1.94 | 3.23 | 2.32 | 2.84 | 2.45 | 2.71 |
| $Y_{47B}$ | 1.43 | 0.72 | 2.15 | 1.07 | 1.79 | 1.29 | 1.57 | 1.36 | 1.50 |
| $Y_{47C}$ | 3.75 | 1.88 | 5.63 | 2.81 | 4.69 | 3.38 | 4.13 | 3.56 | 3.94 |
| $Y_{47D}$ | 0.35 | 0.18 | 0.53 | 0.26 | 0.44 | 0.32 | 0.39 | 0.33 | 0.37 |
| $Y_{47E}$ | 0.71 | 0.36 | 1.07 | 0.53 | 0.89 | 0.54 | 0.78 | 0.67 | 0.75 |
| $Y_{47F}$ | 1.07 | 0.54 | 1.61 | 0.80 | 1.34 | 0.96 | 1.18 | 1.02 | 1.12 |
| $Y_{47G}$ | 7.68 | 3.84 | 11.52 | 5.76 | 9.60 | 6.91 | 8.45 | 7.30 | 8.06 |
| $Y_{47H}$ | 5.41 | 2.71 | 8.12 | 4.06 | 6.76 | 4.87 | 5.95 | 5.14 | 5.68 |
| $Y_{47I}$ | 9.16 | 4.58 | 13.74 | 6.87 | 11.45 | 8.24 | 10.08 | 8.70 | 9.62 |
| $Y_{47J}$ | 0.72 | 0.36 | 1.08 | 0.54 | 0.90 | 0.55 | 0.79 | 0.68 | 0.75 |
| $Y_{67A}$ | 1.61 | 0.91 | 2.42 | 1.21 | 2.01 | 1.45 | 1.77 | 1.53 | 1.69 |
| $Y_{67B}$ | 3.25 | 1.63 | 4.88 | 2.44 | 4.06 | 2.93 | 3.58 | 3.09 | 3.41 |
| $Y_{67C}$ | 5.90 | 2.95 | 8.85 | 4.43 | 7.38 | 5.31 | 6.49 | 5.61 | 6.20 |
| $Y_{67D}$ | 15.21 | 7.60 | 22.81 | 11.41 | 19.01 | 13.69 | 16.73 | 14.45 | 15.97 |
| $Y_{67E}$ | 3.25 | 1.63 | 4.88 | 2.44 | 4.06 | 2.93 | 3.58 | 3.09 | 3.41 |

TABLE D-continued

| | Angular Dimensions (degrees) | | | | | | | |
|---|---|---|---|---|---|---|---|---|
| | Range A | | Range B | | Range C | | Range C | |
| Example | (min) | (max) | (min) | (max) | (min) | (max) | (min) | (max) |
| $Y_{68A}$ | 14.04 | 7.02 | 21.06 | 10.53 | 17.55 | 12.64 | 15.44 | 13.34 | 14.74 |
| $Y_{71A}$ | 4.50 | 2.25 | 6.75 | 3.38 | 5.63 | 4.05 | 4.95 | 4.28 | 4.73 |
| $Y_{72A}$ | 2.50 | 1.25 | 3.75 | 1.88 | 3.13 | 2.25 | 2.75 | 2.38 | 2.63 |
| $Y_{114A}$ | 4.34 | 2.17 | 6.50 | 3.25 | 5.42 | 3.90 | 4.77 | 4.12 | 4.55 |
| $Y_{114B}$ | 13.28 | 6.64 | 19.92 | 9.96 | 16.60 | 11.95 | 14.61 | 12.62 | 13.94 |
| $Y_{116A}$ | 14.79 | 7.39 | 22.18 | 11.09 | 18.48 | 13.31 | 16.27 | 14.05 | 15.53 |

TABLE E

| | Radius Dimensions (mm) | | | | | | | |
|---|---|---|---|---|---|---|---|---|
| | Range A | | Range B | | Range C | | Range D | |
| Example | (min) | (max) | (min) | (max) | (min) | (max) | (min) | (max) |
| $S_{47A}$ | 0.74 | 0.37 | 1.11 | 0.56 | 0.93 | 0.67 | 0.81 | 0.70 | 0.78 |
| $S_{47B}$ | 0.68 | 0.34 | 1.02 | 0.51 | 0.85 | 0.61 | 0.75 | 0.65 | 0.71 |
| $S_{47C}$ | 1.10 | 0.55 | 1.65 | 0.83 | 1.38 | 0.99 | 1.21 | 1.05 | 1.16 |
| $S_{47D}$ | 5.62 | 2.81 | 8.43 | 4.22 | 7.03 | 5.06 | 6.18 | 5.34 | 5.90 |
| $S_{47E}$ | 0.96 | 0.48 | 1.44 | 0.72 | 1.20 | 0.86 | 1.06 | 0.91 | 1.01 |
| $S_{71A}$ | 0.63 | 0.31 | 0.94 | 0.47 | 0.78 | 0.56 | 0.69 | 0.59 | 0.66 |
| $S_{71B}$ | 2.07 | 1.04 | 3.11 | 1.55 | 2.59 | 1.86 | 2.28 | 1.97 | 2.17 |
| $S_{73A}$ | 1.88 | 0.94 | 2.81 | 1.41 | 2.34 | 1.59 | 2.06 | 1.78 | 1.97 |
| $S_{114A}$ | 5.62 | 2.81 | 8.43 | 4.22 | 7.03 | 5.06 | 6.18 | 5.34 | 5.90 |
| $S_{114B}$ | 6.00 | 3.00 | 9.00 | 4.50 | 7.50 | 5.40 | 6.60 | 5.70 | 6.30 |
| $S_{114C}$ | 3.15 | 1.58 | 4.73 | 2.36 | 3.94 | 2.84 | 3.47 | 2.99 | 3.31 |
| $S_{117A}$ | 1.15 | 0.58 | 1.73 | 0.86 | 1.44 | 1.04 | 1.27 | 1.09 | 1.21 |
| $S_{117B}$ | 2.69 | 1.35 | 4.08 | 2.02 | 3.36 | 2.42 | 2.96 | 2.56 | 2.82 |

Referring now to FIGS. 74A, 75A, 76A, 77A, 78A, 79A, 80A, 81A, 82A, and 83A, perspective and cross-sectional views of the device 500A are shown. Referring now to FIG. 74A, the device 500A is shown sliced by cross-section plane 75A near the proximal portion of the coaption element 510A. Referring now to FIG. 75A, a cross-sectional view of the device 500A is shown as viewed from cross-section plane 75A in FIG. 74A. At the location of the plane 75A, the coaption element 510A has a generally rounded rectangular shape. The gaps 542A between the inner paddles 522A and coaption element 510A have a width 542B. As noted above, the gaps 542A have a generally consistent width.

Referring now to FIG. 76A, the device 500A is shown sliced by cross-section plane 77A positioned about three-quarters of the way between the distal portion 507A and the proximal portion 505A of the coaption element 510A. Referring now to FIG. 77A, a cross-sectional view of the device 500A is shown as viewed from cross-section plane 77A in FIG. 76A. As can be seen in FIGS. 76A and 77A, the strip of material 501A forming the device 500A is overlapped to form four layers in the area of the coaption element 510A. A single layer of the strip of material 501A forms each of the inner paddle 522A and the outer paddle 520A. At the location of the plane 75A, the coaption element 510A has a generally rectangular shape oriented along the side-to-side plane 552A. The gaps 542A between the inner paddle 522A and the coaption element 510A are visible. The gaps 542A between the inner paddles 522A and coaption element 510A have a width 542B that is greater than the width 542B seen in FIG. 75A. The gaps 544A between the outer and inner paddles 520A, 522A have a generally consistent width 544B for receiving the attachment portion 524B of the paddle frames 524A.

Referring now to FIG. 78A, the device 500A is shown sliced by cross-section plane 79A positioned about half of the way between the distal portion 507A and the proximal portion 505A of the device 500A. Referring now to FIG. 79A, a cross-sectional view of the device 500A is shown as viewed from cross-section plane 79A in FIG. 78A. As can be seen in FIGS. 78A and 79A, the strip of material 501A forming the device 500A is overlapped to form four layers in the area of the coaption element 510A, two layers in the area of the inner paddle 522A, and one layer in the area of the outer paddle 520A. At the location of the plane 79A, the coaption element 510A has a generally rectangular shape oriented along the side-to-side plane 552A. The gaps 542A between the inner paddles 522A and the coaption element 510A have a width 542B that is the same or about the same as the width 542B seen in FIG. 77A.

Referring now to FIG. 80A, the device 500A is shown sliced by cross-section plane 81A positioned about one-quarter of the way between the distal portion 507A and the proximal portion 505A of the device 500A. Referring now to FIG. 81A, a cross-sectional view of the device 500A is shown as viewed from cross-section plane 81A in FIG. 80A. As can be seen in FIGS. 80A and 81A, the strip of material 501A forming the device 500A is overlapped to form four layers in the area of the coaption element 510A, two layers in the area of the inner paddle 522A, and the outer paddle 520A is formed by a single layer. At the location of the plane 81A, the coaption element 510A has a generally rectangular shape oriented along the side-to-side plane 552A. The gaps 542A between the inner paddle 522A and coaption element 510A have a width 542B that is about the same as the central width 542B seen in FIG. 79A.

Referring now to FIG. 82A, the device 500A is shown sliced by cross-section plane 83A positioned about one-quarter of the way between the distal portion 507A and the proximal portion 505A of the device 500A. Referring now to FIG. 83A, a cross-sectional view of the device 500A is shown as viewed from cross-section plane 83A in FIG. 82A. As can be seen in FIGS. 82A and 83A, the strip of material 501A forming the device 500A is overlapped to form four layers in the area of the coaption element 510A, two layers in the area of the inner paddle 522A, and a single layer forms the outer paddle 520A. At the location of the plane 83A, the coaption element 510A has a generally rectangular shape oriented along the side-to-side plane 552A. The gaps 542A between the inner paddles 522A and coaption element 510A form an arcuate shape with a width 542B that is about the same as the central width 542B seen in FIG. 81A.

Referring now to FIGS. 84-88, 86A, 87A, and 88A, exemplary implantable devices 100, 500, 500A are shown without clasps or articulable gripping members. Rather, the exemplary devices 100, 500, 500A shown in FIGS. 84-88, 86A, 87A, and 88A, have barbs or gripping members 800/800A and/or 802/802A integrated into portions of the coaption element or paddles of the anchor portion of the devices to facilitate grasping of the tissue of the native heart valve.

Figure 84:
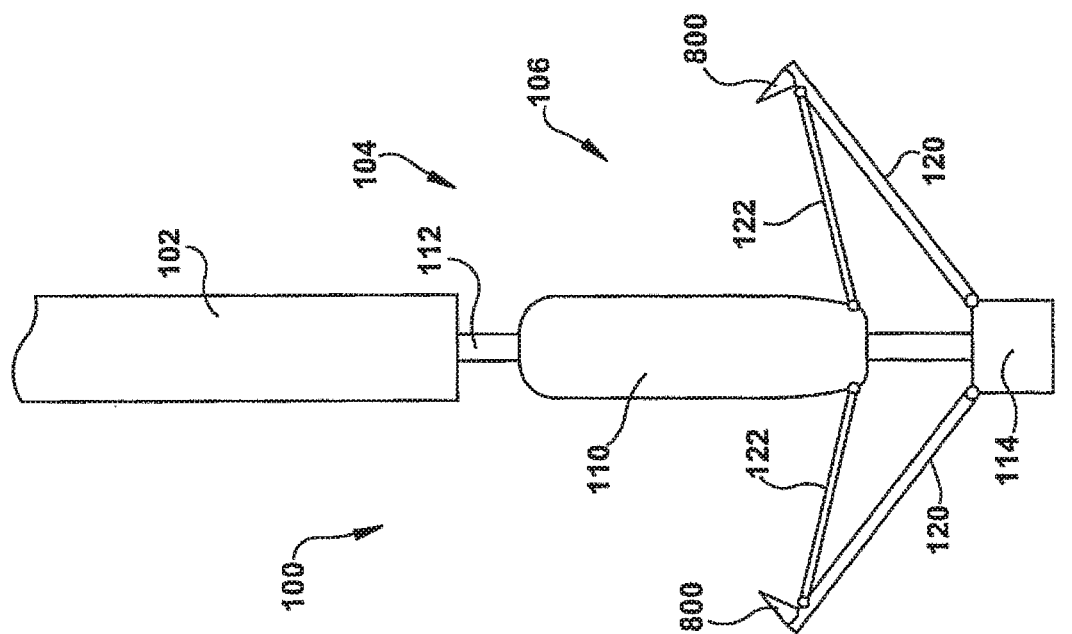
FIG. 84 shows an exemplary embodiment of an implantable prosthetic device with integral barbs.

Referring now to FIG. 84, an exemplary implantable device 100 is shown that does not include articulable clasps or gripping elements. As described above, the device 100 is deployed from a delivery sheath or means for delivery 102 and includes a coaption portion 104 and an anchor portion 106. The coaption portion 104 of the device 100 includes a coaption element or means for coapting 110 that is adapted to be implanted between the leaflets 20, 22 of the native mitral valve MV and is slidably attached to an actuation wire or shaft 112 that extends through the coaption element or means for coapting 110 to a distal cap 114.

The anchor portion 106 of the device 100 includes outer paddles 120 and inner paddles 122 that are connected between the distal cap 114 and the coaption element or means for coapting 110. The anchor portion 106 is actuatable between open and closed conditions and can take a wide variety of forms, such as, for example, paddles, gripping elements, or the like. Actuation of the actuation wire or means for actuating 112 opens and closes the anchor portion 106 of the device 100 to grasp the mitral valve leaflets 20, 22 during implantation.

Rather than articulable clasps or gripping elements, the device 100 shown in FIG. 84 includes barbed portions 800 arranged on the coaption element or means for coapting 110, with each side of the coaption element or means for coapting 110 having at least one barbed portion 800. When the anchor portion 106 of the device 100 is closed, tissue grasped between the inner paddles 122 and the coaption element or means for coapting 110 is pressed against the barbed portions 800. The barbed portions 800 can be sharp so that they engage—and in some embodiments, pierce—the native tissue and prohibit the tissue from retracting from the device 100. In some embodiments, the barbed portions 800 are angled downward to increase engagement with the native tissue.

Figure 85:
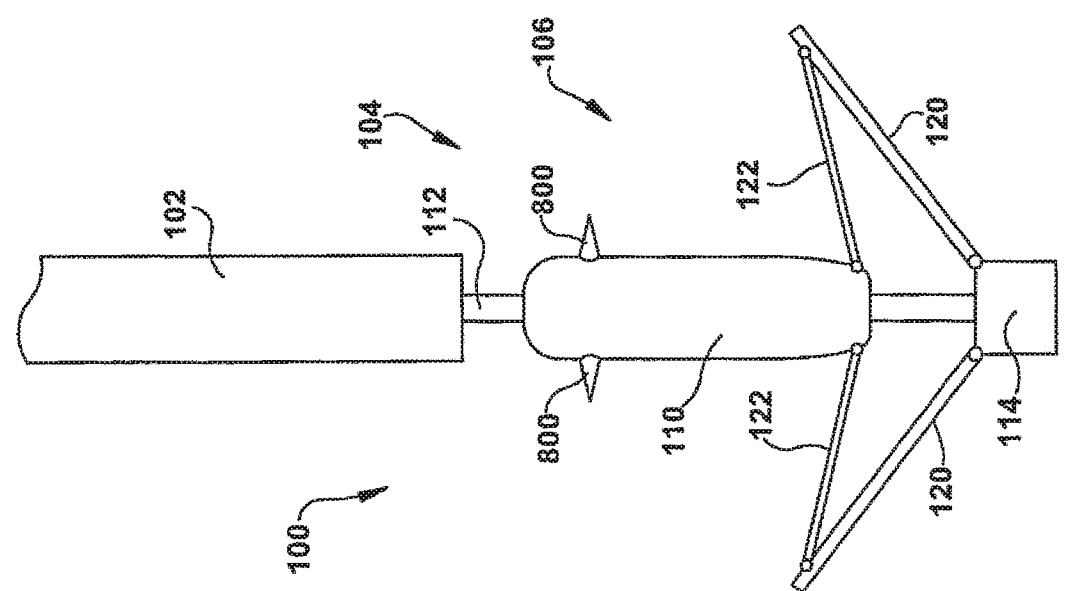
FIG. 85 shows an exemplary embodiment of an implantable prosthetic device with integral barbs.

Referring now to FIG. 85, the exemplary implantable device 100 is shown without separate articulable clasps. As described above, the device 100 is deployed from a delivery sheath or means for delivery 102 and includes a coaption portion 104 and an anchor portion 106. The coaption portion 104 of the device 100 includes a coaption element or means for coapting 110 that is adapted to be implanted between the leaflets 20, 22 of the native mitral valve MV and is slidably attached to an actuation wire or shaft 112 that extends through the coaption element or means for coapting 110 to a distal cap 114.

The anchor portion 106 of the device 100 includes outer paddles 120 and inner paddles 122 that are connected between the distal cap 114 and the coaption element or means for coapting 110. The anchor portion 106 is actuatable between open and closed conditions and can take a wide variety of forms, such as, for example, paddles, gripping elements, or the like. Actuation of the actuation wire or means for actuating 112 opens and closes the anchor portion 106 of the device 100 to grasp the mitral valve leaflets 20, 22 during implantation.

Rather than separate articulable clasps or gripping elements, the device 100 shown in FIG. 85 includes barbed portions 800 arranged on the inner paddles 122, with each inner paddle 122 having at least one barbed portion 800. When the anchor portion 106 of the device 100 is closed, tissue grasped between the inner paddles 122 and the coaption element or means for coapting 110 is pressed against the barbed portions 800. The barbed portions 800 are sharp so that they engage—and in some embodiments, pierce—the native tissue and prohibit the tissue from retracting from the device 100. In some embodiments, the barbed portions 800 are angled downward to increase engagement with the native tissue.

Figure 86:
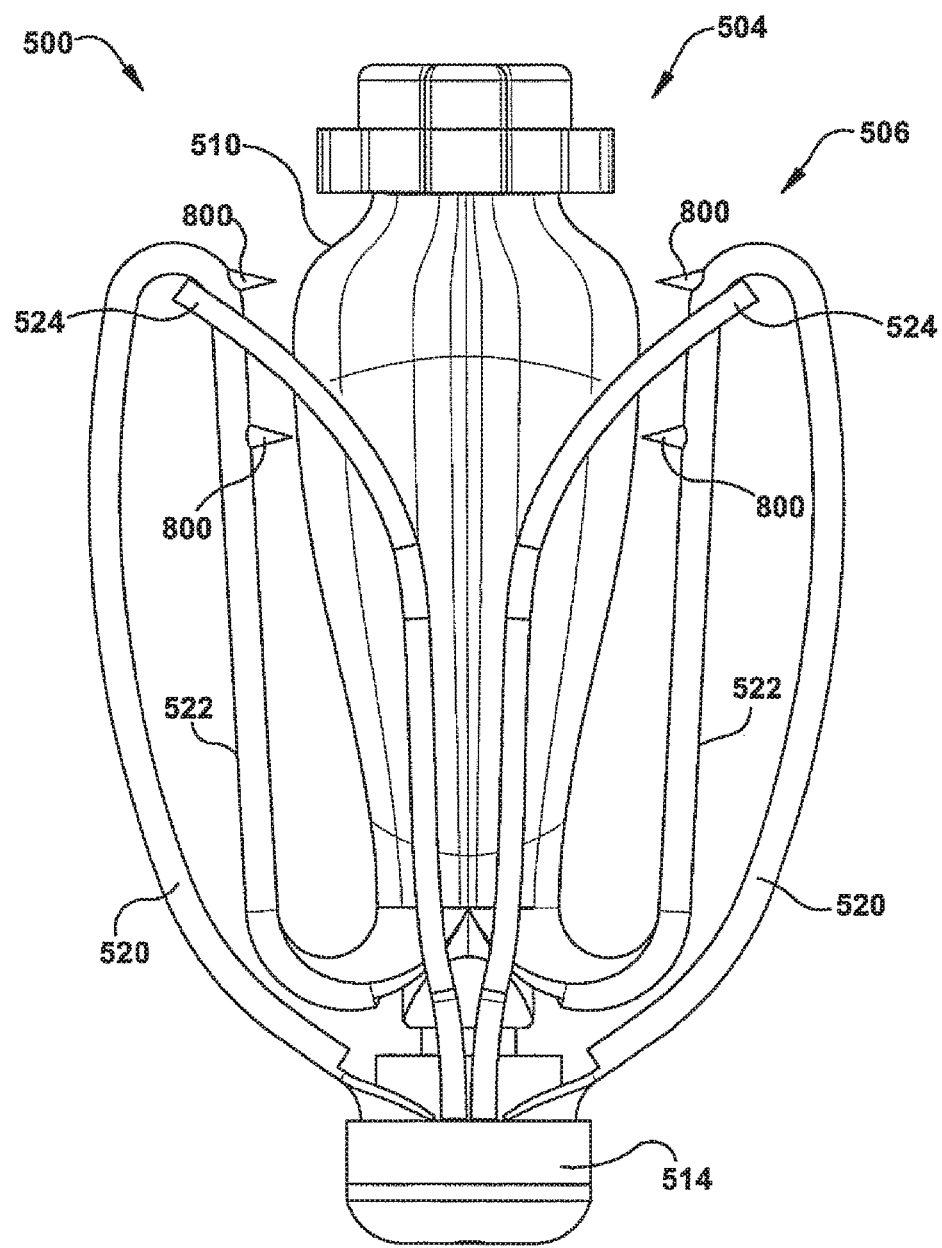
FIG. 86 shows an exemplary embodiment of an implantable prosthetic device with integral barbs.

Referring now to FIG. 86, the exemplary implantable device 500 is shown that does not include articulable clasps or gripping elements. As described above, the device 500 includes a coaption portion 504 and an anchor portion 506. The coaption portion 504 of the device 500 includes a coaption element 510 that is adapted to be implanted between the leaflets 20, 22 of the native mitral valve MV and is slidably attached to an actuation wire or shaft 512 that extends through the coaption element 510 to a distal cap 514.

The anchor portion 506 of the device 500 includes outer paddles 520 and inner paddles 522 that are connected between the distal cap 514 and the coaption element 510. The anchor portion 506 is actuatable between open and closed conditions and can take a wide variety of forms, such as, for example, paddles, gripping elements, or the like. Actuation of the actuation wire 512 opens and closes the anchor portion 506 of the device 500 to grasp the mitral valve leaflets 20, 22 during implantation.

Rather than articulable clasps or gripping elements, the device 500 includes barbed portions 800 arranged on the inner paddles 522, with each inner paddle 522 optionally having more than one barbed portion 800. When the anchor portion 506 of the device 500 is closed, tissue grasped between the inner paddles 522 and the coaption element 510 is pressed against the barbed portions 800. The barbed portions 800 are sharp so that they engage—and in some embodiments, pierce—the native tissue and prohibit the tissue from retracting from the device 500. In some embodiments, the barbed portions 800 are angled downward to increase engagement with the native tissue.

Figure 86A:
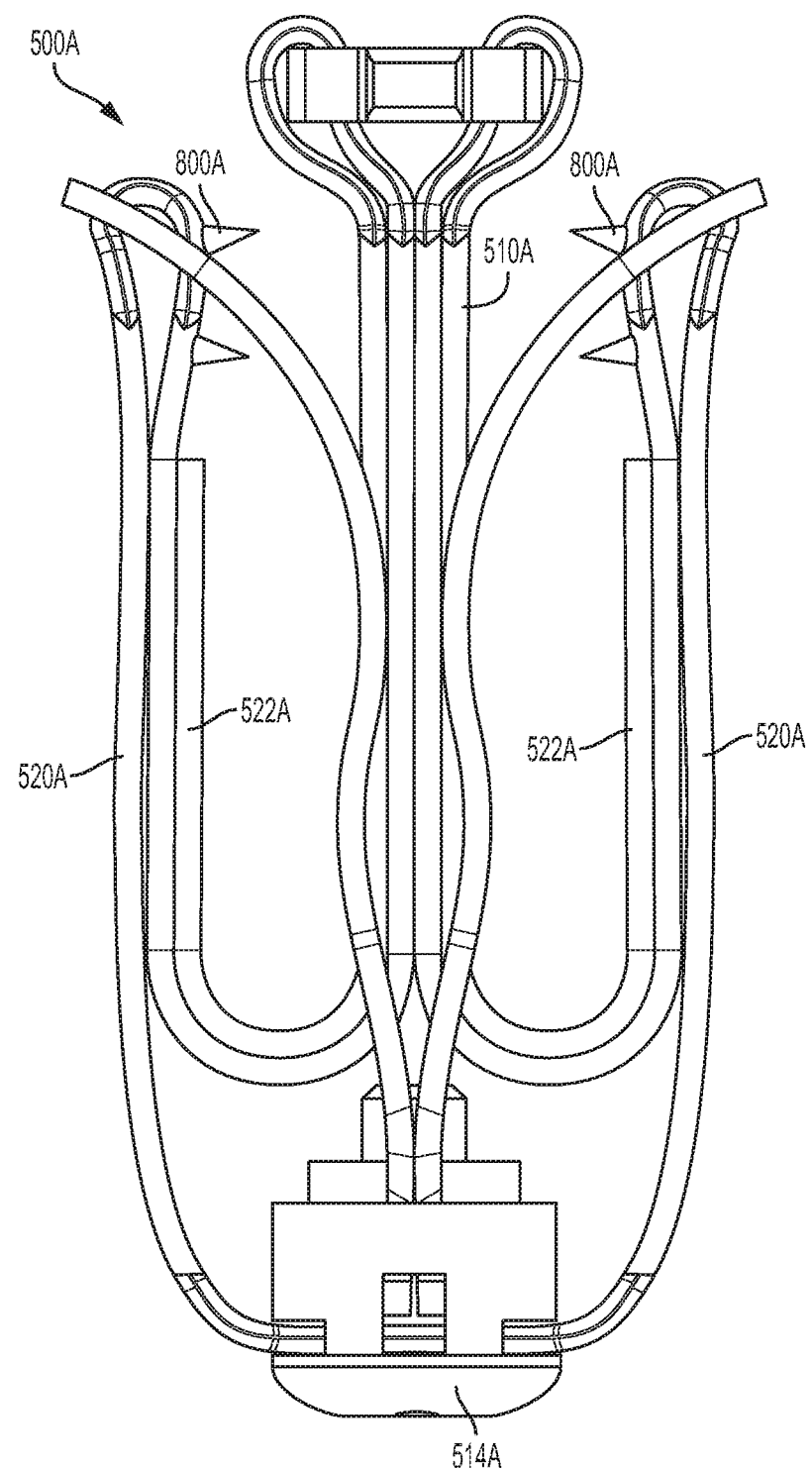
FIG. 86A shows an exemplary embodiment of an implantable prosthetic device with integral barbs.

Referring now to FIG. 86A, the exemplary implantable device 500A is shown that does not include articulable clasps or gripping elements. As described above, the device 500A a coaption element 510A that is adapted to be implanted between the leaflets 20, 22 of the native mitral valve MV and is slidably attached to an actuation wire or shaft (not shown) that extends through the coaption element 510A to a distal cap 514A. The device 500A also includes outer paddles 520A and inner paddles 522A that are connected between the distal cap 514A and the coaption element 510A. The device 500A is actuatable between open and closed conditions and can take a wide variety of forms, such as, for example, paddles, gripping elements, or the like. Actuation of the actuation wire opens and closes the paddles 520A, 522A of the device 500A to grasp the mitral valve leaflets 20, 22 during implantation.

Rather than articulable clasps or gripping elements, the device 500A includes barbed portions 800A arranged on the inner paddles 522A, with each inner paddle 522A optionally having more than one barbed portion 800A. When the device 500A is closed, tissue grasped between the inner paddles 522A and the coaption element 510A is pressed against the barbed portions 800A. The barbed portions 800A are sharp so that they engage—and in some embodiments, pierce—the native tissue and prohibit the tissue from retracting from the device 500A. In some embodiments, the barbed portions 800A are angled downward to increase engagement with the native tissue.

Figure 87:
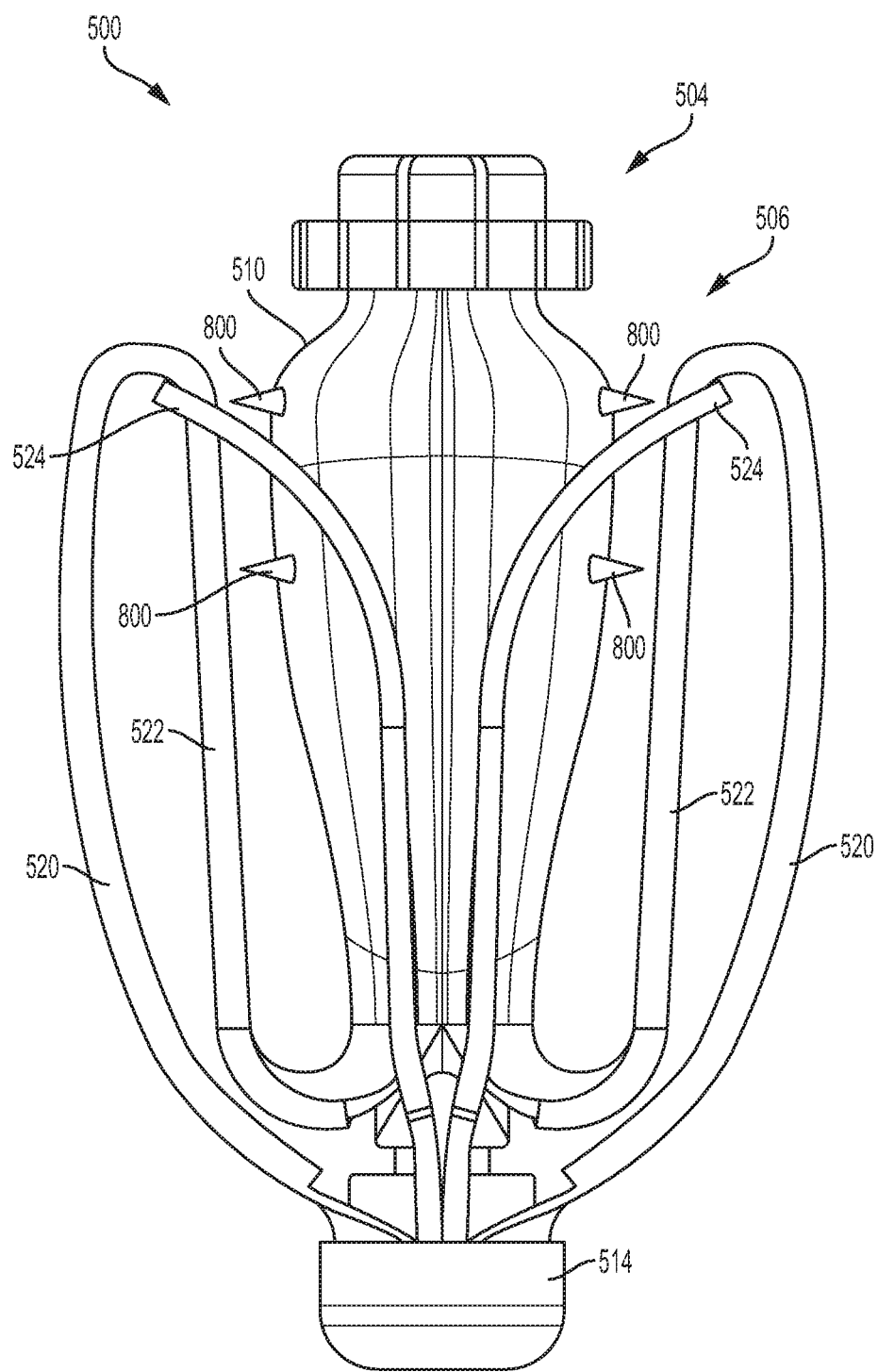
FIG. 87 shows an exemplary embodiment of an implantable prosthetic device with integral barbs.

Referring now to FIG. 87, the exemplary implantable device 500 is shown that does not include separate articulable clasps or gripping elements. As described above, the device 500 includes a coaption portion 502 and an anchor portion 504. The coaption portion 502 of the device 500 includes a coaption element 510 that is adapted to be implanted between the leaflets 20, 22 of the native mitral valve MV and is slidably attached to an actuation wire or shaft 512 that extends through the coaption element 510 to a distal cap 514.

The anchor portion 506 of the device 500 includes outer paddles 520 and inner paddles 522 that are connected between the distal cap 514 and the coaption element 510. The anchor portion 506 is actuatable between open and closed conditions and can take a wide variety of forms, such as, for example, paddles, gripping elements, or the like. Actuation of the actuation wire 512 opens and closes the anchor portion 506 of the device 500 to grasp the mitral valve leaflets 20, 22 during implantation.

Rather than separate articulable clasps or gripping elements, the device 500 includes barbed portions 800 arranged on the coaption element 510, with each side of the coaption element 510 having more than one barbed portion 800. When the anchor portion 506 of the device 500 is closed, tissue grasped between the inner paddles 522 and the coaption element 510 is pressed against the barbed portions 800. The barbed portions 800 are sharp so that they engage—and in some embodiments, pierce—the native tissue and prohibit the tissue from retracting from the device 500. In some embodiments, the barbed portions 800 are angled downward to increase engagement with the native tissue.

Figure 87A:
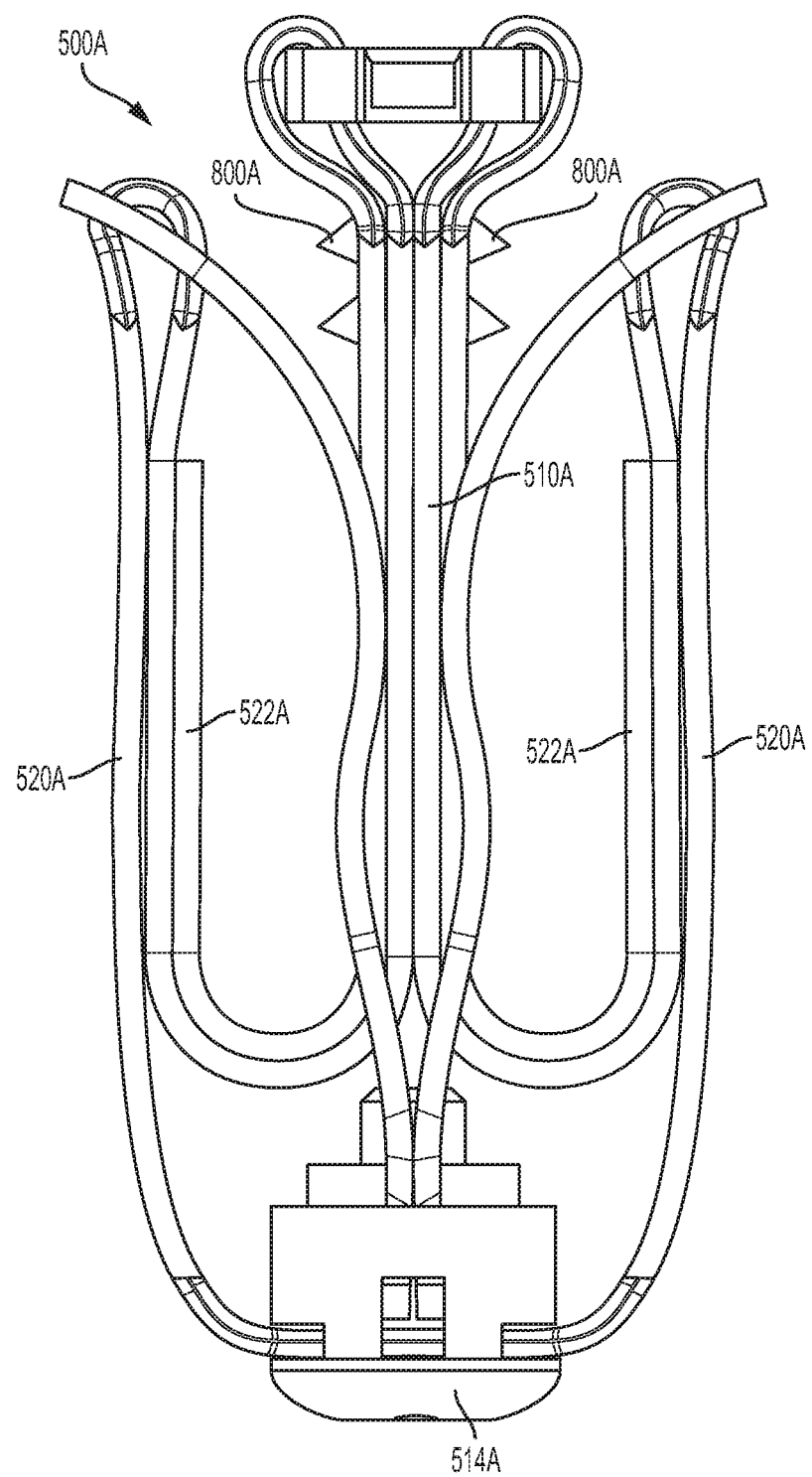
FIG. 87A shows an exemplary embodiment of an implantable prosthetic device with integral barbs.

Referring now to FIG. 87A, the exemplary implantable device 500A is shown that does not include articulable clasps or gripping elements. As described above, the device 500A can have a coaption element 510A that is adapted to be implanted between the leaflets 20, 22 of the native mitral valve MV and is slidably attached to an actuation wire or shaft (not shown) that extends through the coaption element 510A to a distal cap 514A. The device 500A also includes outer paddles 520A and inner paddles 522A that are connected between the distal cap 514A and the coaption element 510A. The device 500A is actuatable between open and closed conditions and can take a wide variety of forms, such as, for example, paddles, gripping elements, or the like. Actuation of the actuation wire opens and closes the paddles 520A, 522A of the device 500A to grasp the mitral valve leaflets 20, 22 during implantation.

Rather than separate articulable clasps or gripping elements, the device 500A includes barbed portions 800A arranged on the coaption element 510A, with each side of the coaption element 510A having more than one barbed portion 800A. When the device 500A is closed, tissue grasped between the inner paddles 522A and the coaption element 510A is pressed against the barbed portions 800A. The barbed portions 800A are sharp so that they engage—and in some embodiments, pierce—the native tissue and prohibit the tissue from retracting from the device 500A. In some embodiments, the barbed portions 800A are angled downward to increase engagement with the native tissue.

Figure 88:
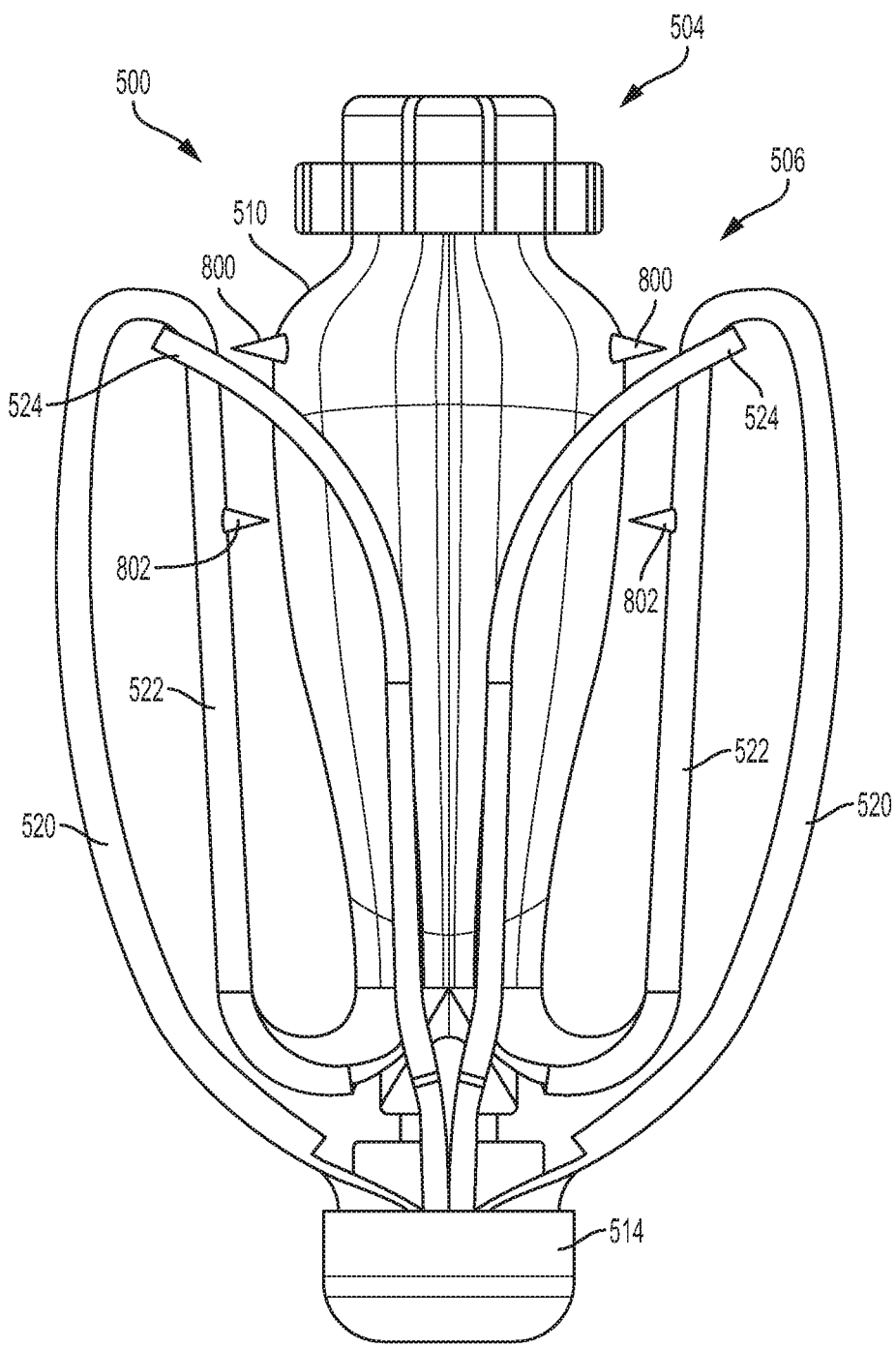
FIG. 88 shows an exemplary embodiment of an implantable prosthetic device with integral barbs.

Referring now to FIG. 88, the exemplary implantable device 500 is shown that does not include separate articulable clasps or gripping elements. As described above, the device 500 includes a coaption portion 502 and an anchor portion 504. The coaption portion 502 of the device 500 includes a coaption element 510 that is adapted to be implanted between the leaflets 20, 22 of the native mitral valve MV and is slidably attached to an actuation wire or shaft 512 that extends through the coaption element 510 to a distal cap 514.

The anchor portion 506 of the device 500 includes outer paddles 520 and inner paddles 522 that are connected between the distal cap 514 and the coaption element 510. The anchor portion 506 is actuatable between open and closed conditions and can take a wide variety of forms, such as, for example, paddles, gripping elements, or the like. Actuation of the actuation wire 512 opens and closes the anchor portion 506 of the device 500 to grasp the mitral valve leaflets 20, 22 during implantation.

Rather than articulable clasps or gripping elements, the device 500 includes barbed portions 800 arranged on the coaption element 510, with each side of the coaption element 510 including at least one barbed portion 800. Similar to device 1500 described above, the device 500 also includes barbed portions 802 arranged on the inner paddles 522, with each inner paddle 522 having at least one barbed portion 802.

When the anchor portion 506 of the device 500 is closed, tissue grasped between the inner paddles 522 and the coaption element 510 is pressed against the barbed portions 800, 802. The barbed portions 800, 802 are sharp so that they engage—and in some embodiments, pierce—the native tissue and prohibit the tissue from retracting from the device 500. In some embodiments, the barbed portions 800, 802 are angled downward to increase engagement with the native tissue. The combination of barbed portions 800 on the coaption element 510 and barbed portions 802 on the inner paddles 522 forms the grasped tissue into an S-shaped tortuous path as it passes over the barbed portions 800, 802. Thus, forces pulling the tissue away from the device 500 will encourage the tissue to further engage the barbed portions 800, 802 before the tissue can escape.

Figure 88A:
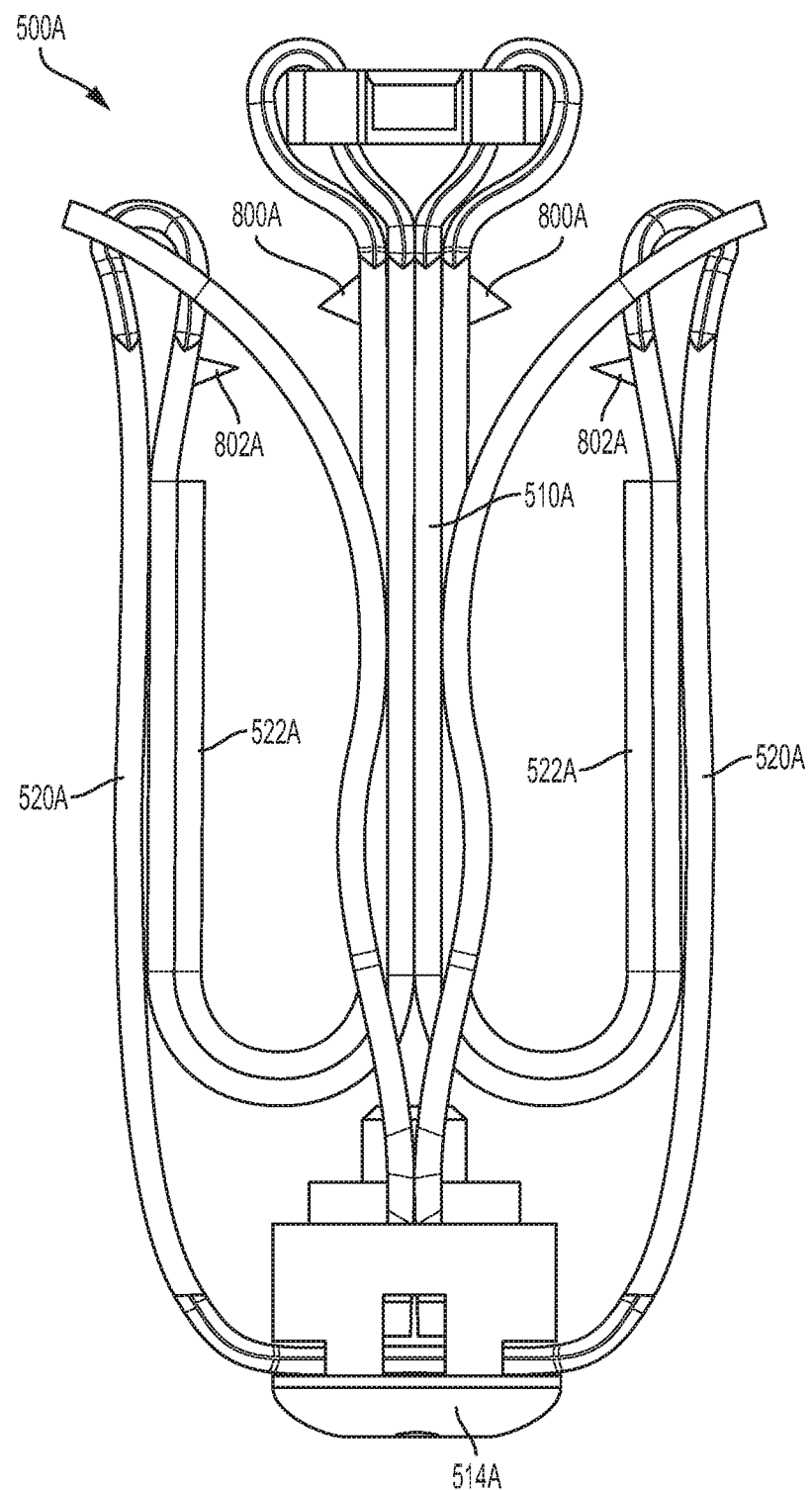
FIG. 88A shows an exemplary embodiment of an implantable prosthetic device with integral barbs.

Referring now to FIG. 88A, the exemplary implantable device 500A is shown that does not include articulable clasps or gripping elements. As described above, the device 500A can have a coaption element 510A that is adapted to be implanted between the leaflets 20, 22 of the native mitral valve MV and is slidably attached to an actuation wire or shaft (not shown) that extends through the coaption element 510A to a distal cap 514A. The device 500A also includes outer paddles 520A and inner paddles 522A that are connected between the distal cap 514A and the coaption element 510A. The device 500A is actuatable between open and closed conditions and can take a wide variety of forms, such as, for example, paddles, gripping elements, or the like.

Actuation of the actuation wire opens and closes the paddles 520A, 522A of the device 500A to grasp the mitral valve leaflets 20, 22 during implantation.

Rather than articulable clasps or gripping elements, the device 500A includes barbed portions 800A arranged on the coaption element 510A, with each side of the coaption element 510A including at least one barbed portion 800A. The device 500A also includes barbed portions 802A arranged on the inner paddles 522A, with each inner paddle 522A having at least one barbed portion 802A.

When the device 500A is closed, tissue grasped between the inner paddles 522A and the coaption element 510A is pressed against the barbed portions 800A, 802A. The barbed portions 800A, 802A are sharp so that they engage—and in some embodiments, pierce—the native tissue and prohibit the tissue from retracting from the device 500A. In some embodiments, the barbed portions 800A, 802A are angled downward to increase engagement with the native tissue. The combination of barbed portions 800A on the coaption element 510A and barbed portions 802A on the inner paddles 522A forms the grasped tissue into an S-shaped tortuous path as it passes over the barbed portions 800A, 802A. Thus, forces pulling the tissue away from the device 500A will encourage the tissue to further engage the barbed portions 800A, 802A before the tissue can escape.

Referring now to FIGS. 89-102, the coaption element 510 and paddles 520, 522 of the exemplary device 500 are shown. The coaption element 510 and the paddles can be made from a wide variety of different materials. The coaption element 510 and paddles 520, 522 may be formed from a material that may be a metal fabric, such as a mesh, woven, braided, electrospun or formed in any other suitable way or a laser cut or otherwise cut flexible material. The material may be cloth, shape-memory alloy wire—such as Nitinol—to provide shape-setting capability, or any other flexible material suitable for implantation in the human body.

In one exemplary embodiment, the coaption element is made from a braided mesh of metal wires, such as a braided mesh of nitinol wires. In one exemplary embodiment, the coaption element 510 is made of a braided mesh of between 25 and 100 wires, such as between 40 and 85 wires, such as between 45 and 60 wires, such as about 48 Nitinol wires or 48 Nitinol wires.

The coaption element can be covered in a cloth, such as a polyethylene cloth. The coaption element 510, can be surrounded in its entirety with a cloth cover, such as a polyethylene cloth of a fine mesh. The cloth cover can provide a blood seal on the surface of the spacer, and/or promote rapid tissue ingrowth.

The use of a shape memory material, such as braided Nitinol wire mesh, for the construction of the coaption element 510 results in a coaption element that can self-expandable, flexible in all directions, and/or results in low strains when the coaption element is crimped and/or bent. The material can be a single piece, two halves joined together, or a plurality of sections or pieces that are fastened or joined together in any suitable manner, such as, by welding, with adhesives, or the like.

Figure 89:
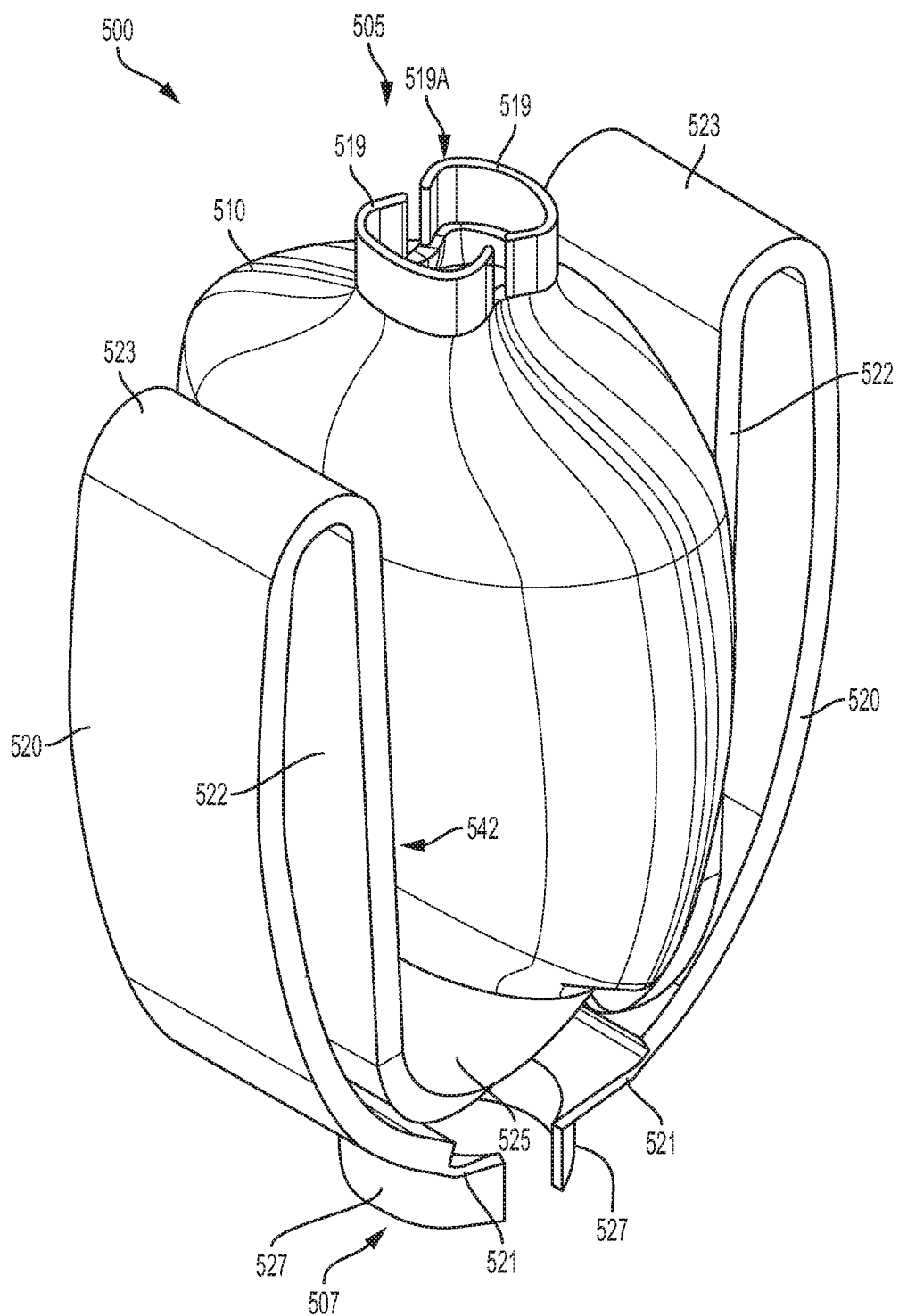
FIG. 89 shows a perspective view of a coapting portion and paddle portions of the implantable prosthetic device illustrated by FIG. 65.
Figure 90:
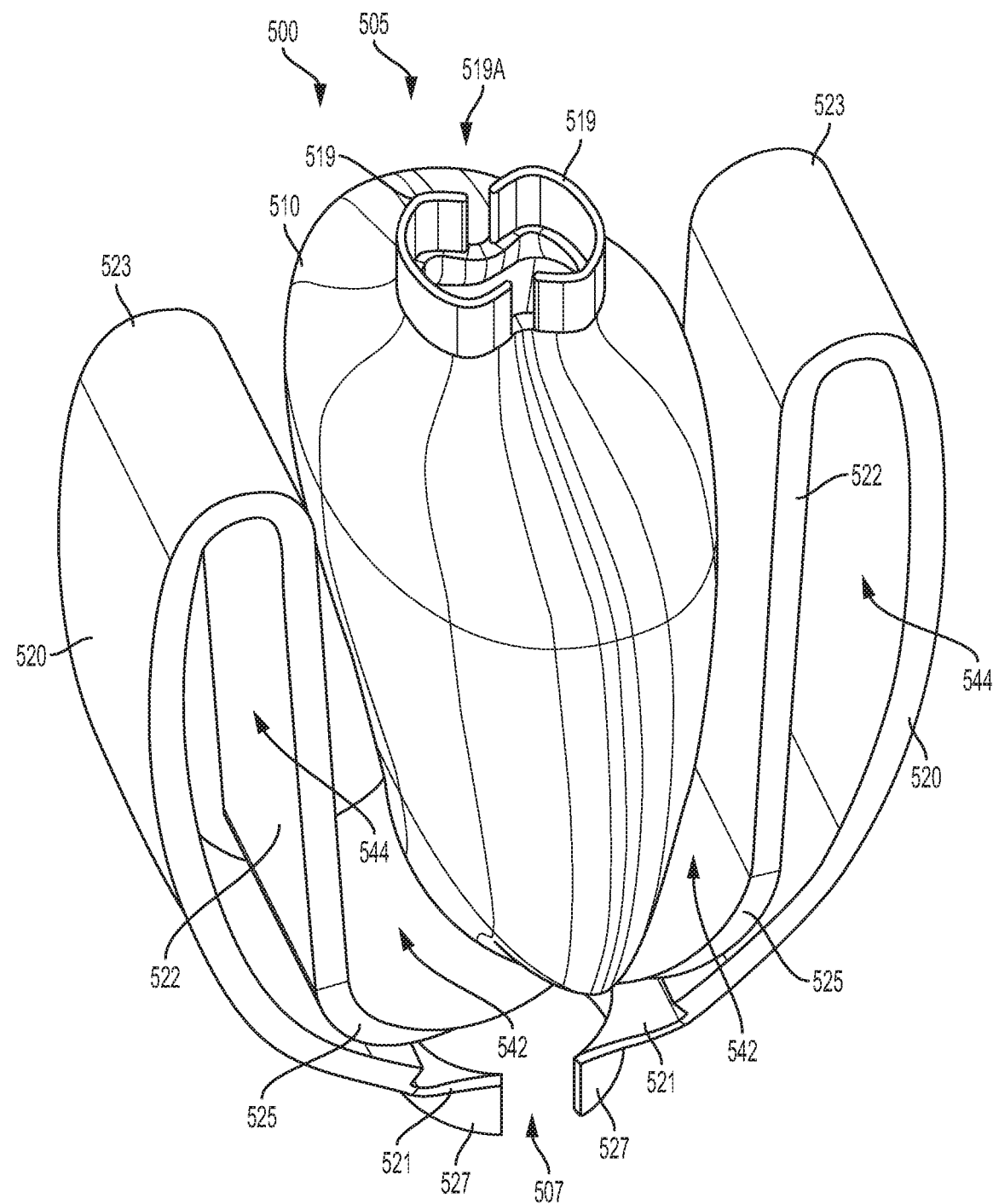
Figure 92:
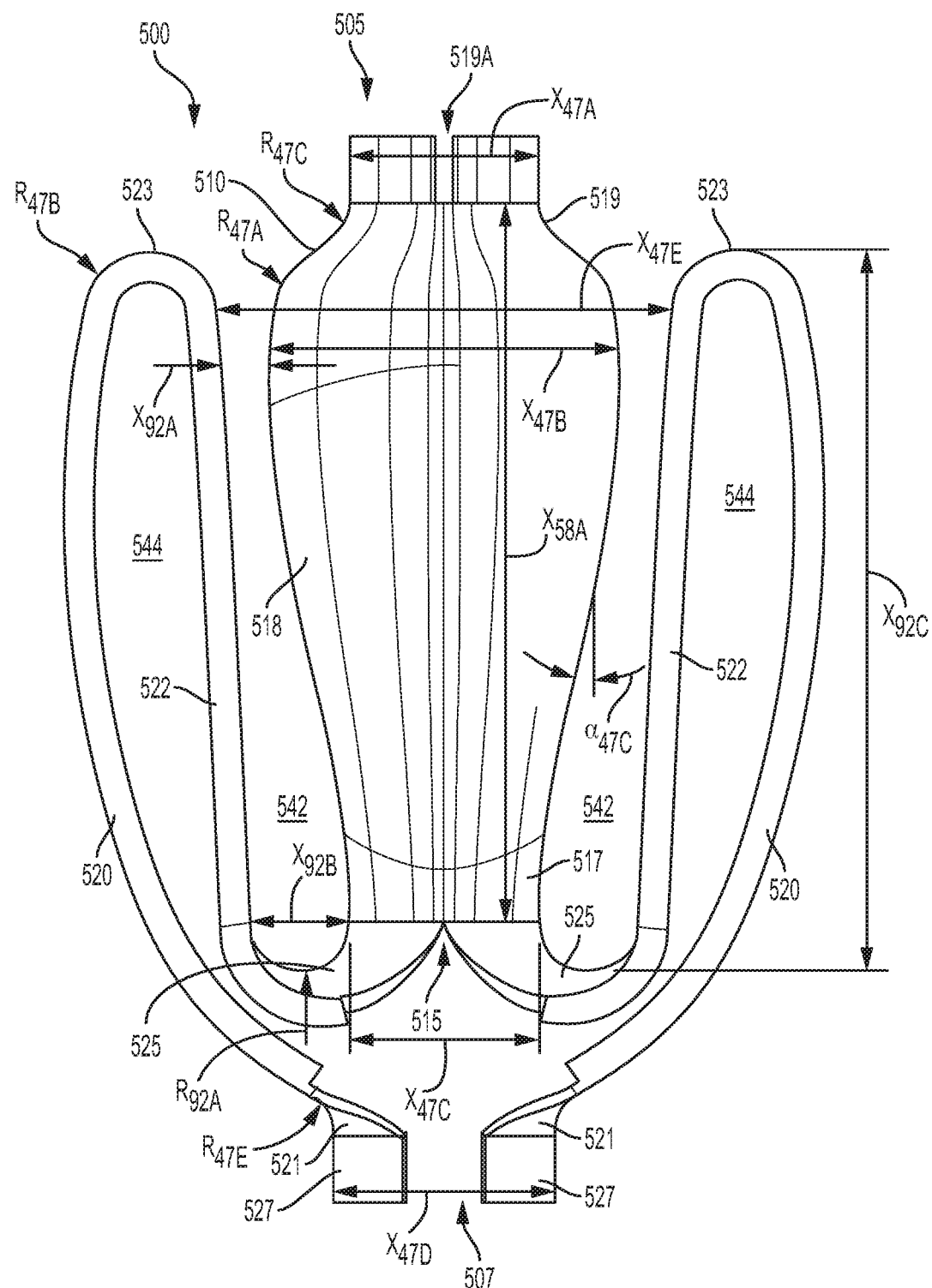
Figure 94:
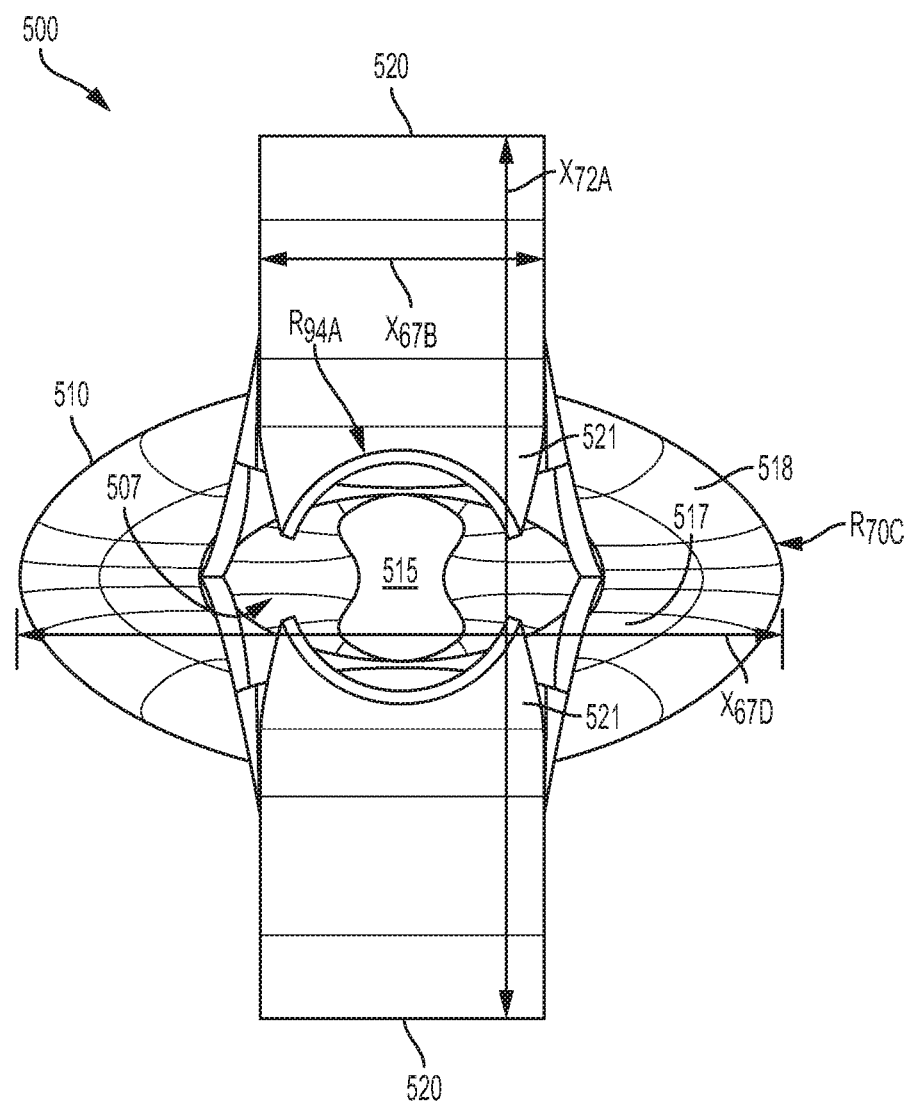

Referring now to FIGS. 89-90, the device 500 extends from a proximal portion 505 to a distal portion 507 and includes a coaption element 510, inner paddles 522, and outer paddles 520. The coaption element 510 includes a proximal opening 519A and a distal opening 515 (FIGS. 92 and 94). The proximal opening 519A of the coaption element 510 is formed in a proximal portion 519 of the coaption element 510. The coaption element 510 is jointably connected to the inner paddles 522 by joint portions 525. The inner paddles 522 are jointably connected to the outer paddles 520 by joint portions 523. The outer paddles 520 are jointably attached to distal portions 527 by joint portions 521. Coaption gaps 542 are formed between the inner paddles 522 and the coaption element 510. Paddle gaps 544 are formed between the inner and outer paddles 520, 522 when the paddles 520, 522 are folded, for example, as shown in FIG. 90.

Figure 91:
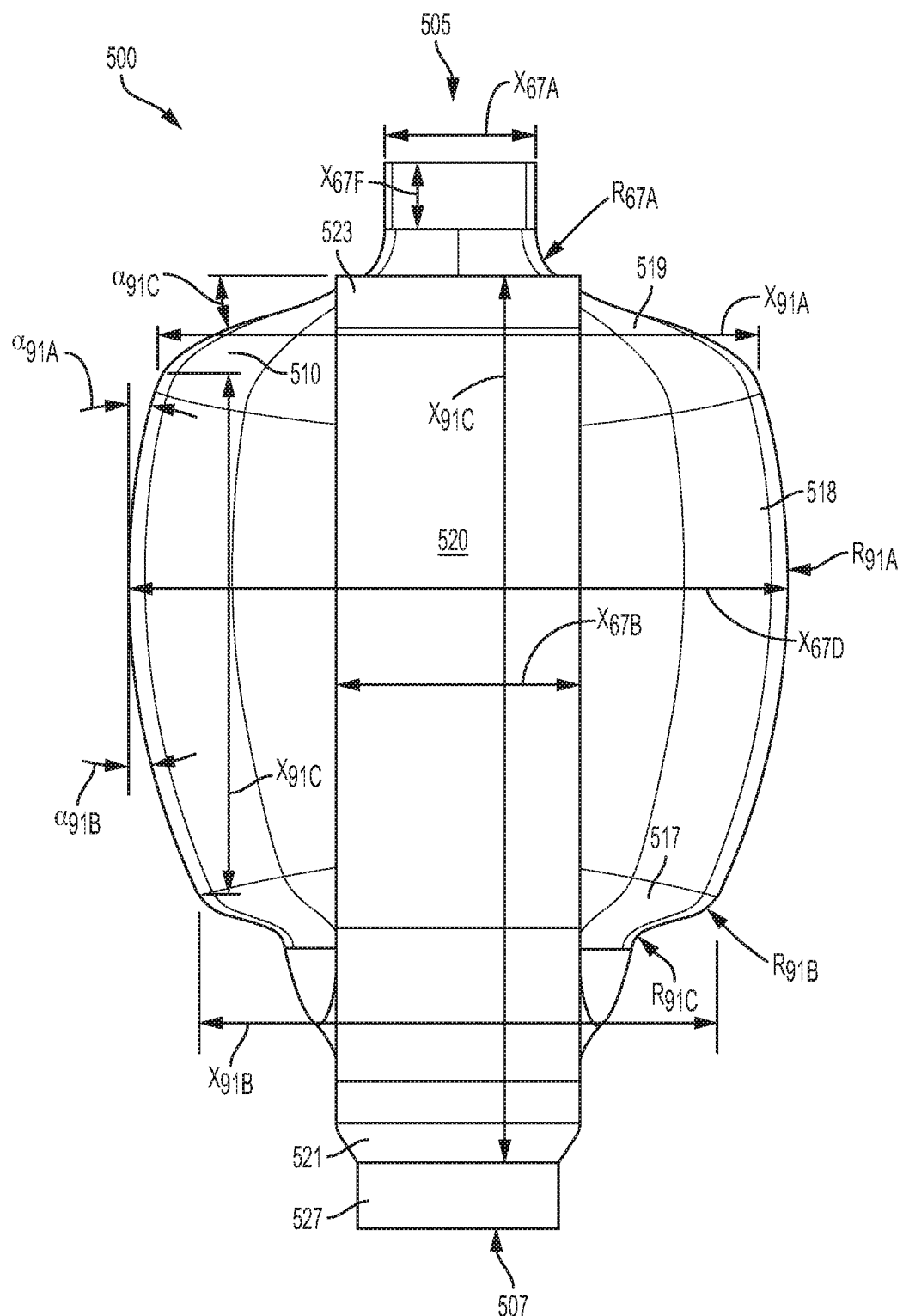

Referring now to FIG. 91, a front view of the device 500 is shown (a back view of which would be identical). The coaption element 510 includes the proximal portion 519, a middle portion 518, and a distal portion 517. The proximal portion 519 includes the proximal opening 519A. The distal portion 517 includes the distal opening 515 and is connected to the joint portions 525. The shape of the coaption element 510 is generally rounded to prevent the device 500 from catching or snagging on structures of the heart, such as the chordae tendineae, during implantation.

Referring now to FIG. 92, a side view of the device 500 is shown. Similar to the device 500 viewed from the front, the distal portion 507 of the device 500 is generally narrower than the proximal portion 505 of the device 500 when the device 500 is viewed from the side. The coaption element 510 flares outwards in the proximal portion 519 from the proximal opening 519A to the middle portion 518. The coaption element 510 then tapers or narrows in the middle portion 518 from the proximal portion 519 to the distal portion 517. The distal portion 517 remains narrow and then splits into the two joint portions 525. The generally rounded features of the device 500 are further demonstrated by the round shape of the joint portions 523 that jointably connect the inner and outer paddles 520, 522 and the outwardly bowed shape of the outer paddles 520.

The coaption gaps 542 formed between the inner paddles 522 and the coaption element 510 are configured to receive native tissue. The narrowing of the coaption element 510 gives the gaps 542 a somewhat teardrop shape that increases in width as the gaps 542 approach the distal portion 507 of the device 500. The widening of the gaps 542 toward the distal portion 507 allows the inner paddles 522 to contact tissue grasped in the gaps 542 nearer to the proximal portion 505 where pinching forces are greater as a result of the mechanical advantage provided by the length of the paddles 520, 522 and other securing or anchoring elements, such as those described in the present application.

Figure 93:
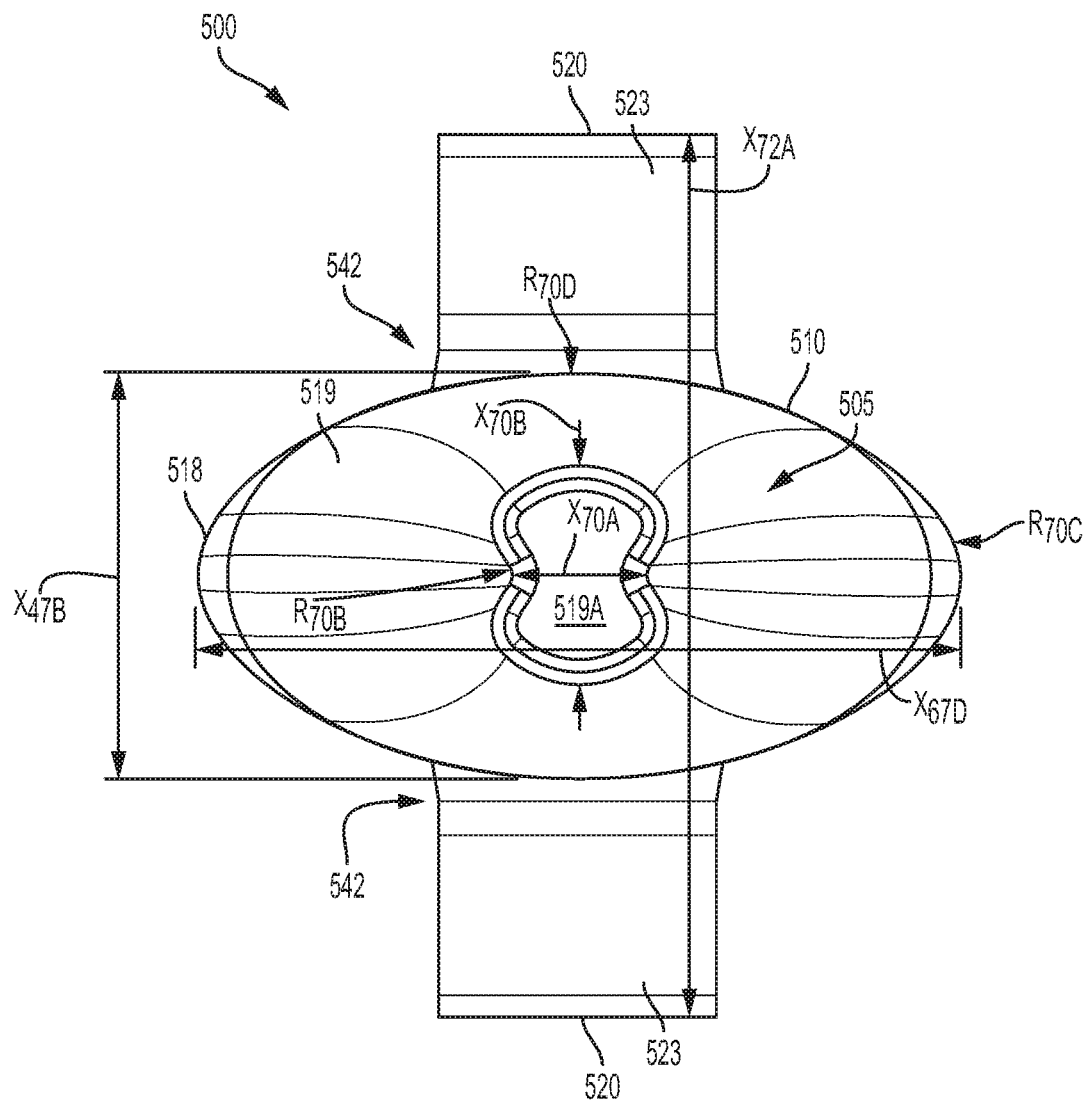

Referring now to FIG. 93, a top view of the device 500 is shown. The proximal opening 519A in the coaption element 510 is visible at the proximal portion 505 of the device 500 and the coaption element 510 can be seen to be hollow inside. The coaption element 510 has a generally oval-shape when viewed from the top. While the paddles 520, 522 appear as protruding rectangular shapes, the paddles 520, 522 can extend laterally and have an arcuate or crescent-like shape.

Referring now to FIG. 94, a bottom view of the device 500 is shown. The distal opening 515 in the coaption element 510 is visible at the distal portion 507 of the device 500 and the coaption element 510 can be seen to be hollow inside. The coaption element 510 has a generally oval-shape when viewed from the top. While the paddles 520, 522 appear as protruding rectangular shapes, the paddles 520, 522 can extend laterally and have an arcuate or crescent-like shape. The distal portion 517 of the coaption element 510 can be seen splitting in two to join with the joint portions 525.

Referring now to FIGS. 89A, 90A, 91A, 92A, 93A, 94A, 95A, 96A, 97A, 98A, 99A, 100A, 101A, and 102A, the portions of the device 500A formed by the single, continuous strip of material 501A, that is, the coaption element 510A and paddles 520A, 522A, are shown. The coaption element 510A and the paddles can be made from a wide variety of different materials. The coaption element 510A, and paddles 520A, 522A may be formed from a material that may be a metal fabric, such as a mesh, woven, braided, electrospun or formed in any other suitable way or a laser cut or otherwise cut flexible material. The material may be cloth, shape-memory alloy wire—such as Nitinol—to provide shape-setting capability, or any other flexible material suitable for implantation in the human body.

In one exemplary embodiment, the coaption element 510A, inner paddle 522A, and outer paddle 520A are made from a single, continuous strip of material 501A. The strip of material 501A may be formed from a material that may be a metal fabric, such as a mesh, woven, braided, electrospun or formed in any other suitable way or a laser cut or otherwise cut flexible material. The material may be cloth, shape-memory alloy wire—such as Nitinol—to provide shape-setting capability, or any other flexible material suitable for implantation in the human body. In one exemplary embodiment, the strip of material 501A is made of a braided mesh of between 25 and 100 strands, such as between 40 and 85 strands, such as between 45 and 60 strands, such as about 48 Nitinol wires or 48 Nitinol wires.

Referring now to FIGS. 205-207, an exemplary woven or braided material 4000 that may be used for the strip of material 501A is shown. Referring now to FIG. 205, an enlarged plan view of the material 4000 is shown. The material 4000 extends from a first edge 4002 to a second edge 4004. The edges 4002, 4004 surround a central portion or field 4006. The material 4000 is formed by braiding or weaving together central strands 4020, such as Nitinol wires. Edge strands 4010 extend longitudinally through the material 4000 along the edges 4002, 4004. The central strands 4020 are woven or braided such that the central strands 4020 wrap around the edge strands 4010. Wrapping the central strands 4020 around the edge strands 4010 causes the material 4000 near the edges 4002, 4004 to be thicker than the material in the central portion 4006, forming a lobed or dog-bone-like shape when the material 4000 is viewed from the end, as is shown in FIG. 206. Thus, the edges 4002, 4004 of the material 4000 are less flexible than the central portion 4006. The edge strands 4010 and central strands 4020 can be similar in diameter and can have a diameter ranging from about 0.06 millimeters to about 0.18 millimeters. In some embodiments, the edge strands 4010 may have a larger diameter than the central strands 4020 to impart more stiffness or rigidity to the edges 4002, 4004 than the central portion 4006. For example, the edge strands 4010 can have a diameter ranging from 0.07 millimeters to about 0.27 millimeters, or about 0.17 millimeters, and the central strands 4020 can have a diameter ranging from about 0.04 millimeters to about 0.15 millimeters, or about 0.009 millimeters. In some embodiments, the edges 4002, 4004 are made less flexible than the central portion 4006 by using different materials for the edge strands 4010 and central strands 4020, such as, for example, a metal material—e.g., Nitinol—for the edge strands 4010 and a cloth or plastic material—e.g., polyethylene—for the central strands 4020. Alternatively, the edge strands 4010 and central strands 4020 may be made from the same material that is subjected to different chemical and or thermal processes that alter the flexibility of the materials so that the central strands 4020 are more flexible than the edge strands 4010.

Referring now to FIG. 207, folded portions of material 4000 are layered on top of each other to form a section that has four layers 4000A, 4000B, 4000C, 4000D. The lobed shape of the individual layers, with thicker edges 4002, 4004 than the central portion 4006, creates three gaps 4001A, 4001B, 4001C between the layers 4000A, 4000B, 4000C, 4000D of material 4000 in the location of the central portion 4006. Outer gaps 4001A, 4001C are formed between outer layers 4000A, 4000D and the adjacent middle layers 4000B, 4000C.

As is discussed in the present disclosure, the coaption element 510A of the device 500A can be formed from four layers of material, such as the material 4000. When layers of the material 4000 are used to form the coaption element 510A, the actuation wire 512A of the device 500A can be inserted through the middle gap 4001B formed in the center of the four layers of material 4000. The actuation wire 512A may have a larger diameter than the width of the gap 4001B, so that inserting the actuation wire 512A causes the middle gap 4001B to stretch open and adjacent outer gaps 4001A, 4001C to reduce in size. In some embodiments, inserting the actuation wire 512A causes the center body portions 4006 on either side to bulge outward to a thickness that is greater than the thickness of the four stacked edge portions 4002, 4004.

The coaption element 510A and paddles 520A, 522A can be covered in a cloth, such as a polyethylene cloth. The coaption element 510A and paddles 520A, 522A can be surrounded in their entirety with a cloth cover (e.g., cover 540A), such as a polyethylene cloth of a fine mesh. The cloth cover can provide a blood seal on the surface of the spacer, and/or promote rapid tissue ingrowth.

The use of a shape memory material, such as braided Nitinol wire mesh, for the construction of the coaption element 510A and paddles 520A, 522A results in a coaption element and paddles that can be self-expandable, flexible in all directions, and/or results in low strains when crimped and/or bent. The material can be a single piece, two halves joined together, or a plurality of sections or pieces that are fastened or joined together in any suitable manner, such as, by welding, with adhesives, or the like.

Figure 89A:
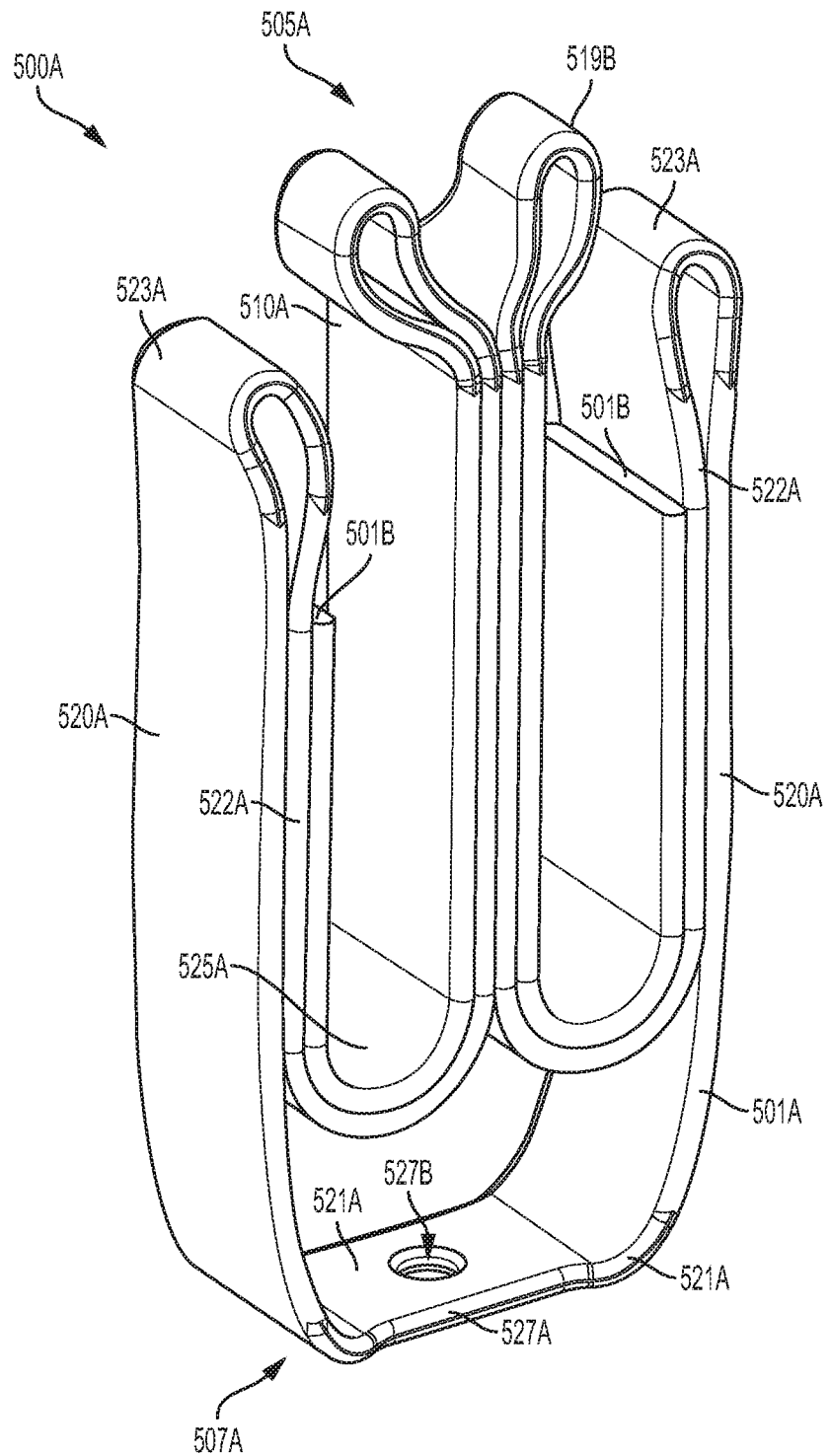
FIG. 89A shows a perspective view of a coapting portion and paddle portions of the implantable prosthetic device illustrated by FIG. 65A.
Figure 90A:
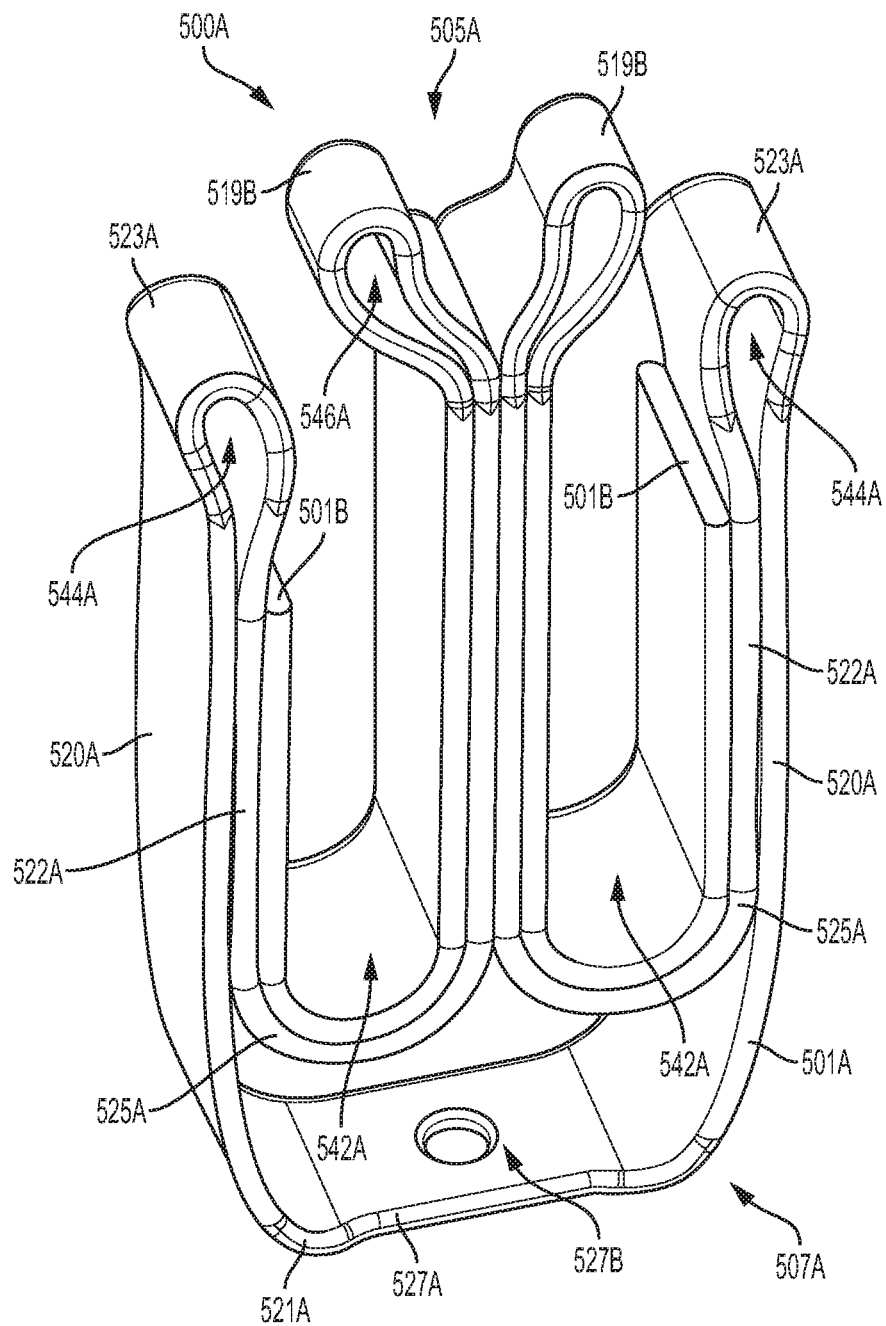

Referring now to FIGS. 89A and 90A, the device 500A extends from a proximal portion 505A to a distal portion 507A and includes a coaption element 510A, inner paddles 522A, and outer paddles 520A. The single, continuous strip of material 501A extends between two ends 501B and is folded to form the coaption element 510A, inner paddles 522A, and outer paddles 520A. Some portions of the device 500A are formed from multiple layers of the strip of material 501A. For example, the strip of material 501A is overlapped to form four layers in the area of the coaption element 510A and two layers in the area of the inner paddle 522A.

The coaption element 510A and paddles 520A, 522A are jointably connected together by joint portions of the strip of material 501A. The coaption element 510A is jointably connected to the inner paddles 522A by joint portions 525A. The inner paddles 522A are jointably connected to the outer paddles 520A by joint portions 523A. The outer paddles 520A are jointably attached to the distal portion 527A by joint portions 521A. The aperture 527B in the distal portion 527A engages the cap 514A.

Various gaps are formed between portions of the device 500A when the strip of material 501A is folded into the desired shape. Coaption gaps 542A are formed between the inner paddles 522A and the coaption element 510A. Paddle gaps 544A are formed between the inner and outer paddles 520A, 522A when the paddles 520A, 522A are folded, for example, as shown in FIG. 90A. Collar gaps 546A are formed when the strip of material 501A is folded to form the proximal portions 519B of the coaption element 510A.

Figure 91A:
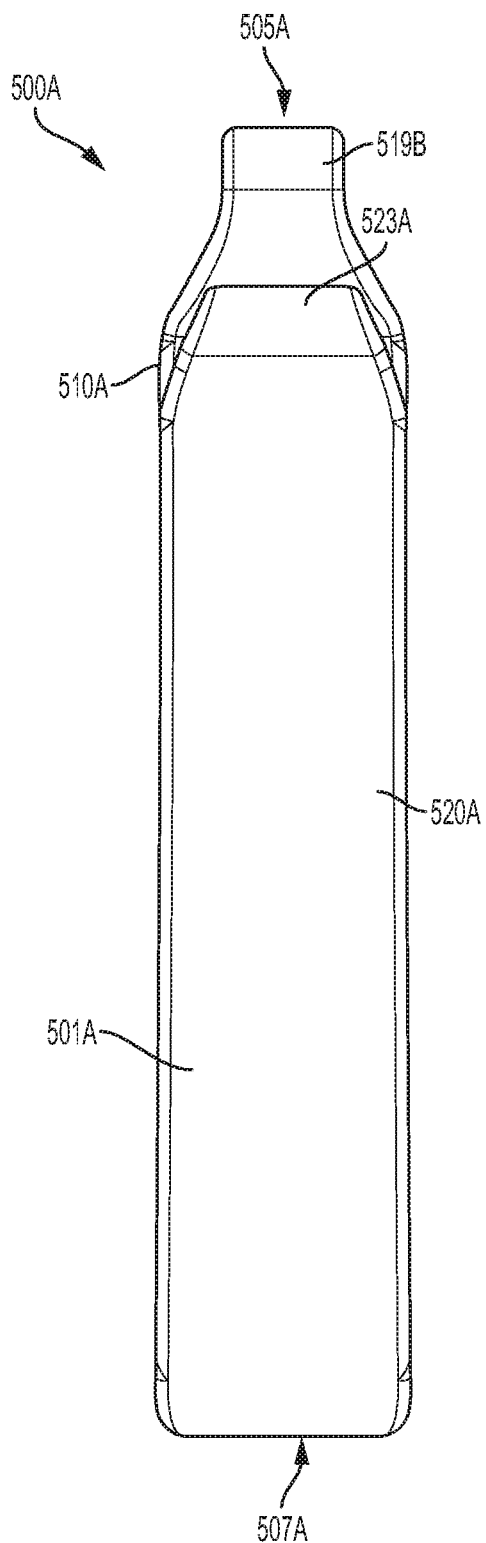

Referring now to FIG. 91A, a front view of the device 500A is shown (a back view of which would be identical). The coaption element 510A includes the proximal portion 519B extending above the joint portions 523A of the paddles 520A, 522A. The distal portion 517A of the coaption element 510A is concealed by the paddles 520A, 522A when viewed from the front or back, giving the device 500A a long and narrow rounded rectangular shape. The shape of the coaption element 510A helps prevent the device 500A from catching or snagging on structures of the heart, such as the chordae tendineae, during implantation.

Figure 92A:
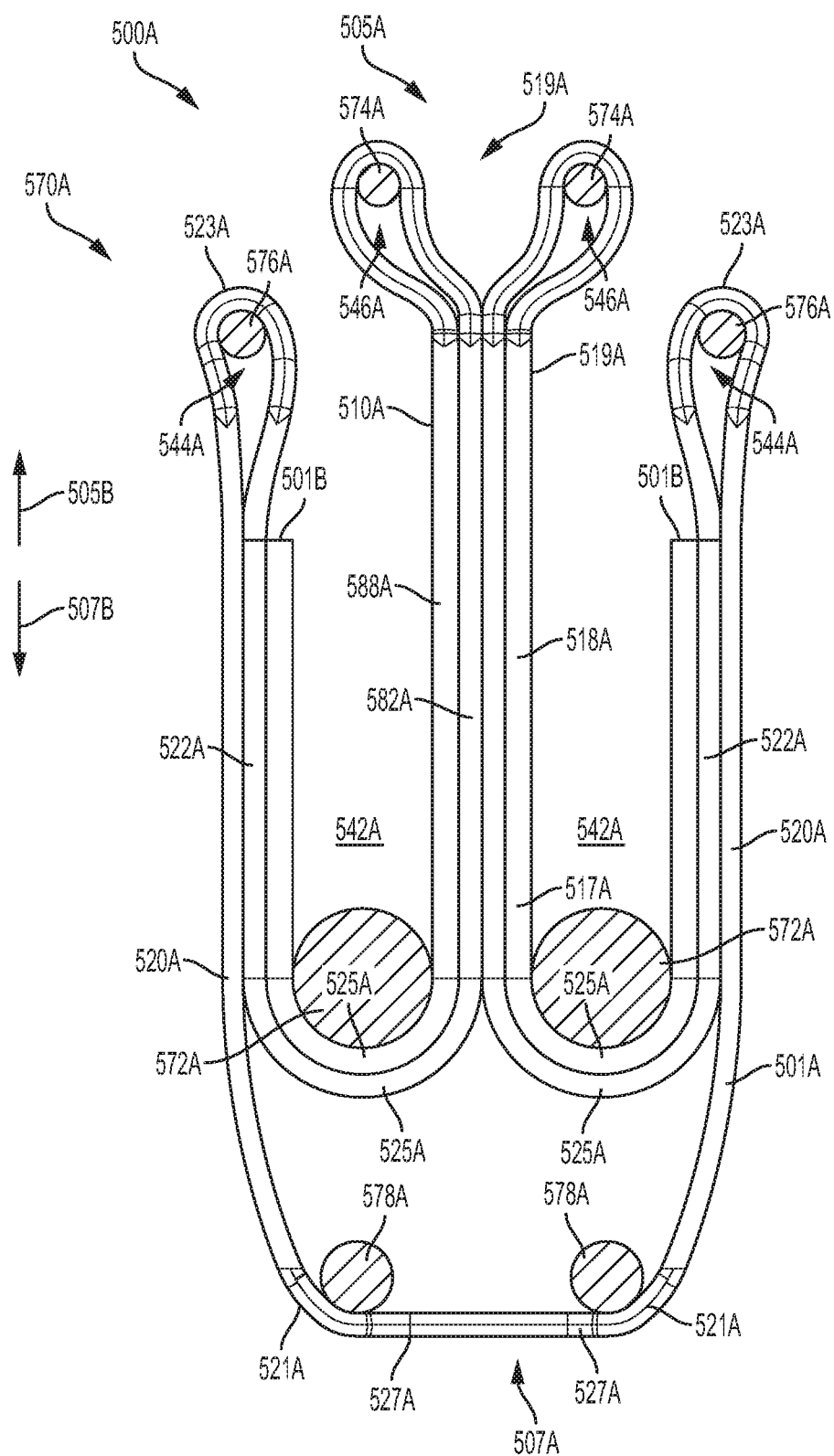

Referring now to FIG. 92A, a side view of the device 500A is shown. The distal end 507A of the device 500A is generally narrower than the proximal end 505A of the device 500A when the device 500A is viewed from the side, forming a generally blunt and rounded shape. The coaption element 510A includes the proximal portion 519B, a middle portion 518A, and the distal portion 517A. The proximal portion 519B flares outward from the middle portion 518A to engage the collar 511D (FIG. 48A). The middle portion 518A of the coaption element 510A is generally straight when viewed from the side. The distal portion 517A is jointably attached to the inner paddles 522A by the joint portions 525A. The generally rounded features of the device 500A are further demonstrated by the round shape of the joint portions 523A that jointably connect the paddles 520A, 522A. The joint portions 521A connecting the outer paddles 520A to the distal portion 527A are also rounded and ease the transition in shape from the strip of material 501A to the cap 514A (FIG. 48A) that is assembled to the generally flat distal portion 527A.

The coaption gaps 542A formed between the inner paddles 522A and the coaption element 510A are configured to receive native tissue. The general straightness of the middle portion 518A of the coaption element 510A and the inner paddles 522A gives the gaps 542A a generally consistent width with a narrow upper end where the proximal portion 519B flares outward to engage the collar 511D (FIG. 48A). Thus, the inner paddles 522A contact the tissue grasped in the gaps 542A nearer to the proximal portion 505A where pinching forces are greater as a result of the mechanical advantage provided by the length of the paddles 520A, 522A and other securing or anchoring elements, such as those described in the present application.

As discussed above, the coaption element 510A and paddles 520A, 522A of the device 500A are formed by folding the strip of material 501A. The strip of material 501A is then unfolded and assembled with other components, such as the collar 511D, cap 514A, and paddle frames 524A. The strip of material 501A is shape-set after being formed into a desired shape so that the strip of material 501A returns to the desired shape after assembly with other components. In some embodiments, a jig is used during folding and shape-setting of the strip of material 501A to ensure that the strip of material 501A is folded in the proper location with the desired radius.

Referring again to FIG. 92A, portions of a jig 570A to aid in folding and shape-setting the device 500A are shown. The strip of material 501A is shown folded around the jig 570A so that the strip of material 501A forms a desired shape. To fold the strip of material 501A into the shape of the device 500A using the jig 570A, the strip of material 501A is arranged with one of the ends 501B at the location of the inner paddle 522A. The strip 501A is extended from the end 501B in a distal direction 507B to form a first layer 581A of the inner paddle 522A, around a first jig portion 572A to form a first layer 581A of the hinge portion 525A, and then in a proximal direction 505B to form the first layer 581A of the coaption element 510A. The first layer 581A of material forms the sides of the inner paddle 522A and coaption element 510A that surround the coaption gap 542A. The strip 501A is then wrapped around a second jig portion 574A to form one of the proximal portions 519B and openings 546A of the coaption element 510A. The strip 501A is then extended in a distal direction 507A along the first layer 581A to form a second layer 582A of the coaption element 510A. The strip 501A is then wrapped back round the first jig portion 574A, forming the second layer 582A of the hinge portion 525A and back in the proximal direction 505A to form the second layer 582A of the inner paddle 522A. The strip 501A is then wrapped around a third jig portion 576A to form the joint portion 523A. The strip 501A then extends in the distal direction 507A along the inner paddle 522A to form the outer paddle 520A before being folded around a fourth jig portion 578A to form the joint portion 521. The strip 501A is then extended laterally to form the distal portion 527. The routing of the strip 501A through the jig 570A is then performed in reverse order on the opposite side of the jig 570A to form the second half of the device 500A. That is, the strip 501A is then wrapped around the fourth, third, first, second, and first jig portions 578A, 576A, 572A, 574A, 572A to form the second half of the device 500A. Once the strip 501A has been wrapped around the jig portions as described above, a shape-setting operation is performed. While the portions of the illustrated jig have a generally round shape, the portions can have any shape to aid in the folding and shaping of the strip of material 501A. The jig 570 may have more or fewer portions for engaging the strip of material 501A.

Figure 93A:
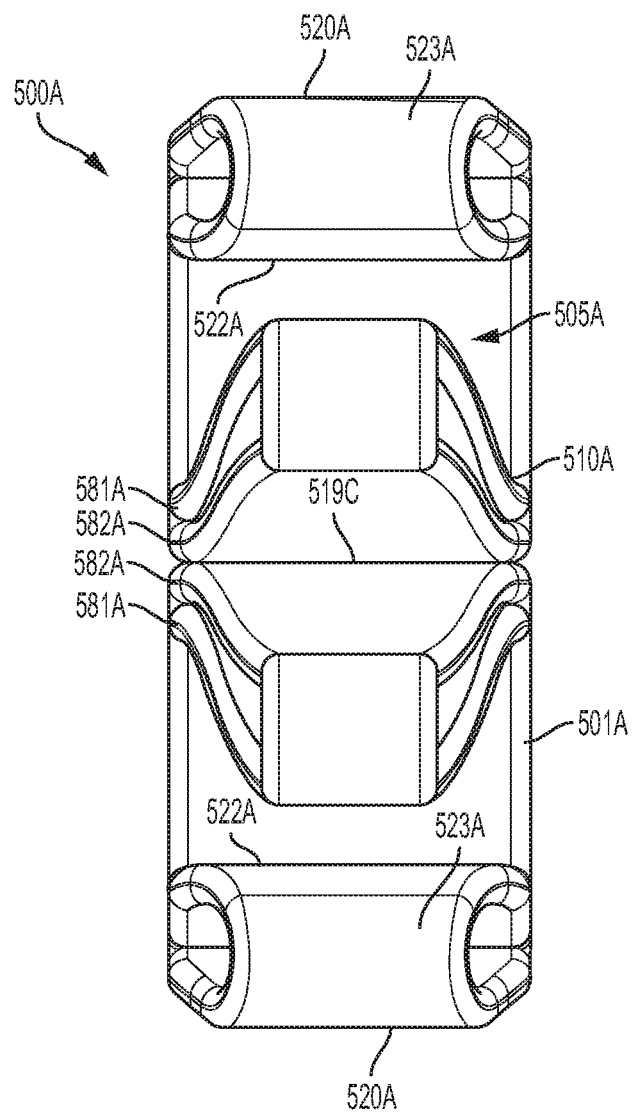

Referring now to FIG. 93A, a top view of the device 500A is shown. The first and second layers 581A, 582A of each half of the device 500A form the four layers of the coaption device 510A. The proximal opening 519C of the coaption device 510A is formed between the two second layers 582A. In some embodiments, the opening 519C is formed by inserting the actuation wire 512A (not shown) between the folded and overlapping layers of the strip of material 501A after shape-setting of the strip of material 501A. In other embodiments, the opening 519C is formed by shape-setting the folded layers 581A, 582A of the strip of material 501A around an additional jig portion (not shown) to give the coaption element 510A a generally rounded shape when viewed from the top.

Figure 94A:
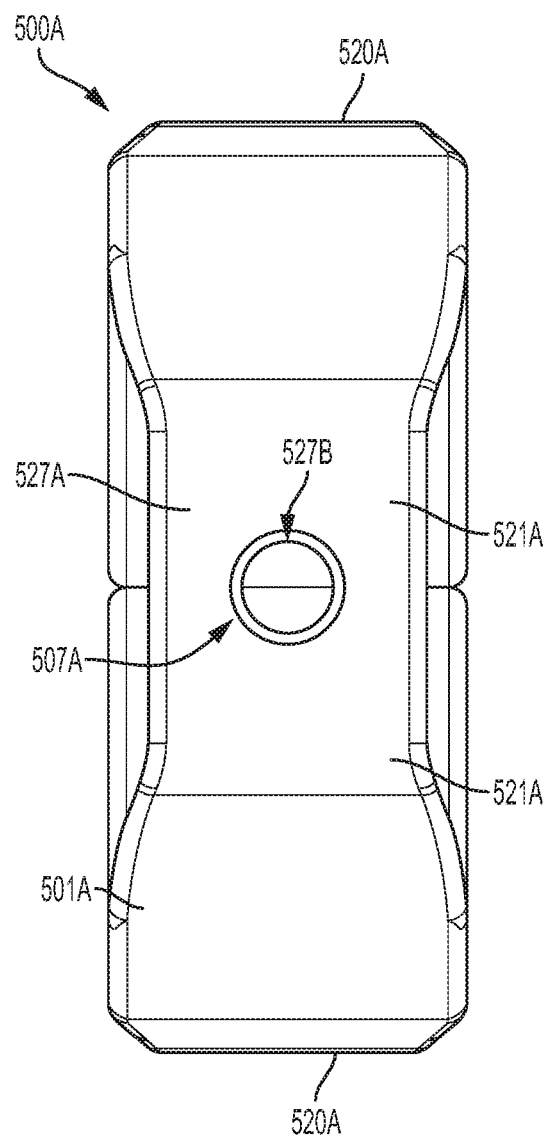

Referring now to FIG. 94A, a bottom view of the device 500A is shown. The distal portion 527A of the strip of material 501A is shown, as is the aperture 527B for receiving the cap 514A. The coaption element 510A and outer paddles 520A have a generally rounded rectangle shape when viewed from below.

Referring now to FIGS. 95-102, perspective and cross-sectional views of the device 500 are shown. Referring now to FIG. 95, the device 500 is shown sliced by cross-section plane 96 near the proximal portion of the coaption element 510. Referring now to FIG. 96, a cross-sectional view of the device 500 is shown as viewed from cross-section plane 96 in FIG. 95. At the location of the plane 96, the coaption element 510 has a generally oval shape with thicker portions along the sides of the coaption element 510. The distal opening 515 is visible from the proximal portion and the coaption element 510 has a hollow interior.

Referring now to FIG. 97, the device 500 is shown sliced by cross-section plane 98 positioned about half of the way between the distal portion 507 and the proximal portion 505 of the coaption element 510. Referring now to FIG. 98, a cross-sectional view of the device 500 is shown as viewed from cross-section plane 98 in FIG. 97. At the location of the plane 98, the coaption element 510 has a generally oval shape that is larger than the oval shape of FIG. 96.

Referring now to FIG. 99, the device 500 is shown sliced by cross-section plane 100 positioned about one-quarter of the way between the distal portion 507 and the proximal portion 505 of the coaption element 510. Referring now to FIG. 99, a cross-sectional view of the device 500 is shown as viewed from cross-section plane 100 in FIG. 99. At the location of the plane 100, the coaption element 510 has a generally oval shape that is narrower than the oval shape seen in FIG. 98.

Referring now to FIG. 101, the device 500 is shown sliced by cross-section plane 102 positioned near the distal portion 507 of the coaption element 510. Referring now to FIG. 102, a cross-sectional view of the device 500 is shown as viewed from cross-section plane 102 in FIG. 101. At the location of the plane 102, the coaption element 510 has a generally oval shape that is smaller than the oval shape seen in FIG. 100 and that is split as the coaption element 510 joins the joint portions 525.

Referring now to FIGS. 95A, 96A, 97A, 98A, 99A, 100A, 101A, and 102A, perspective and cross-sectional views of the portions of the device 500A formed by the single, continuous strip of material 501A are shown. Referring now to FIG. 95A, the device 500A is shown sliced by cross-section plane 96A near the proximal portion of the coaption element 510A. Referring now to FIG. 96A, a cross-sectional view of the device 500A is shown as viewed from cross-section plane 96A in FIG. 95A. At the location of the plane 96A, the coaption element 510 has a generally rectangular shape. In some embodiments, when the actuation wire (not shown) is inserted between the layers 582A of the coaption element 510A, the coaption element 510A remains straight when viewed from the side but bows outward to form a generally round shape when viewed from cross-section plane 96A.

Referring now to FIG. 97A, the device 500A is shown sliced by cross-section plane 98A near the proximal portion of the coaption element 510A. Referring now to FIG. 98A, a cross-sectional view of the device 500A is shown as viewed from cross-section plane 98A in FIG. 97A. At the location of the plane 98A, the coaption element 510 has a generally rectangular shape. In some embodiments, when the actuation wire (not shown) is inserted between the layers 582A of the coaption element 510A, the coaption element 510A remains straight when viewed from the side but bows outward to form a generally round shape when viewed from cross-section plane 98A.

Referring now to FIG. 99A, the device 500A is shown sliced by cross-section plane 100A near the proximal portion of the coaption element 510A. Referring now to FIG. 100A, a cross-sectional view of the device 500A is shown as viewed from cross-section plane 100A in FIG. 99A. At the location of the plane 100A, the coaption element 510 has a generally rectangular shape. In some embodiments, when the actuation wire (not shown) is inserted between the layers 582A of the coaption element 510A, the coaption element 510A remains straight when viewed from the side but bows outward to form a generally round shape when viewed from cross-section plane 100A.

Referring now to FIG. 101A, the device 500A is shown sliced by cross-section plane 102A near the proximal portion of the coaption element 510A. Referring now to FIG. 102A, a cross-sectional view of the device 500A is shown as viewed from cross-section plane 102A in FIG. 101A. At the location of the plane 102A, the coaption element 510 has a generally rectangular shape. In some embodiments, when the actuation wire (not shown) is inserted between the layers 582A of the coaption element 510A, the coaption element 510A remains straight when viewed from the side but bows outward to form a generally round shape when viewed from cross-section plane 102A.

Referring now to FIGS. 103-105, the exemplary implantable prosthetic device 100 is shown having covered and uncovered portions. The device 100 is shown implanted in the native mitral valve MV and secured to the native leaflets 20, 22. As described above, the device 100 includes a coaption element or means for coapting 110, paddles 120, clasps 130, and a cap 114. The paddles 120 and clasps 130 are in a closed position to secure the device 100 to the grasped native leaflets 20, 22 of the mitral valve MV. A proximal portion 105 of the device 100 is exposed to the left atrium LA and a distal portion 107 of the device 100 is exposed to the left ventricle LV.

Referring now to FIG. 103, the device 100 is shown with a covering 900 that covers the entirety of the coaption element or means for coapting 110 and the cap 114. In some embodiments, the covering 900 can be a cloth or fabric such as PET, velour, electrospun or other suitable fabric. In other embodiments, in lieu of or in addition to a fabric, the cover can include a coating (e.g., polymeric) that is applied to the prosthetic spacer device and/or mechanical sealing mechanisms, such as silicone and interlocking joints can be used. The covering 900 can be formed from a metal fabric, such as a mesh, woven, braided, or formed in any other suitable way or a laser cut or otherwise cut flexible material. The covering 900 may be cloth, shape-memory alloy wire—such as Nitinol—to provide shape-setting capability, or any other flexible material suitable for implantation in the human body. The covering 900 prohibits blood flow through coaption element or means for coapting 110 at the proximal portion 105, and also provides a seal between the device 100 and the leaflets 20, 22. Thus, the covering 900 aids in the prohibition of blood flow through the mitral valve MV at the location of the device 100. The covering 900 also prohibits recirculating blood flow from entering the device 100 from the distal portion 107.

Referring now to FIG. 104, the device 100 is shown with a covering 1000 that partially covers the coaption element or means for coapting 110 from the proximal portion 105 of the device 100 to the portion of the coaption element or means for coapting 110 that engages the native leaflets 20, 22. In some embodiments, the cover can be a cloth or fabric such as PET, velour, or other suitable fabric. In other embodiments, in lieu of or in addition to a fabric, the cover can include a coating (e.g., polymeric) that is applied to the prosthetic spacer device. The covering 1000 can be formed from a metal fabric, such as a mesh, woven, braided, or formed in any other suitable way or a laser cut or otherwise cut flexible material. The covering 1000 may be cloth, shape-memory alloy wire—such as Nitinol—to provide shape-setting capability, or any other flexible material suitable for implantation in the human body. Thus, the covering 1000 prohibits blood flow through the coaption element or means for coapting 110 at the proximal portion 105.

Referring now to FIG. 105, the device 100 is shown with a covering 1100 that partially covers the coaption element or means for coapting 110 extending from the portion of the coaption element or means for coapting 110 that engages the native leaflets 20, 22 toward the distal portion 107. The covering 1100 also covers the cap 114. In some embodiments, the cover can be a cloth or fabric such as PET, velour, or other suitable fabric. In other embodiments, in lieu of or in addition to a fabric, the cover can include a coating (e.g., polymeric) that is applied to the prosthetic spacer device. The covering 1100 can be formed from a mesh, woven, braided, or formed in any other suitable way. The covering 1100 may be cloth, electrospun material, and/or shape-memory alloy wire—such as Nitinol—to provide shape-setting capability, or any other flexible material suitable for implantation in the human body. Thus, blood flow can enter the coaption element or means for coapting 110 but is prohibited from passing through the device by the covering 1100 arranged toward the distal portion 107. The covering 1100 also prohibits recirculating blood flow from entering the device 100 from the distal portion 107.

Referring now to FIGS. 106-109, an exemplary coaption element 1200 for an implantable prosthetic device is shown. The coaption element 1200 can be used with any of the implantable prosthetic devices described in the present application. Referring to FIG. 106, the coaption element 1200 has a generally cylindrical shape extending between two caps 1201. However, the coaption element 1200 can have any shape, such as any of the shapes disclosed herein. In one exemplary embodiment, the direction of expansion of the coaption element 1200 can be controlled. For example, the width/size of the coaption element in the Anterior to Posterior direction (when implanted), Medial to Lateral direction (when implanted), or both can be expanded (or contracted) in a controlled manner. The coaption element can be made from a mesh 1200 of material. Referring now to FIG. 107, the mesh wall of the generally cylindrical coaption element 1200 extends outward from the caps 1201 by a distance 1204. Referring now to FIG. 108, axial forces 1208 are applied to the caps 1201 of the coaption element 1200 causing the coaption element 1200 to compress in an axial direction. Compressing the coaption element 1200 axially causes the coaption element 1200 to expand or bulge in an outward direction 1210, such that the distance 1204 increases.

The coaption element 1200 can be compressed in a wide variety of different ways. For example, a threaded connection can be used to draw the two ends of the coaption element together or push the two ends of the coaption element apart. For example, a collar can be provided on each end of the coaption element. One of the collars can threadedly engage a threaded shaft, while the other collar is rotatably connected to the shaft. Rotating the shaft in one direction draws the collars together. Rotating the shaft in the opposite direction moves the collars apart.

Incorporating the coaption element 1200 into an implantable prosthetic device of the present application allows the coaption element to be expanded to press outward against tissue grasped between the coaption element and the paddles and/or gripping members.

Referring now to FIGS. 106A, 108A, 106B, and 108B, exemplary coaption elements 1200, similar to the embodiment illustrated by FIGS. 106-109, for an implantable prosthetic device is shown. The coaption element 1200 can be used with any of the implantable prosthetic devices described in the present application. Referring to FIG. 106A, the coaption element 1200 has a generally cylindrical shape extending between two caps 1201. However, the coaption element 1200 can have any shape, such as any of the shapes disclosed herein. In the example illustrated by FIGS. 106A and 108A, the coaption element 1200 comprises a tube 1203 with slots 1205. For example, the tube 1203 can be made from a shape memory alloy, such as nitinol, and the slots can be cut, such as laser cut, into the tube. The slots can be cut into the material that forms the tube, before the material is formed into a tube.

In one exemplary embodiment, the direction of expansion of the coaption element 1200 can be controlled. For example, the configuration of the slots 1205 and/or a shape-set of the tube can be selected to control the shape of the expanded coaption element 1200. For example, the configuration of the slots 1205 and/or a shape-set can determine the way the width/size of the coaption element in the Anterior to Posterior direction, and/or Medial to Lateral direction expanded (and/or contract). Referring to FIG. 106A, the tube wall of the generally cylindrical coaption element 1200 can extend outward from caps 1201 by a distance 1204. Referring now to FIG. 108A, axial forces 1208 and/or rotational forces 1209 can be applied to the caps 1201 of the coaption element 1200 causing the coaption element 1200 to expand from the configuration illustrated by FIG. 106A to the configuration illustrated by FIG. 108A. In the illustrated example, compressing the coaption element 1200 axially and twisting the coaption element the coaption element 1200 to expand or bulge in an outward direction 1210, such that the distance 1204 increases.

Referring to FIGS. 106B and 108B, the coaption element 1200 can be compressed in a wide variety of different ways. For example, a threaded connection 1221 can be used to draw the two ends of the coaption element together and twist the coaption element in a first direction or push the two ends of the coaption element apart and twist the coaption element in a second direction. For example, a collar can be provided on each end of the coaption element. One of the collars can threadedly engage a threaded shaft, while the other collar is fixedly connected to the shaft. Rotating the shaft in one direction draws the collars together and rotates the collars relative to one another in a first direction. Rotating the shaft in the opposite direction moves the collars apart and rotates the collars relative to one another in a second direction. The pitch of the threaded connection can be selected to set a ratio between the distance the coaption element 1200 is compressed and the angle that the coaption element is twisted.

Incorporating the coaption elements 1200 illustrated by FIGS. 106A, 108A, 106B, and 108B into an implantable prosthetic device of the present application allows the coaption element to be expanded to press outward against tissue grasped between the coaption element and the paddles and/or gripping members.

FIGS. 106C and 108C illustrate another exemplary embodiment of a controllably expandable coaption element 1200 for an implantable prosthetic device. The coaption element 1200 can be used on its own, with a covering, or inside any of the coaption elements described herein (to expand the coaption element). The coaption element 1200 can be used with any of the implantable prosthetic devices described in the present application. Referring to FIG. 106C, the coaption element 1200 has pairs of pivotally connected arms 1231. The pairs of pivotally connected arms 1231 each extending between and pivotally connected to two caps 1201. In the illustrated example, there are two pairs of pivotally connected arms 1231. However, there can be one, three, four, or any number of pairs of pivotally connected arms.

In one exemplary embodiment, the direction of expansion of the coaption element 1200 can be controlled. For example, two pairs (as illustrated) of pivotally connected arms can be included to change the width/size of the coaption element in only one of the Anterior to Posterior direction, and/or Medial to Lateral direction. Four pairs of pivotally connected arms 1231 can be included to change the width/size of the coaption element in both the Anterior to Posterior direction and Medial to Lateral direction. When four pairs of pivotally connected arms 1231 are included, the arms may have different lengths and/or pivot point locations to make the coaption element 1200 expand (or contract) differently in different dictions. For example, the lengths of the arms can be selected to expand more in the Medial to Lateral direction than the Anterior to Posterior direction.

Referring now to FIG. 108C, axial forces 1208 can be applied to the caps 1201 of the coaption element 1200 causing the coaption element 1200 to expand from the configuration illustrated by FIG. 106C to the configuration illustrated by FIG. 108C. In the illustrated example, compressing the pivotally connected arms 1231 axially causes the pivotal connections 1233 or knees to spread apart in an outward direction 1210, such that the distance 1204 increases.

Referring to FIGS. 106C and 108C, the coaption element 1200 can be compressed in a wide variety of different ways. For example, a threaded connection 1221 can be used to draw the two ends of the coaption element together or push the two ends of the coaption element apart. For example, a collar can be provided on each end of the coaption element. One of the collars can threadedly engage a threaded shaft, while the other collar is rotatably connected to the shaft. Rotating the shaft in one direction draws the collars together. Rotating the shaft in the opposite direction moves the collars apart.

Incorporating the coaption element 1200 illustrated by FIGS. 106C, and 108C into an implantable prosthetic device of the present application allows the coaption element to be expanded to press outward against tissue grasped between the coaption element and the paddles and/or gripping members.

FIGS. 106D and 108D illustrate another exemplary embodiment of an expandable coaption element 1200 for an implantable prosthetic device. The coaption element 1200 can be used on its own, with a covering (See FIGS. 106E and 108E), or inside any of the coaption elements described herein (to expand the coaption element). The coaption element 1200 can be used with any of the implantable prosthetic devices described in the present application. Referring to FIG. 106C, the coaption element 1200 has, a central support member 1243, one or more pivotally connected arms 1241, and connection lines 1245. Each arm 1241 extends from a pivotal connection to the central support member 1243. Each connection line 1245 is connected to the central support member 1243 and a pivotally connected arm 1241. The length of the connection line 1245 sets the degree to which the connection arms pivot away from the central support member 1243. In the illustrated example, there are two pivotally connected arms 1241. However, there can be one, three, four, or any number of pivotally connected arms.

In one exemplary embodiment, the direction of expansion of the coaption element 1200 can be controlled. For example, two pivotally connected arms can be included to change the width/size of the coaption element in only one of the Anterior to Posterior direction, and/or Medial to Lateral direction. Four pivotally connected arms 1241 can be included to change the width/size of the coaption element in both the Anterior to Posterior direction and Medial to Lateral direction. When four pivotally connected arms 1241 are included, the arms and/or the connection lines 1245 may have different lengths and/or pivot point locations to make the coaption element 1200 expand (or contract) differently in different dictions. For example, the lengths of the arms and/or the connection lines can be selected to expand more in the Medial to Lateral direction than the Anterior to Posterior direction.

The arms 1241 can be moved from the contracted position (FIG. 106D) to the expanded position (FIG. 108D). For example, the arms 1241 can be biased toward the expanded position 1241 by a spring or other biasing means. In the illustrated example, restraints 1247, such as sutures hold the arms 1241 in the contracted position. The restraints 1247 can be removed or broken to cause the coaption element 1200 to expand from the configuration illustrated by FIG. 106D to the configuration illustrated by FIG. 108D.

FIGS. 106E and 108E illustrate an exemplary embodiment that is similar to the embodiment illustrated by FIGS. 106D and 108D, except that the coaption element includes a covering material 1253. The covering material 1253 can extend from the central support member 1243 to each arm 1241. The covering material 1253 can be used with the connection lines 1245 or the covering material can eliminate the need for the connection lines 1245.

Referring now to FIG. 106F, an exemplary coaption element 1200, similar to the embodiment illustrated by FIGS. 106-109, for an implantable prosthetic device is shown. The coaption element 1200 can be used with any of the implantable prosthetic devices described in the present application. Referring to FIG. 106F, the coaption element 1200 is defined by a coil 1263 extending between two caps 1201. The coaption element 1200 can have any shape, such as any of the shapes disclosed herein. The coil 1263 can be made from a shape memory alloy, such as nitinol.

In one exemplary embodiment, the direction of expansion of the coaption element 1200 can be controlled. For example, the shape-set of the coil 1263 can be selected to control the shape of the expanded coaption element 1200. For example, the configuration of the shape-set can determine the way the width/size of the coaption element in the Anterior to Posterior direction, and/or Medial to Lateral direction expand (and/or contract). Referring to Axial forces 1208 and/or rotational forces 1209 can be applied to caps 1201 of the coaption element 1200 causing the coaption element 1200 to expand or retract from the configuration illustrated by FIG. 106F. In the illustrated example, extending the coil 1263 axially and twisting the coil 1263 contracts the coil in an inward direction 1211 and compressing the coil 1263 axially and twisting the coil in the opposite direction expands or bulge the coil in an outward direction.

Referring to FIG. 106F, the coaption element 1200 can be compressed in a wide variety of different ways. For example, a threaded connection 1221 can be used to draw the two ends of the coaption element together and twist the coaption element in a first direction or push the two ends of the coaption element apart and twist the coaption element in a second direction. For example, a collar can be fixedly connected to each end of the coil 1263. One of the collars can threadedly engage a threaded shaft, while the other collar is fixedly connected to the shaft. Rotating the shaft in one direction draws the collars together and rotates the collars relative to one another in a first direction. Rotating the shaft in the opposite direction moves the collars apart and rotates the collars relative to one another in a second direction. The pitch of the threaded connection can be selected to set a ratio between the distance the coaption element 1200 is compressed and the angle that the coaption element is twisted.

Incorporating the coaption elements 1200 illustrated by FIG. 106F into an implantable prosthetic device of the present application allows the coaption element to be expanded to press outward against tissue grasped between the coaption element and the paddles and/or gripping members.

FIGS. 106G-106I illustrate exemplary embodiments of expandable coaption elements 1200. In the examples illustrated by FIGS. 106G-106I, the coaption elements are inflated by a fluid medium to expand the coaption element. The fluid medium can take a wide variety of different forms. Examples of fluids that can be used to inflate the coaption element 1200 include, but are not limited to, air, gel, water, blood, foaming materials, etc. The coaption element 1200 can be used with any of the implantable prosthetic devices described in the present application.

Referring to FIG. 106G, the coaption element 1200 can have an outer layer 1271 (For example, any of the coaption elements 110, 510 disclosed herein) and an inner layer 1273 or balloon. The coaption element 1200 can have any shape, such as any of the shapes disclosed herein. In the example illustrated by FIGS. 106G and 1086, the inner layer 1273 is disposed in the outer layer 1271 and can have generally the same shape as the inner surface of the outer layer. The inner layer can be made from an expandable material, such as a rubber or other material traditionally used for making balloons and angioplasty devices. The outer layer 1271 can be made from a shape memory alloy, such as nitinol.

Referring to FIGS. 106H and 106I, in one exemplary embodiment, the direction of expansion of the coaption element 1200 can be controlled. In the example illustrated by FIG. 106H, the inner layer 1273 comprises two balloons that are optionally connected together. However, any number of balloons can be used. For example, the inner layer can comprise 3, 4, or any number of balloons. The balloons can be individually inflated to control the shape of expansion of the coaption element 1200. When the balloons are connected together, the connection can also affect the shape of expansion. In the example illustrated by 106H, the balloons are connected together along a plane 1275 or area. Expansion of the inner layer 1273 in the direction 1277 will be less than the expansion in the direction 1279 due to the connection 1275. As such, in this example, the expansion due to inflation can be limited to or substantially limited to expansion in the Medial to Lateral direction.

The use of multiple balloons and the configuration of any connections between the balloons can determine the way the width/size of the coaption element in the Anterior to Posterior direction, and/or Medial to Lateral direction expand (and/or contract).

In the example illustrated by FIG. 106I, the inner layer 1273 comprises one or more supports 1281 or struts. One support 1281 is illustrated, but any number can be used. For example, the inner layer can comprise 2, 3, 4, or any number of supports. The supports 1281 can divide the inner layer into multiple independently inflatable chambers or the supports may not seal off independent chambers and inflation fluid applied to any chamber will fill all of the chambers. When there are independently inflatable chambers, the chambers can be individually inflated to control the shape of expansion of the coaption element 1200. The supports also affect the shape of expansion. In the example illustrated by 106I, the support 1281 will reduce or eliminate expansion of the inner layer 1273 in the direction 1277. As such, in this example, the expansion due to inflation can be limited to or substantially limited to expansion in the Medial to Lateral direction.

The use of multiple independently inflatable chambers and/or the configuration of the support members 1281 can determine the way the width/size of the coaption element in the Anterior to Posterior direction, and/or Medial to Lateral direction expand (and/or contract).

Incorporating the coaption elements 1200 illustrated by FIGS. 106G-106I into an implantable prosthetic device of the present application allows the coaption element to be expanded to press outward against tissue grasped between the coaption element and the paddles and/or gripping members.

Referring now to FIGS. 110-111, an exemplary implantable prosthetic device 1300 is shown. The device 1300 is similar to the device 100, described above, and includes a coaption element 1310, paddles 1320, and clasps or gripping members 1330. Referring now to FIG. 111, a top view of the coaption element 1310 is shown. As can be seen in FIG. 111, the coaption element 1310 has a generally oval-shaped cross-section. The coaption element 1310 does not include a central opening and can be formed from a solid piece of material, such as foam. Forming the coaption element 1310 from a solid piece of foam material prohibits blood from flowing through the center of the coaption element 1310, thereby substantially eliminating a location where blood can be captured. The device 1300 can include any other features for an implantable prosthetic device discussed in the present application, and the device 1300 can be positioned to engage valve tissue 20, 22 as part of any suitable valve repair system (e.g., any valve repair system disclosed in the present application). The prosthetic device 1300 can be opened and closed in a wide variety of different ways. For example, a sleeve can be slidably disposed over the coaption element to engage and open the paddles. Or, the paddles can be opened by pulling a line or suture that opens the clasps and the movement of the clasps can open the paddles. However, any mechanism for opening and closing the device 1300 can be used.

Referring now to FIGS. 112-128, an exemplary paddle frame 1400 for an implantable prosthetic device is shown. The paddle frame 1400 can be used with any of the implantable prosthetic devices described in the present application. The paddle frame 1400 is formed from a piece of material 1402, such as nitinol, or any other suitable material. The paddle frame 1400 extends from a cap attachment portion 1410 to a paddle connection portion 1420 and has a proximal portion 1422, a middle portion 1424, and a distal portion 1426. In some embodiments, the paddle frame 1400 includes attachment portions 1440 for securing a cover (see FIG. 30), the inner paddle 520, and/or the outer paddle 522 to the paddle frame 1400. In some embodiments, the paddle frame 1400 is thinner in the location of the fifth curve 1438 to facilitate bending of both sides of the paddle frame 1400 toward the center plane 1404 during, for example, crimping of the device.

The paddle frame 1400 extends between a first attachment portion 1412 in a generally rounded, three-dimensional shape through the proximal, middle, and distal portions 1422, 1424, 1426 and returns to a second attachment portion 1414. To form a rounded three-dimensional shape, the paddle frame 1400 is bent or curved in multiple locations as the paddle frame 1400 extends between the first and second attachment portions 1412, 1414. The attachment portions 1412, 1414 include notches 1416, 1418 respectively for attachment to the cap. The paddle frame 1400 flexes at the area 1419. The area 1419 can include a wider portion 1417 to distribute the stress that results from flexing the paddle frame 1400 over a greater area. Also, notches 1416, 1418 can include radiused notches 1415 at each end of the notches. The radiused notches 1415 serve as strain reliefs for the bending area 1419 and the area where the paddle frame 1400 connects to the cap.

The paddle frame 1400 curves away from a median or central plane 1404 (FIG. 115) at a first curve 1430 to widen the shape of the paddle frame 1400. As can be seen in FIG. 117, the paddle frame 1400 also curves away from a frontal plane 1406 in the location of the first curve 1430. The paddle frame 1400 curves away from the outward direction of the first curve 1430 at a second curve 1432 to form sides of the frame 1400. The paddle frame continues to slope away from the frontal plane 1406 in the location of the second curve 1432. In some embodiments, the second curve 1432 has a larger radius than the first curve 1430. The paddle frame 1400 curves away from the frontal plane 1406 at a third curve 1434 as the paddle frame 1400 continues to curve in the arc of the second curve 1432 when viewed from the frontal plane 1406. This curvature at the third curve 1434 results in a gradual departure of the frame 1400, and thus the native valve leaflet from the centerline 1406. This departure from the centerline results in spreading of the leaflet tissue toward the valve annulus, which can result in less stress on the leaflet tissue. The paddle frame 1400 curves toward the lateral plane 1404 at a fourth curve 1436 as the frame 1400 continues to curve away from the frontal plane 1406. The rounded three-dimensional shape of the paddle frame 1400 is closed with a fifth curve 1438 that joins both sides of the paddle frame 1400. As can be seen in FIGS. 116 and 118, the paddle frame 1400 has a generally arcuate shape as the frame 1400 extends away from the attachment portion 1420 and to the closed portion 1424. The middle portion 1422 of the frame is closer to the frontal plane 1406 than the closed portion 1424, giving the sides of the middle portion 1422 a rounded, wing-like shape that engages the curved surface of coaption element (not shown) during grasping of native tissue between a paddle (not shown) and coaption element of an implantable device of the present invention.

Referring to FIG. 191, in another exemplary embodiment, a flat blank 1403 of paddle frame 1400 can be cut, for example laser cut, from a flat sheet of material. Referring to FIG. 192, the cut blank 1403 can then be bent to form the three-dimensional shaped paddle frame 1400.

Referring to FIGS. 193 and 194, in one exemplary embodiment, the paddle frames 1400 can be shape-set to provide increased clamping force against or toward the coaption element 510 when the paddles 520, 522 are in the closed configuration. This is because the paddle frames are shape-set relative to the closed position (e.g. FIG. 194) to a first position (e.g., FIG. 193) which is beyond the position where the inner paddle 520 would engage the coaption element, such as beyond the central plane 552 of the device 500, such as beyond the opposite side of the coaption element, such as beyond the outer paddle on the opposite side of the coaption element. Referring to FIG. 194, the paddle frame 194 is flexed and attached to the inner and outer paddles 522, 520, for example by stitching. This results in the paddle frames having a preload (i.e., the clamping force against or toward the coaption element is greater than zero) when the paddle frames 1400 are in the closed configuration. Thus, shape-setting the paddle frames 1400 in the FIG. 193 configuration can increase the clamping force of the paddle frames 1400 compared to paddle frames that are shape-set in the closed configuration (FIG. 194).

The magnitude of the preload of the paddle frames 1400 can be altered by adjusting the degree to which the paddle frames 1400 are shape-set relative to the coaption element 510. The farther the paddle frames 1400 are shape-set past the closed position, the greater the preload.

The curves of the paddle frame 1400 may be independent from one another, that is, one curve is complete before another curve starts, or may be combined, that is, the paddle frame 1400 curves in multiple directions simultaneously.

Referring now to FIGS. 112A, 114A, 115A, 116A, 117A, and 118A, exemplary paddle frames 1400A for an implantable prosthetic device are shown. The paddle frames 1400A can be used with any of the implantable prosthetic devices described in the present application. Each paddle frame 1400A is formed from a piece of material 1402A, such as nitinol, or any other suitable material. Each paddle frame 1400A extends from a cap attachment portion 1410A to a paddle connection portion 1420A and has a proximal portion 1422A, a middle portion 1424A, and a distal portion 1426A.

Each paddle frame 1400A extends between a first attachment portion 1412A in a generally rounded, three-dimensional shape through the proximal, middle, and distal portions 1422, 1424, 1426 and returns to a second attachment portion 1414. To form a rounded three-dimensional shape, each paddle frame 1400A is bent or curved in multiple locations as the paddle frame 1400A extends between the first and second attachment portions 1412A, 1414A. The attachment portions 1412A, 1414A include notches 1416A, 1418A respectively for attachment to the cap. The paddle frames 1400A flex at the area 1419A. The area 1419A can include a wider portion 1417A to distribute the stress that results from flexing the paddle frame 1400A over a greater area. Also, notches 1416A, 1418A can include radiused notches 1415A at each end of the notches 1416A, 1418A. The radiused notches 1415A serve as strain reliefs for the bending area 1419A and the area where the paddle frame 1400A connects to the cap.

Each paddle frame 1400A curves away from a median or central plane 1404A (FIG. 116A) at a first curve 1430A to widen the shape of the paddle frame 1400A. As can be seen in FIG. 114A, the paddle frame 1400A also curves away from a frontal plane 1406A in the location of the first curve 1430A. The paddle frame 1400A curves away from the outward direction of the first curve 1430A at a second curve 1432A to form sides 1433A of the frame 1400A that are substantially parallel to the central plane 1404A when viewed from the frontal plane 1406A. The paddle frame continues to slope away from the frontal plane 1406A in the location of the second curve 1432A. In some embodiments, the second curve 1432A has a larger radius than the first curve 1430A. The paddle frame 1400A curves back toward from the frontal plane 1406A at a third curve 1434A in the middle portion 1424A while the sides 1433A of the paddle frame 1400A remain substantially parallel to the central plane 1404A. The paddle frame 1400A curves away from the central plane 1404A a second time at a fourth curve 1436A and continues to curve away from the central plane 1404A through the remainder of the middle and distal portions 1424A, 1426A. The rounded three-dimensional shape of the paddle frame 1400A is closed by an end portion 1442A connected to the sides 1433A by fifth curves 1438A that form rounded corners of the distal end 1426A of the paddle frame 1400A.

The end portion 1442A may be wider than the remainder of the paddle frame 1400A to accommodate features that allow the paddle frames 1400A to be attached to the paddles (not shown) and cover (not shown). For example, the end portion 1442A may include a slot 1444A for receiving a portion of a strip of material, such as the strip of material 401A, 501A described above. An opening 1446A in the end portion 1442A allows a strip of material to be inserted into the slot 1444A. The end portion 1442A may also include attachment holes 1440A for securing a cover (see FIG. 30A) to the paddle frame 1400A.

As can be seen in FIGS. 116A and 117A, the paddle frame 1400A has a generally rounded rectangle shape as the frame extends away from the attachment portion 1410A to the closed end of the paddle connection portion 1420A. The middle portion 1424A of the frame is closer to the frontal plane 1406A than the distal portion 1426A, giving the sides of the middle portion 1424A a rounded, wing-like shape that engages the front and back surfaces of the coaption element (not shown) during grasping of native tissue between a paddle (not shown) and coaption element of an implantable device described herein.

Referring to FIGS. 195 and 196, the paddle frames 1400A are shown assembled to the collar 514A of an exemplary implantable device, such as the device 500A described above. In one exemplary embodiment, the paddle frames 1400A can be shape-set to provide increased clamping force against or toward a coaption element 510A when the paddles 520A, 522A are in the closed configuration. This is because the paddle frames 1400A are shape-set relative to the closed position (e.g., FIG. 196) to a first position (e.g., FIG. 195) which is beyond the position where the inner paddle 522A would engage the coaption element 510A, such as beyond the central plane 552A of the device 500A (e.g., FIG. 70A), such as beyond the opposite side of the coaption element, such as beyond the outer paddle on the opposite side of the coaption element. In the first position the sides 1433A of the paddle frames 1400A are intertwined in that the sides 1433A of one paddle frame 1400A are moved slightly laterally to allow movement past the sides 1433A of the other paddle frame 1400A until the end portions 1442A of each frame 1400A contact each other and the sides 1433A and prevent further movement.

The magnitude of the preload of the paddle frames 1400A can be altered by adjusting the degree to which the paddle frames 1400A are shape-set relative to the coaption element 510A. The farther the paddle frames 1400A are shape-set past the closed position, the greater the preload force when the paddle frames 1400A are moved into the open position.

The curves of the paddle frame 1400A may be independent from one another, that is, one curve is complete before another curve starts, or may be combined, that is, the paddle frame 1400A curves in multiple directions simultaneously.

Like the paddle frame 1400 shown in FIGS. 191 and 192, in an exemplary embodiment, the paddle frame 1400A can be formed from a flat blank that is cut from a flat sheet of material, for example, by laser cutting. The cut blank can then be bent to form the three-dimensional shape of the paddle frame 1400A.

Referring now to FIGS. 119-120, the paddle frame 1400 is shown in an expanded condition (FIG. 119) and a compressed condition (FIG. 120). The paddle frame 1400 is in a compressed condition when the paddles are disposed in a delivery device 1450. Referring to FIG. 119, the paddle frame 1400 is moved from the expanded condition to the compressed condition by compressing the paddle in the direction X and extending a length of the paddle in the direction Y. When the paddles 1400 are in the compressed condition, the paddles have a width H. The width H can be, for example between about 4 mm and about 7 mm, such as, between about 5 mm and about 6 mm. In alternative embodiments, the width H can be less than 4 mm or more than 7 mm. In certain embodiments, the width H of the compressed paddles 1400 is substantially equal to a width D of the delivery opening 1452 of the delivery device 1450. The ratio between the width W of the paddles in the expanded condition and the width H of the paddles in the compressed condition can be, for example, about 4 to 1 or less, such as about 3 to 1 or less, such as about 2 to 1 or less, such as about 1.5 to 1, such as about 1.25 to 1, such as about 1 to 1. In alternative embodiments, the ratio between the width W and the width H can be more than 4 to 1. FIG. 120 illustrates the connection portions 1410 compressed from the positions illustrated by FIG. 119. However, in some exemplary embodiments, the connection portions 1410 will not be compressed. For example, the connection portions 1410 will not be compressed when the connection portions 1410 are connected to a cap 514. The paddle frame 1400A shown in FIGS. 112A and 114A-118A can be similarly compressed.

Referring now to FIGS. 121-124, the exemplary implantable device 500 is shown in open and closed conditions with paddle frames that are compressed or stretched as the anchor portion 506 of the device is opened and closed. The paddle frames 1524 are like the paddle frame 1400 described above. Referring now to FIG. 121, the anchor portion 506 is shown in a closed condition. Referring now to FIG. 122, the paddle frames 1524 have a first width W1 and a first length L1. Referring now to FIG. 123, the anchor portion 506 is shown in an open condition and the paddle frames 1524 are in an extended condition (FIG. 124). Opening the anchor portion 506 of the device 500 causes the paddle frames 1524 to pivot outward from the coaption portion 510 and transition to the extended condition. In the extended condition, the paddle frames 1524 have a second or extended length L2 and a second or extended width W2. In the extended condition, the paddle frame 1524 lengthens and narrows such that the second length L2 is greater than the first length L1 and the second width W2 is narrower than the first width W1. One advantage of this embodiment is that the paddle frames become narrower and can have less chordal engagement during grasping of the leaflets. However, the paddle frames become wide when the implant is closed to enhance support of the leaflet. Another advantage of this embodiment is that the paddle frames also become narrower and longer in the bailout position. The narrower paddle size in the elongated or bailout position can allow for less chordal entanglement and increased ease of bailout.

Referring now to FIGS. 125-128, the exemplary implantable device 500 is shown in open and closed conditions with paddle frames that are compressed or stretched as the anchor portion 506 of the device is opened and closed. The paddle frames 1624 are similar to the paddle frame 1400 described above. Referring now to FIG. 125, the anchor portion 506 is shown in a closed condition. Referring now to FIG. 126, the paddle frames 1624 have a first width W1 and a first length L1. Referring now to FIG. 127, the anchor portion 506 is shown in an open condition and the paddle frames 1624 are in a compressed condition (FIG. 128). Opening the anchor portion 506 of the device 500 causes the paddle frames 1624 to pivot outward from the coaption portion 510 and transition to the compressed condition. In the compressed condition, the paddle frames 1624 have a second or compressed length L2 and a second or compressed width W2. In the compressed condition, the paddle frame 1624 shortens and widens such that the second length L2 is less than the first length L1 and the second width W2 is wider than the first width W1.

Referring now to FIGS. 129-136, exemplary implantable prosthetic devices are shown that can be locked or fastened closed. Referring now to FIG. 129, the exemplary implantable prosthetic device 500 is shown that can be locked or retained in a closed condition with magnets. As described above, the device 500 includes a coaption element 510 and paddles 520. The paddles 520 open and close to grasp leaflets 20, 22 of the native heart valve, as described in more detail above. The coaption element 510 includes one or more magnets 1700 and the paddles 520 include one or more magnets 1702. The magnets 1700, 1702 have opposite poles facing each other such that the magnets 1702 in the paddles 520 are attracted to the magnets 1700 in the coaption element 510 and the magnetic attractive forces between the magnets 1700, 1702 retain the paddles 520 in a closed condition. In certain embodiments, the magnets 1700, 1702 are programmed or polymagnets with patterns of polarity such that the implantable device 500 can be locked and unlocked by moving—such as rotating—the magnet 1700 within the coaption element. For example, the magnet 1700 can be configured such that the magnet 1700 attracts the magnets 1702 in the paddles 520 in a first orientation and repels the magnets 1702 in the paddles 520 when the magnet 1700 is rotated 90 degrees into a second orientation.

Referring now to FIGS. 130-131, the exemplary implantable prosthetic device 500 is shown that can be locked or retained in a closed condition with an elastic band 1800. The elastic band 1800 can be made from any flexible material and have any configuration. For example, the elastic band can comprise coiled nitinol, can have a stent like structure, etc.

As described above, the device 500 includes a coaption element 510, paddles 520, and barbed clasps 530. The paddles 520 and barbed clasps 530 open and close to grasp leaflets 20, 22 of the native heart valve, as described in more detail above. The paddles 520 move between an open condition (FIG. 130) to a closed condition (FIG. 131) by actuation of an actuation wire or shaft 512, as described above. The elastic band 1800 can be arranged to lock or retain the device 500 in a closed condition. When the device 500 is in the open condition (FIG. 130) the band 1800 is arranged around the paddles 520 in a relaxed or disengaged condition. For example, the band 1800 may be arranged around a narrower portion of the open device 500, such as a tapered portion of the paddles 520 near a distal portion 507 of the device. When the device 500 is in the closed condition (FIG. 131) the band 1800 is arranged around the paddles 520 in an engaged condition. In certain embodiments, when the band 1800 is in the engaged condition it is arranged around the widest portion of the device 500 or can be arranged around the center of the device 500.

The band 1800 is moved from the disengaged condition in a closing or engaging direction 1802 to the engaged condition with sutures (not shown) or other suitable means of moving the band 1800. Movement of the band 1800 can cause the paddles 520 to move in a closing direction 1804, thereby closing and securing the device 500 in a single movement of the band 1800. Alternatively, device 500 may be closed and the band 1800 moved into the engaged location to secure the device 500 in the closed condition.

Referring now to FIG. 132, the exemplary implantable prosthetic device 500 is shown that can be locked or retained in a closed condition with a biasing member 1900. As described above, the device 500 includes a coaption element 510, paddles 520, and barbed clasps 530. The paddles 520 are moved between open and closed positions with an actuation wire 512 extending through the coaption element 510 to a cap 514. The paddles 520 and barbed clasps 530 are opened and closed to grasp leaflets 20, 22 of the native heart valve, as described in more detail above. In the closed condition, the paddles 520 and the clasps 530 engage the tissue of valve leaflets 20, 22 and each other to secure the device 500 to the valve tissue.

The biasing member 1900 (e.g., a spring) is configured to bias the cap 514 toward the coaption element 510, thereby biasing the device 500 toward the closed condition. After the device 500 is delivered to and attached to the valve tissue with a delivery device (not shown), the delivery device is removed from the patient's body and the biasing member 1900 maintains the device 500 in a closed condition to prevent detachment of the device 500 from the valve tissue.

Referring now to FIGS. 133-134, an exemplary implantable prosthetic device 2000 is shown that can be locked or retained in a closed condition with latches. The device 2000 can include any other features for an implantable prosthetic device discussed in the present application, and the device 2000 can be positioned to engage valve tissue 20, 22 as part of any suitable valve repair system (e.g., any valve repair system disclosed in the present application).

The device 2000 is similar to other implantable devices described above and includes paddles 2002 and gripping members or clasps 2004. The paddles 2002 are opened and closed to grasp the native leaflets 20, 22 in a gap 2006 between the paddles 2002 and gripping members 2004. The device 2000 also includes a latch member 2008 attached to the paddles 2002, in which the latch member 2008 is configured to attach the paddles 2002 to the gripping members 2004 when the device 2000 is in the closed position. In some embodiments, the latch member 2008 serves as a secondary latching mechanism and is configured to keep the device 2000 in the closed position when other mechanisms fail.

Referring to FIG. 133, the device 2000 is in an open position with valve tissue 20, 22 disposed in the gap or opening 2006 between the paddles 2002 and the gripping members 2004. Referring to FIG. 134, the device 2000 is moved to the closed position such that the valve tissue 20, 22 is secured between the paddles 2002 and the gripping members 2004. The device 2000 can be moved to the closed position by any suitable manner, such as, for example, any manner described in the present application. When the device 2000 is moved to the closed position, the latch member 2008 punctures the valve tissue 20, 22 and is inserted into or through the gripping member 2004 to secure the paddle 2002 to the gripping member 2004. The latch member 2008 can take any suitable form that can secure the paddles 2002 to the gripping members 2004, such as, for example, metals, plastics, etc.

Referring now to FIGS. 135-136, the exemplary implantable prosthetic device 2000 is shown that can be locked or retained in a closed condition with latches. In FIGS. 135-136, the device 2000 includes a coaption element 2010. Referring to FIG. 135, the device 2000 is in an open position with valve tissue 20, 22 disposed in the gap or opening 2006 between the paddles 2002 and the gripping members 2004. Referring to FIG. 136, the device 2000 is moved to the closed position such that the valve tissue 20, 22 is secured between the paddles 2002 and the gripping members 2004. The device 2000 can be moved to the closed position by any suitable manner, such as, for example, any manner described in the present application. When the device 2000 is moved to the closed position, the latch member 2008 punctures the valve tissue 20, 22 and is inserted into or through the gripping member 2004 to secure the paddle 2002 to the gripping member 2004. In the illustrated embodiment, the latch member 2008 protrudes beyond the gripping members 2004 and into the coaption element 2010. In some embodiments, the latch member 2008 may be secured in the coaption element 2010 by latching onto a portion of the coaption element 2010 or by penetrating the coaption element 2010 material. The latch member 2008 can take any suitable form that can secure the paddles 2002 to the gripping members 2004, such as, for example, metals, plastics, etc.

Referring now to FIGS. 137-145, various embodiments of implantable prosthetic devices and methods of using the same are shown that facilitate release of native tissue grasped by the implantable prosthetic devices. The devices can include any other features for an implantable prosthetic device discussed in the present application, and the devices can be positioned to engage valve tissue 20, 22 as part of any suitable valve repair system (e.g., any valve repair system disclosed in the present application).

Referring now to FIG. 137, a device 2100 with stretchable clasps or gripping members is shown. The device 2100 is delivered from a delivery sheath 2102 and has a coaption element 2110, paddles 2120, and clasps or gripping members 2130. The gripping members 2130 include barbs 2132 and stretchable portions 2134. The stretchable portions 2134 allow the clasps 2130 to be stretched in a stretching direction 2136. Actuation sutures 2104 extend from the delivery sheath 2102 to the clasps 2130. Retracting the sutures 2104 in a retraction direction 2106 opens and stretches the clasps 2130 to a fully extended position. In certain embodiments, the clasps 2130 primarily stretch once the clasps 2130 are in the fully open position. Movement of the barbs 2132 in the stretching direction 2136 allows for clean disengagement from the native tissue. In some embodiments, the stretchable portion 2134 is configured to be moved such that the barbs 2132 exit the valve tissue in a direction substantially opposite the direction in which the barbs entered the native tissue. Alternatively, the clasps 2130 can be otherwise extendable to allow for disengagement from the native tissue without tearing the native tissue. For example, joint portions 2131 can be configured to allow the barbs 2132 of the clasps 2130 to be pulled in the direction 2136.

Referring now to FIGS. 138-143, two exemplary embodiments of methods of releasing valve tissue from the prosthetic device 500 are shown. As described above, the device 500 includes a coaption element 510, inner paddles 522, outer paddles 520, and barbed clasps 530. The device 500 is deployed from a delivery sheath 502. An actuation wire 512 extends through the coaption element 510 to a cap 514. Actuation of the actuation wire 512 opens and closes the paddles 520, 522 to open and close the device. The barbed clasps 530 include barbs 536, moveable arms 534, and stationary arms 532. The stationary arms 532 are attached to the inner paddles 522 so that the clasps 530 move with the movement of the inner paddles 522. Actuation sutures 537 extend from the delivery sheath 502 to the moveable arms 534 of the clasps 530.

Figure 141:
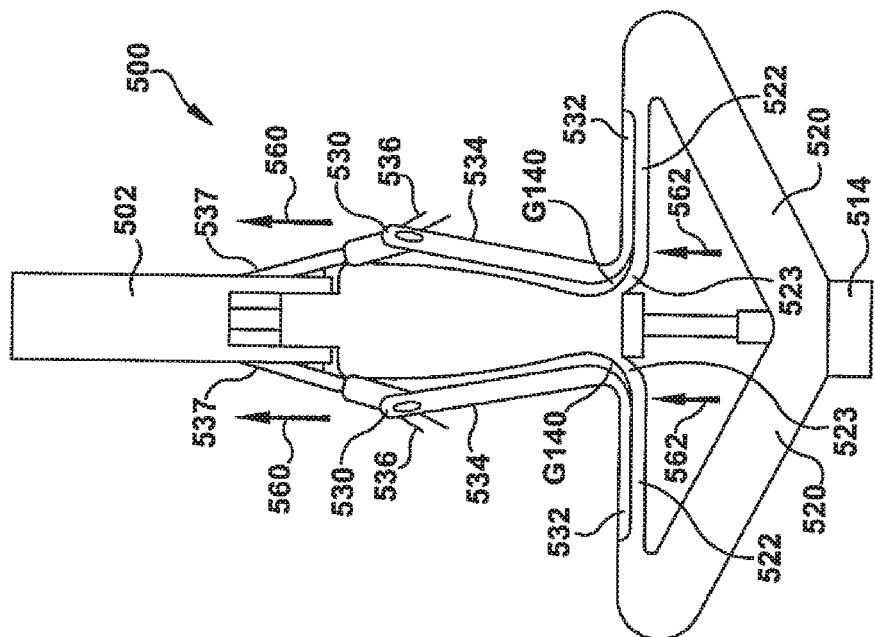
Figure 143:
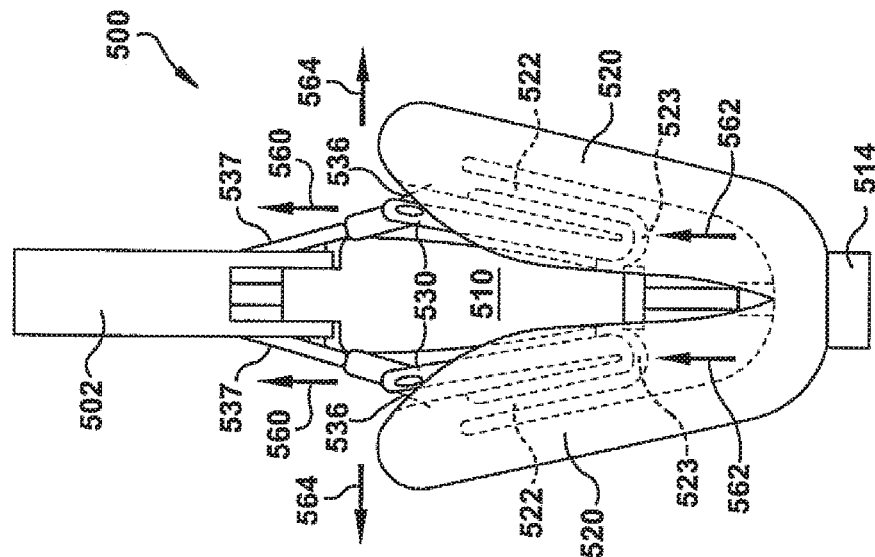
Figure 142:
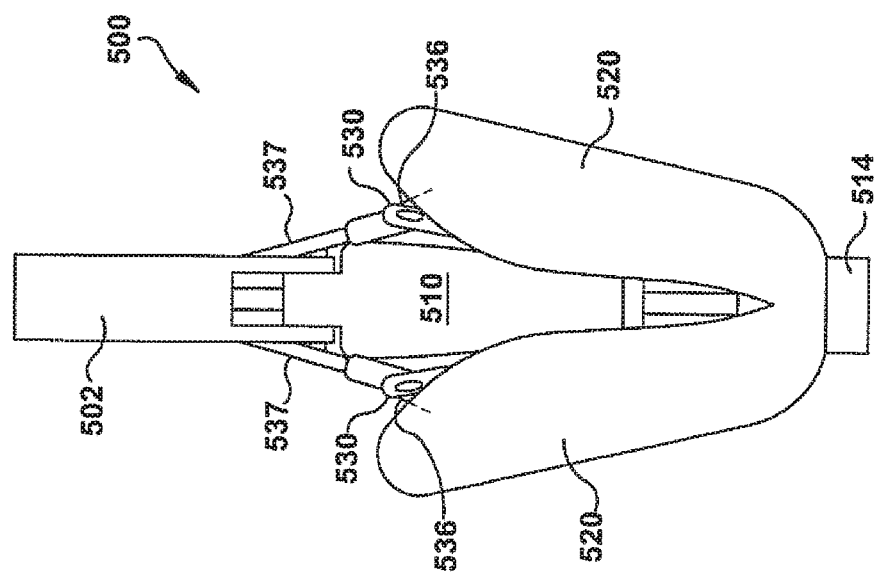

FIGS. 138-141 illustrate an exemplary method of releasing grasped valve tissue. In the example illustrated by FIGS. 138-141, the device is shown in a substantially open position to more clearly illustrate the movements of the parts of the device 500 that are involved with tissue release. However, in practice the tissue release method is more likely to be practiced with the device 500 in the more closed positions illustrated by FIGS. 142 and 143. That is, it is not likely that the paddles and clasps will be substantially opened before moving the clasps to release the valve tissue as illustrated by FIGS. 138-141. It is more likely that the paddles and clasps will only be opened slightly before releasing the valve tissue as illustrated by FIGS. 142 and 143. The same parts that move in the example illustrated by FIGS. 138-141 move in the example illustrated by FIGS. 142-143.

Figure 140:
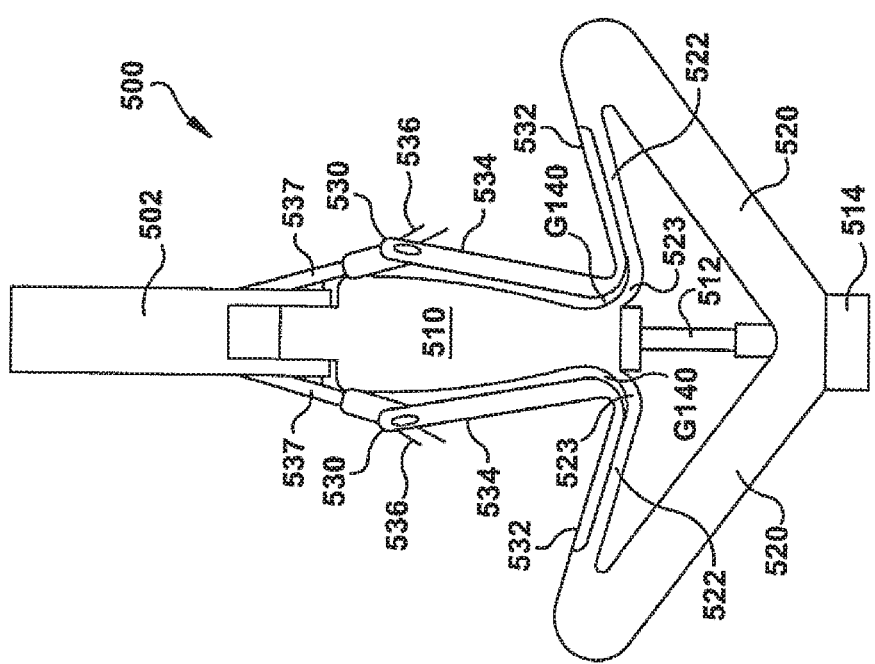

Referring now to FIG. 138, the device 500 is shown in a substantially open position with the clasps 530 in a closed position. Retraction of the actuation sutures 537 pivots the moveable arms 534 of the clasps 530 to a partially open position (FIG. 139) and then to a fully open position (FIG. 140). Referring now to FIG. 141, once the clasps 530 are in the fully open position (FIG. 140), further retraction of the actuation sutures 537 in the retraction direction 560 pulls upward on the moveable arms 534, barbs 536, and inner paddles 522 in a tissue release direction. The portion 523 of the inner paddles 522 closest to the coaption element flex upward in direction 562 to allow this movement in the retraction direction 560. There can optionally be a small gap $G_{140}$ between the claps 530 and the coaption element 510. The inner paddles can flex at the small gap (if there is a small gap) or at the connection 523 between the coaption element 510 and the inner paddles if there is not a gap. This flexing movement 562 of the inner paddles 522 can optionally also cause the outer paddles to pivot downward. Movement of the barbs 536 in the tissue release direction 560 allows for clean disengagement from the native tissue. The barbs can be at an angle θ (see FIG. 138) to the moveable arms 534 that facilitates release from the tissue. For example, the angle θ can be between 10 and 60 degrees, such as 20 and 50 degrees, such as 25 and 45 degrees, such as about 30 degrees, or 30 degrees.

Referring now to FIGS. 142-143, the device 500 is shown in a slightly opened position or a closed position. As mentioned above, the same parts of the device 500 move in the example illustrated by FIGS. 142 and 143 as in the example illustrated by FIGS. 138-141. In the partially open position or closed position, further retraction of the actuation sutures 537 in the retraction direction 560 pulls upward on the moveable arms 534, barbs 536, and inner paddles 522. The portion of the inner paddles 522 closest to the coaption element flexes or is lifted-up in the direction 562 to allow the movement 560. As mentioned above, there can optionally be a small gap $G_{140}$ between the clasps 530 and the coaption element 510. The inner paddles can flex 562 at the small gap (if there is a small gap) or at the connection between the coaption element 510 and the inner paddles if there is not a gap. The movement of the barbs 536 in the direction 560 releases the valve tissue from the barbs. The lifting on the inner paddles 522 can optionally also force the outer paddles 520 to move outward in an opening direction 564. The optional outward movement 564 of the outer paddles 520 relieves the pinching force applied to grasped tissue by the paddles and the coaption element. Relieving the pinching force on the tissue can also assist in the release of the tissue from the barbs. In one exemplary embodiment, the device 500 is moved from the position illustrated by FIG. 143 to the position illustrated by FIG. 140 or 141 to fully disengage the device from the native valve.

FIGS. 144-152 show an exemplary delivery assembly 2200 and its components. Referring to FIG. 144, the delivery assembly 2200 can comprise the implantable prosthetic spacer device 500 (or any other implantable device described in the present application) and a delivery apparatus 2202. The delivery apparatus 2202 can comprise a plurality of catheters and catheter stabilizers. For example, in the illustrated embodiment, the delivery apparatus 2202 includes a first catheter 2204, a second catheter 2206, a third catheter 2208, and catheter stabilizers 2210. The second catheter 2206 extends coaxially through the first catheter 2204, and the third catheter 2208 extends coaxially through the first and second catheters 2204, 2206. The prosthetic spacer device 500 can be releasably coupled to a distal end portion of the third catheter 2208 of the delivery apparatus 2202, as further described below.

In the illustrated embodiment, the delivery assembly 2200 is configured, for example, for implanting the prosthetic spacer device 500 in a native mitral valve via a transseptal delivery approach. In other embodiments, the delivery assembly 2200 can be configured for implanting the prosthetic spacer device 500 in aortic, tricuspid, or pulmonary valve regions of a human heart. Also, the delivery assembly 2200 can be configured for various delivery methods, including transseptal, transaortic, transventricular, etc.

Referring to FIG. 146, the first collar or cap 514 of the prosthetic spacer device 500 can include a bore 516A. In some embodiments, the bore 516A can comprise internal threads configured to releasably engage corresponding external threads on a distal end 512B of the actuation shaft or means of actuating 512 of the delivery apparatus 2202, as shown in FIG. 145.

Referring again to FIG. 146, the second or proximal collar 511 of the prosthetic spacer device 500 can include a central opening 511C that is axially aligned with the bore 516A of the cap 514. The central opening 511C of the proximal collar 511 can be configured to slidably receive the actuation shaft or means of actuating 512 of the delivery apparatus 2202, as shown in FIG. 145. In some embodiments, the proximal collar 511 and/or the coaption element 510 can have a sealing member (not shown, but see, e.g., the sealing member 413 shown in FIG. 23) configured to seal the central opening 511C when the actuation shaft or means of actuating 512 is withdrawn from the central opening 511C.

As shown in FIG. 146, the proximal collar 511 can also include a plurality of engagement portions or projections 511A and a plurality of guide openings 511B. The projections 511A can extending radially outwardly and can be circumferentially offset (e.g., by about 90 degrees) relative to the guide openings 511B. The guide openings 511B can be disposed radially outwardly from the central opening 511C. The projections 511A and the guide openings 511B of the proximal collar 511 can be configured to releasably engage a coupler or means for coupling 2214 of the delivery apparatus 2202, as shown in FIG. 145.

Referring again to FIG. 144 and as mentioned above, the delivery apparatus 2202 can include the first and second catheters 2204, 2206. The first and second catheters 2204, 2206 can be used, for example, to access an implantation location (e.g., a native mitral valve region of a heart) and/or to position the third catheter 2208 at the implantation location.

The first and second catheters 2204, 2206 can comprise first and second sheaths 2216, 2218, respectively. The catheters 2204, 2206 can be configured such that the sheaths 2216, 2218 are steerable. Additional details regarding the first catheter 2204 can be found, for example, in U.S. Published Patent Application No. 2016/0155987, which is incorporated by reference herein in its entirety. Additional details regarding the second catheter 2206 can be found, for example, in U.S. Provisional Patent Application No. 62/418,528, which is incorporated by reference herein in its entirety.

Referring still to FIG. 144, delivery apparatus 2202 can also include the third catheter 2208, as mentioned above. The third catheter 2208 can be used, for example, to deliver, manipulate, position, and/or deploy the prosthetic spacer device 500 at the implantation location.

Referring to FIG. 148, the third catheter 2208 can comprise the actuation or inner shaft 512, the coupler or means for coupling 2214, an outer shaft 2220, a handle 2222 (shown schematically), and clasp control members 537. A proximal end portion 2220a of the outer shaft 2220 can be coupled to and extend distally from the handle 2222, and a distal end portion 2220b of the outer shaft 2220 can be coupled to the coupler or means for coupling 2214. A proximal end portion 512A of the actuation shaft or means of actuating 512 can coupled to an actuation knob 2226. The actuation shaft or means of actuating 512 can extend distally from the knob 2226 (shown schematically), through the handle 2222, through the outer shaft 2220, and through the coupler or means for coupling 2214. The actuation shaft or means of actuating 512 can be moveable (e.g., axially and/or rotationally) relative to the outer shaft 2220 and the handle 2222. The clasp control members 537 can extend through and be axially movable relative to the handle 2222 and the outer shaft 2220. The clasp control members 537 can also be axially movable relative to the actuation shaft or means of actuating 512.

As shown in FIGS. 145-146, the actuation shaft or means of actuating 512 of the third catheter 2208 can be releasably coupled to the cap 514 of the prosthetic spacer device 500. For example, in some embodiments, the distal end portion 512B of the actuation shaft or means of actuating 512 can comprise external thread configured to releasably engage the interior threads of the bore 516A of the prosthetic spacer device 500. As such, rotating the actuation shaft or means of actuating 512 in a first direction (e.g., clockwise) relative to the cap 514 of the prosthetic spacer device 500 releasably secures the actuation shaft or means of actuating 512 to the cap 514. Rotating the actuation shaft or means of actuating 512 in a second direction (e.g., counterclockwise) relative to the cap 514 of the prosthetic spacer device 500 releases the actuation shaft or means of actuating 512 from the cap 514.

Referring now to FIGS. 145-147, the coupler or means for coupling 2214 of the third catheter 2208 can be releasably coupled to the proximal collar 511 of the prosthetic spacer device 500. For example, in some embodiments, the coupler or means for coupling 2214 can comprise a plurality of flexible arms 2228 and a plurality of stabilizer members 2230. The flexible arms 2228 can comprise apertures 2232, ports 2233 (FIG. 146), and eyelets 2234 (FIG. 147). The flexible arms 2228 can be configured to pivot between a first or release configuration (FIG. 146) and a second or coupled configuration (FIGS. 145 and 147). In the first configuration, the flexible arms 2228 extend radially outwardly relative to the stabilizer members 2230. In the second configuration, the flexible arms 2230 extend axially parallel to the stabilizer members 2230 and the eyelets 2234 radially overlap 2234, as shown in FIG. 147. The flexible arms 2228 can be configured (e.g., shape-set) to be biased to the first configuration.

The prosthetic spacer device 500 can be releasably coupled to the coupler or means for coupling 2214 by inserting the stabilizer members 2230 of the coupler or means for coupling 2214 into the guide openings 511B of the prosthetic spacer device 500. The flexible arms 2228 of the coupler or means for coupling 2214 can then be pivoted radially inwardly from the first configuration to the second configuration such that the projections 511A of the prosthetic spacer device 500 extend radially into the apertures 2232 of the flexible arms 2228. The flexible arms 2228 can be retained in the second configuration by inserting the distal end portion 512B of the actuation shaft or means of actuating 512 through openings 2236 of the eyelets 2234, which prevents the flexible arms 2228 from pivoting radially outwardly from the second configuration to the first configuration, thereby releasably coupling the prosthetic spacer device 500 to the coupler or means for coupling 2214.

The prosthetic spacer device 500 can be released from the coupler or means for coupling 2214 by proximally retracting the actuation shaft or means of actuating 512 relative to the coupler or means for coupling 2214 such that the distal end portion 512B of the actuation shaft or means of actuating 512 withdraws from the openings 2236 of the eyelets 2234. This allows the flexible arms 2228 to pivot radially outwardly from the second configuration to the first configuration, which withdraws the projections 511A of the prosthetic spacer device 500 from the apertures 2232 of the flexible arms 2228. The stabilizer members 2230 can remain inserted into the guide openings 511B of the prosthetic spacer device 500 during and after the flexible arms 2228 are released. This can, for example, prevent the prosthetic spacer device 500 from moving (e.g., shifting and/or rocking) while the flexible arms 2228 are released. The stabilizer members 2230 can then be withdrawn from the guide openings 511B of the prosthetic spacer device 500 by proximally retracting the coupler or means for coupling 2214 relative to the prosthetic spacer device 500, thereby releasing the prosthetic spacer device 500 from the coupler or means for coupling 2214.

Referring to FIG. 148, the outer shaft 2220 of the third catheter 2208 can be an elongate shaft extending axially between the proximal end portion 2220a, which is coupled to the handle 2222, and the distal end portion 2220b, which is coupled to the coupler or means for coupling 2214. The outer shaft 2220 can also include an intermediate portion 2220c disposed between the proximal and distal end portions 2220a, 2220b.

Referring to FIG. 149, the outer shaft 2220 can comprise a plurality of axially extending lumens, including an actuation shaft or means of actuating lumen 2238 and a plurality of control member lumens 2240 (e.g., four in the illustrated embodiment). In some embodiments, the outer shaft 2220 can comprise more (e.g., six) or less (e.g., two) than four control member lumens 2240.

The actuation shaft or means of actuating lumen 2238 can be configured to receive the actuation shaft or means of actuating 512, and the control member lumens 2240 can be configured to receive one or more clasp control members 537. The lumens 2238, 2240 can also be configured such that the actuation shaft or means of actuating 512 and clasp control members 537 can be movable axially and/or rotationally) relative to the respective lumens 2238, 2240. In particular embodiments, the lumens 2238, 2240 can comprise a liner or coating configured to reduce friction within the lumens 2238, 2240. For example, the lumens 2238, 2240 can comprise a liner comprising PTFE.

Referring still to FIGS. 148-149, the outer shaft 2220 can be formed from various materials, including metals and polymers. For example, in one particular embodiment, the proximal end portion 2220a can comprise stainless steel and the distal and intermediate portions 2220b, 2220c can comprise PEBAX (e.g., PEBAX®). The outer shaft 2220 can also comprise an outer covering or coating, such as a polymer that is reflowed over the portions 2220a, 2220b, and 2220c.

The outer shaft 2220 can include one or more coil portions 2242 disposed radially outwardly from the lumens 2238, 2240. For example, in one particular embodiment, the outer shaft 2220 can comprise a first coil 2242a, a second coil 2242b, and a third coil 2242c. The first coil 2242a can be the radially outermost coil, the third coil 2242c can be the radially innermost coil, and the second coil 2242b can be radially disposed between the first coil 2242a and the third coil 2242c.

The coil portions 2242 can comprise various materials and/or configurations. For example, the coil portions 2242 can be formed from stainless steel. In one particular embodiment, the first and third coils 2242a, 2242c comprise stainless steel coils wound in a left hand configuration, and the second coil 2242b comprises a stainless steel coil wound in a right hand configuration.

The coil portions 2242 can also comprise various pitches. The pitch of one or more of the coils 2242 can be the same or different than the pitch of one or more other coils 2242. In one particular embodiment, the first and second coils 2242a, 2242b can have a first pitch (e.g., 0.74 in.), and the third coil can comprise a second pitch (e.g., 0.14 in.).

The outer shaft 2220 can also comprise a tie layer 2244 disposed radially inwardly from the third coil 2242c. The tie layer 2244 can be formed of various materials including polymers, such as PEBAX (e.g., PEBAX®).

As shown in FIGS. 150-152, the handle 2222 of the third catheter 2208 can include a housing 2246, an actuation lock mechanism 2248, a clasp control mechanism 2250, and a flushing mechanism 2252. Referring to FIG. 150, a distal end portion of the housing 2246 can be coupled to the proximal end portion 2220a of the outer shaft 2220. The actuation lock mechanism 2248, the clasp control mechanism 2250, and a flushing mechanism 2252 can be coupled to a proximal end of the housing 2246. The actuation lock mechanism 2248 can be configured to selectively lock the position of the actuation shaft or means of actuating 512 relative to the housing 2246 and the outer shaft 2220. The clasp control mechanism 2250 can also be coupled to proximal end portions of the clasp control members 537 and can be configured to secure the clasp control members 537 relative to the handle 2222 and to move the clasp control members 537 relative to the outer shaft 2220 and the actuation shaft or means of actuating 512. The flushing mechanism 2252 can be configured for flushing (e.g., with a saline solution) the outer shaft 2220 prior to inserting the outer shaft 2220 into a patient's vasculature.

As shown in FIGS. 151-152, the housing 2246 of the handle 2222 can comprise a main body 2254 and a nose portion 2256 coupled to a distal end portion of the main body 2254. The main body 2254 and the nose portion 2256 can be coupled together in various manners, including fasteners 2258 and/or pins 2260 (e.g., as shown in the illustrated embodiment), adhesive, and/or other coupling means. The housing 2246 can be formed from various materials, including polymers (e.g., polycarbonate).

The main body 2254 of the housing 2246 can comprise a plurality of lumens, including an actuation shaft or means of actuating lumen 2262, control member lumens 2264 (FIG. 152), and a flushing lumen 2266 that connects with the actuation shaft or means of actuating lumen 2262 (FIG. 151). As shown in FIG. 152, the main body 2254 can also include a plurality of tubes (e.g., hypotubes), including an actuation tube 2268 and control member tubes 2270 that are disposed at least partially in the actuation shaft or means of actuating lumen 2262 and the control member lumens 2264, respectively. The tubes 2268, 2270 can be axially movable (e.g., slidable) relative the lumens 2262, 2264, respectively.

The proximal end of the actuation tube 2268 can extend proximally from the main body 2256 and can be coupled to the knob 2226 and to the proximal end portion 512A of the actuation shaft or means of actuating 512. The proximal ends of the control member tubes 2270 can extend proximally from the main body 2254 and can be coupled to the clasp control mechanism 2250 and the clasp control members 537.

The distal ends of the tubes 2268, 2270 can comprise flanges 2272, 2274 configured to engage a stopper to limit the axial movement of the tubes 2268, 2270 relative to the housing 2224. For example, the flanges 2272, 2274 can be configured to contact respective surfaces of the main body 2254 (e.g., a lip) to prevent to tubes 2268, 2270 from withdrawing completely from the proximal ends of the lumens 2262, 2264, respectively.

The actuation tube 2268 can be configured to receive and be coupled to the proximal end portion of the actuation shaft or means of actuating 512. The control member tubes 2270 can be configured to receive portions of the clasp control mechanism 2250, as further described below. The tubes 2268, 2270 can be formed from various materials, including polymers and metals (e.g., stainless steel).

In some embodiments, the main body 2254 can include a plurality of seal members 2276 (e.g., O-rings) configured to prevent or reduce blood leakage through the lumens and around the shafts and/or tubes. The seal members can be secured relative to the main body 2254, for example, by fasteners 2278 (e.g., hollow-lock or socket-jam set screws).

As shown in FIG. 152, the nose portion 2256 of the housing 2246 can comprise a plurality of lumens, including an actuation shaft or means of actuating lumen 2280 and control member lumens 2282. The actuation shaft or means of actuating lumen 2280 of the nose portion 2256 can be extend coaxially with the actuation shaft or means of actuating lumen 2262 of the main body 2254. Proximal ends of the control member lumens 2282 of the nose portion 2256 can be aligned with the control member lumens 2264 of the main body 2254 at the proximal end of the nose portion 2256 (i.e., the lumens 2282, 2264 are in the same plane). The control member lumens 2282 can extend from the proximal ends at an angle (i.e., relative to the control member lumens 2264 of the main body 2254), and distal ends of the control member lumens 2282 can connect with the actuation shaft or means of actuating lumen 2280 of the nose portion 2256 at a location toward the distal end of the nose portion 2256. In other words, the proximal ends of the lumens 2282 are in a first plane (i.e., the plane of the control member lumens 2264 of the main body 2254), and the distal ends of the lumens 2282 are in a second plane (i.e., the plane of the actuation shaft or means of actuating lumen 2262 of the main body 2254).

As shown in FIG. 151, the actuation shaft or means of actuating lumen 2280 of the nose portion 2256 can be configured to receive the proximal end portion of the outer shaft 2220. The proximal end portion of the outer shaft 2220 can be coupled to the nose portion 2256 in many ways such as with adhesive, fasteners, frictional fit, and/or other coupling means.

Referring still to FIG. 151, the actuation lock mechanism 2248 of the handle 2222 can be coupled to the proximal end portion of the main body 2254 of the housing 2246 and to the actuation tube 2268. The actuation lock mechanism 2248 can be configured to selectively control relative movement between the actuation tube 2268 and the housing 2246. This, in turn, selectively controls relative movement between the actuation shaft or means of actuating 512 (which is coupled to the actuation tube 2268) and the outer shaft 2220 (which is coupled to the nose portion 2256 of the housing 2246).

In some embodiments, the actuation lock mechanism 2248 can comprise a lock configuration, which prevents relative movement between the actuation tube 2268 and the housing 2246, and a release configuration, which allows relative movement between the actuation tube 2268 and the housing 2246. In some embodiments, the actuation lock mechanism 2248 can be configured to include one or more intermediate configurations (i.e., in addition to the lock and release configuration) which allow relative movement between the actuation tube 2268 and the housing 2246, but the force required to cause the relative movement is greater than when the actuation lock mechanism is in the release configuration.

As shown in FIG. 151 of the illustrated embodiment, the actuation lock mechanism 2248 can comprise a lock (e.g., a Tuohy-Borst adapter) 2284 and a coupler (e.g., a female luer coupler) 2286. The coupler 2286 can be attached to the distal end of the lock 2284 and coupled to the proximal end of the main body 2254 of the housing 2246. The actuation tube 2268 can coaxially extend through the lock 2284 and the coupler 2286. As such, rotating a knob 2288 of the lock 2284 in a first direction (e.g., clockwise) can increase the frictional engagement of the lock 2284 on the actuation tube 2268, thus making relative movement between the actuation tube 2268 and the housing 2246 more difficult or preventing it altogether. Rotating a knob 2288 of the lock 2284 in a second direction (e.g., counterclockwise) can decrease the frictional engagement of the lock 2284 on the actuation tube 2268, thus making relative movement between the actuation tube 2268 and the housing 2246 easier.

In other embodiments, actuation lock mechanism 2248 can comprise other configurations configured for preventing relative movement between the actuation tube 2268 and the housing 2246. For example, the locking mechanism 2248 can include lock configured like a stopcock valve in which a plunger portion of valve selectively engages the actuation tube 2268.

The clasp control mechanism 2250 can comprise an actuator member 2290 and one or more locking members 2292 (e.g., two in the illustrated embodiment). A distal end portion of the actuator member 2290 can be coupled to the control member tubes 2270, which extend from the proximal end of the main body 2254 of the housing 2246, as best shown in FIG. 151. The locking members 2292 can be coupled to a proximal end portion of the actuator member 2290.

As shown in the illustrated embodiment, the actuator member 2290 can, optionally, comprise a first side portion 2294 and a second side portion 2296 selectively coupled to the first side portion 2294 by a connecting pin 2298. The actuator member 2290 can be configured such that the first and second side portions 2294, 2296 move together when the connecting pin 2298 is inserted through the first and second side portions 2294, 2296. When the connecting pin 2298 is withdrawn, the first and second side portions 2294, 2296 can be moved relative to each other. This can allow the clasp control members 537 (which are releasably coupled to the first and second side portions 2294, 2296 by the locking elements 2292) to be individually actuated.

The connection between the first and second side portions 2294, 2296 can be configured such that the first and second side portions 2294, 2296 can move axially (i.e., proximally and distally) but not rotationally relative to each other when the connecting pin 2298 is withdrawn. This can be accomplished, for example, by configuring the first side portion 2294 with keyed slot or groove and configuring second side portion 2296 with a keyed projection or tongue that corresponds to the keyed slot or groove of the first side portion 2294. This can, for example, prevent or reduce the likelihood that the clasp control members 537 from twisting relative to the outer shaft 2220.

The first and second side portions 2294, 2296 can include axially extending lumens 2201. Distal ends of the lumens 2201 can be configured to receive the proximal end portions of the control member tubes 2270. Proximal ends of the lumens 2201 can be configured to receive portions of the locking members 2292.

The locking members 2292 can be configured to selectively control relative movement between a clasp control member 2224 and the respective first or second side portion 2294, 2296 of the actuator member 2290. The locking members 2292 can comprise a lock configuration, which prevents relative movement between a clasp control member 2224 and the respective first or second side portion 2294, 2296, and a release configuration, which allows relative movement between a clasp control member 2224 and the respective first or second side portion 2294, 2296. In some embodiments, the locking members 2292 can also comprise one or more intermediate configurations (i.e., in addition to the lock and release configuration) which allows relative movement between a clasp control member 2224 and the respective first or second side portion 2294, 2296, but the force required to cause the relative movement is greater than when the locking members 2292 are in the release configuration.

As shown in the illustrated embodiment, the locking members 2292 can be configured similar to stopcock valves. Thus, rotating knobs 2203 in a first direction (e.g., clockwise) can increase the frictional engagement between the locking members 2292 on the clasp control members 537 and make relative movement between a clasp control member 2224 and the respective first or second side portion 2294, 2296 more difficult or prevent it altogether. Rotating knobs 2203 in a second direction (e.g., counterclockwise) can decrease the frictional engagement between the locking members 2292 on the clasp control members 537 and make relative movement between a clasp control member 2224 and the respective first or second side portion 2294, 2296 easier. In other embodiments, actuation locking members 2292 can comprise other configurations configured for preventing relative movement between the locking members 2292 on the clasp control members 537.

The flushing mechanism 2252 can comprise a flushing tube 2205 and a valve 2207 (e.g., a stopcock valve). A distal end of the flushing tube 2205 can be coupled to and in fluidic communication with the flushing lumen 2266 and thus with the actuation shaft or means of actuating lumen 2262 of the main body 2254. A proximal end of the flushing tube 2205 can be coupled to the valve 2207. In this manner, the flushing mechanism 2252 can be configured for flushing (e.g., with a saline solution) the outer shaft 2220 prior to inserting the outer shaft 2220 into a patient's vasculature.

The clasp control members 537 can be configured to manipulate the configuration of the clasps 530, as further described below. As shown in FIG. 148, each of the clasp control members 537 can be configured as a suture (e.g., wire or thread) loop. Proximal end portions of the control members 537 can extend proximally from the proximal end portion of the clasp control mechanism 2250 and can be releasably coupled to the locking mechanisms 2292 of the clasp control mechanism 2250.

From the locking mechanisms 2292, the clasp control members 537 can form loops extending distally through the lumens 2201 of the clasp control mechanism 2250, through the control member tubes 2270, the control member lumens 2264, 2282 of the handle 2222, and through the control member lumens 2240 of the outer shaft 2220. The clasp control members 537 can extend radially outwardly from the lumens 2240, for example, through the ports 2233 (FIG. 146) of the coupler or means for coupling 2214. The clasp control members 537 can then extend through openings 535 of the clasps 530. The clasp control members 537 can then extend proximally back to the coupler or means for coupling 2214, radially inwardly through the ports 2233 of the coupler or means for coupling 2214, and then proximally through the outer shaft 2220 and the handle 2222, and to the locking mechanisms 2292 of the clasp control mechanism 2250.

In FIG. 148, the clasp control members 537 are shown slacken and the clasps 530 are partially open in order to illustrate the clasp control members 537 extending through the openings 535 of the clasps 530. However, ordinarily when the clasp control members 537 are slacken, the clasps 530 would be in the closed configuration.

As shown in the illustrated embodiment, each of the clasp control members 537 can extend through multiple lumens 2240 of the outer shaft 2220. For example, each of the clasp control members 537 can be looped through two of the lumens 2240. In other embodiments, each of the clasp control members 537 can be disposed in a single lumen 2240. In yet other embodiments, multiple clasp control members 537 can be disposed in a single lumen 2240.

With the clasp control members 537 coupled to the clasps 530, the clasp control mechanism 2250 can be used to actuate the clasps 530 between open and closed configurations. The clasps 530 can be opened by moving the actuator member 2290 proximally relative to the knob 2226 and the housing 2246. This increases tension of the clasp control members 537 and causes the clasp 530 to move from the closed configuration to the open configuration. The clasps 530 can be closed by moving the actuator member 2290 distally relative to the knob 2226 and the housing 2246. This decreases tension on the clasp control members 537 and allows the clasp 530 to move from the open configuration to the closed configuration. The clasps 530 can be individually actuated by removing the pin 2298 and moving the first or second side portions 2294, 2296 relative to each other, the knob 2226, and the housing 2246.

When the handle 2222 is assembled as best shown in FIGS. 150-151, the actuation shaft or means of actuating 512 can extend distally from the knob 2226, through the actuation tube 2268, through the actuation lumens 2262, 2280 of the housing 2246, through the actuation lumen 2238 of the outer shaft 2220, and through the coupler or means for coupling 2214.

Figure 153:
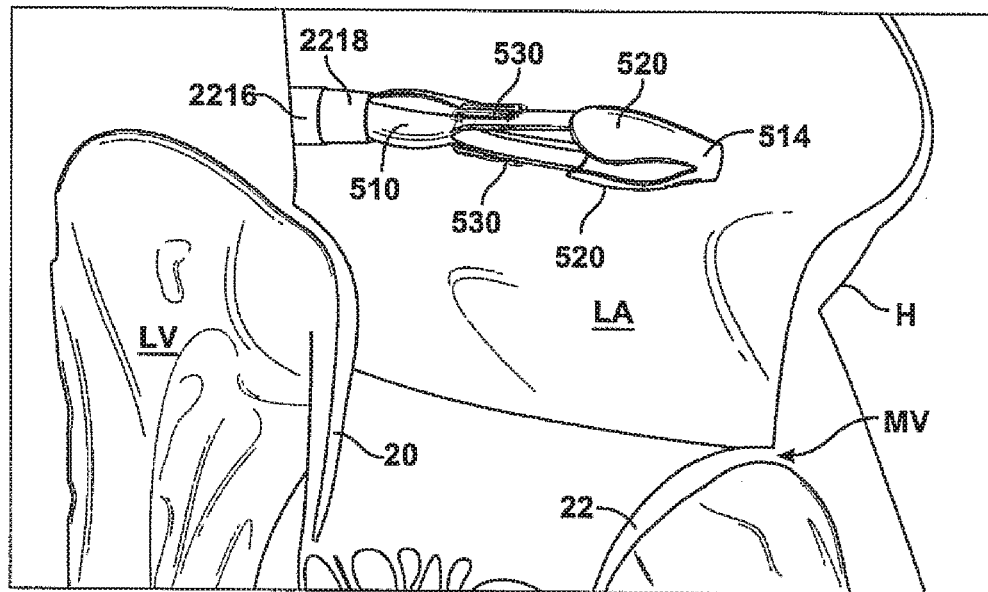
Figure 154:
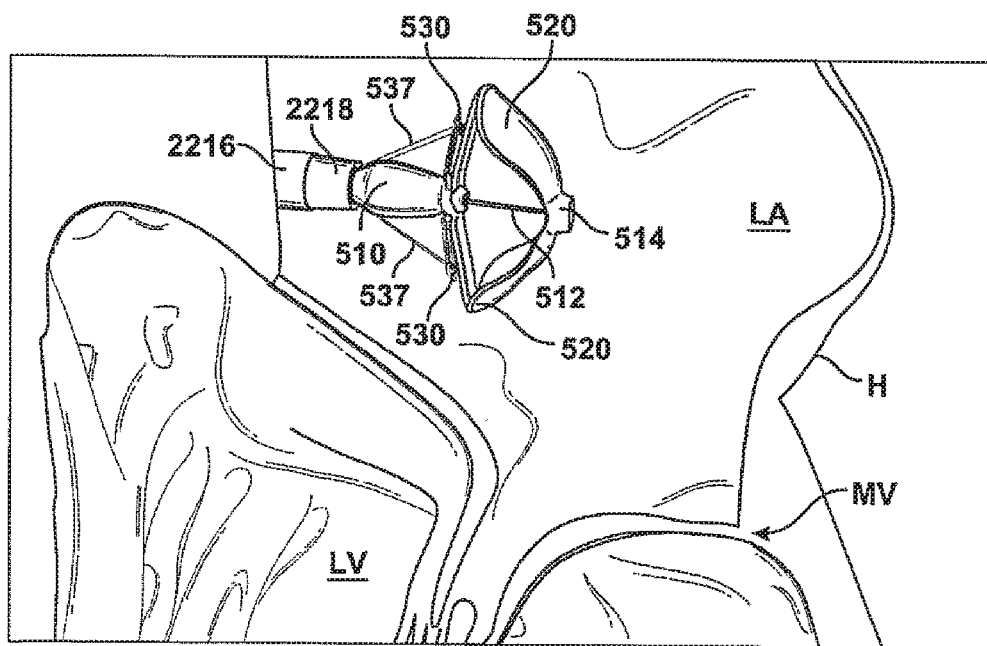

Referring now to FIGS. 153-160, the delivery assembly 2200 is used, for example, to implant the prosthetic spacer device 500 in native mitral valve MV of a heart H using a transseptal delivery approach. FIGS. 153-160 are similar to FIGS. 15-20, described above, that show the implantable prosthetic device 100 being implanted in the heart H and FIGS. 35-46, described above, that show the implantable prosthetic device 500 being implanted in the heart H. Although not shown, a guide wire can be inserted into the patient's vasculature (e.g., a femoral vein) through an introducer sheath. The guide wire can be advanced through the femoral vein, through the inferior vena cava, into the right atrium, through the interatrial septum IAS (e.g., via the fossa ovalis), and into the left atrium LA. The first sheath 2216 of the first catheter 2204 can be advanced over the guide wire such that a distal end portion of the first sheath 2216 is disposed in the left atrium LA, as shown in FIG. 153.

With the prosthetic spacer device 500 coupled to the third catheter 2208 (e.g., as shown in FIG. 145) and configured in a radially compressed, delivery configuration, the prosthetic spacer device 500 can be loaded into the first sheath 2216 at a distal end of the second sheath 2218 of the second catheter 2206. The first sheath 2216 retains the prosthetic spacer device 500 in the delivery configuration. In some embodiments, the radially compressed, delivery configuration can be an axially elongated configuration (e.g., like the configuration shown in FIG. 153). In other embodiments, the radially compressed, delivery configuration can be an axially foreshorten configuration (e.g., similar to the configuration shown in FIG. 155). The second catheter 2206 along with the prosthetic spacer device 500 and the third catheter 2208 can then be advanced together through the first catheter 2204 such that a distal end portion of the sheath 2218 exposed from the distal end portion of the first sheath 2216 and is disposed in the left atrium LA, as shown in FIG. 153.

As shown in FIG. 153, the prosthetic spacer device 500 can be exposed from the first sheath 2216 by distally advancing the outer shaft 2220 and the actuation shaft or means of actuating 512 of the third catheter 2208 relative to the first sheath 2216 and/or retracting the first sheath 2216 relative to the outer shaft 2220 and the actuation shaft or means of actuating 512, thus forcing the paddles 520, 522 of the anchors 508 out of the first sheath 2216. Once exposed from the first sheath 2216, the paddles 520, 522 can be folded by retracting the actuation shaft or means of actuating 512 of the third catheter 2208 relative to the outer shaft 2220 of the third catheter 2208 and/or by advancing the outer shaft 2220 relative to the actuation shaft or means of actuating 512, causing the paddles 520, 522 to bend from the configuration shown in FIG. 153, to the configuration shown in FIG. 154, and then to the configuration shown in FIG. 155. This can be accomplished, for example, by placing the actuation lock mechanism 2248 in the release configuration (e.g., by rotating the knob 2288 counterclockwise relative to the handle 2222) and then moving the knob 2226 proximally relative to the housing 2246. Another option is to set the locking knob 2288 to maintain enough friction that you can actively slide the actuation wire or shaft 512 but the actuation wire or shaft will not move on its own. At any point in the procedure, the physician can lock the relative position of the actuation shaft or means of actuating 512 and the outer shaft 2220, and thus the position of the paddles 520, 522, by actuating the actuation locking mechanism 2248.

Figure 155:
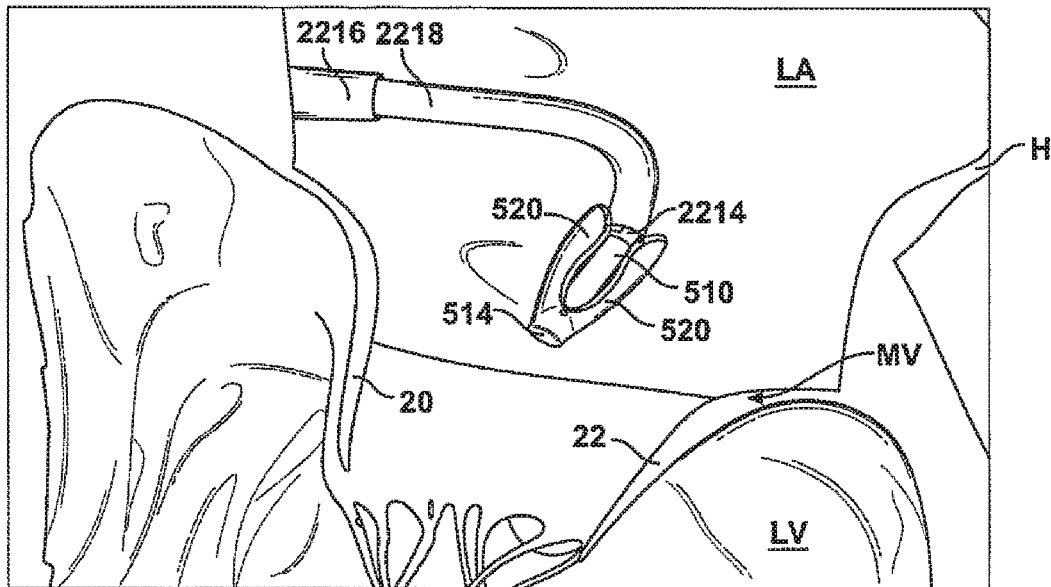

The prosthetic spacer device 500 can then be positioned coaxial relative to the native mitral valve MV by manipulating (e.g., steering and/or bending) the second sheath 2218 of the second catheter 2206, as shown in FIG. 155. The prosthetic spacer device 500 can also be rotated (e.g., by rotating the housing 2246) relative to the native mitral valve MV such that the paddles 520, 522 align with native leaflets 20, 22 of the mitral valve MV.

Figure 156:
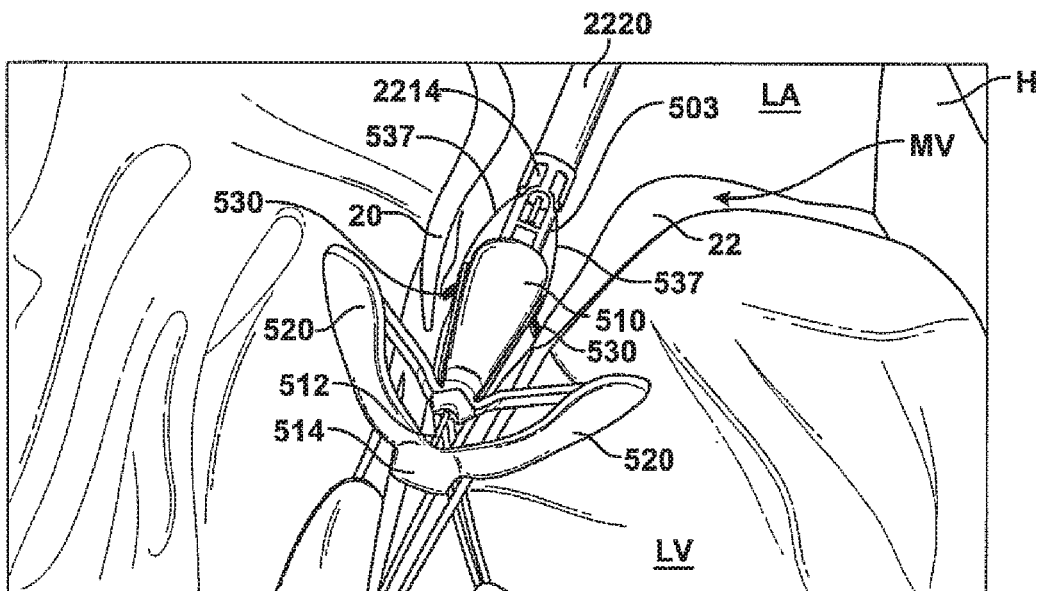

The paddles 520, 522 of the prosthetic spacer device 500 can then be partially opened (i.e., moved radially outwardly relative to the coaption element 510) to the configuration shown in FIG. 156 by moving the knob 2226 distally relative to the housing 2246. The prosthetic spacer device 500 can then be advanced through the annulus of the native mitral valve MV and at least partially into the left ventricle LV. The prosthetic spacer device 500 is then partially retracted such that the paddles 520, 522 are positioned behind the ventricular portions of the leaflets 20, 22 (e.g., at the A2/P2 positions) and the coaption element 510 is disposed on the atrial side of the leaflets 20, 22.

Figure 157:
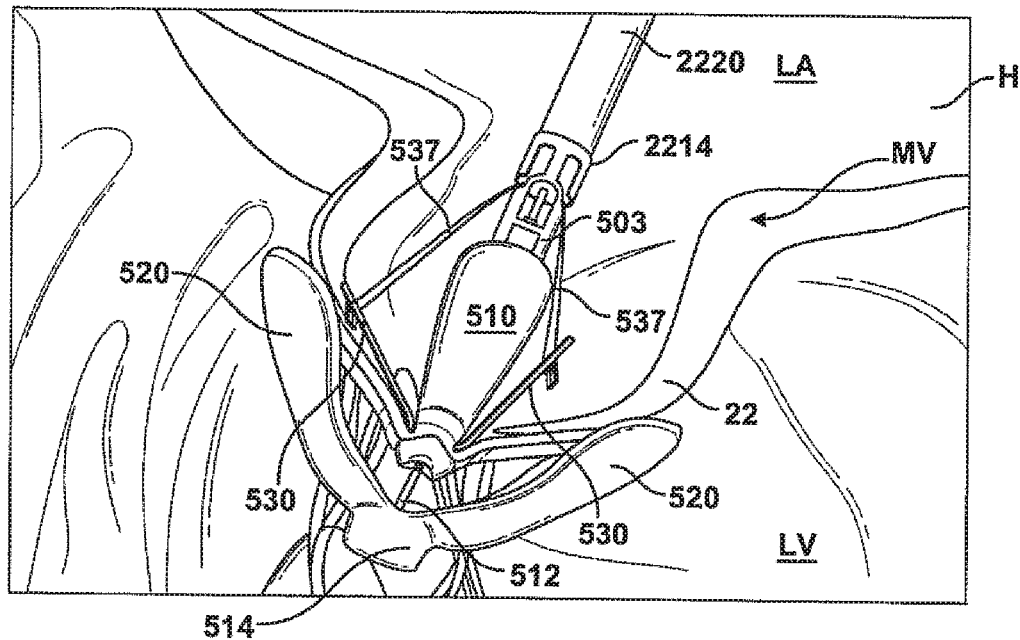

In this configuration, the native leaflets 20, 22 can be secured relative to the paddles 520, 522 by capturing the native leaflets with the clasps 530. The native leaflets 20, 22 can be grasped simultaneously or separately by actuating the actuator member 2290. For example, FIG. 157 shows separate leaflet grasping. This can be accomplished by removing the pin 2298 from the actuator member 2290 and moving the first or second side portions 2294, 2296 relative to each other, the knob 2226, and the housing 2246. Moving the first or second side portions 2294, 2296 distally relative to the knob 2226 and the housing 2246 closes the clasps 530 on the native leaflets 20, 22 (e.g., as shown by the left clasp 530 as illustrated in FIG. 157). Moving the first or second side portions 2294, 2296 proximally relative to the knob 2226 and the housing 2246 opens the clasps 530 (e.g., as shown by the right clasp 530 as illustrated in FIG. 157). Once a clasp 530 is closed, a physician can re-open the clasp 530 to adjust the positioning of the clasp 530.

Figure 158:
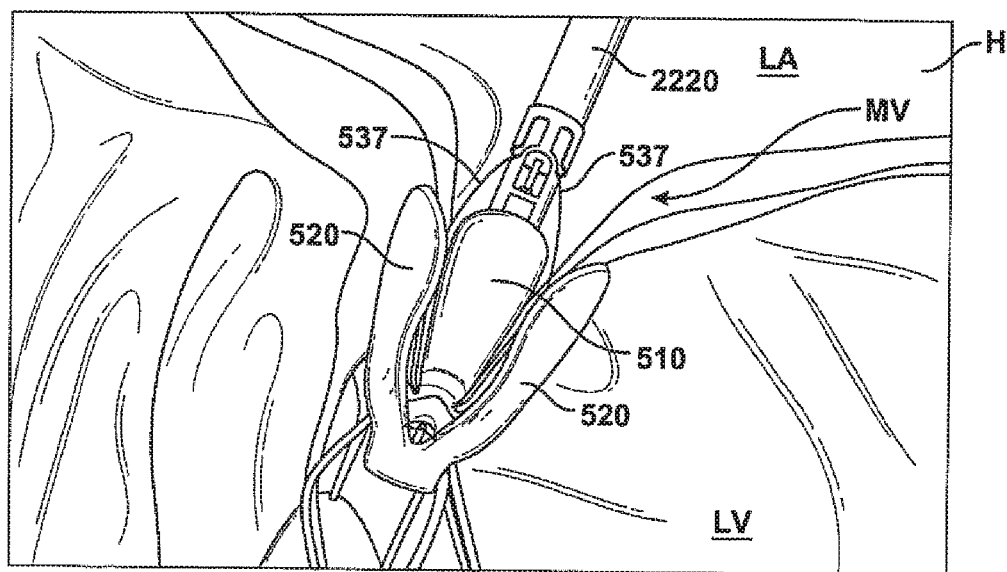

With both of the native leaflets 20, 22 secured within the clasps 530, the physician can move the knob 2226 proximally relative to the housing 2246. This pulls the paddles 520, 522 and thus the native leaflets 20, 22 radially inwardly against the coaption element 510, as shown in FIG. 158. The physician can then observe the positioning and/or reduction in regurgitation. If repositioning or removal is desired the physician can re-open the paddles 520, 522 and/or the clasps 530.

Figure 159:
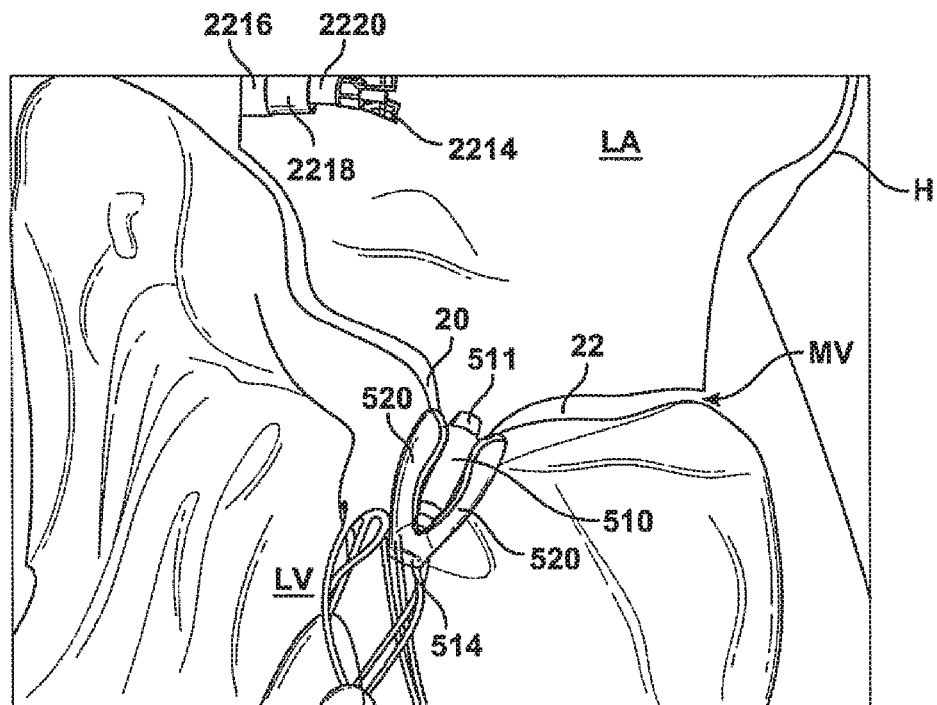

Once the desired positioning and/or reduction in regurgitation is achieved, the physician can release the prosthetic spacer device 500 from the delivery apparatus 2202. The clasps 530 can be released from the delivery apparatus 2202 by releasing the clasp control members 537 from the locking members 2292 and unthreading the clasp control members 537 from the openings 535 of the clasps 530. The cap 514 of the prosthetic spacer device 500 can be released from the delivery apparatus 2202 by rotating the knob 2226 in the second direction relative to the housing 2246 such that the actuation shaft or means of actuating 512 withdraws from the bore 516A. The actuation shaft or means of actuating 512 can then be retracted proximally through the prosthetic spacer device 500 by pulling the knob 2226 proximally relative to the housing 2224. The proximal collar 511 of the prosthetic spacer device 500 can be released from the delivery apparatus 2202 by retracting the actuation shaft or means of actuating 512 proximally relative to the coupler or means for coupling 2214 such that the distal end portion of the actuation shaft or means of actuating 512 withdraws from the eyelets 2234 of the coupler or means for coupling 2214. This allows the flexible arms 2228 of the coupler or means for coupling 2214 to move radially outwardly away from the projections 511A of the proximal collar 511. The stabilizer members 2230 of the coupler or means for coupling 2214 can then be withdrawn from the guide openings 511B of the proximal collar 511 by pulling the housing 2246 proximally, thereby releasing the prosthetic spacer device 500 from the delivery apparatus 2202 as shown in FIG. 159.

The shafts 512, 2220 of the third catheter 2208 can then be retracted proximally into the second sheath 2218 of the second catheter 2206, and the second sheath 2218 of the second catheter 2206 can be retracted proximally into the first sheath 2216 of the first catheter 2204. The catheters 2204, 2206, 2208 can then be retracted proximally and removed from the patient's vasculature.

Figure 160:
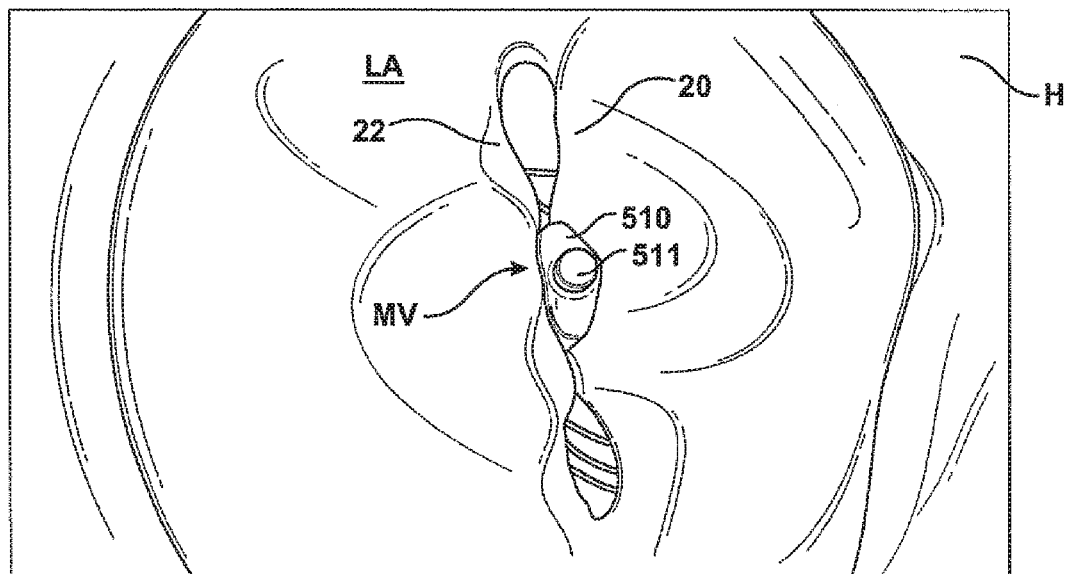

With the prosthetic spacer device 500 implanted at the A2/P2 position, the native mitral valve MV comprises a double orifice during ventricular diastole, as shown in FIG. 160. During ventricular systole, the side surfaces of the native leaflets 20, 22 can coapt all the way around the prosthetic spacer device 500 to prevent or reduce mitral regurgitation.

Referring now to FIGS. 161-162, an exemplary embodiment of a handle 2300 for the delivery apparatus 2200 is shown. Referring to FIG. 161, the handle 2300 can comprise a housing 2302, an actuation control mechanism 2304, the clasp control mechanism 2250, and a flushing mechanism (not shown, but see, e.g., the flushing mechanism 2252 in FIG. 150). The housing 2302 can include a main body 2306 and the nose portion 2256. The nose portion 2256 of the housing 2302 can be coupled to a proximal end portion of the outer shaft 2220. The actuation control mechanism 2304, the clasp control mechanism 2250, and a flushing mechanism 2252 can be coupled to a proximal end of the main body 2306 of the housing 2302.

The handle 2300 can be configured similar to the handle 2222, except that the handle 2300 is configured such that rotational movement of the first knob 2318 of the actuation control mechanism 2304 relative to the housing 2302 causes axial movement of the actuation tube 2268 and the actuation shaft or means of actuating 512; whereas, the handle 2222 is configured such that axial movement of the knob 2226 relative to the housing 2246 causes axial movement of the actuation tube 2268 and the actuation shaft or means of actuating 512.

As mentioned above, the housing 2302 can include a main body 2306 and the nose portion 2256. Referring to FIG. 162, the main body 2306 of the housing 2302 can comprise an actuation lumen 2308, control member lumens 2310, and a flange portion 2312. The flange portion 2312 can extend axially from a proximal end portion of the main body 2306 and annularly around the actuation lumen 2308.

The flange portion 2312 of the main body 2306 can comprise one or more circumferential grooves 2314, a bore (not shown), and a guide pin 2316. The grooves 2314 can be configured to interact with the actuation control mechanism 2304, as further described below. The bore can extend radially inwardly from an outside diameter to an inside diameter of the flange portion 2312 and can be configured to receive the guide pin 2316. The guide pin 2316 can be partially disposed in the bore and can extend radially inwardly from the bore such that the guide pin 2316 protrudes into the actuation lumen 2308.

Referring still to FIG. 162, the actuation control mechanism 2304 can comprise a first knob 2318, attachment pins 2320, a drive screw 2322, a collet 2324, and a second knob 2326. The first knob 2318 can have a distal end portion 2328 and a proximal end portion 2330. The first knob 2318 can be configured such that the inside diameter of the distal end portion 2328 is relatively larger than the inside diameter of the proximal end portion 2330. The distal end portion 2328 can comprise openings 2332 that extend radially inwardly from an outside diameter to the inside diameter of the distal end portion 2328.

Referring again to FIG. 161, the inside diameter of the distal end portion 2328 can be configured such that the distal end portion 2328 of the first knob 2318 can extend over the flange portion 2312 of the main body 2306. The openings 2332 (FIG. 162) can be configured to axially align with the grooves 2314 when the first knob 2318 is disposed over the flange 2312. The attachment pins 2320 can be configured so as to extend through the openings 2332 of the first knob 2318 and into grooves 2314 of the flange 2312. In this manner, the attachment pins 2320 allow relative rotational movement and prevent relative axial movement between the first knob 2318 and the flange 2312.

The inside diameter of the proximal end portion 2330 of the first knob 2318 can have internal threads (not shown) configured to engage corresponding external threads 2334 of the drive screw 2322. As shown in FIG. 162, the drive screw 2322 can have a slot 2336 that extends axially across the external threads 2334. The slot 2336 can be configured to receive the guide pin 2316 of the flange portion 2312. As such, when the handle 2300 is assembled (FIG. 161) and the first knob 2318 is rotated relative to the flange 2316, the guide pin 2316 prevents the drive screw 2322 from rotating together with the first knob 2318 and causes the drive screw 2322 to move axially relative to the first knob 2318 and the flange 2316. In this manner, rotating the first knob 2318 in a first direction (e.g., clockwise) moves the drive screw distally relative to the housing 2306, and rotating the first knob 2318 in a second direction (e.g., counterclockwise) moves the drive screw proximally relative to the housing 2306.

The drive screw 2322 can also have a lumen 2338, as shown in FIG. 162. The lumen 2338 can be configured such that the actuation tube 2268 can extend through the drive screw 2322. The lumen 2338 can be configured such that a distal end portion 2340 of the collet 2324 can also be inserted into a proximal end portion of the lumen 2338.

The second knob 2326 can comprise a first, distal portion 2342 and a second, proximal portion 2344. The first portion 2342 can include internal threads (not shown) corresponding to the external threads 2334 of the drive screw 2322. The second portion 2344 can comprise a conical inside surface configured to engage a proximal end portion 2346 of the collet 2324.

When assembled (FIG. 161), the actuation tube 2268 can extend through the lumen 2338 of the drive screw 2322, through the collet 2324, and through the second knob 2326. The second knob 2326 can be disposed over the collet 2324 and the internal threads of the first portion 2342 of the second knob can threadably engage the external threads 2334 of the drive screw 2322. Accordingly, rotating the second knob 2326 in a first direction (e.g., clockwise) relative to the drive screw 2322 causes the second portion 2344 of the second knob 2326 to move toward the proximal end portion 2346 of the collet 2324 and thus urges the collet 2324 radially inwardly against the actuation tube 2268. As a result, the actuation tube 2268 and the drive screw 2322 move axially together when the first knob 2318 is rotated relative to the housing 2306. Rotating the second knob 2326 in a second direction (e.g., counterclockwise) relative to the drive screw 2322 causes the second portion 2344 of the second knob 2326 to move away from the proximal end portion 2346 of the collet 2324 and thus allows the collet 2324 to move radially outwardly relative to the actuation tube 2268. As a result, the actuation tube 2268 and the drive screw 2322 can move relative to each other.

With the prosthetic spacer device 500 coupled to the actuation shaft or means of actuating 512 and the outer shaft 2220 of the delivery apparatus 2202, the physician can use the actuation control mechanism 2304 of the handle 2300 to manipulate the paddles 520, 522 of the prosthetic spacer device 500 relative to the spacer member 202 of the prosthetic spacer device 500. The actuation control mechanism 2304 can be activated by rotating the second knob 2326 in the first direction relative to the drive screw 2322 to secure the actuation tube 2268 and thus the actuation shaft or means of actuating 512 to the drive screw 2322. The physician can then rotate the first knob 2318 relative to the housing 2302, which causes the drive screw 2322 and thus the actuation tube 2268 and the actuation shaft or means of actuating 512 to move axially relative to the housing 2302 and thus the outer shaft 2220. This, in turn, causes the paddles 520, 522 (which are coupled to the actuation shaft or means of actuating 512 via the cap 514) to move relative to the coaption element 510 (which is coupled to the outer shaft 2220 via coupler or means for coupling 2214 and the proximal collar 511).

The prosthetic spacer device 500 can be released from the delivery apparatus 2202 by rotating the second knob 2326 in the second direction relative to the drive screw 2322. This allows the actuation tube 2268 and thus the actuation shaft or means of actuating 512 to move relative to the drive screw 2322. The shafts 512, 2220 of the delivery apparatus 2202 can then be removed from the respective collars of the prosthetic spacer device 500, as described above.

Configuring a delivery apparatus with the actuation control mechanism 2304 can provide several advantages. For example, the rotational forces required to actuate the first knob 2318 of the handle 2300 can be less than the axial forces required to actuate the knob 2226 of the handle 2300.

The actuation control mechanism 2304 can also provide relatively more precise control of the paddles 520, 522 because the axial movement of the actuation shaft or means of actuating 512 is controlled by rotation of the first knob 2318 and the thread pitch of the drive screw 2322 rather than be axial movement of the knob 2226. In other words, the actuation control mechanism 2304 can be configured, for example, such that one rotation of the first knob 2318 moves the actuation shaft or means of actuating 512 a small axial distance (e.g., 1 mm): whereas, it may be relatively more difficult to axially move the knob 2226 and thus the shaft 512 in small increments (e.g., 1 mm).

Additionally, the actuation control mechanism 2304 can prevent or reduce inadvertent movement and release of the actuation shaft or means of actuating 512. For example, because the actuation control mechanism 2304 requires rotational movement of the first knob 2318 to move the actuation shaft or means of actuating 512, it can prevent or reduce the likelihood that the actuation shaft or means of actuating 512 will move if the knob 2226 is inadvertently contacted. Also, the physician has to rotate the second knob 2326 to release the actuation tube 2268 from the drive screw 2322 before the physician can rotate the knob 2226 to release the actuation shaft or means of actuating 512 from the cap 514 of the prosthetic spacer device 500 and proximally retract the actuation shaft or means of actuating 512. This two-step release process could reduce the likelihood of a physician inadvertently releasing the prosthetic spacer device 500 from the delivery apparatus 2202.

FIGS. 163-164 show exemplary embodiments of a coupler 2400 and a proximal collar 2402. Although not shown, the coupler 2400 can be coupled to the distal end portion of the outer shaft 2220 (FIG. 149) in a manner similar to the coupler or means for coupling 2214. As shown, the proximal collar 2402 can be coupled to a proximal end portion of the coaption element 510 in a manner similar to the proximal collar 511 (FIG. 146). As such, the coupler 2400 and the proximal collar 2402 can be used, for example, in lieu of the coupler or means for coupling 2214 and the proximal collar 514 of the delivery assembly 2200, respectively, to releasably couple the prosthetic spacer device 500 to the outer shaft 2220 (FIG. 149).

Referring to FIG. 164, the coupler 2400 can comprise an axially-extending lumen 2404 and a plurality of radially-extending openings 2406. The lumen 2404 can be configured to receive the actuation shaft or means of actuating 512 (FIG. 163). The openings 2406 can be configured to receive the proximal collar 2402, as further described below.

The proximal collar 2402 can comprise a plurality of proximally-extending tabs or fingers 2408. Free end portions 2410 of the fingers 2408 can have radially-extending projections 2412 formed thereon. The fingers 2408 can be configured to pivot between a first or resting state (FIG. 164) and a second or deflected state (FIG. 163). In the first state, the free end portions 2410 of the fingers 2408 press radially inwardly against each other. In the second state, the free end portions 2410 of the fingers 2408 are radially spaced from each other.

Referring to FIG. 163, the coupler 2400 and the proximal collar 2402 be releasably coupled together by positioning the fingers 2408 of the proximal collar 2402 within the coupler 2400. The actuation shaft or means of actuating 512 can then be advanced through the lumen 2404 of the coupler 2400 and through the fingers 2408 of the proximal collar 2400, thus causing the free ends 2410 of the fingers 2408 to pivot radially-outwardly from the first state to the second state. The projections 2412 of the fingers 2408 and the openings 2406 of the coupler 2400 can be rotationally aligned such that the projections 2412 extend into the openings 2406, thereby releasably coupling the coupler 2400 to the proximal collar 2402. The coupler 2400 can be released from the proximal collar 2402 by retracting the actuation shaft or means of actuating 512 from the finger 2408 of the proximal collar 2402. This allows the free end portions 2410 of the fingers 2408 to pivot from the second state back to the first state and causes the projections 2412 of the fingers 2408 to withdraw from the openings 2406 of the coupler 2402, thus releasing the coupler 2400 from the proximal collar 2402.

In some embodiments, the fingers 2408 of the proximal collar 2402 can be configured to create a hemostatic seal when the fingers 2408 are in the first state. This can, for example, prevent or reduce blood from flowing through the proximal collar 2402 when the prosthetic spacer device 500 is implanted in a patient.

FIGS. 165-166 show exemplary embodiments of a cap 2500, an actuation shaft or means of actuating 2502, and a release member (e.g., wire) 2504, which can be used, for example, with the delivery assembly 2200. Although not shown, the cap 2500 can be coupled to the distal portion of the prosthetic spacer device 500. A proximal portion (not shown) of the actuation shaft or means of actuating 2502 can be coupled to the actuation tube 2268 and the knob 2226. From the proximal end portion, the actuation shaft or means of actuating 2502 can extend distally through the handle 2222 (FIG. 150), through the outer shaft 2220 (FIG. 150), and into the prosthetic spacer device 500 (FIG. 145). A distal end portion of the actuation shaft or means of actuating 2502 can be releasably coupled to the cap 2500 of the prosthetic spacer device 500. As such, the cap 2500 and the actuation shaft or means of actuating 2502 can be used, for example, in lieu of the cap 514 and the actuation shaft or means of actuating 512 of the delivery assembly 2200, respectively.

Referring to FIG. 166, the cap 2500 can comprise a central bore 2506 and a tongue or tab 2508 formed (e.g., laser cut) in a side surface 2510 of the cap 2500. The tongue 2508 can have an opening 2512 formed (e.g., laser cut) therein. The central bore 2506 can be configured to receive a distal end portion of the actuation shaft or means of actuating 2502. The tongue 2508 can be pivotable relative to the side surface 2508 of the cap 2500 from a first or resting configuration (FIG. 166) to a second or deflected configuration (FIG. 165). In the first configuration, the tongue 2508 can be flush with the side surface 2510. In the second configuration, the tongue 2508 can extend radially inwardly relative to the side surface 2510 to protrude into the central bore 2506.

The tongue 2508 can be used, for example, to releasably couple the cap 2500 to the actuation shaft or means of actuating 2502, as shown in FIGS. 165 and 166. For example, the actuation shaft or means of actuating 2502 can be inserted into the central bore 2506 of the cap 2500. The tongue 2508 can then be pushed radially inwardly from the first configuration to the second configuration such that the tongue 2508 presses against the actuation shaft or means of actuating 2502. The release member 2504 can then be advanced distally such that a distal end portion 2514 of the release member 2504 extends through the opening 2512 of the tongue 2508. Thus, the release member 2504 retains the tongue 2508 in the second configuration against the actuation shaft or means of actuating 2502, thereby releasably coupling the cap 2500 to the actuation shaft or means of actuating 2502.

The cap 2500 can be released from the actuation shaft or means of actuating 2500 by retracting the release member 2504 proximally such that the distal end portion 2514 of the release member 2504 withdraws from the opening 2512 of the tongue 2508. This allows the tongue to move radially outwardly from the second state back to the first state, thereby releasing the cap 2500 from the actuation shaft or means of actuating 2502.

This configuration can provide several advantages. For example, in some embodiments, the cap 2500 and the actuation shaft or means of actuating 2502 can be formed without threads. Removing the threads can make manufacturing the cap 2500 and the actuation shaft or means of actuating 2502 easier and/or less expensive. Removing the threads from the actuation shaft or means of actuating 2502 can also reduce the likelihood the actuation shaft or means of actuating 2502 could catch or snag on another component of the delivery assembly 2200.

FIGS. 167-168 show exemplary embodiments of a coupler 2600, a proximal collar 2602, a cap 2604, and an actuation shaft or means of actuating 2606, which can be used, for example, with the delivery assembly 2200. Referring to FIG. 167, the coupler 2600 can be coupled to the distal end portion of the outer shaft 2220. The proximal collar 2602 can be coupled to the proximal portion of the prosthetic spacer device 500 (shown schematically in partial cross-section), and the cap 2604 can be coupled to the distal portion of the prosthetic spacer device 500. A proximal portion (not shown) of the actuation shaft or means of actuating 2606 can be coupled to the actuation tube 2268 and the knob 2226. From the proximal end portion, the actuation shaft or means of actuating 2606 can extend distally through the handle 2222 (FIG. 150), through the outer shaft 2220 (FIG. 150), and into the prosthetic spacer device 200 (FIG. 145). A distal end portion of the actuation shaft or means of actuating 2606 can be releasably coupled to the cap 2604 of the prosthetic spacer device 500. As such, the coupler 2600, the proximal collar 2602, the cap 2604, and the actuation shaft or means of actuating 2606 can be used, for example, in lieu of the coupler or means for coupling 2214, the proximal collar 511, the cap 514, and the actuation shaft or means of actuating 512 of the delivery assembly 2200, respectively.

Referring to FIG. 168, the coupler 2600 can comprise a connection portion 2608, a plurality of pins 2610 (e.g., three in the illustrated embodiment), and one or more securing members 2612 (e.g., three in the illustrated embodiment). The pins 2610 and the securing members can be coupled to and extend distally from the connection portion 2600.

The connection portion 2608 can have an axially-extending lumen 2614 configured to slidably receive the actuation shaft or means of actuating 2606. In some embodiments, the connection portion 2608 can also have a recessed outwardly facing surface 2615 configured to be inserted into the distal end portion of the outer shaft 2220, as shown in FIG. 167.

As best shown in FIG. 168, the pins 2610 can be spaced circumferentially relative to each other and relative to the securing members 2612. The securing members 2612 can be spaced circumferentially relative to each other. In some embodiments, the pins 2610 and the securing members 2612 can be configured in an alternating type pattern (e.g., pin-securing member-pin and so on) on the connection portion 2608.

Referring to FIG. 167, the pins 2610 can be configured to extend into openings 2616 of the proximal collar 2602. In certain embodiments, the securing members 2612 can be suture loops. The securing members 2612 can be configured to extend through the openings 2616 of the proximal collar 2602 and around the actuation shaft or means of actuating 2606. For clarity, only one securing member 2612 is shown extending around the actuation shaft or means of actuating 2606 in FIG. 167.

Referring again to FIG. 168, in addition to the openings 2616, the proximal collar 2602 can comprise a central lumen 2618 disposed radially inward from the openings 2616. The central lumen 2618 can extend axially and can be configured to slidably receive the actuation shaft or means of actuating 2606, as shown in FIG. 167.

The cap 2604 can be configured in a sleeve-like manner such that the actuation shaft or means of actuating 2606 can slidably extend through the cap 2604, as shown in FIG. 167.

The actuation shaft or means of actuating 2606 can comprise a radially-expandable portion 2620 disposed at or near the distal end portion 2622 of the actuation shaft or means of actuating 2606. The radially-expandable portion 2620 can be configured to be selectively expandable from a compressed configuration to an expanded configuration. The radially-expandable portion 2620 can be configured such that an outside diameter of the radially-expandable portion 2620 is less than the inside diameter of the cap 2604, the central lumen 2618 of the proximal collar 2602, and the lumen 2614 of the coupler 2600 when the radially-expandable portion 2620 is in the compressed configuration. When the radially expandable portion 2620 is in the expanded configuration, the outside diameter of the radially-expandable portion 2620 is greater than the inside diameter of the cap 2604. Thus, in the expanded configuration, the radially-expandable portion 2620 can prevent the distal end portion 2622 from moving proximally relative to the cap 2604.

As shown in FIG. 167, the prosthetic spacer device 500 can be releasably coupled to the outer shaft 2220 and the actuation shaft or means of actuating 2606 by inserting the pins 2610 and the securing members 2612 through respective openings 2616 in the proximal collar 2602. With the radially-expandable portion 2620 in the compressed configuration, the actuation shaft or means of actuating 2606 can be advanced distally through the lumen 2614 of the coupler 2600, through the lumen 2618 and the securing members 2612 of the proximal collar 2602, and through the cap 2604 such that the radially-expandable portion 2620 is disposed distal relative to the cap 2604. The radially-expandable portion 2620 of the actuation shaft or means of actuating 2606 can then be expanded from the compressed configuration to the expanded configuration, thus releasably coupling the prosthetic spacer device 500 to the outer shaft 2220 and the actuation shaft or means of actuating 2606.

The prosthetic device 500 can be released from the outer shaft 2220 and the actuation shaft or means of actuating 2606 by compressing the radially-expandable portion 2620 of the actuation shaft or means of actuating 2606 and proximally retracting the actuation shaft or means of actuating 2606 through the cap 2604, through the securing members 2612 and the lumen 2618 of the proximal collar 2602. The outer shaft 2220 can then be retracted proximally relative to the prosthetic spacer device 500 such that the pins 2610 and the securing members 2612 withdraw from the openings 2616 in the proximal collar 2602, thus releasing the prosthetic spacer device 500 from the outer shaft 2220 and the actuation shaft or means of actuating 2606.

FIGS. 169-170 show an exemplary embodiment of clasp control members 2700, which can be used, for example, in lieu of the clasp control members 537 of the delivery assembly 2200. Referring to FIG. 170, the clasp control members 2700 can comprise sleeves 2702, connecting members 2704, and release members 2706. The connecting members 2704 and the release members 2706 can extend axially through and can be movable relative to the sleeves 2702.

Proximal end portions (not shown) of the sleeves 2702 can be coupled to the control member tubes 2270, and distal end portions of the sleeves 2708 can be releasable coupled to the clasps 530 of the prosthetic spacer device 500 by the connecting members 2704 and the release members 2706, as further described below.

The connecting members 2704 can, for example, be suture loops that extend distally from the clasp control mechanism 2250 of the delivery apparatus 2202, through the control member tubes 2270, through the sleeves 2702, and through the openings 535 of the clasps 530. The connecting members 2704 can be releasably coupled to the clasps 530 the prosthetic spacer device 500 by the release members 2706.

The release members 2706 can, for example, be wires that extend distally from the clasp control mechanism 2250 of the delivery apparatus 2202, through the control member tubes 2270, through the sleeves 2702, and through the loops of the connecting members 2704. In this manner, the release members 2706 releasably couple the connecting members 2704 and thus the sleeves 2702 to the clasps 530 by preventing the connection members 2704 from withdrawing through the openings 535 of the clasps 530. The connection members 2704 can be released from the clasps 530 by withdrawing the release members 2706 from the loops of the connecting members 2704 and withdrawing the connecting members 2704 from the openings 535 of the clasps 530.

With the sleeves 2702 releasably coupled to the clasps 530 of the prosthetic spacer device 500 by the connecting members 2704 and the release members 2706, the clasps 530 can be actuated (either together or separately) by moving the sleeves 2702 axially relative to the outer shaft 2220 and the actuation shaft or means of actuating 512. This can be accomplished, for example, by moving the actuator member 2290, which are coupled to the sleeves 2702 via the control tubes 2268, relative to the housing 2246 and actuation tube 2268. Moving the actuation member 2290 proximally relative to the housing 2246 and actuation tube 2268 can open the clasps 530 and moving the actuation member 2290 distally relative to the housing 2246 and actuation tube 2268 can close the clasps 530.

Because the sleeves 2702 are relatively rigid (e.g., compared to the clasp control members 537), the sleeves 2702 can be used to push the clasps 530 closed (either in lieu of or in addition to the bias of the clasps 530 to the closed position). This pushability can help to ensure the native leaflets are grasped within the clasps 530 and thus secured to the paddles 520, 522.

FIG. 171 shows an exemplary embodiment of a guide rail or means for guiding 2800. The guide rail or means for guiding 2800 can, for example, be coupled to the clasps 530 of the prosthetic spacer device 500. In some embodiments, the clasp control member 2700 can be releasably coupled to the guide rail or means for guiding 2800 in a snare-like manner similar to that described above with respect to FIG. 170.

Coupling a clasp control member 2700 to the guide rail or means for guiding 2800 rather than directly to the clasps 530 allows the clasp control member 2700 to slide longitudinally along the guide rail or means for guiding 2800 as the clasp 530 moves between the open and the closed configurations. This can, for example, allow the clasp control member 2700 to maintain a relatively constant angle relative to the paddles 520, 522 as the clasps 530 are actuated. For example, the clasp control member 2700 can slide outwardly toward a first side portion 2802 of the guide rail or means for guiding 2800 when the clasp 206 is pulled open, and the clasp control member 2700 can slide inwardly toward a second side portion 2804 of the guide rail or means for guiding 2800 when the clasp 530 is pushed closed. This can therefore reduce the force required to actuate the clasp control member 2700. For example, the sleeves 2702 can remain more substantially straight as the movable portion of the clasp 530 swings through its full arc of motion. This is due to the sliding movement on the guide rail or means for guiding 2800. By sliding and remaining substantially straight, the amount of bending of the sleeves is limited.

FIG. 172 shows an exemplary embodiment of a shaft 2900. The shaft 2900 can be used, for example, with the delivery apparatus 500 in lieu of the outer shaft 2220 of the third catheter 508. The shaft 2900 can comprise a plurality of axially extending lumens, including an actuation shaft or means of actuating lumen 2902 and a plurality of control member lumens 2904 (e.g., four in the illustrated embodiment) disposed radially outwardly from the actuation shaft or means of actuating lumen 2902. The control member lumens 2904 can be spaced relative to each other and can be evenly distributed circumferentially around the actuation shaft or means of actuating lumen 2902. For example, each of the control member lumens 2904 can be located approximately 90 degrees from an adjacent control member lumen 2904.

The actuation shaft or means of actuating lumen 2902 can be configured to receive the actuation shaft or means of actuating 512, and the control member lumens 2904 can be configured to receive the clasp control members 537. The lumens 2902, 2904 can also be configured such that the actuation shaft or means of actuating 512 and clasp control members 537 can be movable (e.g., axially and/or rotationally) relative to the lumens 2902, 2904, respectively. In particular embodiments, the lumens 2902, 2904 can comprise a liner or coating (e.g., PTFE) configured to reduce friction between the lumens 2902, 2904 and the actuation shaft or means of actuating 512 and clasp control members 537, respectively.

The shaft 2900 can be formed from various materials, including metals and polymers. For example, in one particular embodiment, the shaft 2900 can comprise a first portion 2906, a second portion 2908, and a third portion 2910. The first portion 2906 be the radially outermost portion, the third portion 2910 can be the radially innermost portion, and the second portion 2908 can be disposed radially between the first and third portions 2906, 2910. In certain embodiments, the first and third portions 2906, 2910 can be formed from polymeric material (e.g., PEBAX or other material having a Type D Shore durometer value of SSD), and the second portion 2908 can be formed from a metallic material (e.g., braided stainless steel).

Configuring the shaft 2900 in this manner can, for example, further improve control of the distal end portion of the shaft 2900. For example, this configuration can prevent or reduce "whipping" (e.g., sudden or abrupt movement) at the distal end portion of the shaft 2900 when the shaft 2900 is rotated at the proximal end portion (e.g., by rotating the housing 2246 of the handle 2222). As such, a physician can more precisely control the distal end portion of the shaft 2900 and thus more precisely control the prosthetic spacer device (e.g., the spacer device 500) during the implantation procedure such as when the physician rotates the prosthetic spacer device to align the anchors of the prosthetic spacer device with the native leaflets.

It should be noted that in certain embodiments the housing 2246 of the handle 2222 can comprise four control member lumens 2264, 2282 (i.e., four of each) that are coupled to the control member lumens 2904. As such, each portion of the clasp control members 537 can extend distally in a separate lumen from the clasp control mechanism 2250 of the handle 2222 to the prosthetic spacer device 500.

Referring to FIG. 173, the actuation wire 512 can be hollow so that a tethering line or suture 3000 can be extended through the actuation wire 512 to the device 500. The actuation wire 512 extends through the device 500 and is attached to the cap 514. Retracting the tethering line 3000 in the retraction direction X relative to a coupler of the delivery assembly 2200 reduces the length of the tethering line 3000, thereby moving the coupler of the delivery assembly 2200 toward the device 500 in a recapture direction Y.

Referring again to FIG. 173, the device 500 is shown in a closed position having been delivered and implanted in the native mitral valve. Once the device 500 is implanted, the coupler of the delivery assembly 2200 is opened and moved away from the device in a retraction direction X so that the performance of the device 500 can be monitored to see if any adjustments may be desirable. If further adjustments to the device 500 are desired, the tethering line 3000 is retracted in the retraction direction X so that the coupler of the delivery assembly 2200 moves in the recapture direction Y toward the device 500.

Referring now to FIG. 174, the coupler of the delivery assembly 2200 has been moved into a suitable position to recapture the device 500. Once in position, the actuation lines 3002 for each moveable arm 2228 are retracted in an actuation direction A to cause the moveable arms 2228 to move in a closing direction B close around the proximal collar 511 of the device 500. In some embodiments, the tethering line 3000 is adjusted simultaneously with the actuation lines 3002 to aid in recapturing the device 500 which may be moving around as the native mitral valve MV opens and closes.

Referring now to FIG. 175, the moveable arms 2228 are closed around the proximal collar 511. The actuation wire 512 is then moved in a distal direction C, through the securing portions 2234 of the moveable arms 2228 and into the device 500 along the tethering line 3000. To recapture and secure the device 500, a threaded end 512B of the actuation wire 512 is threaded into a threaded receptacle 516A of the cap 514 as shown in FIG. 176.

FIGS. 174A and 175A illustrate another example of a mechanism that can be used to recouple the coupler of the delivery assembly 2200 to the collar 511 of the device 500. In the example of FIGS. 174A and 175A, the actuation wire 512 can be hollow so that a tethering line or suture 3000 can be extended through the actuation wire 512 to the device 500. As in the embodiment illustrated by FIGS. 174 and 175, retracting the tethering line 3000 in the retraction direction X moves the coupler of the delivery assembly 2200 toward the device 500 in a recapture direction Y.

Referring now to FIGS. 174A and 175A, the coupler of the delivery assembly 2200 has been moved into a suitable position to recapture the device 500. Once in position, a closing sleeve 3003 that fits around the moveable arms 2228 is advanced over the coupler of the delivery assembly 2200 in a closing direction C to press the moveable arms 2228 inward in a closing direction D around the proximal collar 511 of the device 500. In some embodiments, the tethering line 3000 is adjusted simultaneously with the closing sleeve 3003 to aid in recapturing the device 500 which may be moving around as the native mitral valve MV opens and closes.

Referring now to FIG. 175A, the moveable arms 2228 are closed around the proximal collar 511. The actuation wire 512 is then moved in a distal direction E and into the device 500 along the tethering line 3000. To recapture and secure the device 500, a threaded end 512B of the actuation wire 512 is threaded into a threaded receptacle 516A of the cap 514 as shown in FIG. 176.

Referring now to FIGS. 177-178, an exemplary implantable prosthetic device 3100 is shown. The device 3100 includes an implantable prosthetic device 3110 and a coupler 3120. An actuation shaft or means of actuating or wire 3130 can extend through the coupler 3120 to the device 3110 to open and close the device 3110. The device 3110 is similar to exemplary implantable prosthetic devices described in the present application and includes a proximal collar 3112 having an opening 3114 and radially disposed apertures 3116. The coupler 3120 has moveable arms or fingers 3122 that can be moved between open and closed positions. The moveable arms 3122 include protrusions 3124 configured to engage the apertures 3116 of the proximal collar 3112 of the device 3110. The moveable arms 3122 are biased inward so that moving the actuation shaft or means of actuating 3130 in a distal direction Y through the coupler 3120 and between the moveable arms 3122 spreads the moveable arms 3122 outwards so that the protrusions 3124 engage the apertures 3116. In the illustrated embodiment, the protrusions 3124 and apertures 3116 are tapered to ease engagement of the protrusions 3124 with the apertures 3116. Moving the actuation shaft or means of actuating 3130 in a retraction direction X allows the moveable arms 3122 to move inward so that the protrusions 3124 disengage the apertures 3116. In this way the device 3110 can be released and recaptured by the coupler 3120.

Referring now to FIGS. 179-181, an exemplary implantable prosthetic device 3200 is shown. The device 3200 includes an implantable prosthetic device 3210 and a coupler 3220. An actuation shaft or means of actuating or wire 3230 can extend through the coupler 3220 to the device 3210 to open and close the device 3210. The device 3210 is similar to exemplary implantable prosthetic devices described in the present application and includes a proximal collar 3212 having an opening 3214 and radially disposed apertures 3216.

The coupler 3220 has moveable arms or fingers 3222 that can be moved between open and closed positions. The moveable arms 3222 include protrusions 3224 configured to engage the apertures 3216 of the proximal collar 3212 of the device 3210. The moveable arms 3222 are biased inward so that moving the actuation shaft or means of actuating 3230 in a distal direction Y through the coupler 3220 and between the moveable arms 3222 spreads the moveable arms 3222 outwards so that the protrusions 3224 engage the apertures 3216. Moving the actuation shaft or means of actuating 3230 in a retraction direction X allows the moveable arms 3222 to move inward so that the protrusions 3224 disengage the apertures 3216. In this way the device 3210 can be released and recaptured by the coupler 3220.

The actuation wire 3230 can be hollow so that a tethering line or suture 3232 can be extended through the actuation wire 3230 to the device 3210. The actuation wire 3230 extends through the opening 3214 of the device 3210 and is attached to securing portions 3218. Retracting the tethering line 3232 in the retraction direction X (FIG. 180) reduces the length of the tethering line 3232, thereby moving the coupler 3220 toward the device 3210 such that the moveable arms 3222 are inserted into the opening 3214 of the device 3210 as shown in FIG. 180.

Referring now to FIG. 181, once the coupler 3220 has been moved into position to recapture the device 3210 the actuation wire 3230 is moved in the distal direction Y to recouple the coupler 3220 to the device 3210. The actuation wire 3230 engages the moveable arms 3222, thereby causing the protrusions 3224 to move in an outward direction A to engage the apertures 3216 of the device 3210. In the illustrated embodiment, the protrusions 3224 and apertures 3216 are tapered to ease engagement of the protrusions 3224 with the apertures 3216. In some embodiments, the tethering line 3232 is adjusted simultaneously as the actuation shaft or means of actuating 3230 is extended to take up slack in the actuation line and maintain engagement between the coupler 3220 and device 3210.

Referring now to FIGS. 182-183, an exemplary implantable prosthetic device 3300 is shown. The device 3300 includes an implantable prosthetic device 3310 and a coupler 3320. An actuation shaft or means of actuating or wire 3330 can extend through the coupler 3320 to the device 3310 to open and close the device 3310. The device 3310 is similar to exemplary implantable prosthetic devices described in the present application and includes a proximal collar 3312 having an opening 3314 and radially disposed apertures 3316.

The coupler 3320 has moveable arms or fingers 3322 that can be moved between open and closed positions. The moveable arms 3322 include distal protrusions 3324 configured to engage the apertures 3316 of the proximal collar 3312 of the device 3310. The moveable arms 3324 also include internal protrusions 3326 having apertures 3328 configured to receive the actuation shaft or means of actuating 3330. In the closed position, the internal apertures 3328 are offset from the actuation shaft or means of actuating 3330. The actuation shaft or means of actuating 3330 has a tapered end 3332 to engage the offset apertures 3328. As successive apertures 3328 are engaged by the tapered end 3332 of the actuation shaft or means of actuating 3330, the moveable arms 3322 are moved outward to engage the opening 3314.

The moveable arms 3322 are biased inward so that moving the actuation shaft or means of actuating 3330 in a distal direction Y through the coupler 3320 and between the moveable arms 3322 spreads the moveable arms 3322 outwards so that the protrusions 3324 engage the apertures 3316. Moving the actuation shaft or means of actuating 3330 in a retraction direction X allows the moveable arms 3322 to move inward so that the protrusions 3324 disengage the apertures 3316. In this way the device 3310 can be released and recaptured by the coupler 3320. In some embodiments, the prosthetic device 3300 is similar to the device 3200 and includes a tethering line (not shown) that allows the device 3300 to be recaptured.

Referring now to FIGS. 184-185, an exemplary implantable prosthetic device 3400 is shown. The device 3400 includes an implantable prosthetic device 3410 and a coupler 3420. An actuation shaft or means of actuating or wire 3430 can extend through the coupler 3420 to the device 3410 to open and close the device 3410. The device 3410 is similar to exemplary implantable prosthetic devices described in the present application and includes a proximal collar 3412 having an opening 3414 and radially disposed apertures 3416.

The coupler 3420 has moveable arms or fingers 3422 that can be moved between open and closed positions. The moveable arms 3422 include distal protrusions 3424 configured to engage the apertures 3416 of the proximal collar 3412 of the device 3410. The moveable arms 3424 also include internal protrusions 3426 having apertures 3428 configured to receive the actuation shaft or means of actuating 3430. In the closed position, the internal apertures 3428 are offset from the actuation shaft or means of actuating 3430. The actuation shaft or means of actuating 3430 has a tapered end 3432 to engage the offset apertures 3428. As successive apertures 3428 are engaged by the tapered end 3432 of the actuation shaft or means of actuating 3430, the moveable arms 3422 are moved inward to engage the opening 3414.

The moveable arms 3422 are biased outward so that moving the actuation shaft or means of actuating 3430 in a distal direction Y through the coupler 3420 and between the moveable arms 3422 retracts the moveable arms 3422 inwards so that the protrusions 3424 engage the apertures 3416. Moving the actuation shaft or means of actuating 3430 in a retraction direction X allows the moveable arms 4622 to spread outward so that the protrusions 3424 disengage the apertures 3416. In this way the device 3410 can be released and recaptured by the coupler 3420. In some embodiments, the prosthetic device 3400 is similar to the device 3200 and includes a tethering line (not shown) that allows the device 3400 to be recaptured.

Referring to FIG. 186, an actuation shaft or means of actuating 3500 for placing and actuating an implantable prosthetic device is shown. The actuation shaft or means of actuating 3500 includes a hollow positioning shaft 3510 and a hollow device shaft 3520 that fit over a retaining shaft 3530 that holds the hollow positioning and device shafts 3510, 3520 together at a connection 3502. The hollow positioning shaft 3510 extends from a delivery device 3504 and when coupled to the device shaft 3520 allows an implantable device 3506 to be placed in a suitable location for implantation. The location of the connection 3502 between the hollow positioning shaft 3510 and the device shaft 3520 can be at a wide variety of different positions in an implantable device. For example, the connection 3502 may at a proximal portion of a device or may be at a distal portion of a device.

The hollow positioning shaft 3510 can include a protruding portion 3512 and a recessed receiving portion 3514. The device shaft 3520 can also include a protruding portion 3522 and a recessed receiving portion 3524. When the hollow positioning and device shafts 3510, 3520 are coupled, the protruding portion 3512 of the hollow positioning shaft 3510 is received by the receiving portion 3524 of the device shaft 3520, and the protruding portion 3522 of the device shaft 3520 is received by the receiving portion 3514 of the hollow positioning shaft 3510.

The hollow positioning and device shafts 3510, 3520 can be connected in a wide variety of different ways. For example, the hollow positioning shaft 3510 can include a bore or channel 3516 that is aligned with a bore or channel 3526 of the hollow device shaft 3520 when the protruding portions 3512, 3522 are disposed in the receiving portions 3514, 3524, respectively. When the openings 3516, 3526 are aligned and the retaining shaft 3530 is placed into the openings 3516, 3526 in the direction X, the hollow positioning and device shafts 3510, 3520 are retained together. When the retaining shaft 3530 is removed from the openings 3516, 3526 in the direction Z, protruding portions 3512, 3522 can be removed from the receiving portions 3514, 3524, such that the device 3506 is detached from the hollow positioning shaft 3510.

Still referring to FIG. 186, in some embodiments, when the hollow positioning and device shafts 3510, 3520 are secured to each other, an aperture 3540 is created at interface 3542 between the hollow positioning and device shafts 3510, 3520. The aperture 3540 is configured to secure a control line 3544 between the hollow positioning and device shafts 3510, 3520 to allow for separate control of clasps or gripping members (not shown). That is, the aperture 3540 is configured such that the line 3544 does not move relative to the aperture 3540 when the hollow positioning and device shafts 3510, 3520 are joined together. Upon detachment of the hollow positioning and device shafts 3510, 3520, the line 3544 is released from the aperture 3540 and can be removed from the implantable device 3506. The line 3544 can then be retracted into the catheter to release the clasps gripping members.

Referring now to FIG. 187, an actuation or control mechanism 3600 is shown. The control mechanism 3600 can be used to open and close first and second clasps or gripping members 3610, 3620 to grasp native leaflets for implantation of an implantable prosthetic device. The control mechanism 3600 includes a first gripper control member 3612 and a second gripper control member 3622. The first gripper control member 3612 is configured to move the first gripping member 3610 bi-directionally in the direction X, and the second gripper control member 3622 is configured to move the first gripping member 3620 bi-directionally in the direction Z. Movement of the first gripping member 3610 in the direction X adjusts the width W of a first opening 3616 between the first gripping member 3610 and a first paddle 3614, and movement of the second gripping member 3620 in the direction Z will adjust the width H of a second opening 3626 between the second gripping member 3620 and a second paddle 3624.

In the illustrated embodiment, the gripper control members 3610, 3620 include a push/pull link 3611, 3621, such as, for example, a catheter, a flexible rod, or a stiff wire and a coupler 3613, 3623. Each push/pull link 3611, 3621 extends from a delivery device 3602 and is removably attached to the corresponding gripping member 3612, 3622 by the couplers 3613, 3623. The link 3611 is configured to be pushed and pulled in the direction Y. Movement of the link 3611 in the direction Y causes the gripping member 3610 to move in the direction X. Similarly, the link 3621 is configured to be pushed and pulled in the direction M, and movement of the link 3621 in the direction M causes the gripping member 3620 to move in the direction H.

Referring now to FIGS. 188 and 188A, an actuation or control mechanism 3700 for use in implantable prosthetic devices, such as the devices described in the present application, is shown. The actuation mechanism 3700 allows for pushing and pulling of portions of an implantable device, such as the clasps or gripping members described above. The mechanism 3700 includes first and second control members 3710, 3720 that extend from a delivery device 3702. The delivery device 3702 may be any suitable device, such as a sheath or catheter. The first and second control members 3710, 3720 include first and second sutures 3712, 3722 and first and second flexible wires 3714, 3724. The first and second flexible wires 3714, 3724 extend from the delivery device 3702 and each include a loop 3716, 3726 for receiving the first and second sutures 3712, 3722 and for engaging a clasp or gripping member. Each of the first and second sutures 3712, 3722 extends from the delivery device 3702, through a one of the first and second loops 3716, 3726, respectively, and back into the delivery device 3702. In the example illustrated by FIG. 188, each suture 3712, 3722 extends through one of the loops 3716, 3726 once. In the example illustrated by FIG. 188, each suture 3712, 3722 extends through one of the loops 3716, 3726 twice. In some embodiments, the first and second control members 3712, 3722 extend through separate delivery devices 3702. The sutures 3712, 3722 are removably attached to moveable arms of exemplary barbed clasps described above. The first and second loops 3716, 3726 of the respective wires 3714, 3724 are able to move along the corresponding sutures 3712, 3722 such that the loops 3716, 3726 can engage the corresponding barbed clasps to engage the moveable arms. That is, the sutures 3712, 3722 are used to pull the moveable arms in an opening direction and the wires 3714, 3724 are used to push the moveable arms in a closing direction. The wires 3714, 3724 can be made of, for example, steel alloy, nickel-titanium alloy, or any other metal or plastic material. In certain embodiments, the wires 3714, 3724 can have a diameter between about 0.10 mm and about 0.35 mm, between about 0.15 mm and about 0.30 mm, and between about 0.20 mm and about 0.25 mm. While the wires 3714, 3724 are shown as coming out of separate lumens than the sutures 3712, 3722, in another embodiment, the wires 3714, 3724 can share a lumen with a suture.

In the examples of FIGS. 188 and 188A, the wires 3714, 3724 can be replaced with a rigid or semi-rigid tube or pushable coil. The tube or pushable coil can share a lumen with a suture loop, the suture loop can be disposed inside the tube or pushable coil. The tube or pushable coil can be advanced over one side or both sides of each suture loop to push. The tube, pushable coil, or wire can be retracted as necessary into the catheter when not needed.

Referring now to FIG. 189, another exemplary embodiment of an actuation or control mechanism 3800 includes a first catheter 3811, a second catheter 3821, and single line 3830, such as a wire or suture. The first catheter 3811 and line 3830 are configured to move a first gripping member 3810 in the direction X, and the second catheter 3821 and line 3830 configured to move a second gripping member 3820 in the direction Z. Movement of the gripping member 3810 in the direction X will adjust the width W of a first opening 3816 between the first gripping member 3810 and a first paddle 3814, and movement of the second gripping member 3820 in the direction Z will adjust the width H of a second opening 3826 between the second gripping member 3820 and a second paddle 3824. The line 3830 extends from a delivery device 3802 through the catheters 3811, 3821 and is threaded through openings in both gripping member 3810, 3820. Each catheter 3811, 3821 is configured to engage and move the corresponding gripping member 3810, 3820. In particular, the first catheter 3811 is configured to be pushed in the direction Y while the line 3830 is payed out of the second catheter 3821 or tension in the line 3830 is reduced. The first catheter 3811 is configured to be pulled in the direction Y while the line 3830 is pulled into the first catheter 3811 or tension in the line is increased. Movement of the first catheter 3811 in the direction Y causes the first catheter 3811 to move the first gripping member 3810 in the direction X. Similarly, the second catheter 3821 is configured to be pushed in the direction M while the line 3830 is payed out of the first catheter 3811 or tension in the line 3830 is reduced. The second catheter 3821 is configured to be pulled in the direction M while the line 3830 is pulled into the second catheter 3821 or tension in the line 3830 is increased. Movement of the second catheter 3821 in the direction M causes the second catheter 3821 to move the second gripping member 3820 in the direction H. In an alternative embodiment, the control mechanism 3800 described above with reference to FIG. 189 can include a first flexible wire with a loop (e.g., the flexible wire 3714 with the loop 3716 shown in FIG. 188) and a second flexible wire with a loop (e.g., the flexible wire 3724 with the loop 3726 shown in FIG. 188), and the single line 3830 extends through the loop 3716, 3726 of each of the wires 3830.

Referring to FIG. 190, another exemplary embodiment of an actuation or control mechanism 3900 includes a single line 3930, such as a suture or wire, that is removably attached to first and second clasps or gripping members 3910, 3920 and removably fixed between a positioning shaft 3904 and a device shaft 3906 of an implantable device. The shafts 3904, 3906 are similar to the hollow positioning and device shafts 3510, 3520, described in more detail above. The single line 3930 is connected at a connection 3908 between the shafts 3904, 3906, such that the single line 3930 can separately control the gripping members 3910, 3920. That is, movement of a first portion 3832 of the line 3830 in a direction Y will adjust a width W between the first gripping member 3910 and a first paddle 3914, but will not adjust a width H between the second gripping member 3920 and a second paddle 3924. Similarly, movement of a second portion 3934 of the line 3930 in a direction M will adjust a width H between the second gripping member 3920 and a second paddle 3924, but will not adjust the width W between the first gripping member 3910 and the first paddle 3914. After the valve repair device is in a closed position and secured to the native valve tissue, the positioning shaft 3904 is detached from the device shaft 3906. Decoupling the shafts 3904, 3906 releases the line 3930 from the connection 3908. The line 3930 can then be retracted into the catheter 3902 to release the gripping members 3910, 3920 by pulling one end of the line 3930 into the catheter 3902. Pulling one end of the line 3930 into the catheter 3902 pulls the other end of the line 3930 through the gripping members 3910, 3920 and then into the catheter 3902. Any of the lines described herein can be retracted in this manner.

Referring now to FIGS. 208A, 208B, 209A, and 209B, an exemplary implantable prosthetic device 4100, such as the devices described in the present application, is shown anchored to native leaflets 20, 22. The device 4100 includes a coaption or spacer element 4102 and anchors 4104. The anchors 4104 attach the device 4100 to the leaflets 20, 22. As can be seen in FIG. 208B, first and second gaps 26A, 26B remain between the closed leaflets 20, 22 after the device 4100 is deployed. The coaption element 4102 includes first and second auxiliary, inflatable coaption or spacer elements 4106, 4108 that are shown in a deflated condition in FIGS. 208A and 208B.

Referring now to FIGS. 209A, 209B, the device 4100 is shown with the auxiliary coaption elements 4106, 4108 in an inflated condition. The first and second auxiliary coaption elements 4106, 4108 can be inflated to fill the first and second gaps 26A, 26B. Filling the gaps 26A, 26B allows the leaflets 20, 22 to more fully seal around the device 4100. The auxiliary coaption elements 4106, 4108 are independently inflatable so that the first auxiliary coaption element 4106 can be inflated to a different size than the second auxiliary coaption element 4108 to fill different size gaps 26A, 26B.

Referring now to FIGS. 210A and 210B, an exemplary expandable coaption or spacer element 4200 for use with a prosthetic implantable device of the present disclosure is shown. Referring now to FIG. 210A, the expandable coaption element 4200 is shown in a compressed condition. The expandable coaption element 4200 is formed from a coiled wire 4202 that is retained in the compressed condition by a retaining element 4204. Once the coaption element 4200 is in a desired location, an actuation suture 4206 is used to pull the retaining element 4204 in an actuation direction 4208. Removing the retaining element 4204 allows the coaption element 4200 to expand in an expansion direction 4210 to a larger, expanded size. The coaption element 4200 can be used as the auxiliary coaption element 4016, 4018 in the embodiment of FIGS. 208A, 208B, 208C, and 208D.

Referring now to FIGS. 211A and 211B, an exemplary implantable prosthetic device 4300, such as the devices described in the present application, is shown. The device 4300 extends from a proximal end 4301 to a distal end 4303. Like the device 4100 described above, the device 4300 includes a coaption or spacer element 4302 that has first and second auxiliary, inflatable coaption or spacer elements 4306, 4308 that are shown in a deflated condition in FIG. 211A. Each auxiliary coaption element 4306, 4308 extends from a proximal end 4306A, 4308A to a distal end 4306B, 4308B. Referring now to FIG. 211B, the device 4300 is shown with the auxiliary coaption elements 4306, 4308 in an inflated condition. When inflated, the proximal ends 4306A, 4308A and distal end 4306B, 4308B have different sizes such that the auxiliary coaption elements 4306, 4308 increase in size from the proximal 4306A, 4308A to distal ends 4306B, 4308B. In certain embodiments, the proximal ends are larger than the distal ends. The varying width of the auxiliary coaption elements 4306, 4308 improves coaption between leaflets (not shown) and the device 4300 where the gaps between leaflets change in size from the proximal to distal ends 4301, 4303 of the device 4300.

Referring now to FIGS. 212A, 212B, 213A, 213B, 214, 215A, 215B, 216A, 216B, 217A, 217B, and 218 an exemplary implantable prosthetic device 4400, such as the devices described in the present application, is shown. Referring now to FIGS. 212A, 212B, 213A, 213B, and 214, the device 4400 includes a coaption or spacer element 4402, anchors 4404, and an attachment portion 4406. The attachment portion 4406 is a threaded rod that extends from the coaption element 4402 to receive an auxiliary coaption or spacer element 4410. The auxiliary coaption element 4410 has an inverted L-shape with an attachment opening 4412 and a spacer body 4414. The attachment opening 4412 receives the attachment portion 4406 to attach the auxiliary coaption element 4410 to the device 4400. The spacer body 4414 extends along one side of the coaption element 4402 to fill a gap (e.g., gaps 26A, 26B shown in FIG. 208B) between the leaflets. The auxiliary coaption element 4410 may have any suitable shape and may vary in width and size like the inflatable spacers 4106, 4108, 4306, and 4308 described above.

Referring now to FIG. 214, the auxiliary coaption element 4410 is shown being assembled to the device 4400. The auxiliary coaption element 4410 can be attached to the attachment portion 4406 of the device 4400 after the device 4400 has been implanted between the native leaflets (not shown) and anchored in place via the anchors 4404. As can be seen in FIGS. 215A and 215B, the auxiliary coaption element 4410 is secured to the attachment portion 4406 with a nut 4408 after being attached to the device 4400. In certain embodiments, the attachment opening 4412 in the auxiliary coaption element 4410 is a slot to allow for lateral adjustment of the position of the auxiliary coaption element 4410 without fully removing the auxiliary coaption element 4410 from the device 4400. That is, the nut 4408 may be loosened to allow the position of the auxiliary coaption element 4410 to be adjusted after assembly to the device 4400.

Referring now to FIGS. 216A, 216B, 217A, 217B, the device 4400 and auxiliary coaption element or spacer 4410 are shown with different means of attaching the auxiliary coaption element 4410 to the device 4400 than the threaded rod and nut 4408 described above. The device 4400 shown in FIGS. 216A and 216B includes a circular magnet 4407 surrounding the attachment portion 4406. The auxiliary coaption element 4410 shown in FIGS. 217A and 217B includes a similarly shaped magnet 4413 surrounding the attachment opening 4412 (which is shown as a hole, rather than a slot). When the auxiliary coaption element 4410 is assembled to the device 4400 opposite poles two magnets 4407, 4413 face each other and are attracted to each other and retain the auxiliary coaption element 4410 on the device 4400 by way of magnetic attractive forces. In some embodiments, a plurality of magnets are provided on the device 4400 and/or the auxiliary coaption element 4410.

Referring now to FIG. 218, a double-sided auxiliary coaption element 4420 for attachment to the device 4400 is shown. The auxiliary coaption element 4420 has an inverted U-shape with an attachment opening 4422 disposed between two coaption portions 4424. Like the auxiliary coaption element 4410 described above, the attachment opening 4422 receives the attachment portion 4406 to attach the auxiliary coaption element 4420 to the device 4400. The coaption portions 4424 extend along both sides of the coaption element 4402 to fill gaps (e.g., gaps 26A, 26B shown in FIG. 208B) between the leaflets. The auxiliary coaption element 4420 may have any suitable shape and may vary in width and size like the inflatable spacers 4106, 4108, 4306, and 4308 described above.

Referring now to FIGS. 219A, 219B, an exemplary implantable prosthetic device 4500, such as the devices described in the present application, is shown. The device 4500 includes a coaption or spacer element 4502 and attachment portions 4504 arranged on opposite sides of the coaption element 4502. The attachment portions 4504 are configured to receive auxiliary coaption or spacer elements of varying shapes and sizes (FIGS. 220A-220E). In the illustrated embodiment, the attachment portions 4504 are shown as hoops that receive posts or pins 4512 of the auxiliary coaption elements (FIGS. 220A-220E). Like the spacers 4410 shown above, the auxiliary coaption elements 4510A, 4510B, 4520A, 4520B, 4530A, 4530B, 4540A, 4540B, 4550A, 4550B shown in FIGS. 220A-220E extend along one or both sides of the coaption element 4502 to fill a gap (e.g., gaps 26A, 26B shown in FIG. 208B) between the leaflets. To accommodate gaps of different sizes and shapes, the variety of auxiliary coaption elements 4510A, 4510B, 4520A, 4520B, 4530A, 4530B, 4540A, 4540B, 4550A, 4550B are provided with semi-circle, rounded triangular, or other suitable shapes in a range of sizes. Different size and shape auxiliary coaption elements 4510A, 4510B, 4520A, 4520B, 4530A, 4530B, 4540A, 4540B, 4550A, 4550B can be attached to the coaption element 4502 to accommodate gaps that are different shapes and sizes on opposite sides of the coaption element 4502.

Referring now to FIGS. 221-223, an exemplary implantable prosthetic device 4600 is shown. Referring now to FIG. 221, the device 4600 is shown cut from a flat sheet of material 4602, such as Nitinol, into a lattice-like shape formed from a plurality of struts. The coaption portion 4604 of the device 4600 includes auxiliary coaption portions 4606 that expand outwards from the coaption element 4602 when the device 4600 is formed into a three-dimensional shape. The auxiliary coaption portions 4606 can be longer struts that are curved before the prosthetic device is expanded. Referring now to FIG. 223, when the device is expanded, the longer curved struts expand to form the auxiliary coaption portions 4606. The expanded auxiliary coaption portions 4605 fill or partially fill gaps 26 between the native leaflets 20, 22 when the device 4600 is implanted between the native leaflets 20, 22. In some embodiments, the coaption portion 4604 of the device is covered with a cover (not shown) can be a cloth material such as polyethylene cloth of a fine mesh. The cloth cover can provide a blood seal on the surface of the spacer, and/or promote rapid tissue ingrowth.

Referring now to FIGS. 224-225, an exemplary implantable prosthetic device 4700 is shown. Referring now to FIG. 224, the device 4700 is shown cut from a flat sheet of material 4702, such as Nitinol. The device 4700 includes coaption portions 4704, inner paddle portions 4706, outer paddle portions 4708, and a middle portion 4710. Referring now to FIG. 225, the device 4700 is shown folded into a three-dimensional shape. The material 4702 is folded at the middle portion 4710 so that the various portions of each side of the material 4702 align. When the coaption portions 4704 are aligned, a matrix of cut-outs in the material 4702 form the coaption portion 4704 into a three-dimensional shape similar to the shape of the coaption elements described above.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Additionally, even though some features, concepts, or aspects of the disclosures may be described herein as being a preferred arrangement or method, such description is not intended to suggest that such feature is required or necessary unless expressly so stated. Still further, exemplary or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of exemplary methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

What is claimed is:

1. A valve repair device for repairing a native valve of a patient, the valve repair device comprising:
    a coaption element having an oblong cross-section;
    a pair of paddles connected to the coaption element, wherein the paddles are movable between an open position and a closed position and are configured to attach to the native valve of the patient;
    a gripping member attached to each of the paddles;
    a catch point formed between the coaption element and the gripping members when the paddles are in the open position; and
    a cover extending from the coaption element and over a back side of at least one of the gripping members to cover the catch point.

2. The valve repair device of claim 1, wherein the cover extends from the coaption element to the paddles.

3. The valve repair device of claim 1, wherein the cover extends from a proximal end of the device to the paddles.

4. The valve repair device of claim 1, wherein the cover extends from a distal end of the device to the coaption element.

5. The valve repair device of claim 1, wherein the paddles comprise an inner paddle portion and an outer paddle portion.

6. The valve repair device of claim 5, wherein the cover extends from the coaption element to the inner paddle portions.

7. The valve repair device of claim 5, wherein the cover extends from a proximal end of the device to the paddles.

8. The valve repair device of claim 5, wherein the cover extends from a distal end of the device to the inner paddle portions.

9. The valve repair device of claim 5, wherein the gripping members comprise moveable and fixed arms; and wherein the fixed arms are attached to the inner paddle portions of the paddles.

10. The valve repair device of claim 9, wherein the cover extends from the coaption element to the moveable arms of the gripping members.

11. The valve repair device of claim 9, wherein the cover extends from a proximal end of the device to the gripping members.

12. The valve repair device of claim 9, wherein the cover extends from a proximal end of the device to the moveable arms of the gripping members.

13. The valve repair device of claim 9, wherein the cover extends from a distal end of the device to the gripping members.

14. The valve repair device of claim 9, wherein the cover extends from a distal end of the device to the moveable arms of the gripping members.

15. The valve repair device of claim 1, wherein the paddles are each disposed over an extension member.

16. The valve repair device of claim 15, wherein the cover covers at least a portion of the extension member.

17. The valve repair device of claim 15, wherein the cover covers at least a portion of the extension member and paddles.

18. The valve repair device of claim 15, wherein the cover extends from a proximal end of device to cover at least a portion of the extension members and the paddles.

19. The valve repair device of claim 15, wherein the cover extends from a distal end of device to cover at least a portion of the extension members and the paddles.

20. The valve repair device of claim 1, further comprising a base assembly that comprises:
    a shaft;
    a collar that the shaft extends through; and
    a cap attached to the shaft such that the cap can be moved by the shaft away from the collar;
    wherein the pair of paddles are attached to the cap; and
    wherein movement of the cap toward the collar causes the pair of paddles to move to the closed position, and movement of the cap away from the collar causes the pair of paddles to move to the open position.

21. The valve repair device of claim 20, wherein the cover covers at least a portion of the cap and paddles.

22. The valve repair device of claim 1, wherein the catch point is formed between the coaption element and the gripping member when an angle between coaption element and the paddles is greater than about 120 degrees.

23. The valve repair device of claim 1, wherein the catch point is formed between the coaption element and the gripping member when an angle between coaption element and the paddles is greater than about 150 degrees.

24. The valve repair device of claim 1, wherein the catch point is formed between the coaption element and the gripping member when an angle between coaption element and the paddles is greater than about 180 degrees.

25. The valve repair device of claim 1, wherein the cover comprises an electrospun material.

26. The valve repair device of claim 1, wherein the cover comprises a cloth material.

27. The valve repair device of claim 1, wherein the cover comprises polyethylene.

28. The valve repair device of claim 1, wherein the coaption element is configured to close a gap in the native valve of the patient when the valve repair device is attached to the native valve.

29. A valve repair system for repairing a native valve of a patient during a non-open heart procedure, the valve repair system comprising:
    a delivery device having at least one lumen; and
    a valve repair device configured to be delivered through the lumen of the delivery device, and configured to attach to a native valve of a patient, the valve repair device comprising:
        a coaption element having an oblong cross-section;
        a pair of paddles connected to the coaption element, wherein the paddles are movable between an open position and a closed position and are configured to attach to the native valve of the patient;

a gripping member attached to each of the paddles;
a catch point formed between the coaption element and the gripping members when the paddles are in the open position; and
a cover extending from the coaption element and over a back side of at least one of the gripping members to cover the catch point.

* * * * *